United States Patent
Choi et al.

(10) Patent No.: US 6,902,893 B1
(45) Date of Patent: Jun. 7, 2005

(54) LYME DISEASE VACCINES

(76) Inventors: Gil H. Choi, 11429 Potomac Oaks Dr., Rockville, MD (US) 20850; Alice L. Erwin, 7759 26th Ave., NW., Seattle, WA (US) 98119; Mark S. Hanson, 7013 Woodscape Dr., Clarksville, MD (US) 20109; Raju Lathigra, 19051 Steeple Pl., Germantown, MD (US) 20874

( * ) Notice: Subject to any disclaimer, the term of this patent is extended or adjusted under 35 U.S.C. 154(b) by 0 days.

(21) Appl. No.: 09/830,230

(22) PCT Filed: Jun. 18, 1998

(86) PCT No.: PCT/US98/12718

§ 371 (c)(1),
(2), (4) Date: Sep. 27, 2001

(87) PCT Pub. No.: WO98/59071

PCT Pub. Date: Dec. 30, 1998

Related U.S. Application Data

(60) Provisional application No. 60/057,483, filed on Sep. 3, 1997, provisional application No. 60/053,344, filed on Jul. 22, 1997, provisional application No. 60/053,377, filed on Jul. 22, 1997, and provisional application No. 60/050,359, filed on Jun. 20, 1997.

(51) Int. Cl.[7] ............................ C12Q 1/68; C12P 19/34; C07H 21/04
(52) U.S. Cl. ........................ 435/6; 435/91.2; 536/22.1; 536/24.3
(58) Field of Search .................. 435/6, 91.2; 536/22.1, 536/24.3

(56) References Cited

U.S. PATENT DOCUMENTS

| 5,466,577 A | 11/1995 | Weisburg |
| 5,582,990 A | 12/1996 | Bergstrom et al. |

FOREIGN PATENT DOCUMENTS

| WO | WO 95/04145 | 2/1995 |

OTHER PUBLICATIONS

Marconi et al, Journal of Bacteriology, 1996, vol. 178(19), p. 5615–5626.*
Search report accession No. U80956 L78245.*

* cited by examiner

*Primary Examiner*—Kenneth R. Horlick
*Assistant Examiner*—Joyce Tung
(74) *Attorney, Agent, or Firm*—Human Genome Sciences, Inc.

(57) ABSTRACT

The present invention relates to novel vaccines for the prevention or attenuation of Lyme disease. The invention further relates to isolated nucleic acid molecules encoding antigenic polypeptides of *Borrelia burgdorferi*. Antigenic polypeptides are also provided, as are vectors, host cells and recombinant methods for producing the sane. The invention additionally relates to diagnostic methods for detecting, *Borrelia* gene expression.

9 Claims, No Drawings

LYME DISEASE VACCINES

This application claims benefit of provisional application Nos. 60/050,359 filed Jun. 20, 1997 Provisional Appl. 60/053,377 and 60/053,344 both filed Jul. 22, 1997 and Provisional Appl 60/057,483 filed Sep. 3, 1997.

FIELD OF THE INVENTION

The present invention relates to novel vaccines for the prevention or attenuation of Lyme disease. The invention further relates to isolated nucleic acid molecules encoding antigenic polypeptides of *Borrelia burgdorferi*. Antigenic polypeptides are also provided, as are vectors, host cells and recombinant methods for producing the same. The invention additionally relates to diagnostic methods for detecting Borrelia gene expression.

BACKGROUND OF THE INVENTION

Lyme disease (Steere, A. C., *Proc. Natl. Acad Sci. USA* 91:2378–2383 (1991)), or Lyme borreliosis, is presently the most common human disease in the United States transmitted by an arthropod vector (Center for Disease Control, *Morbid Mortal. Week Rep.* 46(23):531–535 (1997)). Further, infection of house-hold pets, such as dogs, is a considerable problem.

While initial symptoms often include a rash at the infection point, Lyme disease is a multisystemic disorder that may include arthritic, cardiac, and neurological manifestations. While antibiotics are currently used to treat active cases of Lyme disease, *B. burgdorferi* persists even after prolonged antibiotic treatment. Further, *B. burgdorferi* can persist for years in a mammalian host in the presence of an active immune response (Straubinger. R. et al., *J. Clin. Microbiol.* 35:111–116 (1997); Steere, A., *N. Engl. J. Med.* 321:586–596 (1989)).

Lyme disease is caused by the related tick-borne-spirochetes classified as *Borrelia burgdorferi* sensu lato (including *B. burgdorferi* sensu stricto, *B. afzelii, B. garinii*). Although substantial progress has been made in the biochemical, ultrastructural, and genetic characterization of the organism; the spirochetal factors responsible for infectivity, immune evasion and disease pathogenesis remain largely obscure.

A number of antigenic *B. burgdorferi* cell surface proteins have been identified. These include the outer membrane surface proteins (Osp) OspA, OspB, OspC and OspD. OspA and OspB are encoded by tightly linked tandem genes which am transcribed as a single transcriptional unit (Brusca, J. et at, *J. Bacteriol.* 173:8004–8008 (1991)). The most-studied *B. burgdorferi* membrane protein is OspA, a lipoprotein antigen expressed by borreliae in testing ticks and the most abundant protein expressed in vitro by most borrelial isolates (Barbour, A. G., et al., *Infection & Immunity* 41:795–804 (1983); Howe, T. R. et al., *Science* 227:645 (1985)).

A number of different types of Lyme disease vaccines have been shown to induce immunological responses. Whole-cell *B. burgdorferi* vaccines, for example, have been shown to induce both immunological responses and protective immunity in several animal models (Reviewed in Wormser, G., *Clin. Infect. Dis.* 21:1267–1274 (1995)). Further, passive immunity has been demonstrated in both humans and other animals using *B. burgdorferi* specific antisera.

While whole-cell Lyme disease vaccines confer protective immunity in animal models, use of such vaccines presents the risk that responsive antibodies will produce an autoimmune response (Reviewed in Wormser, G., supra). This problem is at least partly the result of the production of *B. burgdorferi* specific antibodies which cross-react with hepatocytes and both muscle and nerve cells. *B. burgdorferi* heat shock proteins and the 41-kd flagellin subunit are believed to contain antigens which elicit production of these cross-reactive antibodies.

Single protein subunit vaccines for Lyme disease have also been tested. The cell surface proteins of *B. burgdorferi* are potential candidates for use in such vaccines and several have been shown to elicit protective immune responses in mammals (Probert, W. et al., *Vaccine* 15:15–19 (1997); Fikrig, E. er al., *Infect. Immun.* 63: 1658–1662 (1995); Langerman S. et al., *Nature* 372:552–556 (1994); Fikrig, E. et al., *J. Immunol.* 148:2256–2260 (1992)). Experimental OspA vaccines, for example, have demonstrated efficacy in several animal models (Fikrig, E., et al., *Proc. Natl. Acad. Sci. USA* 89:5418–5421 (1992); Johnson, B. J., et al., *Vaccine* 13:1036–1094 (1996); Fikrig, E., et al., *Infect. Immun.* 60:657–661 (1992); Chang, Y. F., et al., *Infection & Immunity* 63:3543–3549 (1995)), and OspA vaccines for human use are under clinical evaluation (Keller, D., et al., *J. Am. Med. Assoc.* 271:1764–1768 (1994); Van Hoecke, C., et al., *Vaccine* 14:1620–1626 (1996)). Passive immunity is also conferred by antisera containing antibodies specific for the full-length OspA protein. Further, vaccination with plasmid DNA encoding OspA has been demonstrated to elicit protective immune responses in mice (Luke, C. et al., *J. Infect. Dis.* 175:91–97 (1997); Zhong, W. et al., *Eur. J. Immunol.* 26:2749–2757 (1996)).

Recent immunofluorescence assay observations indicate that during tick engorgement the expression of OspA by borreliae diminishes (deSilva, A. M., et al., *J. Exp. Med.* 183:271–275 (1996)) while expression of other proteins, exemplified by OspC, increases (Schwan, T. G., et al., *Proc. Natl. Acad. Sci. USA* 92:2909–2913 (1985)). By the time of transmission to hosts, spirochetes in the tick salivary glands express little or no OspA. This down-modulation of OspA appears to explain the difficulties in demonstrating immune responses to this antigen early in infection following tick bites (Kalish, R. A., et al., *Infect. Immun.* 63:2228–2235 (1995); Gem, L., et al., *J. Infect. Dis.* 167:971–975 (1993); Schiable, U. E., et al., *Immunol. Lett.* 36:219–226 (1993)) or following challenge with limiting doses of cultured borreliae (Schiable, U. E., et al., *Immunol. Lett.* 36:219–226 (1993); Barthold, S. W. and Bockenstedt, L. K., *Infect. Immun.* 61:4696–4702 (1993)).

Furthermore, OspA-specific antibodies are ineffective if administered after a borrelial challenge delivered by syringe (Schiable, U. E., et al., *Proc. Natl. Acad. Sci. USA* 87:3768–3772 (1990)) or tick bite (deSilva, A. M., et al., *J. Exp. Med.* 183:271–275 (1996)). To be efficacious, OspA vaccines must elicit protective levels of antibody which are maintained throughout periods of tick exposure in order to block *borrelia* transmission from the arthropod vector.

Vaccines in current use against other pathogens include in vivo-expressed antigens which could boost anamnestic responses upon infection, potentiate the action of immune effector cells and complement, and inhibit key virulence mechanisms. OspC is both expressed during infection (Montgomery, R. R., et al., *J. Exp. Med.* 183:261–269 (1996)) and a target for protective immunity (Gilmore, R. D., et al., *Infect Immun.* 64:2234–2239 (1996); Probert, W. S. and LeFebvre, R. B., *Infect. Immun.* 62: 1920–1926 (1994); Preac-Mursic, V., et. al., *Infection* 20:342–349 (1992)), but mice immunized with this protein were only protected against challenge with the homologous borrelial isolate (Probert, W. S., et al., *J. Infect Dis.* 175:400–405 (1997)). Identification of in vivo-expressed, and broadly protective, antigens of *B. burgdorferi* has remained elusive.

SUMMARY OF THE INVENTION

The present invention provides isolated nucleic acid molecules comprising polynucleotides encoding the *B. burgdorferi* peptides having the amino acid sequences shown in Table 1. Thus, one aspect of the invention provides isolated nucleic acid molecules comprising polynucleotides having a nucleotide sequence selected from the group consisting of: (a) a nucleotide sequence encoding any of the amino acid sequences of the full-length polypeptides shown in Table 1; (b) a nucleotide sequence encoding any of the amino acid sequences of the full-length polypeptides shown in Table 1 but minus the N-terminal methionine residue, if present; (c) a nucleotide sequence encoding any of the amino acid sequences of the truncated polypeptides shown in Table 1; and (d) a nucleotide sequence complementary to any of the nucleotide sequences in (a), (b), or (c) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), or (d) above, or a polynucleotide which hybridizes under stringent hybridization conditions to a polynucleotide in (a), (b), (c), or (d) above. This polynucleotide which hybridizes does not hybridize under stringent hybridization conditions to a polynucleotide having a nucleotide sequence consisting of only A residues or of only T residues. Additional nucleic acid embodiments of the invention relate to isolated nucleic acid molecules comprising polynucleotides which encode the amino acid sequences of epitope-bearing portions of a *B. burgdorferi* polypeptide having an amino acid sequence in (a), (b), or (c) above.

The present invention also relates to recombinant vectors, which include the isolated nucleic acid molecules of the present invention, and to host cells containing the recombinant vectors, as well as to methods of making such vectors and host cells and for using these vectors for the production of *B. burgdorferi* polypeptides or peptides by recombinant techniques.

The invention further provides isolated *B. burgdorferi* polypeptides having an amino acid sequence selected from the group consisting of: (a) an amino acid sequence of any of the full-length polypeptides shown in Table 1; (b) an amino acid sequence of any of the full-length polypeptides shown in Table 1 but minus the N-terminal methionine residue, if present; (c) an amino acid sequence of any of the truncated polypeptides shown in Table 1; and (d) an amino acid sequence of an epitope-bearing portion of any one of the polypeptides of (a), (b), or (c).

The polypeptides of the present invention also include polypeptides having an amino acid sequence with at least 70% similarity, and more preferably at least 75%, 80%, 85%, 90%, 95%, 96%, 97%, 98%, or 99% similarity to those described in (a), (b), (c), or (d) above, as well as polypeptides having an amino acid sequence at least 70% identical, more preferably at least 75% identical, and still more preferably 80%, 85%, 90%, 95%, 96%, 97%, 98%, or 99% identical to those above; as well as isolated nucleic acid molecules encoding such polypeptides.

The present invention further provides a vaccine, preferably a multi-component vaccine comprising one or more of the *B. burgdorferi* polypeptides shown in Table 1, or fragments thereof, together with a pharmaceutically acceptable diluent, carrier, or excipient, wherein the *B. burgdorferi* polypeptide(s) are present in an amount effective to elicit an immune response to members of the *Borrelia* genus in an animal. The *B. burgdorferi* polypeptides of the present invention may further be combined with one or more immunogens of one or more other borrelial or non-borrelial organisms to produce a multi-component vaccine intended to elicit an immunological response against members of the *Borrelia* genus and, optionally, one or more non borrelial organisms.

The vaccines of the present invention can be administered in a DNA form, e.g., "naked" DNA, wherein the DNA encodes one or more borrelial polypeptides and, optionally, one or more polypeptides of a non-borrelial organism. The DNA encoding one or more polypeptides may be constructed such that these polypeptides are expressed fusion proteins.

The vaccines of the present invention may also be administered as a component of a genetically engineered organism. Thus, a genetically engineered organism which expresses one or more *B. burgdorferi* polypeptides may be administered to an animal. For example, such a genetically engineered organism may contain one or more *B. burgdorferi* polypeptides of the present invention intracellularly, on its cell surface, or in its periplasmic space. Further, such a genetically engineered organism may secrete one or more *B. burgdorferi* polypeptides.

The vaccines of the present invention may be co-administered to an animal with an immune system modulator (e.g., CD86 and GM-CSF).

The invention also provides a method of inducing an immunological response in an animal to one or more members of the *Borrelia* genus, e.g., *B. burgdorferi* sensu stricto, *B. afzelii*, and *B. garinii*, comprising administering to the animal a vaccine as described above.

The invention further provides a method of inducing a protective immune response in an animal, sufficient to prevent or attenuate an infection by members of the *Borrelia* genus, comprising administering to the animal a composition comprising one or more of the polypeptides shown in Table 1, or fragments thereof. Further, these polypeptides, or fragments thereof, may be conjugated to another immunogen and/or administered in admixture with an adjuvant.

The invention further relates to antibodies elicited in an animal by the administration of one or more *B. burgdorferi* polypeptides of the present invention.

The invention also provides diagnostic methods for detecting the expression of genes of members of the *Borrelia* genus in an animal. One such method involves assaying for the expression of a gene encoding *Borrelia* peptides in a sample from an animal. This expression may be assayed either directly (e.g., by assaying polypeptide levels using antibodies elicited in response to amino acid sequences shown in Table 1) or indirectly (e.g., by assaying for antibodies having specificity for amino acid sequences shown in Table 1). An example of such a method involves the use of the polymerase chain reaction (PCR) to amplify and detect *Borrelia* nucleic acid sequences.

The present invention also relates to nucleic acid probes having all or part of a nucleotide sequence shown in Table 1 which are capable of hybridizing under stringent conditions to *Borrelia* nucleic acids. The invention further relates to a method of detecting one or more *Borrelia* nucleic acids in a biological sample obtained from an animal, said one or more nucleic acids encoding *Borrelia* polypeptides, comprising:

a) contacting the sample with one or more of the above-described nucleic acid probes, under conditions such that hybridization occurs, and b) detecting hybridization of said one or more probes to the *Borrelia* nucleic acid present in the biological sample.

DETAILED DESCRIPTION

The present invention relates to recombinant antigenic *B. burgdorferi* polypeptides and fragments thereof. The invention also relates to methods for using these polypeptides to produce immunological responses and to confer immunological protection to disease caused by members of the genus *Borrelia*. The invention further relates to nucleic acid sequences which encode antigenic *B. burgdorferi* polypeptides and to methods for detecting *Borrelia* nucleic acids and polypeptides in biological samples. The invention also relates to *Borrelia* specific antibodies and methods for detecting such antibodies produced in a host animal.

Definitions

The following definitions are provided to clarify the subject matter which the inventors consider to be the present invention.

As used herein, the phrase "pathogenic agent" means an agent which causes a disease state or affliction in an animal. Included within this definition, for examples, are bacteria, protozoans, fungi, viruses and metazoan parasites which either produce a disease state or render an animal infected with such an organism susceptible to a disease state (e.g., a secondary infection). Further included are species and strains of the genus *Borrelia* which produce disease states in animals.

As used herein, the term "organism" means any living biological system, including viruses, regardless of whether it is a pathogenic agent.

As used herein, the term "*Borrelia*" means any species or strain of bacteria which is members of the genus *Borrelia*. Included with this definition are *Borrelia burgdorferi* sensu lato (including *B. burgdorferi* sensu stricto, *B. afzelii*, *B. garinii*), *B. andersonii, B. anserina, B. japonica, B. coriaceae*, and other members of the genus *Borrelia* regardless of whether they are known pathogenic agents.

As used herein, the phrase "one or more *B. burgdorferi* polypeptides of the present invention" means the amino acid sequence of one or more of the *B. burgdorferi* polypeptides disclosed in Table 1. These polypeptides may be expressed as fusion proteins wherein the *B. burgdorferi* polypeptides of the present invention are linked to additional amino acid sequences which may be of borrelial or non-borrelial origin. This phrase further includes fragments of the *B. burgdorferi* polypeptides of the present invention.

As used herein, the phrase "full-length amino acid sequence" and "full-length polypeptide" refer to an amino acid sequence or polypeptide encoded by a full-length open reading frame (ORF). An ORF may be defined as a nucleotide sequence bounded by stop codons which encodes a putative polypeptide. An ORF may also be defined as a nucleotide sequence within a stop codon bounded sequence which contains an initiation codon (e.g., a methionine or valine codon) on the 5' end and a stop codon on the 3' end.

As used herein, the phrase "truncated amino acid sequence" and "truncated polypeptide" refer to a subsequence of a full-length amino acid sequence or polypeptide. Several criteria may also be used to define the truncated amino acid sequence or polypeptide. For example, a truncated polypeptide may-be defined as a mature polypeptide (e.g., a polypeptide which lacks a leader sequence). A truncated polypeptide may also be defined as an amino acid sequence which is a portion of a longer sequence that has been selected for ease of expression in a heterologous system but retains regions which render the polypeptide useful for use in vaccines (e.g., antigenic regions which are expected to elicit a protective immune response).

Additional definitions are provided throughout the specification.

Explanation of Table 1

Table 1 lists *B. burgdorferi* nucleotide and amino acid sequences of the present invention. The nomenclature used therein is as follows:

"nt" refers to nucleotide sequences;

"aa" refers to amino acid sequences;

"f" refers to full-length nucleotide or amino acid sequences; and

"t" refers to truncated nucleotide or amino acid sequences.

Thus, for example, the designation "f101.aa" refers to the full-length amino acid sequence of *B. burgdorferi* polypeptide number 010. Further, "f101.nt" refers to the full-length nucleotide sequence encoding the full-length amino acid sequence of *B. burgdorferi* polypeptide number 101.

Explanation of Table 2

Table 2 lists accession numbers for the closest matching sequences between the polypeptides of the present invention and those available through GeniBank and GeneSeq databases. These reference numbers are the database entry numbers commonly used by those of skill in the art, who will be familiar with their denominations. The descriptions of the nomenclature for GenBank are available from the National Center for Biotechnology Information. Column 1 lists the gene or ORF of the present invention Column 2 lists the accession number of a "match" gene sequence in Genbank or GeneSeq databases. Column 3 lists the description of the "match" gene sequence. Columns 4 and 5 are the high score and smallest sum probability, respectively, calculated by BLAST. Polypeptides of the present invention that do not share significant identity/similarity with any polypeptide sequences of GenBank and GeneSeq are not represented in Table 2. Polypeptides of the present invention that share significant identity/similarity with more than one of the polypeptides of GenBank and GeneSeq are represented more than once.

Explanation of Table 3.

The *B. burgdorferi* polypeptides of the present invention may include one or more conservative amino acid substitutions from natural mutations or human manipulation as indicated in Table 3. Changes are preferably of a minor nature, such as conservative amino acid substitutions that do not significantly affect the folding or activity of the protein. Residues from the following groups, as indicated in Table 3, may be substituted for one another: Aromatic, Hydrophobic, Polar, Basic, Acidic, and Small.

Explanation of Table 4

Table 4 lists residues comprising antigenic epitopes of antigenic epitope-bearing fragments present in each of the full length *B. burgdorferi* polypeptides described in Table 1 as predicted by the inventors using the algorithm of Jameson and Wolf, (1988) Comp. Appl. Biosci. 4:181–186. The Jameson-Wolf antigenic analysis was performed using the computer program PROTEAN (Version 3.11 for the Power MacIntosh, DNASTAR, Inc., 1228 South Park Street Madison, Wis.). *B. burgdorferi* polypeptide shown in Table 1 may one or more antigenic epitopes comprising residues described in Table 4. It will be appreciated that depending on the analytical criteria used to predict antigenic determinants, the exact address of the determinant may vary slightly. The residues and locations shown described in Table 4 correspond to the amino acid sequences for each full length gene sequence shown in Table 1 and in the Sequence Listing. Polypeptides of the present invention that do not have antigenic epitopes recognized by the Jameson-Wolf algorithm are not represented in Table 2.

Selection of Nucleic Acid Sequences Encoding Antigenic *B. burgdorferi* Polypeptides The present invention provides a select number of ORFs from those presented in the fragments of the *Borrelia burgdorferi* genome which may prove useful for the generation of a protective immune response. The sequenced *B. burgdorferi* genomic DNA was obtained from a sub-cultured isolate of ATCC Deposit No. 35210. The sub-cultured isolate was deposited on Aug. 8, 1997 at the American Type Culture Collection, 12301 Park Lawn Drive, Rockville, Md. 20852, and given accession number 202012.

Some ORFs contained in the subset of fragments of the *B. burgdorferi* genome disclosed herein were derived through the use of a number of screening criteria detailed below. The ORFs are generally bounded at the amino terminus by a methionine residue and at the carboxy terminus by a stop codon.

Many of the selected sequences do not consist of complete ORFs. Although a polypeptide representing a complete ORF may be the closest approximation of a protein native to an organism, it is not always preferred to express a complete ORF in a heterologous system. It may be challenging to express and purify a highly hydrophobic protein by common laboratory methods. Some of the polypeptide vaccine candidates described herein have been modified slightly to simplify the production of recombinant protein. For example, nucleotide sequences which encode highly hydrophobic domains, such as those found at the amino terminal signal sequence, have been excluded from some constructs used for in vitro expression of the polypeptides. Furthermore, any highly hydrophobic amino acid sequences occurring at the carboxy terminus have also been excluded from the recombinant expression constructs. Thus, in one embodiment, a polypeptide which represents a truncated or modified ORF may be used as an antigen.

While numerous methods are known in the art for selecting potentially immunogenic polypeptides, many of the ORFs disclosed herein were selected on the basis of screening all theoretical *Borrelia burgdorferi* ORFs for several aspects of potential immunogenicity. One set of selection criteria are as follows:

1. Type I signal sequence: An amino terminal type I signal sequence generally directs a nascent protein across the plasma and outer membranes to the exterior of the bacterial cell. Experimental evidence obtained from studies with *Escherichia coli* suggests that the typical type I signal sequence consists of the following biochemical and physical attributes (Izard, J. W. and Kendall, D. A. *Mol. Microbiol.* 13:765–773 (1994)). The length of the type I signal sequence is approximately 15 to 25 primarily hydrophobic amino acid residues with a net positive charge in the extreme amino terminus. In addition, the central region of the signal sequence adopts an alpha-helical conformation in a hydrophobic environment. Finally, the region surrounding the actual site of cleavage is ideally six residues long, with small side-chain amino acids in the −1 and −3 positions.

2. Type IV signal sequence: The type IV signal sequence is an example of the several types of functional signal sequences which exist in addition to the type I signal sequence detailed above. Although functionally related, the type IV signal sequence possesses a unique set of biochemical and physical attributes (Strom, M. S. and Lory, S., *J. Bacteriol.* 174:7345–7351 (1992)). These are typically six to eight amino acids with a net basic charge followed by an additional sixteen to thirty primarily hydrophobic residues. The cleavage site of a type IV signal sequence is typically after the initial six to eight amino acids at the extreme amino terminus. In addition, type IV signal sequences generally contain a phenylalanine residue at the +1 site relative to the cleavage site.

3. Lipoprotein: Studies of the cleavage sites of twenty-six bacterial lipoprotein precursors has allowed the definition of a consensus amino acid sequence for lipoprotein cleavage. Nearly three-fourths of the bacterial lipoprotein precursors examined contained the sequence L-(A,S)-(G,A)-C at positions −3 to +1, relative to the point of cleavage (Hayashi, S. and Wu, H. C., J. *Bioenerg. Biomembr.* 22:451–471 (1990)).

4. LPXTG motif. It has been experimentally determined that most anchored proteins found on the surface of gram-positive bacteria possess a highly conserved carboxy terminal sequence. More than fifty such proteins from organisms such as *S. pyogenes, S. mutans, B. burgdorferi, S. pneumoniae*, and others, have been identified based on their extracellular location and carboxy terminal amino acid sequence (Fischetti, V. A., *ASM News* 62:405–410 (1996)). The conserved region consists of six charged amino acids at the extreme carboxy terminus coupled to 15–20 hydrophobic amino acids presumed to function as a transmembrane domain. Immediately adjacent to the transmembrane domain is a six amino acid sequence conserved in nearly all proteins examined. The amino acid sequence of this region is L-P-X-T-G-X, where X is any amino acid.

An algorithm for selecting antigenic and immunogenic *Borrelia burgdorferi* polypeptides including the foregoing criteria was developed. The algorithm is similar to that described in U.S. patent application. Ser. No. 08/781,986, filed Jan. 3, 1997, which is fully incorporated by reference herein. Use of the algorithm by the inventors to select immunologically useful *Borrelia burgdorferi* polypeptides resulted in the selection of a number of the disclosed ORFs. Polypeptides comprising the polypeptides identified in this group may be produced by techniques standard in the art and as further described herein.

Nucleic Acid Molecules

The present invention provides isolated nucleic acid molecules comprising polynucleotides encoding the *B. burgdorferi* polypeptides having the amino acid sequences shown in Table 1, which were determined by sequencing the genome of *B. burgdorferi* deposited as ATCC deposit no. 202012 and selected as putative immunogens.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of DNA sequences determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides; and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having a sequence of Table 1 set forth using deoxyribonucleotide abbreviations is intended to indicate an RNA molecule having a sequence in which each deoxyribonucleotide A, G or C of Table 1 has been replaced by the corresponding ribonucleotide A, G or C; and each deoxyribonucleotide T has been replaced by a ribonucleotide U.

Nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

In addition, isolated nucleic acid molecules of the invention include DNA molecules which comprise a sequence substantially different from those described above but which, due to the degeneracy of the genetic code, still encode a *B. burgdorferi* polypeptides and peptides of the present invention (e.g. polypeptides of Table 1). That is, all possible DNA sequences that encode the *B. burgdorferi* polypeptides of the present invention. This includes the genetic code and species-specific codon preferences known in the art. Thus, it would be routine for one skilled in the art to generate the degenerate variants described above, for instance, to optimize codon expression for a particular host (e.g., change codons in the bacteria mRNA to those preferred by a mammalian or other bacterial host such as *E. coli*).

The invention further provides isolated nucleic acid molecules having the nucleotide sequence shown in Table 1 or a nucleic acid molecule having a sequence complementary to one of the above sequences. Such isolated molecules, particularly DNA molecules, are useful as probes for gene mapping and for identifying *B. burgdorferi* in a biological sample, for instance, by PCR, Southern blot, Northern blot, or other form of hybridization analysis.

The present invention is further directed to nucleic acid molecules encoding portions or fragments of the nucleotide sequences-described herein. Fragments include portions of the nucleotide sequences of Table 1 at least 10 contiguous nucleotides in length selected from any two integers, one of which representing a 5' nucleotide position and a second of which representing a nucleotide position, where the first nucleotide for each nucleotide sequence in Table 1 is position 1. That is, every combination of a 5' and 3' nucleotide position that a fragment at least contiguous nucleotides in length could occupy is included in the invention. "At least" means a fragment may be 10 contiguous nucleotide bases in length or any integer between 10 and the length of an entire nucleotide sequence of Table 1 minus 1. Therefore, included in the invention are contiguous fragments specified by any 5' and 3' nucleotide base positions of a nucleotide sequences of Table 1 wherein the contiguous fragment is any integer between 10 and the length of an entire nucleotide sequence minus 1.

Further, the invention includes polynucleotides comprising fragments specified by size, in nucleotides, rather than by nucleotide positions. The invention includes any fragment size, in contiguous nucleotides, selected from integers between 10 and the length of an entire nucleotide sequence minus 1. Preferred sizes of contiguous nucleotide fragments include 20 nucleotides, 30 nucleotides, 40 nucleotides, 50 nucleotides. Other preferred sizes of contiguous nucleotide fragments, which may be useful as diagnostic probes and primers, include fragments 50–300 nucleotides in length which include, as discussed above, fragment sizes representing each integer between 50–300. Larger fragments are also useful according to the present invention corresponding to most, if not all, of the nucleotide sequences shown in Table 1 or of the *B. burgdorferi* nucleotide sequences of the plasimd clones listed in Table 1. The preferred sizes are, of course, meant to exemplify not limit the present invention as all size fragments, representing any integer between 10 and the length of an entire nucleotide sequence minus 1, are included in the invention. Additional preferred nucleic acid fragments of the present invention include nucleic acid molecules encoding epitope-bearing portions of *B. burgdorferi* polypeptides identified in Table 4.

The present invention also provides for the exclusion of any fragment, specified by 5' and 3' base positions or by size in nucleotide bases as described above for any nucleotide sequence of Table 1 or the plasimd clones listed in Table 1. Any number of fragments of nucleotide sequences in Table 1 or the plasimd clones listed in Table 1, specified by 5' and 3' base positions or by size in nucleotides, as described above, may be excluded from the present invention.

Preferred nucleic acid fragments of the present invention also include nucleic acid molecules encoding epitope-bearing portions of the *B. burgdorferi* polypeptides shown in Table 1. Such nucleic acid fragments of the present invention include, for example, nucleic acid molecules encoding polypeptide fragments comprising from about the amino terminal residue to about the carboxy terminal residue of each fragment shown in Table 4. The above referred to polypeptide fragments are antigenic regions of particular *B. burgdorferi* polypeptides shown in Table 1. Methods for determining other such epitope-bearing portions for the remaining polypeptides described in Table 1 are well known in the art and are described in detail below.

In another aspect, the invention provides isolated nucleic acid molecules comprising polynucleotides which hybridize under stringent hybridization conditions to a portion of a polynucleotide in a nucleic acid molecule of the invention described above, for instance, a nucleic acid sequence shown in Table 1. By "stringent hybridization conditions" is intended overnight incubation at 42 C in a solution comprising: 50% formamide, 5× SSC (150 mM NaCl, 15 mM trisodium citrate), 50 mM sodium phosphate (pH 7;6), 5× Denhardt's solution, 10% dextran sulfate, and 20 g/m denatured, sheared salmon sperm DNA, followed by washing the filters in 0.1× SSC at about 65 C.

By polynucleotides which hybridize to a "portion" of a polynucleotide is intended polynucleotides (either DNA or RNA) which hybridize to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Of course, polynucleotides hybridizing to a larger portion of the reference polynucleotide, for instance, a portion 50–100 nt in length, or even to the entire length of the reference polynucleotide, are also useful as probes according to the present invention, as are polynucleotides corresponding to most, if not all, of a nucleotide sequence as shown in Table 1. By a portion of a polynucleotide of "at least 20 nt in length," for example, is intended 20 or more contiguous nucleotides from the nucleotide sequence of the reference polynucleotide (e.g., a nucleotide sequences as shown in Table 1). As noted above, such portions are useful diagnostically either as probes according to conventional DNA hybridization techniques or as primers for amplification of a target sequence by PCR as described, for instance, in *Molecular Cloning, A Laboratory Manual,* 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since nucleic acid sequences encoding the *B. burgdorferi* polypeptides of the present invention are provided in Table 1, generating polynucleotides which hybridize to portions of these sequences would be routine to the skilled artisan. For example, the hybridizing polynucleotides of the present invention could be generated synthetically according to known techniques.

As indicated, nucleic acid molecules of the present invention which encode *B. burgdorferi* polypeptides of the present invention may include, but are not limited to those encoding the amino acid sequences of the polypeptides by themselves; and additional coding sequences which code for additional amino acids, such as those which provide additional functionalities. Thus, the sequences encoding these polypeptides may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the resulting fusion protein.

Thus, the present invention also includes genetic fusions wherein the *B. burgdorferi* nucleic acid sequences coding sequences provided in Table 1 are linked to additional nucleic acid sequences to produce fusion proteins. These fusion proteins may include epitopes of borrelial or non-borrelial origin designed to produce proteins having enhanced immunogenicity. Further, the fusion proteins of the present invention may contain antigenic determinants known to provide helper T-cell stimulation, peptides encoding sites for post-translational modifications which enhance immunogenicity (e.g., acylation), peptides which facilitate purification (e.g. histidine "tag"), or amino acid sequences which target the fusion protein to a desired location (e.g., a heterologous leader sequence). For instance, hexa-histidine provides for convenient purification of the fusion protein. See Gentz et al. (1989) Proc. Natl. Acad. Sci. 86:821–24. The "HA" tag is another peptide useful for purification which corresponds to an epitope derived from the influenza hemagglutinin protein. See Wilson et al. (1984) Cell 37:767. As discussed below, other such fusion proteins include the *B. burgdorferi* polypeptides of the present invention fused to Fc at the N- or C-terminus.

Post-translational modification of the full-length *B. burgdorferi* OspA protein expressed in *E. coli* is believed to increase the immunogenicity of this protein. Erdile, L: et al., *Infect Immun.* 61:81–90 (1993). *B. burgdorferi* OspA when expressed in *E. coli*, for example, is post-translationally modified in at least two ways. First, a signal peptide is cleaved; second, lipid moieties are attached. The presence of these lipid moieties is believed to confer enhanced immunogenicity and results in the elicitation of a strong protective immunological response.

Variant and Mutant Polynucleotides

The present invention thus includes nucleic acid molecules and sequences which encode fusion proteins comprising one or more *B. burgdorferi* polypeptides of the present invention fused to an amino acid sequence which allows for post-translational modification to enhance immunogenicity. This post-translational modification may occur either in vitro or when the fusion protein is expressed in vivo in a host cell. An example of such a modification is the introduction of an amino acid sequence which results in the attachment of a lipid moiety. Such a lipid moiety attachment site of OspA, which is lipidated upon expression in *E. coli*, has been identified. Bouchon, B. et al., *Anal. Biochem.* 246:52–61 (1997).

Thus, as indicated above, the present invention includes genetic fusions wherein a *B. burgdorferi* nucleic acid sequence provided in Table 1 is linked to a nucleotide sequence encoding another amino acid sequence. These other amino acid sequences may be of borrelial origin (e.g., another sequence selected from Table 1) or non-borrelial origin. An example of such a fusion protein is reported in Fikrig, E. et al., *Science.* 250:553–556 (1990) where an OspA-glutathione-S-transferase fusion protein was produced and shown to elicit protective immunity against Lyme disease in immune competent mice.

The present invention further relates to variants of the nucleic acid molecules of the present invention, which encode portions, analogs or derivatives of the *B. burgdorferi* polypeptides shown in Table 1. Variants may occur naturally, such as a natural allelic variant. By an "allelic variant" is intended one of several alternate forms of a gene occupying a given locus on a chromosome of an organism. *Genes II,* Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. These variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the *B. burgdorferi* polypeptides disclosed herein or portions thereof. Also especially preferred in this regard are conservative substitutions.

The present application is further directed to nucleic acid molecules at least 90%, 95%, 96%, 97%, 98% or 99% identical to a nucleic acid sequence shown in Table 1. The above nucleic acid sequences are included irrespective of whether they encode a polypeptide having *B. burgdorferi* activity. This is because even where a particular nucleic acid molecule does not encode a polypeptide having *B. burgdorferi* activity, one of skill in the art would still know how to use the nucleic acid molecule, for instance, as a hybridization probe. Uses of the nucleic acid molecules of the present invention that do not encode a polypeptide having *B. burgdorferi* activity include, inter alia, isolating an *B. burgdorferi* gene or allelic variants thereof from a DNA library, and detecting *B. burgdorferi* mRNA expression samples, environmental samples, suspected of containing *B. burgdorferi* by Northern Blot analysis.

Embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding any of the amino acid sequences of the full-length polypeptides shown in Table 1; (b) a nucleotide sequence encoding any of the amino acid sequences of the full-length polypeptides shown in Table 1 but minus the N-terminal methionine residue, if present; (c) a nucleotide sequence encoding any of the amino acid sequences of the truncated polypeptides shown in Table 1; and (d) a nucleotide sequence complementary to any of the nucleotide sequences in (a), (b), or (c) above.

Preferred, are nucleic acid molecules having sequences at least 90%, 95%, 96%, 97%, 98% or 99% identical to the nucleic acid sequence shown in Table 1, which do, in fact, encode a polypeptide having *B. burgdorferi* protein activity By "a polypeptide having *B. burgdorferi* activity" is intended polypeptides exhibiting activity similar, but not necessarily identical, to an activity of the *B. burgdorferi* protein of the invention, as measured in a particular biological assay suitable for measuring activity of the specified protein.

Due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequences shown in Table 1 will encode a polypeptide having *B. burgdorferi* protein activity. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having *B. burgdorferi* protein activity: This is because the skilled artisan is fully aware of amino acid substitutions that are either less likely or not likely to significantly effect protein function (e.g., replacing one aliphatic amino acid with a second aliphatic amino acid), as further described below.

The biological activity or function of the polypeptides of the present invention are expected to be similar or identical to polypeptides from other bacteria that share a high degree of structural identity/similarity. Tables 2 lists accession numbers and descriptions for the closest matching sequences of polypeptides available through Genbank and Derwent databases. It is therefore expected that the biological activity or function of the polypeptides of the present invention will be similar or identical to those polypeptides from other bacterial genuses, species, or strains listed in Table 2.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the *B. burgdorferi* polypeptide. In other words, to obtain a polynucleotide having a nucleotide sequence at least 95% identical to a reference nucleotide sequence, up to 5% (5 of 100) of the nucleotides in the reference sequence may be deleted, inserted, or substituted with another nucleotide. The query sequence may be an entire sequence shown in Table. 1, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. See Brutlag et al. (1990) Comp. App. Biosci. 6:237–245. In a sequence alignment the query and subject sequences are both DNA sequences. An RNA sequence can be compared by first converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the lenght of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only nucleotides outside the 5' and 3' nucleotides of the subject sequence, as displayed by the FASTDB alignment, which are not matched/aligned with the query sequence, are calculated for the purposes of manually adjusting the percent identity score.

For example, a 90 nucleotide subject sequence is aligned to a 100 nucleotide query sequence to determine percent identity. The deletions occur at the 5' end of the subject sequence and therefore, the FASTDB alignment does not show a matched/alignment of the first 10' nucleotides at 5' end. The 10 unpaired nucleotides represent 10% of the sequence (number of nucleotides at the 5' and 3' ends not matched/total number of nucleotides in the query sequence) so 10% is subtracted from the percent identity score calculated by the FASTDB program. If the remaining 90 nucleotides were perfectly matched the final percent identity would be 90%. In another example, a 90 nucleotide subject sequence is compared with a 100 nucleotide query sequence. This time the deletions are internal deletions so that there are no nucleotides on the 5' or 3' of the subject sequence which are not matched/aligned with the query. In this case the percent identity calculated by FASTDB is not manually corrected. Once again, only nucleotides 5' and 3' of the subject sequence which are not matched/aligned with the query sequence are manually corrected for. No other manual corrections are to made for the purposes of the present invention.

Vectors and Host Cells

The present invention also relates to vectors which include the isolated DNA molecules of the present invention, host cells which are genetically engineered with the recombinant vectors, and the production of B. burgdorferi polypeptides or fragments thereof by recombinant techniques.

Recombinant constructs may be introduced into host cells using well known techniques such as infection, transduction, transfection transvection, electroporation and transformation. The vector may be for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors-comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal- , episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating site at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A available from Stratagene; pET series of vectors available from Novagen; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the E. coli lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

Transcription of DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated polypeptide into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See Bennett, D. et al., *J. Molec. Recogn.* 8:52–58 (1995) and Johanson, K. et al., *J. Biol. Chem.* 270 (16):9459–9471 (1995).

The *B. burgdorferi* polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, lectin chromatography and high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells.

Polypeptides and Fragments

The invention further provides isolated polypeptides having the amino acid sequences in Table 1, and peptides or polypeptides comprising portions of the above polypeptides. The terms "peptide" and "oligopeptide" are considered synonymous (as is commonly recognized) and each term can be used interchangeably as the context requires to indicate a chain of at least to amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

As discussed in detail below, immunization using *B. burgdorferi* sensu stricto isolate B31 decorin-binding protein elicits the production of antiserum which confers passive immunity against *Borrelia* species and strains which express divergent forms of this protein. Cassatt, D. et al., *Protection of Borrelia burgdorferi Infection by Antibodies to Decorin-binding Protein*, in VACCINES97, Cold Spring Harbor Press 1997), pages 191–195. Thus, some amino acid sequences of the *B. burgdorferi* polypeptides shown in Table 1 can be varied without significantly effecting the antigenicity of the polypeptides. If such differences in sequence are contemplated, it should be remembered that there will be critical areas on the polypeptide which determine antigenicity. In general, it is possible to replace residues which do not form part of an antigenic epitope without significantly effecting the antigenicity of a polypeptide.

Variant and Mutant Polypeptides

To improve or alter the characteristics of *B. burgdorferi* polypeptides of the present invention, protein engineering may be employed. Recombinant DNA technology known to those skilled in the art can be used to create novel mutant proteins or muteins including single or multiple amino acid substitutions, deletions, additions, or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

It is known in the art that one or more amino acids may be deleted from the N-terminus or C-terminus without substantial loss of biological function. For instance, Ron et al. *J. Biol. Chem.*, 268:2984–2988 (1993), reported modified KGF proteins that had heparin binding activity even if 3, 8, or 27 N-terminal amino acid residues were missing. Accordingly, the present invention provides polypeptides having one or more residues deleted from the amino terminus of the amino acid sequence of the *B. burgdorferi* polypeptides shown in Table 1, and polynucleotides encoding such polypeptides.

Similarly, many examples of biologically functional C-terminal deletion muteins are known. For instance, Interferon gamma shows up to ten times higher activities by deleting 8–10 amino acid residues from the carboxy terminus of the protein See, e.g., Dobeli, et al. (1988) J. Biotechnology 7:199–216. Accordingly, the present invention provides polypeptides having one or more residues from the carboxy terminus of the amino acid sequence of the *B. burgdorferi* polypeptides shown in Table 1. The invention also provides polypeptides having one or more amino acids deleted from both the amino and the carboxyl termini as described below.

The present invention is further directed to polynucleotide encoding portions or fragments of the amino acid sequences described herein as well as to portions or fragments of the isolated amino acid sequences described herein. Fragments include portions of the amino acid sequences of Table 1, are at least 5 contiguous amino acid in length, are selected from any two integers, one of which representing a N-terminal position. The initiation codon of the polypeptides of the present inventions position 1. Every combination of a N-terminal and C-terminal position that a fragment at least 5 contiguous amino acid residues in length could occupy, on any given amino acid sequence of Table 1 is included in the invention. At least means a fragment may be 5 contiguous amino acid residues in length or any integer between 5 and the number of residues in a full length amino acid sequence minus 1. Therefore, included in the invention are contiguous fragments specified by any N-terminal and C-terminal positions of amino acid sequence set forth in Table 1 wherein the contiguous fragment is any integer between 5 and the number of residues in a full length sequence minus 1.

Further, the invention includes polypeptides comprising fragments specified by size, in amino acid residues, rather than by N-terminal and C-terminal positions. The invention includes any fragment size, in contiguous amino acid residues, selected from integers between 5 and the number of residues in a full length sequence minus 1. Preferred sizes of contiguous polypeptide fragments include about 5 amino acid residues, about 10 amino acid residues, about 20 amino acid residues, about 30 amino acid residues, about 40 amino acid residues, about 50 amino acid residues, about 100 amino acid residues, about 200 amino acid residues, about 300 amino acid residues, and about 400 amino acid residues. The preferred sizes are, of course, meant to exemplify, not limit, the present invention as all size fragments representing any integer between 5 and the number of residues in a full length sequence minus 1 are included in the invention. The to present invention also provides for the exclusion of any fragments specified by N-terminal and C-terminal positions or by size in amino acid residues as described above. Any number of fragments specified by N-terminal and C-terminal positions or by size in amino acid residues as described above may be excluded.

The above fragments need not be active since they would be useful, for example, in immunoassays, in epitope mapping, epitope tagging, to generate antibodies to a particular portion of the protein, as vaccines, and as molecular weight markers.

Other Mutants

In addition to N- and C-terminal deletion forms of the protein discussed above, it also will be recognized by one of ordinary skill in the art that some amino acid sequences of the B. burgdorferi polypeptide can be varied without significant effect of the structure or function of the protein. If such differences in sequence are contemplated, it should be remembered that there will be critical areas on the protein which determine activity.

Thus, the invention further includes variations of the B. burgdorferi polypeptides which show substantial B. burgdorferi polypeptide activity or which include regions of B. burgdorferi protein such as the protein portions discussed below. Such mutants include deletions, insertions, inversions, repeats, and type substitutions selected according to general rules known in the art so as to have little effect on activity. For example, guidance concerning how to make phenotypic ally silent amino acid substitutions is provided. There are two main approaches for studying the tolerance of an amino acid sequence to change. See, Bowie, J. U. et al. (1990), Science 247:1306–1310. The first method relies on the process of evolution, in which mutations are either accepted or rejected by natural selection. The second approach uses genetic engineering to introduce amino acid changes at specific positions of a cloned gene and selections or screens to identify sequences that maintain functionality.

These studies have revealed that proteins are surprisingly tolerant of amino acid substitutions. The studies indicate which amino acid changes are likely to be permissive at a certain position of the protein. For example, most buried amino acid residues require nonpolar side chains, whereas few features of surface side chains are generally conserved. Other such phenotypically silent substitutions are described by Bowie et al. (supra) and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the, amide residues Asn and Gln, exchange of the basic residues Lys and Arg and replacements among the aromatic residues Phe, Tyr.

Thus, the fragment; derivative, analog, or homolog of the polypeptide of Table 1, or that encoded by the plaimds listed in Table 1, may be: (i) one in which one or more of the amino acid residues are substituted with a conserved or non-conserved amino acid residue (preferably a conserved amino acid residue) and such substituted amino acid residue may or may not be one encoded by the genetic code: or (ii) one in which one or more of the amino acid residues includes a substituent group: or (iii) one in which the B. burgdorferi polypeptide is fused with another compound, such as a compound to increase the half-life of the polypeptide (for example, polyethylene glycol): or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein.

Thus, the B. burgdorferi polypeptides of the present invention may include one or more amino acid substitutions, deletions, or additions, either from natural mutations or human manipulation. As indicated, changes are preferably of a minor nature, such as conservative amino acid substitutions that do not significantly affect the folding or activity of the protein (see Table 3).

Amino acids in the B. burgdorferi proteins of the present invention that are essential for function can be identified by methods known in the art, such as site-directed mutagenesis or alanine-scanning mutagenesis. See, e.g., Cunningham et al. (1989) Science 244:1081–1085. The latter procedure introduces single alanine mutations at every residue in the molecule. The resulting mutant molecules are then tested for biological activity using assays appropriate for measuring the function of the particular protein.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic. See, e.g., Pinckard et al., (1967) Clin. Exp. Immunol. 2:331–340; Robbins, et al., (1987) Diabetes 36:838–845; Cleland, et al., (1993) Crit. Rev. Therapeutic Drug Carrier Systems 10:307–377.

The polypeptides of the present invention are preferably provided in an isolated form, and preferably are substantially purified. A recombinantly produced version of the B. burgdorferi polypeptide can be substantially purified by the one-step method described by Smith et al. (1988) Gene 67:31–40. Polypeptides of the invention also can be purified from natural or recombinant sources using antibodies directed against the polypeptides of the invention in methods which are well known in the art of protein purification.

The invention further provides for isolated B. burgdorferi polypeptides comprising an amino acid sequence selected from the group consisting of: (a) the amino acid sequence of a full-length B. burgdorferi polypeptide having the complete amino acid sequence shown in Table 1 (b) the amino acid sequence of a full-length B. burgdorferi polypeptide having the complete amino acid sequence shown in Table 1 excepting the N-terminal methionine; (c) the complete amino acid sequence encoded by the plasmids listed in Table 1; and (d) the complete amino-acid sequence excepting the N-terminal methionine encoded by the plasmids listed in Table 1. The polypeptides of the present invention also include polypeptides having an amino acid sequence at least 80% identical, more preferably at least 90% identical, and still more preferably 95%, 96%, 97%, 98% or 99% identical to those described in (a), (b), (c), and (d) above.

Further polypeptides of the present invention include polypeptides which have at least 90% similarity, more preferably at least 95% similarity, and still more preferably at least 96%, 97%, 98% or 99% similarity to those described above.

A further embodiment of the invention relates to a polypeptide which comprises the amino acid sequence of a *B. burgdorferi* polypeptide having an amino acid sequence which contains at least one conservative amino acid substitution, but not more than 50 conservative amino acid substitutions, not more than 40 conservative amino acid substitutions, not more than 30 conservative amino acid substitutions, and not more than 20 conservative amino acid substitutions. Also provided are polypeptides which comprise the amino acid sequence of a *B. burgdorferi* polypeptide, having at least one, but not more than 10, 9, 8, 7, 6, 5, 4, 3, 2 or 1 conservative amino acid substitutions.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in Table 1 or to the amino acid sequence encoded by the plaimds listed in Table 1 can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., (1990) Comp. App. Biosci. 6:237–245. In a sequence alignment the query and subject sequences are both amino acid sequences. The result of said global sequence alignment is in percent identity. Preferred parameters used in a FASTDB amino acid alignment are: Matrix= PAM 0, k-tuple=2, Mismatch Penalty=1, Joining Penalty= 20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, the results, in percent identity, must be manually corrected. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query amino acid residues outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not match/align with the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal so there are no residues at the N- or C-termini of the subject sequence which are not matched/ aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other manual corrections are to made for the purposes of the present invention.

The above polypeptide sequences are included irrespective of whether they have their normal biological activity. This is because even where a particular polypeptide molecule does not have biological activity, one of skill in the art would still know how to use the polypeptide, for instance, as a vaccine or to generate antibodies. Other uses of the polypeptides of the present invention that do not have *B. burgdorferi* activity include, inter alia, as epitope tags, in epitope mapping, and as molecular weight markers on SDS-PAGE gels or on molecular sieve gel filtration columns using methods known to those of skill in the art.

As described below, the polypeptides of the present invention can also be used to raise polyclonal and monoclonal antibodies, which are useful in assays for detecting *B. burgdorferi* protein expression or as agonists and antagonists capable of enhancing or inhibiting *B. burgdorferi* protein function. Further, such polypeptides can be used in the yeast two-hybrid system to "capture" *B. burgdorferi* protein binding proteins which are also candidate agonists and antagonists according to the present invention. See, e.g., Fields et al. (1989) Nature 340:245–246.

Epitope-Bearing Portions

In another aspect, the invention provides peptides and polypeptides comprising epitope-bearing portions of the *B. burgdorferi* polypeptides of the present invention. These epitopes are immunogenic or antigenic epitopes of the polypeptides of the present invention. An "immunogenic epitope" is defined as a part of a protein that elicits an antibody response when the whole protein or polypeptide is the immunogen. These immunogenic epitopes are believed to be confined to a few loci on the molecule. On the other hand, a region of a protein molecule to which an antibody can bind is defined as an "antigenic determinant" or "antigenic epitope." The number of immunogenic epitopes of a protein generally is less than the number of antigenic epitopes. See, e.g., Geysen, et al. (1983) Proc. Natl. Acad.

Sci. USA 81:3998–4002. Predicted antigenic epitopes are shown in Table 4, below. It is pointed out that Table 4 only lists amino acid residues comprising epitopes predicted to have the highest degree of antigenicity. The polypeptides not listed in Table 4 and portions of polypeptides not listed in Table 4 are not considered non-antigenic. This is because they may still be antigenic in vivo but merely not recognized as such by the particular algorithm used. Thus, Table 4 lists the amino acid residues comprising preferred antigenic epitopes but not a complete list. Amino acid residues comprising other anigenic epitopes may be determined by algorithms similar to the Jameson-Wolf analysis or by in vivo testing for an antigenic response using the methods described herein or those known in the art.

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, e.g., Sutcliffe, et al., (1983) Science 219:660–666. Peptides capable of eliciting protein-reactive sera are frequently represented in the primary sequence of a protein, can be characterized by a set of simple chemical rules, and are confined neither to immunodominant regions of intact proteins (i.e. immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. See, Sutcliffe, et al., supra, p. 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. See Sutcliffe, et al., supra, p. 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, e.g., Wilson, et al., (1984) Cell 37:767–778. The anti-peptide antibodies of the invention also are useful for purification of the mimicked protein, for instance, by adsorption chromatography using methods known in the art.

Antigenic epitope-bearing peptides and polypeptides of the invention designed according to the above guidelines preferably contain a sequence of at least seven, more preferably at least nine and most preferably between about 10 to about 50 amino acids (i.e. any integer between 7 and 50) contained within the amino acid sequence of a polypeptide of the invention. However, peptides or polypeptides comprising a larger portion of an amino acid sequence of a polypeptide of the invention, containing about 50 to about 100 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate an *Borrelia*-specific immune response or antibodies include portions of the amino acid sequences identified in Table 1. More specifically, Table 4 discloses a list of non-limiting residues that are involved in the antigenicity of the epitope-bearing fragments of the present invention. Therefore, the present inventions provides for isolatd and purified antigenic epitope-bearing fragments of the polypeptides of the present invention comprising a peptide sequences of Table 4. The antigenic epitope-bearing fragments comprising a peptide sequence of Table 4 preferably contain a sequence of at least seven, more preferably at least nine and most preferably between about 10 to about 50 amino acids (i.e. any integer between 7 and 50) of a polypeptide of the present invention. That is, included in the present invention are antigenic polypeptides between the integers of 7 and 50 amino acid in length comprising one or more of the sequences of Table 4. Therefore, in most cases, the polypeptides of Table 4 make up only a portion of the antigenic polypeptide. All combinations of sequences between the integers of 7 and 50 amino acid in length comprising one or more of the sequences of Table 4 are included. The antigenic epitope-bearing fragements may be specified by either the number of contiguous amino acid residues or by specific N-terminal and C-terminal positions as described above for the polypeptide fragments of the present invention, wherein the initiation codon is residue 1. Any number of the described antigenic epitope-bearing fragments of the present invention may also be excluded from the present invention in the same manner.

The epitope-bearing peptides and polypeptides of the invention may be produced by any conventional means for making peptides or polypeptides including recombinant means using nucleic acid molecules of the invention. For instance, an epitope-bearing amino acid sequence of the present invention may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks (Houghten, R. A. Proc. Natl. Acad. Sci. USA 82:5131–5135 (1985)). This "Simultaneous Multiple Peptide Synthesis (SMPS)" process is further described in U.S. Pat. No. 4,631,211 to Houghten and coworkers (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously (Houghten et al. (1985) Proc. Natl. Acad. Sci. 82:5131–5135 at 5134.

Epitope-bearing peptides and polypeptides of the invention are used to induce antibodies according to methods well known in the art. See, e.g., Sutcliffe, et al., supra; Wilson, et al., supra; and Bittle, et al. (1985) J. Gen. Virol. 66:2347–2354. Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 $\mu$g peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen, et al., supra, discloses a procedure for rapid concurrent synthesis on solid supports of hundreds of peptides of sufficient purity to react in an ELISA. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. supra with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392, to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092, also to Geysen (1989), describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods. The entire disclosure of each document-cited in this section on "Polypeptides and Fragments" is hereby incorporated herein by reference.

As one of skill in the art will appreciate, the polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins. (EPA 0,394,827; Traunecker et al. (1988) Nature 331:84–86. Fusion proteins that have a disulfide-linked dimeric structure due to the IgG part can also be more efficient in binding and neutralizing other molecules than a monomeric B. burgdorferi polypeptide or fragment thereof alone. See Fountoulakis et al. (1995) J. Biochem. 270:3958–3964. Nucleic acids encoding the above epitopes of B. burgdorferi polypeptides can also be recombined with a gene of interest as an epitope tag to aid in detection and purification of the expressed polypeptide.

Antibodies

B. burgdorferi protein-specific antibodies for use in the present invention can be raised against the intact B. burgdorferi protein or an antigenic polypeptide fragment thereof, which may be presented together with a carrier protein, such as an albumin, to an animal system (such as rabbit or mouse) or, if it is long enough (at least-about 25 amino acids), without a carrier.

As used herein, the term "antibody" (Ab) or "monoclonal antibody" (Mab) is meant to include intact molecules, single chain whole antibodies, and antibody fragments. Antibody fragments of the present invention include Fab and F(ab')2 and other fragments including single-chain Fvs (scFv) and disulfide-linked Fvs (sdFv). Also included in the present invention are chimeric and humanized monoclonal antibodies and polyclonal antibodies specific for the polypeptides of the present invention. The antibodies of the present invention may be prepared by any of a variety of methods. For example, cells expressing a polypeptide of the present invention or an antigenic fragment thereof can be administered to an animal in order to induce the production of sera containing polyclonal antibodies. For example, a preparation of B. burgdorferi polypeptide or fragment thereof is prepared and purified to render it substantially free of natural contaminants. Such a preparation is then introduced into an animal in order to produce polyclonal antisera of greater specific activity.

In a preferred method, the antibodies of the present invention are monoclonal antibodies or binding fragments thereof. Such monoclonal antibodies can be prepared using hybridoma technology. See, e.g., Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563–681 (Elsevier, N.Y., 1981). Fab and F(ab')2 fragments may be produced by proteolytic cleavage, using enzymes such as papain (to produce Fab fragments) or pepsin (to produce F(ab')2 fragments). Alternatively, B. burgdorferi polypeptide-binding fragments, chimeric, and humanized antibodies can be produced through the application of recombinant DNA technology or through synthetic chemistry using methods known in the art.

Alternatively, additional antibodies capable of binding to the polypeptide antigen of the present invention may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, B. burgdorferi polypeptide-specific antibodies are used to immunize an animal, preferably a mouse. The splenocytes of such an animal are then used to produce hybridoma cells, and the hybridoma cells are screened to identify clones which produce an antibody whose ability to bind to the B. burgdorferi polypeptide-specific antibody can be blocked by the B. burgdorferi polypeptide antigen. Such antibodies comprise anti-idiotypic antibodies to the B. burgdorferi polypeptide-specific antibody and can be used to immunize an animal to induce formation of further B. burgdorferi polypeptide-specific antibodies.

Antibodies and fragments thereof of the present invention may be described by the portion of a polypeptide of the present invention recognized or specifically bound by the antibody. Antibody binding fragments of a polypeptide of the present invention may be described or specified in the same manner as for polypeptide fragments discussed above., i.e, by N-terminal and C-terminal positions or by size in contiguous amino acid residues. Any number of antibody binding fragments, of a polypeptide of the present invention, specified by N-terminal and C-terminal positions or by size in amino acid residues, as described above, may also be excluded from the present invention. Therefore, the present invention includes antibodies the specifically bind a particularly described fragment of a polypeptide of the present invention and allows for the exclusion of the same.

Antibodies and fragments thereof of the present invention may also be described or specified in terms of their cross-reactivity. Antibodies and fragments that do not bind polypeptides of any other species of Borrelia other than B. burgdorferi are included in the present invention. Likewise, antibodies and fragments that bind only species of Borrelia, i.e. antibodies and fragments that do not bind bacteria from any genus other than Borrelia, are included in the present invention.

Diagnostic Assays

The present invention further relates to methods for assaying staphylococcal infection in an animal by detecting the expression of genes encoding staphylococcal polypeptides of the present invention. The methods comprise analyzing tissue or body fluid from the animal for Borrelia-specific antibodies, nucleic acids, or proteins. Analysis of nucleic acid specific to Borrelia is assayed by PCR or hybridization techniques using nucleic acid sequences of the present invention as either hybridization probes or primers. See, e.g., Sambrook et al. Molecular cloning. A Laboratory Manual (Cold Spring Harbor Laboratory Press, 2nd ed., 1989, page 54 reference); Eremeeva et al. (1994) J. Clin. Microbiol. 32:803–810 (describing differentiation among spotted fever group Rickettsiae species by analysis of restriction fragment length polymorphism of PCR-amplified DNA) and Chen et al. 1994 J. Clin. Microbiol. 32:589–595 (detecting B. burgdorferi nucleic acids via PCR).

Where diagnosis of a disease state related to infection with Borrelia has already been made, the present invent on is useful for monitoring progression or regression of the disease state whereby patients exhibiting enhanced Borrelia gene expression will experience a worse clinical outcome relative to patients expressing these gene(s) at a lower level.

By "biological sample" is intended any biological sample obtained from an animal, cell line, tissue culture, or other source which contains Borrelia polypeptide, mRNA, or DNA. Biological samples include body fluids (such as saliva, blood, plasma, urine, mucus, synovial fluid, etc.) tissues (such as muscle, skin, and cartilage) and any other biological source suspected of containing Borrelia polypeptides or nucleic acids. Methods for obtaining biological samples such as tissue are well known in the art.

The present invention is useful for detecting diseases related to Borrelia infections in animals. Preferred animals include monkeys, apes, cats, dogs, birds, cows, pigs, mice, horses, rabbits and humans. Particularly preferred are humans.

Total RNA can be isolated from a biological sample using any suitable technique such as the single-step guanidinium-thiocyanate-phenol-chloroform method described in Chomczynski et al. (1987) Anal. Biochem. 162:156–159 mRNA encoding Borrelia polypeptides having sufficient homology to the nucleic acid sequences identified in Table 1 to allow for hybridization between complementary sequences are then assayed using any appropriate method. These include Northern blot analysis, S1 nuclease mapping; the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al. (1990) Cell 63:303–312. Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. A B. burgdorferi polynucleotide sequence shown in Table 1 labeled according to any appropriate method (such as the $^{32}$P-multiprimed DNA labeling system (Amersham)) is used as probe. After hybridization overnight, the filter is washed and exposed to x-ray film. DNA for use as probe according to the present invention is described in the sections above and will preferably at least 15 nucleotides in length.

S1 mapping can be performed as described in Fujita et al. (1987) Cell 49:357–367. To prepare probe DNA for use in S1 mapping, the sense strand of an above-described B. burgdorferi DNA sequence of the present invention is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding Borrelia polypeptides).

Levels of mRNA encoding Borrelia polypeptides are assayed, for e.g., using the RT-PCR method described in Makino et al. (1990) Technique 2:295–301. By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the Borrelia polypeptides of the present invention) are quantified using an imaging analyzer. RT and PCR reaction ingredients and conditions, reagent and gel concentrations, and labeling methods are well known in the art. Variations on the RT-PCR method will be apparent to the skilled artisan. Other PCR methods that can detect the nucleic acid of the present invention can be found in PCR PRIMER: A LABORATORY MANUAL (C. W. Dieffenbach et al. eds., Cold Spring Harbor Lab Press, 1995).

The polynucleotides of the present invention, including both DNA and RNA, may be used to detect polynucleotides of the present invention or Borrelia species including B. burgdorferi using bio chip technology. The present invention includes both high density chip arrays (>1000 oligonucleotides per $cm^2$) and low density chip arrays (<1000 oligonucleotides per $cm^2$). Bio chips comprising arrays of polynucleotides of the present invention may be used to detect Borrelia species, including B. burgdorferi, in biological and environmental samples and to diagnose an animal, including humans, with an B. burgdorferi or other Borrelia infection. The bio chips of the present invention may comprise polynucleotide sequences of other pathogens including bacteria, viral, parasitic, and fungal polynucleotide sequences, in addition to the polynucleotide sequences of the present invention, for use in rapid diffenertial pathogenic detection and diagnosis. The bio chips can also be used to monitor an B. burgdorferi or other Borrelia infections and to monitor the genetic changes (deletions, insertions, mismatches, etc.) in response to drug therapy in the clinic and drug development in the laboratory. The bio chip technology comprising arrays of polynucleotides of the present invention may also be used to simultaneously monitor the expression of a multiplicity of genes, including those of the present invention. The polynucleotides used to comprise a selected array may be specified in the same manner as for the fragments, i.e, by their 5' and 3' positions or length in contigious base pairs and include from. Methods and particular uses of the polynucleotides of the present invention to detect Borrelia species, including B. burgdorferi, using bio chip technology include those known in the art and those of: U.S. Pat. Nos. 5,510,270; 5,545,531, 5,445,934, 5,677,195, 5,532,128, 5,556,752, 5,527,681, 5,451,683, 5,424,186, 5,607,646, 5,658,732 and World Patent Nos. WO/9710365, WO/9511995, WO/9743447, WO/9535505, each incorporated herein in their entireties.

Biosensors using the polynucleotides of the present invention may also be used to detect, diagnose, and monitor B. burgdorferi or other Borrelia species and infections thereof. Biosensors using the polynucleotides of the present invention may also be used to detect particular polynucleotides of the present invention. Biosensors using the polynucleotides of the present invention may also be used to monitor the genetic changes (deletions, insertions, mismatches, etc.) in response to drug therapy in the clinic and drug development in the laboratory. Methods and particular uses of the polynucleotides of the present invention to detect Borrelia species, including B. burgdorferi, using biosensors include those known in the art and those of: U.S. Pat. Nos. 5,721, 102, 5,638,732, 5,631,170, and World Patent Nos. WO97/35011, WO/9720203, each incorporated herein in their entireties.

Thus, the present invention includes both bio chips and biosensors comprising polynucleotides of the present invention and methods of their use.

Assaying Borrelia polypeptide levels in a biological sample can occur using any art-known method, such as antibody-based techniques. For example, Borrelia polypeptide expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of Borrelia polypeptides for Western-blot or dot/slot assay. See, e.g., Jalkanen, M. et al. (1985) J. Cell. Biol: 101:976–985; Jalkanen, M. et al. (1987) J. Cell. Biol. 105:3087–3096. In this technique, which is based on the use of cationic solid phases, quantitation of a Borrelia polypeptide can be accomplished using an isolated Borrelia polypeptide as a standard. This technique can also be applied to body fluids.

Other antibody-based methods useful for detecting Borrelia polypeptide gene expression include immunoassays, such as the ELISA and the radioimmnunoassay (RIA). For example, a Borrelia polypeptide-specific monoclonal antibodies can be used both as an immunoabsorbent and as an enzyme-labeled probe to detect and quantify a Borrelia polypeptide. The amount of a Borrelia polypeptide present in the sample can be calculated by reference to the amount present in a standard preparation using a linear regression computer algorithm; Such an ELISA is described in Iacobelli et al. (1988) Breast Cancer Research and Treatment 11:19–30. In another ELISA assay, two distinct specific monoclonal antibodies can be used to detect Borrelia polypeptides in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting the Borrelia polypeptide with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample. Variations of the above and other immunological methods included in the present invention can also be found in Harlow et al., ANTIBODIES: A LABORATORY MANUAL, (Cold Spring Harbor Laboratory Press, 2nd ed. 1988).

Suitable enzyme labels include, for example, those from the oxidase group, which catalyze the production of hydrogen peroxide by reacting with substrate. Glucose oxidase is particularly preferred as it has good stability and its substrate (glucose) is readily available.

Activity of an oxidase label may be assayed by measuring the concentration of hydrogen peroxide formed by the enzyme-labeled antibody/substrate reaction. Besides enzymes, other suitable labels include radioisotopes, such as iodine ($^{125}I$, $^{121}I$), carbon ($^{14}C$), sulphur ($^{35}S$), tritium (3H), indium ($^{112}In$), and technetium ($^{99m}Tc$), and fluorescent labels, such as fluorescein and rhodamine, and biotin.

Further suitable labels for the Borrelia polypeptide-specific antibodies of the present invention are provided below. Examples of suitable enzyme labels include malate dehydrogenase, *Borrelia* nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging. See, e.g., Perkins et al. (1985) Eur. J. Nucl. Med. 10:296–301; Carasquillo et al. (1987) J. Nucl. Med. 28:281–287. For example, $^{111}$In coupled to monoclonal antibodies with 1-(P-isothiocyanatobenzyl)-DPTA has shown little uptake in non-tumors tissues, particularly the liver, and therefore enhances specificity of tumor localization. See, Esteban et al. (1987) J. Nucl. Med. 28:861–870.

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include, *Pseudomonas* toxin, diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al. (1976) Clin. Chim. Acta 70:1–31, and Schurs et al. (1977) Clin. Chim. Acta 81:1–40. Coupling techniques mentioned in the latter are the glutaraldehyde method, the periodate method, the dimaleimide method, the m-maleimidobenzyl-N-hydroxy-succinimide ester method, all of which methods are incorporated by reference herein.

In a related aspect, the invention includes a diagnostic kit for use in screening serum containing antibodies specific against *B. burgdorferi* infection. Such a kit may include an isolated *B. burgdorferi* antigen comprising an epitope which is specifically immunoreactive with at least one anti-*B. burgdorferi* antibody. Such a kit also includes means for detecting the binding of said antibody to the antigen. In specific embodiments, the kit may include a recombinantly produced or chemically synthesized peptide or polypeptide antigen. The peptide or polypeptide antigen may be attached to a solid support.

In a more specific embodiment, the detecting means of the above-described kit includes a solid support to which said peptide or polypeptide antigen is attached. Such a kit may also include a non-attached reporter-labeled anti-human antibody. In this embodiment, binding of the antibody to the *B. burgdorferi* antigen can be detected by binding of the reporter labeled antibody to the anti-*B. burgdorferi* polypeptide antibody.

In a related aspect, the invention includes a method of detecting *B. burgdorferi* infection in a subject. This detection method includes reacting a body fluid, preferably serum, from the subject with an isolated *B. burgdorferi* antigen, and examining the antigen for the presence of bound antibody. In a specific embodiment, the method includes a polypeptide antigen attached to a solid support, and serum is reacted with the support. Subsequently, the support is reacted with a reporter-labeled anti-human antibody. The support is then examined for the presence of reporter-labeled antibody.

The solid surface reagent employed in the above assays and kits is prepared by known techniques for attaching protein material to solid support material, such as polymeric beads, dip sticks, 96-well plates or filter material. These attachment methods generally include non-specific adsorption of the protein to the support or covalent attachment of the protein., typically through a free amine group, to a chemically reactive group on the solid support, such as an activated carboxyl, hydroxyl, or aldehyde group. Alternatively, streptavidin coated plates can be used in conjunction with biotinylated antigen(s).

The polypeptides and antibodies of the present invention, including fragments thereof, may be used to detect *Borrelia* species including *B. burgdorferi* using bio chip and biosensor technology. Bio chip and biosensors of the present invention may comprise the polypeptides of the present invention to detect antibodies, which specifically recognize *Borrelia* species, including *B. burgdorferi*. Bio chip and biosensors of the present invention may also comprise antibodies which specifically recognize the polypeptides of the present invention to detect *Borrelia* species, including *B. burgdorferi* or specific polypeptides of the present invention. Bio chips or biosensors comprising polypeptides or antibodies of the present invention may be used to detect *Borrelia* species, including *B. burgdorferi*, in biological and environmental samples and to diagnose an animal, including humans, with an *B. burgdorferi* or other *Borrelia* infection. Thus, the present invention includes both bio chips and biosensors comprising polypeptides or antibodies of the present invention and methods of their use.

The bio chips of the present invention may further comprise polypeptide sequences of other pathogens including bacteria, viral, parasitic, and fungal polypeptide sequences, in addition to the polypeptide sequences of the present invention, for use in rapid diffenertial pathogenic detection and diagnosis. The bio chips of the present invention may further comprise-antibodies or fragments thereof specific for other pathogens including bacteria, viral, parasitic, and fungal polypeptide sequences, in addition to the antibodies or fragments thereof of the present invention, for use in rapid diffenertial pathogenic detection and diagnosis. The bio chips and biosensors of the present invention may also be used to monitor an *B. burgdorferi* or other *Borrelia* infection and to monitor the genetic changes (amio acid deletions, insertions, substitutions, etc.) in response to drug therapy in the clinic and drug development in the laboratory. The bio chip and biosensors comprising polypeptides or antibodies of the present invention may also be used to simultaneously monitor the expression of a multiplicity of polypeptides, including those of the present invention. The polypeptides used to comprise a bio chip or biosensor of the present invention may be specified in the same manner as for the fragments, i.e, by their N-terminal and C-terminal positions or length in contigious amino acid residue. Methods and particular uses of the polypeptides and antibodies of the present invention to detect *Borrelia* species, including *B. burgdorferi*, or specific polypeptides using bio chip and biosensor technology include those known in the art, those of the U.S. patent Nos. and World Patent Nos. listed above for bio chips and biosensors using polynucleotides of the present invention, and those of: U.S. Pat. Nos. 5,658,732, 5,135,852, 5,567,301, 5,677,196, 5,690,894 and World Patent Nos. W09729366, WO9612957, each incorporated herein in their entireties.

Treatment:

Agonists and Antagonists—Assays and Molecules

The invention also provides a method of screening compounds to identify those which enhance or block the biological activity of the B. burgdorferi polypeptides of the present invention. The present invention further provides where the compounds kill or slow the growth of B. burgdorferi. The ability of B. burgdorferi antagonists, including B. burgdorferi ligands, to prophylactically or therapeutically block antibiotic resistance may be easily tested by the skilled artisan. See, e.g., Straden et al. (1997) J. Bacteriol. 179(1) :9–16.

An agonist is a compound which increases the natural biological function or which functions in a manner similar to the polypeptides of the present invention, while antagonists decrease or eliminate such functions. Potential antagonists include small organic molecules, peptides, polypeptides, and antibodies that bind to a polypeptide of the invention and thereby inhibit or extinguish its activity.

The antagonists may be employed for instance to inhibit peptidoglycan cross bridge formation. Antibodies against B. burgdorferi may be employed to bind to and inhibit B. burgdorferi activity to treat antibiotic resistance. Any of the above antagonists may be employed in a composition with a pharmaceutically acceptable carrier.

Vaccines

The present invention also provides vaccines comprising one or more polypeptides of the present invention. Heterogeneity in the composition of a vaccine may be provided by combining B. burgdorferi polypeptides of the present invention. Multi-component vaccines of this type are desirable because they are likely to be more effective in eliciting protective immune responses against multiple species and strains of the Borrelia genus than single polypeptide vaccines. Thus, as discussed in detail below, a multi-component vaccine of the present invention may contain one or more, preferably 2 to about 20, more preferably 2 to about 15, and most preferably 3 to about 8, of the B. burgdorferi polypeptides shown in Table 1, or fragments thereof.

Multi-component vaccines are known in the art to elicit antibody production to numerous immunogenic components. Decker, M. and Edwards, K., J. Infect. Dis. 174:S270–275 (1996). In addition, a hepatitis B, diphtheria, tetanus, pertussis tetravalent vaccine has recently been demonstrated to elicit protective levels of antibodies in human infants against all four pathogenic agents. Aristegui, J. et al., Vaccine 15:7–9 (1997).

The present invention thus also includes multi-component vaccines. These vaccines comprise more than one polypeptide, immunogen or antigen. An example of such a multi-component vaccine would be a vaccine comprising more than one of the B. burgdorferi polypeptides shown in Table 1. A second example is a vaccine comprising one or more, for example 2 to 10, of the B. burgdorferi polypeptides shown in Table 1 and one or more, for example 2 to 10, additional polypeptides of either borrelial or non-borrelial origin. Thus, a multi-component vaccine which confers protective immunity to both a borrelial infection and infection by another pathogenic agent is also within the scope of the invention.

As indicated above, the vaccines of the present invention are expected to elicit a protective immune response against infections caused by species and strains of Borrelia other than B. burgdorferi sensu stricto isolate B31 (ATCC Accession No. 35210). Immunizations using decorin-binding protein and OspA derived from one strain of B. burgdorferi has been shown to elicit the production of antiserum which confers passive immunity against other strains of B. burgdorferi. Cassatt, D. et al., Protection of Borrelia burgdorferi Infection by Antibodies to Decorin-binding Protein, in VACCINES97; Cold Spring Harbor Press (1997), pages 191–195. Further, the inventors have found using an in vitro assay that antiserum produced in response to B. burgdorferi decorin-binding protein will kill several species of Borrelia. The amino acid sequences of decorin-binding protein expressed by different strains of B. burgdorferi are believed to diverge by as much as 25%. Thus, antisera elicited against decorin-binding proteins confers passive immunity against Borrelia expressing proteins having only 75% or less amino acid sequence similarity.

Further within the scope of the invention are whole cell and whole viral vaccines. Such vaccines may be produced recombinantly and involve the expression of one or more of the B. burgdorferi polypeptides shown in Table 1. For example, the B. burgdorferi polypeptides of the present invention may be either secreted or localized intracellular, on the cell surface, or in the periplasmic space. Further, when a recombinant virus is used, the B. burgdorferi polypeptides of the present invention may, for example, be localized in the viral envelope, on the surface of the capsid, or internally within the capsid. Whole cells vaccines which employ cells expressing heterologous proteins are known in the art. See, e.g., Robinson, K. et al., Nature Biotech. 15:653–657 (1997); Sirard, J. et al., Infect. Immun. 65:2029–2033 (1997); Chabalgoity, J. et al., Infect. Immun. 65:2402–2412 (1997). These cells may be administered live or may be killed prior to administration. Chabalgoity, J. et al., supra, for example, report the successful use in mice of a live attenuated Salmonella vaccine strain which expresses a portion of a platyhelminth fatty acid-binding protein as a fusion protein on its cells surface.

A multi-component vaccine can also be prepared using techniques known in the art by combining one or more B. burgdorferi polypeptides of the present invention, or fragments thereof, with additional non-borrelial components (e.g., diphtheria toxin or tetanus toxin, and/or other compounds known to elicit an immune response). Such vaccines are useful for eliciting protective immune responses to both members of the Borrelia genus and non-borrelial pathogenic agents.

The vaccines of the present invention also include DNA vaccines. DNA vaccines are currently being developed for a number of infectious diseases. Boyer, J et al., Nat. Med. 3:526–532 (1997); reviewed in Spier, R., Vaccine 14:1285–1288 (1996). Such DNA vaccines contain a nucleotide sequence encoding one or more B. burgdorferi polypeptides of the present invention oriented in a manner that allows for expression of the subject polypeptide. The direct administration of plasmid DNA encoding OspA has been shown to elicit protective immunity in mice against borrelial challenge. Luke, C. et al., J. Infect. Dis. 175:91–97 (1997).

The present invention also relates to the administration of a vaccine which is co-administered with a molecule capable of modulating immune responses. Kim, J. et al., Nature Biotech. 15:641–646 (1997), for example, report the enhancement of immune responses produced by DNA immunizations when DNA sequences encoding molecules which stimulate the immune response are co-administered.

In a similar fashion, the vaccines of the present invention may be co-administered with either nucleic acids encoding immune modulators or the immune modulators themselves. These immune modulators include granulocyte macrophage colony stimulating factor (GM-CSF) and CD86.

The vaccines of the present invention may be used to confer resistance to borrelial infection by either passive or active immunization. When the vaccines of the present invention are used to confer resistance to borrelial infection through active immunization, a vaccine of the present invention is administered to an animal to elicit a protective immune response which either prevents or attenuates a borrelial infection. When the vaccines of the present invention are used to confer resistance to borrelial infection through passive immunization, the vaccine is provided to a host animal (e.g., human, dog, or mouse), and the antisera elicited by this antisera is recovered and directly provided to a recipient suspected of having an infection caused by a member of the *Borrelia* genus.

The ability to label antibodies, or fragments of antibodies, with toxin molecules provides an additional method for treating borrelial infections when passive immunization is conducted. In this embodiment, antibodies, or fragments of antibodies, capable of recognizing the *B. burgdorferi* polypeptides disclosed herein, or fragments thereof, as well as other *Borrelia* proteins, are labeled with toxin molecules prior to their administration to the patient. When such toxin derivatized antibodies bind to *Borrelia* cells, toxin moieties will be localized to these cells and will cause their death.

The present invention thus concerns and provides a means for preventing or attenuating a borrelial infection resulting from organisms which have antigens that are recognized and bound by antisera produced in response to the polypeptides of the present invention. As used herein, a vaccine is said to prevent or attenuate a disease if its administration to an animal results either in the total or partial attenuation (i.e., suppression) of a symptom or condition of the disease, or in the total or partial immunity of the animal to the disease.

The administration of the vaccine (or the antisera which it elicits) may be for either a "prophylactic" or "therapeutic" purpose. When provided prophylactically, the compound(s) are provided in advance of any symptoms of borrelial infection. The prophylactic administration of the compound (s) serves to prevent or attenuate any subsequent infection. When provided therapeutically, the compound(s) is provided upon or after the detection of symptoms which indicate that an animal may be infected with a member of the *Borrelia* genus. The therapeutic administration of the compound(s) serves to attenuate any actual infection. Thus, the *B. burgdorferi* polypeptides, and fragments thereof, of the present invention may be provided either prior to the onset of infection (so as to prevent or attenuate an anticipated infection) or after the initiation of an actual infection.

The polypeptides of the invention, whether encoding a portion of a native protein or a functional derivative thereof, may be administered in pure form or may be coupled to a macromolecular carrier. Example of such carriers are proteins and carbohydrates. Suitable proteins which may act as macromolecular carrier for enhancing the immunogenicity of the polypeptides of the present invention include keyhole limpet hemacyanin (KLH) tetanus toxoid, pertussis toxin, bovine serum albumin, and ovalbumin. Methods for coupling the polypeptides of the present invention to such macromolecular carriers are disclosed in Harlow et al., *Antibodies: A Laboratory Manual, 2nd Ed.*; Cold Spring Harbor Laboratory Press, Cold Spring Harbor, N.Y. (1988), the entire disclosure of which is incorporated by reference herein.

A composition is said to be "pharmacologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

While in all instances the vaccine of the present invention is administered as a pharmacologically acceptable compound, one skilled in the art would recognize that the composition of a pharmacologically acceptable compound varies with the animal to which it is administered. For example, a vaccine intended for human use will generally not be co-administered with Freund's adjuvant. Further, the level of purity of the *B. burgdorferi* polypeptides of the present invention will normally be higher when administered to a human than when administered to a non-human animal.

As would be understood by one of ordinary skill in the art, when the vaccine of the present invention is provided to an animal, it may be in a composition which may contain salts, buffers, adjuvants, or other substances which are desirable for improving the efficacy of the composition. Adjuvants are substances that can be used to specifically augment a specific immune response. These substances generally perform two functions: (1) they protect the antigen(s) from being rapidly catabolized after administration and (2) they nonspecifically stimulate immune responses.

Normally, the adjuvant and the composition are mixed prior to presentation to the immune system, or presented separately, but into the same site of the animal being immunized. Adjuvants can be loosely divided into several groups based upon their composition. These groups include oil adjuvants (for example, Freund's complete and incomplete), mineral salts (for example, $AlK(SO_4)_2$, $AlNa(SO_4)_2$, $AlNH_4(SO_4)$, silica, kaolin, and carbon), polynucleotides (for example, poly IC and poly AU acids), and certain natural substances (for example, wax D from *Mycobacterium tuberculosis*, as well as substances found in *Corynebacterium parvum*, or *Bordetella pertussis*, and members of the genus *Brucella*. Other substances useful as adjuvants are the saponins such as, for example, Quil A. (Superfos A/S, Denmark). Preferred adjuvants for use in the present invention include aluminum salts, such as $AlK(SO_4)_2$, $AlNa(SO_4)_2$, and $AlNH_4(SO_4)$. Examples of materials suitable for use in vaccine compositions are provided in *Remington's Pharmaceutical Sciences* (Osol, A, Ed, Mack Publishing Co, Easton, Pa., pp. 1324–1341 (1980), which reference is incorporated herein by reference).

The therapeutic compositions of the present invention can be administered parenterally by injection, rapid infusion, nasopharyngeal absorption (intranasopharangeally), dermoabsorption, or orally. The compositions may alternatively be administered intramuscularly, or intravenously Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

Therapeutic compositions of the present invention can also be administered in encapsulated form. For example, intranasal immunization of mice against *Bordetella pertussis* infection using vaccines encapsulated in biodegradable microsphere composed of poly(DL-lactide-co-glycolide) has been shown to stimulate protective immune responses. Shahin; R. et al., *Infect. Immun.* 63:1195–1200 (1995). Similarly, orally administered encapsulated *Salmonella typhimurium* antigens have also been shown to elicit protective immunity in mice. Allaoui-Attarki, K. et al., *Infect. Immun.* 65:853–857 (1997). Encapsulated vaccines of the present invention can be administered by a variety of routes including those involving contacting the vaccine with mucous membranes (e.g., intranasally, intracolonicly, intraduodenally).

Many different techniques exist for the timing of the immunizations when a multiple administration regimen is utilized. It is possible to use the compositions of the invention more than once to increase the levels and diversities of expression of the immunoglobulin repertoire expressed by the immunized animal. Typically, if multiple immunizations are given, they will be given one to two months apart.

According to the present invention, an "effective amount" of a therapeutic composition is one which is sufficient to achieve a desired biological effect. Generally, the dosage needed to provide an effective amount of the composition will vary depending upon such factors as the animal's or human's age, condition, sex, and extent of disease, if any, and other variables which can be adjusted by one of ordinary skill in the art.

The antigenic preparations of the invention can be administered by either single or multiple dosages of an effective amount. Effective amounts of the compositions of the invention can vary from 0.01–1,000 μg/ml per dose, more preferably 0.1–500 μg/ml per dose, and most preferably 10–300 μg/ml per dose.

Having now generally described the invention, the same will be more readily understood through reference to the following example which is provided by way of illustration, and is not intended to be limiting of the present invention, unless specified.

EXAMPLES

1. Preparation of PCR Primers and Amplification of DNA

Various fragments of the *Borrelia burgdorferi* genome, such as those of Table 1, can be used, in accordance with the present invention, to prepare PCR primers for a variety of users. The PCR primers are preferably at least 15 bases, and more preferably at least 18 bases in length. When selecting a primer sequence, it is preferred that the primer pairs have approximately the same G/C ratio, so that melting temperatures are approximately the same. The PCR primers and amplified DNA of this Example find use in the Examples that follow.

2. Isolation of a Selected DNA Clone From *B. burgdorferi*

Three approaches are used to isolate a *B. burgdorferi* clone comprising a polynucleotide of the present invention from any *B. burgdorferi* genomic DNA library. The *B. burgdorferi* strain B31PU has been deposited as a convienent source for obtaining a *B. burgdorferi* strain although a wide varity of strains *B. burgdorferi* strains can be used which are known in the art.

*B. burgdorferi* genomic DNA is prepared using the following method. A 20 ml overnight bacterial culture grown in a rich medium (e.g., Trypticase Soy Broth, Brain Heart Infusion broth or Super broth), pelleted, ished two times with TES (30 mM Tris-pH 8.0, 25 mM EDTA, 50 mM NaCl), and resuspended in 5 ml high salt TES (2.5M NaCl). Lysostaphin is added to final concentration of approx 50 ug/ml and the mixture is rotated slowly 1 hour at 37 C to make protoplast cells. The solution is then placed in incubator (or place in a shaking water bath) and warmed to 55 C. Five hundred micro liter of 20% sarcosyl in TES (final concentration 2%) is then added to lyse the cells. Next, guanidine HCl is added to a final concentration of 7M (3.69 g in 5.5 ml). The mixture is swirled slowly at 55 C for 60–90 min (solution should clear). A CsCl gradient is then set up in SW41 ultra clear tubes using 2.0 ml 5.7M CsCl and overlaying with 2.85M CsCl. The gradient is carefully overlayed with the DNA-containing GuHCl solution. The gradient is spun at 30,000 rpm, 20 C for 24 hr and the lower DNA band is collected. The volume is increased to 5 ml with TE buffer. The DNA is then treated with protease K (10 ug/ml) overnight at 37 C, and precipitated with ethanol. The precipitated DNA is resuspended in a desired buffer.

In the first method, a plasmid is directly isolated by screening a plasmid *B. burgdorferi* genomic DNA library using a polynucleotide probe corresponding to a polynucleotide of the present invention. Particularly, a specific polynucleotide with 30–40 nucleotides is synthesized using an Applied Biosystems DNA synthesizer according to the sequence reported. The oligonucleotide is labeled, for instance, with $^{32}$P-γ-ATP using T4 polynucleotide kinase and purified according to routine methods. (See, e.g., Maniatis et al., Molecular Cloning: A Laboratory Manual, Cold Spring Harbor Press, Cold Spring, N.Y. (1982).) The library is transformed into a suitable host, as indicated above (such as XL-1 Blue (Stratagene)) using techniques known to those of skill in the art. See, e.g., Sambrook et al. MOLECULAR CLONING: A LABORATORY MANUAL (Cold Spring Harbor, N.Y. 2nd ed. 1989); Ausubel et al., CURRENT PROTOCALS IN MOLECULAR BIOLOGY (John Wiley and Sons, N.Y. 1989). The transformants are plated on 1.5% agar plates (containing the appropriate selection agent, e.g., ampicillin) to a density of about 150 transformants (colonies) per plate. These plates are screened using Nylon membranes according to routine methods for bacterial colony screening. See, e.g., Sambrook et al. MOLECULAR CLONING: A LABORATORY MANUAL (Cold Spring Harbor, N.Y. 2nd ed. 1989); Ausubel et al., CURRENT PROTOCALS IN MOLECULAR BIOLOGY (John Wiley and Sons, N.Y. 1989) or other techniques known to those of skill in the art.

Alternatively, two primers of 15–25 nucleotides derived from the 5' and 3' ends of a polynucleotide of Table 1 are synthesized and used to amplify the desired DNA by PCR using a *B. burgdorferi* genomic DNA prep as a template. PCR is carried out under routine conditions, for instance, in 25 μl of reaction mixture with 0.5 ug of the above DNA template. A convenient reaction mixture is 1.5–5 mM $MgCl_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Finally, overlapping oligos of the DNA sequences of Table 1 can be chemically synthesized and used to generate a nucleotide sequence of desired length using PCR methods known in the art.

3(a). Expression and Purification Borrelia Polypeptides in E. coli

The bacterial expression vector pQE60 is used for bacterial expression of some of the polypeptide fragments of the present invention. (QIAGEN, Inc., 9259 Eton Avenue, Chatsworth, Calif., 91311). pQE60 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin (QIAGEN, Inc., supra) and suitable single restriction enzyme cleavage sites. These elements are arranged such that an inserted DNA fragment encoding a polypeptide expresses that polypeptide with the six His residues (i.e., a "6× His tag") covalently linked to the carboxyl terminus of that polypeptide.

The DNA sequence encoding the desired portion of a *B. burgdorferi* protein of the present invention is amplified from *B. burgdorferi* genomic DNA using PCR oligonucleotide primers which anneal to the 5' and 3' sequences coding for the portions of the *B. burgdorferi* polynucleotide shown in Table 1. Additional nucleotides containing restriction sites to facilitate cloning in the pQE60 vector are added to the 5' and 3' sequences, respectively.

For cloning the mature protein, the 5' primer has a sequence containing an appropriate restriction site followed by nucleotides of the amino terminal coding sequence of the desired *B. burgdorferi* polynucleotide sequence in Table 1. One of ordinary skill in the art would appreciate that the point in the protein coding sequence where the 5' and 3' primers begin may be varied to amplify a DNA segment encoding any desired portion of the complete protein shorter or longer than the mature form. The 3' primer has a sequence containing an appropriate restriction site followed by nucleotides complementary to the 3' end of the polypeptide coding sequence of Table 1, excluding a stop codon, with the coding sequence aligned with the restriction site so as to maintain its reading frame with that of the six His codons in the pQE60 vector.

The amplified *B. burgdorferi* DNA fragment and the vector pQE60 are digested with restriction enzymes which recognize the sites in the primers and the digested DNAs are then ligated together. The *B. burgdorferi* DNA is inserted into the restricted pQE60 vector in a mariner which places the *B. burgdorferi* protein coding region downstream from the IPTG-inducible promoter and in-frame with an initiating AUG and the six histidine codons.

The ligation mixture is transformed into competent *E. coli* cells using standard procedures such as those described by Sambrook et al., supra. *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing a *B. burgdorferi* polypeptide, is available commercially (QIAGEN, Inc., supra). Transformants are identified by their ability to grow on LB agar plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-β-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the *B. burgdorferi* polypeptide is loaded onto a nickel-nitrilo-tri-acetic acid ("Ni-NTA") affinity resin column (QIAGEN, Inc., supra). Proteins with a 6× His tag bind to the Ni-NTA resin with high affinity are purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the *B. burgdorferi* polypeptide is eluted with 6 M guanidine-HCl, pH 5.

The purified protein is then renatured by dialyzing it against phosphate-buffered saline (PBS) or 50 μM Na-acetate, pH 6 buffer plus 200 mM NaCl. Alternatively, the protein could be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

The polypeptide of the present invention are also prepared using a non-denaturing protein purification method. For these polypeptides, the cell pellet from each liter of culture is resuspended in 25 mls of Lysis Buffer A at 4° C. (Lysis Buffer A=50 mM Na-phosphate, 300 mM NaCl, 10 mM 2-mercaptoethanol, 10% Glycerol, pH 7.5 with 1 tablet of Complete EDTA-free protease inhibitor cocktail (Boehringer Mannheim #1873580) per 50 ml of buffer). Absorbance at 550 nm is approximately 10–20 O.D./ml. The suspension is then put through three freeze/thaw cycles from −70° C. (using a ethanol-dry ice bath) up to room temperature. The cells are lysed via sonication in short 10 sec bursts over 3 minutes at approximately 80 W while kept on ice. The sonicated sample is then centrifuged at 15,000 RPM for 30 minutes at 4° C. The supernatant is passed through a column containing 1.0 ml of CL-4B resin to pre-clear the sample of any proteins that may bind to agarose non-specifically, and the flow-through fraction is collected.

The pre-cleared flow-through is applied to a nickel-nitrilo-tri-acetic acid ("Ni-NTA") affinity resin column (Quiagen, Inc., supra). Proteins with a 6× His tag bind to the Ni-NTA resin with high affinity and can be purified in a simple one-step procedure. Briefly, the supernatant is loaded onto the column in Lysis Buffer A at 4° C., the column is first washed with 10 volumes of Lysis Buffer A until the A280 of the eluate returns to the baseline. Then, the column is washed with 5 volumes of 40 mM Imidazole (92% Lysis Buffer A/8% Buffer B) (Buffer B=50 mM Na-Phosphate, 300 mM NaCl, 10% Glycerol, 10 mM 2-mercaptoethanol, 500 mM Imidazole, pH of the final buffer should be 7.5).

The protein is eluted off of the column with a series of increasing Imidazole solutions made by adjusting the ratios of Lysis Buffer A to Buffer B. Three different concentrations are used: 3 volumes of 75 mM imidazole, 3 volumes of 150 mM Imidazole, 5 volumes of 500 mM Imidazole. The fractions containing the purified protein are analyzed using 8%, 10% or 14% SDS-PAGE depending on the protein size. The purified protein is then dialyzed 2× against phosphate-buffered saline (PBS) in order to place it into an easily workable buffer. The purified protein is stored at 4° C. or frozen at −80°.

The following alternative method may be used to purify *B. burgdorferi* expressed in *E. coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the *B. burgdorferi* polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded *B. burgdorferi* polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise marker. The absorbance at 280 mm of the effluent is continuously monitored. Fractions are collected and further analyzed by SDS-PAGE.

Fractions containing the *B. burgdorferi* polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the *B. burgdorferi* polypeptide (determined, for instance, by 16% SDS-PAGE) are then pooled.

The resultant *B. burgdorferi* polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 ng/ml according to LAL assays.

3(b). Alternative Expression and Purification *Borrelia* Polypeptides in *E. coli*

Tthe vector pQE10 is alternatively used to clone and express some of the polypeptides of the present invention for use in the soft tissue and systemic infection models discussed below. The difference being such that an inserted DNA fragment encoding a polypeptide expresses that polypeptide with the six His residues (i.e., a "6× His tag") covalently linked to the amino terminus of that polypeptide. The bacterial expression vector pQE 10 (QIAGEN, Inc., 9259 Eton Avenue, Chatsworth, Calif., 91311) was used in this example. The components of the pQE10 plasmid are arranged such that the inserted DNA sequence encoding a polypeptide of the present invention expresses the polypeptide with the six His residues (i.e., a "6× His tag")) covalently linked to the amino terminus.

The DNA sequences encoding the desired portions of a polypeptide of Table 1 were amplified using PCR oligonucleotide primers from genomic *B. burgdorferi* DNA. The PCR primers anneal to the nucleotide sequences encoding the desired amino acid sequence of a polypeptide of the present invention. Additional nucleotides containing restriction sites to facilitate cloning in the pQE10 vector were added to the 5' and 3' primer sequences, respectively.

For cloning a polypeptide of the present invention, the 5' and 3' primers were selected to amplify their respective nucleotide coding sequences. One of ordinary skill in the art would appreciate that the point in the protein coding sequence where the 5' and 3' primers begins may be varied to amplify a DNA segment encoding any desired portion of a polypeptide of the present invention. The 5' primer was designed so the coding sequence of the 6× His tag is aligned with the restriction site so as to maintain its reading frame with that of *B. burgdorferi* polypeptide. The 3' was designed to include an stop codon. The amplified DNA fragment was then cloned, and the protein expressed, as described above for the pQE60 plasmid.

The DNA sequences of Table 1 encoding amino acid sequences may also be cloned and expressed as fusion proteins by a protocol similar to that described directly above, wherein the pET-32b(+) vector (Novagen, 601 Science Drive, Madison, Wis. 53711) is preferentially used in place of pQE10.

The above methods are not limited to the polypeptide fragments actually produced. The above method, like the methods below, can be used to produce either full length polypeptides or desired fragments thereof.

3(c). Alternative Expression and Purification of *Borrelia* Polypeptides in *E. coli*

The bacterial expression vector pQE60 is used for bacterial expression in this example (QIAGEN, Inc., 9259 Eton Avenue, Chatsworth, Calif., 9131.1). However, in this example, the polypeptide coding sequence is inserted such that translation of the six His codons is prevented and, therefore, the polypeptide is produced with no 6× His tag.

The DNA sequence encoding the desired portion of the *B. burgdorferi* amino acid sequence is amplified from an *B. burgdorferi* genomic DNA prep the deposited DNA clones using PCR oligonucleotide primers which anneal to the 5' and 3' nucleotide sequences corresponding to the desired portion of the *B. burgdorferi* polypeptides. Additional nucleotides containing restriction sites to facilitate cloning in the pQE60 vector are added to the 5' and 3' primer sequences.

For cloning a *B. burgdorferi* polypeptides of the present invention, 5' and 3' primers are selected to amplify their respective nucleotide coding sequences. One of ordinary skill in the art would appreciate that the point in the protein coding sequence where the 5' and 3' primers begin may be varied to amplify a DNA segment encoding any desired portion of a polypeptide of the present invention. The 3' and 5' primers contain appropriate restriction sites followed by nucleotides complementary to the 5' and 3' ends of the coding sequence respectively. The 3' primer is additionally designed to include an in-frame stop codon.

The amplified *B. burgdorferi* DNA fragments and the vector pQE60 are digested with restriction enzymes recognizing the sites in the primers and the digested DNAs are then ligated together. Insertion of the *B. burgdorferi* DNA into the restricted pQE60 vector places the *B. burgdorferi* protein coding region including its associated stop codon downstream from the IPTG-inducible promoter and in-frame with an initiating AUG. The associated stop codon prevents translation of the six histidine codons downstream of the insertion point.

The ligation mixture is transformed into competent *E. coli* cells using standard procedures such as those described by Sambrook et al. *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing *B. burgdorferi* polypeptide, is available commercially (QIAGEN, Inc., supra). Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 $\mu$g/ml) and kanamycin (25 $\mu$g/ml). The O/N culture is used to inoculate a large culture, at a dilution of approximately 1:25 to 1:250. The cells are grown to an optical density at 600 nm ("OD600") of between 0.4 and 0.6 isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

To purify the *B. burgdorferi* polypeptide, the cells are then stirred for 3–4 hours at 4° C. in 6M guanidine-HCl, pH 8. The cell debris is removed by centrifugation, and the supernatant containing the *B. burgdorferi* polypeptide is dialyzed against 50 mM Na-acetate buffer pH 6, supplemented with 200 mM NaCl. Alternatively, the protein can be successfully refolded by dialyzing it against 500 mM NaCl, 20% glycerol, 25 mM Tris/HCl pH 7.4, containing protease inhibitors. After renaturation the protein can be purified by ion exchange, hydrophobic interaction and size exclusion chromatography. Alternatively, an affinity chromatography step such as an antibody column can be used to obtain pure *B. burgdorferi* polypeptide. The purified protein is stored at 4° C. or frozen at −80° C.

The following alternative method may be used to purify *B. burgdorferi* polypeptides expressed in *E. coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the *B. burgdorferi* polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded *B. burgdorferi* polypeptide solution, a previously prepared tangential filtration unit equipped with 0.16 $\mu$m membrane filter with appropriate surface area (e.g., Filtron), equilibrated with 40 mM sodium acetate, pH 6.0 is employed. The filtered sample is loaded onto a cation exchange resin (e.g., Poros HS-50, Perspective Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the *B. burgdorferi* polypeptide are then pooled and mixed with 4 volumes of water. The diluted sample is then loaded onto a previously prepared set of tandem columns of strong anion (Poros HQ-50, Perspective Biosystems) and weak anion (Poros CM-20, Perspective Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the *B. burgdorferi* polypeptide (determined, for instance, by 16% SDS-PAGE) are then pooled.

The resultant *B. burgdorferi* polypeptide exhibits greater than 95% purity after the above refolding and purification steps. No major contaminant bands are observed from Commassie blue stained 16% SDS-PAGE gel when 5 µg of purified protein is loaded. The purified protein is also tested for endotoxin/LPS contamination, and typically the LPS content is less than 0.1 ng/ml according to LAL assays.

3(d). Cloning and Expression of *B. burgdorferi* in Other Bacteria

*B. burgdorferi* polypeptides can also be produced in: *B. burgdorferi* using the methods of S. Skinner et al., (1988) Mol. Microbiol. 2:289–297 or J. I. Moreno (1996) Protein Expr. Purif. 8(3):332–340; *Lactobacillus* using the methods of C. Rush et al., 1997 Appl. Microbiol. Biotechnol. 47(5): 537–542; or in *Bacillus subtilis* using the methods Chang et al., U.S. Pat. No. 4,952,508.

4. Cloning and Expression in COS Cells

A *B. burgdorferi* expression plasmid is made by cloning a portion of the DNA encoding a *B. burgdorferi* polypeptide into the expression vector pDNAI/Amp or pDNAIII (which can be obtained from, Invitrogen, Inc.). The expression vector pDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a DNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al. 1984 Cell 37:767. The fusion of the HA tag to the target protein allows easy detection and recovery of the recombinant protein with an antibody that recognizes the HA epitope. pDNAIII contains, in addition, the selectable neomycin marker.

A DNA fragment encoding a *B. burgdorferi* polypeptide is cloned into the polylinker region of the vector so that recombinant protein expression is directed by the CMV promoter. The plasmid construction strategy is as follows. The DNA from a *B. burgdorferi* genomic DNA prep is amplified using primers that contain convenient restriction sites, much as described above for construction of vectors for expression of *B. burgdorferi* in *E. coli*. The 5' primer contains a Kozak sequence, an AUG start codon, and nucleotides of the 5' coding region of the *B. burgdorferi* polypeptide. The 3' primer, contains nucleotides complementary to the 3' coding sequence of the *B. burgdorferi* DNA, a stop codon, and a convenient restriction site.

The PCR amplified DNA fragment and the vector, pDNAI/Amp, are digested with appropriate restriction enzymes and then ligated. The ligation mixture is transformed into an appropriate *E. coli* strain such as SURE™ (Stratagene Cloning Systems, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the *B. burgdorferi* polypeptide.

For expression of a recombinant *B. burgdorferi* polypeptide, COS cells are transfected with an expression vector, as described above, using DEAE-dextran, as described, for instance, by Sambrook et al. (supra). Cells are incubated under conditions for expression of *B. burgdorferi* by the vector.

Expression of the *B. burgdorferi*-HA fusion protein is detected by radiolabeling and immunoprecipitation, using methods described in, for example Harlow et al., supra. To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. (supra). Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

5. Cloning and Expression in CHO Cells

The vector pC4 is used for the expression of *B. burgdorferi* polypeptide in this example. Plasmid pC4 is a derivative of the plasmid pSV2-dhfr (ATCC Accession No. 37146). The plasmid contains the mouse DHFR gene under control of the SV40 early promoter. Chinese hamster ovary cells or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented. See, e.g., Alt et al., 1978, J. Biol. Chem. 253:1357–1370; Hamlin et al., 1990, Biochem. et Biophys. Acta, 1097:107–143; Page et al., 1991, Biotechnology 9:64–68. Cells grown in increasing concentrations of MTX develop resistance to the drug by overproducing the target enzyme, DHFR, as a result of amplification of the DHFR gene. If a second gene is linked to the DHFR gene, it is usually co-amplified and overexpressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains the strong promoter of the long terminal repeat (LTR) of the Rouse Sarcoma Virus, for expressing a polypeptide of interest, Cullen, et al. (1985) Mol. Cell. Biol. 5:438–447; plus a fragment isolated from the enhancer of the immediate early gene of human cytomegalovirus (CMV), Boshart, et al., 1985, Cell 41:521–530. Downstream of the promoter are the following single restriction enzyme cleavage sites that allow the integration of the genes: Bam HI, Xba I, and Asp 718. Behind these cloning sites the plasmid contains the 3' intron and polyadenylation site of the rat preproinsulin gene. Other high efficiency promoters can also be used for the expression, e.g., the human. β-actin promoter, the SV40 early or late promoters or the long terminal repeats from other retroviruses, e.g., HIV and HTLVI. Clontech's Tet-Off and Tet-On gene expression systems and similar systems can be used to express the *B. burgdorferi* polypeptide in a regulated way in mammalian cells (Gossen et al., 1992, Proc. Natl. Acad. Sci. USA 89:5547–5551. For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes and then dephosphorylated using calf intestinal phosphates by procedures known in the art. The vector is then isolated from a 1% agarose gel. The DNA sequence encoding the *B. burgdorferi* polypeptide is amplified using PCR oligonucleotide primers corresponding to the 5' and 3' sequences of the desired portion of the gene. A 5' primer containing a restriction site, a Kozak sequence, an AUG start codon, and nucleotides of the 5' coding region of the. *B. burgdorferi* polypeptide is synthesized and used. A 3' primer, containing a restriction site, stop codon, and nucleotides complementary to the 3' coding sequence of the *B. burgdorferi* polypeptides is synthesized and used. The amplified fragment is digested with the restriction endonucleases and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance; restriction enzyme analysis.

Chinese hamster ovary cells lacking an active DHFR gene are used for transfection. Five μg of the expression plasmid pC4 is cotransfected with 0.5 μg of the plasmid pSV neo using a lipid-mediated transfection agent such as Lipofectin™ or LipofectAMINE™ (LifeTechnologies Gaithersburg, Md.). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

6. Immunization and Detection of Immune Responses

6(a). *B. burgdorferi* Propagation

*B. burgdorferi* sensu stricto isolate B31 is propagated in tightly-closed containers at 34° C. in modified Barbour-Stoenner-Kelly (BSKII) medium (Barbour, A. G., *Yale J. Biol. Med.* 57:521–525 (1984)) overlaid with a 5% $O_2$/5% $CO_2$/90% $N_2$ gas mixture. Cell densities of these cultures are determined by darkfield microscopy at 400×.

Immunization of Mice and Challenge with *B. burgdorferi*. For active immunizations BALB/cByJ mice (BALB, Jackson Laboratories) are injected intraperitoneally (i.p.) at week 0 with 20 g of recombinant borrelial protein, or phosphate-buffered saline (PBS), emulsified with complete Freund's adjuvant (CFA), given a similar booster immunization in incomplete Freund's adjuvant (IFA) at week 4, and challenged at week 6. For challenge *B. burgdorferi* are diluted in BSKII from exponentially-growing cultures and mice are injected subcutaneously (s.c.) at the base of the tail with 0.1 ml of these dilutions (typically $10^3$–$10^4$ borreliae; approximately 10–100 times the median infectious dose). Borreliae used for challenge are passaged fewer than six times in vitro. To assess infection, mice are sacrificed at 14–17 days post-challenge, and specimens derived from ear, bladder, and tibiotarsal joints are placed in BSKII plus 1.4% gelatin, 13 g/ml amphotericin B, 1.5 g/ml phosphomycin, and 15 g/ml rifampicin, and *borrelia* outgrowth at two or three weeks is quantified by darkfield microscopy. Batches of BSKII are qualified for infection testing by confirming that they supported the growth of 1–5 cells of isolate B31. In some instances seroconversion for protein P39 reactivity is also used to confirm infections (see below). Others have previously shown that mice elicited antibodies to P39 when inoculated with live borreliae by syringe or tick bite, but not with killed borreliae (Simpson, W. J., et al., *J. Clin. Microbiol.* 29:236–243 (1991)).

6(b). Immunoassays

Several immunoassay formats are used to quantify levels of *borrelia*-specific antibodies (ELISA and immunoblot), and to evaluate the functional properties of these antibodies (growth inhibition assay). The ELISA and immunoblot assays are also used to detect and quantify antibodies elicited in response to borrelial infection that react with specific borrelial antigens. Where antibodies to certain borrelial antigens are elicited by infection this is taken as evidence that the borrelial proteins in question are expressed in vivo. Absence of infection-derived antibodies (seroconversion) following borrelial challenge is evidence that infection is prevented or suppressed. The immunoblot assay is also used to ascertain whether antibodies raised against recombinant borrelial antigens recognize a protein of similar size in extracts of whole borreliae. Where the natural protein is of similar, or identical, size in the immunoblot assay to the recombinant version of the same protein, this is taken as evidence that the recombinant protein is the product of a full-length clone of the respective gene.

Enzyme-Linked Immunosorbant Assay (ELISA). The ELISA is used to quantify levels of antibodies reactive with borrelial antigens elicited in response to immunization with these borrelial antigens. Wells of 96 well microtiter plates (Immunlon 4, Dynatech, Chantilly, Va., or equivalent) are coated with antigen by incubating 50 l of 1 g/ml protein antigen solution in a suitable buffer, typically 0.1 M sodium carbonate buffer at pH 9.6. After decanting unbound antigen, additional binding sites are blocked by incubating 100 l of 3% nonfat milk in wash buffer (PBS, 0.2% Tween 20, pH 7.4). After washing, duplicate serial two-fold dilutions of sera in PBS, Tween 20, 1% fetal bovine serum, are incubated for 1 hr, removed, wells are washed three times, and incubated with horseradish peroxidase-conjugated goat anti-mouse IgG. After three washes, bound antibodies are detected with $H_2O_2$ and 2,2'-azino-di-(3-ethylbenzthiazoline sulfonate) (Schwan, T. G., et al., *Proc. Natl. Acad Sci. USA* 92:2909–2913 (1985)) (ABTS®, Kirkegaard & Perry Labs., Gaithersburg, Md.) and $A_{405}$ is quantified with a Molecular Devices, Corp. (Menlo Park, Calif.) Vmax™ plate reader. IgG levels twice the background level in serum from naive mice are assigned the minimum titer of 1:100.

6(c). In Vitro Growth Inhibition Assay

Unlike other bacteria, borreliae can be killed by the binding of specific antibodies to their surface antigens. The mechanism for this in vitro killing or growth-inhibitory effect is not known, but can occur in the absence of serum complement, or other immune effector functions. Antibodies elicited in animals receiving immunizations with specific borrelial antigens that result in protection from borrelial challenge usually will directly kill borreliae in vitro. Thus, the in vitro growth inhibition assay also has a high predictive value for the protective potency of the borrelial antibodies, although exceptions, such as antibodies against OspC which are weak at in vitro growth inhibition, have been observed.

Also, this assay can be used to evaluate the serologic conservation of epitope binding protective antibodies. A microwell antibody titration assay (Sadziene, A., et al., *J. Infect. Dis.* 167:165–172 (1993)) is used to evaluate the growth inhibition (GI) properties of antisera against recombinant borrelial antigens against the homologous B31 isolate, and against various strains of *borrelia*. Briefly, $10^5$ *borrelia* in 100 l BSKII are added to serial two-fold dilutions of sera in 100 l BSKII in 96-well plates, and the plates are covered and incubated at 34° C. in a 5% $O_2$/5% $CO_2$/90% $N_2$ gas mixture for 72 h prior to quantification of *borrelia* growth by darkfield microscopy.

6(d). Sodiumdodecylsulfate-Polyacrylamide Gel Electrophoresis (SDS-PAGE) and Immunoblotting Using a single well format, total borrelial protein extracts, recombinant borrelial antigen, or recombinant P39 samples (2 g of purified protein, or more for total borrelial extracts) are boiled in SDS/2-ME sample buffer before electrophoresis through 3% acrylamide stacking gels, and resolving gels of higher acrylamide concentration, typically 10–15% acrylamide monomer. Gels are electro-blotted to nitrocellulose membranes and lanes are probed with dilutions of antibody to be tested for reactivity with specific borrelial antigens, followed by the appropriate secondary antibody-enzyme (horseradish peroxidase) conjugate. When it is desirable to confirm that the protein had transferred following electro-blotting, membranes are stained with Ponceau S. Immunoblot signals from bound antibodies are detected on x-ray film as chemiluminescence using ECL™ reagents (Amersham Corp., Arlington Heights, Ill.).

6(e). Detection of *Borrelia* mRNA Expression

Northern blot analysis is carried out using methods described by, among others, Sambrook et al., supra. to detect the expression of the *B. burgdorferi* nucleotide sequences of the present invention in animal tissues. A cDNA probe containing an entire nucleotide sequence shown in Table 1 is labeled with $^{32}P$ using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to detect the expression of *Borrelia* mRNA in an animal tissue sample.

Animal tissues, such as blood or spinal fluid, are examined with the labeled probe using ExpressHyb™ hybridization solution (Clontech) according to manufacturer's protocol number PT1190-1. Following hybridization and washing, the blots are mounted and exposed to film at –70 C overnight, and films developed according to standard procedures.

The disclosure of all publications (including patents, patent applications, journal articles, laboratory manuals, books, or other documents) cited herein are hereby incorporated by reference in their entireties.

Thee present invention is not to be limited in scope by the specific embodiments described herein, which are intended as single illustrations of individual aspects of the invention. Functionally equivalent methods and components are within the scope of the invention, in addition to those shown and described herein and will become apparant to those skilled in the art from the foregoing description and accompanying drawings. Such modifications are intended to fall within the scope of the appended claims.

Provisional Application Ser. No. 60/057,483 filed 3 Sep. 1997 is incorporated by reference herein in its entirety.

TABLE 1

Nucleotide and Amino Acid Sequences.

f101.aa (SEQ ID NO:1)
MSKIFLLFNAGFFFLKIIYVFSYPEIKNFSRQDPVFSDLKIKVLKYNKKQHIPLFFYSYKVKKGDTFFKI
ANKINGWQSGIATINLLDSPAVSVGQEILIPSKKGVFVFDSKDYRFNNLLLATRDLAKAEKVKIKRN
DRVYEFYFFDFVKNPDFGLFSGTELLFFLNANFIFPLKKFIVSSDFGFRNDPFTGNKSFHTGIDLAAPM
NAEVYLLLLE t101.aa (SEQ ID NO:2)
SYPEIKNFSRQDPVFSDLKIKVLKYNKKQHIPLFFYSYKVKKGDTFFKIANKINGWQSGIATINLLDSP
AVSVGQEILIPSKKGVFVFDSKDYRFNNLLLATRDLAKAEKVKIKRNDRVYEFYFFDFVKNPDFGLF
SGTELLFFLNANFIFPLKKFIVSSDFGFRNDPFTGNKSFHTGIDLAAPMNAEVYLLLLE f101.nt (SEQ ID NO:3)
ATGAGTAAAATTTTTTATTATTTAATGCAGGTTTCTTTTTTTTAAAAATAATTTATGTTTTTCT
TATCCAGAAATAAAAAATTTCTCAAGGCAAGATCCTGTTTTTTCTGATCTTAAAATTAAAGTTTT
AAAATATAACAAAAAACAACATATTCCTCTGTTTTTTTACTCATATAAAGTTAAAAAAGGGGAT
ACTTTTTTTAAAATTGCCAATAAAATAAATGGATGGCAGTCCGGCATTGCTACTATTAATTTATT
AGATTCTCCTGCTGTGAGTGTTGGGCAAGAGATTCTTATTCCCAGTAAAAAAGGAGTTTTTGTT
TTTGATAGTAAAGATTATAGATTTAATAATTTGCTTTTAGCAACAAGGGATCTTGCTAAAGCTG
AAAAGGTAAAAATTAAAAGGAACGACAGAGTTTATGAATTTTATTTTTTTGATTTTGTTAAGAA
TCCAGATTTTGGACTTTTTTCAGGCACAGAATTGCTTTTTTTCTTAAATGCCAATTTTATTTTTCC
TTTAAAAAAATTTATTGTTAGTTCTGATTTTGGATTTAGAAATGACCCTTTCACTGGCAACAAAA
GTTTCCATACAGGAATAGATCTTGCAGCTCCAATGAATGCTGAAGTGTATCTTCTTCTTCTGGA
ATAG t101.nt (SEQ ID NO:4)
TCTTATCCAGAAATAAAAAATTTCTCAAGGCAAGATCCTGTTTTTTCTGATCTTAAAATTAAAGT
TTTAAAATATAACAAAAAACAACATATTCCTCTGTTTTTTTACTCATATAAAGTTAAAAAAGGG
GATACTTTTTTTAAAATTGCCAATAAAATAAATGGATGGCAGTCCGGCATTGCTACTATTAATT
TATTAGATTCTCCTGCTGTGAGTGTTGGGCAAGAGATTCTTATTCCCAGTAAAAAAGGAGTTTT
TGTTTTTGATAGTAAAGATTATAGATTTAATAATTTGCTTTTAGCAACAAGGGATCTTGCTAAA
GCTGAAAAGGTAAAAATTAAAAGGAACGACAGAGTTTATGAATTTTATTTTTTTGATTTTGTTA
AGAATCCAGATTTTGGACTTTTTTCAGGCACAGAATTGCTTTTTTTCTTAAATGCCAATTTTATT
TTTCCTTTAAAAAAATTTATTGTTAGTTCTGATTTTGGATTTAGAAATGACCCTTTCACTGGCAA
CAAAAGTTTCCATACAGGAATAGATCTTGCAGCTCCAATGAATGCTGAAGTGTATCTTCTTCTT

TABLE 1-continued

Nucleotide and Amino Acid Sequences.

CTGGAATAG f11.aa (SEQ ID NO:5)
VKKYIKTIFLISMVYFYCCTTIKINHDYETDFKVLESPSKYINIDVIKATNEYIYIQITNNSLDVVKINW
QNTSLNNDKIVLKKEDLTINNETGYKNKYREFFIGPKTSFKFKVYPLKIHSKNKNSNNLSSTIKYPSIF
KLNITKVGIEAKKTINVLITRTTKINITNK t11.aa (SEQ ID NO:6)
CCTTIKINHDYETDFKVLESPSKYINIDVIKATNEYIYIQITNNSLDVVKINWQNTSLNNDKIVLKKED
LTINNETGYKNKYREFFIGPKTSFKFKVYPLKIHSKNKNSNNLSSTIKYPSIFKLNITKVGIEAKKTINV
LITRTTKINITNK f11.nt (SEQ ID NO:7)
GTGGAAAAATTTCTTTTATTCCAGGAAATGAAAATATTGCAGATCTTGGTTTTCATAAAACTAA
GTAGAAATATTGTCAAAAAATACATAAAAACAATATTTCTGATTTCAATGGTTTATTTTTATTGT
TGTACGACAATAAAAATAAACCATGATTATGAAACTGATTTTAAAGTTCTAGAATCTCCCTCTA
AATACATCAATATAGATGTAATTAAAGCTACAAATGAATATATTTATATTCAAATTACAAACAA
TAGCTTAGACGTAGTAAAAATAAATTGGCAAAACACTAGTCTTAACAACGATAAGATCGTCTTA
AAAAAAGAAGATCTTACAATAAACAATGAAACAGGGTATAAAAATAAATACAGAGAGTTTTTT
ATTGGTCCTAAAACTTCATTTAAATTTAAAGTATATCCACTAAAAATTCATTCTAAAAACAAAA
ATAGCAATAACTTAAGCTCAACTATTAAATATCCGTCTATTTTTAAGCTCAACATAACAAAAGT
AGGAATTGAAGCAAAAAAAACAATAAATGTTTTAATAACAAGAACTACAAAAATTAATATTAC
TAATAAATGA t11.nt (SEQ ID NO:8)
TGTTGTACGACAATAAAAATAAACCATGATTATGAAACTGATTTTAAAGTTCTAGAATCTCCCT
CTAAATACATCAATATAGATGTAATTAAAGCTACAAATGAATATATTTATATTCAAATTACAAA
CAATAGCTTAGACGTAGTAAAAATAAATTGGCAAAACACTAGTCTTAACAACGATAAGATCGTC
TTAAAAAAAGAAGATCTTACAATAAACAATGAAACAGGGTATAAAAATAAATACAGAGAGTTT
TTTATTGGTCCTAAAACTTCATTTAAATTTAAAGTATATCCACTAAAAATTCATTCTAAAAACAA
AAATAGCAATAACTTAAGCTCAACTATTAAATATCCGTCTATTTTTAAGCTCAACATAACAAAA
GTAGGAATTGAAGCAAAAAAAACAATAAATGTTTTAATAACAAGAACTACAAAAATTAATATT
ACTAATAAATGA f12.aa (SEQ ID NO:9)
MREFLYRNVFKKSFIVFLIFLTFSNAIFAQTIDDENSKKRDKLTLSQKSYLRELELSTDEDLKKWALK
EGLKETDVSKIRELLLKKFGIDPELFIKGKGLAGSGRYKIIIETADNLENFTYGLTKDESIIFEGRVNIL
VEDIKENKKHNIKGDRIVLNKNSKKLYAIGNVEYILDMDTNEKLYFYGNEFLVDFDSQNFLLKNGIL
QKKMQKNQIDHILSFGGKVLKKIDNDVTILEQAFATTSKIPEPYYSIKASKIWALPSGDFGFLNAIFY
MGRVPVFYIPFFFRPGDSLFFNPSLGLNPRKGFSVFNTVYLFGNKSSSEDSSFLDFDFNSVYNSGKKP
YIRNGYLTYFFAENLAPSVNKDYVKLIFDIYANLGFYSGIDFNLGNTLGHFKTLEGNFGLGFTRNVY
SYDGGYYPFDNRTLKQSLFSFSNLNKGDVFGFEVPFRYLFKFKTEFLLSDALFSVVLEHYSDPYVNID
FRDRIESATFFSLLNLDKDSVKEQTSISTFDWNLSSFYKRTFNDGSILDYKLNNLGLSFKLSGYENLY
VKSPLEKPKDVNDPTRKWFYLERIYAPYIDLNFQKDLYNNQWTFPADTKEMIMRPEIKNLEDKDND
KKSVKEKNTKKTTELTKDLYIPPEPITLKNIDQSDSFFIRFGINPYLRNNVFFDNYGITSPKDFNYEIKN
YLFDIKNKTDIKIHADFYNRLITFENLLYLNTIEYSPLNKDFKVEDKDKKSEHSIINQINLNLLPFTIYP
LFSRSTLKFENKATLYSFNKKYDSDVKSLVNKNSSIFLSDPETFYQSLTASLIYDYDYFTTELSGELK
NSFEDIKASSELKLSLDFPYLLQEAGIGIKYYKKFKEDAMKNSGISAVQSPLEPQKPSSPYKNLEMSP
ALYYKIEPRYLDYFKFSFLVAYDPLINRVSELSFKLNVFDFQFLFAMKDDFEYNYDPLKGDFSKIGTT
TKLVPYSLDSSYKKELYVLTFFFDNKLSFTLGVDVGWKINLQKFTDNELRSALTLKFKYTEFLEIYFST
LSNTKIFKYFKGYMDQIGLEPVNFFVDLSKSFNFFNSQDRKDSLFKIKKFSSGFKFNFYDWKFVGE
YNLEPDLLRGSDGIYSPIWRNNFTIYISWNFFAPIKASFENNKDTNYEFIINRKTKK t12.aa (SEQ ID NO:10)
IFAQTIDDENSKKRDKLTLSQKSYLRELELSTDEDLKKWALKEGLKETDVSKIRELLLKKFGIDPELFI
KGKGLAGSGRYKIIIETADNLENFTYGLTKDESIIFEGRVNILVEDIKENKKHNIKGDRIVLNKNSKKL
YAIGNVEYILDMDTNEIKLYFYGNEFLVDFDSQNFLLKNGILQKKMQKNQIDHILSFGGKVLKKIDN
DVTILEQAFATTSKIPEPYYSIKASKIWALPSGDFGFLNAIFYMGRVPVFYIPFFFRPGDSLFFNPSLGL
NPRKGPSVFNTVYLFGNKSSSEDSSFLDFDFNSVYNSGKKPYIRNGYLTYFFAENLAPSVNKDYVKL
IFDIYANLGFYSGIDFNLGNTLGHFKTLEGNFGLGFTRNVYSYDGGYYPFDNRTLKQSLFSFSNLNK
GDVFGFEVPFRYLFKFKTEFLLSDALFSVVLEHYSDPYVNIDFRDRIESATFFSLLNLDKDSVKEQTSI
STFDWNLSSFYKRTFNDGSILDYKLNNLGLSFKLSGYENLYVKSPLEKPKDVNDPTRKWFYLERIYA
PYIDLNFQKDLYNNQWTFPADTKEMIMRPEIKNLEDKDNDKKSVKEKNTKKTTELTKDLYIPPEPIT
LKNIDQSDSFFIRFGINPYLRNNVFFDNYGITSPKDFNYEIKNYLFDIKNKTDIKIHADFYNRLITFENL
LYLNTIEYSPLNKDFKVEDKDKKSEHSIINQINLNLLPFIRYPLFSRSTLKFENKATLYSFNKKYDSDV
KSLVNKNSSIFLSDPETFYQSLTASLIYDYDYFTTELSGELKNSFEDIKASSELKLSLDFPYLLQEAGIG
IKYYKKFKEDAMKNSGISAVQSPLEPQKPSSPYKNLEMSPALYYKIEPRYLDYFKFSFLVAYDPLINR
VSELSFKLNVFDFQFLFAMKDDFEYNYDPLKGDFSKIGTTTKLVPYSLDSSYKKELYVLTFFDNKLS
FTLGVDVGWKINLQKFTDNELRSALTLKFKYTEFLEIYFSTLSINTKTFKYFKGYMDQIGLEPVNFFV
DLSKSFNFFNSQDRKDSLFKIKKFSSGFKFNFYDWKFVGEYNLEPDLLRGSDGIYSPIWRNNFTIYIS
WNFFAPIKASFENNKDTNYEFIINRKTKK f12.nt (SEQ ID NO:11)
ATGCGAGAATTCCTATACAGGAATGTTTTAAAAAATCTTTTATAGTATTTTTAATTTTTTTAAC
ATTTTCTAATGCAATTTTTGCCCAGACTATAGATGATGAAAATTCTAAAAAAAGGGATAAGCTA
ACTTTAAGTCAAAAATCTTATTTAAGAGAACTTGAGCTTTCAACCGATGAGGATTTAAAAAAAT
GGGCCTTAAAAGAGGGTTTAAAAGAAACAGATGTTTCAAAAATACGAGAATTGCTTTTAAAA

TABLE 1-continued

Nucleotide and Amino Acid Sequences.

AGTTTGGAATAGATCCTGAGCTTTTTATCAAAGGAAAGGGACTTGCCGGATCTGGTAGATATAA
AATAATCATTGAAACTGCAGATAATCTTGAAAATTTCACTTATGGACTTACTAAAGATGAAAGT
ATTATTTTTGAAGGAAGAGTTAATATCTTGGTTGAAGATATTAAAGAAAATAAAAAGCACAATA
TTAAAGGCGACAGAATAGTCCTTAATAAGAACTCTAAAAAACTTTATGCTATTGGAAATGTTGA
ATATATTCTTGATATGGATACCAATGAAAAGCTTTATTTTTATGGCAATGAATTTCTTGTCGATT
TTGATTCTCAAAATTTTTTATTAAAAAATGGTATTCTTCAAAAAAAAATGCAAAAAAATCAAAT
AGATCATATTCTTTCGTTTGGAGGAAAGGTTTTAAAAAAGATAGACAATGATGTTACCATTTTG
GAACAAGCTTTTGCAACAACTAGTAAAATTCCAGAGCCTTACTATTCAATCAAGGCTTCTAAAA
TATGGGCATTGCCCTCGGGAGATTTTGGGTTTTTAAATGCCATATTTTACATGGGAAGAGTTCC
AGTATTTTATATTCCTTTTTTTTCCAGACCGGGAGATAGTTTGTTTTTTAATCCATCTTTAGGTCT
AAATCCACGAAAAGGTTTTTCTGTTTTTAATACCGTTTATCTTTTTGGTAATAAATCTTCAAGTG
AAGATTCTTCTTTTTTGGATTTTGATTTCAATTCTGTTTATAATTCGGGTAAAAAAACCTTATATA
AGAAATGGATATTTAACTTATTTTTTTGCAGAAAATTTAGCACCCAGTGTTAATAAAGATTATG
TTAAGCTTATTTTTGACATTTATGCTAATCTGGGATTTTATTCTGGAATTGATTTTAATTTGGGC
AATACTTTGGGGCATTTTAAAACTTTGGAAGGAAATTTTGGATTGGGTTTTACCAGGAATGTTT
ATAGTTACGATGGAGGATATTATCCTTTTGATAATAGGACTTTAAAACAATCTCTTTTTAGTTTT
TCCAATCTTAACAAAGGAGATGTATTTGGGTTTGAAGTTCCTTTTAGATATTTATTTAAATTTAA
AACAGAATTTCTTTTAAGTGATGCACTTTTCTCGGTTGTTTTAGAGCACTATTCTGACCCGTATG
TTAATATTGATTTTAGAGATAGGATAGAAAGTGCTACATTTTTTTCTCTTTTAAATTTAGATAAA
GATTCGGTTAAAGAGCAAACTAGCATTAGCACTTTTGATTGGAATTTATCTTCTTTTTATAAGCG
AACATTTAATGACGGTTCGATTTTAGATTATAAATTAAATAATTTAGGTTTAAGTTTTAAATTGT
CGGGCTATGAAAATCTTTATGTTAAATCTCCTTTAGAGAAACCAAAAGATGTTAATGATCCTAC
AAGAAAATGGTTTTATTTGGAGAGAATTTATGCTCCATATATTGATTTGAATTTTCAAAAAGAT
CTTTACAATAACCAATGGACATTTCCAGCTGATACTAAAGAAATGATAATGCGCCCAGAAATTA
AAAATCTAGAAGATAAAGATAATGATAAAAAGAGTGTGAAGGAGAAAAATACTAAAAAAACA
ACAGAATTAACCAAAGATTTATATATTCCTCCAGAACCAATTACTTTAAAAAAATATTGATCAAT
CCGATTCTTTTTTTATTAGGTTTGGCATTAATCCTTATTTAAGAAATAATGTTTTTTTTTGATAATT
ATGGCATAACAAGTCCAAAGGACTTTAATTATGAAATAAAAAATTATTTATTTGATATAAAAAA
TAAAACGGATATAAAAATTCATGCTGATTTTTACAATCGTTTAATTACTTTTGAAAATTTATTAT
ATCTTAATACTATTGAGTATAGTCCTTTAAATAAAGATTTTAAAGTTGAAGATAAAGATAAAAA
AAGTGAGCACTCTATTATTAACCAAATAAATTTAAACTTGCTTCCTTTTATTAGATATCCTTTAT
TTTCTAGAAGTACTTTAAAGTTTGAAAATAAGGCTACTTTATATTCATTTAATAAAAATATGA
TTCTGATGTAAAATCTTTGGTTAATAAGAATAGTAGTATTTTTTATCTGATCCGGAAACTTTTT
ATCAAAGTTTAACAGCCTCTTTAATTTATGATTATGATTATTTTACTACTGAGCTTTCAGGTGAA
TTAAAAAATAGTTTTGAAGATATTAAAGCTTCTTCTGAGCTTAAACTTTCTTTAGATTTTCCTTA
TTTGCTACAAGAAGCTGGGATTGGAATTAAATATTATAAAAAGTTTAAAGAAGATGCTATGAA
AAACTCTGGAATTTCTGCTGTTCAAAGTCCTTTGGAGCCTCAAAAACCATCATCGCCCTTATAAA
AATTTAGAAATGTCTCCTGCTTTGTATTATAAAATTGAGCCGAGATATTTGGATTATTTTAAATT
TAGTTTTTTAGTCGCCTATGATCCTTTGATAAATAGAGTTTCTGAACTTTCTTTTAAGCTTAATG
TTTTTGATTTTCAATTTTTGTTTGCTATGAAAGACGACTTTGAATATAATTATGATCCTTTAAAA
GGAGATTTTTCCAAGATTGGTACTACAACCAAACTTGTTCCATATTCTTTAGATTCTAGTTACAA
AAAGGAATTGTACGTTTTAACTTTTTTTGACAATAAGCTTTCTTTTACCTTGGGGGTAGATGTTG
GTTGGAAAATAAATTTGCAGAAATTTACGGATAATGAACTTCGATCTGCATTGACTTTGAAGTT
TAAATATACAGAATTTTTAGAAATTTACTTTTCTACTTTATCTATTAATACTAAGACTTTTAAAT
ATTTTAAAGGGTATATGGACCAAATTGGTCTAGAACCTGTTAATTTCTTTGTTGATTATCAAAA
TCTTTCAATTTCTTTAATTCTCAAGACAGAAAAGATTCACTTTTTAAAATTAAAAAATTTTCATC
AGGCTTTAAATTCAATTTTTATGATTGGAAATTTGTTGGAGAATATAATTTAGAACCAGATTTA
TTAAGGGGATCTGATGGGATTTATTCTCCTATTTGGAGAAATAATTTTACAATTTATATTTCTTG
GAACTTTTTTGCTCCTATAAAAGCGTCATTTGAAAACAACAAAGATACAAACTACGAGTTTATT
ATTAATAGAAAAACAAAAAAATAA t12.nt (SEQ ID NO:12)
ATTTTTTGCCCAGACTATAGATGATGAAAATTCTAAAAAAAGGGATAAGCTAACTTTAAGTCAAA
AATCTTATTTAAGAGAACTTGAGCTTTCAACCGATGAGGATTTAAAAAAATGGGCCTTAAAAGA
GGGTTTAAAAGAAACAGATGTTTCAAAAATACGAGAATTGCTTTTAAAAAAGTTTGGAATAGA
TCCTGAGCTTTTTATCAAAGGAAAGGGACTTGCCGGATCTGGTAGATATAAAATAATCATTGAA
ACTGCAGATAATCTTGAAAATTTCACTTATGGACTTACTAAAGATGAAAGTATTATTTTTGAAG
GAAGAGTTAATATCTTGGTTGAAGATATTAAAGAAAATAAAAAGCACAATATTAAAGGCGACA
GAATAGTCCTTAATAAGAACTCTAAAAAACTTTATGCTATTGGAAATGTTGAATATATTCTTGA
TATGGATACCAATGAAAAGCTTTATTTTTATGGCAATGAATTTCTTGTCGATTTTGATTCTCAAA
ATTTTTTATTAAAAAATGGTATTCTTCAAAAAAAAATGCAAAAAAATCAAATAGATCATATTCT
TTCGTTTGGAGGAAAGGTTTTAAAAAAGATAGACAATGATGTTACCATTTTGGAACAAGCTTTT
GCAACAACTAGTAAAATTCCAGAGCCTTACTATTCAATCAAGGCTTCTAAAATATGGGCATTGC
CCTCGGGAGATTTTGGGTTTTTAAATGCCATATTTTACATGGGAAGAGTTCCAGTATTTTTATATT
CCTTTTTTTTCAGACCGGGAGATAGTTTGTTTTTTAATCCATCTTTAGGTCTAAATCCACGAAAA
GGTTTTTCTGTTTTTAATACCGTTTATCTTTTTGGTAATAAATCTTCAAGTGAAGATTCTTCTTT
TTTGGATTTTGATTTCAATTCTGTTTATAATTCGGGTAAAAAACCTTATATAAGAAATGGATATT
TAACTTATTTTTTTGCAGAAAATTTAGCACCCAGTGTTAATAAAGATTATGTTAAGCTTATTTTT
GACATTTATGCTAATCTGGGATTTTATTCTGGAATTGATTTTAATTTGGGCAATACTTTGGGGCA
TTTTAAAACTTTGGAAGGAAATTTTGGATTGGGTTTTACCAGGAATGTTTATAGTTACGATGGA
GGATATTATCCTTTTGATAATAGGACTTTAAAACAATCTCTTTTTAGTTTTTCCAATCTTAACAA
AGGAGATGTATTTGGGTTTGAAGTTCCTTTTAGATATTTATTTAAATTTAAAACAGAATTTCTTT
AAGTGATGCACTTTTCTCGGTTGTTTTAGAGCACTATTCTGACCCGTATGTTAATATTGATTTT
AGAGATAGGATAGAAAGTGCTACATTTTTTTCTCTTTTAAATTTAGATAAAGATTCGGTTAAAG
AGCAAACTAGCATTAGCACTTTTGATTGGAATTTATCTTCTTTTTATAAGCGAACATTTAATGAC
GGTTCGATTTTAGATTATAAATTAAATAATTTAGGTTTAAGTTTTAAATTGTCGGGCTATGAAA
ATCTTTATGTTAAATCTCCTTTAGAGAAACCAAAAGATGTTAATGATCCTACAAGAAAATGGTT

TABLE 1-continued
Nucleotide and Amino Acid Sequences.

```
TTATTTGGAGAGAATTTATGCTCCATATATTGATTTGAATTTTCAAAAAGATCTTTACAATAACC
AATGGACATTTCCAGCTGATACTAAAGAAATGATAATGCGCCCAGAAATTAAAAATCTAGAAG
ATAAAGATAATGATAAAAAGAGTGTGAAGGAGAAAAATACTAAAAAAACAACAGAATTAACCA
AAGATTTATATATTCCTCCAGAACCAATTACTTTAAAAAATATTGATCAATCCGATTCTTTTTTT
ATTAGGTTTGGCATTAATCCTTATTTAAGAAATAATGTTTTTTTTGATAATTATGGCATAACAAG
TCCAAAGGACTTTAATTATGAAATAAAAAATTATTTATTTGATATAAAAAATAAAACGGATATA
AAAATTCATGCTGATTTTTACAATCGTTTAATTACTTTTGAAAATTTATTATATCTTAATACTAT
TGAGTATAGTCCTTTAAATAAAGATTAAAGTTGAAGATAAAGATAAAAAAAGTGAGCACTCT
ATTATTAACCAAATAAATTTAAACTTGCTTCCTTTTATTAGATATCCTTTATTTTCTAGAAGTAC
TTTAAAGTTTGAAAATAAGGCTACTTATATTCATTTAATAAAAAATATGATTCTGATGTAAAA
TCTTTGGTTAATAAGAATAGTAGTATTTTTTATCTGATCCGGAAACTTTTTATCAAAGTTTAAC
AGCCTCTTTAATTTATGATTATGATTATTTTACTACTGAGCTTTCAGGTGAATTAAAAAATAGTT
TTGAAGATATTAAAGCTTCTTCTGAGCTTAAACTTTCTTTAGATTTTCCTTATTTGCTACAAGAA
GCTGGGATTGGAATTAAATATTATAAAAAGTTTAAAGAAGATGCTATGAAAAACTCTGGAATTT
CTGCTGTTCAAAGTCCTTTGGAGCCTCAAAAACCATCATCGCCTTATAAAAATTTAGAAATGTC
TCCTGCTTTGTATTATAAAATTGAGCCGAGATATTTGGATTATTTTAAATTTAGTTTTTTAGTCG
CCTATGATCCTTTGATAAATAGAGTTTCTGAACTTTCTTTTAAGCTTAATGTTTTTGATTTTCAA
TTTTTGTTTGCTATGAAAGACGACTTTGAATATAATTATGATCCTTTAAAAGGAGATTTTTCCAA
GATTGGTACTACAACCAAACTTGTTCCATATTCTTTAGATTCTAGTTACAAAAAGGAATTGTAC
GTTTTAACTTTTTTTGACAATAAGCTTTCTTTTACCTTGGGGGTAGATGTTGGTTGGAAAATAAA
TTTGCAGAAATTTACGGATAATGAACTTCGATCTGCATTGACTTTGAAGTTTAAATATACAGAA
TTTTTAGAAATTTACTTTTCTACTTTATCTATTAATACTAAGACTTTTAAATATTTTAAAGGGTA
TATGGACCAAATTGGTCTAGAACCTGTTAATTTCTTTGTTGATTTATCAAAATCTTTCAATTTCT
TTAATTCTCAAGACAGAAAAGATTCACTTTTTAAAATTAAAAAATTTTCATCAGGCTTTAAATTC
AATTTTTATGATTGGAAATTTGTTGGAGAATATAATTTAGAACCAGATTTATTAAGGGGATCTG
ATGGGATTTATTCTCCTATTTGGAGAAATAATTTTACAATTTATATTTCTTGGAACTTTTTTGCT
CCTATAAAAGCGTCATTTGAAAACAACAAAGATACAAACTACGAGTTTATTATTAATAGAAAAA
CAAAAAAATAA f129.aa (SEQ ID NO:13)
MTKKLFVRVLIFLISNNYAFAKDTIKDLFFIQDILIKKEKYSEVLNNASLEGIIEIEHNGPYIKDHDSEV
KLILKENGYRRNFNFFNLLNTSNIIKSLSLFDSRPKNIKENEIILLETKMIKENPYKRYKDDDDFELKLS
VTRKNNQIYLILDFNFLFDQRKTFPSIYIKEEDVSTIINSTMKLQDSSFLSPQAS t129.aa (SEQ ID NO:14)
KDTIKDLFFIQDILIKKEKYSEVLNNASLEGIIEIEHNGPYIKDHDSEVKLILKENGYRRNFNFFNLLNT
SNIIKSLSLFDSRPKNIKENEIILLETKMIKENPYKRYKDDDDFELKLSVTRKNNQIYLILDFNFLFDQR
KTFPSIYIKEEDVSTIINSFMKLQDSSFLSPQAS f129.nt (SEQ ID NO:15)
ATGACAAAAAAATTGTTTGTGAGGGTATTAATCTTTTTAATATCCAATAATTATGCTTTTGCAAA
AGACACAATCAAAGATTTGTTCTTTATACAAGATATACTAATAAAAAAAGAGAAATATTCCGAG
GTTCTAAATAATGCAAGCCTTGAAGGCATTATTGAAATTGAACATAACGGACCATACATTAAAG
ATCACGATTCAGAAGTTAAACTTATCCTAAAAGAAAACGGATATAGAAGAAATTTCAACTTTTT
TAATCTTTTAAATACTAGTAATATAATCAAAAGTCTAAGCTTATTTGACAGCAGACCAAAAAAC
ATTAAAGAAAATGAAATCATATTATTAGAGACAAAAATGATTAAAGAAAATCCCTATAAACGA
TACAAAGACGATGATGATTTTGAATTAAAACTAAGTGTAACTCGAAAAAATAATCAAATTTATT
TAATTCTTGATTTCAATTTCCTATTTGATCAAAGAAAAACGTTTCCATCAATTTACATCAAAGAA
GAAGATGTATCAACAATAATAAACAGCTTCATGAAACTACAAGATTCAAGCTTTTTATCTCCTC
AAGCTTCTTAA t129.nt (SEQ ID NO:16)
AAAGACACAATCAAAGATTTGTTCTTTATACAAGATATACTAATAAAAAAAGAGAAATATTCCG
AGGTTCTAAATAATGCAAGCCTTGAAGGCATTATTGAAATTGAACATAACGGACCATACATTAA
AGATCACGATTCAGAAGTTAAACTTATCCTAAAAGAAAACGGATATAGAAGAAATTTCAACTTT
TTTAATCTTTTAAATACTAGTAATATAATCAAAAGTCTAAGCTTATTTGACAGCAGACCAAAAA
ACATTAAAGAAAATGAAATCATATTATTAGAGACAAAAATGATTAAAGAAAATCCCTATAAAC
GATACAAAGACGATGATGATTTTGAATTAAAACTAAGTGTAACTCGAAAAAATAATCAAATTTA
TTTAATTCTTGATTTCAATTTCCTATTTGATCAAAGAAAAACGTTTCCATCAATTTACATCAAAG
AAGAAGATGTATCAACAATAATAAACAGCTTCATGAAACTACAAGATTCAAGCTTTTTATCTCC
TCAAGCTTCTTAA f142.aa (SEQ ID NO:17)
MDKISILYTLINIIIMLILISIVYLCKRKNVSFTKRVFIALAIGIVFGMTIQYFYGTNSEITNETINWISILG
DGYVRLLKMIIIPLIITSIISAIIKLTNSKDVGKMSLLVILTLVFTAGIAAIIGIFTALALGLTAEGLQAGTI
EILQSEKLQKGLEILNQTTITKKITDLIPQNIFEDFAGLRKNSTIGVVIFSAIIGIAALKTSIKKPESIEFFK
KIILTLQDIILGVVTLILKLTPYAILALMTKITATSEIKSIIKLGETVIASYIAIGLTFLMHMTLIAINKLNP
ITFIKKIFPALSFAFISRSSAATIPINIEIQTKNLGVSEGIANLSSSFGTSIGQNGCAALHPAMLAIMIAPT
QGINPTDISFILTLIGLIIITSFGAAGAGGGATTASLMVLSAMNFPVGLVGLVISVEPIIDMGRTAVNVG
GSMLAGVISAKQLKQFNHNIYNQKELVNK t142.aa (SEQ ID NO:18)
CKRKNVSFTKRVFIALAIGIVFGMTIQYFYGTNSEITNETINWISILGDGYVRLLKMIIIPLIITSIISAIIK
LTNSKDVGKMSLLVILTLVFTAGIAAIIGIFTALALGLTAEGLQAGTIEILQSEKLQKGLEILNQTTITK
KITDLIPQNIFEDFAGLRKNSTIGVVIFSAIIGIAALKTSIKKPESIEFFKKIILTLQDIILGVVTLILKLTPY
AILALMTKITATSEIKSIIKLGEFVIASYIAIGLTFLMHMTLIAINKLNPITFIKKIFPALSFAFISRSSAATI
PINIEIQTKNLGVSEGIANLSSSFGTSIGQNGCAALHPAMLAIMIAPTQGINPTDISFILTLIGLIIITSFGA
```

TABLE 1-continued

Nucleotide and Amino Acid Sequences.

AGAGGGATTASLMVLSAMNFPVGLVGLVISVEPIIDMGRTAVNVGGSMLAGVISAKQLKQFNHNIY
NQKELVNK f142.nt (SEQ ID NO:19)
TAAGAGGTAATAATGGATAAAATAAGTATATTATATACATTAATCAATATTATAATAATGCTTA
TTCTAATAAGCATAGTTTATCTTTGTAAAAGAAAAAATGTTTCTTTTACAAAAAGAGTGTTTAT
AGCGTTAGCAATCGGAATAGTATTTGGAATGACCATTCAATATTTTTATGGAACAAATTCAGAA
ATAACAAACGAAACTATAAATTGGATAAGTATTTTGGGCGATGGATACGTAAGGCTCCTTAAAA
TGATTATAATCCCCTTAATAATAACATCAATAATCTCTGCAATAATAAAACTAACCAATAGTAA
AGATGTTGGGAAAATGAGCCTACTTGTAATATTAACACTAGTATTTACAGCAGGTATTGCTGCC
ATAATTGGCATTTTCACTGCTTTAGCATTGGGATTAACAGCCGAAGGACTACAAGCGGGAACCA
TCGAAATTTTACAAAGTGAAAAATTGCAAAAAGGCCTTGAAATATTAAATCAAACAACAATCAC
AAAAAAAAATCACAGATCTTATTCCACAAAATATATTTGAAGATTTTGCAGGGCTTAGAAAAAAC
TCAACCATCGGGGTCGTGATATTTTCAGCTATCATAGGAATAGCCGCCCTTAAAACATCTATCA
AAAAGCCAGAATCAATAGAATTTTTTAAAAAAAATAATATTAACACTCCAAGACATAATATTAGG
TGTAGTAACTTTGATTTTAAAACTAACGCCTTATGCTATATTAGCTTTAATGACAAAAATTACAG
CAACCAGCGAAATCAAAAGCATAATAAAGCTTGGAGAATTTGTAATTGCTTCCTACATTGCCAT
AGGTCTTACATTTCTTATGCATATGACATTAATTGCAATAAATAAATTAAACCCAATTACTTTTA
TAAAAAAAATATTCCCAGCACTATCATTTGCATTCATATCTAGGTCGAGTGCTGCAACCATACC
CATTAATATAGAAATTCAAACTAAAAATCTGGGAGTAAGCGAAGGAATAGCAAATTTATCAAG
CTCCTTTGGAACATCAATTGGGCAAAATGGTTGTGCAGCACTACACCCCGCTATGCTTGCAATA
ATGATAGCACCAACTCAGGGAATAAACCCCACAGATATTTCATTTATACTCACACTTATTGGAT
TAATAATAATAACTTCATTTGGAGCTGCTGGCGCTGGTGGAGGCGCAACAACAGCCTCACTAAT
GGTGCTCTCAGCAATGAACTTTCCAGTGGGATTGGTAGGACTTGTAATATCTGTTGAGCCTATA
ATTGACATGGGAAGAACAGCTGTTAATGTAGGCGGCTCAATGCTTGCAGGCGTTATATCTGCTA
AACAGCTCAAACAATTCAACCATAATATATACAACCAAAAAGAGCTTGTAAACAAATAA t142.nt (SEQ ID NO:20)
TGTAAAAGAAAAAATGTTTCTTTTACAAAAAGAGTGTTTATAGCGTTAGCAATCGGAATAGTAT
TTGGAATGACCATTCAATATTTTTATGGAACAAATTCAGAAATAACAAACGAAACTATAAATTG
GATAAGTATTTTGGGCGATGGATACGTAAGGCTCCTTAAAATGATTATAATCCCCTTAATAATA
ACATCAATAATCTCTGCAATAATAAAACTAACCAATAGTAAAGATGTTGGGAAAATGAGCCTAC
TTGTAATATTAACACTAGTATTTACAGCAGGTATTGCTGCCATAATTGGCATTTTCACTGCTTTA
GCATTGGGATTAACAGCCGAAGGACTACAAGCGGGAACCATCGAAATTTTACAAAGTGAAAAA
TTGCAAAAAGGCCTTGAAATATTAAATCAAACAACAATCACAAAAAAAAATCACAGATCTTATTC
CACAAAATATATTTGAAGATTTTGCAGGGCTTAGAAAAAACTCAACCATCGGGGTCGTGATATT
TTCAGCTATCATAGGAATAGCCGCCCTTAAAACATCTATCAAAAAGCCAGAATCAATAGAATTT
TTTAAAAAAATAATATTAACACTCCAAGACATAATATTAGGTGTAGTAACTTTGATTTTAAAAC
TAACGCCTTATGCTATATTAGCTTTAATGACAAAAATTACAGCAACCAGCGAAATCAAAAGCAT
AATAAAGCTTGGAGAATTTGTAATTGCTTCCTACATTGCCATAGGTCTTACATTTCTTATGCATA
TGACATTAATTGCAATAAATAAATTAAACCCAATTACTTTTATAAAAAAAATATTCCCAGCACT
ATCATTTGCATTCATATCTAGGTCGAGTGCTGCAACCATACCCATTAATATAGAAATTCAAACT
AAAAATCTGGGAGTAAGCGAAGGAATAGCAAATTTATCAAGCTCCTTTGGAACATCAATTGGG
CAAAATGGTTGTGCAGCACTACACCCCGCTATGCTTGCAATAATGATAGCACCAACTCAGGGAA
TAAACCCCACAGATATTTCATTTATACTCACACTTATTGGATTAATAATAATAACTTCATTTGGA
GCTGCTGGCGCTGGTGGAGGCGCAACAACAGCCTCACTAATGGTGCTCTCAGCAATGAACTTTC
CAGTGGGATTGGTAGGACTTGTAATATCTGTTGAGCCTATAATTGACATGGGAAGAACAGCTGT
TAATGTAGGCGGCTCAATGCTTGCAGGCGTTATATCTGCTAAACAGCTCAAACAATTCAACCAT
AATATATACAACCAAAAAGAGCTTGTAAACAAATAA f147.aa (SEQ ID NO:21)
MKIIIIGGTSAGTSAAAKANRLNKKLDITIYEKTNIVSFGTCGLPYFVGGFFDNPNTMISRTQEEFEKT
GISVKTNHEVIKVDAKNNTIVIKNQKTGTIFNNTYDQLMIATGAKPIIPPINNINLENFHTLKNLEDGQ
KIKKLMDREEIKNIVIIGGGYIGIEMVEAAKNRKNVRLIQLDKHILIDSFDEEIVTIMEEELTKKGVN
LHTNEFVKSLIGEKKAEGVVTNKNTYQADAVILATGIKPDTEFLENQLKTTKNGAIIVNEYGETSIKN
IFSAGDCATIYNIVSKKNEYIPLATTANKLGRIVGENLAGNHTAFKGTLGSASIKILSLEAARTGLTEK
DAKKLQIKYKTIFVKDKNHTNYYPGQEDLYIKLIYEENTKIILGAQAIGKNGAVIRIHALSIAIYSKLT
TKELGMMDFSYSPPFSRTWDILNIAGNAAK t147.aa (SEQ ID NO:22)
AAAKANRLNKKLDITIYEKTNIVSFGTCGLPYFVGGFFDNPNTMISRTQEEFEKTGISVKTNHEVIKV
DAKNNTIVIKNQKTGTIFNNTYDQLMIATGAKPIIPINNINLENFHTLKNLEDGQKIKKLMDREEIKN
IVIIGGGYIGIEMVEAAKNRKNVRLIQLDKHILIDSFDEEIVTIMEEELTKKGVNLHTNEFVKSLIGE
KKAEGVVTNKNTYQADAVILATGIKPDTEFLENQLKTTKNGAIIVNEYGETSIKNIFSAGDCATIYNI
VSKKNEYIPLATTANKLGRIVGENLAGNHTAFKGTLGSASIKILSLEAARTGLTEKDAKKLQIKYKTI
FVKDKNHTNYYPGQEDLYIKLIYEENTKIILGAQAIGKNGAVIRIHALSIAIYSKLTTKELGMMDFSY
SPPFSRTWDILNIAGNAAK f147.nt (SEQ ID NO:23)
ATGAAAATAATAATTATTGGGGGCACATCAGCAGGAACTAGTGCCGCAGCTAAAGCAAACCGC
TTAAACAAAAAGCTAGACATTACTATCTATGAAAAAACAAATATTGTATCTTTTGGAACCTGTG
GCCTGCCTTACTTTGTGGGGGATTCTTTGACAACCCCAATACAATGATCTCAAGAACACAAGA
AGAATTCGAAAAAACTGGAATCTCTGTTAAAACTAACCACGAAGTTATCAAAGTAGATGCAAA
AAACAATACAATTGTAATAAAAAATCAAAAAACAGGAACCATTTTTAACAATACTTACGATCAA
CTTATGATAGCAACTGGTGCAAAACCTATTATTCCACCAATCAATAATATCAATCTAGAAAATT
TTCATACTCTGAAAAATTTAGAAGACGGTCAAAAAATAAAAAAATTAATGGATAGAGAAGAGA
TTAAAAATATAGTGATAATTGGTGGTGGATACATTGGAATTGAAATGGTAGAAGCAGCAAAAA

TABLE 1-continued

Nucleotide and Amino Acid Sequences.

ATAAAAGAAAAAATGTAAGATTAATTCAACTAGATAAGCACATACTCATAGATTCCTTTGACGA
AGAAATAGTCACAATAATGGAAGAAGAACTAACAAAAAAGGGGGTTAATCTTCATACAAATGA
GTTTGTAAAAAGTTTAATAGGAGAAAAAAAGGCAGAAGGAGTAGTAACAAACAAAAATACTTA
TCAAGCTGACGCTGTTATACTTGCTACCGGAATAAAACCTGACACTGAATTTTTAGAAAACCAG
CTTAAAACTACTAAAAATGGAGCAATAATTGTAAATGAGTATGGCGAAACTAGCATAAAAAAT
ATTTTTTCTGCAGGAGATTGTGCAACTATTTATAATATAGTAAGTAAAAAAAATGAATACATAC
CCTTGGCAACAACAGCCAACAAACTTGGAAGAATAGTTGGTGAAAATTTAGCTGGGAATCATA
CAGCATTTAAAGGCACATTGGGCTCAGCTTCAATTAAAATACTATCTTTAGAAGCTGCAAGAAC
AGGACTTACAGAAAAAGATGCAAAAAAGCTCCAAATAAAATATAAAACGATTTTTGTAAAGGA
CAAAAATCATACAAATTATTATCCAGGCCAAGAAGATCTTTATATTAAATTAATTTATGAGGAA
AATACCAAAATAATCCTTGGGGCACAAGCAATAGGAAAAAATGGAGCCGTAATAAGAATTCAT
GCTTTATCAATTGCAATCTATTCAAAACTTACAACAAAAGAGCTAGGGATGATGGATTTCTCAT
ATTCCCCACCCTTCTCAAGAACTTGGGATATATTAAATATTGCTGGCAATGCTGCCAAATAG t147.nt (SEQ ID NO:24)
GCCGCAGCTAAAGCAAACCGCTTAAACAAAAAGCTAGACATTACTATCTATGAAAAAACAAAT
ATTGTATCTTTTGGAACCTGTGGCCTGCCTTACTTTGTGGGGGGATTCTTTGACAACCCCAATAC
AATGATCTCAAGAACACAAGAAGAATTCGAAAAAACTGGAATCTCTGTTAAAACTAACCACGA
AGTTATCAAAGTAGATGCAAAAAACAATACAATTGTAATAAAAAATCAAAAAACAGGAACCAT
TTTTAACAATACTTACGATCAACTTATGATAGCAACTGGTGCAAAACCTATTATTCCACCAATC
AATAATATCAATCTAGAAAATTTTCATACTCTGAAAAATTTAGAAGACGGTCAAAAAATAAAAA
AATTAATGGATAGAGAAGAGATTAAAAATATAGTGATAATTGGTGGTGGATACATTGGAATTG
AAATGGTAGAAGCAGCAAAAAATAAAAGAAAAAATGTAAGATTAATTCAACTAGATAAGCACA
TACTCATAGATTCCTTTGACGAAGAAATAGTCACAATAATGGAAGAAGAACTAACAAAAAAGG
GGGTTAATCTTCATACAAATGAGTTTGTAAAAAGTTTAATAGGAGAAAAAAAGGCAGAAGGAG
TAGTAACAAACAAAAATACTTATCAAGCTGACGCTGTTATACTTGCTACCGGAATAAAACCTGA
CACTGAATTTTTAGAAAACCAGCTTAAACTACTAAAAATGGAGCAATAATTGTAAATGAGTAT
GGCGAAACTAGCATAAAAAATATTTTTTCTGCAGGAGATTGTGCAACTATTTATAATATAGTAA
GTAAAAAAAATGAATACATACCCTTGGCAACAACAGCCAACAAACTTGGAAGAATAGTTGGTG
AAAATTTAGCTGGGAATCATACAGCATTTAAAGGCACATTGGGCTCAGCTTCAATTAAAATACT
ATCTTTAGAAGCTGCAAGAACAGGACTTACAGAAAAAGATGCAAAAAAGCTCCAAATAAAATA
TAAAACGATTTTTGTAAAGGACAAAAATCATACAAATTATTATCCAGGCCAAGAAGATCTTTAT
ATTAAATTAATTTATGAGGAAAATACCAAAATAATCCTTGGGGCACAAGCAATAGGAAAAAT
GGAGCCGTAATAAGAATTCATGCTTTATCAATTGCAATCTATTCAAAACTTACAACAAAAGAGC
TAGGGATGATGGATTTCTCATATTCCCCACCCTTCTCAAGAACTTGGGATATATTAAATATTGCT
GGCAATGCTGCCAAATAG f152.aa (SEQ ID NO:25)
MLKFEFSDRFLLFSYFVLIMFIGSLLLMLPISWEGDGKLAYIDALFTAVSAVSITGLTTVKMEGFSTFG
FILIMLLIQLGGLGFISITTFYLLIPKKKMNLTDARIIKQYSLSNIEYNPIRILKSILFITFSIEMIGLILILIC
FKLRGVNISFLEALFTTISAFCNAGFSMHSESIYAWRDVPEAIVVVSILIICGGLGFMVYRDVNNTIKN
KKKLSLHAKIVFSLSFFLIIIGAILFFFTEMHKLKAGYSMSTLIFNSIFYSISTRTAGFNYLDNSLISGRT
QIISLPFMFIGGAPGSTAGGIKITTFFLIVLAVVKNQNGNGYIIGSYKVSIDSIRFALLFFARAIFILSFSFF
MLLFFEGGSGNWKVIDLGYEVFSAFGTVGLSVGVTQDLSFWGKVIIIFTMFAGRIGLFSMAVFVSRK
SRFEEFTRPRQDILVG t152.aa (SEQ ID NO:26)
WEGDGKLAYIDALFTAVSAVSITGLTTVKMEGFSTFGFILIMLLIQLGGLGFISITTFYLLIPKKKMNL
TDARIIKQYSLSNIEYNPIRILKSILFITFSIEMIGLILILICFKLRGVNISFLEALFTTISAFCNAGFSMHSE
SIYAWRDVPEAIVVVSILIICGGLGFMVYRDVNNTIKNKKKLSLHAKIVFSLSFFLIIIGAILFFFTEMH
KLKAGYSMSTLIFNSIFYSISTRTAGFNYLDNSLISGRTQIISLPFMFIGGAPGSTAGGIKITTFFLIVLAV
VKNQNGNGYIIGSYKVSIDSIRFALLFFARAIFILSFSFFMLLFFEGGSGNWKVIDLGYEVFSAFGTVG
LSVGVTQDLSFWGKVIIIFTMFAGRIGLFSMAVFVSRKSRFEEFTRPRQDILVG f152.nt (SEQ ID NO:27)
ATGTTGAAATTTGAATTTAGCGACAGGTTTTTACTTTTTAGTTATTTTGTTTTAATTATGTTTAT
AGGCTCTCTTTTGTTGATGTTGCCTATTTCCTGGGAAGGTGATGGCAAATTAGCATACATTGAT
GCTCTTTTTACTGCTGTTTCTGCTGTAAGTATTACGGGCCTTACAACGGTTAAAATGGAAGGCTT
TTCTACTTTTGGATTTATTTTGATAATGTTGCTAATCCAGCTTGGGGGACTTGGATTTATAAGTA
TTACTACTTTTTATTTGCTTATACCTAAAAAGAAAATGAATTTAACAGATGCAAGAATAATAAA
GCAGTATTCCCTTTCAAATATAGAATATAATCCTATTAGAATTTTAAAAAGCATATTGTTTATAA
CTTTTTCAATTGAAATGATAGGTTTAATATTAATACTTATTTGTTTTAAACTTAGGGGAGTGAAT
ATTTCATTCTTAGAGGCTTTGTTTACGACAATTTCTGCTTTTTGCAATGCAGGTTTTTCCATGCA
TTCTGAGAGTATTTATGCATGGCGAGATGTTCCTGAAGCTATAGTTGTGGTCTCTATTTTAATAA
TTTGTGGTGGGCTTGGGTTTATGGTCTATAGAGATGTAAATAACACTATTAAAAACAAAAAAAA
ACTATCGCTTCATGCCAAGATAGTTTTTTCTTTAAGCTTCTTTTTAATTATAATTGGTGCAATTTT
ATTTTTTTTTTACAGAGATGCATAAATTAAAAGCTGGTTATTCAATGAGCACTTTAATATTTAATT
CAATTTTTTATTCGATTAGTACCAGAACAGCTGGTTTTAATTATCTTGATAATTCTTTAATAAGC
GGAAGAACTCAAATAATTTCTCTACCATTCATGTTTATTGGTGGTGCACCCGGATCAACTGCAG
GAGGGATTAAGATTACAACATTTTTTTTAATTGTATTGGCTGTTGTTAAAAATCAAAACGGCAA
TGGATATATTATTGGTTCTTACAAGGTTTCAATAGATAGTATAAGATTTGCACTTTTATTTTTTG
CAAGAGCTATTTTTATTTTAAGTTTTTCTTTTTTCATGCTTCTTTTTTTGAGGGAGGATCTGGCA
ATTGGAAGGTTATTGATTTAGGTTATGAAGTATTTTCTGCTTTTGGAACGGTTGGTCTTTCAGTT
GGAGTAACTCAGGATTTGTCATTTTGGGGAAAGTCATTATAATTTTTACTATGTTTGCAGGAC
GAATAGGGCTTTTTTCAATGGCTGTTTTTGTTTCAAGAAAGTCGCGTTTTGAAGAATTTACAAG
GCCAAGGCAAGATATTTTGGTTGGTTGA

TABLE 1-continued

Nucleotide and Amino Acid Sequences.

t152.nt (SEQ ID NO:28)
TGGGAAGGTGATGGCAAATTAGCATACATTGATGCTCTTTTTACTGCTGTTTCTGCTGTAAGTA
TTACGGGCCTTACAACGGTTAAAATGGAAGGCTTTTCTACTTTTGGATTTATTTTGATAATGTTG
CTAATCCAGCTTGGGGGACTTGGATTTATAAGTATTACTACTTTTTATTTGCTTATACCTAAAAA
GAAAATGAATTTAACAGATGCAAGAATAATAAAGCAGTATTCCCTTTCAAATATAGAATATAAT
CCTATTAGAATTTTAAAAAGCATATTGTTTATAACTTTTTCAATTGAAATGATAGGTTTAATATT
AATACTTATTTGTTTTAAACTTAGGGGAGTGAATATTTCATTCTTAGAGGCTTTGTTTACGACAA
TTTCTGCTTTTTGCAATGCAGGTTTTTCCATGCATTCTGAGAGTATTTATGCATGGCAGATGTT
CCTGAAGCTATAGTTGTGGTCTCTATTTTAATAATTTGTGGTGGGCTTGGGTTTATGGTCTATAG
AGATGTAAATAACACTATTAAAAACAAAAAAAAACTATCGCTTCATGCCAAGATAGTTTTTTCT
TTAAGCTTCTTTAATTATAATTGGTGCAATTTTATTTTTTTTTACAGAGATGCATAAATTAAA
AGCTGGTTATTCAATGAGCACTTTAATATTTAATTCAATTTTTTATTCGATTAGTACCAGAACAG
CTGGTTTTAATTATCTTGATAATTCTTTAATAAGCGGAAGAACTCAAATAATTTCTCTACCATTC
ATGTTTATTGGTGGTGCACCCGGATCAACTGCAGGAGGGATTAAGATTACAACATTTTTTTTAA
TTGTATTGGCTGTTGTTAAAAATCAAAACGGCAATGGATATATTATTGGTTCTTACAAGGTTTC
AATAGATAGTATAAGATTTGCACTTTTATTTTTTGCAAGAGCTATTTTTATTTTAAGTTTTTCTTT
TTTCATGCTTCTTTTTTTGAGGGAGGATCTGGCAATTGGAAGGTTATTGATTTAGGTTATGAAG
TATTTTTCTGCTTTTGGAACGGTTGGTCTTTCAGTTGGAGTAACTCAGGATTTGTCATTTTGGGGG
AAAGTCATTATAATTTTTACTATGTTTGCAGGACGAATAGGGCTTTTTTCAATGGCTGTTTTTGT
TTCAAGAAAGTCGCGTTTTGAAGAATTTACAAGGCCAAGGCAAGATATTTTGGTTGGTTGA f154.aa (SEQ ID NO:29)
MKINKTFILLFLFTKFSFVQAQANQILTEISPLSISLKNGKGSVYLKVSKSSDYILTLDKSSNSDFVFKI
YDISNKKYITDKVKRRDFKIRLDKNSLYAIIYVGTKNENIKFSLTDLDFSILSSDSLKAKTSKIEKEDLF
FTLKDLPVLNLTAKLKKYVLRIYKSNIYIAYQLENSDDIKVAEFIEDVGWFNLDSSVNRNITNIVNFD
FSINSKGNLYIAFVTKSGADFASELIVKKFNSRKWIDISPGHIENFGSLLNISIDLKDRLYLAYLREIRG
EYKINLISNMGYGSIWTDVIHAYLSKGDSNVNSSNIGLISEPFLGIFYNYKSNNEIKSEFIVNNENAWV
NANIPSVYMANFIKGFFDSNFNQIIMSFVSENRPIVNICPLKSSRWINISPNVEMEGLSADIGLYKNNL
FLAFEDNNNVRLIYFKNKNWYFLNKLENFKSNVKSPQIGIYGNQGLVISTLSSNSNELFFTLICQ t154.aa (SEQ ID NO:30)
NQILTEISPLSILSKNGKGSVYLKVSKSSDYILTLDKSSNSDFVFKIYDISNKKYITDKVKRRDFKIRLD
KNSLYAIIYVGTKNENIKFSLTDLDFSILSSDSLKAKTSKIEKEDLFFTLKDLPVLNLTAKLKKYVLRI
YKSNIYIAYQLENSDDIKVAEFIEDVGWFNLDSSVNRNITNIVNFDFSINSKGNLYIAFVTKSGADFAS
ELIVKKFNSRKWIDISPGHIENFGSLLNISIDLKDRLYLAYLREIRGEYKINLISNMGYGSIWTDVIHAY
LSKGDSNVNSSNIGLISEPFLGIFYNYKSNNEIKSEFIVNNENAWVNANIPSVYMANFIKGFFDSNFNQ
IIMSFVSENRPIVNICPLKSSRWINISPNVEMEGLSADIGLYKNNLFLAFEDNNNVRLIYFKNKNWYFL
NKLENFKSNVKSPQIGIYGNQGLVISTLSSNSNELFFTLICQ f154.nt (SEQ ID NO:31)
ATGAAAATAAATAAGACATTCATTTTGCTATTTTTATTTACAAAATTTTTCTTTTGTTCAAGCTCA
AGCAAATCAAATATTAACAGAAATTAGTCTTTAAGTATTTTAAGCAAAAATGGGAAAGGAAG
TGTTTACTTAAAAGTTAGCAAATCTTCCGATTATATTTTAACCCTAGATAAGAGTTCAAATTCCG
ATTTTGTTTTTAAAAATTTATGACATTTCTAATAAAAAATATATAACCGATAAAGTAAAAAGAAG
AGATTTAAAATAAGATTAGATAAAAATTCTCTTTATGCAATAATATATGTTGGTACTAAAAAT
GAAAACATAAAGTTTTCGCTTACAGATTTAGATTTTTCAATTTTAAGTAGCGATTCCCTGAAAG
CTAAAACATCTAAGATTGAAAAAGAAGATTTATTTTTTACTTTAAAAGATTTGCCTGTTTTAAAT
TTAACTGCCAAGCTTAAAAAATATGTATTAAGGATTTATAAAAGCAATATTTATATTGCTTATC
AGCTAGAAAATAGCGATGATATTAAAGTTGCTGAATTTATTGAGGATGTTGGTTGGTTTAATCT
TGATTCATCTGTTAATAGAAATATTACTAATATAGTTAATTTTGATTTTTCAATTAATTCTAAAG
GAAATTTATATATTGCTTTTGTTACGAAATCAGGGGCTGATTTTGCCAGCGAGCTTATAGTTAA
AAAATTTAATAGTAGAAAATGGATTGATATTAGTCCTGGTCACATAGAAAATTTTGGATCTTTA
TTAAATATTAGCATTGATTTAAAAGATAGGTTGTATTTAGCATATTTAAGGGAAATTAGGGGTG
AATATAAAATTAATTTAATCTCGAATATGGGTTACGGAAGTATTTGGACCGATGTAATACATGC
TTATTTAAGTAAAGGTGATTCTAATGTTAATTCATCAAACATTGGTTTAATATCTGAACCTTTT
TGGGCATTTTTATAATTATAAGTCAAATAATGAGATTAAATCTGAATTTATTGTAAACAATGA
AAATGCTTGGGTAAATGCAAATATTCCTTCTGTTTATATGGCCAATTTTATTAAAGGCTTTTTG
ATTCTAATTTTAATCAAATAATTATGAGTTTTGTTTCTGAAAATAGACCTATTGTAAACATTTGT
CCTTTGAAAAGTAGTAGATGGATTAATATAAGTCCTAATGTTGAAATGGAAGGTTTAAGTGCTG
ACATTGGGCTTTATAAAAATAATTTGTTTTTAGCTTTTGAGGACAATAATAATGTGAGATTAAT
TTATTTTAAGAATAAAAATTGGTATTTTTTAAATAAGCTTGAGAATTTTAAGAGTAATGTTAAA
AGCCCTCAGATTGGAATTTATGGCAATCAAGGGCTTGTAATCTCTACTTTAAGCTCTAATTCCA
ATGAATTATTTTTTACTTTGATTTGCCAATGA t154.nt (SEQ ID NO:32)
AATCAAATATTAACAGAAATTAGTCCTTTAAGTATTTTAAGCAAAAATGGGAAAGGAAGTGTTT
ACTTAAAAGTTAGCAAATCTTCCGATTATATTTTAACCCTAGATAAGAGTTCAAATTCCGATTTT
GTTTTTAAAAATTTATGACATTTCTAATAAAAAATATATAACCGATAAAGTAAAAAGAAGATT
TTAAAATAAGATTAGATAAAAATTCTCTTTATGCAATAATATATGTTGGTACTAAAAATGAAAA
CATAAAGTTTTCGCTTACAGATTTAGATTTTTCAATTTTAAGTAGCGATTCCCTGAAAGCTAAAA
CATCTAAGATTGAAAAGAAGATTTATTTTTTACTTTAAAAGATTTGCCTGTTTTAAATTTAACT
GCCAAGCTTAAAAAATATGTATTAAGGATTTATAAAAGCAATATTTATATTGCTTATCAGCTAG
AAAATAGCGATGATATTAAAGTTGCTGAATTTATTGAGGATGTTGGTTGGTTTAATCTTGATTC
ATCTGTTAATAGAAATATTACTAATATAGTTAATTTTGATTTTTCAATTAATTCTAAAGGAAATT
TATATATTGCTTTTGTTACGAAATCAGGGGCTGATTTTGCCAGCGAGCTTATAGTTAAAAAATT
TAATAGTAGAAAATGGATTGATATTAGTCCTGGTCACATAGAAAATTTTGGATCTTTATTAAAT
ATTAGCATTGATTTAAAAGATAGGTTGTATTTAGCATATTTAAGGGAAATTAGGGGTGAATATA

TABLE 1-continued

Nucleotide and Amino Acid Sequences.

```
AAATTAATTTAATCTCGAATATGGGTTACGGAAGTATTTGGACCGATGTAATACATGCTTATTT
AAGTAAAGGTGATTCTAATGTTAATTCATCAAACATTGGTTTAATATCTGAACCTTTTTTGGGCA
TTTTTTATAATTATAAGTCAAATAATGAGATTAAATCTGAATTTATTGTAAACAATGAAAATGC
TTGGGTAAATGCAAATATTCCTTCTGTTTATATGGCCAATTTTATTAAAGGCTTTTTTGATTCTA
ATTTTAATCAAATAATTATGAGTTTTGTTTCTGAAAATAGACCTATTGTAAACATTTGTCCTTTG
AAAAGTAGTAGATGGATTAATATAAGTCCTAATGTTGAAATGGAAGGTTTAAGTGCTGACATTG
GGCTTTATAAAAATAATTTGTTTTTAGCTTTTGAGGACAATAATAATGTGAGATTAATTTATTTT
AAGAATAAAAATTGGTATTTTTAAATAAGCTTGAGAATTTTAAGAGTAATGTTAAAAGCCCTC
AGATTGGAATTTATGGCAATCAAGGGCTTGTAATCTCTACTTTAAGCTCTAATTCCAATGAATT
ATTTTTTACTTTGATTTGCCAATGA f157.aa (SEQ ID NO:33)
MKIFLKVIGRGILGRLMVFRKNYDYLALISLLIVSFVGILLIYSSDYNISGSLTKNEYIKQTFW
VIIGFFLIFIVGKYDLKFVYSMVYPLYFLLILALIFTAFFGMTVNGARSWIGIWKLGGQPSEFGKVVIIL
TLSKFYTEKKGYNEFFTFITAFLLIFPSVILILLQPDFGTAIVYLTIFIFISFFAGIDLHYVLAFALIGFFSF
VFAILPVWYEYKVNMGNVFYLIFSNPFYFRVIMGVLLLILLISVLGFFISKYGLSIKIIYFYVFFASSILL
VSIVFSKVLSKLMKTYQIKRFLVFLDPAIDAKGAGWNLNQVKIAIGSGGLLGKGFLKGPYTHANYVP
SQSTDFIFSILAEEFGFLGVSTILILFFFLFFKFLIIMNKSQDRYMALVISGILGLLFFHTSFNVGMSLGV
LPITGIPFPFLSYGGSSTITFFLAMSFYFNIESIVAMD t157.aa (SEQ ID NO:34)
RKNYDYLALISLLIVSFVGILLIYSSDYNISGSLTKNEYIKQTFWVIIGFFLIFIVGKYDLKFVYSMVYP
LYFLLILALIFTAFFGMTVNGARSWIGIWKLGGQPSEFGKVVIILTLSKFYTEKKGYNEFFTFITAFLLI
FPSVILILLQPDFGTAIVYLTIFIFISFFAGIDLHYVLAFALIGFFSFVFAILPVWYEYKVNMGNVFYLIFS
NPFYFRVIMGVLLLILLISVLGFFISKYGLSIKIIYFYVFFASSILLVSIVFSKVLSKLMKTYQIKRFLVFL
DPAIDAKGAGWNLNQVKIAIGSGGLLGKGFLKGPYTHANYVPSQSTDFIFSILAEEFGFLGVSTILILF
FFLFFKFLIIMNKSQDRYMALVISGILGLLFFHTSFNVGMSLGVLPITGIPFPFLSYGGSSTITFFLAMSF
YFNIESIVAMD f157.nt (SEQ ID NO:35)
ATGAAGATATTCTTAAAGGTTATAGGCCGTGGTATATTAGGTAGATTAATGGTTTTTAGAAAAA
ATTATGATTATTTGGCTTTGATAAGCTTACTTATAGTTTCTTTTGTTGGTATATTGTTGATTATT
CTAGCGATTATAATATTAGTGGATCTTTAACCAAGAATGAATATATAAAACAAACCTTTTGGGT
AATTATTGGATTTTTTCTAATTTTTATAGTGGGCAAATATGATTTAAAATTTGTTTATAGCATGG
TATATCCTTTATATTTTTATTAATATTGGCTTTAATTTTTACTGCATTTTTTGGAATGACAGTAA
ATGGAGCAAGATCTTGGATTGGCATATGGAAACTTGGAGGACAGCCTTCTGAATTTGGTAAAGT
TGTTATTATTTTAACCCTTTCAAAATTTTACACTGAAAAAAAGGGTTATAATGAATTTTTTACCT
TTATTACTGCATTTTTATTAATTTTTCCATCGGTAATTCTTATATTATTGCAACCTGATTTTGGTA
CAGCAATAGTATATTTAACCATTTTTATATTTATTTCTTTTTTTGCAGGAATAGATTTGCACTAT
GTTTTAGCATTTGCGTTGATAGGGTTTTTTTCTTTTGTTTTTGCAATTTTACCGGTTTGGTATGA
ATATAAGGTGAATATGGGTAATGTATTTTATCTTATTTTCTCAAATCCTTTTTATTTTAGAGTAA
TAATGGGAGTGCTGCTTTTAATTCTTTTGATTTCTGTTTTAGGATTTTTCATTTCTAAATATGGTT
TGAGTATTAAAATAATTTATTTTTATGTATTTTTTGCAAGTTCTATTTTATTAGTTTCAATAGTGT
TTTCAAAGGTTCTTTCAAAGTTAATGAAGACTTATCAGATTAAACGGTTTTTGGTATTCTTAGAT
CCGGCTATTGATGCTAAGGGTGCTGGTTGGAATTTAAATCAGGTTAAAATAGCAATTGGTTCTG
GCGGTCTTTTGGGCAAAGGATTTTAAAGGGACCTTATACCCACGCTAATTATGTGCCATCTCA
AAGCACAGATTTTATTTTTTCTATTCTTGCCGAAGAGTTTGGGTTTTTGGGTGTTAGCACTATTT
TAATATTATTTTTTTTCCTTTTTTTTAAATTTTTGATAATAATGAATAAAAGTCAAGATAGATAT
ATGGCCTTAGTAATATCTGGAATTTTGGGACTTTTATTTTTTCATACTTCTTTTAATGTTGGAAT
GTCTTTAGGAGTTCTTCCTATTACCGGGATTCCCTTTCCTTTTCTCTCTTATGGAGGTTCTTCTAC
TATTACATTTTTTTAGCAATGTCTTTTTATTTTAATATTGAATCAATAGTTGCTATGGATTGA t157.nt (SEQ ID NO:36)
AGAAAAAATTATGATTATTTGGCTTTGATAAGCTTACTTATAGTTTCTTTTGTTGGTATATTGTT
GATTTATTCTAGCGATTATAATATTAGTGGATCTTTAACCAAGAATGAATATATAAAACAAACC
TTTTGGGTAATTATTGGATTTTTTCTAATTTTTATAGTGGGCAAATATGATTTAAAATTTGTTTA
TAGCATGGTATATCCTTTATATTTTTATTAATATTGGCTTTAATTTTTACTGCATTTTTTGGAAT
GACAGTAAATGGAGCAAGATCTTGGATTGGCATATGGAAACTTGGAGGACAGCCTTCTGAATTT
GGTAAAGTTGTTATTATTTTAACCCTTTCAAAATTTTACACTGAAAAAAAGGGTTATAATGAAT
TTTTTACCTTTATTACTGCATTTTTATTAATTTTTCCATCGGTAATTCTTATATTATTGCAACCTG
ATTTTGGTACAGCAATAGTATATTTAACCATTTTTATATTTATTTCTTTTTTTGCAGGAATAGAT
TTGCACTATGTTTTAGCATTTGCGTTGATAGGGTTTTTTTCTTTTGTTTTTGCAATTTTACCGGTT
TGGTATGAATATAAGGTGAATATGGGTAATGTATTTTATCTTATTTTCTCAAATCCTTTTTATTT
TAGAGTAATAATGGGAGTGCTGCTTTTAATTCTTTTGATTTCTGTTTTAGGATTTTTCATTTCTA
AATATGGTTTGAGTATTAAAATAATTTATTTTTATGTATTTTTTGCAAGTTCTATTTTATTAGTTT
CAATAGTGTTTTCAAAGGTTCTTTCAAAGTTAATGAAGACTTATCAGATTAAACGGTTTTTGGT
ATTCTTAGATCCGGCTATTGATGCTAAGGGTGCTGGTTGGAATTTAAATCAGGTTAAAATAGCA
ATTGGTTCTGGCGGTCTTTTGGGCAAAGGATTTTAAAGGGACCTTATACCCACGCTAATTATG
TGCCATCTCAAAGCACAGATTTTATTTTTTCTATTCTTGCCGAAGAGTTTGGGTTTTTGGGTGTT
AGCACTATTTTAATATTATTTTTTTTCCTTTTTTTTAAATTTTTGATAATAATGAATAAAAGTCA
AGATAGATATATGGCCTTAGTAATATCTGGAATTTTGGGACTTTTATTTTTTCATACTTCTTTTA
ATGTTGGAATGTCTTTAGGAGTTCTTCCTATTACCGGGATTCCCTTTCCTTTTCTCTCTTATGGA
GGTTCTTCTACTATTACATTTTTTTAGCAATGTCTTTTTATTTTAATATTGAATCAATAGTTGCT
ATGGATTGA f17.aa (SEQ ID NO:37)
MIVFLFFSIYLIILFKRSSNSPLYFVPDTKFETLSIRIVLSCSLLLIFFCTMLDARPSTIAVFPTPGSPISIAL
```

TABLE 1-continued

Nucleotide and Amino Acid Sequences.

FLFLLKSIFVRVLISASLPTKGSNFLAFASAVKFLTYFPISKCSFSSRISSSNSL t17.aa (SEQ ID NO:38)
PLYFVPDTKFETLSIRIVLSCSLLLIFFCTMLDARPSTIAVFPTPGSPISIALFLFLLKSIFVRVLISASLPT
KGSNFLAFASAVKFLTYFPISKCSFSSRISSSNSL f17.nt (SEQ ID NO:39)
ATGATTGTGTTTTTGTTTTTTTCAATATACTTAATTATATTATTTAAACGATCTTCAAACTCGCCT
CTATATTTTGTTCCCGATACCAAGTTTGAAACCTTAAGCATTAGAATTGTTTTGTCTTGTAGTTT
GCTACTTATTTTTTTTTGCACTATGCTTGATGCAAGGCCTTCAACTATTGCTGTTTTTCCCACACC
AGGTTCGCCTATTAGCATTGCACTATTTTTATTTCTTCTCAAGAGTATATTTGTAAGAGTTTTAA
TCTCTGCTTCTCTTCCAACCAAGGGGTCTAATTTTTTGGCTTTTGCAAGTGCTGTTAAATTTTTG
ACATACTTTCCAATTTCAAAGTGCTCATTTTCAAGTCGTATTTCTTCATCAAATTCTTTGTAG t17.nt (SEQ ID NO:40)
CCTCTATATTTTGTTCCCGATACCAAGTTTGAAACCTTAAGCATTAGAATTGTTTTGTCTTGTAG
TTTGCTACTTATTTTTTTTTGCACTATGCTTGATGCAAGGCCTTCAACTATTGCTGTTTTTCCCAC
ACCAGGTTCGCCTATTAGCATTGCACTATTTTTATTTCTTCTCAAGAGTATATTTGTAAGAGTTT
TAATCTCTGCTTCTCTTCCAACCAAGGGGTCTAATTTTTTGGCTTTTGCAAGTGCTGTTAAATTT
TTGACATACTTTCCAATTTCAAAGTGCTCATTTTCAAGTCGTATTTCTTCATCAAATTCTTTGTA
G f170.aa (SEQ ID NO:41)
MKAFKVKNLRRFSNFIRILVIVLFLNSLLSLFVFLAGSYNIFVYNFQKFYLDLAIILSSVSFGLESTRLIF
FYFLKNKKIKYYLILIFSFIIFFIALVFKIFLSGNK t170.aa (SEQ ID NO:42)
YNIFVYNFQKFYLDLAIILSSVSFGLESTRLIFFYFLKNKKIKYYLILIFSFIIFFIALVFKIFLSGNK f170.nt (SEQ ID NO:43)
ATGAAAGCTTTTAAAGTAAAAAATCTAAGACGTTTTTCAAATTTTATTAGAATTTTGGTTATTGT
ATTGTTTTTAAATTCTTTGTTAAGTTTGTTCGTGTTTTTGGCTGGTTCTTACAATATTTTTGTTTA
CAATTTTCAGAAATTTTATCTTGATCTTGCTATTATTTTAAGCTCTGTTTCTTTTGGACTTGAATC
TACTAGACTGATATTTTTTTATTTTTTGAAAAATAAAAAAATTAAGTATTATTTAATTTTAATTT
TTAGTTTTATAATTTTTTTTATTGCTCTTGTTTTTAAAATTTTTCTTTCTGGTAATAA
ATAG t170.nt (SEQ ID NO:44)
TACAATATTTTTGTTTACAATTTTCAGAAATTTTATCTTGATCTTGCTATTATTTTAAGCTCTGTT
TCTTTTGGACTTGAATCTACTAGACTGATATTTTTTTATTTTTTGAAAAATAAAAAAATTAAGTA
TTATTTAATTTTAATTTTTAGTTTTATAATTTTTTTTATTGCTCTTGTTTTTAAAATTTTTCTTTCT
GGTAATAAATAG f186.aa (SEQ ID NO:45)
MKKLIIIFTLFLSQACNLSTMHKIDTKEDMKILYSEIAELRKKLNLNHLEIDDTLEKVAKEYAIKLGEN
RTITHTLFGTTPMQRIHKYDQSFNLTREILASGIELNRVVNAWLNSPSHKEALINTDTDKIGGYRLKT
TDNIDIFVVLFGKRKYKN t186.aa (SEQ ID NO:46)
TMHKIDTKEDMKILYSEIAELRKKLNLNHLEIDDTLEKVAKEYAIKLGENRTITHTLFGTTPMQRIHK
YDQSFNLTREILASGIELNRVVNAWLNSPSHKEALINTDTDKIGGYRLKTTDNIDIFVVLFGKRKYKN f186.nt (SEQ ID NO:47)
ATGAAAAAATTGATTATAATTTTTACACTGTTTTTATCTCAAGCATGCAATTTAAGTACAATGCA
TAAAATAGATACAAAAGAAGATATGAAAATTCTATATTCAGAAATTGCTGAATTGAGAAAAAA
ATTAAATCTAAACCATCTAGAAATAGATGATACCCTTGAAAAAGTTGCAAAAGAATATGCCATT
AAACTGGGAGAAAATAGAACAATAACTCACACCCTTTTTGGCACAACCCCAATGCAAAGAATA
CATAAATACGATCAATCCTTTAATTTAACAAGAGAAATACTGGCATCAGGAATTGAACTTAACA
GAGTAGTTAATGCATGGCTTAATAGTCCAAGCCACAAAGAAGCTCTTATTAATACAGATACCGA
TAAAATAGGTGGCTATAGATTAAAAACGACTGACAATATAGATATATTTGTAGTTCTTTTTGGA
AAAAGAAAATATAAGAATTGA t186.nt (SEQ ID NO:48)
ACAATGCATAAAATAGATACAAAAGAAGATATGAAAATTCTATATTCAGAAATTGCTGAATTG
AGAAAAAAATTAAATCTAAACCATCTAGAAATAGATGATACCCTTGAAAAGTTGCAAAAGAA
TATGCCATTAAACTGGGAGAAAATAGAACAATAACTCACACCCTTTTTGGCACAACCCCAATGC
AAAGAATACATAAATACGATCAATCCTTTAATTTAACAAGAGAAATACTGGCATCAGGAATTGA
ACTTAACAGAGTAGTTAATGCATGGCTTAATAGTCCAAGCCACAAAGAAGCTCTTATTAATACA
GATACCGATAAAATAGGTGGCTATAGATTAAAAACGACTGACAATATAGATATATTTGTAGTTC
TTTTTGGAAAAAGAAAATATAAGAATTGA f196.aa (SEQ ID NO:49)
MKLKARMLLLVLILIAFFISILFFAFGMLINSKLVDQQFNLMINLIESIKSSFNLYISSMEEKVR
VSSMYFNSAEKFNEASKIKSKRLSFISDQSEILIQTGSNMMVTDKEGKIVFTTAVKDNSDFGKSIGDR
EYFTKLKESNSIVYNSFVMLADPGSIEESLLKDISKIKNKKGQIPYILIGMPLRDFETDNIFGYFMFLYS
MDYIYRSFRGINFGILSSGRALAYDTTGRLLVHHVVLPGDILTDISASYSNIIKKTSEDLLQKNKEIST
VYYYDPKSNKKYVGISQKVLLNLSNNKFILLMRTSEDDFYYMSRATTIILAISFVFTLLMLAIATLYL

TABLE 1-continued

Nucleotide and Amino Acid Sequences.

VKKLSSSLNKILEYSERLASGNFTADINFGKWDTVELYSLYEGLEQLRTNFSSVAKGVIENLDYLYE
NAIQIANASQNLSSGAVEQASTLEQMTANIEQISQGVSENTENAATTEKIAVNTNERTKEGHKSVVK
AIEAMTVITEKIGIIDEITRQTNLLALNASIEAARVGEKGKGFEVVAAEVRKLADQSKESAREIIDIAN
RSLTVASRAGENFEQIVPGMEQTARLVKNISNESYKQSVQIEQFKNAIEQVSQLVQTTASSSEELSAM
SEKMLESVKDLKESVDYFKIEK t196.aa (SEQ ID NO:50)
MLINSKLVDQQFNLMINLIESIKSSFNLYISSMEEKVRVSSMYFNSAEKFNEASKIKSKRLSFISDQSEI
LIQTGSNMMVTDKEGKIVFTTAVKDNSDFGKSIGDREYFTKLKESNSIVYNSFVMLADPGSIEESLLK
DISKIKKKGQIPYILIGMPLRDFETDNIFGYFMFLYSMDYIYRSFRGINFGILSSGRALAYDTTGRLL
VHHVVLPGDILTDISASYSNIIKKTSEDLLQKNKEISTVYYYDPKSNKKYVGISQKVLLNLSNNKFILL
MRTSEDDFYYMSRATTIILAISFVFTLLMLAIATLYLVKKLSSSLNKILEYSERLASGNFTADINFGKW
DTVELYSLYEGLEQLRTNFSSVAKGVIENLDYLYENAIQIANASQNLSSGAVEQASTLEQMTANIEQI
SQGVSENTENAATTEKIAVNTNERTKEGHKSVVKAIEAMTVITEKIGIIDEITRQTNLLALNASIEAAR
VGEKGKGFEVVAAEVRKLADQSKESAREIIDIANRSLTVASRAGENFEQIVPGMEQTARLVKNISNE
SYKQSVQIEQFKNAIEQVSQLVQTTASSSEELSAMSEKMLESVKDLKESVDYFKIEK f196.nt (SEQ ID NO:51)
ATGAAGCTTAAAGCTAGGATGTTGCTACTTGTTCTTATTCTGATAGCATTCTTTATATCA
ATTTTGTTTTTTGCTTTTGGAATGCTTATTAATAGTAAATTGGTGGATCAACAGTTTAATCTTAT
GATAAATCTTATTGAAAGCATTAAAAGTTCTTTTAATCTTTACATCTCTTCAATGGAAGAGAAA
GTTAGGGTTAGTTCCATGTATTTCAACTCTGCTGAAAAATTTAATGAGGCTAGTAAAATTAAAT
CCAAAAGGTTGAGCTTTATTTCAGATCAATCTGAAATTCTTATTCAAACCGGTAGTAATATGAT
GGTTACAGACAAAGAAGGTAAAATAGTGTTTACTACGGCGGTTAAGGATAATAGTGATTTTGG
CAAATCTATTGGGGATAGAGAATATTTTACAAAACTTAAGGAGTCTAATAGTATTGTTTACAAT
TCCTTTGTCATGTTGGCAGATCCCGGGTCTATTGAGGAGTCTTTACTTAAAGATATTTCCAAGAT
AAAAAATAAAAAAGGTCAGATTCCTTACATATTAATAGGTATGCCATTAAGAGATTTTGAAACA
GATAACATTTTTGGTTATTTTATGTTTCTTTATTCAATGGATTATATATATAGGTCTTTTAGAGG
GATTAATTTTGGAATACTCTCTAGCGGTCGTGCGCTAGCTTATGATACTACGGGTAGATTGTTG
GTTCATCATGTAGTATTGCCAGGTGATATTTTGACTGATATTAGTGCTTCTTATTCCAATATTAT
TAAGAAAACATCTGAAGATTTGTTGCAAAAGAATAAAGAAATTTCAACTGTTTATTATTATGAT
CCTAAAAGCAATAAGAAATATGTGGGAATTAGTCAAAAGGTGTTATTAAACTTGTCTAATAATA
AATTTATTCTTTTAATGAGAACTTCAGAGGACGATTTTTATTACATGTCACGAGCTACAACTATA
ATCTTAGCAATTAGTTTTGTATTTACATTACTTATGCTTGCTATTGCAACTCTTTATCTTGTGAA
AAAGTTAAGCTCTTCTTTGAATAAGATACTGGAATATTCTGAGAGAGTTGCTTCTGGTAATTTT
ACTGCTGATATTAATTTTGGCAAATGGGATACTGTAGAGCTTTACAGTTTGTACGAAGGGCTTG
AGCAGTTGAGAACCAATTTTTCTTCAGTTGCAAAAGGAGTTATTGAAAATCTAGATTATCTTTA
TGAAAATGCAATTCAAATAGCAAATGCAAGCCAGAATTTAAGTTCTGGCGCTGTTGAGCAGGCT
TCTACTTTAGAGCAAATGACAGCAAATATTGAGCAAATTTCAAAGGTGTTTCTGAGAATACTG
AAAATGCAGCTACTACTGAAAAAATTGCTGTTAATACTAATGAAAGGACTAAAGAGGGGCATA
AATCTGTTGTTAAGGCTATTGAGGCAATGACTGTAATTACTGAAAAAATTGGAATTATTGATGA
GATAACAAGGCAAACCAATTTGCTTGCTTTAAATGCCTCGATTGAAGCTGCACGAGTGGGAGAA
AAGGGCAAGGGATTTGAAGTGGTAGCTGCTGAGGTTAGAAAGCTTGCAGATCAAAGCAAAGAA
TCAGCAAGAGAGATTATTGATATTGCAAACAGAAGTTTAACTGTTGCAAGTCGTGCTGGGGAA
AATTTTGAACAAATAGTTCCTGGTATGGAACAAACAGCCAGACTTGTAAAAAATATTTCTAATG
AAAGTTATAAGCAAAGTGTTCAAATAGAGCAATTTAAAAATGCAATAGAGCAGGTTAGTCAGT
TAGTCCAAACTACAGCCTCAAGCAGTGAAGAGCTTTCTGCAATGTCTGAAAAGATGTTAGAGAG
TGTAAAAGATTTAAAAGAATCTGTTGATTATTTTAAGATCGAAAAGTAA t196.nt (SEQ ID NO:52)
ATGCTTATTAATAGTAAATTGGTGGATCAACAGTTTAATCTTATGATAAATCTTATTGAAAGCA
TTAAAAGTTCTTTTAATCTTTACATCTCTTCAATGGAAGAGAAAGTTAGGGTTAGTTCCATGTAT
TTCAACTCTGCTGAAAAATTTAATGAGGCTAGTAAAATTAAATCCAAAAGGTTGAGCTTTATTT
CAGATCAATCTGAAATTCTTATTCAAACCGGTAGTAATATGATGGTTACAGACAAAGAAGGTAA
AATAGTGTTTACTACGGCGGTTAAGGATAATAGTGATTTTGGCAAATCTATTGGGGATAGAGAA
TATTTTACAAAACTTAAGGAGTCTAATAGTATTGTTTACAATTCCTTTGTCATGTTGGCAGATCC
CGGGTCTATTGAGGAGTCTTTACTTAAAGATATTTCCAAGATAAAAAATAAAAAAGGTCAGATT
CCTTACATATTAATAGGTATGCCATTAAGAGATTTTGAAACAGATAACATTTTTGGTTATTTTAT
GTTTCTTTATTCAATGGATTATATATATAGGTCTTTTAGAGGGATTAATTTTGGAATACTCTCTA
GCGGTCGTGCGCTAGCTTATGATACTACGGGTAGATTGTTGGTTCATCATGTAGTATTGCCAGG
TGATATTTTGACTGATATTAGTGCTTCTTATTCCAATATTATTAAGAAAACATCTGAAGATTTGT
TGCAAAAGAATAAAGAATTTCAACTGTTTATTATTATGATCCTAAAAGCAATAAGAAATATGT
GGGAATTAGTCAAAAGGTGTTATTAAACTTGTCTAATAATAAATTTATTCTTTTAATGAGAACT
TCAGAGGACGATTTTTATTACATGTCACGAGCTACAACTATAATCTTAGCAATTAGTTTTGTATT
TACATTACTTATGCTTGCTATTGCAACTCTTTATCTTGTGAAAAAGTTAAGCTCTTCTTTGAATA
AGATACTGGAATATTCTGAGAGACTTGCTTCTGGTAATTTTACTGCTGATATTAATTTTGGCAA
ATGGGATACTGTAGAGCTTTACAGTTTGTACGAAGGGCTTGAGCAGTTGAGAACCAATTTTTCT
TCAGTTGCAAAAGGAGTTATTGAAAATCTAGATTATCTTTATGAAAATGCAATTCAAATAGCAA
ATGCAAGCCAGAATTTAAGTTCTGGCGCTGTTGAGCAGGCTTCTACTTTAGAGCAAATGACAGC
AAATATTGAGCAAATTTCACAAGGTGTTTCTGAGAATACTGAAAATGCAGCTACTACTGAAAAA
ATTGCTGTTAATACTAATGAAAGGACTAAAGAGGGGCATAAATCTGTTGTTAAGGCTATTGAGG
CAATGACTGTAATTACTGAAAAAATTGGAATTATTGATGAGATAACAAGGCAAACCAATTTGCT
TGCTTTAAATGCCTCGATTGAAGCTGCACGAGTGGGAGAAAAGGGCAAGGGATTTGAAGTGGT
AGCTGCTGAGGTTAGAAAGCTTGCAGATCAAAGCAAAGAATCAGCAAGAGAGATTATTGATAT
TGCAAACAGAAGTTTAACTGTTGCAAGTCGTGCTGGGGAAAATTTTGAACAAATAGTTCCTGGT
ATGGAACAAACAGCCAGACTTGTAAAAAATATTTCTAATGAAAGTTATAAGCAAAGTGTTCAA
ATAGAGCAATTTAAAAATGCAATAGAGCAGGTTAGTCAGTTAGTCCAAACTACAGCCTCAAGC

TABLE 1-continued

Nucleotide and Amino Acid Sequences.

AGTGAAGAGCTTTCTGCAATGTCTGAAAAGATGTTAGAGAGTGTAAAAGATTTAAAAGAATCT
GTTGATTATTTTAAGATCGAAAAGTAA f899.aa (SEQ ID NO:53)
MRFIIAFLMILNQGFSNLFSLPPEDIIFESSYEVAIKKAQKLNKNVLILVGRDIKENLIKDFLNS
FTNGEIIHKVSRKSVFLVIDKDNEIFNKINLQKSPTIFFVDSKNEQIKAAYVGAVLSSVQFDKDFLNYV
MGAIKSTSVLKKQKDYEINTADERTFFYKTLKGDWRLKFNGKDRKLVLFDTDLKEFLVFKDINENK
LYAIPKSRIGNIYFSLLGNEEWKLFGKIK t899.aa (SEQ ID NO:54)
LPPEDIIFESSYEVAIKKAQKLNKNVLILVGRDIKENLIKDFLNSFTNGEIIHKVSRKSVFLVIDKDNEIF
NKINLQKSPTIFFVDSKNEQIKAAYVGAVLSSVQFDKDFLNYVMGAIKSTSVLKKQKDYEINTADER
TFFYKTLKGDWRLKFNGKDRKLVLFDTDLKEFLVFKDINENKLYAIPKSRIGNIYFSLLGNEEWKLF
GKIK f899.nt (SEQ ID NO:55)
ATGAGATTTATAATTGCATTTTTAATGATTTTAAATCAAGGATTTTCAAATTTGTTTTCT
TTGCCTCCGGAAGATATTATTTTTGAGAGTTCTTATGAGGTTGCAATTAAAAAAGCTCAAAAAT
TGAATAAAAAATGTTTTAATTTTGGTTGGTAGAGATATTAAAGAAAATTTAATAAAAGATTTTTT
AAACTCTTTTACAATGGTGAAATTATTCACAAAGTATCTAGAAAAAGTGTTTTTTTAGTTATTG
ATAAGGATAATGAAATTTTTAATAAAATTAATCTACAAAAAAGTCCGACTATTTTTTTTGTTGA
TTCTAAGAATGAGCAAATAAAGGCAGCTTATGTGGGAGCTGTTTTGAGCAGTGTTCAATTTGAT
AAGGATTTTTTAAACTATGTTATGGGAGCTATAAAATCAACAAGTGTTTTAAAAAGCAAAAAG
ATTATGAAATTAATACTGCTGATGAGAGAACCTTTTTTTACAAAACATTAAAAGGTGATTGGCG
ATTAAAGTTTAATGGTAAAGACAGAAAGCTTGTTCTTTTTGATACAGATCTTAAAGAATTTTTA
GTTTTTAAAGATATTAATGAAAACAAGCTTTATGCTATTCCTAAGTCTAGGATTGGTAATATTTA
TTTTTCATTATTGGGAAATGAAGAATGGAAGCTTTTTGGAAAAATAAAATAA t899.nt (SEQ ID NO:56)
TTGCCTCCGGAAGATATTATTTTTGAGAGTTCTTATGAGGTTGCAATTAAAAAAGCTCAAAAAT
TGAATAAAAAATGTTTTAATTTTGGTTGGTAGAGATATTAAAGAAAATTTAATAAAAGATTTTTT
AAACTCTTTTACAAATGGTGAAATTATTCACAAAGTATCTAGAAAAAGTGTTTTTTTAGTTATTG
ATAAGGATAATGAAATTTTTAATAAAATTAATCTACAAAAAAGTCCGACTATTTTTTTTGTTGA
TTCTAAGAATGAGCAAATAAAGGCAGCTTATGTGGGAGCTGTTTTGAGCAGTGTTCAATTTGAT
AAGGATTTTTTAAACTATGTTATGGGAGCTATAAAATCAACAAGTGTTTTAAAAAAGCAAAAAG
ATTATGAAATTAATACTGCTGATGAGAGAACCTTTTTTTACAAAACATTAAAAGGTGATTGGCG
ATTAAAGTTTAATGGTAAAGACAGAAAGCTTGTTCTTTTTGATACAGATCTTAAAGAATTTTTA
GTTTTTAAAGATATTAATGAAAACAAGCTTTATGCTATTCCTAAGTCTAGGATTGGTAATATTTA
TTTTTCATTATTGGGAAATGAAGAATGGAAGCTTTTTGGAAAAATAAAATAA f924.aa (SEQ ID NO:57)
MQDRKFSFRKYFLISVFLIFIVSGITYFYSTQMLEKSQKCVEDNLDAKVKLVDMEDFYFDLNECLNM
DDFFIPRPDFLNENLNKNLVVDGLIKNKFLDENFFKDLWIKKENLFNVDIEKENEKLIDKILEISK t924.aa (SEQ LD NO:58)
TQMLEKSQKCVEDNLDAKVKLVDMEDFYFDLNECLNMDDFFIPRPDFLNENLNKNLVVDGLIKNK
FLDENFFKDLWIKKENLFNVDIEKENEKLIDKILEISK f924.nt (SEQ ID NO:59)
ATGCAAGATAGAAAGTTTAGTTTTAGAAAATATTTTTTAATTTCAGTATTTTTGATTTTTATTGT
TTCTGGTATTACTTATTTCTATTCAACACAAATGTTGGAAAAATCTCAAAAGTGTGTTGAAGAC
AATTTAGACGCTAAGGTTAAATTAGTTGATATGGAAGATTTTTATTTTGATTTAAATGAATGTCT
AAATATGGATGATTTTTTTATTCCAAGACCTGATTTTTTAAATGAAAATTTAAATAAGAATTTAG
TTGTTGATGGATTGATTAAAAATAAATTTCTTGATGAGAATTTTTTCAAGGATCTTTGGATTAAA
AAGGAAAATTTATTTAACGTTGATATTGAGAAGGAGAATGAAAAATTAATAGATAAGATTTTA
GAAATTTCCAAATGA t924.nt (SEQ ID NO:60)
ACACAAATGTTGGAAAAATCTCAAAAGTGTGTTGAAGACAATTTAGACGCTAAGGTTAAATTA
GTTGATATGGAAGATTTTTATTTTGATTTAAATGAATGTCTAAATATGGATGATTTTTTTATTCC
AAGACCTGATTTTTTAAATGAAAATTTAAATAAGAATTTAGTTGTTGATGGATTGATTAAAAAT
AAATTTCTTGATGAGAATTTTTTCAAGGATCTTTGGATTAAAAAGGAAAATTTATTTAACGTTG
ATATTGAGAAGGAGAATGAAAAATTAATAGATAAGATTTTAGAAATTTCCAAATGA f925.aa (SEQ ID NO:61)
MIRKYLIYISLLFIVFEVYSKPAFISQDDSYELDFSSGEVDISVNTNSKFNLSFKDESWIYIKSIENEAFI
KLIGESYDNGAVFTFQTFKKEGKIKLVFTYQNVKDSSEFNKIIILKITKNFEVAIPQGVGGGSSRDNNI
ETGNNLELGGGSISGATSKEIIVRALNLSYINDYKGAIDLLNKYNFNDDKYILLKAEIHYKNGDYLKS
YENYLKLKSKYFQSIVFDLIRLAIELNIKEEVLENARYLVEKNVDFSESIYLEIFEFLVTRGEHEFALNF
SSLYFPKYTNSSFSDKYSYLLGKLYESESKHKDFLKALHYYKLVIDNYPFSYYYERAKIRYLFLKRFF
t925.aa (SEQ ID NO:62)
KPAFISQDDSYELDFSSGEVDISVNTNSKFNLSFKDESWIYIKSIENEAFIKLIGESYDNGAVFTFQTFK
KEGKIKLVFTYQNVKDSSEFNKIIILKITKNFEVAIPQGVGGGSSRDNNIETGNNLELGGGSISGATSK
EIIVRALNLSYINDYKGAIDLLNKYNFNDDKYILLKAEIHYKNGDYLKSYENYLKLKSKYFQSIVFDL
IRLAIELNIKEEVLENARYLVEKNVDFSESIYLEIFEFLVTRGEHEFALNFSSLYFPKYINSSFSDKYSYL
LGKLYESESKHKDFLKALHYYKLVIDNYPFSYYYERAKIRYLFLKRFF

TABLE 1-continued

Nucleotide and Amino Acid Sequences.

f925.nt (SEQ ID NO:63)
ATGATTAGAAAATATTTGATTTATATAAGTTTGCTATTTATTGTTTTTGAAGTTTACTCTAAGCC
AGCTTTTATAAGTCAAGACGATTCGTATGAGCTTGATTTTAGTAGTGGAGAGGTAGATATTAGT
GTAAATACCAATTCAAAATTTAATCTTTCTTTTAAAGATGAGTCTTGGATTTATATCAAAAGCAT
TGAAAATGAAGCTTTTATTAAGTTAATTGGAGAATCTTATGATAACGGTGCTGTTTTTACTTTTC
AGACTTTTAAAAAAGAAGGCAAAATTAAATTGGTTTTCACTTATCAAAATGTTAAAGATTCAAG
TGAATTTAATAAAATAATTATCTTGAAAATTACAAAGAATTTTGAAGTTGCAATTCCACAAGGC
GTTGGTGGTGGCTCTAGCAGGGACAATAACATTGAAACTGGTAATAATCTTGAACTTGGGGGG
GGGAGTATTAGCGGGGCAACTTCTAAAGAGATTATTGTTAGGGCTTTAAATTTGTCCTACATAA
ATGATTACAAAGGAGCAATAGATTTGCTTAATAAGTATAATTTCAATGACGATAAATATATTTT
ATTGAAGGCGGAAATTCATTATAAAAATGGTGATTATTTAAAATCTTATGAAAATTATTTGAAA
TTGAAGAGTAAATATTTTCAAAGCATTGTTTTTGATCTAATTAGGCTTGCTATAGAATTAAATAT
TAAAGAAGAGGTTTTAGAGAACGCTAGATATTTAGTTGAAAAGAATGTTGATTTTTCTGAGAGC
ATTTATCTTGAGATCTTTGAATTCTTAGTAACAAGGGGAGAGCATGAGTTTGCTTTAATTTTA
GCTCTCTTTACTTTCCTAAGTATATTAATTCAAGCTTTTCAGACAAATATAGTTATTTGTTGGGA
AAACTTTATGAGTCTGAGAGCAAGCATAAAGATTTTTTAAAGGCTTTGCATTACTATAAATTGG
TTATTGATAATTACCCTTTTAGTTATTATTATGAGAGAGCCAAGATAAGATATTTATTTTTAAAG
CGGTTTTTTTAG t925.nt (SEQ ID NO:64)
AAGCCAGCTTTTATAAGTCAAGACGATTCGTATGAGCTTGATTTTAGTAGTGGAGAGGTAGATA
TTAGTGTAAATACCAATTCAAAATTTAATCTTTCTTTTAAAGATGAGTCTTGGATTTATATCAAA
AGCATTGAAAATGAAGCTTTTATTAAGTTAATTGGAGAATCTTATGATAACGGTGCTGTTTTTA
CTTTTCAGACTTTTAAAAAAGAAGGCAAAATTAAATTGGTTTTCACTTATCAAAATGTTAAAGA
TTCAAGTGAATTTAATAAAATAATTATCTTGAAAATTACAAAGAATTTTGAAGTTGCAATTCCA
CAAGGCGTTGGTGGTGGCTCTAGCAGGGACAATAACATTGAAACTGGTAATAATCTTGAACTTG
GGGGGGGGAGTATTAGCGGGGCAACTTCTAAAGAGATTATTGTTAGGGCTTTAAATTTGTCCTA
CATAAATGATTACAAAGGAGCAATAGATTTGCTTAATAAGTATAATTTCAATGACGATAAATAT
ATTTTATTGAAGGCGGAAATTCATTATAAAAATGGTGATTATTTAAAATCTTATGAAAATTATT
TGAAATTGAAGAGTAAATATTTTCAAAGCATTGTTTTTGATCTAATTAGGCTTGCTATAGAATT
AAATATTAAAGAAGAGGTTTTAGAGAACGCTAGATATTTAGTTGAAAAGAATGTTGATTTTTCT
GAGAGCATTTATCTTGAGATCTTTGAATTCTTAGTAACAAGGGGAGAGCATGAGTTTGCTTTTAA
ATTTTAGCTCTCTTTACTTTCCTAAGTATATTAATTCAAGCTTTTCAGACAAATATAGTTATTTG
TTGGGAAAACTTTATGAGTCTGAGAGCAAGCATAAAGATTTTTTAAAGGCTTTGCATTACTATA
AATTGGTTATTGATAATTACCCTTTTAGTTATTATTATGAGAGAGCCAAGATAAGATATTTATTT
TTAAAGCGGTTTTTTTAG f929.aa (SEQ ID NO:65)
MTKVLVVSAIALLSKDKELIPFYKFLFLFFFFTLLACSKVSKDFIVFNKDVKTSSRIDNPNSNVLEVNK
MEDFFGDIIDLKGYKILSVQQENLNLDVYFEQVVLAQNFSNLNAYLFIIGFDPKIKAGTILFKTQIDID
PKNSYNMYLEDITGDYDFNIVIQGFLKDKSVLYVFQKSVLNDVSSYRPIFFDKVNGTVLINKYARSS
AYEENRSRESYPISLEKYEKVGEDLIISKIEKYEYSNVQGRYCLSSVSEKVGKIDNNIYKTLKNLSKD
EVYKFLHGVWYDVHDYNKMHVKDIDEVLFLSFERQSSEINLFRKNSQEVAKIEYISKPAYNTLNVS
AKSLFSDLIVYNFWIKIVDKENIEIKIDTSTNSYDNSGFSGTFKRFDENVLNVKKGSSDIYFIPSGNYV
YKDKIYDFSYPHLTYIDENKIYYGIFNIFPLKNNFVLEYEIDMGSYKLVESFFLEHSERIVQKQKFSTII
LNPIKILKDDVSLVKGQKLKLERIEKI t929.aa (SEQ ID NO:66)
KDKELIPFYKFLFLFFFFTLLACSKVSKDFIVFNKDVKTSSRIDNPNSNVLEVNKMEDFFGDIIDLKGY
KILSVQQENLNLDVYFEQVVLAQNFSNLNAYLFIIGFDPKIKAGTILFKTQIDIDPKNSYNMYLEDITG
DYDFNIVIQGFLKDKSVLYVFQKSVLNDVSSYRPIFFDKVNGTVLINKYARSSAYEENRSRESYPISL
EKYEKVGEDLIISKIEKYEYSNVQGRYCLSSVSEKVGKIDNNIYKTLKNLSKDEVYKFLHGVWYDV
HDYNKMHVKDIDEVLFLSFERQSSEINLFRKNSQEVAKIEYISKPAYNTLNVSAKSLFSDLIVYNFWI
KIVDKENIEIKIDTSTNSYDNSGFSGTFKRFDENVLNVKKGSSDIYFIPSGNYVYKDKIYDFSYPHLTY
IDENKIYYGIFNIFPLKNNFVLEYEIDMGSYKLVESFFLEHSERIVQKQKTSTIILNPIKILKDDVSLVKG
QKLKLERIEKI f929.nt (SEQ ID NO:67)
ATGACAAAGGTTTTGGTTGTTAGTGCGATTGCTCTTCTGAGTAAGGATAAAGAATTAAT
CCCATTTTATAAATTTTTGTTTTTATTCTTTTTTTTTACATTACTTGCTGTTCCAAGGTAAGCAA
AGATTTTATTGTTTTTAACAAAGATGTAAAGACTTCTTCCAGGATCGATAATCCAAATTCCAAT
GTTTTAGAAGTTAATAAAATGGAAGATTTTTTTGGAGATATTATAGATTTAAAAGGTTATAAAA
TTCTTTCAGTTCAGCAGGAAAATTTAAATTTAGATGTGTATTTTGAGCAGGTGGTTTAGCTCAA
AATTTTTCAAATCTTAATGCATATTTGTTTATTATTGGTTTTGATCCTAAAATTAAAGCTGGAAC
GATTCTTTTTAAAACTCAAATAGATATTGATCCAAAAAATTCTTATAACATGTATCTTGAAGAT
ATTACAGGTGATTATGATTTTAATATAGTTATTCAAGGATTTTTAAAAGATAAATCTGTTTTGTA
TGTTTTTTCAAAAATCTGTTTTAAATGATGTGTCTTCTTATAGGCCTATATTTTTTGACAAAGTTA
ATGGAACTGTTCTTATTAATAAGTATGCAAGATCTTCAGCTTATGAAGAAACAGATCAAGAGA
AAGCTATCCTATTTCTTTAGAAAAATATGAAAAAGTGGGGGAAGATTTAATAATTAGCAAGATT
GAAAAATATGAATATTCTAATGTTCAGGGTAGATATTGTCTTTCTTCTGTGAGCGAAAAAGTTG
GTAAAATTGATAATAATATTTATAAAACTTTAAAGAATTTAAGCAAAGATGAAGTTTATAAATT
TTTGCATGGAGTTTGGTATGATGTTCATGACTATAATAAAATGCATGTCAAAGATATTGATGAA
GTTTTATTCTTGTCTTTGAAAGGCAATCAAGCGAGATTAATCTTTTCAGGAAAAATTCTCAAG
AAGTTGCAAAGATTGAATATATTTCAAAACCTGCTTACAATACTCTTAATGTTAGTGCAAAGTC
TCTTTTTTCAGATTTGATAGTTTATAACTTTTGGATCAAAATTGTAGATAAAGAAAACATTGAA
ATCAAAATTGACACTAGCACAAATTCTTATGATAATAGTGGATTTTCGGGTACATTTAAGAGGT
TTGATGAGAATGTCTTAAATGTTAAAAAAGGGAGTAGTGATATTTATTTTATTCCTAGTGGAAA

TABLE 1-continued

Nucleotide and Amino Acid Sequences.

TTACGTGTATAAGGATAAAATTTATGATTTTTCTTACCCCCATTTAACTTATATTGATGAGAATA
AAATTTATTATGGCATTTTTAATATTTTTCCTTTAAAAAATAATTTTGTTCTTGAATATGAGATT
GACATGGGTAGTTACAAGCTTGTTGAATCTTTTTTCCTTGAGCATAGCGAAAGAATTGTTCAAA
AGCAAAAATTTTCTACAATCATTTTAAATCCTATTAAAATTTTAAAAGATGATGTAAGCTTAGTT
AAAGGGCAAAAATTAAAGCTTGAGCGAATAGAAAAAATATGA t929.nt (SEQ ID NO:68)
AAGGATAAAGAATTAATCCCATTTTATAAATTTTGTTTTTATTCTTTTTTTTTACATTACTTGCT
TGTTCCAAGGTAAGCAAAGATTTTATTGTTTTTAACAAAGATGTAAAGACTTCTTCCAGGATCG
ATAATCCAAATTCCAATGTTTTAGAAGTTAATAAAATGGAAGATTTTTTTGGAGATATTATAGA
TTTAAAAGGTTATAAAATTCTTTCAGTTCAGCAGGAAAATTTAAATTTAGATGTGTATTTTGAG
CAGGTGGTTTTAGCTCAAAATTTTTCAAATCTTAATGCATATTTGTTTATTATTGGTTTTGATCC
TAAAATTAAAGCTGGAACGATTCTTTTTAAAACTCAAATAGATATTGATCCAAAAAATTCTTAT
AACATGTATCTTGAAGATATTACAGGTGATTATGATTTTAATATAGTTATTCAAGGATTTTTAA
AAGATAAATCTGTTTTGTATGTTTTTCAAAAATCTGTTTTAAATGATGTGTCTTCTTATAGGCCT
ATATTTTTTGACAAAGTTAATGGAACTGTTCTTATTAATAAGTATGCAAGATCTTCAGCTTATGA
AGAAAACAGATCAAGAGAAAGCTATCCTATTTCTTTAGAAAAATATGAAAAAGTGGGGGAAGA
TTTAATAATTAGCAAGATTGAAAAATATGAATATTCTAATGTTCAGGGTAGATATTGTCTTTCTT
CTGTGAGCGAAAAAGTTGGTAAAATTGATAATAATATTTATAAAACTTTAAAGAATTTAAGCAA
AGATGAAGTTTATAAATTTTTGCATGGAGTTTGGTATGATGTTCATGACTATAATAAAATGCAT
GTCAAAGATATTGATGAAGTTTTATTCTTGTCTTTTGAAAGGCAATCAAGCGAGATTAATCTTTT
CAGGAAAAATTCTCAAGAAGTTGCAAAGATTGAATATATTTCAAAACCTGCTTACAATACTCTT
AATGTTAGTGCAAAGTCTCTTTTTTCAGATTTGATAGTTTATAACTTTTGGATCAAAATTGTAGA
TAAAGAAAACATTGAAATCAAAATTGACACTAGCACAAATTCTTATGATAATAGTGGATTTTCG
GGTACATTTAAGAGGTTTGATGAGAATGTCTTAAATGTTAAAAAAGGGAGTAGTGATATTTATT
TTATTCCTAGTGGAAATTACGTGTATAAGGATAAAATTTATGATTTTTCTTACCCCCATTTAACT
TATATTGATGAGAATAAAATTTATTATGGCATTTTTAATATTTTTCCTTTAAAAAATAATTTTGT
TCTTGAATATGAGATTGACATGGGTAGTTACAAGCTTGTTGAATCTTTTTTCCTTGAGCATAGCG
AAAGAATTGTTCAAAAGCAAAAATTTTCTACAATCATTTTAAATCCTATTAAAATTTTAAAAGA
TGATGTAAGCTTAGTTAAAGGGCAAAAATTAAAGCTTGAGCGAATAGAAAAAATATGA f933.aa (SEQ ID NO:69)
MNKLLIFVLATFCVFSSFAQANDSKNGAFGMSAGEKLLVYETSKQDPIVPFLLNLFLGFGIGSFAQG
DILGGSLILGFDAVGIGLILAGAYLDIKALDGITKKAAFQWTWGKGVMLAGVVTMAVTRLTEIILPF
TFANSYNRKLKNSLNVALGGFEPSFDVAMGQSSALGFELSFKKSY t933.aa (SEQ ID NO:70)
NDSKNGAFGMSAGEKLLVYETSKQDPIVPFLLNLFLGFGIGSFAQGDILGGSLILGFDAVGIGLILAG
AYLDIKALDGITKKAAFQWTWGKGVMLAGVVTMAVTRLTEIILPFTFANSYNRKLKNSLNVALGG
FEPSFDVAMGQSSALGFELSFKKSY f933.nt (SEQ ID NO:71)
ATGAATAAACTTTTAATTTTTGTTTTGGCAACCTTTTGTGTTTTTTCTAGCTTTGCTCAAGCTAAT
GATTCTAAAAATGGTGCGTTTGGGATGAGTGCTGGAGAAAAACTTTTGGTTTATGAAACTAGCA
AGCAAGATCCTATTGTACCATTTTTATTGAACCTTTTTTTAGGGTTTGGAATAGGCTCCTTTGCT
CAAGGAGATATTCTTGGAGGTTCTCTTATTCTTGGATTTGATGCGGTTGGTATAGGGCTTATACT
TGCGGGGCTTATTTGGATATCAAAGCGCTTGATGGTATTACTAAAAAAGCTGCTTTTCAATGG
ACTTGGGGTAAGGGAGTTATGTTAGCAGGTGTGGTTACTATGGCTGTGACAAGATTAACAGAA
ATTATTCTTCCATTTACATTTGCTAATAGTTATAATAGGAAGCTAAAAAATAGCCTTAATGTAGC
TTTAGGAGGATTTGAACCTAGTTTTGATGTTGCAATGGGCCAATCCAGTGCTCTTGGGTTTGAA
CTGTCTTTCAAAAAAAGCTATTAA t933.nt (SEQ ID NO:72)
AATGATTCTAAAAATGGTGCGTTTGGGATGAGTGCTGGAGAAAAACTTTTGGTTTATGAAACTA
GCAAGCAAGATCCTATTGTACCATTTTTATTGAACCTTTTTTTAGGGTTTGGAATAGGCTCCTTT
GCTCAAGGAGATATTCTTGGAGGTTCTCTTATTCTTGGATTTGATGCGGTTGGTATAGGGCTTA
TACTTGCGGGGGCTTATTTGGATATCAAAGCGCTTGATGGTATTACTAAAAAAGCTGCTTTTCA
ATGGACTTGGGGTAAGGGAGTTATGTTAGCAGGTGTGGTTACTATGGCTGTGACAAGATTAAC
AGAAATTATTCTTCCATTTACATTTGCTAATAGTTATAATAGGAAGCTAAAAAATAGCCTTAAT
GTAGCTTTAGGAGGATTTGAACCTAGTTTTGATGTTGCAATGGGCCAATCCAGTGCTCTTGGGT
TTGAACTGTCTTTCAAAAAAAGCTATTAA f940.aa (SEQ ID NO:73)
MRKYIFIILIAVLLIGVNIKKIAAAANIDRHTNSTLGIDLSVGIPIFYNDLSKAYPTNLYPGGIGAIKYQY
HILNNLAIGLELRYMFNFDINHSFNILNPDSSVGKIFYSVPITFSINYIFDIGELFQIPVFTNIGFSLNTYG
DRNNNITNLRTFDALPTISFGSGILWNFNYKWAFGATASWWMMFEFGNSAKMAHFALVSLSVTVN
VNKL t940.aa (SEQ ID NO:74)
ANIDRHTNSTLGIDLSVGIPIFYNDLSKAYPTNLYPGGIGAIKYQYHILNNLAIGLELRYMFNFDINHS
FNILNPDSSVGKIFYSVPITFSINYIFDIGELFQIPVFTNIGFSLNTYGDRNNNITNLRTFDALPTISFGSGI
LWNFNYKWAFGATASWWMMFEFGNSAKMAHFALVSLSVTVNVNKL f940.nt (SEQ ID NO:75)
ATGAGAAAGTATATTTTTATAATACTAATTGCAGTCTTGCTAATTGGTGTAAACATAAAAAAAA
TTGCGGCCGCAGCCAATATTGATAGGCATACAAACTCCACTTTAGGAATAGATTTAAGTGTAGG
AATCCCTATTTTTTACAACGACTTATCAAAAGCTTATCCTACCAATTTATATCCAGGAGGTATTG

TABLE 1-continued

Nucleotide and Amino Acid Sequences.

```
GGGCAATAAAATACCAGTACCATATTTTAAACAATTTAGCAATTGGACTTGAACTAAGGTATAT
GTTTAACTTTGATATTAACCATTCTTTTAATATATTAAATCCAGATTCAAGTGTAGGTAAAATTT
TTTATAGCGTGCCTATTACATTTTCAATAAATTATATATTTGATATAGGAGAATTATTTCAAATT
CCAGTCTTCACAAATATAGGGTTTTCTCTTAATACATATGGAGATAGAAACAACAATATTACAA
ATTTAAGAACTTTTGATGCACTCCCTACAATCTCTTTTGGATCTGGAATTTTATGGAACTTTAAC
TATAAATGGGCTTTTGGAGCAACAGCATCTTGGTGGATGATGTTTGAATTTGGAAATTCTGCTA
AAATGGCACATTTTGCACTTGTATCATTATCAGTTACAGTGAATGTAAATAAATTGTAG t940.nt (SEQ ID NO:76)
GCCAATATTGATAGGCATACAAACTCCACTTTAGGAATAGATTTAAGTGTAGGAATCCCTATTT
TTTACAACGACTTATCAAAAGCTTATCCTACCAATTTATATCCAGGAGGTATTGGGGCAATAAA
ATACCAGTACCATATTTTAAACAATTTAGCAATTGGACTTGAACTAAGGTATATGTTTAACTTT
GATATTAACCATTCTTTTAATATATTAAATCCAGATTCAAGTGTAGGTAAAATTTTTTATAGCGT
GCCTATTACATTTTCAATAAATTATATATTTGATATAGGAGAATTATTTCAAATTCCAGTCTTCA
CAAATATAGGGTTTTCTCTTAATACATATGGAGATAGAAACAACAATATTACAAATTTAAGAAC
TTTTGATGCACTCCCTACAATCTCTTTTGGATCTGGAATTTTATGGAACTTTAACTATAAATGGG
CTTTTGGAGCAACAGCATCTTGGTGGATGATGTTTGAATTTGGAAATTCTGCTAAAATGGCACA
TTTTGCACTTGTATCATTATCAGTTACAGTGAATGTAAATAAATTGTAG f943.aa (SEQ ID NO:77)
MKNQFLNSYFQLITTIFLISSITIAAEEITSTLKVPNGFKVEIFLNNTIEKPRGITSDQDGNIFIGSGSTFA
YFVTKNRKIYTIAKTLQKPIGIDYWDNKLYISSVDKIYVVKNVKEEINKSIKSHKDYTWKMQIFALLP
KNNSQMHSGRYIKVDSKNNKLIVNIGSQHNVKIPPKKEAVILSINLKTKKEEIVAFGVRNSVGFDFHP
ISNEIYFSDNGQDGLGDNIPPDEINVITEYKEHTGFPYVFGKNQKNYGFYNKAPKNTKFIPSIYELPAH
VAPLGIHFYRGNNFPKEYINKLFIAEHGSWNRSSPVGYKITTLDIDSKTRTARNYKTFLYGFLKHDKS
KFGRPVDIITYYDGSILFTDDFGNKIYRVYYEKI t943.aa (SEQ ID NO:78)
EITSTLKVPNGFKVEIFLNNTIEKPRGITSDQDGNIFIGSGSTFAYFVTKNRKIYTIAKTLQKPIGIDYW
DNKLYISSVDKIYVVKNVKEEINKSIKSHKDYTWKMQIFALLPKNNSQMHSGRYIKVDSKNNKLIV
NIGSQHNVKIPPKKEAVILSINLKTKKEEIVAFGVRNSVGFDFHPISNEIYFSDNGQDGLGDNIPPDEIN
VITEYKEHFGFPYVFGKNQKNYGFYNKAPKNTKFIPSIYELPAHVAPLGIHFYRGNNFPKEYINKLFI
AEHGSWNRSSPVGYKITTLDIDSKTRTARNYKTFLYGFLKHDKSKFGRPVDIITYDDGSILFTDDFGN
KIYRVYYEKI f943.nt (SEQ ID NO:79)
ATGAAAAATCAATTTTTAAATAGCTATTTTCAATTAATTACAACTATTTTCTTAATCTCATCTAT
AACTATTGCAGCAGAAGAAATAACAAGCACACTAAAAGTTCCTAATGGATTTAAAGTCGAAAT
TTTTTTAAACAATACAATTGAAAAACCTAGAGGAATCACAAGCGATCAAGATGGAAATATATTC
ATAGGATCTGGAAGCACTTTTGCATACTTTGTAACAAAAAACAGAAAAATTTATACCATAGCAA
AAACCCTGCAAAAACCTATTGGTATTGATTATTGGGATAATAAACTCTACATATCTTCTGTCGA
TAAAAATATATGTAGTTAAAAATGTAAAAGAAGAAATTAATAAAAGCATAAAATCACATAAAGA
CTATACATGGAAAATGCAAATTTTTGCACTTTTGCCAAAAAATAATTCTCAAATGCACTCAGGA
CGTTACATTAAAGTAGATTCTAAAAATAACAAATTAATAGTAAATATAGGATCCCAGCACAATG
TTAAAATTCCCCCAAAAAAGAAGCAGTAATCCTTAGTATTAATTTAAAAACAAAAAAGAAG
AAATAGTAGCTTTTGGAGTGAGAAACTCAGTTGGGTTTGATTTTCACCCAATTAGCAATGAAAT
ATATTTTAGCGACAATGGCCAAGACGGATTAGGAGACAACATTCCCCCAGATGAAATAAACGT
AATAACCGAATATAAAGAACATTTTGGATTTCCCTATGTGTTTGGAAAAAATCAAAAAAATTAC
GGTTTTTATAACAAAGCACCCAAAAACACTAAGTTTATCCCATCTATTTACGAACTTCCCGCAC
ATGTAGCTCCACTTGGAATACACTTTACCGGGGAAATAACTTTCCAAAAGAATACATAAATAA
ATTATTCATAGCAGAACACGGCTCGTGGAACAGATCTTCTCCTGTTGGCTACAAAATAACAACA
CTAGACATTGATTCTAAAACCAGAACAGCAAGAAATTACAAGACTTTTTTATATGGATTTTAA
AGCACGACAAATCTAAATTTGGACGCCCTGTTGATATAATCACATATTATGACGGTTCAATTCT
TTTTACAGATGACTTTGGAAATAAAATATACAGAGTTTACTACGAAAAGATTTAA t943.nt (SEQ ID NO:80)
GAAATAACAAGCACACTAAAAGTTCCTAATGGATTTAAAGTCGAAATTTTTTTAAACAA
TACAATTGAAAAACCTAGAGGAATCACAAGCGATCAAGATGGAAATATATTCATAGGATCTGG
AAGCACTTTTGCATACTTTGTAACAAAAAACAGAAAAATTTATACCATAGCAAAAACCCTGCAA
AAACCTATTGGTATTGATTATTGGGATAATAAACTCTACATATCTTCTGTCGATAAAAATATATGT
AGTTAAAAATGTAAAAGAAGAAATTAATAAAAGCATAAAATCACATAAAGACTATACATGGAA
AATGCAAATTTTTGCACTTTTGCCAAAAAATAATTCTCAAATGCACTCAGGACGTTACATTAAA
GTAGATTCTAAAAATAACAAATTAATAGTAAATATAGGATCCCAGCACAATGTTAAAATTCCCC
CAAAAAAGAAGCAGTAATCCTTAGTATTAATTTAAAAACAAAAAAGAAGAAATAGTAGCTT
TTGGAGTGAGAAACTCAGTTGGGTTTGATTTTCACCCAATTAGCAATGAAATATATTTTAGCGA
CAATGGCCAAGACGGATTAGGAGACAACATTCCCCCAGATGAAATAAACGTAATAACCGAATA
TAAAGAACATTTTGGATTTCCCTATGTGTTTGGAAAAAATCAAAAAAATTACGGTTTTTATAAC
AAAGCACCCAAAAACACTAAGTTTATCCCATCTATTACGAACTTCCCGCACATGTAGCTCCAC
TTGGAATACACTTTTACCGGGGAAATAACTTTCCAAAAGAATACATAAATAAATTATTCATAGC
AGAACACGGCTCGTGGAACAGATCTTCTCCTGTTGGCTACAAAATAACAACACTAGACATTGAT
TCTAAAACCAGAACAGCAAGAAATTACAAGACTTTTTTATATGGATTTTAAAGCACGACAAAT
CTAAATTTGGACGCCCTGTTGATATAATCACATATTATGACGGTTCAATTCTTTTTACAGATGAC
TTTGGAAATAAAATATACAGAGTTTACTACGAAAAGATTTAA f952.aa (SEQ ID NO:81)
MNYARFAVLIVLLFFYIWFFIILRMKRTNLFLLEKIQNGAKILDIRSPKEYSKSHYLKSINIPFNNLFAK
KDKLGDFESPIIVYGKSFNKSYEAKKVLKSMGFKNVFVAGTLKDMPQAKKEVG
```

TABLE 1-continued

Nucleotide and Amino Acid Sequences.

t952.aa (SEQ ID NO:82)
RMKRTNLFLLEKIQNGAKILDIRSPKEYSKSHYLKSINIPFNNLFAKKDKLGDFESPIIVYGKSFNKSY
EAKKVLKSMGFKNVFVAGTLKDMPQAKKEVG f952.nt (SEQ ID NO:83)
ATGAATTATGCAAGATTTGCAGTATTAATAGTTCTGCTTTTTTTTTATATTTGGTTTTTTATTATC
CTTAGGATGAAAAGAACTAATCTGTTTTTGTTAGAAAAATCCAAAATGGAGCAAAAATTTTGG
ATATTCGGTCTCCCAAAGAATATAGCAAGTCTCATTATTTGAAGTCAATTAACATTCCTTTTAAT
AATTTATTTGCTAAAAAGGATAAATTAGGTGATTTTGAGTCCCCAATAATTGTTTATGGTAAAA
GTTTTAATAAGTCTTACGAGGCTAAAAAAGTTTTAAAAAGCATGGGATTTAAGAATGTGTTTGT
TGCTGGAACCTTGAAAGACATGCCACAAGCAAAAAAAGAAGTTGGTTGA t952.nt (SEQ ID NO:84)
AGGATGAAAAGAACTAATCTGTTTTTGTTAGAAAAAATCCAAAATGGAGCAAAAATTTTGGAT
ATTCGGTCTCCCAAAGAATATAGCAAGTCTCATTATTTGAAGTCAATTAACATTCCTTTTAATAA
TTTATTTGCTAAAAAGGATAAATTAGGTGATTTTGAGTCCCCAATAATTGTTTATGGTAAAAGT
TTTAATAAGTCTTACGAGGCTAAAAAAGTTTTAAAAAGCATGGGATTTAAGAATGTGTTTGTTG
CTGGAACCTTGAAAGACATGCCACAAGCAAAAAAAGAAGTTGGTTGA f378.aa (SEQ ID NO:85)
MIKKFLLFAMLNIFLTNKAHSNEEIIEISTEIQKEKYIPFLISRGKTQLEDLVKYTLEINPELDKNYVNT
VAKTYIDESLIEGVNYDIAYAQMLLETGALKFNGIVSKEQHNFSGIGATNNLTKGNSFSNITEGIKAH
IQHLKAYASKQNIKSNMVDPRFYLVKRGSAPTIYDLTGKWAKDKLYDKKLKKILLELLEYNNANKS t378.aa (SEQ ID NO:86)
NEEIIEISTEIQKEKYIPFLISRGKTQLEDLVKYTLEINPELDKNYVNTVAKTYIDESLIEGVNYDIAYA
QMLLETGALKFNGIVSKEQHNFSGIGATNNLTKGNSFSNITEGIKAHIQHLKAYASKQNIKSNMVDP
RFYLVKRGSAPTIYDLTGKWAKDKLYDKKLKKILLELLEYNNANKS f378.nt (SEQ ID NO:87)
ATGATAAAAAAATTCTTGCTATTTGCAATGCTCAACATCTTTTTAACAAATAAAGCTCATAGTA
ATGAAGAGATAATCGAAATAAGTACTGAAATACAAAAGGAAAAATATATTCCCTTTTTAATAA
GTAGAGGAAAAACTCAACTAGAAGACCTTGTAAAATATACTCTAGAAATAAATCCAGAGCTTG
ACAAAAACTATGTAAATACTGTTGCTAAAACCTATATAGACGAATCTTTGATTGAAGGGGTTAA
TTATGACATTGCCTATGCTCAAATGTTACTAGAAACAGGAGCTCTAAAATTCAATGGAATAGTT
TCAAAAGAACAACACAATTTTTCAGGAATAGGCGCTACTAATAATCTTACAAAAGGAAATTCTT
TTTTCCAATATTACAGAAGGAATTAAAGCTCATATTCAACATTTAAAAGCTTATGCTTCAAAACA
AAATATCAAATCAAATATGGTTGATCCTAGATTTTACCTTGTTAAAAGAGGATCTGCTCCAACA
ATATATGATTTGACTGGGAAATGGGCAAAAGACAAACTTTACGACAAAAAACTTAAAAAAATA
TTATTAGAACTATTAGAATATAATAATGCAAATAAAAGCTAA t378.nt (SEQ ID NO:88)
AATGAAGAGATAATCGAAATAAGTACTGAAATACAAAAGGAAAAATATATTCCCTTTTTAATA
AGTAGAGGAAAAACTCAACTAGAAGACCTTGTAAAATATACTCTAGAAATAAATCCAGAGCTT
GACAAAAACTATGTAAATACTGTTGCTAAAACCTATATAGACGAATCTTTGATTGAAGGGGTTA
ATTATGACATTGCCTATGCTCAAATGTTACTAGAAACAGGAGCTCTAAAATTCAATGGAATAGT
TTCAAAAGAACAACACAATTTTTCAGGAATAGGCGCTACTAATAATCTTACAAAAGGAAATTCT
TTTTTCCAATATTACAGAAGGAATTAAAGCTCATATTCAACATTTAAAAGCTTATGCTTCAAAAC
AAAATATCAAATCAAATATGGTTGATCCTAGATTTTACCTTGTTAAAAGAGGATCTGCTCCAAC
AATATATGATTTGACTGGGAAATGGGCAAAAGACAAACTTTACGACAAAAAACTTAAAAAAAT
ATTATTAGAACTATTAGAATATAATAATGCAAATAAAAGCTAA f4.aa (SEQ ID NO:89)
MKLFRRNVMIKMPSSFTIIFSLIVFVTILTYVIPAGKFDKEFKQMGDGSKREIIVAGTYQYVDRGSRGF
LHPIMTILTAMSKGMEHAVEVIVFVLIVGGAYGIIMKTGAIDVGIYFLIKKLGHKDKLLIPLLMFIFSI
GGTVTGMSEETLPFYFVMIPLIVALGYDSLVGAAIIALGAGVGTMASTVNPFATGIASAIASISLQDG
FYFRIVLYFVSVLAAITYVCVYASKIKKDPSKSLVYSQKDEHYQYFVKKDGLSTGDNAQNALEFTFA
HKLVLLLFGFMILILIFSIVNLGWWMQEMTMLYLGVAIISAFICKLGETEMWDAFVKGSESLLTAAL
VIGLARGVMIVCDDGLITDTMLNAATNFLYNLPRPLFIILNEIIQIFIGFVVPSSSGHASLTMPIMAPLA
DFLSIPRASVVIAMQTASGLINLITPTSGVIMAVLGISRLSYGTWFKFVLPLFMIEFFISILVIIANIYLSF t4.aa (SEQ ID NO:90)
KFDKEFKQMGDGSKREIIVAGTYQYVDRGSRGTLHPIMTILTAMSKGMEHAVEVIVFVLIV
GGAYGIIMKTGAIDVGIYFLIKKLGHKDKLLIPLLMFIFSIGGTVTGMSEETLPFYFVMIPLIVALGYD
SLVGAAIIALGAGVGTMASTVNPFATGIASAIASISLQDGFYFRIVLYFVSVLAAITYVCVYASKIKKD
PSKSLVYSQKDEHYQYFVKKDGLSTGDNAQNALEFTFAHKLVLLLFGFMILILIFSIVNLGWWMQE
MTMLYLGVAIISAFICKLGETEMWDAFVKGSESLLTAALVIGLARGVMIVCDDGLITDTMLNAATN
FLYNLPRPLFIILNEIIQIFIGFVVPSSSGHASLTMPIMAPLADFLSIPRASVVIAMQTASGLINLITPTSG
VIMAVLGISRLSYGTWFKFVLPLFMIEFFISILVIIANIYLSF f4.nt (SEQ ID NO:91)
ATGAAATTATTTAGGAGAAACGTTATGATCAAAATGCCAAGTAGTTTTACAATAATATTTTCTT
TAATTGTATTTGTTACCATTTTAACGTATGTGATTCCTGCCGGTAAGTTTGATAAAGAATTTAAG
CAAATGGGTGATGGATCTAAAAGGGAAATAATTGTTGCTGGAACTTATCAATATGTAGATCGA
GGCTCTAGGGGATTTTTACATCCTATTATGACTATTTTAACCGCAATGTCAAAGGGGATGGAAC
ATGCAGTTGAAGTTATTGTTTTTGTTTTAATTGTTGGGGGTGCTTATGGGATTATTATGAAAACT

TABLE 1-continued

Nucleotide and Amino Acid Sequences.

GGAGCAATAGATGTGGGAATTTATTTTTTAATCAAGAAGTTGGGGCACAAAGATAAGTTGCTTA
TTCCTTTGTTAATGTTTATTTTTTCAATTGGTGGAACTGTAACCGGAATGAGTGAAGAGACCCTT
CCTTTTTATTTTGTTATGATTCCCTTGATAGTAGCTTTGGGTTATGATAGTCTTGTTGGAGCGGC
TATTATTGCTTTAGGAGCTGGAGTGGGAACTATGGCTTCTACTGTAAATCCATTTGCGACAGGA
ATTGCATCTGCAATAGCTTCTATTAGCTTGCAGGATGGATTTTATTTTAGAATTGTTCTTTATTT
TGTATCAGTATTGGCTGCTATAACCTATGTTTGTGTTTATGCGTCTAAAATTAAAAAGGATCCCT
CAAAATCGCTTGTGTATTCTCAAAAAGATGAACATTATCAATATTTTGTTAAAAAAGATGGACT
TTCTACCGGAGATAATGCTCAGAATGCTCTTGAGTTTACTTTTGCTCATAAATTAGTTTTACTTT
TATTTGGATTTATGATATTGATTTTGATATTTAGCATTGTTAATCTTGGTTGGTGGATGCAAGAA
ATGACAATGTTGTATCTTGGAGTTGCTATTATATCGGCTTTATTTGTAAATTAGGTGAAACTGA
AATGTGGGATGCGTTTGTGAAAGGTTCTGAAAGTCTGCTAACCGCTGCTCTTGTTATTGGACTT
GCTAGAGGTGTTATGATAGTATGTGATGATGGGTTGATTACAGATACTATGTTAAATGCTGCTA
CTAATTTTTTATACAATCTTCCAAGACCCCTTTTTATCATATTGAATGAAATTATTCAAATATTT
ATAGGATTTGTTGTTCCATCTTCATCAGGACATGCTAGTCTCACTATGCCAATAATGGCTCCTCT
TGCCGATTTTTTGTCAATTCCAAGAGCTTCAGTTGTTATTGCCATGCAGACTGCATCTGGGCTTA
TTAATTTGATAACACCTACCAGCGGAGTTATAATGGCTGTATTGGGGATATCCAGATTGAGTTA
TGGTACGTGGTTTAAGTTTGTTTTACCATTATTTATGATTGAGTTTTTATCTCTATTTTAGTTAT
TATAGCTAACATTTATTTAAGTTTTTAG t4.nt (SEQ ID NO:92)
AAGTTTGATAAAGAATTTAAGCAAATGGGTGATGGATCTAAAAGGGAAATAATTGTTG
CTGGAACTTATCAATATGTAGATCGAGGCTCTAGGGGATTTTTACATCCTATTATGACTATTTTA
ACCGCAATGTCAAAGGGGATGGAACATGCAGTTGAAGTTATTGTTTTTGTTTTAATTGTTGGGG
GTGCTTATGGGATTATTATGAAAACTGGAGCAATAGATGTGGGAATTTATTTTTTAATCAAGAA
GTTGGGGCACAAAGATAAGTTGCTTATTCCTTTGTTAATGTTTATTTTTCAATTGGTGGAACTG
TAACCGGAATGAGTGAAGAGACCCTTCCTTTTTATTTTGTTATGATTCCCTTGATAGTAGCTTTG
GGTTATGATAGTCTTGTTGGAGCGGCTATTATTGCTTTAGGAGCTGGAGTGGGAACTATGGCTT
CTACTGTAAATCCATTTGCGACAGGAATTGCATCTGCAATAGCTTCTATTAGCTTGCAGGATGG
ATTTTATTTTAGAATTGTTCTTTATTTTGTATCAGTATTGGCTGCTATAACCTATGTTTGTGTTTA
TGCGTCTAAAATTAAAAAGGATCCCTCAAAATCGCTTGTGTATTCTCAAAAAGATGAACATTAT
CAATATTTTGTTAAAAAAGATGGACTTTCTACCGGAGATAATGCTCAGAATGCTCTTGAGTTTA
CTTTTGCTCATAAATTAGTTTTACTTTTATTTGGATTTATGATATTGATTTTGATATTTAGCATTG
TTAATCTTGGTTGGTGGATGCAAGAAATGACAATGTTGTATCTTGGAGTTGCTATTATATCGGC
TTTTTATTTGTAAATTAGGTGAAACTGAAATGTGGGATGCGTTTGTGAAAGGTTCTGAAAGTCTG
CTAACCGCTGCTCTTGTTATTGGACTTGCTAGAGGTGTTATGATAGTATGTGATGATGGGTTGA
TTACAGATACTATGTTAAATGCTGCTACTAATTTTTTATACAATCTTCCAAGACCCCTTTTTATC
ATATTGAATGAAATTATTCAAATATTTATAGGATTTGTTGTTCCATCTTCATCAGGACATGCTAG
TCTCACTATGCCAATAATGGCTCCTCTTGCCGATTTTTTGTCAATTCCAAGAGCTTCAGTTGTTA
TTGCCATGCAGACTGCATCTGGGCTTATTAATTTGATAACACCTACCAGCGGAGTTATAATGGC
TGTATTGGGGATATCCAGATTGAGTTATGGTACGTGGTTTAAGTTTGTTTTACCATTATTTATGA
TTGAGTTTTTATCTCTATTTTAGTTATTATAGCTAACATTTATTTAAGTTTTTAG f43.aa (SEQ ID NO:93)
MKYFYFLFFLLIFNVYAQNVNSPALPSPPLLPEITENKPVERENSSKGENFSNVGLDGKYVN
DTILYGLDSQVTSIIKALKKSSDSQYNFSLKKRLEKTFNAELKREILELFISLKYSGGIDTANYILENYE
SKRYSNALFGLAISYLKEFDDKEKLKKTLIDILENKEGNVVSIAAYYLGELNSLEYSKNMMEVFEKY
SGNDGARREILIALGKMSAVDYQDRIYEISLDNYEGPSIKAAAIEALSYLASDKVTENADLYLQSNN
NNLNVKLAIIASLSKDPSLKSKEILQGFLRDSDDNIRFKAINAIKGHRDSSAKDILIYKLKSDPSLKVRE
ASAKALIDMDLGNIEIKNIMFDFKIDNNFKISMFSYLLDKDSLKALSIALEIVNKENINRPSNVLRGVA
SMLAGKKGNFDNFYSKIIDSKNIDLRHLALKGAVYNKSSSLSDKLKKIKSETNSEYIKMLLKDY t43.aa (SEQ ID NO:94)
LPSPPLLPEITENKPVERENSSKGENFSNVGLDGKYVNDTILYGLDSQVTSIIKALKKSSDSQYNFSLK
KRLEKTFNAELKREILELFISLKYSGGIDTANYILENYESKRYSNALFGLAISYLKEFDDKEKLKKTLI
DILENKEGNVVSIAAYYLGELNSLEYSKNMMEVFEKYSGNDGARREILIALGKMSAVDYQDRIYEIS
LDNYEGPSIKAAAIEALSYLASDKVTENADLYLQSNNNNLNVKLAIIASLSKDPSLKSKEILQGFLRD
SDDNIRFKAINAIKGHRDSSAKDILIYKLKSDPSLKVREASAKALIDMDLGNIEIKNIMFDFKIDNNFKI
SMFSYLLDKDSIKALSIALEIVNKENINRPSNVLRGVASMLAGKKGNFDNFYSKIIDSKNIDLRHLAL
KGAVYNKSSSLSDKLKKIKSETNSEYIKMLLKDY f43.nt (SEQ ID NO:95)
ATGAAATACTTTTATTTTTATTTTTTTACTTATTTTTAATGTGTATGCTCAAAATGTT
AATTCTCCAGCTCTTCCTAGTCCGCCTTTGTTGCCCGAAATTACAGAAAATAAGCCTGTTGAGA
GAGAAAATTCTTCTAAGGGAGAGAATTTTTCTAATGTTGGTTTAGATGGTAAGTATGTTAACGA
TACAATTCTTTATGGGCTTGATAGTCAAGTGACAAGCATTATAAAAGCTCTTAAAAAATCAAGC
GATAGTCAATATAATTTTTCTCTTAAAAAAAGACTTGAGAAAACTTTTAATGCTGAGCCTAAAA
GGGAAATACTTGAATTGTTTATTTCTCTTAAGTATTCGGGGGGCATTGATACAGCAAATTATAT
TCTTGAAAATTATGAGAGTAAAAGATATTCAAACGCTTTATTTGGCTTGGCAATTTCGTATCTTA
AGGAGTTTGATGATAAAGAAAAATTAAAAAAAACTCTTATTGACATTCTTGAAAATAAAGAGG
GCAATGTGGTATCTATTGCAGCTTATTATTAGGAGAGCTTAATTCTCTTGAGTATTCTAAAAAC
ATGATGGAAGTTTTTGAAAAATATTCTGGAAATGATGGGGCTAGAAGAGAAATACTTATTGCTC
TTGGAAAAATGTCCGCTGTTGATTATCAGGATAGAATTTATGAAATTTCGCTAGATAATTACGA
GGGCCCATCAATTAAGGCTGCTGCAATCGAAGCGTTGTCATATCTTGCTTCAGATAAAGTAACT
GAAAATGCTGATTTGTATCTTCAGAGTAATAACAATAATTTAAATGTTAAATTAGCTATTATTG
CTTCTTTGTCCAAAGATCCTTCTTTAAAGTCTAAAGAGATTTTACAAGGATTTTTAAGAGATTCT
GATGATAATATTAGGTTTAAAGCTATTAATGCAATCAAAGGACATAGGGACTCTTCTGCAAAGG
ATATTTTGATTTATAAGCTTAAAAGCGATCCATCTCCTTAAAGTTAGGGAGGCTTCTGCTAAGGC

TABLE 1-continued

Nucleotide and Amino Acid Sequences.

CTTAATTGATATGGATCTTGGGAATATTGAGATAAAAAACATTATGTTTGATTTTAAGATTGAC
AATAATTTTAAAATTTCAATGTTTAGTTACCTTTTAGATAAGGATTCTCTAAAAGCATTGTCAAT
TGCTTTAGAAATTGTTAATAAAGAAAATATTAATAGACCCTCAAATGTTTTAAGGGGCGTTGCT
TCAATGTTGGCTGGTAAAAAGGGTAATTTTGATAATTTTTATTCTAAAATCATTGACAGCAAAA
ATATTGATTTAAGGCATTTAGCATTAAAAGGAGCTGTTTATAATAAATCTTCATCGCTTTCTGAT
AAGCTTAAAAAAATTAAAAGTGAAACGAACTCCGAATATATTAAAATGCTTTTAAAAGATTATT
GA t43.nt (SEQ ID NO:96)
CTTCCTAGTCCGCCTTTGTTGCCCGAAATTACAGAAAATAAGCCTGTTGAGAGAGAAAA
TTCTTCTAAGGGAGAGAATTTTTCTAATGTTGGTTTAGATGGTAAGTATGTTAACGATACAATT
CTTTATGGGCTTGATAGTCAAGTGACAAGCATTATAAAAGCTCTTAAAAAATCAAGCGATAGTC
AATATAATTTTTCTCTTAAAAAAAGACTTGAGAAAACTTTTAATGCTGAGCTTAAAAGGGAAAT
ACTTGAATTGTTTATTCCTCTTAAGTATTCGGGGGGCATTGATACAGCAAATTATATTCTTGAAA
ATTATGAGAGTAAAAGATATTCAAACGCTTTATTTGGCTTGGCAATTTCGTATCTTAAGGAGTT
TGATGATAAAGAAAAATTAAAAAAAACTCTTATTGACATTCTTGAAAATAAAGAGGGCAATGT
GGTATCTATTGCAGCTTATTATTTAGGAGAGCTTAATTCTCTTGAGTATTCTAAAAACATGATG
GAAGTTTTTGAAAAATATTCTGGAAATGATGGGGCTAGAAGAGAAATACTTATTGCTCTTGGAA
AAATGTCCGCTGTTGATTATCAGGATAGAATTTATGAAATTTCGCTAGATAATTACGAGGGCCC
ATCAATTAAGGCTGCTGCAATCGAAGCGTTGTCATATCTTGCTTCAGATAAAGTAACTGAAAAT
GCTGATTTGTATCTTCAGAGTAATAACAATAATTTAAATGTTAAATTAGCTATTATTGCTTCTTT
GTCCAAAGATCCTTCTTTAAAGTCTAAAGAGATTTTACAAGGATTTTTAAGAGATTCTGATGAT
AATATTAGGTTTAAAGCTATTAATGCAATCAAAGGACATAGGGACTCTTCTGCAAAGGATATTT
TGATTTATAAGCTTAAAAGCGATCCATCTCTTAAAGTTAGGGAGGCTTCTGCTAAGGCCTTAAT
TGATATGGATCTTGGGAATATTGAGATAAAAAACATTATGTTTGATTTTAAGATTGACAATAAT
TTTAAAATTTCAATGTTTAGTTACCTTTTAGATAAGGATTCTCTAAAAGCATTGTCAATTGCTTT
AGAAATTGTTAATAAAGAAAATATTAATAGACCCTCAAATGTTTTAAGGGGCGTTGCTTCAATG
TTGGCTGGTAAAAAGGGTAATTTTGATAATTTTTATTCTAAAATCATTGACAGCAAAAATATTG
ATTTAAGGCATTTAGCATTAAAAGGAGCTGTTTATAATAAATCTTCATCGCTTTCTGATAAGCTT
AAAAAAATTAAAAGTGAAACGAACTCCGAATATATTAAAATGCTTTTAAAAGATTATTGA f50.aa (SEQ ID NO:97)
MKFVLNNLFKGCLICFFLFFSCLTTDRSIQDSHISDIVEKKKEAVIIDDNNVVLGSNEGKFKR
DYLIGLKDNESFFLSDAFLKENNFYFKKARESYAKKNIGLTNYYLNKIVTNENQHSRELLAKANLFF
GYVNYENGFYDLSEYNFDLFLKDYKYSHASLRLAELKYLVKEKSDAISAFKEINEFSISGYDREIYGF
LSNKLGVSHLNLESLGFLDNSVFDTFVFNDNIFVTNILGGLLRYNIKKNDCRVYLKDKKSIFLNGIRG
FADYNGTIYIGGKNVVYYIDDVDGDLKQINYPGNADFSNVQVLLAVKNGIFVGTLNSGLWFYDLK
NWKNIPLGSNKISSLCFDSLKNLLLVGTVDKAIYSVNVDNLKKIEHLDFFSKNDNEKNINFIKEYKDS
YFVGTYGGGLFELNLNKNSYKKHVIANNIDVNYFMDMEIKDKKLLFATFDHGLLIYDSENDNWDY
FGPNNGLLNLNLIKVSRFENYVILGTINNGLVFVDENIKKQL t50.aa (SEQ ID NO:98)
CLTTDRSIQDSHISDIVEKKKEAVIIDDNNVVLGSNEGKFKRDYLIGLKDNESFFLSDAFLKE
NNFYFKKARESYAKKNIGLTNYYLNKIVTNENQHSRELLAKANLFFGYVNYENGFYDLSEYNFDLF
LKDYKYSHASLRLAELKYLVKEKSDAISAFKEINEFSISGYDREIYGFLSNKLGVSHLNLESLGFLDNS
VFDTFVFNDNIFVTNILGGLLRYNIKKNDCRVYLKDKKSIFLNGIRGFADYNGTIYIGGKNVVYYIDD
VDGDLKQINVPGNADFSNVQVLLAVKNGIFVGTLNSGLWFYDLKNWKNIPLGSNKISSLCFDSLKN
LLLVGTVDKAIYSVNVDNLKKIEHLDFFSKNDNEKNINFIKEYKDSYFVGTYGGGLFELNLNKNSYK
KHVIANNIDVNYFMDMEIKDKKLLFATFDHGLLIYDSENDNWDYFGPNNGLLNLNLIKVSRFENYV
ILGTINNGLVTVDENIKKQL f50.NT (SEQ ID NO:99)
ATGAAATTTGTTTTGAATAATTTATTTAAAGGTTGTCTTATATGTTTTTTCTTGTTTTTT
TCCTGCCTTACTACAGATAGATCTATTCAAGATTCTCATATTAGTGATATTGTAGAGAAGAAAA
AAGAAGCAGTCATTATTGATGATAATAATGTTGTTCTTGGGAGTAATGAGGGTAAATTTAAAAG
AGACTATTTGATAGGATTAAAAGATAATGAATCTTTTTTCTTAGTGATGCTTTTTTAAAAGAA
AATAATTTTTATTTTAAAAAGCCAGGGAAAGTTATGCTAAAAAAAATATTGGCTTGACAAATT
ATTATTTGAATAAAATAGTAACTAATGAGAATCAGCACAGCAGAATTGCTAGCTAAAGCGA
ATTTGTTTTTGGATATGTAAATTATGAGAATGGTTTTTATGATCTTTTCCGAATATAATTTTGAT
CTATTTTTAAAAGACTATAAATATTCTCATGCTAGTTTAAGATTAGCTGAATTAAAATATCTTGT
TAAAGAAAAATCTGATGCAATTTCTGCATTTAAAGAGATTAATGAATTTTCTATCTCAGGTTAT
GATAGAGAGATTTATGGCTTTTTAAGTAATAAACTTGGAGTAAGTCATTTAAACTTAGAGTCTT
TAGGATTTCTTGACAACAGCGTTTTGATACATTTGTCTTTAATGACAATATATTTGTAACTAAT
ATATTGGGAGGGCTTTTAAGATATAATATTAAAAAAAATGATTGTAGAGTCTATCTTAAGGATA
AAAAAAGCATTTTTTTAAATGGCATTAGGGGTTTTGCGGATTATAATGGAACAATTTATATTGG
TGGTAAAAATGTTGTTTATTATAGATGATGTTGATGGGGATTTAAAGCAAATAAATGTTCCC
GGTAATGCTGATTTTAGCAATGTACAAGTTTTGCTTGCTGTTAAAAATGGAATATTTGTTGGCA
CTCTAAATTCTGGATTATGGTTTTATGATTTAAAAAATTGGAAAAATATACCGCTTGGATCTAA
TAAAATTTCTTCACTCTGCTTTGATAGTTTAAAAAATTTATTATTAGTTGGAACAGTTGACAAGG
CTATTTATAGTGTTAATGTCGATAATTTGAAAAAGATTGAACATTTGGATTTTTTAGCAAAAA
TGATAATGAAAAAATATTAATTTTATAAAAGAATATAAAGATAGTTATTTTGTTGGAACATAT
GGTGGGGTCTTTTGAATTAAATTTAAATAAAAATAGTTGCAAAAGCACGTTATTGCCAATA
ATATTGATGTTAATTATTTTATGGATATGGAGATTAAAGATAAAAAGCTATTGTTTGCAACCTT
TGATCATGGGTTATTGATTTATGGATTCTGAAAATGACAACTGGGATTATTTTGGACCCAATAAT
GGGCTTCTTAATTTGAATTTAATAAAAGTTTCTAGATTTGAAAATTATGTCATACTGGGCACTAT
TAATAACGGTTTGGTTTTTGTAGATGAAAATATTAAAAAACAGTTATGA

TABLE 1-continued

Nucleotide and Amino Acid Sequences.

t50.nt (SEQ ID NO:100)
TGCCTTACTACAGATAGATCTATTCAAGATTCTCATATTAGTGATATTGTAGAGAAGAAAAG
AAGCAGTCATTATTGATGATAATAATGTTGTTCTTGGGAGTAATGAGGGTAAATTTAAAAGAGA
CTATTTGATAGGATTAAAAGATAATGAATCTTTTTTTCTTAGTGATGCTTTTTTAAAAGAAATA
ATTTTTATTTTAAAAAAGCCAGGGAAAGTTATGCTAAAAAAAATATTGGCTTGACAAATTATTA
TTTGAATAAAATAGTAACTAATGAGAATCAGCACAGCAGAGAATTGCTAGCTAAAGCGAATTT
GTTTTTTGGATATGTAAATTATGAGAATGGTTTTTATGATCTTTCCGAATATAATTTTGATCTAT
TTTTAAAAGACTATAAATATTCTCATGCTAGTTTAAGATTAGCTGAATTAAAATATCTTGTTAAA
GAAAAATCTGATGCAATTTCTGCATTTAAAGAGATTAATGAATTTTCTATCTCAGGTTATGATA
GAGAGATTTATGCTTTTTAAGTAATAAACTTGGAGTAAGTCATTTAAACTTAGAGTCTTTAGG
ATTTCTTGACAACAGCGTTTTTGATACATTTGTCTTTAATGACAATATATTTGTAACTAATATAT
TGGGAGGCTTTTAAGATATAATATTAAAAAAATGATTGTAGAGTCTATCTTAAGGATAAAAA
AAGCATTTTTTAAATGGCATTAGGGGTTTTGCGGATTATAATGGAACAATTTATATTGGTGGT
AAAAATGTTGTTTATTATATAGATGATGTTGATGGGGATTTAAAGCAAATAAATGTTCCCGGTA
ATGCTGATTTTAGCAATGTACAAGTTTTGCTTGCTGTTAAAAATGGAATATTTGTTGGCACTCTA
AATTCTGGATTATGGTTTTATGATTTAAAAAATTGGAAAAATATACCGCTTGGATCTAATAAAA
TTTCTTCACTCTGCTTTGATAGTTTAAAAAATTTATTATTAGTTGGAACAGTTGACAAGGCTATT
TATAGTGTTAATGTCGATAATTTGAAAAAGATTGAACATTTGGATTTTTTTAGCAAAAATGATA
ATGAAAAAAATATTAATTTTATAAAAGAATATAAAGATAGTTATTTTGTTGGAACATATGGTGG
GGGTCTTTTTGAATTAAATTTAAATAAAAATAGTTACAAAAAGCACGTTATTGCCAATAATATT
GATGTTAATTATTTTATGGATATGGAGATTAAAGATAAAAAGCTATTGTTTGCAACCTTTGATC
ATGGGTTATTGATTTATGATTCTGAAAATGACAACTGGGATTATTTTGGACCCAATAATGGGCT
TCTTAATTTGAATTTAATAAAAGTTTCTAGATTTGAAAATTATGTCATACTGGGCACTATTAATA
ACGGTTTGGTTTTTGTAGATGAAAATATTAAAAAACAGTTATGA f65.aa (SEQ ID NO:101)
MHIFKNVPFQINLILFLLVSVAKINASSKFYYAEQWYVIFNSQMKKKPENYKKNIFFLQKALKYPFG
NPKYSLTKIETKEQWEKYKLLFKMHVNLLLVRQNLHLGDLFDTRNLYFFKTPEKDGIISNLEKSKKL
YKLAINYYSEALKYHKKLENYTTVKLENDGITNWEDEYHKISLKELNYYDIIKKELLRIDETKAFFE
QGPNYY t65.aa (SEQ ID NO:102)
KINASSKFYYAEQWYVIFNSQMKKKPENYKKNIFFLQKALKYPFGNPKYSLTKIETKEQWEKYKLL
FKMHVNLLLVRQNLHLGDLFDTRNLYFFKTPEKDGIISNLEKSKKLYKLAINYYSEALKYHKKLEN
YTTVKLENDGITNWEDEYHKISLKELNYYDIIKKELLRIDETKAFFEQGPNYY f65.nt (SEQ ID NO:103)
ATGCATATTTTCAAAAATGTCCCCTTCCAAATAAATTTAATTTTATTTCTTTTAGTATCAGTTGC
AAAGATAAATGCATCGTCCAAATTTTATTACGCAGAACAATGGTATGTAATTTTTAATTCTCAA
ATGAAAAAAAAACCTGAAAACTATAAAAAAAATATATTTTTTCTTCAAAAAGCCTTAAAATACC
CATTTGGAAATCCAAAATATTCTCTAACTAAAATAGAAACCAAAGAACAGTGGGAAAAATATA
AACTTCTTTTCAAAATGCATGTAAACTTGCTTCTACTTAGGCAAAATTTACATTTAGGAGATTTA
TTCGACACAAGAAATTTATATTTTTTCAAAACTCCAGAAAAAGATGGAATTATTTCCAATCTAG
AAAAATCAAAAAAATTATATAAACTAGCTATTAATTACTACAGCGAAGCACTAAAATACCACAA
AAAACTTGAAAATTACACAACTGTTAAACTAGAAAACGATGGAATAACAAACTGGGAAGATGA
ATATCATAAAATTTCTCTTAAAGAGCTTAATTACTATGACATTATTAAAAAAGAACTACTAAGA
ATTGACGAAACTAAAGCATTTTTTGAACAAGGGCCAAACTATTATTAA t65.nt (SEQ ID NO:104)
AAGATAAATGCATCGTCCAAATTTTATTACGCAGAACAATGGTATGTAATTTTTAATTCTCAAA
TGAAAAAAAAACCTGAAAACTATAAAAAAAATATATTTTTTCTTCAAAAAGCCTTAAAATACCC
ATTTGGAAATCCAAAATATTCTCTAACTAAAATAGAAACCAAAGAACAGTGGGAAAAATATAA
ACTTCTTTTCAAAATGCATGTAAACTTGCTTCTAGTAGGCAAAATTTACATTTAGGAGATTTAT
TCGACACAAGAATTTATATTTTTCAAAACTCCAGAAAAGATGGAATTATTTCCAATCTAGA
AAAATCAAAAAAATTATATAAACTAGCTATTAATTACTACAGCGAAGCACTAAAATACCACAAA
AACTTGAAAATTACACAACTGTTAAACTAGAAAACGATGGAATAACAAACTGGGAAGATGAA
TATCATAAAATTTCTCTTAAAGAGCTTAATTACTATGACATTATTAAAAAAGAACTACTAAGAA
TTGACGAAACTAAAGCATTTTTTGAACAAGGGCCAAACTATTATTAA f8.aa (SEQ ID NO:105)
MKNINRLILLILTTHTLLFSCALIADNKSKNLSTSEIILTQKTLLESSLIKNPSNVEYRIPISSIQEILNNN
NDSFLIKKTAAKIKISPQKLEEIKNYLNAYKNYLNNETEWIKFIDQSSVNGNLTIKIDTAFEKKTNFNH
TNSDNENLTELIELQMHLEKEILNLIEQTFHDKNLGYIQLSHINSFFPQENINSITKEIIDGKEYIAPHIIA
NQLLKIKDKKYFEQFMHFLKVENSKIKTIIEKQKISDLHNELYYSKQSPPRRRKRSTADSDNNNKYDI
IPKIIDPNTGIEITPKNLRSILSNGDIILIKPKIDWTEFFYFWQHVGIFDEEKYEATKKIATNGIDSFDIKSI
ITSNQIKFDTASTQGSGYEKLSTYVQSRILKIFSPITDIRTIQKAINFGRSRYIDNNFGYMVPLISSNLWT
DSFNLEEIHNKTYCSLMVDRIYKIAGLNVSRNYEISGIITPGEINAAAYNFYMSYTIAGILPSVLPKRLI
KPTLKEKFIGYNKEIVDAIELKKSKEKIFGRACNITNLWCSGS t8.aa (SEQ ID NO:106)
CALIADNKSKNLSTSEIILTQKTLLESSLIKNPSNVEYRIPISSIQEILNNNNDSFLIKKTAAKIKISPQKL
EEIKNYLNAYKNYLNNETEWIKFIDQSSVNGNLTIKIDTAFEKKTNFNHTNSDNENLTELIELQMHLE
KEILNLIEQTFHDKNLGYIQLSHINSFFPQENINSITKEIIDGKEYIAPHIIANQLLKIKDKKYFEQFMHF
LKVENSKIKTIIEKQKISDLHNELYYSKQSPPRRRKRSTADSDNNNKYDIIPKIIDPNTGIEITPKNLRSI
LSNGDIILIKPKIDWTEFFYFWQHVGIFDEEKYEATKKIAFNGIDSFDIKSIITSNQIKFDTASTQGSGY
EKLSTYVQSRILKIFSPITDIRTIQKAINFGRSRYIDNNFGYMVPLISSNLWTDSFNLEEIHNKTYCSLM
VDRIYKIAGLNVSRNYEISGIITPGEINAAAYNFYMSYTIAGILPSVLPKRLIKPTLKEKFIGYNKEIVD

TABLE 1-continued

Nucleotide and Amino Acid Sequences.

AIELKKSKEKIFGRACNITNLWCSGS f8.nt (SEQ ID NO:107)
ATGAAGAATATTAATAGATTAATATTATTAATATTAACTACACACACTTTATTATTCTCTTGTGC
CTTAATTGCAGATAATAAGTCAAAAAATTTAAGCACATCAGAAATCATATTAACACAAAAAACA
CTACTAGAAAGCTCTTTAATAAAAAATCCTTCTAATGTAGAATATCGAATACCAATATCCAGTA
TCCAAGAAATTTTAAACAATAACAATGATTCTTTTTTAATAAAAAAAAACAGCAGCAAAAATCAA
AATAAGCCCTCAAAAACTTGAAGAAATAAAAAACTATCTAAATGCTTATAAAAATTATCTAAAT
AATGAAACAGAATGGATAAAGTTTATAGATCAAAGTAGCGTCAATGGAAATTTAACAATTAAA
ATTGATACTGCTTTTGAAAAAAAAACAAATTTTAATCATACAAATTCAGATAATGAAAATTTAA
CAGAACTAATAGAACTACAAATGCATCTGGAAAAAGAAATTTTAAACTTAATTGAGCAAACATT
TCATGATAAAAATTTAGGATATATACAATTAAGTCACATCAACTCATTCTTTCCTCAAGAAAAT
ATAAACTCAATAACAAAAGAAATAATAGATGGAAAAGAATATATTGCACCGCACATAATAGCA
AATCAATTATTAAAAATAAAAGATAAAAATATTTTGAACAATTTATGCACTCTTTTTAAAAGTTG
AAAACAGCAAAATAAAAACAATAATTGAAAAACAAAAAAATTTCAGATCTTCACAATGAACTGT
ATTATTCAAAACAATCCCCGCCCAGAAGAAGAAAAAGGTCAACTGCCGATTCCGATAATAACA
ATAAATACGATATAATACCAAAAATAATAGACCCAAATACAGGCATTGAAATAACTCCTAAAA
ATTTAAGATCTATTTTATCAAATGGCGACATAATACTAATAAAACCAAAAATAGATTGGACAGA
ATTTTTTTATTTTTGGCAACATGTGGGAATATTTGATGAAGAAAAATATGAAGCCACTAAAAAA
ATTGCATTCAATGGAATTGATAGCTTTGATATAAAATCAATAATTACAAGCAATCAAATCAAAT
TCGATACAGCATCTACTCAAGGTTCAGGATACGAAAAGCTTTCAACATACGTACAATCAAGAAT
ATTAAAAATATTCTCACCAATAACAGACATAAGAACAATTCAAAAAGCTATTAATTTTGGAAGA
AGTAGATACATTGACAATAACTTTGGATATATGGTTCCATTAATATCCTCTAATTTATGGACAG
ATTCATTCAATCTTGAAGAAATTCACAACAAAACCTATTGCTCTTTAATGGTTGATAGAATATA
TAAAATAGCAGGACTTAATGTATCAAGAAATTACGAAATTTCGGGAATAATTACTCCTGGAGAA
ATAAATGCAGCAGCTTACAATTTTTACATGTCTTATACGATTGCAGGAATACTTCCAAGCGTGC
TTCCAAAAAGGCTCATTAAACCAACATTAAAAGAAAAATTCATTGGTTACAATAAAGAAATAGT
AGATGCAATAGAATTAAAAAAAATCGAAAGAAAAAATTTTTGGGAGAGCTTGCAACATTACAAA
TCTCTGGTGCTCAGGAAGTTAA t8.nt (SEQ ID NO:108)
TGTGCCTTAATTGCAGATAATAAGTCAAAAAATTTAAGCACATCAGAAATCATATTAACACAAA
AAACACTACTAGAAAGCTCTTTAATAAAAAATCCTTCTAATGTAGAATATCGAATACCAATATC
CAGTATCCAAGAAATTTTAAACAATAACAATGATTCTTTTTTAATAAAAAAAAACAGCAGCAAAA
ATCAAAATAAGCCCTCAAAAACTTGAAGAAATAAAAAACTATCTAAATGCTTATAAAAATTATC
TAAATAATGAAACAGAATGGATAAAGTTTATAGATCAAAGTAGCGTCAATGGAAATTTAACAA
TTAAAATTGATACTGCTTTTGAAAAAAAAACAAATTTTAATCATACAAATTCAGATAATGAAAA
TTTAACAGAACTAATAGAACTACAAATGCATCTGGAAAAAGAAATTTTAAACTTAATTGAGCAA
ACATTTCATGATAAAAATTTAGGATATATACAATTAAGTCACATCAACTCATTCTTTCCTCAAGA
AAATATAAACTCAATAACAAAAGAAATAATAGATGGAAAAGAATATATTGCACCGCACATAAT
AGCAAATCAATTATTAAAAATAAAGATAAAAATATTTTGAACAATTTATGCACTTTTTAAAA
GTTGAAAACAGCAAAATAAAAACAATAATTGAAAAACAAAAAAATTTCAGATCTTCACAATGAA
CTGTATTATTCAAAACAATCCCCGCCCAGAAGAAGAAAAAGGTCAACTGCCGATTCCGATAATA
ACAATAAATACGATATAATACCAAAAATAATAGACCCAAATACAGGCATTGAAATAACTCCTA
AAAATTTAAGATCTATTTTATCAAATGGCGACATAATACTAATAAAACCAAAAATAGATTGGAC
AGAATTTTTTTATTTTTGGCAACATGTGGGAATATTTGATGAAGAAAAATATGAAGCCACTAAA
AAAATTGCATTCAATGGAATTGATAGCTTTGATATAAAATCAATAATTACAAGCAATCAAATCA
AATTCGATACAGCATCTACTCAAGGTTCAGGATACGAAAAGCTTTCAACATACGTACAATCAAG
AATATTAAAAATATTCTCACCAATAACAGACATAAGAACAATTCAAAAAGCTATTAATTTTGGA
AGAAGTAGATACATTGACAATAACTTTGGATATATGGTTCCATTAATATCCTCTAATTTATGGA
CAGATTCATTCAATCTTGAAGAAATTCACAACAAAACCTATTGCTCTTTAATGGTTGATAGAAT
ATATAAAATAGCAGGACTTAATGTATCAAGAAATTACGAAATTTCGGGAATAATTACTCCTGGA
GAAATAAATGCAGCAGCTTACAATTTTTACATGTCTTATACGATTGCAGGAATACTTCCAAGCG
TGCTTCCAAAAAGGCTCATTAAACCAACATTAAAAGAAAAATTCATTGGTTACAATAAAGAAAT
AGTAGATGCAATAGAATTAAAAAAAATCGAAAGAAAAAATTTTTGGGAGAGCTTGCAACATTAC
AAATCTCTGGTGCTCAGGAAGTTAA f82.aa (SEQ ID NO:109)
MTRVFSKFFLFFCFSMLLFANSEDSNEKDIVSKDENPVFENEVLGYWVGYNDVSNIKNSIIYIYKYN
GEVYGRILTIIKDGKKYDAKNPSGDTVVGFENLAIEGLDFMWGLKYSSSSKKWDRGKIIDPKNGKIY
NSEMRVDSKTGNLITKGKVWIFGRSKIWTRAKDDEIPKLDLHNLVPAPPVKK t82.aa (SEQ ID NO:110)
EDSNEKDIVSKDENPVFENEVLGYWVGYNDVSNIKNSIIYIYKYNGEVYGRILTIIKDGKKYDAKNP
SGDTVVGFENLAIEGLDFMWGLKYSSSSKKWDRGKIIDPKNGKIYNSEMRVDSKTGNLITKGKVWI
FGRSKIWTRAKDDEIPKLDLHNLVPAPPVKK f82.nt (SEQ ID NO:111)
ATGACTAGAGTTTTTTCAAAGTTTTTTCTTTTTTTTGTTTTTCAATGCTTTTATTTGCAAATTCA
GAAGATTCAAATGAAAAGGACATTGTTAGCAAGGATGAAAACCCTGTTTTTGAAAATGAAGTT
TTAGGATATTGGGTTGGTTATAATGATGTAAGTAACATAAAGAATTCTATTATCTATATTTATA
AATATAATGGGAAGTTTATGGCCGAATTTTAACTATAATAAAAGATGGCAAAAAGTATGATG
CTAAAAATCCTTCAGGAGATACTGTAGTTGGGTTTGAAAATCTTGCAATAGAGGGTCTTGATTT
TATGTGGGGTCTTAAGTATTCTTCTTCTTCTAAAAAGTGGGATAGGGGCAAAATAATAGATCCT
AAAAACGGTAAAATTTATAATTCTGAGATGCGTGTTGATAGTAAAACCGGAAATCTTATTACCA
AGGGGAAAGTTTGGATTTTTGGTAGAAGTAAAATTTGGACAAGAGCTAAAGATGATGAAATAC
CAAAATTAGATTTGCATAATCTTGTTCCAGCGCCCCCTGTGAAAAAATAA

TABLE 1-continued

Nucleotide and Amino Acid Sequences.

f82.nt (SEQ ID NO:112)
GAAGATTCAAATGAAAAGGACATTGTTAGCAAGGATGAAAACCCTGTTTTTGAAAATGAAGTT
TTAGGATATTGGGTTGGTTATAATGATGTAAGTAACATAAAGAATTCTATTATCTATATTTATA
AATATAATGGGGAAGTTTATGGCCGAATTTTAACTATAATAAAAGATGGCAAAAAGTATGATG
CTAAAAATCCTTCAGGAGATACTGTAGTTGGGTTTGAAAATCTTGCAATAGAGGGTCTTGATTT
TATGTGGGGTCTTAAGTATTCTTCTTCTTCTAAAAAGTGGGATAGGGGCAAAATAATAGATCCT
AAAAACGGTAAAATTTATAATTCTGAGATGCGTGTTGATAGTAAAACCGGAAATCTTATTACCA
AGGGGAAAGTTTGGATTTTTGGTAGAAGTAAAATTTGGACAAGAGCTAAAGATGATGAAATAC
CAAAATTAGATTTGCATAATCTTGTTCCAGCGCCCCCTGTGAAAAAATAA f86.aa (SEQ ID NO:113)
MNKLMLMLITFATSLLAQTNKASTGLKTDQSTNNSLSESVKLKEIADIYPTNTNFLTGIGIV
AGLAGKGDSIKQKDLIIKILEENNIINEIGSNNIESKNIALVNVSLQVKGNTIKGSKHKACVASILDSKD
LTNGILLKTNLKNKEGEIIAIASGITQPNNKLKGSGYTIDSVIINENQNINHSYNIILKKGNYTLINRIHK
ILTSKKINNKIKSDSTIEIEAKNISLLEEIENIKIETNPKILIDKKNGIILASENAKIGTFTFSIEKDNQNIFL
SKNNKTTIQVNSMKLNEFILKNSNNLSNKELIQIIQAAQKINKLNGELILEEIDGNQN t86.aa (SEQ ID NO:114)
LKTDQSFNNSLSESVKLKEIADIYPTNTNFLTGIGIVAGLAGKGDSIKQKDLIIKILEENNIINEIGSNNI
ESKNIALVNVSLQVKGNTIKGSKHKACVASILDSKDLTNGILLKTNLKNKEGEIIAIASGITQPNNKLK
GSGYTIDSVIINENQNINHSYNIILKKGNYTLINRIHKILTSKKINNKIKSDSTIEIEAKNISLLEEIENIKI
ETNPKILIDKKNGIILASENAKIGTFTFSIEKDNQNIFLSKNNKTTIQVNSMKLNEFILKNSNNLSNKEL
IQIIQAAQKINKLNGELILEEIDGNQN f86.nt (SEQ ID NO:115)
ATGAACAAACTAATGTTGATGTTAATTACATTTGCAACGAGTCTATTAGCCCAAACAAACAAAG
CTTCAACAGGACTAAAAACAGATCAATCATTTAACAATAGCCTATCTGAAAGCGTAAAATTAAA
AGAAATTGCGGATATTTATCCCACAAATACAAATTTTTTAACAGGTATTGGAATAGTAGCGGGA
CTTGCTGGAAAAGGAGACTCTATAAAACAAAAAGACCTTATAATTAAAATTTTAGAAGAAAAC
AATATAATAAATGAAATAGGCTCTAATAACATAGAAAGTAAAATATATTGCACTAGTAAATGTC
AGTCTCCAAGTAAAAGGTAATACAATCAAAGGTTCAAAACATAAAGCTTGCGTTGCATCAATAC
TGGACTCAAAAGATTTAACAAATGGAATACTTTTAAAAACAAATCTTAAAAATAAAGAGGGGG
AAATAATAGCAATTGCATCAGGAATTACACAGCCCAATAATAAATTAAAAGGATCTGGATATA
CTATAGATAGTGTAATAATAAATGAGAATCAAAATATTAACCACAGTTATAATATAATTCTTAA
AAAAGGAAATTATACATTAATAAATAGAATTCATAAAATATTAACCTCTAAAAAAATCAACAAC
AAAATTAAATCAGACAGCACAATAGAAATAGAAGCAAAAAACATAAGCCTATTAGAAGAGATT
GAAAATATTAAAATAGAAACCAACCCCAAGATATTAATAGACAAAAAAAATGGTATTATTTTA
GCAAGTGAAAATGCAAAAATAGGAACTTTTACATTTTCCATTGAAAAAGACAATCAAAACATTT
TTTTAAGTAAAAATAACAAAACAACAATTCAAGTAAACTCAATGAAATTAAATGAATTTATATT
AAAAAAATTCCAACAATCTTAGCAATAAAGAATTAATTCAAATAATTCAAGCTGCGCAAAAAATT
AATAAATTAAATGGGGAACTTATCTTGGAGGAAATTGATGGAAACCAAAATTAA t86.nt (SEQ ID NO:116)
CTAAAAACAGATCAATCATTTAACAATAGCCTATCTGAAAGCGTAAAATTAAAAGAAATTGCG
GATATTTATCCCACAAATACAAATTTTTTAACAGGTATTGGAATAGTAGCGGGACTTGCTGGAA
AAGGAGACTCTATAAAACAAAAAGACCTTATAATTAAAATTTTAGAAGAAAACAATATAATAA
ATGAAATAGGCTCTAATAACATAGAAAGTAAAATATTGCACTAGTAAATGTCAGTCTCCAAGT
AAAAGGTAATACAATCAAAGGTTCAAAACATAAAGCTTGCGTTGCATCAATACTGGACTCAAA
AGATTTAACAAATGGAATACTTTTAAAAACAAATCTTAAAAATAAAGAGGGGGAAATAATAGC
AATTGCATCAGGAATTACACAGCCCAATAATAAATTAAAAGGATCTGGATATACTATAGATAGT
GTAATAATAAATGAGAATCAAAATATTAACCACAGTTATAATATAATTCTTAAAAAAGGAAATT
ATACATTAATAAATAGAATTCATAAAATATTAACCTCTAAAAAAATCAACAACAAAATTAAATC
AGACAGCACAATAGAAATAGAAGCAAAAAACATAAGCCTATTAGAAGAGATTGAAAATATTAA
AATAGAAACCAACCCCAAGATATTAATAGACAAAAAAAATGGTATTATTTTAGCAAGTGAAAA
TGCAAAAATAGGAACTTTTACATTTTCCATTGAAAAAGACAATCAAAACATTTTTTTAAGTAAA
AATAACAAAACAACAATTCAAGTAAACTCAATGAAATTAAATGAATTTATATTAAAAAAATTCCA
ACAATCTTAGCAATAAGAATTAATTCAAATAATTCAAGCTGCGCAAAAAATTAATAAATTAAA
TGGGGAACTTATCTTGGAGGAAATTGATGGAAACCAAAATTAA f90.aa (SEQ ID NO:117)
MCPITFTIPFFLAIFFAFSSSFVTDSSVSLLSRNTSLFSTLTPISLPIISGTLPAIVTLSKKYLSISLSFSKMIF
IKSLFEVIKLPIWLFIIFASGYFLNAFSIFLCISSFLSFMFI t90.aa (SEQ ID NO:118)
SSFVTDSSVSLLSRNTSLFSTLTPISLPIISGTLPAIVTLSKKYLSISLSFSKMIFIKSLFEVIKLPIWLFIIFA
SGYFLNAFSIFLCISSFLSFMFI f90.nt (SEQ ID NO:119)
ATGTGTCCTATTACTTTTACCATTCCATTTTTTCTAGCAATATTTTTTGCTTTTTCAAGCTCCTTT
GTTACGGACTCTTCTGTGTCTTTGCTATCAAGAAATACGTCTCTTTTTTCTACTTTAACTCCAATT
TCTTTGCCTATTATTTCTGGTACGCTTCCTGCAATAGTTACGCTGTCGAAAAAATATCTGTCAAT
CTCTTTAAGCTTTTCTAAAATGATTTTCATCAAATCTTTATTTGAAGTGATTAAACTTCCCATAT
GGTTATTCATTATTTTTGCATCAGGATACTTTTTAAATGCTTTTTCGATTTTTTTGTGTATTTCTT
CTTTTTTATCTTTTATGTTTATATGA t90.nt (SEQ ID NO:120)

TABLE 1-continued

Nucleotide and Amino Acid Sequences.

AGCTCCTTTGTTACGGACTCTTCTGTGTCTTTGCTATCAAGAAATACGTCTTTTTTCTACTTTA
ACTCCAATTTCTTTGCCTATTATTTCTGGTACGCTTCCTGCAATAGTTACGCTGTCGAAAAAATA
TCTGTCAATCTCTTTAAGCTTTTCTAAAATGATTTTCATCAAATCTTTATTTGAAGTGATTAAAC
TTCCCATATGGTTATTCATTATTTTTGCATCAGGATACTTTTTAAATGCTTTTTCGATTTTTTGT
GTATTTCTTCTTTTTTATCTTTTATGTTTATATGA f469.aa (SEQ ID NO:121)
MANVALSSGFISQKIFGIIIMVFLPTIIATPIINFLFKINKSGLKKELPIDQNTHICVSFEYDNLAKILIWD
FKNELRKEGFFTQQIKNDSSQYINARKNNISFSIKREGSKITFECPNNHLIIIQDLFRETILNLEKITKEV
ETVSLRAKKLDYSINYDKILSNINLNKRIKKENIILELKSSNKADVIRELLSVINIEIDKERIFQDLMERE
KLITTALKEGFAIPHLKTNLISKIHIAIGISHEGIDFNALDKNLSHVFILILCPAKDYVSYPRILASVVGK
VDLYKKEILNAKTDKEIYNIIVS t469.aa (SEQ ID NO:122)
VFLPTIIATPIINFLFKINKSGLKKELPIDQNTHICVSFEYDNLAKILIWDFKNELRKEGFFTQQIKNDSS
QYINARKNNISFSIKREGSKITFECPNNHLIIIQDLFRETILNLEKITKEVETVSLRAKKLDYSINYDKIL
SNINLNKRIKKENIILELKSSNKADVIRELLSVINIEIDKERIFQDLMEREKLITTALKEGFAIPHLKTNLI
SKIHLAIGISHEGIDFNALDKNLSHVFILILCPAKDYVSYPRILASVVGKVDLYKKEILNAKTDKEIYNII
VS f469.nt (SEQ ID NO:123)
ATGGCAAATGTAGCATTATCTTCAGGATTTATTAGCCAAAAAATATTTGGAATCATAATAATAA
TGGTGTTTTTGCCAACAATCATTGCAACACCCATAATAAACTTTTTATTTAAAATAAATAAAAG
TGGACTTAAAAAAGAACTCCCAATAGATCAAAATACACACATATGCGTATCATTTGAATATGAT
AATTTAGCCAAAATTCTTATATGGGACTTTAAAAATGAGTTAAGAAAAGAAGGATTTTTTACAC
AACAAATTAAAAATGATTCTTCACAATATATTAATGCAAGAAAAAACAATATATCCTTCTCAAT
AAAACGAGAAGGTAGCAAAATCACATTTGAATGCCCAAATAATCATTTAATTATAATACAAGAT
CTTTTTAGAGAAACAATCTTAAACCTAGAAAAAATAACCAAAGAAGTTGAAACAGTCTCTTTAA
GAGCAAAAAAACTAGATTACTCAATAAATTACGATAAAATCCTTAGTAATATCAACCTAAATAA
AAGAATAAAAAAGGAAAACATTATTCTAGAATTAAAATCAAGCAATAAGGCTGATGTAATAAG
AGAGCTTCTAAGCGTAATAAACATTGAAATTGATAAAGAAAGAATATTCCAAGATTTAATGGA
AAGAGAAAAGTTAATTACTACTGCACTAAAAGAAGGCTTTGCCATTCCCCATTTAAAAACAAAT
TTAATATCAAAAATACATATTGCAATAGGAATAAGCCATGAGGGAATTGACTTTAATGCTCTTG
ACAAGAACTTAAGTCATGTTTTTATATTAATACTGTGCCCAGCAAAAGATTACGTTAGCTACCC
TAGAATTTTAGCATCTGTTGTGGGCAAAGTTGATCTGTACAAAAAAGAAATTTTAAATGCAAAA
ACAGATAAAGAAATTTATAATATAATAGTGAGCTAA t469.nt (SEQ ID NO:124)
TTTTTGCCAACAATCATTGCAACACCCATAATAAACTTTTTATTTAAAATAAATAAAAGTGGAC
TTAAAAAAGAACTCCCAATAGATCAAAATACACACATATGCGTATCATTTGAATATGATAATTT
AGCCAAAATTCTTATATGGGACTTTAAAAATGAGTTAAGAAAAGAAGGATTTTTTACACAACAA
ATTAAAAATGATTCTTCACAATATATTAATGCAAGAAAAAACAATATATCCTTCTCAATAAAAC
GAGAAGGTAGCAAAATCACATTTGAATGCCCAAATAATCATTTAATTATAATACAAGATCTTTT
TAGAGAAACAATCTTAAACCTAGAAAAAATAACCAAAGAAGTTGAAACAGTCTCTTTAAGAGC
AAAAAAACTAGATTACTCAATAAATTACGATAAAATCCTTAGTAATATCAACCTAAATAAAGA
ATAAAAAAGGAAAACATTATTCTAGAATTAAAATCAAGCAATAAGGCTGATGTAATAAGAGAG
CTTCTAAGCGTAATAAACATTGAAATTGATAAAGAAAGAATATTCCAAGATTTAATGGAAAGA
GAAAAGTTAATTACTACTGCACTAAAAGAAGGCTTTGCCATTCCCCATTTAAAAACAAATTTAA
TATCAAAAATACATATTGCAATAGGAATAAGCCATGAGGGAATTGACTTTAATGCTCTTGACAA
GAACTTAAGTCATGTTTTTATATTAATACTGTGCCCAGCAAAAGATTACGTTAGCTACCCTAGA
ATTTTAGCATCTGTTGTGGGCAAAGTTGATCTGTACAAAAAAGAAATTTTAAATGCAAAAACAG
ATAAAGAAATTTATAATATAATAGTGAGCTAA f477.aa (SEQ ID NO:125)
MEKPQGVSIVGAISGAMHVHLMAEHYGVPVVLHTDHCAKNLLPWVEGLLEYGEKYYSQHKKPLF
SSHMLDLSEEPIKENIEISKKFLERMAKIEMFLEIELGITGGEEDGVDNSDRALHELFSTPEDIYYGYSE
LLKVSPNFQIAAAFGNVHGVYKPGNVKLTPKVLKDGQDYVISKTGVNMAKPVSYVFHGGSGSTIDE
INEALSYGVVKMNIDTDTQWAAWEGVLNYYKKNESRLQGQLGDGKDIDIPNKKFYDPRVWLREA
EVSMKDRVKIACKNLNNINRN t477.aa (SEQ ID NO:126)
MHVHLMAEHYGVPVVLHTDHCAKNLLPWVEGLLEYGEKYYSQHKKPLFSSHMLDLSEEPIKENIEI
SKKFLERMAKIEMFLEIELGITGGEEDGVDNSDRALHELFSTPEDIYYGYSELLKVSPNFQIAAAFGN
VHGVYKPGNVKLTPKVLKDGQDYVISKTGVNMAKPVSYVFHGGSGSTIDEINEALSYGVVKMNID
TDTQWAAWEGVLNYYKKNESRLQGQLGDGKDIDIPNKKFYDPRVWLREAEVSMKDRVKIACKNL
NNINRN f477.nt (SEQ ID NO:127)
ATGGAAAAACCACAAGGAGTTTCAATAGTTGGAGCTATTTCTGGTGCTATGCATGTTCATTTAA
TGGCAGAGCATTATGGTGTTCCTGTTGTTCTTCATACTGATCACTGTGCTAAAAATTTGCTTCCT
TGGGTTGAAGGCCTTTTAGAATATGGAGAGAAATACTATAGTCAGCACAAAAAACCATTATTTT
CTTCACATATGTTAGATTTATCAGAAGAACCTATTAAAGAAAATATTGAAATTTCTAAAAAATT
CTTAGAAAGAATGGCAAAAATTGAAATGTTTTTGGAAATAGAGCTTGGAATTACGGGTGGGGA
AGAGGATGGAGTTGACAATTCAGATAGAGCTTTGCATGAACTATTTTCTACTCCTGAGGATATT
TATTATGGATATTCAGAACTTTTAAAAGTTAGCCCAAATTTTCAGATTGCAGCAGCTTTTGGAA
ATGTTCATGGGTATATAAACCGGGGAATGTTAAGCTTACTCCAAAAGTTTTAAAAGATGGTCA
AGATTATGTCATATCAAAAACAGGAGTAAATATGGCTAAGCCAGTTTCTTATGTTTTTCATGGA

TABLE 1-continued

Nucleotide and Amino Acid Sequences.

GGGTCTGGATCTACAATTGATGAGATTAATGAGGCGCTTTCTTATGGCGTTGTAAAGATGAATA
TTGACACAGATACACAGTGGGCTGCCTGGGAGGGTGTTTTAAATTATTACAAAAAAAATGAAA
GTCGTTTGCAAGGTCAATTAGGAGATGGCAAGGATATTGATATTCCAAATAAGAAATTTTATGA
TCCAAGGGTTTGGTTAAGAGAAGCTGAAGTTTCTATGAAAGACCGTGTGAAGATTGCATGCAA
AAATCTTAATAATATTAATAGAAATTAA t477.nt (SEQ ID NO:128)
ATGCATGTTCATTTAATGGCAGAGCATTATGGTGTTCCTGTTGTTCTTCATACTGATCACTGTGC
TAAAAATTTGCTTCCTTGGGTTGAAGGCCTTTTAGAATATGGAGAGAAATACTATAGTCAGCAC
AAAAAAACCATTATTTTCTTCACATATGTTAGATTTATCAGAAGAACCTATTAAAGAAAATATTG
AAATTTCTAAAAAAATTCTTAGAAAGAATGGCAAAAATTGAAATGTTTTTGGAAATAGAGCTTGG
AATTACGGGTGGGGAAGAGGATGGAGTTGACAATTCAGATAGAGCTTTGCATGAACTATTTTCT
ACTCCTGAGGATATTTATTATGGATATTCAGAACTTTTAAAAGTTAGCCCAAATTTTCAGATTGC
AGCAGCTTTTGGAAATGTTCATGGGGTATATAAACCGGGGAATGTTAAGTTACTCCAAAAGTT
TTAAAAGATGGTCAAGATTATGTCATATCAAAAACAGGAGTAAATATGGCTAAGCCAGTTTCTT
ATGTTTTTCATGGAGGGTCTGGATCTACAATTGATGAGATTAATGAGGCGCTTTCTTATGGCGT
TGTAAAGATGAATATTGACACAGATACACAGTGGGCTGCCTGGGAGGGTGTTTTAAATTATTAC
AAAAAAAATGAAAGTCGTTTGCAAGGTCAATTAGGAGATGGCAAGGATATTGATATTCCAAAT
AAGAAATTTTATGATCCAAGGGTTTGGTTAAGAGAAGCTGAAGTTTCTATGAAAGACCGTGTGA
AGATTGCATGCAAAAATCTTAATAATATTAATAGAAATTAA f488.aa (SEQ ID NO:129)
MPSSFPFLLVNGSSGIAVGMATNMAPHNLREICDAIVYMLDNENASIFDLLKIVKGPDFPTFGEIVYN
DNLIKAYKTGKGSVVIRARYHIEERAEDRNAIIVTEIPYTVNKSALLMKVALLAKEEKLEGLLDIRDE
SDREGIRIVLEVKRGFDPHVIMNLLYEYTEFKKHFSINNLALVNGIPKQLNLEELLFEFIEHRKNIIERR
IETDLRKAKEKAHVLEGLNIALNNIDEVIKIIKSSKLAKDARERLVSNFGLSEIQANSVLDMRLQKLT
ALEIFKLEEELNILLSLIKDYEDILLNPVRIINIIREETINLGLKFGDERRTKIIYDEEVLKTSMSDLMQK
ENIVVMLTKKGFLKRLSQNEYKLQGTGGKGLSSFDLNDGDEIVIALCVNTHDYLFMISNEGKLYLIN
AYEIKDSSRASKGQNISELINLGDQEEILTIKNSKDLTDDAYLLLTTASGKIARFESTDFKAVKSRGVI
VIKLNDKDFVTSAEIVFKDEKVICLSKKGSAFIFNSRDVRLTNRGTQGVCGMKLKEGDLFVKVLSVK
ENPYLLIVSENGYGKRLNMSKISELKRGATGYTSYKKSDKKAGSVVDAIAVSEDDEILLVSKRSKAL
RTVAGKVSEQGKDARGIQVLFLDNDSLVSVSKFIK t488.aa (SEQ ID NO:130)
MATNMAPHNLREICDAIVYMLDNENASIFDLLKIVKGPDFPTFGEIVYNDNLIKAYKTGKGSVVIRA
RYHIEERAEDRNAIIVTEIPYTVNKSALLMKVALLAKEEKLEGLLDIRDESDREGIRIVLEVKRGFDPH
VIMNLLYEYTEFKKHFSINNLALVNGIPKQLNLEELLFEFIEHRKNIIERRIEFDLRKAKEKAHVLEGL
NIALNNIDEVIKIIKSSKLAKDARERLVSNFGLSEIQANSVLDMRLQKLTALEIFKLEEELNILLSLIKD
YEDILLNPVRIINIIREETINLGLKFGDERRTKIIYDEEVLKTSMSDLMQKENIVVMLTKKGFLKRLSQ
NEYKLQGTGGKGLSSFDLNDGDEIVIALCVNTHDYLFMISNEGKLYLINAYEIKDSSRASKGQNISEL
INLGDQEEILTIKNSKDLTDDAYLLLTTASGKIARFESTDFKAVKSRGVIVIKLNDKDFVTSAEIVFKD
EKVICLSKKGSAFIFNSRDVRLTNRGTQGVCGMKLKEGDLFVKVLSVKENPYLLIVSENGYGKRLN
MSKISELKRGATGYTSYKKSDKKAGSVVDAIAVSEDDEILLVSKRSKALRTVAGKVSEQGKDARGI
QVLFLDNDSLVSVSKFIK f488.nt (SEQ ID NO:131)
ATGCCGTCATCATTTCCATTTCTTTTGGTAAATGGCTCTAGTGGAATTGCTGTTGGAATGGCTAC
TAATATGGCACCTCATAATTTAAGAGAAATTTGTGATGCCATTGTTTACATGCTAGATAATGAG
AATGCTTCTATATTTGATTTGCTTAAAATAGTTAAAGGGCCTGATTTCCCAACTTTTGGAGAGAT
TGTTTATAATGATAATTTAATTAAAGCATACAAAACTGGCAAGGGAAGTGTTGTTATTAGGGCA
AGATATCATATTGAAGAAAGAGCAGAAGATAGAAATGCTATAATTGTTACAGAAATACCTTAT
ACGGTAAATAAATCTGCACTTCTTATGAAAGTTGCGCTTTTAGCAAAAGAAGAAAAGCTAGAA
GGACTTTTAGATATAAGAGATGAATCTGATCGAGAAGGTATTAGGATAGTTCTTGAAGTTAAAA
GAGGGATTTGATCCTCATGTTATTATGAATTTGCTTTATGAATATACTGAATTTAAAAAGCATTTT
AGTATAAATAATTTAGCCCTTGTTAATGGTATTCCCAAACAGTTAAATTTAGAAGAATTGTTAT
TTGAATTTATTGAGCATAGAAAAAATTATTATCGAAAGACGTATTGAATTTGACTTGAGAAAGGC
AAAAGAGAAAGCACATGTTCTTGAGGGATTAAATATTGCTTTAAATAATATAGATGAGGTTATT
AAGATTATTAAATCATCTAAATTAGCAAAAGATGCAAGGGAGAGGCTTGTTTCGAATTTTGGTC
TTTCAGAGATTCAGGCCAATTCAGTTCTTGATATGAGGTTACAAAAACTTACAGCCCTTGAGAT
TTTTAAAGCTTGAAGAGGAGCTTAATATACTGTTAAGCTTAATAAAAGATTATGAAGATATTCTC
TTGAATCCAGTAAGGATTATTAATATTATAAGAGAAGAAACTATTAATTTAGGTTTGAAATTTG
GCGATGAACGTCGAACTAAAATAATTTATGATGAGGAGGTTTTAAAAACTAGTATGTCGGATTT
AATGCAAAAAGAAAATATTGTTGTTATGCTTACAAAGAAAGGTTTCCTTAAAAGACTTTCACAA
AATGAGTATAAATTGCAAGGTACGGGAGGAAAAGGCTAAGTTCGTTTGATCTAAATGATGGA
GATGAGATTGTTATTGCTTTGTGTGTCAATACTCATGATTATTTATTTATGATTTCAAATGAAGG
AAAGCTTTATTTAATCAATGCTTATGAAATAAAAGATTCTTCAAGAGCTTCAAAAGGTCAGAAT
ATTAGTGAGCTTATTAATTTAGGAGATCAAGAAGAAATATTAACTATTAAGAATAGTAAAGATT
TAACTGATGATGCTTATTTATTGCTTACAACTGCAAGTGGAAAGATAGCTAGATTCGAATCTAC
AGATTTTAAAGCAGTAAAGTCACGAGGTGTTATTGTTATTAAACTGAATGATAAAGATTTTGTT
ACAAGTGCAGAGATTGTTTTTAAGGATGAAAAAGTAATTTGTCTTTCTAAAAAGGGTAGTGCAT
TTATATTTAATTCAAGGGATGTTAGGCTTACTAATAGAGGTACCCAAGGTGTTTGTGGAATGAA
ATTAAAAGAAGGTGATTTGTTTGTTAAAGTTTTATCGGTTAAAGAAAATCCTTATCTTTTGATTG
TTTCTGAAAATGGGTATGGAAAAAGGTTAAACATGTCTAAAATATCTGAGCTTAAAAGAGGAG
CCACTGGTTATACTAGTTATAAAAAATCTGATAAAAAAGCGGGTAGTGTTGTTGATGCTATAGC
AGTTTCAGAGGATGATGAAATCTTGCTTGTAAGTAAACGTTCAAAAGCTTTAAGAACAGTAGCT
GGAAAAGTATCTGAACAAGGCAAAGATGCTAGAGGAATTCAAGTATTATTTCTTGATAATGAC
AGCTTGGTTTCTGTTTCAAAATTTATTAAATAA

TABLE 1-continued

Nucleotide and Amino Acid Sequences.

t488.nt (SEQ ID NO:132)
ATGGCTACTAATATGGCACCTCATAATTTAAGAGAAATTTGTGATGCCATTGTTTACATGCTAG
ATAATGAGAATGCTTCTATATTTGATTTGCTTAAAATAGTTAAAGGGCCTGATTTCCCAACTTTT
GGAGAGATTGTTTATAATGATAATTTAATTAAAGCATACAAAACTGGCAAGGGAAGTGTTGTTA
TTAGGGCAAGATATCATATTGAAGAAAGAGCAGAAGATAGAAATGCTATAATTGTTACAGAAA
TACCTTATACGGTAAATAAATCTGCACTTCTTATGAAAGTTGCGCTTTTAGCAAAAGAAGAAAA
GCTAGAAGGACTTTTAGATATAAGAGATGAATCTGATCGAGAAGGTATTAGGATAGTTCTTGA
AGTTAAAAGAGGATTTGATCCTCATGTTATTATGAATTTGCTTTATGAATATACTGAATTTAAA
AAGCATTTTAGTATAAATAATTTAGCCCTTGTTAATGGTATTCCCAAACAGTTAAATTTAGAAG
AATTGTTATTTGAATTTATTGAGCATAGAAAAAATATTATCGAAAGACGTATTGAATTTGACTT
GAGAAAGGCAAAAGAGAAAGCACATGTTCTTGAGGGATTAAATATTGCTTTAAATAATATAGA
TGAGGTTATTAAGATTATTAAATCATCTAAATTAGCAAAAGATGCAAGGGAGAGGCTTGTTTCG
AATTTTGGTCTTTCAGAGATTCAGGCCAATTCAGTTCTTGATATGAGGTTACAAAAACTTACAG
CCCTTGAGATTTTTAAGCTTGAAGAGGAGCTTAATATACTGTTAAGCTTAATAAAAGATTATGA
AGATATTCTCTTGAATCCAGTAAGGATTATTAATATTATAAGAGAAGAAACTATTAATTTAGGT
TTGAAATTTGGCGATGAACGTCGAACTAAAATAATTTATGATGAGGAGGTTTTAAAAACTAGTA
TGTCGGATTTAATGCAAAAAGAAAATATTGTTGTTATGCTTACAAAGAAAGGTTTCCTTAAAAG
ACTTTCACAAAATGAGTATAAATTGCAAGGTACGGGAGGAAAAGGACTAAGTTCGTTTGATCT
AAATGATGGAGATGAGATTGTTATTGCTTTGTGTGTCAATACTCATGATTATTTATTTATGATTT
CAAATGAAGGAAAGCTTTATTTAATCAATGCTTATGAAATAAAAGATTCTTCAAGAGCTTCAAA
AGGTCAGAATATTAGTGAGCTTATTAATTTAGGAGATCAGGAAGAAATATTAACTATTAAGAAT
AGTAAAGATTTAACTGATGATGCTTATTTATTGCTTACAACTGCAAGTGGAAAGATAGCTAGAT
TCGAATCTACAGATTTTAAAGCAGTAAAGTCACGAGGTGTTATTGTTATTAAACTGAATGATAA
AGATTTTGTTACAAGTGCAGAGATTGTTTTTAAGGATGAAAAAGTAATTTGTCTTTCTAAAAAG
GGTAGTGCATTTATATTTAATTCAAGGGATGTTAGGCTTACTAATAGAGGTACCCAAGGTGTTT
GTGGAATGAAATTAAAAGAAGGTGATTTGTTTGTTAAAGTTTTATCGGTTAAAGAAAATCCTTA
TCTTTTGATTGTTTCTGAAAATGGGTATGGAAAAAGGTTAAACATGTCTAAAATATCTGAGCTT
AAAAGAGGAGCCACTGGTTATACTAGTTATAAAAAATCTGATAAAAAAGCGGGTAGTGTTGTT
GATGCTATAGCAGTTTCAGAGGATGATGAAATCTTGCTTGTAAGTAAACGTTCAAAAGCTTTAA
GAACAGTAGCTGGAAAAGTATCTGAACAAGGCAAAGATGCTAGAGGAATTCAAGTATTATTTC
TTGATAATGACAGCTTGGTTTCTGTTTCAAAATTTATTAAATAA f494.aa (SEQ ID NO: 133)
MFALIRKIFMIYFLCITLAGFAMIFIDSKFTEQPNVKENQSKINQHTIEPNLIMFTSSIGGFLGVYVGIWI
FNYDKSNFYLNWGNLIILIYNIALIITVYSKSHS t494.aa (SEQ ID NO:134)
MIFIDSKFTEQPNVKENQSKINQHTIEPNLIMFTSSIGGFLGVYVGIWIFNYDKSNFYLNWGNLIILIYN
IALIITVYSKSHS f494.nt (SEQ ID NO:135)
ATGTTTGCATTAATTAGAAAAATATTTATGATCTATTTTTTATGCATTACTCTTGCAGGTTTTGC
CATGATTTTTATTGACAGCAAATTTACCGAACAGCCTAATGTTAAAGAAAATCAAAGCAAAATT
AATCAACATACAATTGAACCCAATTTAATCATGTTTACATCTTCTATAGGAGGATTTTTAGGTGT
TTATGTTGGAATTTGGATCTTTAACTATGACAAAAGCAATTTTTACCTAAATTGGGGAAATTTA
ATAATATTAATATACAACATAGCCCTAATTATCACTGTATACTCAAAATCACATAGTTAG t494.nt (SEQ ID NO:136)
ATGATTTTTATTGACAGCAAATTTACCGAACAGCCTAATGTTAAAGAAAATCAAAGCAAAATTA
ATCAACATACAATTGAACCCAATTTAATCATGTTTACATCTTCTATAGGAGGATTTTTAGGTGTT
TATGTTGGAATTTGGATCTTTAACTATGACAAAAGCAATTTTTACCTAAATTGGGGAAATTTAA
TAATATTAATATACAACATAGCCCTAATTATCACTGTATACTCAAAATCACATAGTTAG f516.aa (SEQ ID NO:137)
MKKTPNTCIFLTLLIISNLNALANEEGNTNEKNDQPKQISNFFSPERGFIYSTGIGIGVGFFLNSNIKHLI
FRPYYTFSNNTFDFLIVAMILTRESLNIPKKMQYFKSYIGGGINWHIANLIKKTKYFSATIGIGGRFYL
STNFIEDIRFYEKLPYVIEPYMFIEISSKKAIPLMGLDFKIDFLFLDTFNISFNFTIRYNFKDKNEMET t516.aa (SEQ ID NO:138)
NEEGNTNEKNDQPKQISNFFSPERGFIYSTGIGIGVGFFLNSNIKHLIFRPYYTFSNNTFDFLIVAMILT
RESLNIPKKMQYFKSYIGGGINWHIANLIKKTKYFSATIGIGGRFYLSTNFIEDIRFYEKLPYVIEPYMF
IEISSKKAIPLMGLDFKIDFLFLDTFNISFNFTIRYNFKDKNEMET f516.nt (SEQ ID NO:139)
ATGAAAAAAACTCCAAACACTTGTATTTTCTTAACATTGCTTATCATTTCCAATTTAAATGCACT
TGCAAATGAAGAAGGCAATACTAATGAAAAAAATGATCAACCCAAACAAATCTCTAATTTTTTT
AGCCCAGAAAGAGGGTTCATATATTCAACAGGAATTGGGATTGGAGTTGGATTTTTCTAAATT
CAAATATTAAACACCTTATCTTTAGACCTTATTATACATTCTCTAATAATACTTTTGATTTTTA
ATCGTTGCTATGATATTAACAAGGGAAAGCCTTAATATCCCAAAAAAATGCAATACTTTAAAT
CTTATATTGGAGGAGGAATAAACTGGCACATTGCAAACTTAATTAAAAAAACAAAATATTTTTC
CGCCACCATTGGCATAGGTGGTCGTTTTTACCTATCTACAAACTTCTATAGAAGACATTCGATTTT
ACGAAAAATTGCCTTATGTAATAGAGCCTTATATGTTTATTGAAATTTCTTCTAAAAAGGCAAT
TCCTTTAATGGGGTTAGACTTTAAAATTGATTTTTTATTTTTAGATACATTAACATTTCTTTTAA
TTTTACTATTAGATATAATTTTAAGGACAAAAACGAGATGGAAACATGA t516.nt (SEQ ID NO:140)

TABLE 1-continued

Nucleotide and Amino Acid Sequences.

```
AATGAAGAAGGCAATACTAATGAAAAAAATGATCAACCCAAACAAATCTCTAATTTTTTAGCC
CAGAAAGAGGGTTCATATATTCAACAGGAATTGGGATTGGAGTTGGATTTTTTCTAAATTCAAA
TATTAAACACCTTATCTTTAGACCTTATTATACATTCTCTAATAATACTTTTGATTTTTAATCGT
TGCTATGATATTAACAAGGGAAAGCCTTAATATCCCCAAAAAAATGCAATACTTTAAATCTTAT
ATTGGAGGAGGAATAAACTGGCACATTGCAAACTTAATTAAAAAAACAAAATATTTTTCCGCCA
CCATTGGCATAGGTGGTCGTTTTTACCTATCTACAAACTTTATAGAAGACATTCGATTTTACGAA
AAATTGCCTTATGTAATAGAGCCTTATATGTTTATTGAAATTTCTTCTAAAAAGGCAATTCCTTT
AATGGGGTTAGACTTTAAAATTGATTTTTTATTTTTAGATACATTTAACATTTCTTTTAATTTTA
CTATTAGATATAATTTTAAGGACAAAAACGAGATGGAAACATGA
``` f517.aa (SEQ ID NO:141)
```
MIPVVASGGILIALSIAFVGIGPDGPNFAEHPFYKQIADIGSIAFGMMLPVLAGFIAMAIADKPGLTPG
LVGGVMSGNVKAGFLGAIFAGFLAGYVARFLARRSVPEWLRPVMPIFVIPLISTIIVGFFMLYFGVYI
GKFMGVLESGLKSLQSNSETFGVLGKIFLGLVLGSMITVDMGGPFNKVAFLFGVGLIPQVPEIMGMV
AAAIPVPPMAMGLATFLAPKLFENEEKESGKIAFLISFIGISEGAIPFAASDPGRVIPSIVVGGAVSSIIA
AFLGVANHAPHGGPIVLPVIDNKFGFIIAIAVGVAVATALVIFLKSLKLKESE
``` t517.aa (SEQ ID NO:142)
```
DKPGLTPGLVGGVMSGNVKAGFLGAIFAGFLAGYVARFLARRSVPEWLRPVMPIFVIPLISTIIVGFF
MLYFGVYIGKFMGVLESGLKSLQSNSETFGVLGKIFLGLVLGSMITVDMGGPFNKVAFLFGVGLIPQ
VPEIMGMVAAAIPVPPMAMGLATFLAPKLFENEEKESGKIAFLISFIGISEGAIPFAASDPGRVIPSIVV
GGAVSSIIAAFLGVANHAPHGGPIVLPVIDNKFGFIIAIAVGVAVATALVIFLKSLKLKESE
``` f517.nt (SEQ ID NO:143)
```
ATGATTCCTGTTGTTGCAAGTGGAGGAATTTTAATTGCTCTTAGCATTGCTTTTGTTGGGATTGG
ACCTGATGGGCCTAATTTTGCTGAGCATCCATTTTATAAGCAGATTGCAGATATTGGTTCTATA
GCTTTTGGGATGATGTTGCCCGTGCTTGCTGGTTTTATTGCAATGGCAATTGCTGATAAGCCTG
GTCTTACCCCCGGTCTTGTTGGTGGAGTAATGTCTGGGAATGTAAAAGCAGGTTTCTTGGGCGC
AATATTTGCGGGCTTTCTTGCAGGTTATGTTGCAAGGTTTTTAGCAAGAAGATCTGTTCCTGAG
TGGTTAAGACCTGTAATGCCTATATTTGTAATTCCGCTAATAAGCACCATTATTGTCGGCTTTTT
TATGCTGTATTTTGGTGTTTATATTGGAAAATTTATGGGGGTGCTTGAGAGTGGGCTTAAATCT
TTACAGAGTAATTCGGAAACTTTTGGCGTGTTGGGTAAAATTTTCTTAGGCTTAGTACTAGGTT
CAATGATTACTGTTGATATGGGCGGACCTTTTAATAAAGTGGCATTTCTTTTTGGTGTAGGGCT
AATTCCTCAAGTGCCAGAAATAATGGGAATGGTAGCAGCAGCAATTCCTGTTCCTCCTATGGCT
ATGGGGCTTGCAACCTTTTTAGCACCTAAATTGTTTGAAAATGAAGAAAAAGAATCTGGTAAAA
TAGCCTTTTTAATTTCATTTATTGGTATTAGCGAAGGAGCTATTCCTTTTGCTGCTAGTGATCCC
GGACGGGTAATCCCTTCGATAGTGGTAGGGGGAGCTGTATCAAGCATTATTGCCGCTTTTTTAG
GCGTTGCTAATCATGCTCCACACGGAGGACCAATAGTACTTCCTGTTATTGATAATAAATTTGG
GTTTATTATTGCAATTGCTGTTGGAGTTGCGGTTGCAACAGCTTTGGTAATTTTTTTGAAATCTT
TAAAATTAAAGGAATCTGAATGA
``` t517.nt (SEQ ID NO:144)
```
GATAAGCCTGGTCTTACCCCCGGTCTTGTTGGTGGAGTAATGTCTGGGAATGTAAAAGCAGGTT
TCTTGGGCGCAATATTTGCGGGCTTTCTTGCAGGTTATGTTGCAAGGTTTTTAGCAAGAAGATC
TGTTCCTGAGTGGTTAAGACCTGTAATGCCTATATTTGTAATTCCGCTAATAAGCACCATTATTG
TCGGCTTTTTTATGCTGTATTTTGGTGTTTATATTGGAAAATTTATGGGGGTGCTTGAGAGTGGG
CTTAAATCTTTACAGAGTAATTCGGAAACTTTTGGCGTGTTGGGTAAAATTTTCTTAGGCTTAGT
ACTAGGTTCAATGATTACTGTTGATATGGGCGGACCTTTTAATAAAGTGGCATTTCTTTTTGGTG
TAGGGCTAATTCCTCAAGTGCCAGAAATAATGGGAATGGTAGCAGCAGCAATTCCTGTTCCTCC
TATGGCTATGGGGCTTGCAACCTTTTTAGCACCTAAATTGTTTGAAAATGAAGAAAAAGAATCT
GGTAAAATAGCCTTTTTAATTTCATTTATTGGTATTAGCGAAGGAGCTATTCCTTTTGCTGCTAG
TGATCCCGGACGGGTAATCCCTTCGATAGTGGTAGGGGGAGCTGTATCAAGCATTATTGCCGCT
TTTTTAGGCGTTGCTAATCATGCTCCACACGGAGGACCAATAGTACTTCCTGTTATTGATAATA
AATTTGGGTTTATTATTGCAATTGCTGTTGGAGTTGCGGTTGCAACAGCTTTGGTAATTTTTTTG
AAATCTTTAAAATTAAAGGAATCTGAATGA
``` t519.aa (SEQ ID NO:145)
```
MIKIFKKIYILTLVLGMAHLSFASDNYMVRCSKEEDSTTCIAKLKEIKEKKNYDLFSMGIGIGDPIANI
MITIPYINIDFGYGGFIGLKSNNFENYLNGGIDVIFKKQIGQYMKIGGGIGIGADWSKTSLIPPNEEEET
DYERIGAVIRIPFIMEYNFAKNLSIGFKIYPAVGPTILLTKPSILFEGIKFNFFGFGFIKFAFN
``` t519.aa (SEQ ID NO:146)
```
DNYMVRCSKEEDSTTCIAKLKEIKEKKNYDLFSMGIGIGDPIANIMITIPYINIDFGYGGFIGLKSNNFE
NYLNGGIDVIFKKQIGQYMKIGGGIGIGADWSKTSLIPPNEEEETDYERIGAVIRIPFIMEYNFAKNLSI
GFKIYPAVGPTILLTKPSILFEGIKFNFFGFGFIKFAFN
``` f519.nt (SEQ ID NO:147)
```
ATGATAAAAATTTTTAAAAAAAATATACATTTTAACATTAGTATTAGGTATGGCACACCT
TTCTTTTGCATCTGACAATTATATGGTCAGATGCAGCAAGGAAGAAGATTCAACCACCTGTATC
GCAAAGCTTAAAGAAATAAAAGAAAAGAAAAATTATGACTTATTTTCAATGGGCATTGGAATA
GGAGATCCTATTGCAAATATTATGATTACAATTCCTTATATAAATATTGATTTTGGATATGGAG
GTTTTATTGGCCTTAAGTCAAACAATTTTGAAAATTATCTAAATGGTGGAATAGACGTTATTTTT
AAAAAGCAAATTTGACAATATATGAAAATTGGCGGCGGCATTGGAATAGGTGCGGATTGGTCA
AAAACATCCCTTATACCCCCTAATGAAGAAGAAGAAACTGATTATGAGAGAATAGGCGCTGTT
ATAAGAATTCCTTTTATAATGGAATATAATTTTGCAAAAAATTTATCCATAGGATTCAAAATTT
ATCCTGCAGTAGGGCGAACAATATTACTAACAAAACCAAGCATTTTATTTGAAGGAATTAAATT
CAATTTTTTTGGATTTGGATTCATAAAATTTGCATTTAATTAA
```

TABLE 1-continued

Nucleotide and Amino Acid Sequences.

t519.nt (SEQ ID NO:148)
GACAATTATATGGTCAGATGCAGCAAGGAAGAAGATTCAACCACCTGTATCGCAAAGCTTAAA
GAAATAAAAGAAAAGAAAAATTATGACTTATTTTCAATGGGCATTGGAATAGGAGATCCTATT
GCAAATATTATGATTACAATTCCTTATATAAATATTGATTTTGGATATGGAGGTTTTATTGGCCT
TAAGTCAAACAATTTTGAAAATTATCTAAATGGTGGAATAGACGTTATTTTTAAAAAGCAAATT
GGACAATATATGAAAATTGGCGGCGGCATTGGAATAGGTGCGGATTGGTCAAAAACATCCCTT
ATACCCCCTAATGAAGAAGAAGAAACTGATTATGAGAGAATAGGCGCTGTTATAAGAATTCCTT
TTATAATGGAATATAATTTTGCAAAAAATTTATCCATAGGATTCAAAATTTATCCTGCAGTAGG
GCCAACAATATTACTAACAAAACCAAGCATTTTATTTGAAGGAATTAAATTCAATTTTTTTGGA
TTTGGATTCATAAAATTTGCATTTAATTAA f520.aa (SEQ ID NO:149)
MRMLLATIILILTTGLLAAQSKSKSMTEDDFDFDKLLAKEESVRRLFGIGFGVGYPLANITISVPYVDI
DLGYGGFVGLKPNNFLPYVVMGVDLLFKDEIHKNTMISGGIGIGADWSKGSPEKSNEKLEEEEENE
AQQVASLQNRIGVVIRLPLVIEYSFLKNIVIGFKAVATIGTTMLLGSPMSFEGARFNFLGTGFIKIYI t520.aa (SEQ ID NO:150)
QSKSKSMTEDDFDFDKLLAKEESVRRLFGIGFGVGYPLANITISVPYVDIDLGYGGFVGLKPNNFLPY
VVMGVDLLFKDEIHKNTMISGGIGIGADWSKGSPEKSNEKLEEEEENEAQQVASLQNRIGVVIRLPL
VIEYSFLKNIVIGTKAVATIGTTMLLGSPMSFEGARFNFLGTGFIKIYI f520.nt (SEQ ID NO:151)
ATGAGAATGCTATTAGCAACAATAATACTTATATTAACAACGGGTTTATTAGCTGCACA
ATCCAAAAGCAAAAGTATGACTGAAGATGACTTTGATTTTGATAAACTTCTTGCAAAAGAAGAG
TCTGTGCGCCGTTTATTTGGCATAGGTTTTGGAGTTGGATATCCACTTGCAAACATTACAATATC
TGTTCCATATGTAGACATAGACCTTGGGTACGGAGGATTCGTAGGGCTTAAACCCAACAATTTC
TTGCCCTATGTTGTGATGGGTGTAGATCTTCTATTTAAAGATGAAATACACAAAAACACTATGA
TTTCTGGAGGCATTGGAATAGGTGCAGATTGGTCAAAAGGAAGTCCTGAAAAATCAAATGAAA
AACTTGAAGAAGAGGAAGAAAATGAAGCACAACAAGTAGCTTCTCTTCAAAATAGAATAGGGG
TTGTGATAAGATTGCCTTTGGTAATAGAGTACAGCTTTCTTAAAAATATTGTGATTGGATTTAA
AGCTGTTGCTACTATTGGAACAACTATGCTACTTGGCAGCCCAATGTCATTTGAAGGAGCTAGA
TTTAATTTCTTAGGCACAGGCTTTATAAAAATATATATATAG t520.nt (SEQ ID NO:152)
CAATCCAAAAGCAAAAGTATGACTGAAGATGACTTTGATTTTGATAAACTTCTTGCAAAAGAAG
AGTCTGTGCGCCGTTTATTTGGCATAGGTTTTGGAGTTGGATATCCACTTGCAAACATTACAAT
ATCTGTTCCATATGTAGACATAGACCTTGGGTACGGAGGATTCGTAGGGCTTAAACCCAACAAT
TTCTTGCCCTATGTTGTGATGGGTGTAGATCTTCTATTTAAAGATGAAATACACAAAAACACTA
TGATTTCTGGAGGCATTGGAATAGGTGCAGATTGGTCAAAAGGAAGTCCTGAAAAATCAAATG
AAAAACTTGAAGAAGAGGAAGAAAATGAAGCACAACAAGTAGCTTCTCTTCAAAATAGAATAG
GGGTTGTGATAAGATTGCCTTTGGTAATAGAGTACAGCTTTCTTAAAAATATTGTGATTGGATT
TAAAGCTGTTGCTACTATTGGAACAACTATGCTACTTGGCAGCCCAATGTCATTTGAAGGAGCT
AGATTTAATTTCTTAGGCACAGGCTTTATAAAAATATATATATAG f523.aa (SEQ ID NO:153)
MNIKINFFFTLPIGIFLGLFFPLGIYSSLSHAFIRLSYLSLIPFLIFSIPLGIENIIENKNFKKLFGKTIYYGIL
TNLSGVAVSIIAATIYLPQRIPILEKTIQNTCFFEKEALLETFFPKNIFKIFTSSNPNLLSIYMISIIIGTSFY
YAKQKGRIARELMLSASNLFYHANGFIVNILNIGIIFITANYAANLKNFKDYPNYTNSITFFLAWTIIIL
FVILPTISYRLTKSFKMIYKGIFVSFQNIIFSGLAKDSYSPYVILIEDIKNERINIKKSIIINIPLINFVSKFG
TIFVSVISFFIILKSYSSLPISIYEISYMSTLSFVFVFAFPHIPNSLIYIITMLCSTYTKGIELNVSNITPMLPI
LISLALLIDFAFNIAIIHIINFKELKDQEKIN t523.aa (SEQ ID NO:154)
IENIIENKNFKKLFGKTIYYGILTNLSGVAVSIIAATIYLPQRIPILEKTIQNTCFFEKEALLETFFPKNIF
KIFTSSNPNLLSIYMISIIIGTSFYYAKQKGRIARELMLSASNLFYHANGFIVNILNIGIIFITANYAANLK
NFKDYPNYTNSITFFLAWTIIILFVILPTISYRLTKSFKMIYKGIFVSFQNIIFSGLAKDSYSPYVILIEDIK
NERINIKKSIIINIPLINFVSKFGTIFVSVISFFIILKSYSSLPISIYEISYMSTLSFVFVFAFPHIPNSLIYIITM
LCSTYTKGIELNVSNITPMLPILISLALLIDFAFNIAIIHIINFKELKDQEKIN f523.nt (SEQ ID NO:155)
ATGAATATAAAAATCAATTTTTTTTTCACTTTGCCTATTGGAATCTTTTTAGGATTGTTTTTCCCT
CTTGGAATTTATAGCTCCTTATCACATGCTTTTATAAGATTATCATACTTATCTCTTATTCCCTTT
TTAATATTTTCAATTCCATTAGGAATTGAAAATATTATTGAAAATAAAACTTTAAAAAGCTTTT
TGGTAAAACAATTTATTATGGAATTTTAACTAACCTATCTGGAGTTGCTGTATCAATAATAGCT
GCAACAATATATCTTCCGCAAAGAATTCCAATACTAGAAAAAACAATACAAAATACATGTTTTT
TTGAAAAAGAAGCTTTACTAGAAACATTCTTTCCAAAAAATATTTTCAAAATATTTACATCTAG
CAATCCAAATCTACTAAGCATTTACATGATTTCAATAATAATAGGCACAAGTTTTTATTATGCA
AAACAAAAAGGCAGAATAGCTAGAGAACTGATGCTAAGCGCATCCAATCTTTTTTACCATGCAA
ATGGGTTTATTGTAAACATATTAAATATAGGGATCATTTTTATAACAGCAAATTACGCTGCAAA
CTTAAAAAACTTCAAAGATTACCCAAATTATACAAACAGCATAACATTCTTTTTGGCATGGACA
ATTATAATTTTATTCGTAATATTGCCAACAATTAGTTATAGATTAACAAAAAGTTTTAAAATGAT
ATATAAAGGCATTTTTGTATCATTTCAAAACATAATATTTTCAGGACTTGCAAAAGATTCTTATT
CCCCTTATGTGATATTAATAGAAGATATTAAAAACGAAAGAATAAATATAAAAAAATCCATAAT
TATAAACATACCTTTAATAAATTTTGTATCTAAATTTGGCACTATTTTTGTTTCAGTAATATCAT
TTTTTTATAATTTTAAAATCATATTCTAGCTTACCCATTTCTATTTATGAAATAAGCTATATGAGC
ACTTTATCATTTGTTTTTGTCTTTGCATTTCCTCATATACCAAATAGTTTAATTTATATAATTACA

TABLE 1-continued

Nucleotide and Amino Acid Sequences.

ATGCTTTGCTCTACATATACAAAAGGAATAGAGCTAAATGTTTCAAACATAACACCAATGCTGC
CGATATTAATCTCTTTGGCTTTACTAATCGACTTTGCTTTTAACATTGCAATCATTCATATAATA
AACTTCAAAGAATTAAAAGATCAAGAAAAAATTAATTAA f523.nt (SEQ ID NO:156)
ATTGAAAATATTATTGAAAATAAAAACTTTAAAAAGCTTTTTGGTAAAACAATTTATTA
TGGAATTTTAACTAACCTATCTGGAGTTGCTGTATCAATAATAGCTGCAACAATATATCTTCCGC
AAAGAATTCCAATACTAGAAAAAACAATACAAAATACATGTTTTTTTGAAAAAGAAGCTTTACT
AGAAACATTCTTTCCAAAAAATATTTTCAAAATATTTACATCTAGCAATCCAAATCTACTAAGC
ATTTACATGATTTCAATAATAATAGGCACAAGTTTTTATTATGCAAAACAAAAAGGCAGAATAG
CTAGAGAACTGATGCTAAGCGCATCCAATCTTTTTTACCATGCAAATGGGTTTATTGTAAACAT
ATTAAATATAGGGATCATTTTTATAACAGCAAATTACGCTGCAAACTTAAAAAACTTCAAAGAT
TACCCAAATTATACAAACAGCATAACATTCTTTTTGGCATGGACAATTATAATTTTATTCGTAAT
ATTGCCAACAATTAGTTATAGATTAACAAAAAGTTTTAAAATGATATATAAAGGCATTTTTGTA
TCATTTCAAAACATAATATTTTCAGGACTTGCAAAAGATTCTTATTCCCCTTATGTGATATTAAT
AGAAGATATTAAAAACGAAAGAATAAATATAAAAAAATCCATAATTATAAACATACCTTTAAT
AAATTTTGTATCTAAATTTGGCACTATTTTTGTTTCAGTAATATCATTTTTTATAATTTTAAAATC
ATATTCTAGCTTACCCATTTCTATTTATGAAATAAGCTATATGAGCACTTTATCATTTGTTTTTG
TCTTTGCATTTCCTCATATACCAAATAGTTTAATTTATATAATTACAATGCTTTGCTCTACATAT
ACAAAAGGAATAGAGCTAAATGTTTCAAACATAACACCAATGCTGCCGATATTAATCTCTTTGG
CTTTTACTAATCGACTTTGCTTTTAACATTGCAATCATTCATATAATAAACTTCAAAGAATTAAAA
GATCAAGAAAAAATTAATTAA f526.aa (SEQ ID NO:157)
MKKEFIMLLLLLQTIMNLNSINTNTSTSIVKELQKNLYIFNSKEYQKDKDTLNEFINSININDKEILQSL
EKIKNELFIISVFFNNKKGILIALNLGAEINFKYKISPISISIINNEFEITKILIDYGISLNQIDDTGYSPIFW
AIYTNNEKIFEFLKESGADLSFTLKNRKTPMQAAIETENIKLIKSLEKKKIYIDDNFKKLKKLKNKEI
VRILVK t526.aa (SEQ ID NO:158)
NSINTNTSTSIVKELQKNLYIFNSKEYQKDKDTLNEFINSININDKEILQSLEKIKNELFIISVFFNKKG
ILIALNLGAEINFKYKISPISISIINNEFEITKILIDYGISLNQIDDTGYSPIFWAIYTNNEKIFEFLKESGAD
LSFTLKNRKTPMQAAIETENIKLIKSLEKKKIYIDDNFKKKLKKLKNKEIVRILVK f526.nt (SEQ ID NO:159)
ATGAAAAAAGAATTCATTATGCTTTTACTGTTATTGCAAACAATAATGAATTTAAACTCAATAA
ATACTAATACAAGTACTTCAATAGTAAAAGAATTGCAAAAAAATTTATATATTTTCAATAGCAA
AGAATATCAAAAAGATAAAGACACTTTAAATGAATTTATAAATTCAATAAATATAAATGACAA
AGAAATCTTACAAAGTTTAGAAAAAATCAAAAATGAGCTTTTTATAATATCTGTTTTTTTCAAC
AATAAAAAAGGGATTTTAATTGCACTAAATCTTGGAGCAGAAATAAACTTTAAATATAAATAT
CTCCAATTTCAATTTCAATAATAAACAATGAATTTGAAATCACAAAAATATTGATAGATTACGG
AATAAGCCTTAATCAAATAGATGATACAGGTTATTCTCCAATATTTTGGGCAATATATACTAAT
AACGAAAAAATATTTGAATTTTTAAAAGAAAGCGGAGCTGATTTAAGTTTCACACTTAAAAATA
GAAAAACACCAATGCAAGCCGCAATAGAAACAGAAAATATAAAACTAATTAAATCTCTGGAAA
AGAAAAAAATTTACATTGACGACAATTTCAAAAAAAAAACTTAAAAAGCTTAAAAACAAAGAAA
TAGTTCGAATTTTAGTAAAATAG t526.nt (SEQ ID NO:160)
AACTCAATAAATACTAATACAAGTACTTCAATAGTAAAAGAATTGCAAAAAAATTTATATATTT
TCAATAGCAAAGAATATCAAAAAGATAAAGACACTTTAAATGAATTTATAAATTCAATAAATAT
AAATGACAAAGAAATCTTACAAAGTTTAGAAAAAATCAAAAATGAGCTTTTTATAATATCTGTT
TTTTTCAACAATAAAAAAGGGATTTTAATTGCACTAAATCTTGGAGCAGAAATAAACTTTAAAT
ATAAAATATCTCCAATTTCAATTTCAATAATAAACAATGAATTTGAAATCACAAAAATATTGAT
AGATTACGGAATAAGCCTTAATCAAATAGATGATACAGGTTATTCTCCAATATTTTGGGCAATA
TATACTAATAACGAAAAAATATTTGAATTTTTAAAAGAAAGCGGAGCTGATTTAAGTTTCACAC
TTAAAAATAGAAAAACACCAATGCAAGCCGCAATAGAAACAGAAAATATAAAACTAATTAAAT
CTCTGGAAAAGAAAAAAATTTACATTGACGACAATTTCAAAAAAAAAACTTAAAAAGCTTAAAA
ACAAAGAAATAGTTCGAATTTTAGTAAAATAG f544.aa (SEQ ID NO:161)
MTKNRIIWLLVLMVSSTFTATIISNYQNLMLSLVVLANFIPLLMDTSGNAGSQASALIIRELALGTVK
VKDFFKVFLKEICVSILVGAILASVNFLRIVFFVAPHHSDKLKIAFVVSSCLMVSLTVAKILGGLLPIV
AKLLKLDPALMAGPLITTIADAITLIAYFNIAKWVLVSYAV t544.aa (SEQ ID NO:162)
STFTATIISNYQNLMLSLVVLANFIPLLMDTSGNAGSQASALIIRELALGTVKVKDFFKVFLKEICVSIL
VGAILASVNFLRIVFFVAPHHSDKLKIAFVVSSCLMVSLTVAKILGGLLPIVAKLLKLDPALMAGPLIT
TIADAITLIAYFNIAKWVLVSYAV f544.nt (SEQ ID NO:163)
ATGACAAAAAATAGAATAATTTGGCTTTTAGTTCTTATGGTGTCTTCTACTTTTACAGC
TACAATTATTTCAAATTATCAAAATTTAATGTTGTCTTTAGTGGTTTTAGCTAATTTTATTCCCC
TTTTAATGGATACTTCAGGCAATGCCGGCTCTCAGGCATCTGCGCTAATAATTCGTGAGCTTGC
TCTTGGTACTGTCAAGGTAAAAGATTTTTTTAAAGTGTTTTTAAAGGAAATATGTGTTAGCATTC
TAGTGGGAGCAATTCTTGCTAGTGTTAATTTTTTAAGAATTGTCTTTTTTGTAGCTCCACACCAT
TCTGATAAGCTGAAAATAGCTTTTGTAGTTTCATCTTGCTTGATGGTAAGTTTGACAGTAGCAA
AGATATTGGAGGTCTTTTACCCATTGTTGCTAAACTTTTAAAGTTGGATCCAGCACTTATGGC

TABLE 1-continued

Nucleotide and Amino Acid Sequences.

AGGCCCTTTAATCACTACAATTGCAGATGCTATTACTTTAATAGCTTATTTTAATATAGCAAAAT
GGGTTTTAGTTAGCTATGCTGTTTAA t544.nt (SEQ ID NO:164)
TCTACTTTTACAGCTACAATTATTTCAAATTATCAAAATTTAATGTTGTCTTTAGTGGTT
TTAGCTAATTTTATTCCCCTTTTAATGGATACTTCAGGCAATGCCGGCTCTCAGGCATCTGCGCT
AATAATTCGTGAGCTTGCTCTTGGTACTGTCAAGGTAAAAGATTTTTTTAAAGTGTTTTTAAAG
GAAATATGTGTTAGCATTCTAGTGGGAGCAATTCTTGCTAGTGTTAATTTTTTAAGAATTGTCTT
TTTTGTAGCTCCACACCATTCTGATAAGCTGAAAATAGCTTTTGTAGTTTCATCTTGCTTGATGG
TAAGTTTGACAGTAGCAAAGATATTGGGAGGTCTTTTACCCATTGTTGCTAAACTTTTAAAGTT
GGATCCAGCACTTATGGCAGGCCCTTTAATCACTACAATTGCAGATGCTATTACTTTAATAGCTT
ATTTTAATATAGCAAAATGGGTTTTAGTTAGCTATGCTGTTTAA f545.aa (SEQ ID NO:165)
MTKNRIIWLLVLMVSSTFTATIISNYQNLMLSLVVLANFIPLLMDTSGNAGSQASALIIRELALGTVK
VKDFFKVFLKEICVSILVGAILASVNFLRIVFFVAPHHSDKLKIAFVVSSCLMVSLTVAKILGGLLPIV
AKLLKLDPALMAGPLITTIADAITLIAYFNIAKWVLVSYAV t545.aa (SEQ ID NO:166)
GSQASALIIRELALGTVKVKDFFKVFLKEICVSILVGAILASVNFLRIVFFVAPHHSDKLKIAFVVSSCL
MVSLTVAKILGGLLPIVAKLLKLDPALMAGPLITTIADAITLIAYFNIAKWVLVSYAV f545.nt (SEQ ID NO:167)
ATGACAAAAAATAGAATAATTTGGCTTTTAGTTCTTATGGTGTCTTCTACTTTTACAGCTACAAT
TATTTCAAATTATCAAAATTTAATGTTGTCTTTAGTGGTTTTAGCTAATTTTATTCCCCTTTTAAT
GGATACTTCAGGCAATGCCGGCTCTCAGGCATCTGCGCTAATAATTCGTGAGCTTGCTCTTGGT
ACTGTCAAGGTAAAAGATTTTTTTAAAGTGTTTTTAAAGGAAATATGTGTTAGCATTCTAGTGG
GAGCAATTCTTGCTAGTGTTAATTTTTTAAGAATTGTCTTTTTTGTAGCTCCACACCATTCTGAT
AAGCTGAAAATAGCTTTTGTAGTTTCATCTTGCTTGATGGTAAGTTTGACAGTAGCAAAGATAT
TGGGAGGTCTTTTACCCATTGTTGCTAAACTTTTAAAGTTGGATCCAGCACTTATGGCAGGCCC
TTTAATCACTACAATTGCAGATGCTATTACTTTAATAGCTTATTTTAATATAGCAAAATGGGTTT
TAGTTAGCTATGCTGTTTAA t545.nt (SEQ ID NO:168)
GGCTCTCAGGCATCTGCGCTAATAATTCGTGAGCTTGCTCTTGGTACTGTCAAGGTAAAAGATT
TTTTTAAAGTGTTTTTAAAGGAAATATGTGTTAGCATTCTAGTGGGAGCAATTCTTGCTAGTGTT
AATTTTTTAAGAATTGTCTTTTTTGTAGCTCCACACCATTCTGATAAGCTGAAAATAGCTTTTGT
AGTTTCATCTTGCTTGATGGTAAGTTTGACAGTAGCAAAGATATTGGGAGGTCTTTTACCCATT
GTTGCTAAACTTTTAAAGTTGGATCCAGCACTTATGGCAGGCCCTTTAATCACTACAATTGCAG
ATGCTATTACTTTAATAGCTTATTTTAATATAGCAAAATGGGTTTTAGTTAGCTATGCTGTTTAA f577.aa (SEQ ID NO:169)
MRIKNLILIAILLISPSCSTNKNIVVLTDNKTIPFYINQFNIENKANFIIKFRNNIDLQTIEKENAQIIISKNI
GNTNIANHFKSVKINVNPDYPILKHIFKQFNYKIIPLGFDIPILIYKNTHHIKKYINTKYLKEEYENFIK
DGKFFISPYVSENLFYVISQINNVRFSFEKNKLNYNENQILKMLEYFSSFLNTKQMDLQKDFFNKYG
YLKLNKILLNKKSLLIAGLSDITFYNSLSEQEKSQIKFSYLINDNNEIVISNPNFIGILETSVLTKKFINWI
LYKKTQKTLIGFNNQSQSNICFGFANGFTPYKELNLKIKHSIDGISPFIIDETQINSHSYVLSKKTIEKE
NLLINEWFFSKANNLKKNKN t577.aa (SEQ ID NO:170)
NKNIVVLTDNKTIPFYINQFNIENKANFIIKFRNNIDLQTIEKENAQIIISKNIGNTNIANHFKSVKINYN
PDYPILKHIFKQFNYKIIPLGFDIPILIYKNTHHIKKYINTKYLKEEYENFIKDGKFFISPYVSENLFYVIS
QINNVRFSFEKNKLNYNENQILKMLEYFSSFLNTKQMDLQKDFFNKYGYLKLNKILLNKKSLLIAGL
SDITFYNSLSEQEKSQIKFSYLINDNNEIVISNPNFIGILETSVLTKKFINWILYKKTQKTLIGFNNQSQS
NICFGFANGFTPYKELNLKIKHSIDGISPFIIDETQINSHSYVLSKKTIEKENLLINEWFFSKANNLKKN
KN f577.nt (SEQ ID NO:171)
ATGAGAATAAAAAATTTAATACTAATAGCAATTTTATTAATTAGCCCTAGCTGTTCAAC
AAATAAGAACATCGTTGTACTAACTGACAATAAAACAATACCATTTTATATAAATCAATTTAAT
ATAGAAAATAAAGCAAATTTTATAATTAAGTTTAGAAATAATATTGATCTGCAAACAATAGAAA
AAGAAAATGCACAAATAATTATTTCTAAAAACATTGGTAACACAAATATTGCTAACCATTTTAA
ATCTGTAAAAATCAATTATAATCCAGATTATCCTATCTTAAAGCATATTTTCAAGCAATTTAACT
ACAAAATTATTCCATTGGGCTTTGACATTCCTATTTTAATCTATAAAAATACACATCATATTAAA
AAATACATAAACACTAAATATCTAAAAGAAGAATACGAAAATTTCATTAAAGATGGAAAATTTT
TTATATCGCCTTATGTTTCTGAAAATTTATTTTATGTGATTTCTCAAATAAATAATGTGAGATTT
TCTTTTGAAAAAAATAAATTAAATTATAATGAGAATCAAATTTTAAAAATGCTAGAATATTTCT
CATCATTTTTAAATACAAAACAAATGGACTTGCAAAAAGATTTCTTTAATAAATACGGCTACCT
AAAGTTAAATAAAATATTGCTTAATAAAAAATCTCTTTTAATAGCAGGATTGAGCGATATAACC
TTCTACAATAGCTTAAGCGAACAAGAGAAGTCACAAATAAAATTTTCCTATTTAATAAACGATA
ACAATGAAATTGTTATCTCAAACCCAAATTTTATTGGCATTTTAGAAACATCTGTTTTAACTAAA
AAATTTATCAACTGGATATTGTATAAAAAAACTCAAAAAACCCTAATTGGATTTAACAATCAAT
CCCAATCAAATATATGTTTTGGATTTGCCAATGGTTTTACCCCTTACAAAGAATTAAATTTAAAA
ATAAAACATTCAATTGATGGAATATCTCCTTTTATTATTGACGAAACTCAAATCAATAGCCATTC
CTATGTATTAAGCAAAAAAACAATTGAAAAGAAAACTTACTAATAAATGAATGGTTTTTCTCT
AAAGCTAATAATCTAAAAAAAAATAAAAATTAA

TABLE 1-continued

Nucleotide and Amino Acid Sequences.

t577.nt (SEQ ID NO:172)
AATAAGAACATCGTTGTACTAACTGACAATAAAACAATACCATTTTATATAAATCAATTTAATA
TAGAAAATAAAGCAAATTTTATAATTAAGTTTAGAAATAATATTGATCTGCAAACAATAGAAAA
AGAAAATGCACAAATAATTATTTCTAAAAACATTGGTAACACAAATATTGCTAACCATTTTAAA
TCTGTAAAAATCAATTATAATCCAGATTATCCTATCTTAAAGCATATTTTCAAGCAATTTAACTA
CAAAATTATTCCATTGGGCTTTGACATTCCTATTTTAATCTATAAAAATACACATCATATTAAAA
AATACATAAACACTAAATATCTAAAAGAAGAATACGAAAATTTCATTAAAGATGGAAAATTTTT
TATATCGCCTTATGTTTCTGAAAATTTTATTTTATGTGATTTCTCAAATAAATAATGTGAGATTTT
CTTTTGAAAAAAATAAATTAAATTATAATGAGAATCAAATTTTAAAAATGCTAGAATATTTCTC
ATCATTTTTAAATACAAAACAAATGGACTTGCAAAAAGATTTCTTTAATAAATACGGCTACCTA
AAGTTAAATAAAATATTGCTTAATAAAAAATCTCTTTTAATAGCAGGATTGAGCGATATAACCT
TCTACAATAGCTTAAGCGAACAAGAGAAGTCACAAATAAAATTTTCCTATTTAATAAACGATAA
CAATGAAATTGTTATCTCAAACCCAAATTTTATTGGCATTTTAGAAACATCTGTTTTAACTAAAA
AATTTATCAACTGGATATTGTATAAAAAAACTCAAAAAACCTAATTGGATTTAACAATCAATC
CCAATCAAATATATGTTTTGGATTTGCCAATGGTTTTACCCCTTACAAAGAATTAAATTTAAAA
ATAAAACATTCAATTGATGGAATATCTCCTTTTATTATTGACGAAACTCAAATCAATAGCCATTC
CTATGTATTAAGCAAAAAAACAATTGAAAAGAAAACTTACTAATAAATGAATGGTTTTTCTCT
AAAGCTAATAATCTAAAAAAAAATAAAAATTAA f584.aa (SEQ ID NO:173)
MIKTILLLVLYPVVVFSQISANQYFEGIYAKYQNIEDMQATINFTLKGLKQTGVLLYKFPDKFIINLDS
NNQVFVSDGEFLTVYVPSLGTSFNQQLLKGSSGGGLMKVLNSEYSVSYTNSPNLEDLDSSEPGKYIK
LTFSRKLYKGAATINSFILAFAPDGIIRRITAFPTSGGREIVIDLTAVKFNVGILDSKFKYDPPKSSNKVD
NFLYDIKKN t584.aa (SEQ ID NO:174)
QISANQYFEGIYAKYQNIEDMQATINFTLKGLKQTGVLLYKFPDKFIINLDSNNQVFVSDGEFLTVY
VPSLGTSFNQQLLKGSSGGGLMKVLNSEYSVSYTNSPNLEDLDSSEPGKYIKLTFSRKLYKGAATINS
FIIAFAPDGIIRRITAFPTSGGREIVIDLTAVKFNVGILDSKFKYDPPKSSNKVDNFLYDIKKN t584.nt (SEQ ID NO:175)
ATGATAAAAACAATACTTTTATTAGTTTTGTATCCTGTTGTTGTGTTTTCTCAAATATCTGCAAA
TCAATATTTTGAAGGAATTTATGCTAAATATCAAAATATAGAGGACATGCAAGCAACAATTAAT
TTTACTTTAAAGGGGTTAAAGCAAACAGGTGTTTTGCTTTATAAGTTTCCAGACAAGTTTATTAT
CAATTTAGATTCAAATAATCAAGTTTTTGTAAGTGATGGTGAATTTTTGACAGTTTATGTTCCAT
CTCTTGGGACTTCTTTTAATCAGCAATTATTAAAGGGTAGTAGTGGGGGAGGTCTTATGAAAGT
TTTAAATAGTGAGTATAGCGTATCTTATACCAATTCTCCAAATTTAGAAGATCTCGATTCATCTG
AGCCTGGAAAATATATTAAATTAACCTTTTCTAGAAAGCTTTACAAGGGGGCTGCTACTATTAA
TTCTTTTATTATTGCTTTTGCTCCGGATGAATAATTAGAAGAATTACTGCTTTTCCTACTAGTG
GTGGGCGCGAAATAGTTATTGATTTGACTGCTGTGAAGTTTAATGTTGGAATTCTTGATAGCAA
ATTTAAATATGATCCTCCAAAATCTTCAAATAAGGTAGATAATTTTTTATATGATATTAAAAA
AATTAA t584.nt (SEQ ID NO:176)
CAAATATCTGCAAATCAATATTTTGAAGGAATTTATGCTAAATATCAAAATATAGAGGACATGC
AAGCAACAATTAATTTTACTTTAAAGGGGTTAAAGCAAACAGGTGTTTTGCTTTATAAGTTTCC
AGACAAGTTTATTATCAATTTAGATTCAAATAATCAAGTTTTTGTAAGTGATGGTGAATTTTTG
ACAGTTTATGTTCCATCTCTTGGGACTTCTTTTAATCAGCAATTATTAAAGGGTAGTAGTGGGG
GAGGTCTTATGAAAGTTTTAAATAGTGAGTATAGCGTATCTTATACCAATTCTCCAAATTTAGA
AGATCTCGATTCATCTGAGCCTGGAAAATATATTAAATTAACCTTTTCTAGAAAGCTTTACAAG
GGGGCTGCTACTATTAATTCTTTTATTATTGCTTTTGCTCCGGATGAATAATTAGAAGAATTAC
TGCTTTTCCTACTAGTGGTGGGCGCGAAATAGTTATTGATTTGACTGCTGTGAAGTTTAATGTTG
GAATTCTTGATAGCAAATTTAAATATGATCCTCCAAAATCTTCAAATAAGGTAGATAATTTTTT
ATATGATATTAAAAAAAATTAA t596.aa (SEQ ID NO:177)
MKERCLYLLVFVALCVNNLFSDDYLIYDFDLSLNEFLEVSTRKDNLEPMVDSNRILLFYPPKKEIRKI
FAAFDFDQYSKKYLFKKNEHGVFFVKVNIPHGTSSIKYRLIVDGVWTNDEYNKNVVYNEDLIPFSKI
EIAKEKSSYISLRNPIQSYDNNEIEIFYIGRPGQIVTIAGSFNNFNPFLNRLIEKEDNKGIYTIKLKNLPK
DRIYYYFIDSGNKVIDKNNVNRINLYFVEGIDNKIDFEVSYFDHK t596.aa (SEQ ID NO:178)
DDYLIYDFDLSLNEFLEVSTRKDNLEPMVDSNRILLFYPPKKEIRKIFAAFDFDQYSKKYLFKKNEHG
VFFVKVNIPHGTSSIKYRLIVDGVWTNDEYNKNVVYNEDLIPFSKIEIAKEKSSYISLRNPIQSYDNNE
IEIFYIGRPGQIVTIAGSFNNFNPFLNRLIEKEDNKGIYTIKLKNLPKDRIYYYFIDSGNKVIDKNNVNRI
NLYFVEGIDNKIDFEVSYFDHK t596.nt (SEQ ID NO:179)
ATGAAAGAAAGGTGTTTGTATTTATTGGTTTTTGTAGCTTTATGTGTTAACAATCTTTTTTCAGA
TGATTATTTAATTTATGACTTTGATTTAAGTTTAAATGAATTTCTAGAAGTTTCAACAAGAAAAG
ACAATCTTGAGCCTATGGTTGATTCCAATCGTATATTATTGTTTTATCCTCCTAAAAAGAAATT
AGAAAAATTTTTGCTGCCTTTGACTTTGATCAGTATTCTAAGAAATATTTATTCAAAAAAATG
AGCATGGAGTTTTTTTTGTTAAAGTTAATATTCCTCATGGCACAAGCAGTATAAAATATAGGCT
TATTGTAGACGGTGTTTGGACTAATGACGAGTATAATAAAAATGTAGTTTATAATGAGGATTTA
ATCCCATTTTCTAAAATTGAGATCGCTAAAGAGAAGTCCAGCTATATTTCTTTGAGAAATCCAA
TACAATCATATGATAACAATGAAATTGAAATTTTTTACATAGGTCGTCCTGGACAAATAGTTAC
AATAGCTGGTAGTTTTAACAATTTTAATCCTTTTTTAAATAGGCTTATTGAGAAAGAGGACAAT

TABLE 1-continued
Nucleotide and Amino Acid Sequences.

AAGGGAATTTATACTATTAAGCTTAAAAATTTACCCAAGGATAGAATTTATTATTATTTTATTG
ATTCTGGTAACAAAGTAATAGATAAAAATAATGTTAATAGAATTAATTTATATTTTGTTGAGGG
AATTGATAATAAAATAGATTTCGAAGTTTCCTATTTTGATCATAAGTAA t596.nt (SEQ ID NO:180)
GATGATTATTTAATTTATGACTTTGATTTAAGTTTAAATGAATTTCTAGAAGTTTCAAC
AAGAAAAGACAATCTTGAGCCTATGGTTGATTCCAATCGTATATTATTGTTTTATCCTCCTAAAA
AAGAAATTAGAAAAATTTTTGCTGCCTTTGACTTTGATCAGTATTCTAAGAAATATTTATTCAA
AAAAAAATGAGCATGGAGTTTTTTTTGTTAAAGTTAATATTCCTCATGGCACAAGCAGTATAAAA
TATAGGCTTATTGTAGACGGTGTTTGGACTAATGACGAGTATAATAAAAATGTAGTTTATAATG
AGGATTTAATCCCATTTTCTAAAATTGAGATCGCTAAAGAGAAGTCCAGCTATATTTCTTTGAG
AAATCCAATACAATCATATGATAACAATGAAATTGAAATTTTTTACATAGGTCGTCCTGGACAA
ATAGTTACAATAGCTGGTAGTTTTAACAATTTTAATCCTTTTTTAAATAGGCTTATTGAGAAAGA
GGACAATAAGGGAATTTATACTATTAAGCTTAAAAATTTACCCAAGGATAGAATTTATTATTAT
TTTATTGATTCTGGTAACAAAGTAATAGATAAAAATAATGTTAATAGAATTAATTTATATTTTGT
TGAGGGAATTGATAATAAAATAGATTTCGAAGTTTCCTATTTTGATCATAAGTAA f598.aa (SEQ ID NO:181)
MRQRVMIAMALSCHPSLLIADEPTTALDVTIQEQILLLIKNLSKKFNTSTIFITHDLAVVAEICDTVSV
MYQGKIVEEGTVEEIFNNPKHPYTIGLLKSILTLEHDPNKKLYSTKENPMKITKTSTEEF t598.aa (SEQ ID NO:182)
EPTTALDVTIQEQILLLIKNLSKKFNTSTIFITHDLAVVAEICDTVSVMYQGKIVEEGTVEEIFNNPKH
PYTIGLLKSILTLEHDPNKKLYSTKENPMKITKTSTEEF f598.nt (SEQ ID NO:183)
ATGAGACAAAGAGTTATGATTGCCATGGCTCTTAGCTGTCATCCATCCTTATTAATAGCAGATG
AACCAACAACAGCCCTTGATGTTACAATCCAAGAGCAAATATTATTATTAATCAAAAACCTATC
TAAAAAATTCAATACTTCTACCATATTTATAACTCATGATCTTGCGGTTGTTGCTGAAATTTGTG
ATACAGTATCTGTAATGTATCAAGGAAAAATTGTAGAAGAAGGAACAGTAGAGGAAATATTTA
ACAATCCTAAGCATCCTTACACCATTGGGCTTTTAAAATCAATTCTTACGCTAGAACACGATCC
AAATAAAAAGCTTTATTCAACAAAAGAAAACCCTATGAAGATCACAAAAACCAGCACCGAGGA
GTTTTAA t598.nt (SEQ ID NO:184)
GAACCAACAACAGCCCTTGATGTTACAATCCAAGAGCAAATATTATTATTAATCAAAAACCTAT
CTAAAAAATTCAATACTTCTACCATATTTATAACTCATGATCTTGCGGTTGTTGCTGAAATTTGT
GATACAGTATCTGTAATGTATCAAGGAAAAATTGTAGAAGAAGGAACAGTAGAGGAAATATTT
AACAATCCTAAGCATCCTTACACCATTGGGCTTTTAAAATCAATTCTTACGCTAGAACACGATC
CAAATAAAAAGCTTTATTCAACAAAAGAAAACCCTATGAAGATCACAAAAACCAGCACCGAGG
AGTTTTAA f600.aa (SEQ ID NO:185)
MAIMERSIIGLFIALAFVSWLTVARVVRGQVQSLSSSEFIQAAKTLGATNQRIILKHLIPNSIGMIVIFT
TIRVPSFIMAEAFLSFLGLGISAPMTSWGELVQNGIATFVEYPWKVFIPAIVMTIFLLFMNFLGDGLRD
AFDPKDSI t600.aa (SEQ ID NO:186)
RVVRGQVQSLSSSEFIQAAKTLGATNQRIILKHLIPNSIGMIVIFTTIRVPSFIMAEAFLSFLGLGISAPM
TSWGELVQNGIATFVEYPWKVFIPAIVMTIFLLFMNFLGDGLRDAFDPKDSI f600.nt (SEQ ID NO:187)
ATGGCAATAATGGAAAGAAGTATAATCGGCTTATTCATAGCACTTGCATTTGTATCATGGTTAA
CAGTAGCTCGAGTTGTACGAGGCCAAGTACAATCACTATCAAGTTCGGAATTTATACAAGCAGC
CAAAACCCTTGGTGCAACAAATCAAAGAATAATCTTAAAACACTTGATCCCTAATAGCATTGGA
ATGATAGTTATATTCACAACAATAAGGGTTCCAAGCTTTATTATGGCTGAAGCATTTTTATCCTT
TTTAGGACTTGGAATTTCAGCTCCAATGACAAGCTGGGGAGAATTAGTGCAAAATGGAATTGCT
ACATTTGTTGAATATCCATGGAAAGTTTTTATTCCAGCTATAGTTATGACAATATTTCTATTATT
TATGAACTTTTTAGGTGATGGGCTAAGGGATGCTTTTGATCCAAAAGATAGCATCTAA t600.nt (SEQ ID NO:188)
CGAGTTGTACGAGGCCAAGTACAATCACTATCAAGTTCGGAATTTATACAAGCAGCCAAAACCC
TTGGTGCAACAAATCAAAGAATAATCTTAAAACACTTGATCCCTAATAGCATTGGAATGATAGT
TATATTCACAACAATAAGGGTTCCAAGCTTTATTATGGCTGAAGCATTTTTATCCTTTTTAGGAC
TTGGAATTTCAGCTCCAATGACAAGCTGGGGAGAATTAGTGCAAAATGGAATTGCTACATTTGT
TGAATATCCATGGAAAGTTTTTATTCCAGCTATAGTTATGACAATATTTCTATTATTTATGAACT
TTTTAGGTGATGGGCTAAGGGATGCTTTTGATCCAAAAGATAGCATCTAA f603.aa (SEQ ID NO:189)
MLKFTLKKILGIIPTLLVIIFLCFFVMRMAPGSPFDSEKPIDPQVKARLMEKYHLDKPFYIQAFYYITN
ALRGDLGPSLKKKDLTVSQYIKLGFPKSLTLGVISLIISLSIGIPIGILAAIYKNTYVDYIITSIAILGISIPL
FVIGPILQYFFAIKWGLLYTSGWITERGGFSNLILPIITLSMPNVAIFARIIRGSMLEIIQSDFIRTARAKG
LSFKKIVIKHMLRGAMLPVVSYIGPAFAAIISGSVVIEKIFRIAGMGMFITESALNRDYPVLMGGLLV
YSIILLISILISDIIYKILDPRV t603.aa (SEQ ID NO:190)
SPFDSEKPIDPQVKARLMEKYHLDKPFYIQAFYYITNALRGDLGPSLKKKDLTVSQYIKLGFPKSLTL

TABLE 1-continued

Nucleotide and Amino Acid Sequences.

GVISLIISLSIGIPIGILAAIYKNTYVDYIITSIAILGISIPLFVIGPILQYFFAIKWGLLYTSGWITERGGFSN
LILPIITLSMPNVAIFARIIRGSMLEIIQSDFIRTARAKGLSFKKIVIKHMLRGAMLPVVSYIGPAFAAIIS
GSVVIEKIFRIAGMGMFITESALNRDYPVLMGGLLVYSIILLISILISDIIYKILDPRV f603.nt (SEQ ID NO:191)
ATGTTAAAGTTTACTTTAAAGAAAATATTAGGAATAATACCAACTTTACTGGTAATAATTTTTTT
ATGCTTTTTTGTAATGAGAATGGCTCCTGGAAGTCCATTTGATTCTGAAAAACCTATTGATCCTC
AAGTAAAAGCAAGATTGATGGAAAAATATCACCTTGACAAGCCTTTTTATATTCAAGCTTTTTA
TTACATTACAAACGCTCTCAGGGGAGATCTGGGACCTTCTTTGAAAAAGAAAGACCTTACAGTT
AGTCAATACATAAAATTAGGATTTCCAAAATCACTTACACTAGGAGTAATATCCCTTATTATAT
CACTATCAATAGGAATACCAATAGGTATATTAGCTGCCATTTATAAAAATACTTATGTGGATTA
TATAATAACATCAATAGCAATATTGGGGATTTCAATACCATTATTCGTAATAGGGCCAATTTTA
CAATATTTTTTTGCAATTAAATGGGGTTTGCTTTATACCTCTGGATGGATTACAGAAAGAGGAG
GATTTTCAAATTTAATTCTACCCATAATAACTCTTAGCATGCCCAACGTAGCTATTTTCGCAAGA
ATAATCAGAGGATCAATGCTAGAAATAATACAAAGCGACTTTATAAGAACTGCGCGTGCAAAA
GGGCTAAGCTTCAAAAAGATAGTTATAAAGCATATGTTAAGAGGAGCAATGTTGCCTGTAGTA
AGCTATATAGGTCCAGCATTTGCTGCTATAATATCTGGAAGCGTGGTTATTGAAAAAATATTTA
GAATTGCTGGAATGGGAATGTTTATAACAGAATCCGCACTAAACAGAGATTACCCAGTATTAAT
GGGCGGATTGTTAGTATATTCAATAATACTGCTTATTTCTATATTAATATCAGATATTATATATA
AAATATTAGATCCAAGAGTATAA t603.nt (SEQ ID NO:192)
AGTCCATTTGATTCTGAAAAACCTATTGATCCTCAAGTAAAAGCAAGATTGATGGAAAAATATC
ACCTTGACAAGCCTTTTTATATTCAAGCTTTTTATTACATTACAAACGCTCTCAGGGGAGATCTG
GGACCTTCTTTGAAAAAGAAAGACCTTACAGTTAGTCAATACATAAAATTAGGATTTCCAAAAT
CACTTACACTAGGAGTAATATCCCTTATTATATCACTATCAATAGGAATACCAATAGGTATATT
AGCTGCCATTTATAAAAATACTTATGTGGATTATATAATAACATCAATAGCAATATTGGGGATT
TCAATACCATTATTCGTAATAGGGCCAATTTTACAATATTTTTTTGCAATTAAATGGGGTTTGCT
TTATACCTCTGGATGGATTACAGAAAGAGGAGGATTTTCAAATTTAATTCTACCCATAATAACT
CTTAGCATGCCCAACGTAGCTATTTTCGCAAGAATAATCAGAGGATCAATGCTAGAAATAATAC
AAAGCGACTTTATAAGAACTGCGCGTGCAAAAGGGCTAAGCTTCAAAAAGATAGTTATAAAGC
ATATGTTAAGAGGAGCAATGTTGCCTGTAGTAAGCTATATAGGTCCAGCATTTGCTGCTATAAT
ATCTGGAAGCGTGGTTATTGAAAAAATATTTAGAATTGCTGGAATGGGAATGTTTATAACAGAA
TCCGCACTAAACAGAGATTACCCAGTATTAATGGGCGGATTGTTAGTATATTCAATAATACTGC
TTATTTCTATATTAATATCAGATATTATATATAAAATATTAGATCCAAGAGTATAA f607.aa (SEQ ID NO:193)
MKYIKIALMLIIFSLIACISNAKKEKIVFRVSNLSEPSSLDPQLSTDLYGSNIITNLFLGLAVKDSQTGK
YKPGLAKSWNISEDGIIYTFNLREDIVWSDGVAITAEEIKKSYLRILNKKTAAMYANLIKSTIKNAQE
YFDETVPESELGIKAIDSKTLEITLTSPKPYFPDMLTHSAYIPVPMHIVEKYGENWTNPENIVVSGAY
KLKERSINDKIVIEKNEKYYNAKNVEIDEVIFYPTEGSVAYNMYINGELDFLQGAEKNNLEEIKIRDD
YYSGLKNGMAYIAFNTTIKPLDNLKVRQAISLAIDRETLTKVVLKGSSDPTRNLTPKFDDYSYGKNL
ILFDPENAKKLLAEAGYPDGKGFPTLKYKISEGRPTTAEFLQEQFKKILNINLEIENEEWTTFLGSRRT
GNYQMSSVGWIGDYFDPLTFLDSLFTTENHFLGAYKYSNKEYDALIKKSNFELDPIKRQDILRQAEEI
IAEKDFPMAPLYIPKSHYLFRNDKWTGWVPNIAESYLYEDIKTKK t607.aa (SEQ ID NO:194)
CISNAKKEKIVFRVSNLSEPSSLDPQLSTDLYGSNIITNLFLGLAVKDSQTGKYKPGLAKSWNISEDGI
IYTFNLREDIVWSDGVAITAEEIKKSYLRILNKKTAAMYANLIKSTIKNAQEYFDETVPESELGIKAID
SKTLEITLTSPKPYFPDMLTHSAYIPVPMHIVEKYGENWTNPENIVVSGAYKLKERSINDKIVIEKNE
KYYNAKNVEIDEVIFYPTEGSVAYNMYINGELDFLQGAEKNNLEEIKIRDDYYSGLKNGMAYIAFN
TTIKPLDNLKVRQAISLAIDRETLTKVVLKGSSDPTRNLTPKFDDYSYGKNLILFDPENAKKLLAEAG
YPDGKGTPFLKYKISEGRPTTAEFLQEQFKKILNINLEIENEEWTTFLGSRRTGNYQMSSVGWIGDYF
DPLTFLDSLFTTENHTLGAYKYSNKEYDALIKKSNFELDPIKRQDILRQAEEIIAEKDFPMAPLYIPKS
HYLFRNDKWTGWVPNIAESYLYEDIKTKK f607.nt (SEQ ID NO:195)
ATGAAATATATAAAAATAGCCTTAATGCTAATAATTTTTTCTTTAATAGCATGTATTAGTAATGC
TAAAAAAGAAAAAATAGTTTTCAGAGTATCAAACTTAAGCGAGCCATCATCACTTGATCCTCAA
CTCTCAACAGACCTTTACGGTAGCAACATTATTACAAACCTATTCTTAGGCCTAGCGGTAAAAG
ATTCTCAAACTGGAAAATATAAACCAGGACTTGCAAAAAGTTGGAATATTTCTGAAGATGGAAT
TATTTACACATTTAACCTAAGAGAAGATATAGTTTGGAGCGATGGAGTTGCCATTACTGCCGAG
GAGATAAAAAAATCATACCTAAGAATTTTAAATAAAAAAACAGCTGCAATGTATGCTAATTTAA
TAAAATCTACAATAAAAAATGCACAAGAATATTTCGATGAGACAGTGCCTGAATCTGAGCTTGG
CATAAAGGCTATTGACAGCAAAACCTTAGAGATAACATTAACATCTCCAAAGCCTTATTTTCCT
GATATGCTAACACACTCAGCATACATACCAGTTCCAATGCATATTGTTGAAAAATATGGAGAAA
ATTGGACAAATCCTGAAAATATAGTTGTTAGTGGCGCATACAAACTTAAAGAAAGATCAATTAA
CGATAAAATCGTAATAGAAAAAAATGAAAAATACTATAATGCAAAAAATGTAGAAATTGATGA
AGTAATATTTTACCCAACAGAAGGTAGCGTGGCTTACAATATGTACATAAACGGTGAACTCGAT
TTTCTACAAGGAGCAGAAAAGAATAATTTAGAAGAAATTAAAATAAGAGATGATTATTATTCTG
GGTTAAAAAACGGAATGGCATACATAGCATTCAATACAACAATAAAACCACTAGACAATTTAA
AAGTTAGACAAGCCATCTCCCTTGCCATTGACAGAGAAACTTTAACTAAAGTAGTTTTAAAGGG
AAGTTCAGATCCAACAAGAAATCTAACTCCAAAATTTGATGATTATTCTTATGGAAAAAATTTA
ATACTATTTGATCCTGAGAATGCAAAAAAACTTTTAGCTGAAGCTGGATATCCGGATGGGAAAG
GATTCCCCACATTAAAAATATAAATATCGGAGGGAAGACCAACAACAGCAGAATTTTTGCAAG
AACAATTTAAAAAAATACTAAACATTAACTTAGAAATCGAGAATGAAGAATGGACAACATTCC
TAGGAAGCAGAAGAACTGGAAATTACCAAATGTCAAGCGTGGGGTGGATAGGAGATTATTTTG

TABLE 1-continued

Nucleotide and Amino Acid Sequences.

ATCCCTTAACATTCTTAGACAGCTTATTTACAACAGAAAATCATTTTTTAGGAGCGTACAAATA
TTCAAACAAAGAGTATGATGCTTTAATAAAAAAATCTAATTTTGAACTTGATCCAATAAAAAGA
CAAGACATTTTAAGACAAGCTGAAGAGATAATAGCAGAAAAAGACTTTCCTATGGCACCTTTAT
ATATACCCAAATCTCATTATCTTTTCAGAAATGATAAATGGACAGGGTGGGTACCAAATATCGC
AGAAAGCTATTTATATGAAGATATTAAAACTAAAAAATAA t607.nt (SEQ ID NO:196)
TGTATTAGTAATGCTAAAAAAGAAAAAATAGTTTTCAGAGTATCAAACTTAAGCGAGCCATCAT
CACTTGATCCTCAACTCTCAACAGACCTTTACGGTAGCAACATTATTACAAACCTATTCTTAGGC
CTAGCGGTAAAAGATTCTCAAACTGGAAAATATAAACCAGGACTTGCAAAAAGTTGGAATATT
TCTGAAGATGGAATTATTTACACATTTAACCTAAGAGAAGATATAGTTTGGAGCGATGGAGTTG
CCATTACTGCCGAGGAGATAAAAAAATCATACCTAAGAATTTTAAATAAAAAACAGCTGCAA
TGTATGCTAATTTAATAAAATCTACAATAAAAAATGCACAAGAATATTTCGATGAGACAGTGCC
TGAATCTGAGCTTGGCATAAAGGCTATTGACAGCAAAACCTTAGAGATAACATTAACATCTCCA
AAGCCTTATTTTCCTGATATGCTAACACACTCAGCATACATACCAGTTCCAATGCATATTGTTGA
AAAATATGGAGAAAATTGGACAAATCCTGAAAATATAGTTGTTAGTGGCGCATACAAACTTAA
AGAAAGATCAATTAACGATAAAATCGTAATAGAAAAAAATGAAAAATACTATAATGCAAAAAA
TGTAGAAATTGATGAAGTAATATTTTACCCAACAGAAGGTAGCGTGGCTTACAATATGTACATA
AACGGTGAACTCGATTTTCTACAAGGAGCAGAAAAGAATAATTTAGAAGAAATTAAAATAAGA
GATGATTATTATTCTGGGTTAAAAAACGGAATGGCATACATAGCATTCAATACAACAATAAAAC
CACTAGACAATTTAAAAGTTAGACAAGCCATCTCCCTTGCCATTGACAGAGAAACTTTAACTAA
AGTAGTTTTAAAGGGAAGTTCAGATCCAACAAGAAATCTAACTCCAAAATTTGATGATTATTCT
TATGGAAAAAATTTAATACTATTTGATCCTGAGAATGCAAAAAAACTTTTAGCTGAAGCTGGAT
ATCCGGATGGGAAAGGATTCCCCACATTAAAATATAAAATATCGGAGGGAAGACCAACAACAG
CAGAATTTTTGCAAGAACAATTTAAAAAAATACTAAACATTAACTTAGAAATCGAGAATGAAG
AATGACAACATTCCTAGGAAGCAGAAGAACTGGAAATTACCAAATGTCAAGCGTGGGTGGA
TAGGAGATTATTTTGATCCCTTAACATTCTTAGACAGCTTATTTACAACAGAAAATCATTTTTTA
GGAGCGTACAAATATTCAAACAAAGAGTATGATGCTTTAATAAAAAAATCTAATTTTGAACTTG
ATCCAATAAAAAGACAAGACATTTTAAGACAAGCTGAAGAGATAATAGCAGAAAAAGACTTTC
CTATGGCACCTTTATATATACCCAAATCTCATTATCTTTTCAGAAATGATAAATGGACAGGGTG
GGTACCAAATATCGCAGAAAGCTATTTATATGAAGATATTAAAACTAAAAAATAA f611.aa (SEQ ID NO:197)
MKKIFLFLFISFYLFGFEDSSLKIGIDDVYVEAHEEGFHLFIRKKPAIKSVILTESFEIPDKKKDVATYSF
RTLSYNKVNGDEIRILNGRVIKNKELLSLTSSTPVPNKKTGEAFHILIPKKLKYGFPNFSTRSGDIDLE
VLKSKKEPFWFSIRSFEKKYNDYLGRYQDNAYELLFKDDQNQGKIEFNELKDTFTKFSDEVVIANN
GIDIVDKINKILKNSEDSVVDLDLVLVVDVTDSMKSNIEILKEHLTSIIEPQLQKFKSYRIGLVFYKDY
LEDFLTKAFDFNTIPYLNNILKYVNVGGGGDYPEAVFEGIDAAVTQFDWRAERRFIIVIGDAPPHEYP
RGSIVYKDVINSAKEKDITIYGIIFQ t611.aa (SEQ ID NO:198)
FEDSSLKIGIDDVYVEAHEEGFHLFIRKKPAIKSVILTESFEIPDKKKDVATYSFRTLSYNKVNGDEIRI
LNGRVIKNKELLSLTSSTPVPNKKTGEAFHILIPKKLKYGFPNFSTRSGDIDLEVLKSKKEPFWFSIRSF
EKKYNDYLGRYQDNAYELLFKDDQNQGKIEFNELKDTFTKFSDEVVIANNGIDIVDKINKILKNSED
SVYDLDLVLVVDVTDSMKSNIEILKEHLFSIIEPQLQKFKSYRIGLVFYKDYLEDFLTKAFDFNTIPYL
NNILKYVNVGGGGDYPEAVFEGIDAAVTQFDWRAERRFIIVIGDAPPHEYPRGSIVYKDVINSAKEK
DITIYGIIFQ f611.nt (SEQ ID NO:199)
ATGAAGAAAATTTTTTTATTTCTTTTTATTAGTTTTTATTTGTTTGGATTTGAAGATAGTTCTTTG
AAAATAGGTATTGATGATGTTTATGTTGAGGCTCATGAAGAGGGATTTCATCTTTTTATTAGAA
AAAAACCTGCAATCAAATCAGTAATATTGACAGAGTCTTTTGAAATTCCTGATAAGAAAAAGA
TGTGGCTACTTATTCATTTCGTACATTAAGTTATAATAAGGTTAATGGAGATGAAATTCGGATT
TTAAATGGAAGAGTTATTAAGAATAAAGAACTTTTATCATTGACATCTTCCACCCCTGTTCCTA
ATAAAAAGTTTGGAGAAGCTTTTCATATATTGATTCCAAAAAAATTAAAATATGGATTTCCAAA
TTTTTCAACAAGAAGTGGTGATATTGACTTAGAAGTATTAAAAAGTAAAAAAGAGCCCTTTTGG
TTTTCTATAAGATCTTTTGAGAAAAAATATAATGATTATTTGGGCAGATATCAAGACAATGCTT
ATGAATTGCTTTTCAAGGATGATCAAAATCAGGGAAAAATTGAATTTAATGAATTAAAAGATAC
TTTTACAAAATTTTCAGATGAGGTTGTTATTGCTAATAATGGCATTGATATTGTTGATAAAATA
AACAAAATTTTAAAAAACTCAGAAGATTCAGTTTATGATTTAGATTTAGTGCTTGTTGTTGATG
TTACTGATAGTATGAAAAGCAATATTGAGATTCTAAAAGAGCATTTGTTTTCAATAATAGAACC
TCAACTTCAAAAGTTTAAATCCTACAGAATAGGTCTTGTTTTTTATAAAGACTATCTTGAAGATT
TTTTAACCAAAGCTTTTGATTTTAATACTATTCCTTATTTAAATAATATTCTTAAGTATGTTAAT
GTTGGTGGCGGTGGGGATTATCCAGAAGCTGTTTTTGAGGGGATTGATGCTGCTGTGACCCAAT
TTGATTGGCGGGCAGAAAGAAGGTTTATTATTGTTATAGGAGATGCACCTCCTCATGAGTATCC
AAGAGGGTCTATTGTTTATAAAGATGTTATCAATTCTGCAAAGGAAAAAGATATTACAATTTAT
GGAATAATATTTCAGTAA t611.nt (SEQ ID NO:200)
TTTGAAGATAGTTCTTTGAAAATAGGTATTGATGATGTTTATGTTGAGGCTCATGAAGAGGGAT
TTCATCTTTTTATTAGAAAAAAACCTGCAATCAAATCAGTAATATTGACAGAGTCTTTTGAAATT
CCTGATAAGAAAAAAGATGTGGCTACTTATTCATTTCGTACATTAAGTTATAATAAGGTTAATG
GAGATGAAATTCGGATTTTAAATGGAAGAGTTATTAAGAATAAAGAACTTTTATCATTGACATC
TTCCACCCCTGTTCCTAATAAAAAGTTTGGAGAAGCTTTTCATATATTGATTCCAAAAAAATTA
AAATATGGATTTCCAAATTTTTCAACAAGAAGTGGTGATATTGACTTAGAAGTATTAAAAAGTA
AAAAAGAGCCCTTTTGGTTTTCTATAAGATCTTTTGAGAAAAAATATAATGATTATTTGGGCAG
ATATCAAGACAATGCTTATGAATTGCTTTTCAAGGATGATCAAAATCAGGGAAAAATTGAATTT

TABLE 1-continued

Nucleotide and Amino Acid Sequences.

AATGAATTAAAAGATACTTTTACAAAATTTTCAGATGAGGTTGTTATTGCTAATAATGGCATTG
ATATTGTTGATAAAATAAACAAAATTTTAAAAAACTCAGAAGATTCAGTTTATGATTTAGATTT
AGTGCTTGTTGTTGATGTTACTGATAGTATGAAAAGCAATATTGAGATTCTAAAAGAGCATTTG
TTTTCAATAATAGAACCTCAACTTCAAAAGTTTAAATCCTACAGAATAGCTCTTGTTTTTTATAA
AGACTATCTTGAAGATTTTTTAACCAAAGCTTTTGATTTTAATACTATTCCTTATTTAAATAATA
TTCTTAAGTATGTTAATGTTGGTGGCGGTGGGGATTATCCAGAAGCTGTTTTTGAGGGGATTGA
TGCTGCTGTGACCCAATTTGATTGGCGGGCAGAAAGAAGGTTTATTATTGTTATAGGAGATGCA
CCTCCTCATGAGTATCCAAGAGGGTCTATTGTTTATAAAGATGTTATCAATTCTGCAAAGGAAA
AAGATATTACAATTTATGGAATAATATTTCAGTAA f617.aa (SEQ ID NO:201)
MIFFRNSFMALIFSFSILSISYFFGDFFQFSYIKMISWRFILFLIMATGIATCAKSNSLNLGNEGQIYFGA
FLVYIFSSFFGLTYFNFVFLILLSSFFVGLLGLIPFFITFFFGLNKALTGLLISYGNQRLVDGFILNMLKT
GSFSNQTKRINSLFALDSSLIYLFLLLGVSVWLFYVFIHKKTIYGLQLEILSNKKKIDIFFNINEFKYKFF
AVFGSAFLNGLAGSMFVVFFRPYLVLGLTSGLGWSSLIVAVISGFNYVYVLFFSLLFSILIEFNNFLNI
NYDFKYEFIGLCQSIAIFISLFLIKARKK t617.aa (SEQ ID NO:202)
AKSNSLNLGNEGQIYFGAFLVYIFSSFFGLTYFNFVFLILLSSFFVGLLGLIPFFITFFFGLNKALTGLLIS
YGNQRLVDGFILNMLKTGSFSNQTKRINSLFALDSSLIYLFLLGVSVWLFYVFIHKKTIYGLQLEILSN
KKKIDIFFNINEFKYKFFAVFGSAFLNGLAGSMFVVFFRPYLVLGLTSGLGWSSLIVAVISGFNYVYV
LFFSLLFSILIEFNNFLNINYDFKYEFIGLCQSIAIFISLFLIKARKK f617.nt (SEQ ID NO:203)
ATGATCTTTTTTAGAAATAGCTTTATGGCATTAATTTTTTCTTTTTCAATATTAAGTATTAGCTAT
TTTTCGGTGATTTTTTTCAATTTTCTTATATTAAAATGATATCTTGGCGCTTTATTTTATTTTA
ATTATGGCTACGGGGATTGCTACTTGTGCCAAGAGTAATTCATTAAATCTTGGGAATGAAGGTC
AGATTTATTTTGGGGCATTTTTAGTTTATATATTTTCAAGTTTTTTTGGATTAACCTATTTTAATT
TTGTATTTTTGATACTTTTAAGTTCTTTTTTTGTAGGACTTTTGGGGCTTATCCCCTTTTTTATTA
CTTTTTCTTCGGATTAAATAAAGCCTTAACAGGTCTTTTAATATCTTATGGAAATCAAAGATTG
GTGGATGGATTTATTTTAAATATGTTAAAAACAGGTAGTTTTTCTAATCAGACAAAAAGGATTA
ATAGTTTGTTTGCTTTAGATTCATCACTTATTTACTTGTTTTTGCTTGGTGTATCAGTTTGGCTTT
TTTATGTTTTTATTCACAAAAAAACTATTTATGGTCTTCAGCTTGAAATATTAAGCAATAAAAAA
AAGATAGACATTTTTTTCAATATAAATGAATTTAAATATAAGTTTTTCGCTGTATTTGGCAGTGC
TTTTTTAAATGGTCTTGCAGGTTCTATGTTTGTAGTGTTTTTTAGACCATATTTGGTTTTAGGGC
TAACTTCAGGACTTGGTTGGAGTAGTCTAATTGTTGCTGTAATTTCAGGATTTAATTATGTTTAT
GTATTATTTTTTAGCTTATTGTTTTCAATATTAATTGAATTTAATAATTTTCTTAATATAAATTAT
GACTTTAAGTATGAATTTATTGGGCTTTGTCAATCAATTGCTATTTTTATCTCTTTATTTTTGATT
AAAGCTAGGAAAAAGTAG t617.nt (SEQ ID NO:204)
GCCAAGAGTAATTCATTAAATCTTGGGAATGAAGGTCAGATTTATTTTGGGGCATTTTTACTTT
ATATATTTTCAAGTTTTTTTGGATTAACCTATTTTAATTTTGTATACTTTTAAGTTCTT
TTTTTGTAGGACTTTTGGGGCTTATCCCCTTTTTTATTACTTTTTTCTTCGGATTAAATAAAGCCT
TAACAGGTCTTTTAATATCTTATGGAAATCAAAGATTGGTGGATGGATTTATTTTAAATATGTT
AAAAACAGGTAGTTTTTCTAATCAGACAAAAAGGATTAATAGTTTGTTTGCTTTAGATTCATCA
CTTATTTACTTGTTTTTGCTTGGTGTATCAGTTTGGCTTTTTTATGTTTTTATTCACAAAAAAACT
ATTTATGGTCTTCAGCTTGAAATATTAAGCAATAAAAAAAAGATAGACATTTTTTTCAATATAA
ATGAATTTAAATATAAGTTTTTCGCTGTATTTGGCAGTGCTTTTTTAAATGGTCTTGCAGGTTCT
ATGTTTGTAGTGTTTTTTAGACCATATTTGGTTTTAGGGCTAACTTCAGGACTTGGTTGGAGTAG
TCTAATTGTTGCTGTAATTTCAGGATTTAATTATGTTTATGTATTATTTTTTAGCTTATTGTTTTC
AATATTAATTGAATTTAATAATTTTCTTAATATAAATTATGACTTTAAGTATGAATTTATTGGGC
TTTGTCAATCAATTGCTATTTTTATGTCTTATTTTTGATTAAAGCTAGGAAAAAGTAG f631.aa (SEQ ID NO:205)
MVVEINSLRTCYLLVLLLLVAYGLVVFYTSSFFLSLELTGNPNFLFFTRLNYLFLSFMVFLVFERISLN
FLKKSIFPVLIITLFLIMATFLSPSISGAKRWIFFQGVSIQPSEIFKTSFTIYLSAYLSKFDPRKNNGISYWI
KPMLIFAIFWVLIILQNDYSTAIYFAILFFIVLFVSNMAFSYVFAIVVTFLPVSAIFLMLEPYRVSRIFAF
LNPYDDPSGKGYQIIASLNALKSGGILGKGLGMGEVKLGKLPEANSDFIFSVLGEELGFLGVLFAISL
FFLFFYFGYFIAIHSNSRFKFFIAFISSLAIFLQSMMNILIAIGLLPPTGINLPFFSSGGSSIIVTMALSGLIS
NVSKNLSNN t631.aa (SEQ ID NO:206)
RISLNFLKKSIFPVLIITLFLIMATFLSPSISGAKRWIFFQGVSIQPSEIFKISFTIYLSAYLSKFDPRKNNG
ISYWIKPMLIFAIFWVLIILQNDYSTAIYFAILFFIVLFVSNMAFSYVFAIVVTFLPVSAIFLMLEPYRVS
RIFAFLNPYDDPSGKGYQIIASLNALKSGGILGKGLGMGEVKLGKLPEANSDFIFSVLGEELGFLGVL
FAISLFFLFFYFGYFIAIHSNSRFKFFIAFISSLAIFLQSMMNILIAIGLLPPTGINLPFFSSGGSSIIVTMAL
SGLISNVSKNLSNN f631.nt (SEQ ID NO:207)
ATGGTTGTAGAGATAAATTCACTTAGGACATGTTATTTGCTTGTTTTGCTGCTATTGGTAGCCTA
TGGCCTTGTAGTTTTTTATACTTCTTCCTTTTTTCTAAGCTTAGAATTGACAGGTAATCCAAATT
TTTTATTTTTCACAAGACTTAATTATCTTTTTTTAAGTTTTATGGTTTTTCTTGTTTTTGAAAGGA
TTTCTTTAAATTTTTAAAAAAATCAATATTTCCTGTATTGATTATAACTCTTTTTTTAATTATGG
CAACTTTTTTATCTCCAAGTATTTCTGGAGCAAAGAGATGGATATTCTTTCAAGGTGTTAGCATT
CAACCTTCTGAGATTTTTAAAATATCTTTTACTATTTATCTTTCAGCTTATTTGAGCAAGTTTGA
CCCAAGAAAAAACAATGGTATTTCATACTGGATAAAGCCAATGTTGATTTTTGCAATTTTTTGG

TABLE 1-continued

Nucleotide and Amino Acid Sequences.

GTGTTAATAATTTTGCAAAACGATTATTCAACAGCTATTTATTTTGCCATTCTTTTTTTTATTGTT
TTGTTTGTTTCTAATATGGCATTTAGCTATGTTTTTGCTATTGTGGTTACTTTTTTTACCAGTTTCT
GCTATATTCTTGATGCTTGAACCTTATAGGGTTTCTAGAATTTTTGCCTTTCTCAATCCTTACGA
TGATCCTTCTGGCAAAGGTTACCAGATAATAGCATCTCTTAATGCTTTAAAAAGTGGAGGAATT
TTAGGTAAAGGGCTGGGAATGGGAGAGGTAAAACTTGGAAAATTACCAGAGGCCAATTCGGAT
TTTATTTTTTCAGTTCTTGGAGAAGAATTAGGATTTTTAGGGGTTTTGTTTGCTATAAGCTTGTT
TTTTTTGTTTTTTTACTTTGGTTATTTTATAGCTATTCATTCTAATAGTAGGTTTAAATTTTTTAT
TGCATTTATTTCAAGTCTTGCAATTTTTCTTCAAAGCATGATGAATATTTTAATTGCAATCGGTC
TTTTGCCTCCTACAGGGATAAATTTACCATTTTTTTCATCTGGGGGATCTTCTATTATTGTTACC
ATGGCATTGTCTGGCCTTATTTCAAATGTTTCAAAAAATTTAAGTAATAATTGA t631.nt (SEQ ID NO:208)
AGGATTTCTTTAAATTTTTTAAAAAAATCAATATTTCCTGTATTGATTATAACTCTTTTTTTAATT
ATGGCAACTTTTTTATCTCCAAGTATTTCTGGAGCAAAGAGATGGATATTCTTTCAAGGTGTTA
GCATTCAACCTTCTGAGATTTTTAAAATATCTTTTACTATTTATCTTTCAGCTTATTTGAGCAAG
TTTGACCCAAGAAAAAACAATGGTATTTCATACTGGATAAAGCCAATGTTGATTTTTGCAATTT
TTTGGGTGTTAATAATTTTGCAAAACGATTATTCAACAGCTATTTATTTTGCCATTCTTTTTTTA
TTGTTTTGTTTGTTTCTAATATGGCATTTAGCTATGTTTTTGCTATTGTGGTTACTTTTTTACCAG
TTTCTGCTATATTCTTGATGCTTGAACCTTATAGGGTTTCTAGAATTTTTGCCTTTCTCAATCCTT
ACGATGATCCTTCTGGCAAAGGTTACCAGATAATAGCATCTCTTAATGCTTTAAAAAGTGGAGG
AATTTTAGGTAAAGGGCTGGGAATGGGAGAGGTAAAACTTGGAAAATTACCAGAGGCCAATTC
GGATTTTATTTTTTCAGTTCTTGGAGAAGAATTAGGATTTTTAGGGGTTTTGTTTGCTATAAGCT
TGTTTTTTTTGTTTTTTTACTTTGGTTATTTTATAGCTATTCATTCTAATAGTAGGTTTAAATTTT
TTATTGCATTTATTTCAAGTCTTGCAATTTTTCTTCAAAGCATGATGAATATTTTAATTGCAATC
GGTCTTTTGCCTCCTACAGGGATAAATTTACCATTTTTTTCATCTGGGGGATCTTCTATTATTGT
TACCATGGCATTGTCTGGCCTTATTTCAAATGTTTCAAAAAATTTAAGTAATAATTGA f647.aa (SEQ ID NO:209)
MKVNNFLSFFFRAFFLLFLIVILFFFVLFFIDFIGMYNTKRYFPEFVRTKLLGETSLVFDHNSNIILDEA
RLVKEREAIDIKNQQIEKLKEDLKLKEDSLNKLEFELKQKQKDLDLKQKIIDDIINKYNDEEANILQT
AVYLMNMPPEDAVKRLEDLNPELAISYMRKIEELSKKEGRLSIVPYWLSLMDSKKAAILIRKMSVSS
LE t647.aa (SEQ ID NO:210)
IDFIGMYNTKRYFPEFVRTKLLGETSLVFDHNSNIILDEARLVKEREAIDIKNQQIEKLKEDLKLKEDS
LNKLEFELKQKQKDLDLKQKIIDDIINKYNDEEANILQTAVYLMNMPPEDAVKRLEDLNPELAISYM
RKIEELSKKEGRLSIVPYWLSLMDSKKAAILIRKMSVSSLE f647.nt (SEQ ID NO:211)
ATGAAAGTGAATAATTTTTTATCGTTCTTTTTTAGGGCATTTTTTTTGTTATTTTTAATTGTTATT
TTATTTTTCTTTGTATTATTCTTTATTGATTTTATTGGAATGTATAATACTAAAAGATATTTCCCC
GAATTTGTAAGAACCAAGTTGTTAGGAGAAACTTCTCTGGTCTTTGATCATAATTCTAATATAA
TTCTTGATGAAGCTAGACTTGTGAAGGAAAGAGAAGCTATTGATATTAAGAATCAGCAGATTG
AAAAGCTTAAAGAAGATCTAAAGTTAAAAGAAGACAGTTTAAATAAGCTTGAATTTGAGCTTA
AGCAAAAGCAGAAAGATTTAGATTTAAAACAAAAAATAATAGATGACATTATAAATAAATATA
ATGATGAGGAAGCAAATATTTTGCAAACAGCTGTATATTTAATGAATATGCCACCAGAAGATGC
TGTTAAGCGGCTTGAAGATTTAAATCCCGAGCTTGCAATATCTTATATGCGGAAAATTGAAGAG
CTTTCCAAAAAAGAAGGTCGTTTATCAATTGTTCCTTATTGGTTATCTCTTATGGATTCTAAAAA
AGCTGCTATATTGATTAGAAAAATGTCTGTTAGTTCATTGGAGTAG t647.nt (SEQ ID NO:212)
ATTGATTTTATTGGAATGTATAATACTAAAAGATATTTCCCCGAATTTGTAAGAACCAAGTTGT
TAGGAGAAACTTCTCTGGTCTTTGATCATAATTCTAATATAATTCTTGATGAAGCTAGACTTGTG
AAGGAAAGAGAAGCTATTGATATTAAGAATCAGCAGATTGAAAAGCTTAAAGAAGATCTAAAG
TTAAAAGAAGACAGTTTAAATAAGCTTGAATTTGAGCTTAAGCAAAAGCAGAAAGATTTAGAT
TTAAAACAAAAAATAATAGATGACATTATAAATAAATATAATGATGAGGAAGCAAATATTTTG
CAAACAGCTGTATATTTAATGAATATGCCACCAGAAGATGCTGTTAAGCGGCTTGAAGATTTAA
ATCCCGAGCTTGCAATATCTTATATGCGGAAAATTGAAGAGCTTTCCAAAAAAGAAGGTCGTTT
ATCAATTGTTCCTTATTGGTTATCTCTTATGGATTCTAAAAAAGCTGCTATATTGATTAGAAAAA
TGTCTGTTAGTTCATTGGAGTAG f653.aa (SEQ ID NO:213)
MLTYGDMVTLLLVFFVTMFSLNDIIFQENVIRIMSASFTGAGFFKGGKTLDFSKLSYLSNSFMSLPST
VRNKQASQTAKNKSMIEFIEKIQSKNIVVRQEERGIVISLAADAFFDSASADVKLEENRDSIQKIASFI
GFLSPRGYNFKIEGHTDNIDTDVNGPWKSNWELSAARSVNMLEHILNYLDQSDVKRIENNFEVSGF
GGSRPIATDDTPEGRAYNRRIDILITTDASLSTPKEIKQ t653.aa (SEQ ID NO:214)
NDIIFQENVIRIMSASFTGAGFFKGGKTLDFSKLSYLSNSFMSLPSTVRNKQASQTAKNKSMIEFIEKI
QSKNIVVRQEERGIVISLAADAFFDSASADVKLEENRDSIQKIASFIGFLSPRGYNFKIEGHTDNIDTD
VNGPWKSNWELSAARSVNMLEHILNYLDQSDVKRIENNFEVSGFGGSRPIATDDTPEGRAYNRRIDI
LITTDASLSFPKEIKQ f653.nt (SEQ ID NO:215)
ATGTTGACTTATGGAGACATGGTTACTTTGCTGCTTGTGTTTTTTGTTACAATGTTTTCATTAAA
TGATATTATTTTTCAAGAAAATGTGATAAGAATAATGTCTGCTTCTTCACGGGTGCTGGATTTT
TCAAGGGCGGTAAAACTTTAGATTTTAGTAAATTATCTTATTTGAGTAATAGCTTTATGTCTTTG

TABLE 1-continued

Nucleotide and Amino Acid Sequences.

CCTTCTACTGTGCGCAATAAACAAGCATCTCAGACTGCTAAAAATAAATCCATGATTGAATTTA
TTGAGAAGATTCAGTCTAAAAATATTGTAGTTAGGCAAGAAGAAAGAGGTATTGTAATATCTCT
TGCAGCAGATGCATTTTTTGATTCTGCTAGTGCAGATGTTAAGCTTGAAGAGAATAGAGATTCT
ATTCAAAAAATAGCATCTTTTATTGGCTTTTTAAGTCCTAGAGGCTATAATTTTAAAATAGAAG
GGCATACAGATAATATTGATACTGATGTAAATGGACCTTGGAAAAGCAATTGGGAACTTTCGGC
TGCTAGATCTGTTAATATGCTGGAACATATTTTGAACTATTTAGATCAATCTGATGTTAAAAGA
ATTGAAAATAATTTTGAAGTATCTGGTTTTGGTGGAAGTAGGCCTATTGCAACAGACGATACCC
CTGAGGGTAGGGCTTATAATAGAAGAATTGATATATTAATTACTACAGATGCATCTTTAAGTTT
CCCTAAGGAAATTAAGCAGTAA t653.nt (SEQ ID NO:216)
AATGATATTATTTTTCAAGAAAATGTGATAAGAATAATGTCTGCTTCTTTCACGGGTGC
TGGATTTTTCAAGGGCGGTAAAACTTTAGATTTTAGTAAATTATCTTATTTGAGTAATAGCTTTA
TGTCTTTGCCTTCTACTGTGCGCAATAAACAAGCATCTCAGACTGCTAAAAATAAATCCATGAT
TGAATTTATTGAGAAGATTCAGTCTAAAAATATTGTAGTTAGGCAAGAAGAAAGAGGTATTGTA
ATATCTCTTGCAGCAGATGCATTTTTTGATTCTGCTAGTGCAGATGTTAAGCTTGAAGAGAATA
GAGATTCTATTCAAAAAATAGCATCTTTTATTGGCTTTTTAAGTCCTAGAGGCTATAATTTTAAA
ATAGAAGGGCATACAGATAATATTGATACTGATGTAAATGGACCTTGGAAAAGCAATTGGGAA
CTTTCGGCTGCTAGATCTGTTAATATGCTGGAACATATTTTGAACTATTTAGATCAATCTGATGT
TAAAAGAATTGAAAATAATTTTGAAGTATCTGGTTTTGGTGGAAGTAGGCCTATTGCAACAGAC
GATACCCCTGAGGGTAGGGCTTATAATAGAAGAATTGATATATTAATTACTACAGATGCATCTT
TAAGTTTCCCTAAGGAAATTAAGCAGTAA f664.aa (SEQ ID NO:217)
MRMSVYTMGFAYIRSIMGYVVLFFFASLAVNFFVNIIQVGFFITFKSLEPRWDKISFNFSRWAKNSFF
SAGAFFNLFKSLLKVVIICLIYYFIIENNIGKISKLSEYTLQSGISIVLVIAYKICFFSVMFLAIVGVFDYL
FQRSQYIESLKMTKEEVKQERKEMEGDPLLRSRIKERMRVILSTNLRVAIPQADVVITNPEHFAVAIK
WDSETMLAPKVLAKGQDEIALTIKKIARENNVPLMENKLLARALYANVKVNEEIPREYWEIVSKILV
RVYSITKKFN t664.aa (SEQ ID NO:218)
FVNIIQVGFFITFKSLEPRWDKISFNFSRWAKNSFFSAGAFFNLFKSLLKVVIICLIYYFIIENNIGKISKL
SEYTLQSGISIVLVIAYKICFFSVMFLAIVGVFDYLFQRSQYIESLKMTKEEVKQERKEMEGDPLLRSR
IKERMRVILSTNLRVAIPQADVVITNPEHFAVAIKWDSETMLAPKVLAKGQDEIALTIKKIARENNVP
LMENKLLARALYANVKVNEEIPREYWEIVSKILVRVYSITKKFN f664.nt (SEQ ID NO:219)
ATGCGTATGAGTGTTTATACTATGGGTTTTGCATATATTAGATCTATCATGGGGTATGTCGTTTT
GTTTTTTTTCGCATCTTTAGCTGTTAATTTTTTTGTTAATATTATTCAAGTAGGCTTTTTTATTAC
TTTTAAATCTTTGGAGCCAAGGTGGGATAAAATTAGTTTTAATTTTTCCAGATGGGCAAAAAAT
TCTTTTTTTTCAGCAGGGGCTTTTTTCAATTTGTTTAAAAGTTTGTTAAAAGTTGTTATAATATG
CTTGATATATTATTTTATTATAGAAAACAATATAGGCAAAATTTCTAAGCTTTCGGAGTATACA
CTTCAATCTGGAATTTCTATTGTGTTAGTGATTGCCTATAAGATATGTTTTTTTTCAGTAATGTT
TTTGGCAATTGTAGGGGTGTTTGATTATTTGTTTCAAAGATCTCAGTACATTGAGAGTTTGAAA
ATGACAAAAGAAGAGGTAAAGCAGGAAAGAAAGGAAATGGAAGGTGATCCTTTACTTCGATCT
AGAATAAAAGAGAGAATGAGGGTTATTTTAAGTACCAATTTAAGAGTAGCTATTCCTCAAGCA
GATGTAGTAATTACAAATCCAGAACATTTTGCAGTTGCTATTAAATGGGATAGCGAAACAATGT
TAGCTCCAAAGGTGCTTGCAAAAGGTCAAGATGAAATAGCTCTCACAATTAAAAAAATTGCAA
GAGAAAATAATGTTCCTTTAATGGAAAATAAGCTCCTTGCAAGAGCTCTTTATGCTAATGTTAA
GGTTAATGAAGAGATTCCAAGAGAATATTGGGAGATTGTTTCAAAAATTCTTGTGAGAGTATAT
TCTATTACTAAAAAGTTTAATTAG t664.nt (SEQ ID NO:220)
TTTGTTAATATTATTCAAGTAGGCTTTTTTATTACTTTTAAATCTTTGGAGCCAAGGTGGGATAA
AATTAGTTTTAATTTTTCCAGATGGGCAAAAAATTCTTTTTTTTCAGCAGGGGCTTTTTTCAATT
TGTTTAAAAGTTTGTTAAAAGTTGTTATAATATGCTTGATATATTATTTTATTATAGAAAACAAT
ATAGGCAAAATTTCTAAGCTTTCGGAGTATACACTTCAATCTGGAATTTCTATTGTGTTAGTGAT
TGCCTATAAGATATGTTTTTTTTCAGTAATGTTTTTGGCAATTGTAGGGGTGTTTGATTATTTGT
TTCAAAGATCTCAGTACATTGAGAGTTTGAAAATGACAAAAGAAGAGGTAAAGCAGGAAAGAA
AGGAAATGGAAGGTGATCCTTTACTTCGATCTAGAATAAAAGAGAGAATGAGGGTTATTTTAA
GTACCAATTTAAGAGTAGCTATTCCTCAAGCAGATGTAGTAATTACAAATCCAGAACATTTTGC
AGTTGCTATTAAATGGGATAGCGAAACAATGTTAGCTCCAAAGGTGCTTGCAAAAGGTCAAGA
TGAAATAGCTCTCACAATTAAAAAAATTGCAAGAGAAAATAATGTTCCTTTAATGGAAAATAAG
CTCCTTGCAAGAGCTCTTTATGCTAATGTTAAGGTTAATGAAGAGATTCCAAGAGAATATTGGG
AGATTGTTTCAAAAATTCTTGTGAGAGTATATTCTATTACTAAAAAGTTTAATTAG f680.aa (SEQ ID NO:221)
MFTLSFVLINFIITGILILMLEFNFLKVDFKGNILLAGIFMGLMQGLGALPGISRSGITIFSASVTGFNRK
SAFEISFLSLIPIVFGAILLKHKEFYDIFMVLNFFEINLGALVAFVVGIFSINFFFKMLNNKKLYYFSIYL
FALSIIVCYFVRI t680.aa (SEQ ID NO:222)
ITGILILMLEFNFLKVDFKGNILLAGIFMGLMQGLGALPGISRSGITIFSASVIGFNRKSAFEISFLSLIPI
VFGAILLKHKEFYDIFMVLNFFEINLGALVAFVVGIFSINFFFKMLNNKKLYYFSIYLFALSIIVCYFVR
I f680.nt (SEQ ID NO:223)

TABLE 1-continued

Nucleotide and Amino Acid Sequences.

ATGTTTACATTGTCTTTCGTTTTAATTAATTTTATTATAACAGGGATTTTAATCTTGATGCTAGA
ATTTAATTTTTTAAAAGTTGATTTTAAAGGTAATATTTTGTTAGCAGGAATTTTTATGGGGCTGA
TGCAAGGCTTGGGTGCGCTTCCAGGAATCTCTCGTTCAGGAATTACGATCTTTTCGGCATCGGT
TATTGGATTTAATAGAAAAAGTGCATTTGAAATTTCATTTTTATCTTTAATTCCAATAGTTTTTG
GAGCGATTTTATTAAAACATAAAGAATTTTATGATATTTTTATGGTTTTAAATTTTTTTGAAATA
AACTTAGGAGCATTAGTTGCTTTTGTTGTTGGTATTTTCTCAATAAATTTCTTTTTTAAAATGCT
TAATAACAAAAAACTGTATTATTTTTCTATATATTTATTTGCACTTTCAATTATAGTTTGTTATTT
TGTTAGAATATGA t680.nt (SEQ ID NO:224)
ATAACAGGGATTTTAATCTTGATGCTAGAATTTAATTTTTTAAAAGTTGATTTTAAAGGTAATAT
TTTGTTAGCAGGAATTTTTATGGGGCTGATGCAAGGCTTGGGTGCGCTTCCAGGAATCTCTCGT
TCAGGAATTACGATCTTTTCGGCATCGGTTATTGGATTTAATAGAAAAAGTGCATTTGAAATTT
CATTTTTATCTTTAATTCCAATAGTTTTTGGAGCGATTTTATTAAAACATAAAGAATTTTATGAT
ATTTTTATGGTTTTAAATTTTTTTGAAATAAAACTTAGGAGCATTAGTTGCTTTTGTTGTTGGTAT
TTTCTCAATAAATTTCTTTTTTAAAATGCTTAATAACAAAAAACTGTATTATTTTTCTATATATTT
ATTTGCACTTTCAATTATAGTTTGTTATTTTGTTAGAATATGA f688.aa (SEQ ID NO:225)
MIVLLISIGCANAVHIINEIFKLIKKEQLSKESIKATIKKLKTPILLTSFTTAFGFLSLTTSSINAYKTMGI
FMSIGVIISMIISLTVLPGIITLIPFAKKKSFEKEKENKLNKISFLERLAKLNTQITKSILRKYTSSIMVLI
ILGISFVGLLKIEINFDEKDYFKESTSVKKTLNLMQKEMGGISIFKIEIEGRPGEFKNAKAMQILDLITD
KLDAFSAKTQSSSINGILKFTNFKIKKESPLEYKLPENKIILNKLINLIDKSDWTKDNKRMYINDDWSL
ISIIVRIEDNSTEGIKKFEKYAINTINEYMKNNKYHFSGVYDKVLIAKTMVKEQVINIITTLGSITLLLM
FFFKSIKTGIIIAIPVAWSVFLNFAVMRLFGITLNPATATIASVSMGVGVDYSIHFFNTFILQYQKNQIY
KTALLESIPNVFNGIFANSISVGIGFLTLTFSSYKIISTLGAIIAFTMLTTSLASLTLLPLLIYLFKPRVKL
ASNNNFKKLKQ t688.aa (SEQ ID NO:226)
YKTMGIFMSIGVIISMIISLTVLPGIITLIPFAKKKSFEKEKENKLNKISFLERLAKLNTQITKSILRKYT
SSIMVLIILGISFVGLLKIEINFDEKDYFKESTSVKKTLNLMQKEMGGISIFKIEIEGRPGEFKNAKAMQ
ILDLITDKLDAFSAKTQSSSINGILKFTNFKIKKESPLEYKLPENKIILNKLINLIDKSDWTKDNKRMYI
NDDWSLISIIVRIEDNSTEGIKKFEKYAINTINEYMKNNKYHFSGVYDKVLIAKTMVKEQVINIITTLG
SITLLLMFFFKSIKTGIIIAIPVAWSVFLNFAVMRLFGITLNPATATIASVSMGVGVDYSIHFFNTFILQY
QKNQIYKTALLESIPNVFNGIFANSISVGIGFLTLTFSSYKIISTLGAIIAFTMLTTSLASLTLLPLLIYLF
KPRVKLASNNNFKKLKQ f688.nt (SEQ ID NO:227)
ATGATTGTTTTACTTATTTCAATCGGATGCGCCAATGCTGTACATATAATAAATGAAATATTTAA
ATTAATAAAAAAAGAACAGCTCTCAAAAGAATCCATAAAAGCAACAATTAAAAAACTTAAAAC
ACCCATCCTGCTAACATCTTTTACAACTGCATTTGGATTTTTATCTCTTACAACCTCTTCAATTA
ATGCCTACAAAACAATGGGTATTTTCATGTCAATTGGAGTAATTATCTCAATGATAATCTCATT
AACCGTTTTACCTGGAATAATAACATTAATCCCATTTGCAAAAAAAAGTCTTTTGAAAAAGAA
AAAGAAAATAAACTAAATAAAAATATCCTTCCTTGAAAGACTTGCCAAACTAAATACGCAAATAA
CAAAATCTATATTAAAAAGAAAATATACATCCTCTATAATGGTCCTCATCATACTGGGAATTTC
TTTTGTAGGTCTTTTAAAAATCGAAATCAATTTTGATGAAAAAGATTACTTTAAAGAAAGCACA
AGTGTAAAAAAAACATTAAACCTAATGCAAAAAGAAATGGGGGAAATATCGATTTTCAAAATA
GAAATTGAAGGCAGGCCCGGTGAATTTAAAAATGCTAAAGCAATGCAAATATTAGACTTAATT
ACAGATAAGCTTGATGCATTTTCTGCAAAAACTCAATCTAGTTCTATTAATGGCATTTTAAAATT
TACAAATTTTAAAATTAAAAAAGAATCCCCACTAGAGTATAAACTGCCTGAAAATAAAATTATA
CTAAACAAACTAATAAATTTGATAGATAAAAGCGATTGGACTAAGGACAATAAAAGAATGTAC
ATTAACGATGACTGGTCATTAATATCTATCATAGTAAGAATTGAAGACAACTCAACCGAAGGAA
TAAAAAAATTTGAAAAATATGCTATTAACACAATTAATGAATATATGAAAAATAATAAATATCA
TTTCTCAGGTGTTTATGATAAGGTATTAATAGCTAAAACAATGGTAAAAGAACAGGTTATAAAC
ATTATAACAACTCTTGGATCAATAACACTACTACTTATGTTTTTCTTTAAATCTATAAAAACCGG
AATAATTATTGCAATCCCAGTAGCATGGTCAGTGTTTTTAAACTTTGCTGTAATGAGATTATTTG
GGATAACCCTTAAACCCCGCAACGGCAACAATTGCATCTGTAAGCATGGGAGTAGGAGTAGATT
ATTCAATTCATTTTTTCAATACATTTATTTTACAATACCAAAAAAATCAAATCTACAAAACTGCA
CTTCTTGAATCAATACCCAATGTATTTAATGGAATATTTGCAAATTCTATTTCTGTTGGAATAGG
ATTTTTAACTCTAACATTTTCGTCTTATAAAATAATATCAACTCTTGGAGCAATAATTGCTTTTA
CAATGCTAACGACATCTCTTGCATCACTAACTCTTCTTCCATTATTAATTTATTTATTTAAACCT
AGAGTAAAGCTAGCCTCAAACAACAATTTTAAAAAATTAAAACAATAA t688.nt (SEQ ID NO:228)
TACAAAACAATGGGTATTTTCATGTCAATTGGAGTAATTATCTCAATGATAATCTCATTAACCG
TTTTACCTGGAATAATAACATTAATCCCATTTGCAAAAAAAAGTCTTTTGAAAAAGAAAAAGA
AAATAAACTAAATAAAAATATCCTTCCTTGAAAGACTTGCCAAACTAAATACGCAAATAACAAAA
TCTATATTAAAAAGAAAATATACATCCTCTATAATGGTCCTCATCATACTGGGAATTTCTTTTGT
AGGTCTTTTAAAAATCGAAATCAATTTTGATGAAAAAGATTACTTTAAAGAAAGCACAAGTGTA
AAAAAAACATTAAACCTAATGCAAAAAGAAATGGGGGAATATCGATTTTCAAAATAGAAATT
GAAGGCAGGCCCGGTGAATTTAAAAATGCTAAAGCAATGCAAATATTAGACTTAATTACAGAT
AAGCTTGATGCATTTTCTGCAAAAACTCAATCTAGTTCTATTAATGGCATTTTAAAATTTACAAA
TTTTAAAATTAAAAAAGAATCCCCACTAGAGTATAAACTGCCTGAAAATAAAATTATACTAAAC
AAACTAATAAATTTGATAGATAAAAGCGATTGGACTAAGGACAATAAAAGAATGTACATTAAC
GATGACTGGTCATTAATATCTATCATAGTAAGAATTGAAGACAACTCAACCGAAGGAATAAAA
AAATTTGAAAAATATGCTATTAACACAATTAATGAATATATGAAAAATAATAAATATCATTTCT
CAGGTGTTTATGATAAGGTATTAATAGCTAAAACAATGGTAAAAGAACAGGTTATAAACATTAT

TABLE 1-continued

Nucleotide and Amino Acid Sequences.

```
AACAACTCTTGGATCAATAACACTACTACTTATGTTTTTCTTTAAATCTATAAAAACCGGAATAA
TTATTGCAATCCCAGTAGCATGGTCAGTGTTTTTAAACTTTGCTGTAATGAGATTATTTGGGATA
ACCTTAAACCCCGCAACGGCAACAATTGCATCTGTAAGCATGGGAGTAGGAGTAGATTATTCAA
TTCATTTTTTCAATACATTTATTTTACAATACCAAAAAAATCAAATCTACAAAACTGCACTTCTT
GAATCAATACCCAATGTATTTAATGGAATATTTGCAAATTCTATTTCTGTTGGAATAGGATTTTT
AACTCTAACATTTTCGTCTTATAAAATAATATCAACTCTTGGAGCAATAATTGCTTTTACAATGC
TAACGACATCTCTTGCATCACTAACTCTTCTTCCATTATTAATTTATTTATTTAAACCTAGAGTA
AAGCTAGCCTCAAACAACAATTTTAAAAAATTAAAACAATAA f704.aa (SEQ ID NO:229)
MNYTKFQEFISEFLGTFILLALGTGSVAMTVLFSSSPEIPGEIIKGGYTNIVFGWGLGVTFGIYTAARM
SGAHLNPAVSIGLASVGKFPVSKLLHYIVAQILGAFTGALMTLVVFYPKWIEMDPGLENTQGIMATF
PAVPGFLPGFIDQIFGTFLLMFLISVVGDFTKKHSDNPFIPFIVGAVVLSIGISFGGMNGYAINPARDLG
PRILLLFAGFKNHGFNNLSIVIVPIIGPIIGAILGATIYEFTLKNNKD t704.aa (SEQ ID NO:230)
GEIIKGGYTNIVFGWGLGVTFGIYTAARMSGAHLNPAVSIGLASVGKFPVSKLLHYIVAQIL
GAFTGALMTLVVFYPKWIEMDPGLENTQGIMATFPAVPGFLPGFIDQIFGTFLLMFLISVVGDFTKK
HSDNPFIPFIVGAVVLSIGISFGGMNGYAINPARDLGPRILLLFAGFKNHGFNNLSIVIVPIIGPIIGAILG
ATIYEFTLKNNKD f704.nt (SEQ ID NO:231)
ATGAATTATACAAAATTCCAAGAATTTATATCGGAATTTTTGGGAACATTTATCCTATTGGCTCT
AGGAACTGGATCTGTTGCAATGACAGTATTATTTTCCTCAAGTCCCGAAATACCAGGAGAAATA
ATAAAAGGAGGATATACAAATATAGTATTTGGATGGGGATTGGGTGTAACGTTTGGTATTTACA
CAGCAGCAAGAATGAGCGGAGCACACCTAAACCCAGCTGTTAGCATAGGATTAGCAAGTGTTG
GAAAGTTTCCCGTTTCAAAACTTTTACATTACATTGTAGCACAAATATTAGGAGCTTTTACAGG
TGCATTAATGACACTTGTCGTATTTTATCCTAAATGGATAGAAATGGATCCTGGCTTAGAAAAT
ACTCAAGGAATAATGGCAACTTTCCCTGCTGTTCCTGGATTTTTGCCTGGATTTATTGATCAAAT
TTTTTGGAACTTTTTTGCTAATGTTTTTAATTTCTGTTGTTGGAGATTTTACAAAAAAACACAGCG
ACAATCCATTTATTCCTTTTATTGTAGGAGCAGTGGTTTTATCAATAGGGATAAGTTTCGGAGG
AATGAACGGTTATGCTATTAATCCTGCAAGGGATCTGGGACCAAGAATTTTACTCTTATTTGCT
GGATTTAAAAATCACGGATTTAACAATCTAAGTATAGTTATTGTACCAATAATTGGCCCAATAA
TTGGAGCAATTTTGGGAGCTACAATTTACGAATTTACACTAAAAAATAACAAAGACTAA t704.nt (SEQ ID NO:232)
GGAGAAATAATAAAAGGAGGATATACAAATATAGTATTTGGATGGGGATTGGGTGTAACGTTT
GGTATTTACACAGCAGCAAGAATGAGCGGAGCACACCTAAACCCAGCTGTTAGCATAGGATTA
GCAAGTGTTGGAAAGTTTCCCGTTTCAAAACTTTTACATTACATTGTAGCACAAATATTAGGAG
CTTTTACAGGTGCATTAATGACACTTGTCGTATTTTATCCTAAATGGATAGAAATGGATCCTGG
CTTAGAAAATACTCAAGGAATAATGGCAACTTTCCCTGCTGTTCCTGGATTTTTGCCTGGATTTA
TTGATCAAATTTTTGGAACTTTTTTGCTAATGTTTTTAATTTCTGTTGTTGGAGATTTTACAAAA
AAACACAGCGACAATCCATTTATTCCTTTTATTGTAGGAGCAGTGGTTTTATCAATAGGGATAA
GTTTCGGAGGAATGAACGGTTATGCTATTAATCCTGCAAGGGATCTGGGACCAAGAATTTTACT
CTTATTTGCTGGATTTAAAAATCACGGATTTAACAATCTAAGTATAGTTATTGTACCAATAATTG
GCCCAATAATTGGAGCAATTTTGGGAGCTACAATTTACGAATTTACACTAAAAAATAACAAAG
ACTAA f707.aa (SEQ ID NO:233)
MRRLFLLYILCSFVFLNLFAQGSSSYIDKQKELAIFYYEVGQRYINVGKIKKGKLFQAKALKIYPDLK
KGFDIKLAVKELDARIKDDNPKVVMLEDIKLEEIPGIVHEKIEINDFTNAPKIEYIAQRERSKNQDKII
KFQFGKFARALISRNFDLFDSVIADKVNVMGQFESKNDFISTLSSASSKADADELEYLSVDDYYDLK
SLKISKSNDTSFAVNVNAKKNDVTKNFPFWKERQTLIFTTEDDNNWFLSSIN t707.aa (SEQ ID NO:234)
MRRLFLLYILCSFVFLNLFAQGSSSYIDKQKELAIFYYEVGQRYINVGKIKKGKLFQAKALKIYPDLK
KGFDIKLAVKELDARIKDDNPKVVMLEDIKLEEIPGIVHEKIEINDFTNAPKIEYIAQRERSKNQDKII
KFQFGKFARALISRNFDLFDSVIADKVNVMGQFESKNDFISTLSSASSKADADELEYLSVDDYYDLK
SLKISKSNDTSFAVNVNAKKNDVTKNFPFWKERQTLIFTTEDDNNWFLSSIN f707.nt (SEQ ID NO:235)
ATGAGAAGATTATTTCTTCTATATATTTTATGTTCTTTTGTTTTTTGAATTTATTTGCTC
AAGGTAGTTCTTCTTATATTGATAAGCAAAAAGAGCCTGCTATTTTTTATTATGAGGTTGGTCA
AAGATATATAAACGTTGGTAAAATTAAAAAAGGAAAGCTTTTTCAAGCAAAAGCTTTAAAGAT
TTATCCAGATTTGAAAAAGGGGTTTGATATCAAGCTTGCAGTTAAAGAGCTTGATGCTAGGATT
AAAGATGACAATCCCAAGGTTGTTATGCTTGAGGATATTAAGCTTGAGGAGATACCTGGAATA
GTGCACGAAAAAATAGAAATCAATGATTTTACAAATGCTCCTAAAATAGAATATATTGCTCAAA
GAGAGAGAAGCAAAAATCAAGATAAAATTATTAAGTTTCAATTTGGAAAGTTTGCAAGAGCTT
TAATTTCTAGGAACTTTGATTTGTTTGATTCAGTTATTGCGGATAAAGTTAACGTTATGGGTCAA
TTTGAATCAAAAAATGATTTTATATCAACTTTATCAAGTGCTTCATCTAAGGCCGATGCTGATG
AGTTAGAGTATTTATCAGTTGATGATTATTACGATTTAAAGTCTTTAAAAATTTCAAATCCAA
CGATACTTCTTTTGCTGTTAATGTTAATGCCAAAAAAAATGATGTTACTAAAAATTTTCCATTTT
GGAAAGAACGTCAAACTTTAATTTTTACTACAGAGGATGATAATAATTGGTTTTTGTCTTCCAT
AAATTGA t707.nt (SEQ ID NO:236)
CAAGGTAGTTCTTCTTATATTGATAAGCAAAAAGAGCTTGCTATTTTTTATTATGAGGTTGGTCA
```

TABLE 1-continued

Nucleotide and Amino Acid Sequences.

AAGATATATAAACGTTGGTAAAATTAAAAAAGGAAAGCTTTTTCAAGCAAAAGCTTTAAAGAT
TTATCCAGATTTGAAAAAGGGGTTTGATATCAAGCTTGCAGTTAAAGAGCTTGATGCTAGGATT
AAAGATGACAATCCCAAGGTTGTTATGCTTGAGGATATTAAGCTTGAGGAGATACCTGGAATA
GTGCACGAAAAAATAGAAATCAATGATTTTACAAATGCTCCTAAAATAGAATATATTGCTCAAA
GAGAGAGAAGCAAAAATCAAGATAAAATTATTAAGTTTCAATTTGGAAAGTTTGCAAGAGCTT
TAATTTCTAGGAACTTTGATTTGTTTGATTCAGTTATTGCGGATAAAGTTAACGTTATGGGTCAA
TTTGAATCAAAAAATGATTTTATATCAACTTTATCAAGTGCTTCATCTAAGGCCGATGCTGATG
AGTTAGAGTATTTCAGTTGATGATTATTACGATTTAAAGTCTTTAAAAATTTCAAATCCAA
CGATACTTCTTTTGCTGTTAATGTTAATGCCAAAAAAAATGATGTTACTAAAAATTTTCCATTTT
GGAAAGAACGTCAAACTTTAATTTTTACTACAGAGGATGATAATAATTGGTTTTTGTCTTCCAT
AAATTGA f709.aa (SEQ ID NO:237)
MLIFGFIGLFFLNIFSLHAQGIVTNKDAQEEFKWALNSYNNGIYDDALLSFKKILSFDPNNLDYHFWT
GNVYYRLGYVEEALMEWRNLKDQGYKVPYLRHLISTIEQRRGIFSNYELNFKKLVKVASLDNSIYK
RPHGYQITSLRADKYGGYYAANFVGNEILYFDVNNNVNALVKDGFSYLKSPYDVIEANNLLYVTLY
SSDEIGVYDKVLGVKRKSIGNKGTKDGELLAPQYMAIDKRNYIYVSEWGNKRVSKFGLEGDFILHF
GSRTSGYKGLLGPTGVTYLNENIYVADSLRNTIEVFDTSGNHLYSVFTSIEGIEGLSSDFVGNNVIVSS
KDGVYKYSIAKKTITKILKADKMNSKISSSILDANNQMIVSDFNNAKVSVYKSDASLYDSLNVDVRR
IIRLGGPKIYVELNVSSKSGLPVVGLKSENFSISNENYYIVNPKVAYNVNASKDINIAVVFDKSSYMK
KYDTDQIVGLNALMELSKNKNFSFINATSVPIIDNIESLTNSIRNTSSLGPYSTDAVKTDVSLKLAGSG
LMSKSSRRAVVYFSGGILNRKAFEKYSLDTIVSYYKNNDIRFYLILFGNDPINSKLQYLVNETGGAVI
PFSSYEGVSKVYDLILEQKTGTYLLEYYYPGPQEPNKYFNLSVEANINQQTGRGEFAYFIN t709.aa (SEQ ID NO:238)
QGIVTNKDAQEEFKWALNSYNNGIYDDALLSFKKILSFDPNNLDYHFWTGNVYYRLGYVEEALME
WRNLKDQGYKVPYLRHLISTIEQRRGIFSNYELNFKKLVKVASLDNSIYKRPHGYQITSLRADKYGG
YYAANFVGNEILYFDVNNNVNALVKDGFSYLKSPYDVIEANNLLYVTLYSSDEIGVYDKVLGVKRK
SIGNKGTKDGELLAPQYMAIDKRNYIYVSEWGNKRVSKFGLEGDFILHFGSRTSGYKGLLGPTGVT
YLNENIYVADSLRNTIEVFDTSGNHLYSVFTSIEGIEGLSSDFVGNNVIVSSKDGVYKYSIAKKTITKI
LKADKMNSKISSSILDANNQMIVSDFNNAKVSVYKSDASLYDSLNVDVRRIIRLGGPKIYVELNVSS
KSGLPVVGLKSENFSISNENYYIVNPKVAYNVNASKDINIAVVFDKSSYMKKYDTDQIVGLNALME
LSKNKNFSFINATSVPIIDNIESLTNSIRNTSSLGPYSTDAVKTDVSLKLAGSGLMSKSSRRAVVYFSG
GILNRKAFEKYSLDTIVSYYKNNDIRFYLILFGNDPINSKLQYLVNETGGAVIPFSSYEGVSKVYDLIL
EQKTGTYLLEYYYPGPQEPNKYFNLSVEANINQQTGRGEFAYFIN f709.nt (SEQ ID NO:239)
ATGTTAATTTTTGGTTTTATTGGTTTGTTTTTTTAAATATTTTTAGTTTGCATGCCCAAGGAATA
GTTACTAATAAAGATGCTCAAGAAGAGTTTAAATGGGCTCTTAATTCTTATAATAATGGAATTT
ACGATGATGCTCTTTTATCTTTTAAAAAAATTTTAAGCTTTGATCCTAATAATCTTGATTATCAT
TTTTTGGACTGGCAATGTTTATTATAGACTGGGTTATGTTGAAGAAGCTTTAATGGAATGGAGAA
ATTTAAAAGATCAAGGCTATAAGGTTCCCTATCTTAGACATTTGATTTCTACTATTGAGCAAAG
GAGAGGTATTTTTTCAAATTATGAACTTAATTTTAAAAAACTTGTAAAAGTTGCTTCTCTTGATA
ATTCTATTTATAAAAGGCCACATGGGTACCAGATTACATCTTTAAGGGCTGATAAGTACGGCGG
ATATTACGCTGCTAACTTTGTAGGCAATGAAATATTGTATTTTGATGTTAATAACAATGTTAAT
GCTTTAGTTAAAGATGGCTTTAGTTATTTAAAATCACCTTATGATGTTATTGAAGCTAATAATCT
GCTTTATGTGACTCTTTATTCAAGTGATGAAATTGGTGTTTATGACAAAGTTCTTGGAGTTAAA
AGGAAATCTATTGGGAATAAAGGCACAAAAGATGGCGAATTGCTTGCTCCTCAGTATATGCT
ATTGATAAGAGAAACTATATTTATGTAAGTGAGTGGGGAAATAAAAGAGTAAGTAAATTTGGA
CTTGAAGGTGATTTTATTTTGCATTTTGGTTCTAGAACTTCAGGCTATAAGGGCCTTTTAGGTCC
CACAGGCGTTACTTATTTGAATGAAAACATTTATGTTGCAGATTCTCTGAGAAATACCATTGAA
GTTTTTTGATACTAGTGGTAATCATTTATATTCAGTTTTTACTTCTATTGAGGGAATAGAGGGGCT
TAGCAGTGATTTTGTAGGTAATAATGTTATAGTATCCTCAAAAGATGGTGTTTATAAATATAGC
ATTGCTAAAAAGACAATTACAAAAATTTTAAAAGCAGATAAAATGAATTCTAAAATTTCTTCAT
CTATTTTGGATGCCAATAATCAGATGATTGTCTCAGATTTTAATAATGCCAAGGTTTCAGTTTAC
AAGAGTGATGCAAGCCTTTATGATAGTTTAAATGTTGATGTTAGAAGAATAATTAGGCTTGGAG
GGCCTAAAATTTACGTTGAGCTTAATGTTAGCAGTAAAAGCGGATTACCAGTTGTTGGGCTTAA
AAGTGAAAATTTTTCAATTTCAAATGAAAATTATTACATTGTCAATCCCAAGGTGGCATATAAT
GTAAATGCTTCAAAAGACATTAATATAGCAGTTGTTTTTGATAAATCTTCTTATATGAAAAAAT
ATGATACAGATCAAATTGTAGGGTTAAATGCCCTAATGGAGTTGTCAAAAAATAAAAACTTTAG
TTTTTATAAATGCAACAAGTGTGCCCATTATAGATAATATTGAAAGCTTAACAAATAGCATTAGA
AATACAAGTTCTCTTGGTCCTTATAGTACAGATGCTGTAAAAACAGACGTTAGTTTGAAGTTGG
CAGGTTCTGGGCTTATGTCAAAAAGCTCAAGAAGAGCAGTAGTTTATTTTAGTGGTGGTATTTT
AAATCGTAAAGCTTTTGAAAAGTACTCTTTAGATACAATAGTAAGTTATTATAAAAATAATGAT
ATAAGGTTTTACTTAATACTATTTGGTAATGATCCTATTAATAGTAAGCTTCAGTATTTAGTTAA
TGAAACAGGCGGTGCTGTAATTCCTTTTTCATCTTATGAAGGTGTATCTAAAGTTTATGATTTAA
TTTTAGAACAAAAAACGGGCACTTATTTGTTGGAATATTATTATCCAGGCCCTCAAGAACCTAA
TAAATATTTTAATTTATCTGTTGAAGCAAATATAAATCAACAGACAGGAAGAGGGGAGTTTGCA
TATTTTATTAATTAG t709.nt (SEQ ID NO:240)
CAAGGAATAGTTACTAATAAAGATGCTCAAGAAGAGTTTAAATGGGCTCTTAATTCTTA
TAATAATGGAATTTACGATGATGCTCTTTTATCTTTTAAAAAAATTTTAAGCTTTGATCCTAATA
ATCTTGATTATCATTTTTTGGACTGGCAATGTTTATTATAGACTGGGTTATGTTGAAGAAGCTTTA
ATGGAATGGAGAAATTTAAAAGATCAAGGCTATAAGGTTCCCTATCTTAGACATTTGATTTCTA
CTATTGAGCAAAGGAGAGGTATTTTTTCAAATTATGAACTTAATTTTAAAAAACTTGTAAAAGT
TGCTTCTCTTGATAATTCTATTTATAAAAGGCCACATGGGTACCAGATTACATCTTTAAGGGCTG

TABLE 1-continued

Nucleotide and Amino Acid Sequences.

ATAAGTACGGCGGATATTACGCTGCTAACTTTGTAGGCAATGAAATATTGTATTTTGATGTTAA
TAACAATGTTAATGCTTTAGTTAAAGATGGCTTTAGTTATTTAAAATCACCTTATGATGTTATTG
AAGCTAATAATCTGCTTTATGTGACTCTTTATTCAAGTGATGAAATTGGTGTTTATGACAAAGTT
CTTGGAGTTAAAAGGAAATCTATTGGGAATAAAGGCACAAAAGATGGCGAATTGCTTGCTCCT
CAGTATATGGCTATTGATAAGAGAAACTATATTTATGTAAGTGAGTGGGGAAATAAAAGAGTA
AGTAAATTTGGACTTGAAGGTGATTTTATTTTGCATTTTGGTTCTAGAACTTCAGGCTATAAGG
GCCTTTTAGGTCCCACAGGCGTTACTTATTTGAATGAAAACATTTATGTTGCAGATTCTCTGAGA
AATACCATTGAAGTTTTTGATACTAGTGGTAATCATTTATATTCAGTTTTTACTTCTATTGAGGG
AATAGAGGGGCTTAGCAGTGATTTTGTAGGTAATAATGTTATAGTATCCTCAAAAGATGGTGTT
TATAAATATAGCATTGCTAAAAAGACAATTACAAAAATTTTAAAAGCAGATAAAATGAATTCTA
AAATTTCTTCATCTATTTTGGATGCCAATAATCAGATGATTGTCTCAGATTTTAATAATGCCAAG
GTTTCAGTTTACAAGAGTGATGCAAGCCTTTATGATAGTTTAAATGTTGATGTTAGAAGAATAA
TTAGGCTTGGAGGGCCTAAAATTTACGTTGAGCTTAATGTTAGCAGTAAAAGCGGATTACCAGT
TGTTGGGCTTAAAAGTGAAAATTTTTCAATTTCAAATGAAAATTATTACATTGTCAATCCCAAG
GTGGCATATAATGTAAATGCTTCAAAAGACATTAATATAGCAGTTGTTTTTGATAAATCTTCTT
ATATGAAAAAATATGATACAGATCAAATTGTAGGGTTAAATGCCCTAATGGAGTTGTCAAAAA
ATAAAAACTTTAGTTTTATAAATGCAACAAGTGTGCCCATTATAGATAATATTGAAAGCTTAAC
AAATAGCATTAGAAATACAAGTTCTCTTGGTCCTTATAGTACAGATGCTGTAAAAACAGACGTT
AGTTTGAAGTTGGCAGGTTCTGGGCTTATGTCAAAAAGCTCAAGAAGAGCAGTAGTTTATTTTA
GTGGTGGTATTTTAAATCGTAAAGCTTTTGAAAAGTACTCTTTAGATACAATAGTAAGCTATTA
TAAAAATAATGATATAAGGTTTTACTTAATACTATTTGGTAATGATCCTATTAATAGTAAGCTTC
AGTATTTAGTTAATGAAACAGGCGGTGCTGTAATTCCTTTTTCATCTTATGAAGGTGTATCTAA
AGTTTATGATTTAATTTTAGAACAAAAAACGGGCACTTATTTGTTGGAATATTATTATCCAGGC
CCTCAAGAACCTAATAAATATTTTAATTTATCTGTTGAAGCAAATATAAATCAACAGACAGGAA
GAGGGGAGTTTGCATATTTTATTAATTAG f730.aa (SEQ ID NO:241)
MIKSILDYLLTLHPVLLGLLGSTFTWFTTAFGAAAVFFFRKVDNKIMDAMLGFSAGIMIAASFFSLIQ
PAIERAEELGYITWVPAVFGFLVGAFFIYIVVDVFVPDLDKLTFIDEDLTKHGKKDFLLFTAVTLHNFP
EGLAVGVAFGALASNPDIQTLVGAMLLTLGIGIQNIPEGAAISLPLRRGNVALAKCFNYGQMSGLVE
IVGGLMGAYAVYSFTRILPFALAFSAGAMIYVSIEQLIPEAKRKDIDNKVPSIFGVIGFTLMMFLDVSL
G t730.aa (SEQ ID NO:242)
AVFFFRKVDNKIMDAMLGFSAGIMIAASFFSLIQPAIERAEELGYITWVPAVFGFLVGAFFIYIVDVFV
PDLDKLTFIDEDLTKHGKKDFLLFTAVTLHNFPEGLAVGVAFGALASNPDIQTLVGAMLLTLGIGIQ
NIPEGAAISLPLRRGNVALAKCFNYGQMSGLVEIVGGLMGAYAVYSFTRILPFALAFSAGAMIYVSIE
QLIPEAKRKDIDNKVPSIFGVIGFTLMMFLDVSLG f730.nt (SEQ ID NO:243)
ATGATAAAATCAATTTTAGATTATTTATTAACTTTGCATCCTGTATTATTGGGACTTTTAGGTTC
TACTTTCACTTGGTTTACTACAGCTTTTGGAGCAGCAGCAGTTTTTTTCTTTAGAAAGGTAGATA
ATAAAATAATGGACGCTATGCTTGGTTTTTCAGCTGGCATTATGATAGCGGCCAGTTTTTTTTCG
CTTATTCAGCCTGCTATAGAAAGAGCTGAAGAGCTTGGATACATTACTTGGGTGCCGGCTGTTT
TTGGATTTCTTGTTGGGGCATTTTTTATATATATTGTAGATGTATTTGTTCCAGATCTGGATAAA
CTTACTTTTATTGATGAAGACTTAACTAAACATGGTAAAAAAGATTTTTTACTCTTTACTGCTGT
TACTTTACATAATTTTCCAGAAGGATTGGCTGTTGGAGTTGCTTTTGGAGCCTTGGCGTCTAATC
CAGATATTCAAACTTTAGTTGGGGCTATGCTTCTTACGCTTGGTATTGGTATTCAAAATATTCCC
GAAGGAGCAGCTATTTCTCTGCCTTTAAGAAGAGGTAATGTTGCTTTGGCAAAATGCTTTAACT
ATGGCCAAATGTCAGGATTGGTAGAAATTGTGGGGGGCTTATGGGTGCTTATGCGGTTTATTC
TTTTACTCGAATTTTACCTTTTGCTTTGGCTTTTTCTGCAGGAGCTATGATTTATGTGTCAATTG
AACAATTAATACCTGAAGCTAAGAGAAAAGACATTGACAATAAAGTGCCAAGTATATTTGGTG
TTATTGGTTTTACATTAATGATGTTCTCGATGTTTCACTAGGTTAA t730.nt (SEQ ID NO:244)
GCAGTTTTTTTCTTTAGAAAGGTAGATAATAAAATAATGGACGCTATGCTTGGTTTTTCAGCTG
GCATTATGATAGCGGCCAGTTTTTTTTCGCTTATTCAGCCTGCTATAGAAAGAGCTGAAGAGCT
TGGATACATTACTTGGGTGCCGGCTGTTTTTGGATTTCTTGTTGGGGCATTTTTTATATATATTG
TAGATGTATTTGTTCCAGATCTGGATAAACTTACTTTTATTGATGAAGACTTAACAAACATGGT
AAAAAAGATTTTTTACTCTTTACTGCTGTTACTTTACATAATTTTCCAGAAGGATTGGCTGTTGG
AGTTGCTTTTGGAGCCTTGGCGTCTAATCCAGATATTCAAACTTTAGTTGGGGCTATGCTTCTTA
CGCTTGGTATTGGTATTCAAAATATTCCCGAAGGAGCAGCTATTTCTCTGCCTTTAAGAAGAGG
TAATGTTGCTTTGGCAAAATGCTTTAACTATGGCCAAATGTCAGGATTGGTAGAAATTGTGGGG
GGGCTTATGGGTGCTTATGCGGTTTATTCTTTTACTCGAATTTTACCTTTTGCTTTGGCTTTTTCT
GCAGGAGCTATGATTTATGTGTCAATTGAACAATTAATACCTGAAGCTAAGAGAAAAGACATTG
ACAATAAAGTGCCAAGTATATTTGGTGTTATTGGTTTTACATTAATGATGTTTCTCGATGTTTCA
CTAGGTTAA f197.aa (SEQ ID NO:245)
MLLKLKYRFVGFLLLFLIFILLLFSTIFNFVLCGYLEDYYKQLTRAQVRRAAFSLQSFLDTLHVIINGA
ASNLALETISEFAMSENRGKDFSESELIDLRKNPKFVIDSVKVSKKYRQYLYNFMANLKNDTLFEEF
AFFDFEGRVIVSTRHENNMDFGHSEANTNYFKKAVEDYRQNQLKFIGWYSNLSEGISAEVAIRSKQS
EKKAFAIIVPVYSPEDKLVCGYLAGYLLNDIVADSFDRFRFGFYKRGNFIYVDPNNIAVNPFEEYNET
SRVSSKFLNVLKDVFSKPPFPSNIASEVSVYTIDRILLSEMGEDCYYAMLPISSKLGEKSGVLIARLPY
KDIYGVISSLRFQYILYSVLGIIALSIVLSIRIDRIISFRLNAIRVLVQDMVKGNLDKDYALDDDENTLD
ELGMLSLQVVKMKKAISVAISSVLRNISYVNKASLEVASSSQNLSSSALQQASALEEMSANVEQIAS
GVNMSANNSYETEQIALKTNENSQIGGRAVEESVIAMQDIVEKVSVIEEIARKTNLLALNAAIEAAR

TABLE 1-continued

Nucleotide and Amino Acid Sequences.

AGDEGKGFAVVASEIRKLADLSKISALEIGELVEDNSKVATEAGVIFKEMLPEIEETANLVKKISEGSS
KQSDQIAQFKMALDQVGEVVQSSASSSEQLSSMSDKMLEKSKELRKSVLFFKIKDSKIENPENDDYD
FRLIDCPENSFKDENQNLKSNGISTSNASGHNNYSLDIESESSSVRTINKRVDPKKAIDIADKDLNFDDD
FSEF t197.aa (SEQ ID NO:246)
VLCGYLEDYYKQLTRAQVRRAAFSLQSFLDTLHVIINGAASNLALETISEFAMSENRGKDFSESELID
LRKNPKFVIDSVKVSKKYRQYLYNFMANLKNDTLFEEFAFFDFEGRVIVSTRHENNMDFGHSEANT
NYFKKAVEDYRQNLKFIGWYSNLSEGISAEVAIRSKQSEKKAFAIIYPVYSPEDKLVCGYLAGYLL
NDIVADSFDRFRFGFYKRGNFIYVDPNNIAVNPFEEYNETSRVSSKFLNVLKDVFSKPPFPSNIASEVS
VYTIDRILLSEMGEDCYYAMLPISSKLGEKSGVLIARLPYKDIYGVISSLRFQYILYSVLGIIALSIVLSI
RIDRIISFRLNAIRVLVQDMVKGNLDKDYALDDDENTLDELGMLSLQVVKMKKAISVAISSVLRNIS
YVNKASLEVASSSQNLSSSALQQASALEEMSANVEQIASGVNMSANNSYETEQIALKTNENSQIGGR
AVEEESVIAMQDIVEKVSVIEEIARKTNLLALNAAIEAARAGDEGKGFAVVASEIRKLADLSKISALEIG
ELVEDNSKVATEAGVIFKEMLPEIEETANLVKKISEGSSKQSDQIAQFKMALDQVGEVVQSSASSSE
QLSSMSDKMLEKSKELRKSVLFFKIKDSKIENPENDDYDFRLIDCPENSFKDENQNLKSNGISTSNAS
GHNNYSLDIESESSSVRTINKRVDPKKAIDIADKDLNFDDDFSEF f197.nt (SEQ ID NO:247)
ATGTTATTGAAGCTTAAATACAGGTTTGTTGGATTTTTATTATTGTTTTAATTTTTATA
CTGCTACTTTTTTCCACGATTTTTAATTTTGTTTTATGCGGTTATTTAGAAGATTATTATAAGCA
GCTTACAAGGGCGCAAGTAAGAAGAGCAGCTTTTTCTTTGCAATCTTTTTTAGACACCCTGCAT
GTCATAATCAATGGTGCAGCTTCTAATTTGGCACTTGAAACCATATCAGAATTTGCAATGTCTG
AGAATAGAGGAAAAGATTTCTCTGAGTCGGAATTGATAGATTTAAGAAAAAATCCAAAATTTG
TTATTGACTCTGTAAAGGTGAGCAAAAAATATCGACAATACTTATACAATTTTATGGCCAATCT
TAAAAATGATACCCTTTTTGAAGAATTCGCTTTTTTTGATTTTGAAGGGAGAGTAATTGTTAGC
ACAAGACATGAGAATAATATGGATTTTGGTCATTCTGAGGCTAATACCAATTATTTTAAAAAAG
CTGTTGAGGATTATAGGCAAAACCAATTAAAATTTATAGGTTGGTATTCAAATCTTTCTGAAGG
AATATCCGCAGAAGTTGCTATTAGGTCTAAACAAAGCGAAAAAAGGCTTTTGCAATAATTGTA
CCTGTATATTCCCCAGAAGATAAACTTGTTTGTGGGTATTTGGCCGGATATTTGCTTAATGATAT
TGTGGCAGATAGTTTTGATAGATTTAGATTCGGTTTTTATAAAAGAGGCAATTTTATTTATGTG
GATCCCAACAATATAGCAGTTAATCCTTTTGAAGAATATAATGAAACCAGCAGGGTTAGTTCTA
AATTTTTGAATGTTCTTAAAGATGTTTTCTCTAAGCCCCCTTTTCCATCAAACATTGCCAGTGAA
GTGTCGGTTTACACTATTGATAGAATACTTTTGTCCGAAATGGGAGAAGATTGTTATTATGCAA
TGTTGCCCATAAGTAGTAAATTGGGAGAAAAGAGTGGAGTACTTATTGCTAGGCTTCCTTATAA
GGATATTTTACGGAGTAATATCTAGTCTAAGATTTCAGTATATTTTATATTCAGTCTTAGGCATTA
TAGCATTAAGTATTGTTCTTTCAATTAGAATAGACAGGATTATTAGTTTTCGTTTAAACGCAATT
AGAGTTCTAGTTCAAGATATGGTTAAGGGCAATTTAGATAAAGATTATGCTCTTGATGATGATG
AAAATACTCTTGATGAACTTGGCATGTTAAGTCTTCAGGTTGTTAAAATGAAAAAAGCTATTTC
TGTAGCAATTTCTAGTGTTTTGAGAAATATTAGCTATGTAAATAAGGCAAGTTTAGAAGTTGCC
AGTTCAAGTCAAAATTTAAGCTCTAGTGCATTGCAACAGGCATCTGCTCTTGAAGAAATGTCAG
CTAATGTTGAGCAAATAGCCTCAGGTGTCAACATGAGCGCCAATAATTCTTATGAAACAGAACA
AATAGCTTTAAAGACGAATGAAAATTCTCAGATAGGTGGTAGGGCCGTTGAAGAATCTGTTATT
GCTATGCAAGACATTGTGGAGAAAGTTAGTGTTATTGAAGAGATAGCTAGAAAAACCAATTTA
CTTGCTTTGAATGCGGCTATTGAAGCTGCAAGAGCAGGAGATGAGGGAAAGGGATTTGCTGTT
GTGGCCAGTGAGATTAGAAAGTTGGCTGATTTGAGTAAAATTTCTGCTCTTGAGATTGGAGAGT
TAGTTGAAGATAACTCTAAGGTAGCAACTGAAGCGGGAGTGATTCTTTAAAGAAATGCTACCCG
AAATTGAAGAAACGGCTAATCTTGTTAAGAAGATTTCAGAAGGTAGCTCTAAGCAAAGCGATC
AGATTGCTCAATTTAAAATGGCTTTAGATCAGGTTGGAGAAGTTGTTCAATCTTCAGCTTCAAG
CAGTGAGCAGCTTTCTAGTATGTCCGATAAAATGTTAGAAAAGTCTAAGGAACTTAGAAAATCT
GTATTATTTTTCAAAATTAAAGATTCTAAAATTGAAAATCCAGAAAATGATGATTATGATTTCA
GGTTAATAGATTGTCCTGAAAATTCTTTTAAAGATGAAAATCAAAATTTGAAAAGCAATGGAAT
TTCTACTTCAAATGCCAGTGGGCATAATAATTATTCTTTAGATATTGAGAGCGAATCTTCTGTAA
GAACTATTAATAAGCGAGTTGATCCTAAAAAAGCTATCGATATTGCTGATAAGGATTTAAATTT
TGATGATGATTTTTCAGAGTTTTAG t197.nt (SEQ ID NO:248)
GTTTTATGCGGTTATTTAGAAGATTATTATAAGCAGCTTACAAGGGCGCAAGTAAGAA
GAGCAGCTTTTTCTTTGCAATCTTTTTTAGACACCCTGCATGTCATAATCAATGGTGCAGCTTCT
AATTTGGCACTTGAAACCATATCAGAATTTGCAATGTCTGAGAATAGAGGAAAAGATTTCTCTG
AGTCGGAATTGATAGATTTAAGAAAAAATCCAAAATTTGTTATTGACTCTGTAAAGGTGAGCAA
AAAATATCGACAATACTTATACAATTTTATGGCCAATCTTAAAAATGATACCCTTTTTGAAGAA
TTCGCTTTTTTTGATTTTGAAGGGAGAGTAATTGTTAGCACAAGACATGAGAATAATATGGATT
TTGGTCATTCTGAGGCTAATACCAATTATTTTAAAAAAGCTGTTGAGGATTATAGGCAAAACCA
ATTAAAATTTATAGGTTGGTATTCAAATCTTTCTGAAGGAATATCCGCAGAAGTTGCTATTAGG
TCTAAACAAAGCGAAAAAAGGCTTTTGCAATAATTGTACCTGTATATTCCCCAGAAGATAAAC
TTGTTTGTGGGTATTTGGCCGGATATTTGCTTAATGATATTGTGGCAGATAGTTTTGATAGATTT
AGATTCGGTTTTTATAAAGAGGCAATTTTATTTATGTGGATCCCAACAATATAGCAGTTAATC
CTTTTGAAGAATATAATGAAACCAGCAGGGTTAGTTCTAAATTTTTGAATGTTCTTAAAGATGT
TTTCTCTAAGCCCCCTTTTCCATCAAACATTGCCAGTGAAGTGTCGGTTTACACTATTGATAGAA
TACTTTTGTCCGAAATGGGAGAAGATTGTTATTATGCAATGTTGCCCATAAGTAGTAAATTGGG
AGAAAAGAGTGGAGTACTTATTGCTAGGCTTCCTTATAAGGATATTTTACGGAGTAATATCTAGT
CTAAGATTTCAGTATATTTTATATTCAGTCTTAGGCATTATAGCATTAAGTATTGTTCTTTCAAT
TAGAATAGACAGGATTATTAGTTTTCGTTTAAACGCAATTAGAGTTCTAGTTCAAGATATGGTT
AAGGGCAATTTAGATAAAGATTATGCTCTTGATGATGATGAAAATACTCTTGATGAACTTGGCA
TGTTAAGTCTTCAGGTTGTTAAAATGAAAAAAGCTATTTCTGTAGCAATTTCTAGTGTTTTGAG
AAATATTAGCTATGTAAATAAGGCAAGTTTAGAAGTTGCCAGTTCAAGTCAAAATTTAAGCTCT

TABLE 1-continued

Nucleotide and Amino Acid Sequences.

```
AGTGCATTGCAACAGGCATCTGCTCTTGAAGAAATGTCAGCTAATGTTGAGCAAATAGCCTCAG
GTGTCAACATGAGCGCCAATAATTCTTATGAAACAGAACAAATAGCTTTTAAAGACGAATGAAA
ATTCTCAGATAGGTGGTAGGGCCGTTGAAGAATCTGTTATTGCTATGCAAGACATTGTGGAGAA
AGTTAGTGTTATTGAAGAGATAGCTAGAAAAACCAATTTACTTGCTTTGAATGCGGCTATTGAA
GCTGCAAGAGCAGGAGATGAGGGAAAGGGATTTGCTGTTGTGGCCAGTGAGATTAGAAAGTTG
GCTGATTTGAGTAAAATTTCTGCTCTTGAGATTGGAGAGTTAGTTGAAGATAACTCTAAGGTAG
CAACTGAAGCGGGAGTGATCTTTAAAGAAATGCTACCCGAAATTGAAGAAACGGCTAATCTTG
TTAAGAAGATTTCAGAAGGTAGCTCTAAGCAAAGCGATCAGATTGCTCAATTTAAAATGGCTTT
AGATCAGGTTGGAGAAGTTGTTCAATCTTCAGCTTCAAGCAGTGAGCAGCTTTCTAGTATGTCC
GATAAAATGTTAGAAAAGTCTAAGGAACTTAGAAAATCTGTATTATTTTTCAAAATTAAAGATT
CTAAAATTGAAAATCCAGAAAATGATGATTATGATTTCAGGTTAATAGATTGTCCTGAAAATTC
TTTTTAAAGATGAAAATCAAAATTTGAAAAGCAATGGAATTTCTACTTCAAATGCCAGTGGGCAT
AATAATTATTCTTTAGATATTGAGAGCGAATCTTCTGTAAGAACTATTAATAAGCGAGTTGATC
CTAAAAAAGCTATCGATATTGCTGATAAGGATTTAAATTTTGATGATGATTTTTCAGAGTTTTA
G f200.aa (SEQ ID NO:249)
MTISKNVFSKFILKFLNSSAFVSVFALFVGFLIVGLVVMGLGHSPFRMYFIILEIIFSSPKHLGYVLSYS
APLIFTGLSIGISLKAGLFNIGVEGQFILGSIVALIASVLLDLPPILHVITIFIITFLASGSLGILIGYLKAKF
NISEVISGIMFNWILFHLNNIILDFSFIKRDNSDFSKPIKESAYIDFLASWKLSPEGLAYRSSHPFVNELL
KAPLHFGIILGIIFAILIWFLLNKTIIGFKINATGSNIEASRCMGINVKAVLIFSMFLSAAVAGLAGAIQL
MGVNKAIFKLSYMQGIGFNGIAASLMGNNSPIGIIFSSILFSILLYGSSRVQSLMGLPSSIVSLMMGIIV
LVISASYFLNKIVLKGVKRVKYNNILD t200.aa (SEQ ID NO:250)
LVVMGLGHSPFRMYFIILEIIFSSPKHLGYVLSYSAPLIFTGLSIGISLKAGLFNIGVEGQFILGSIVALIA
SVLLDLPPILHVITIFIITFLASGSLGILIGYLKAKFNISEVISGIMFNWILFHLNNIILDFSFIKRDNSDFSK
PIKESAYIDFLASWKLSPEGLAYRSSHPFVNELLKAPLHFGIILGIIFAILIWFLLNKTIIGFKINATGSNI
EASRCMGINVKAVLIFSMFLSAAVAGLAGAIQLMGVNKAIFKLSYMQGIGFNGIAASLMGNNSPIGII
FSSILFSILLYGSSRVQSLMGLPSSIVSLMMGIIVLVISASYFLNKIVLKGVKRVKYNNILD f200.nt (SEQ ID NO:251)
ATGACAATTAGTAAAAACGTATTTAGTAAATTTATTTTGAAATTTTTAAATTCTTCAGC
ATTTGTTAGTGTATTTGCTCTATTTGTTGGATTTTTAATTGTTGGGCTAGTGGTGATGGGCTTG
GTCATTCTCCTTTTAGAATGTATTTTATAATATTAGAAATTATTTTTTCTTCTCCCAAACATTTG
GTTATGTTTTAAGTTATTCAGCTCCTTTGATTTTTACAGGTCTTTCTATTGGTATTTCTTTAAAAG
CGGGTCTTTTTAATATTGGGGTTGAAGGCCAGTTTATACTAGGATCTATTGTTGCTTTAATAGCA
TCAGTTTTACTTGATTTGCCTCCAATTTTACATGTAATTACTATTTTTATTATTACTTTTTTAGCT
TCAGGCAGTTTAGGAATTTTAATCGGATATTTAAAAGCCAAATTCAATATTAGCGAAGTGATTT
CAGGAATAATGTTTAATTGGATATTATTTCATTTAAATAATATAATTTTAGATTTTAGTTTTATT
AAAAGAGATAATAGTGATTTTTCAAAACCCATTAAAGAAAGCGCATATATTGATTTTTTAGCTT
CTTGGAAGCTCTCACCAGAAGGTCTTGCTTATAGATCTTCTCATCCTTTTGTTAATGAGCTTTTA
AAAGCACCTCTTCATTTTGGAATAATTTTAGGTATAATTTTTGCTATTTTAATATGGTTTTACT
TAATAAAAACTATTATTGGATTTAAAATAAATGCCACAGGAAGTAATATTGAAGCTTCAAGATGT
ATGGGTATTAATGTAAAAGCTGTGCTAATTTTTTCAATGTTTCTCTCAGCAGCTGTTGCAGGTCT
TGCTGGTGCTATTCAACTTATGGGTGTTAATAAAGCTATATTTAAGCTTTCTTATATGCAAGGA
ATTGGTTTTAATGGGATAGCTGCTTCTCTTATGGGGAAACAATTCGCCAATTGGCATAATATTTC
TAGCATTCTTTTTTCTATATTGCTTTATGGAAGCAGTAGAGTTCAAAGTTTAATGGGCCTTCCAT
CTTCAATTGTATCTTTGATGATGGGAATAATTGTTCTTGTAATTTCTGCTAGCTATTTTTTAAAT
AAAATTGTTTTAAAAGGTGTTAAGCGTGTCAAATATAATAATATTCTTGATTAG t200.nt (SEQ ID NO:252)
GGGCTAGTGGTGATGGGCTTGGTCATTCTCCTTTTAGAATGTATTTTATAATATTAGA
AATTATTTTTTCTTCTCCCAAACATTTAGGTTATGTTAAGTTATTCAGCTCCTTTGATTTTTAC
AGGTCTTTCTATTGGTATTTCTTTAAAAGCGGGTCTTTTTAATATTGGGGTTGAAGGCCAGTTTA
TACTAGGATCTATTGTTGCTTTAATAGCATCAGTTTTACTTGATTTGCCTCCAATTTTACATGTA
ATTACTATTTTTATTATTACTTTTTTAGCTTCAGGCAGTTTAGGAATTTTAATCGGATATTTAAA
AGCCAAATTCAATATTAGCGAAGTGATTTCAGGAATAATGTTTAATTGGATATTATTTCATTTA
AATAATATAATTTTAGATTTTAGTTTTATTAAAAGAGATAATAGTGATTTTTCAAAACCCATTAA
AGAAAGCGCATATATTGATTTTTTAGCTTCTTGGAAGCTCTCACCAGAAGGTCTTGCCTATAGA
TCTTCTCATCCTTTTGTTAATGAGCTTTTAAAAGCACCTCTTCATTTTGGAATAATTTTAGGTAT
AATTTTTGCTATTTTAATATGGTTTTTACTTAATAAAACTATTATTGGATTTAAAATAAATGCCA
CAGGAAGTAATATTGAAGCTTCAAGATGTATGGGTATTAATGTAAAAGCTGTGCTAATTTTTTC
AATGTTTCTCTCAGCAGCTGTTGCAGGTCTTGCTGGTGCTATTCAACTTATGGGTGTTAATAAAG
CTATATTTAAGCTTTCTTATATGCAAGGAATTGGTTTTAATGGGATAGCTGCTTCTCTTATGGGA
AACAATTCGCCAATTGGCATAATATTTCTAGCATTCTTTTTTCTATATTGCTTTATGGAAGCAG
TAGAGTTCAAAGTTTAATGGGCCTTCCATCTTCAATTGTATCTTTGATGATGGGAATAATTGTTC
TTGTAATTTCTGCTAGCTATTTTTTAAATAAAATTGTTTTAAAAGGTGTTAAGCGTGTCAAATAT
AATAATATTCTTGATTAG f208.aa (SEQ ID NO:253)
MVKKFSIFLKAIIIFSIFELLIEELSIILFLPYKIRFALIFLGFLFDTIFIFIFLYKITKAYLSQRLEIYVRNNL
FFDIIHCLIPLAFYSSYQLKNIIVAHETILNPIMLSLFKLRFLRLLRFNDLIIEIYYNSKEKNLILLAFARTF
SMSLLIPFTFFIIISSSKIVNSIPEKQEFNIIKNISIINEKAYIKEKYPFILIIKEKDDIIYSKSDEIFVYYSPSE
YRVIEMEKTKFYIDKYLQRKSDSILGIFLFTLFASFTIFLMNFYKFFKASFLNPIILMTKILQDPLEYRKI
QIPFTLSEEKVYELAKSFNNLLLKEKLNSKRKSKIPLEIEKVKKIINKNQEIK
```

TABLE 1-continued

Nucleotide and Amino Acid Sequences.

t208.aa (SEQ ID NO:254)
IIIFSIFELLIEELSIILFLPYKIRFALIFLGFLFDTIFIFIFLYKITKAYLSQRLEIYVRNNLFFDIIHCLIPLAF
YSSYQLKNIIVAHETILNPIMLSLFKLRFLRLLRFNDLIIEIYYNSKEKNLILIAFARTFSMSLLIPFTFFIII
SSSKIVNSIPEKQEFNIIKNISIINEKAYIKEKYPFILIIKEKDDIIYSKSDEIFVYYSPSEYRVIEMEKTKF
YIDKYLQRKSDSILGIFLFTLFASFTIFLMNFYKFFKASFLNPIILMTKILQDPLEYRKIQIPFTLSEEKV
YELAKSFNNLLLKEKLNSKRKSKIPLEIEKVKKHIINKNQEIK f208.nt (SEQ ID NO:255)
ATGGTAAAAAAATTTTCAATTTTCTTAAAAGCAATAATAATTTTTTCAATATTTGAACTTTTAAT
CGAAGAACTCTCAATAATTCTTTTTTTACCATACAAAATACGATTTGCACTAATATTTCTTGGGT
TTCTATTTGACACAATTTTTATTTTCATTTTTTTATACAAAATAACCAAGGCCTACCTTTCCCAA
AGATTAGAAATCTACGTCAGAAACAATCTATTCTTCGATATAATCCACTGCCTTATTCCTTTAGC
GTTTTATAGCTCATATCAGCTTAAAAACATAATTGTCGCCCATGAAACAATATTTAAATCCAATA
ATGCTATCACTTTTCAAGTTAAGATTTTTAAGACTTCTTAGGTTTAATGACCTAATAATAGAAT
ATATTACAATTCAAAAGAAAAGAACCTAATACTAATAGCATTTGCTAGGACATTTTCAATGAGC
TTATTAATACCATTTACATTTTTTATAATAATATCAAGCTCAAAAATTGTAAATTCAATACCAGA
AAAACAAGAATTTAATATCATTAAAAATATATCAATAATAAATGAAAAAGCTTACATTAAAGA
AAAATATCCCTTCATCTTAATAATCAAGGAAAAAGATGACATAATATACTCAAAATCAGACGAA
ATATTTGTTTACTACAGTCCCAGTGAATATAGAGTAATAGAAATGGAGAAAACAAAATTTTATA
TAGATAAATATTTGCAAAGAAAAAGCGATTCTATTCTTGGAATTTTTCTATTTACATTGTTTGCA
TCATTTACTATTTTTTTAATGAATTTTTATAAATTTTTTAAAGCAAGGTTTTTAAATCCTATTATT
TTAATGACAAAAATTTTACAAGACCCATTAGAATATCGAAAAATTCAAATTCCTTTTACTTTAA
GCGAAGAAAAAGTATATGAACTTGCAAAATCATTTAACAATCTCTTGCTAAAAGAAAAACTAA
ACTCAAAGCGAAAAAGCAAAATACCTTTAGAAATTGAAAAAGTAAAAAAAATAATTAATAAAA
ACCAGGAAATAAAATGA t208.nt (SEQ ID NO:256)
ATAATAATTTTTTCAATATTTGAACTTTTAATCGAAGAACTCTCAATAATTCTTTTTTTACCATA
CAAAATACGATTTGCACTAATATTTCTTGGGTTTCTATTTGACACAATTTTTATTTTCATTTTTTT
ATACAAAATAACCAAGGCCTACCTTTCCCAAAGATTAGAAATCTACGTCAGAAACAATCTATTC
TTCGATATAATCCACTGCCTTATTCCTTTAGCGTTTTATAGCTCATATCAGCTTAAAAACATAAT
TGTCGCCCATGAAACAATATTTAAATCCAATAATGCTATCACTTTTCAAGTTAAGATTTTTAAGA
CTTCTTAGGTTTAATGACCTAATAATAGAAATATATTACAATTCAAAAGAAAAGAACCTAATAC
TAATAGCATTTGCTAGGACATTTTCAATGAGCTTATTAATACCATTTACATTTTTTATAATAATA
TCAAGCTCAAAAATTGTAAATTCAATACCAGAAAAACAAGAATTTAATATCATTAAAAATATAT
CAATAATAAATGAAAAAGCTTACATTAAAGAAAAATATCCCTTCATCTTAATAATCAAGGAAAA
AGATGACATAATATACTCAAAATCAGACGAAATATTTGTTTACTACAGTCCCAGTGAATATAGA
GTAATAGAAATGGAGAAAACAAAATTTTATATAGATAAATATTTGCAAAGAAAAAGCGATTCT
ATTCTTGGAATTTTTCTATTTACATTGTTTGCATCATTTACTATTTTTTTAATGAATTTTTATAAA
TTTTTTAAAGCAAGCTTTTTAAATCCTATTATTTTAATGACAAAAATTTTACAAGACCCATTAGA
ATATCGAAAAATTCAAATTCCTTTTACTTTAAGCGAAGAAAAAGTATATGAACTTGCAAAATCA
TTTAACAATCTCTTGCTAAAAGAAAAACTAAACTCAAAGCGAAAAAGCAAAATACCTTTAGAA
ATTGAAAAAGTAAAAAAAATAATTAATAAAAACCAGGAAATAAAATGA f210.aa (SEQ ID NO:257)
MKIQIIIMLLALLDFPLNARLLDISIEKRADEEIKKYSSYNLILEKEYYTNFPTSEIEKNIYKLTEHFVKS
IMLNKTNYSLLNSNYKEANKYLIQSELIDKKFLKYKIFKIKNINGIFKSHSLIYTKKGFYKLELYIENN
AEPLKIFNLNITYFLKNLDKISNEMIFFPREKREVNMIQKTTIAADSSSKPRGINYDTGIPFNVLIVDDS
VFTVKQLTQIFTSEGFNIIDTAADGEEAVIKYKNHYPNIDIVTLDITMPKMDGITCLSNIMEFDKNAR
VIMISALGKEQLVKDCLIKGAKTFIVKPLDRAKVLQRVMSVFVK t210.aa (SEQ ID NO:258)
RLLDISIEKRADEEIKKYSSYNLILEKEYYTNFPTSEIEKNIYKLTEHFVKSIMLNKTNYSLLN
SNYKEANKYLIQSELIDKKFLKYKIFKIKNINGIFKSHSLIYTKKGFYKLELYIENNAEPLKIFNLNITY
FLKNLDKISNEMIFFPREKREVNMIQKTTIAADSSSKPRGINYDTGIPFNVLIVDDSVFTVKQLTQIFTS
EGFNIIDTAADGEEAVIKYKNHYPNIDIVTLDITMPKiMDGITCLSNIMEFDKNARVIMISALGKEQLV
KDCLIKGAKTFIVKPLDRAKVLQRVMSVFVK f210.nt (SEQ ID NO:259)
ATGAAAATTCAAATAATTATAATGCTGCTTGCATTGTTAGATTTTCCACTTAATGCCAG
ACTTTTGGACATTTCAATTGAAAAAGAGCAGATGAAGAAATAAAAAAATATTCGTCTTATAAT
TTAATTTTAGAAAAAGAATACTATACCAATTTTCCAACAAGCGAAATAGAAAAAAATATTTATA
AACTAACAGAACATTTTGTAAAAAGCATAATGCTCAATAAAACTAACTACAGCTTAATTAAATTC
AAACTACAAAGAAGCAAATAAATATCTAATTCAAAGCGAACTCATTGATAAAAAATTTTTAAAA
TATAAAATATTTAAAATCAAAAATATAAATGGAATTTTTAAAAGCCATTCACTAATATATACAA
AAAAAGGATTTTACAAATTAGAACTTTACATAGAAAATAATGCAGAACCTCTAAAAATATTTAA
CCTTAACATTACTTATTTTTTAAAGAATTTAGATAAAATAAGTAATGAAATGATTTTTTTCCCAA
GGGAATGA t210.nt (SEQ ID NO:260)
AGACTTTTTGGACATTTCAATTGAAAAAGAGCAGATGAAGAAATAAAAAAATATTCGTCTTATA
ATTTAATTTTAGAAAAAGAATACTATACCAATTTTCCAACAAGCGAAATAGAAAAAAATATTTA
TAAACTAACAGAACATTTTGTAAAAAGCATAATGCTCAATAAAACTAACTACAGCTTATTAAAT
TCAAACTACAAAGAAGCAAATAAATATCTAATTCAAAGCGAACTCATTGATAAAAAATTTTTAA
AATATAAAATATTTAAAATCAAAAATATAAATGGAATTTTTAAAAGCCATTCACTAATATATAC
AAAAAAAGGATTTTACAAATTAGAACTTTACATAGAAAATAATGCAGAACCTCTAAAAATATTT
AACCTTAACATTACTTATTTTTTAAAGAATTTAGATAAAATAAGTAATGAAATGATTTTTTTCC

TABLE 1-continued

Nucleotide and Amino Acid Sequences.

AAGGGAATGA f22.aa (SEQ ID NO:261)
MLKTLTKIITISCLIVGCASLPYTPPKQNLNYLMELLPGANLYAHVNLIKNRSIYNSLSPKYKSVLGLI
SNLYFSYKKENNDFALLIMGNFPKDIFWGIHKNRNTESIGNIFTNPKWKLKNSNIYIIPNKARTSIAIT
QKDITAKDNNMLTTKYIGEIEKNEMFFWIQDPTLLLPNQIVSSKNLIPFSSGTLSINSLNQEEYIFKSLI
KTNNPPILKILSKKLIPTVLTNMTNLTISSHIKTTIKDQNTVEIEFNIQKSSVESLIEKLASNIQT t22.aa (SEQ ID NO:262)
PYTPPKQNLNYLMELLPGANLYAHVNLIKNRSIYNSLSPKYKSVLGLISNLYFSYKKENNDFALLIM
GNFPKDIFWGIHKNRNTESIGNIFTNPKWKLKNSNIYIIPNKARTSIAITQKDITAKDNNMLTTKYIGEI
EKNEMFFWIQDPTLLLPNQIVSSKNLIPFSSGTLSINSLNQEEYIFKSLIKTNNPPILKILSKKLIPTVLTN
MTNLTISSHIKTTIKDQNTVEIEFNIQKSSVESLIEKLASNIQT f22.nt (SEQ ID NO:263)
ATGTTAAAAACATTAACAAAAATAATTACCATTTCATGCCTCATAGTGGGATGCGCAAGCCTGC
CTTACACTCCTCCAAAACAAAATCTAAATTACTTAATGGAACTTTTACCTGGCGCAAATTTATAC
GCCCATGTAAATTTAATTAAAAACAGGTCTATTTATAACTCTTTAAGCCCTAAATATAAATCAG
TTCTTGGGCTTATAAGCAATTTATACTTTAGCTATAAAAAGAAAATAACGATTTTGCTCTACTA
ATAATGGGTAATTTCCCAAAAGATATTTTCTGGGGAATTCATAAAAATAGAAATACAGAATCAA
TAGGCAATATATTTACAAATCCAAAATGGAAACTTAAAAATTCAAATATATACATTATTCCAAA
CAAAGCTAGAACTAGCATTGCAATAACCCAAAAAGATATAACCGCAAAAGACAATAATATGCT
AACAACAAAATATATTGGGGAAATAGAAAAAAATGAAATGTTTTTTTGGATTCAAGATCCAAC
ATTATTGCTCCCAAACCAAATAGTAAGCAGCAAAAATTTAATTCCCTTTAGCAGTGGAACTTTG
TCTATAAACAGCTTAAATCAAGAAGAATATATTTTTAAATCCTTAATCAAAACAAATAATCCAC
CAATACTAAAAATATTGTCAAAAAAGTTAATTCCAACCGTCTTGACAAACATGACAAACCTCAC
AATATCAAGCCACATAAAGACCACAATAAAAGACCAAAATACGGTTGAAATAGAATTTAATAT
TCAAAAATCTAGTGTTGAAAGCCTTATAGAAAAACTAGCTTCAAATATTCAAACCTAA t22.nt (SEQ ID NO:264)
CCTTACACTCCTCCAAAACAAAATCTAAATTACTTAATGGAACTTTTACCTGGCGCAAATTTATA
CGCCCATGTAAATTTAATTAAAAACAGGTCTATTTATAACTCTTTAAGCCCTAAATATAAATCA
GTTCTTGGGCTTATAAGCAATTTATACTTTAGCTATAAAAAGAAAATAACGATTTTGCTCTAC
TAATAATGGGTAATTTCCCAAAAGATATTTTCTGGGGAATTCATAAAAATAGAAATACAGAATC
AATAGGCAATATATTTACAAATCCAAAATGGAAACTTAAAAATTCAAATATATACATTATTCCA
AACAAAGCTAGAACTAGCATTGCAATAACCCAAAAAGATATAACCGCAAAAGACAATAATATG
CTAACAACAAAATATATTGGGGAAATAGAAAAAAATGAAATGTTTTTTTGGATTCAAGATCCAA
CATTATTGCTCCCAAACCAAATAGTAAGCAGCAAAAATTTAATTCCCTTTAGCAGTGGAACTTT
GTCTATAAACAGCTTAAATCAAGAAGAATATATTTTTAAATCCTTAATCAAAACAAATAATCCA
CCAATACTAAAAATATTGTCAAAAAAGTTAATTCCAACCGTCTTGACAAACATGACAAACCTCA
CAATATCAAGCCACATAAAGACCACAATAAAAGACCAAAATACGGTTGAAATAGAATTTAATA
TTCAAAAATCTAGTGTTGAAAGCCTTATAGAAAAACTAGCTTCAAATATTCAAACCTAA f221.aa (SEQ ID NO:265)
MGITVFYLFSIFASFVLGSSMDSVKENVLKSTIFYYDVEEVEFPYARKQTLQFIAKTHLKYAVFNFDK
NKMFSYTFVFDKKLISQYAIFIEVKKKFGEATLVTPLNYLWDLGDSIIVLNKNILRITLKSYISNYNK t221.aa (SEQ ID NO:266)
SMDSVKENVLKSTIFYYDVEEVEFPYARKQTLQFIAKTHLKYAVFNFDKNKMFSYTFVFDKKLISQ
YAIFIEVKKKFGEATLVTPLNYLWDLGDSIIVLNKNILRITLKSYISNYNK f221.nt (SEQ ID NO:267)
ATGGGTATTACAGTTTTTTATTTATTTTCTATTTTTGCATCTTTTGTTCTGGGTTCTAGCATGGAT
TCTGTTAAAGAGAATGTTCTCAAGAGCACTTTTTTATTATGATGTTGAAGAAGTTGAATTTCC
TTATGCTAGGAAGCAGACTTTACAATTTATTGCTAAAACCCATTTAAAATATGCTGTTTTTAATT
TTGACAAAAATAAAATGTTTTCGTACACTTTTGTTTTTGATAAAAAATTAATATCTCAGTATGCA
ATTTTTATTGAGGTAAAGAAAAAGTTTGGCGAGGCTACACTAGTAACGCCTTTGAATTATTTAT
GGGATCTTGGTGATTCTATTATTGTTTTAAATAAAAATATTTTAAGAATTACTTTAAAATCTTAT
ATTTCAAATTATAATAAATGA t221.nt (SEQ ID NO:268)
AGCATGGATTCTGTTAAAGAGAATGTTCTCAAGAGCACTATTTTTTATTATGATGTTGAAGAAG
TTGAATTTCCTTATGCTAGGAAGCAGACTTTACAATTTATTGCTAAAACCCATTTAAAATATGCT
GTTTTTAATTTTGACAAAAATAAAATGTTTTCGTACACTTTTGTTTTTGATAAAAAATTAATATC
TCAGTATGCAATTTTTATTGAGGTAAAGAAAAAGTTTGGCGAGGCTACACTAGTAACGCCTTTG
AATTATTTATGGGATCTTGGTGATTCTATTATTGTTTTAAATAAAAATATTTTAAGAATTACTTT
AAAATCTTATATTTCAAATTATAATAAATGA f253.aa (SEQ ID NO:269)
MYMENIEVRGQPNFFGLIPFFVFIIIYLGTGIYLGVIGVEMAFYQLPASVAMFFASIVCFLVFKGKFSD
KIHIFIKGAAQYDIILMCLIFMLSGAFSSLCKEIGCVETVANLGIKYINPNWIVSGIFFVTCFLSFSAGTS
VGSIVAIAPIAFNIAVKSGINPNLIAASVMCGAMFGDNLSLISDTTIVSSRTQGSSILDVFISSSFYAFPS
AILTFFSFFFLSENLSNATNFLHESSIDLVKTVPYLMIIFFSLAGMNVFIVLFLGILSICLISVLYGNLYFL
DVMKNINKGFLNMADLIFLSILTGGVSFAVIHNGGFKWLLIKLKSLIRGKSSAEFSIGAFVSIVDVFLA
NNTIAILICGKVAKKIAFENNISVQRSASILDMFSCIFQGIIPYGAQMIILVNFSNGLVSPISILPFLVYFG
FLLFFVILSILGLDIKKVFLFFLKK

TABLE 1-continued

Nucleotide and Amino Acid Sequences.

t253.aa (SEQ ID NO:270)
LVFKGKFSDKIHIFIKGAAQYDIILMCLIFMLSGAFSSLCKEIGCVETVANLGIKYINPNWIVSGIFFVT
CFLSFSAGTSVGSIVAIAPIAFNIAVKSGINPNLIAASVMCGAMFGDNLSLISDTTIVSSRTQGSSILDVF
ISSSFYAFPSAILTFFSFFFLSENLSNATNFLHESSIDLVKTVPYLMIIFFSLAGMNVFIVLFLGILSICLIS
VLYGNLYFLDVMKNINKGFLNMADLIFLSILTGGVSFAVHKNGGFKWLLIKLKSLIRGKSSAEFSIGA
FVSIVDVFLANNTIAILICGKVAKKIAFENNISVQRSASILDMFSCIFQGIIPYGAQMIILVNFSNGLVSPI
SILPFLVYFGFLLFFVILSILGLDIKKVFLFFLKK f253.n (SEQ ID NO:271)
ATGTATATGGAAAATATTGAAGTAAGAGGGCAGCCAAATTTTTTTGGGCTTATTCCTTTTTTTGT
TTTTTATTATTATCTATTTAGGCACGGGGATTTATTTGGGAGTTATTGGTGTAGAAATGGCCTTTT
ATCAACTGCCGGCTAGTGTTGCAATGTTTTTTGCTTCCATTGTTTGTTTTTTGGTATTTAAAGGA
AAATTTTCCGACAAAATTCACATATTTATTAAAGGAGCAGCTCAGTACGATATTATACTAATGT
GTCTTATTTTTATGCTTTCGGGAGCTTTCTCTTCTCTTTGTAAAGAAATAGGCTGCGTTGAAACT
GTAGCAAATTTGGGAATTAAATATATTAATCCTAATTGGATTGTTTCTGGTATATTTTTTGTAAC
CTGCTTTCTTTCTTTTTCTGCCGGCACTTCTGTTGGATCTATCGTTGCAATTGCTCCTATTGCTTT
TAATATTGCTGTTAAAAGCGGCATTAATCCGAATTTAATAGCAGCATCTGTAATGTGTGGAGCT
ATGTTTGGAGATAATCTTTCTTTAATATCAGATACAACTATTGTTTCTAGTCGAACTCAAGGTAG
TAGCATCTTAGATGTTTTTATTAGTAGCAGTTTTTATGCTTTTCCATCCGCCATACTAACTTTTTT
TTCTTTTTTCTTTCTTTCTGAAAATTTGTCCAATGCCACAAACTTTTTACACGAAAGTTCAATAG
ATTTAGTGAAAACTGTGCCTTATTTAATGATTATATTTTCTCTTTAGCTGGAATGAATGTTTTT
ATAGTTCTTTTTTTAGGTATTCTTTCTATATGTCTTATTAGCGTTTTGTATGGTAATTTATACTTT
CTAGATGTAATGAAAAACATTAATAAAGGGTTTTTAAATATGGCGGATTTGATTTTTCTTTCAA
TTTTAACAGGGGGAGTTTCTTTTGCCGTGATTCATAATGGAGGCTTTAAATGGCTACTTATTAA
ATTAAAATCCTTGATTAGAGGAAAAAGTTCAGCGGAATTTTCTATTGGGGCTTTTGTTTCAATA
GTTGATGTTTTTCTTGCTAATAACACAATTGCCATACTTATTTGCGGCAAAGTAGCAAAAAAGA
TAGCTTTTGAAAATAACATCAGTGTTCAAAGAAGTGCTTCTATTTTAGATATGTTCTCTTGTATT
TTTCAAGGCATTATTCCTTATGGTGCGCAAATGATTATTTTAGTGAATTTTTCAAATGGACTTGT
GTCGCCAATTAGTATTTTGCCATTTTTAGTTTATTTTGGATTTTTATTGTTTTTTGTTATTTTATC
TATTTTTGGGCCTTGATATAAAAAAAGTTTTTTATTTTTTTTAAAAAAATAA t253.nt (SEQ ID NO:272)
TTGGTATTTAAAGGAAAATTTTCCGACAAAATTCACATATTTATTAAAGGAGCAGCTCAGTACG
ATATTATACTAATGTGTCTTATTTTTATGCTTTCGGGAGCTTTCTCTTCTCTTTGTAAAGAAATA
GGCTGCGTTGAAACTGTAGCAAATTTGGGAATTAAATATATTAATCCTAATTGGATTGTTTCTG
GTATATTTTTTGTAACCTGCTTTCTTTCTTTTTCTGCCGGCACTTCTGTTGGATCTATCGTTGCAA
TTGCTCCTATTGCTTTTAATATTGCTGTTAAAAGCGGCATTAATCCGAATTTAATAGCAGCATCT
GTAATGTGTGGAGCTATGTTTGGAGATAATCTTTCTTTAATATCAGATACAACTATTGTTTCTAG
TCGAACTCAAGGTAGTAGCATCTTAAGATGTTTTTATTAGTAGCAGTTTTTATGCTTTTCCATCCG
CCATACTAACTTTTTTTTCTTTTTTCTTTCTTTCTGAAAATTTGTCCAATGCCACAAACTTTTTAC
ACGAAAGTTCAATAGATTTAGTGAAAACTGTGCTTATTTAATGATTATATTTTCTCTTTAGCT
GGAATGAATGTTTTTATAGTTCTTTTTTTAGGTATTCTTTCTATATGTCTTATTAGCGTTTTGTAT
GGTAATTTATACTTTCTAGATGTAATGAAAAACATTAATAAAGGGTTTTTAAATATGGCGGATT
TGATTTTTCTTTCAATTTTAACAGGGGGAGTTTCTTTTGCCGTGATTCATAATGGAGGCTTTAAA
TGGCTACTTATTAAATTAAAATCCTTGATTAGAGGAAAAAGTTCAGCGGAATTTTCTATTGGGG
CRTTTGTTTCAATAGTTGATGTTTTTCTTGCTAATAACACAATTGCCATACTTATTTGCGGCAAA
GTAGCAAAAAAGATAGCTTTTGAAAATAACATCAGTGTTCAAAGAAGTGCTTCTATTTTAGATA
TGTTCTCTTGTATTTTTCAAGGCATTATTCCTTATGGTGCGCAAATGATTATTTTAGTGAATTTT
TCAAATGGACTTGTGTCGCCAATTAGTATTTTGCCATTTTTAGTTTATTTTGGATTTTTATTGTTT
TTTGTTATTTTATCTATTTTTGGGCCTTGATATAAAAAAAGTTTTTTATTTTTTTTAAAAAAATA
A f265.aa (SEQ ID NO:273)
MRKCFVSLSLLLIFFACSSNVEIELNDDISGIVSIFVNVNREFEKIRKELLTTLVGEEIANMPLFPVDEIK
KYFKNGEEKLGLKLLSIKTQGDSINLVVKFDNLIKILGDYMKKPDISVFKIEKKDGKNIIELNINLENA
TKNINENKEYISDALAALLPSDEIPMSAKEYKDVLVYFLSDFTSKASELIDNSKLNLVVKTSRNVQEQ
FGFKQINSNTLRFEMDMVKGLSLETPIKLRLV
Y t265.aa (SEQ ID NO:274)
SNVEIELNDDISGIVSIFVNVNREFEKIRKELLTTLVGEEIANMPLFPVDEIKKYFKNGEEKLGLKLLSI
KTQGDSINLVVKFDNLIKILGDYMKKPDISVFKIEKKDGKNIIELNINLENATKNINENKEYISDALAA
LLPSDEIPMSAKEYKDVLVYFLSDFTSKASELIDNSKLNLVVKTSRNVQEQFGFKQINSNTLRFEMD
MVKGLSLETPIKLRLVY f265.nt (SEQ ID NO:275)
ATGAGAAAGTGTTTTGTTAGCTTGAGTTTATTGTTGATTTTTTTTGCTTGTAGCTCTAATGTTGA
AATTGAGTTAAATGATGATATTAGTGGTATTGTTTCAATATTTGTTAATGTTAATAGAGAATTT
GAAAAAATTAGAAAAGAACTCTTAACAACTTTGGTGGGAGAAGAAATTGCAAATATGCCTCTTT
TTCCTGTAGATGAAATAAAAAAATACTTTAAAAATGGAGAGGAAAAGCTTGGGCTTAAGCTTTT
GAGTATTAAAACCCAAGGAGATTCTATTAATTTAGTTGTTAAGTTTGATAATTTAATTAAAATTT
TAGGCGATTATATGAAAAAACCCGATATATCTGTGTTTAAGATAGAAAAAAAAGATGGTAAAA
ATATTATTGAACTTAATATTAATTTGGAAAACGCTACTAAGAATATTAATGAAAATAAAGAATA
TATTAGTGATGCACTTGCTGCTCTTTTGCCATCGGATGAGATCCCAATGTCTGCCAAAGAATAT
AAAGATGTTTTGGTTTATTTTTATCGGATTTTACTTCCAAAGCAAGTGAACTTATTGACAATTC
CAAACTTAATCTTGTAGTTAAGACTTCTAGAAATGTTCAAGAACAATTTGGATTCAAACAAATT
AACTCAAACACACTGCGGTTTGAGATGGATATGGTTAAAGGATTAAGTCTTGAAACACCAATAA

TABLE 1-continued

Nucleotide and Amino Acid Sequences.

AACTTAGATTAGTTTATTGA t265.nt (SEQ ID NO:276)
TCTAATGTTGAAATTGAGTTAAATGATGATATTAGTGGTATTGTTTCAATATTTGTTAATGTTAA
TAGAGAATTTGAAAAAATTAGAAAAGAACTCTTAACAACTTTGGTGGGAGAAGAAATTGCAAA
TATGCCTCTTTTTCCTGTAGATGAAATAAAAAAATACTTTAAAAATGGAGAGGAAAAGCTTGGG
CTTAAGCTTTTGAGTATTAAAACCCAAGGAGATTCTATTAATTTAGTTGTTAAGTTTGATAATTT
AATTAAAATTTTAGGCGATTATATGAAAAAACCCGATATATCTGTGTTTAAGATAGAAAAAAAA
GATGGTAAAAATATTATTGAACTTAATATTAATTTGGAAAACGCTACTAAGAATATTAATGAAA
ATAAAGAATATATTAGTGATGCACTTGCTGCTCTTTTGCCATCGGATGAGATCCCAATGTCTGC
CAAAGAATATAAAGATGTTTTGGTTTATTTTTTATCGGATTTTACTTCCAAAGCAAGTGAACTTA
TTGACAATTCCAAACTTAATCTTGTAGTTAAGACTTCTAGAAATGTTCAAGAACAATTTGGATT
CAAACAAATTAACTCAAACACACTGCGGTTTGAGATGGATATGGTTAAAGGATTAAGTCTTGAA
ACACCAATAAAACTTAGATTAGTTTATTGA f269.aa (SEQ ID NO:277)
MNIRKLLFCIFFMNISFLLFAGDYKGLDFKIKFFNQSIYRVNSNVFIEVSLSNASESVLTLEIG
DINSFGFDFDVTDTTNIKVKRPLEYVKKRSKNVAIPVRNMSLRPNEKFSVVINLNQFVKFSKDGVYF
VKGIFFPDISDPSKKKESNIITLFLNDGFDENPGSIDLVNLSENNDIQDILKKKKLSPDEIVKYLLKALQ
LGKKEKFFLYLDIEGLLLNDKGKAYLYKQKLSPIPNKNVVEEYKEYLWNSNNSDISKAPNKFSIIETT
YSDTSGKVIADLYFDDGQFYISKRYTFFFKKYDYYWIIYDYIVQNTGIKEK t269.aa (SEQ ID NO:278)
GDYKGLDFKIKFFNQSIYRVNSNVFIEVSLSNASESVLTLEIGDINSFGFDFDVTDTTNIKVKRPIEYV
KKRSKNVAIPVRNMSLRPNEKFSVVTINLNQFVKFSKDGVYFVKGIFFPDISDPSKKKESNIITLFLNDG
FDENPGSIDLVNLSENNDIQDILKKKKLSPDEIVKYLLKALQLGKKEKFFLYLDIEGLLLNDKGKAYL
YKQKLSPIPNKNVVEEYKEYLWNSNNSDISKAPNKFSIIETTYSDTSGKVIADLYFDDGQFYISKRYT
FFFKKYDYYWIIYDYIVQNTGIKEK f269.nt (SEQ ID NO:279)
ATGAATATTAGAAAATTGCTTTTTTGTATCTTTTTTTATGAATATTTCTTTTCTTTTGTTTG
CGGGAGATTACAAGGGCCTTGATTTTAAAATCAAGTTTTTAATCAATCTATTTATCGTGTCAAT
AGTAATGTTTTTATTGAAGTTTCTCTTAGTAATGCGTCTGAGAGTGTTTTAACTTTAGAAATAGG
CGATATTAATTCTTTTGGCTTTGATTTTGATGTTACTGATACCACCAATATTAAAGTTAAAAGAC
CTATTGAATATGTTAAAAAGAGATCTAAAAATGTTGCAATTCCTGTTAGAAATATGAGCTTGAG
ACCTAATGAAAAATTTTCTGTAGTTATTAACTTAAATCAATTTGTTAAGTTTAGTAAAGATGGA
GTTTATTTTGTTAAGGGTATTTTTTTCCCAGACATTTCAGATCCATCTAAAGAAAAAGAATCCAA
TATTATTACGCTTTTTTTGAATGATGGTTTTGATGAAAATCCAGGTAGCATAGACCTTGTTAATT
TGTCTGAAAATAATGATATTCAAGATATCTTGAAAAAGAAAAAATTATCTCCCGATGAAATTGT
TAAATATTTGTTAAAGGCATTGCAGCTTGGGAAAAAAGAAAAGTTCTTTTTATATCTTGATATT
GAAGGTTTGTTATTAAATGACAAGGGCAAGGCATACCTTTATAAGCAAAAGTTATCACCTATTC
CCAATAAAAATGTAGTTGAAGAGTATAAAGAATATTTGTGGAATTCTAATAATTCGGATATTTC
AAAAGCACCAAATAAATTTTCTATTATTGAAACTACTTATTCTGATACTTCTGGCAAGGTGATT
GCTGATTTATATTTTGACGATGGGCAATTTTATATTTCCAAAAGATATACTTTCTTCTTTAAAAA
ATATGATTATTATTGGATAATTTATGATTACATTGTTCAAAATACTGGCATTAAGGAAAAGTAA t269.nt (SEQ ID NO:280)
GGAGATTACAAGGGCCTTGATTTTAAAATCAAGTTTTTTAATCAATCTATTTATCGTGTCAATAG
TAATGTTTTTATTGAAGTTTCTCTTAGTAATGCGTCTGAGAGTGTTTTAACTTTAGAAATAGGCG
ATATTAATTCTTTTGGCTTTGATTTTGATGTTACTGATACCACCAATATTAAAGTTAAAAGACCT
ATTGAATATGTTAAAAAGAGATCTAAAAATGTTGCAATTCCTGTTAGAAATATGAGCTTGAGAC
CTAATGAAAAATTTTCTGTAGTTATTAACTTAAATCAATTTGTTAAGTTTAGTAAAGATGGAGT
TTATTTTGTTAAGGGTATTTTTTTCCCAGACATTTCAGATCCATCTAAGAAAAAAGAATCCAATA
TTATTACGCTTTTTTTGAATGATGGTTTTGATGAAAATCCAGGTAGCATAGACCTTGTTAATTTG
TCTGAAAATAATGATATTCAAGATATCTTGAAAAAGAAAAAATTATCTCCCGATGAAATTGTTA
AATATTTGTTAAAGGCATTGCAGCTTGGGAAAAAAGAAAAGTTCTTTTTATATCTTGATATTGA
AGGTTTGTTATTAAATGACAAGGGCAAGGCATACCTTTATAAGCAAAAGTTATCACCTATTCCC
AATAAAAATGTAGTTGAAGAGTATAAAGAATATTTGTGGAATTCTAATAATTCGGATATTTCAA
AAGCACCAAATAAATTTTCTATTATTGAAACTACTTATTCTGATACTTCTGGCAAGGTGATTGCT
GATTTATATTTTGACGATGGGCAATTTTATATTTCCAAAAGATATACTTTCTTCTTTAAAAAATA
TGATTATTATTGGATAATTTATGATTACATTGTTCAAAATACTGGCATTAAGGAAAAGTAA f29.aa (SEQ ID NO:281)
MNWLSFFYVLLFLLIFPFELQSNNKENIENLIKLHMLYDLTNNLSKELETINKIKNFDLEQHYLLITKY
YLKIKKYKEANDFLKKINQKKIKNQKIKNEIISLKLRINEDNINEEEIKKILNNEKNIDVKIIYQIFSLIK
FKNKJKLKLANKIKNIILTNYPKSIYSYKIKRNE t29.aa (SEQ ID NO:282)
NNKENIENLIKLHMLYDLTNNLSKELETINKIKNFDLEQHYLLITKYYLKIKKYKEANDFLKKINQKK
IKNQKIKNEIISLKLRINEDNINEEEIKKILNNEKNIDVKIIYQIFSLIKFKNKKLANKIKNIILTNYPKSIY
SYKIKRNE f29.nt (SEQ ID NO:283)
ATGAACTGGCTATCCTTTTTTTATGTTTTATTATTTTTATTAATTTTCCTTTTGAATTACAGAGT
AATAATAAAGAAAATATAGAAAATTTAATAAAGCTACATATGCTTTATGATTTAACCAATAACC
TGTCAAAAGAATTAGAAACAATAAATAAAATTAAAAATTTTGACTTAGAACAACATTATCTGCT
AATTACAAAATATTATCTAAAAATAAAAAAATATAAAGAAGCTAATGATTTTTTAAAAAAAATA

TABLE 1-continued

Nucleotide and Amino Acid Sequences.

AACCAAAAAAAGATCAAAAATCAAAAAATAAAAAACGAAATCATTTCGCTAAAATTAAGAATA
AATGAAGATAATATTAATGAAGAAGAAATCAAAAAAATTTTAAATAACGAAAAAAATATAGAT
GTCAAAATAATTTATCAAATATTCAGTCTTATAAAATTTAAAAATAAAAAATTAGCAAATAAAA
TTAAAAACATAATACTAACAAACTATCCCAAAAGCATTTATTCTTATAAAATAAAAAGAAATGA
ATAA t29.nt (SEQ ID NO:284)
AATAATAAAGAAAATATAGAAAATTTAATAAAGCTACATATGCTTTATGATTTAACCAATAACC
TGTCAAAAGAATTAGAAACAATAAATAAAATTAAAAATTTTGACTTAGAACAACATTATCTGCT
AATTACAAAATATTATCTAAAAATAAAAAAATATAAAGAAGCTAATGATTTTTTAAAAAAAATA
AACCAAAAAAAGATCAAAAATCAAAAAATAAAAAACGAAATCATTTCGCTAAAATTAAGAATA
AATGAAGATAATATTAATGAAGAAGAAATCAAAAAAATTTTAAATAACGAAAAAAATATAGAT
GTCAAAATAATTTATCAAATATTCAGTCTTATAAAATTTAAAAATAAAAAATTAGCAAATAAAA
TTAAAAACATAATACTAACAAACTATCCCAAAAGCATTTATTCTTATAAAATAAAAAGAAATGA
ATAA f290.aa (SEQ ID NO:285)
MNSIYVIGKLLLTLFLIFFPFCYNLFAVNLAEINKLSEYAKSIVLIDFDTKRILYSKKPNLVFPPASLTKI
VTIYTALIEAEKRNIKLKSIVPISDSASYYNAPPNSSLMFLEKGQIVNFEEILKGLSVSSGNDSSIAIAEF
VVGNLNSFVNLMNINVLNLGLFNMHFVEPSGYSSENKITALDMAFFVKSYIEKFKFMLNIHSLKYFI
YPKSRNLGTALSSKFLNLKQRNANLLIYDYPYSDGIKTGYIKESGLNLVATAKKGERRLIAVVLGVE
KGINGFGEKMRSSIAKNLFEYGFNKYSKFPLIVKLKEKVYNGTVDTVALFSKEPFYYILTKDEFDKIN
ISYTVDKLVAPLSGDMPVGRAMIFLENEKIGDVALFSGKVKRLGFWQGLYKSFINLFSREY t290.aa (SEQ ID NO:286)
VNLAEINKLSEYAKSIVLIDFDTKRILYSKKPNLVFPPASLTKIVTIYTALIEAEKRNIKLKSIVPISDSA
SYYNAPPNSSLMFLEKGQIVNFEEILKGLSVSSGNDSSIAIAEFVVGNLNSFVNLMNINVLNLGLFNM
HFVEPSGYSSENKITALDMAFFVKSYIEKFKFMLNIHSLKYFIYPKSRNLGTALSSKFLNLKQRNANL
LIYDYPYSDGIKTGYIKESGLNLVATAKKGERRLIAVVLGVEKGINGFGEKMRSSIAKINLFEYGFNK
YSKFPLIVKLKEKVYNGTVDTVALFSKEPFYYILTKDEFDKINISYTVDKLVAPLSGDMPVGRAMIFL
NEKIGDVALFSGKVKRLGFWQGLYKSFINLFSREY f290.nt (SEQ ID NO:287)
ATGAATAGTATCTATGTTATTGGGAAATTGTTATTAACTTTATTTTTAATTTTTTTCCCGTTTTGT
TATAATCTTTTTGCAGTTAATTTAGCTGAGATTAATAAATTATCAGAGTATGCAAAGTCAATAG
TTTTAATAGATTTTGATACTAAGCGAATACTTTATTCTAAGAAGCCCAATTTGGTTTTTCCTCCA
GCATCTCTTACAAAGATTGTTACAATTTATACAGCTTTAATTGAAGCTGAAAAGCGAAATATAA
AATTAAAAAGCATAGTTCCTATTAGCGATTCTGCTTCATATTATAATGCACCCCCCAATTCTTCT
TTGATGTTTTAGAAAAAGGTCAAATTGTTAATTTTGAAGAGATTTTAAAAGGACTTTCAGTTT
CTTCGGGTAATGATTCTTCTATTGCAATTGCTGAGTTTGTAGTAGGCAATTTAAATAGCTTGTT
AATTTAATGAATATTAATGTTTTAAATTTAGGGCTTTTTAATATGCATTTTGTTGAACCTTCTGG
ATATAGCAGCGAGAATAAGATTACAGCACTAGATATGGCTTTTTTTGTGAAATCTTATATAGAA
AAGTTTAAATTTATGCTTAATATTCATTCTTTAAAGTATTTTATTTATCCAAAGAGTAGAAATTT
AGGAACTGCTTTGTCATCAAAATTTTTAAACTTAAAACAAAGAAATGCTAATTTATTAATATAT
GATTACCCTTATTCAGATGGCATTAAAACGGGATATATTAAGGAATCAGGCTTAAATCTTGTTG
CTACTGCTAAAAAGGGTGAGAAGATTAATAGCAGTTGTATTGGGGGTTGAAAAAGGAATTA
ATGGATTTGGAGAGAAAATGAGATCTTCGATTGCAAAAAATTTATTTGAATATGGATTTAATAA
ATATTCTAAATTTCCTTTAATAGTAAAATTAAAAGAAAAAGTCTATAATGGTACAGTGGATACA
GTTGCTCTTTTTTCTAAAGAGCCTTTTTATTATATTTTAACTAAAGATGAATTTGATAAAATTAA
TATAAGTTATACTGTTGATAAATTGGTTGCTCCACTTAGTGGGGATATGCCTGTTGGGAGGGCT
ATGATTTTTTTAGAAAATGAAAAAATAGGGGATGTTGCTTTGTTTAGTGGCAAGGTAAAAAGAT
TAGGGTTTTGGCAAGGTCTTATAAGAGTTTTATAAATCTTTTTTCAAGAGAGTATTAA t290.nt (SEQ ID NO:288)
GTTAATTTAGCTGAGATTAATAAATTATCAGAGTATGCAAAGTCAATAGTTTTAATAGATTTTG
ATACTAAGCGAATACTTTATTCTAAGAAGCCCAATTTGGTTTTTCCTCCAGCATCTCTTACAAAG
ATTGTTACAATTTATACAGCTTTAATTGAAGCTGAAAAGCGAAATATAAAATTAAAAAGCATAG
TTCCTATTAGCGATTCTGCTTCATATTATAATGCACCCCCCAATTCTTCTTTGATGTTTTTAGAA
AAAGGTCAAATTGTTAATTTTGAAGAGATTTTAAAAGGACTTTCAGTTTCTTCGGGTAATGATT
CTTCTATTGCAATTGCTGAGTTTGTAGTAGGCAATTTAAATAGCTTTGTTAATTTAATGAATATT
AATGTTTTAAATTTAGGGCTTTTTAATATGCATTTTGTTGAACCTTCTGGATATAGCAGCGAGAA
TAAGATTACAGCACTAGATATGGCTTTTTTTGTGAAATCTTATATAGAAAAGTTTAAATTTATGC
TTAATATTCATTCTTTAAAGTATTTTATTTATCCAAAGAGTAGAAATTTAGGAACTGCTTTGTCA
TCAAAATTTTTAAACTTAAAACAAAGAAATGCTAATTTATTAATATATGATTACCCTTATTCAGA
TGGCATTAAAACGGGATATATTAAGGAATCAGGCTTAAATCTTGCTACTGCTAAAAAGGGT
GAGAGAAGATTAATAGCAGTTGTATTGGGGGTTGAAAAAGGAATTAATGGATTTGGAGAGAAA
ATGAGATCTTCGATTGCAAAAAATTTATTTGAATATGGATTTAATAAATATTCTAAATTTCCTTT
AATAGTAAAATTAAAAGAAAAAGTCTATAATGGTACAGTGGATACAGTTGCTCTTTTTTCTAAA
GAGCCTTTTTATTATATTTTAACTAAAGATGAATTTGATAAAATTAATATAAGTTATACTGTTGA
TAAATTGGTTGCTCCACTTAGTGGGGATATGCCTGTTGGGAGGGCTATGATTTTTTTAGAAAAT
GAAAAAATAGGGGATGTTGCTTTGTTTAGTGGCAAGGTAAAAAGATTAGGGTTTTGGCAAGGT
CTTTATAAGAGTTTTATAAATCTTTTTTCAAGAGAGTATTAA f291.aa (SEQ ID NO:289)
MNSYDFITALVPIILIIIGLGIIKKPAYYVIPISLIATVAIVIFYKNLGIVNTSLAMLEGALMGIWPIATVII
AAIFTYKMSEDQKDIETIKNILSNVSSDRRIIVLLVAWGFGNFLEGVAGYGTAVAIPVSILIAMGFEPF
FACLICLIMNTSSTAYGSVGIPITSLAQATNLDVNIVSSEIAFQLILPTLTIPFVLILTGGGIKGLKGVF
LLTLLSGMSMAISQVFISKTLGPELPAILGSILSMTITIVYARFFGNKETTERQSKNTISLSKGIIACSPYI

TABLE 1-continued

Nucleotide and Amino Acid Sequences.

LIVTFIVLVSPLFNKIHEYLKTFQSTISIYPEANPLHFKWIISPGFLIILATTISYSIRGVPMLKQLKIFTLT
LKKMALSSFIIICIVAISRLMTHSGMIRDLANGISIITGKFGPLFSPLIGAIGTFLTGSDTVSNVLFGPLQT
QMAENIGANPYWLAAANTTGATGGKMISPQNITIATTYAGLIGQEGKLLSKTIIYALYYILATGLLVY
LV t291.aa (SEQ ID NO:290)
QKDIETIKNILSNVSSDRRIIVLLVAWGFGNFLEGVAGYGTAVAIPVSILIAMGFEPFFACLICLIMNTS
STAYGSVGIPITSLAQATNLDVNIVSSEIAFQLILPLTLTIPFVLVILTGGGIKGLKGVFLLTLLSGMSMAI
SQVFISKTLGPELPAILGSILSMTITIVYARFFGNKETTERQSKNTISLSKGIIACSPYILIVTFIVLVSPLF
NKIHEYLKTFQSTISIYPEANPLHFKWIISPGFLIILATTISYSIRGVPMLKQLKIFTLTLKKMALSSFIIIC
IVAISRLMTHSGMIRDLANGISIITGKFGPLFSPLIGAIGTFLTGSDTVSNVLFGPLQTQMAENIGANPY
WLAAANTTGATGGKMISPQNITIATTTAGLIGQEGKLLSKTIIYALYYILATGLLVYLV f291.nt (SEQ ID NO:291)
ATGAATTCTTATGATTTTATAACAGCTTTGGTACCAATAATCCTAATAATTATTGGACTTGGCAT
AATAAAAAAGCCAGCTTACTATGTAATACCCATATCATTAATAGCCACCGTTGCTATAGTTATA
TTTTTATAAAAACTTGGGAATAGTAAACACAAGTCTTGCAATGCTTGAGGGCGCCTTAATGGGGA
TATGGCCAATAGCAACTGTAATTATTGCTGCCATATTTACATACAAAATGTCAGAAGATCAAAA
AGATATAGAAACTATTAAAAATATTTTATCAAACGTATCTTCTGATAGAAGAATTATAGTATTA
CTAGTTGCATGGGGATTTGGAAATTTTTTAGAAGGAGTTGCTGGATATGGAACTGCTGTTGCAA
TTCCTGTATCAATATTAATAGCAATGGGATTTGAACCATTTTTTGCCTGCTTAATCTGTTTAATA
ATGAACACCTCATCAACCGCCTACGGATCTGTGGGAATCCCTATAACATCTTTAGCTCAAGCAA
CTAACTTGGATGTTAACATTGTTTTCATCTGAGATTGCATTCCAACTAATACTTCCAACCTTAACA
ATACCTTTTGTACTGGTAATTCTTACAGGAGGGGCATTAAAGGATTAAAAGGAGTATTCCTTC
TTACCTTACTCTCAGGAATGTCAATGGCAATATCTCAAGTATTTATATCAAAACTTTGGGTCCA
GAACTTCCTGCAATCCTTGGAAGCATTCTTTCTATGACAATAACAATAGTTTATGCAAGGTTTTT
TGGAAATAAAGAAACTACTGAGCGCCAAAGCAAAAACACAATATCCTTATCAAAGGAATTAT
TGCCTGCTCACCCTACATTTTAATAGTAACTTTTATAGTGCTTGTATCTCCTCTTTTTAACAAAA
TTCATGAATACCTAAAAACTTTTCAAAGCACTATTAGCATTTATCCAGAAGCAAATCCCTTACA
CTTTAAATGGATTATCTCTCCGGGCTTCTTGATTATACTTGCAACAACAATATCCTATTCAATAC
GGGGAGTTCCAATGTTAAAACAGCTAAAAATATTTACATTAACCTTGAAAAAAATGCATTATC
TTCCTTTATAATCATATGCATTGTTGCAATATCAAGATTAATGACACATAGTGGAATGATAAGA
GATCTTGCTAATGGAATCTCAATAATAACAGGTAAATTTGGACCATTATTTAGCCCACTAATTG
GAGCTATTGGGACATTTTTAACAGGAAGTGATACGGTTTCAAATGTTCTTTTTGGACCTTTACA
AACACAAATGGCAGAAAATATTGGAGCAAATCCTTACTGGCTTGCAGCAGCAAATACAACAGG
AGCAACTGGAGGGAAAATGATTTCTCCCCAAAACATCACAATAGCAACAACAACTGCTGGATT
AATTGGACAAGAAGGCAAGCTTTTATCAAAAACAATAATTTATGCTTTATACTACATTTTAGCA
ACAGGATTGCTAGTTTATTTAGTATAA t291.nt (SEQ ID NO:292)
CAAAAAGATATAGAAACTATTAAAAATATTTTATCAAACGTATCTTCTGATAGAAGAATTATAG
TATTACTAGTTGCATGGGGATTTGGAAATTTTTTAGAAGGAGTTGCTGGATATGGAACTGCTGT
TGCAATTCCTGTATCAATATTAATAGCAATGGGATTTGAACCATTTTTTGCCTGCTTAATCTGTT
TAATAATGAACACCTCATCAACCGCCTACGGATCTGTGGGAATCCCTATAACATCTTTAGCTCA
AGCAACTAACTTGGATGTTAACATTGTTTCATCTGAGATTGCATTCCAACTAATACTTCCAACCT
TAACAATACCTTTTGTACTGGTAATTCTTACAGGAGGGGCATTAAAGGATTAAAAGGAGTATT
CCTTCTTACCTTACTCTCAGGAATGTCAATGGCAATATCTCAAGTATTTATATCAAAAACTTTGG
GTCCAGAACTTCCTGCAATCCTTGGAAGCATTCTTTCTATGACAATAACAATAGTTTATGCAAG
GTTTTTTGGAAATAAAGAAACTACTGAGCGCCAAAGCAAAAACACAATATCCTTATCAAAGG
AATTATTGCCTGCTCACCCTACATTTTAATAGTAACTTTTATAGTGCTTGTATCTCCTCTTTTTAA
CAAAATTCATGAATACCTAAAAACTTTTCAAAGCACTATTAGCATTTATCCAGAAGCAAATCCC
TTACACTTTAAATGGATTATCTCTCCGGGCTTCTTGATTATACTTGCAACAACAATATCCTATTC
AATACGGGGAGTTCCAATGTTAAAACAGCTAAAAATATTTACATTAACCTTGAAAAAAATGGCA
TTATCTTCCTTTATAATCATATGCATTGTTGCAATATCAAGATTAATGACACATAGTGGAATGAT
AAGAGATCTTGCTAATGGAATCTCAATAATAACAGGTAAATTTGGACCATTATTTAGCCCACTA
ATTGGAGCTATTGGGACATTTTTAACAGGAAGTGATACGGTTTCAAATGTTCTTTTTGGACCTTT
ACAAACACAAATGGCAGAAAATATTGGAGCAAATCCTTACTGGCTTGCAGCAGCAAATACAAC
AGGAGCAACTGGAGGGAAAATGATTCTCCCCAAAACATCACAATAGCAACAACAACTGCTGGA
TTAATTGGACAAG f296.aa (SEQ ID NO:293)
MPSPIRVFFLVLLFIFIFNPVLIAMLFILFPFILILFSFLGVFRIYFTRDYSYSRSREFEFYKLSFLLMAKLL
SILGTVTGEQLNYVNFIINSLNLSERGKSELYTIFHSAITKNNNADKILYTLKLGYFQHKDLFIWLFAT
LKEINRLSRYKNLEAEKFISYVGVFLELESDGYEAYKDINIKIVNPYSVLGLTYSASDDEVKKAYKSL
VIKYHPDKFANDPVRQKDANDKFIKIQDAYEKICKERNIR t296.aa (SEQ ID NO:294)
IYFTRDYSYSRSREFEFYLLSFKLMAKLLSILGTVTGEQLNYVNFIINSLNLSERGKSELYTIFHSAITK
NNNADKILYTLKLGYFQHKDLFIWLFATLKEINRLSRYKNLEAEKFISYVGVFLELESDGYEAYKDI
NIKIVNPYSVLGLTYSASDDEVKKAYKSLVIKYHPDKFANDPVRQKDANDKFIKIQDAYEKICKEPN
IR f296.nt (SEQ ID NO:295)
ATGCCAAGCCCAATTAGAGTGTTTTTTTTAGTGTTGTTGTTTATTTTTATTTTTAATCCCGTTTTA
ATAGCAATGCTTTTTATTTTATTTCCTTTTATTTTGATATTATTTAGTTTTTTAGGTGTTTTTAGA
ATATACTTTACAAGGGATTACTCATATTCTAGATCTAGAGAGTTTGAATTTTATAAACTTTCTTT
TTTATTAATGGCTAAATTGCTATCTATTTTAGGAACTGTAACTGGGGAGCAGCTAAATTATGTC

TABLE 1-continued

Nucleotide and Amino Acid Sequences.

AATTTTATTATCAATTCTTTGAATTTGTCTGAACGTGGTAAATCAGAATTGTATACCATTTTTCA
TTCTGCTATTACTAAAAATAATAATGCTGATAAAATTTTATATACCCTTAAGCTTGGTTATTTTC
AGCACAAAGATCTTTTTATATGGCTTTTTGCCACTCTTAAAGAAATTAACAGGCTCTAGGTAT
AAAAATTTAGAAGCTGAAAAATTTATTTCTTATGTTGGTGTTTTTTTAGAACTTGAATCTGATGG
TTATGAAGCTTATAAAGATATTAATATTAAAATTGTAAATCCTTATAGTGTTTTGGGGTTAACA
TATAGTGCTAGCGATGATGAGGTTAAAAAGGCGTATAAAAGCCTTGTTATAAATATCATCCTG
ATAAGTTTGCAAATGATCCTGTAAGACAAAAAGATGCAAATGATAAATTTATAAAAATTCAAG
ATGCTTATGAAAAAATTTGCAAGGAAAGAAATATAAGGTAA t296.nt (SEQ ID NO:296)
ATATACTTTACAAGGGATTACTCATATTCTAGATCTAGAGAGTTTGAATTTTATAAACT
TTCTTTTTTATTAATGGCTAAATTGCTATCTATTTTAGGAACTGTAACTGGGGAGCAGCTAAATT
ATGTCAATTTTATTATCAATTCTTTGAATTTGTCTGAACGTGGTAAATCAGAATTGTATACCATT
TTTCATTCTGCTATTACTAAAAATAATAATGCTGATAAAATTTTATATACCCTTAAGCTTGGTTA
TTTTCAGCACAAAGATCTTTTTATATGGCTTTTTGCCACTCTTAAAGAAATTAACAGGCTTTCTA
GGTATAAAAATTTAGAAGCTGAAAAATTTATTTCTTATGTTGGTGTTTTTTTAGAACTTGAATCT
GATGGTTATGAAGCTTATAAAGATATTAATATTAAAATTGTAAATCCTTATAGTGTTTTGGGGT
TAACATATAGTGCTAGCGATGATGAGGTTAAAAAGGCGTATAAAAGCCTTGTTATAAATATCA
TCCTGATAAGTTTGCAAATGATCCTGTAAGACAAAAAGATGCAAATGATAAATTTATAAAAATT
CAAGATGCTTATGAAAAAATTTGCAAGGAAAGAAATATAAGGTAA f3.aa (SEQ ID NO:297)
MKKKNLSIYMIMLISLLSCNTSDPNELTRKKMQDKNVKILGFLEKIQADNKEIVEKHIEKKEKQMVQ
AASVAPINVESNFPYYLQEEIEIKEEELVPNTDEEKKAEKAISDGSLEFAKLVDDENKLKNESAQLES
SFNNVYKEILELADLIQAEVHVAGRINSYIKKRKTTKEKEYKKREIKNKIEKQALIKLFNQLLEKRGD
IENLHTQLNSGLSERASAKYFFEKAKETLKAAITERLNNKRKNRPWWARRTHSNLAIQAKNEAEDA
LNQLSTSSFRILEAMKIKEDVKQLLEEVKSFLDSSKSKIFSSGDRLYDFLETSK t3.aa (SEQ ID NO:298)
NELTRKKMQDKNVKILGFLEKIQADNKEIVEKHIEKKEKQMVQAASVAPINVESNFPYYLQEEIEIK
EEELVPNTDEEKKAEKAISDGSLEFAKLVDDENKLKNESAQLESSFNNVYKEILELADLIQAEVHVA
GRINSYIKKRKTTKEKEYKKREIKNKIEKQALIKLFNQLLEKRGDIENLHTQLNSGLSERASAKYFFE
KAKETLKAAITERLNNKRKNRPWWARRTRSNLAIQAKNEAEDALNQLSTSSFRILEAMKIKEDVKQ
LLEEVKSFLDSSKSKIFSSGDRLYDFLETSK f3.nt (SEQ ID NO:299)
ATGAAAAAAAAAAATTTATCAATTTACATGATAATGCTAATAAGTTTATTATCATGTAATACAA
GTGACCCCAATGAATTAACTCGTAAAAAAATGCAAGACAAGAACGTGAAAATTTTAGGATTTTT
AGAGAAAATTCAAGCAGATAATAAAGAAATTGTTGAAAAACATATAGAAAAAAAAGAAAAAC
AAATGGTGCAGGCTGCTTCTGTAGCACCTATTAATGTAGAGAGTAATTTCCCATATTATCTTCA
AGAAGAAATAGAGATAAAAGAAGAAGAGTTGGTTCCAAATACTGATGAAGAAAAGAAGGCAG
AGAAGGCAATTAGCGATGGGAGTCTTGAATTTGCTAAATTAGTTGATGATGAAAATAAACTTAA
AAATGAATCTGCGCAATTAGAATCTAGTTTTAATAATGTTTATAAAGAAATCTTAGAACTTGCA
GATTTAATACAAGCAGAGGTGCATGTTGCAGGAAGGATAAATAGCTATATAAAAAAAAGAAAG
ACCACTAAAGAAAAGAATATAAGAAGAGAGAAATTAAGAATAAGATAGAAAACAGGCTCT
AATTAAGTTGTTCAATCAGTTATTAGAAAAAGAGGCGATATTGAAAATCTTCATACTCAATTA
AATAGTGGACTTAGCGAGAGAGCATCTGCAAAATACTTTTTTGAGAAAGCCAAAGAAACTTTA
AAAGCTGCTATTACTGAAAGATTAAATAACAAACGTAAAAATCGGCCATGGTGGGCAAGAAGA
ACACATAGTAATTTAGCAATACAGGCAAAAAATGAGGCAGAGGATGCTTTAAACCAATTAAGT
ACTTCTTCTTTTAGGATACTTGAAGCAATGAAAATAAAGGAAGATGTAAAACAGCTTCTTGAAG
AAGTAAAATCTTTTCTAGATTCTTCAAAGAGCAAAATCTTTTCTAGTGGCGATAGATTATATGA
TTTTTTAGAGACGAGTAAATAA t3.nt (SEQ ID NO:300)
AATGAATTAACTCGTAAAAAAATGCAAGACAAGAACGTGAAAATTTTAGGATTTTTAGAGAAA
ATTCAAGCAGATAATAAAGAAATTGTTGAAAACATATAGAAAAAAAAGAAAAACAAATGGTG
CAGGCTGCTTCTGTAGCACCTATTAATGTAGAGAGTAATTTCCCATATTATCTTCAAGAAGAAA
TAGAGATAAAAGAAGAAGAGTTGGTTCCAAATACTGATGAAGAAAAGAAGGCAGAGAAGGCA
ATTAGCGATGGGAGTCTTGAATTTGCTAAATTAGTTGATGATGAAAATAAACTTAAAAATGAAT
CTGCGCAATTAGAATCTAGTTTTAATAATGTTTATAAAGAAATCTTAGAACTTGCAGATTTAAT
ACAAGCAGAGGTGCATGTTGCAGGAAGGATAAATAGCTATATAAAAAAAAGAAAGACCACTAA
AGAAAAAGAATATAAGAAGAGAGAAATTAAGAATAAGATAGAAAACAGGCTCTAATTAAGTT
GTTCAATCAGTTATTAGAAAAAGAGGCGATATTGAAAATCTTCATACTCAATTAAATAGTGGA
CTTAGCGAGAGAGCATCTGCAAAATACTTTTTTGAGAAAGCCAAAGAAACTTTAAAAGCTGCTA
TTACTGAAAGATTAAATAACAAACGTAAAAATCGGCCATGGTGGGCAAGAAGAACACATAGTA
ATTTAGCAATACAGGCAAAAAATGAGGCAGAGGATGCTTTAAACCAATTAAGTACTTCTTCTTT
TAGGATACTTGAAGCAATGAAAATAAAGGAAGATGTAAAACAGCTTCTTGAAGAAGTAAAATC
TTTTCTAGATTCTTCAAAGAGCAAAATCTTTTCTAGTGGCGATAGATTATATGATTTTTTAGAGA
CGAGTAAATAA f30.aa (SEQ ID NO:301)
MNKKILTLLVLILSISSVLMLSKSITKKSKYKIIRDYFINSNYVLVKIENKDLKFTISKPIYDKKLNNYF
FKGQTTSHFLISNNVDIAINTSPYEVKQNMFFPKGLYIYNKKMISKQINNYGEIVIKHNKIILNPKEDEI
ENCDYGFSGFFVLIKNGKYKKNFKETRHPRTIIGTDKNNKHLFLVTIEGRGVNNSKGASLNEAIDFA
LSYGMTNAINLDGGGSSTLVVKSNNAPYKLNFTANIFGQERPVPFHLGIKLPN t30.aa (SEQ ID NO:302)
LSKSITKKSKYKIIRDYFINSNYVLVKIENKDLKFTISKPIYDKKLNNYFFKGQTTSHFLISNNVDIAIN

TABLE 1-continued

Nucleotide and Amino Acid Sequences.

TSPYEVKQNMFFPKGLYIYNKKMISKQINNYGEIVIKHNKIILNPKEDEIENCDYGFSGFFVLIKNGK
YKKNFKETRHPRTIIGTDKNNKHLFLVTIEGRGVNNSKGASLNEAIDFALSYGMTNAINLDGGGSST
LVVKSNNAPYKLNFTANIFGQERPVPFHLGIKLPN f30.nt (SEQ ID NO:303)
ATGAATAAAAAAATATTAACACTGCTAGTATTGATTTTAAGTATTTCATCAGTACTAAT
GCTGTCCAAATCAATCACCAAAAAATCCAAATACAAAATTATTAGGGATTATTTCATAAACAGC
AATTATGTTCTGGTGAAAATTGAAAATAAAGATCTAAAATTTACCATATCAAAACCTATTTACG
ACAAAAAGCTAAATAATTACTTCTTTAAAGGCCAAACAACAAGCCATTTCTTAATTTCTAACAA
TGTTGACATTGCAATTAACACAAGTCCATACGAAGTTAAACAAAACATGTTTTTCCCAAAAGGA
CTATACATATATAATAAAAAAATGATTTCAAAACAAATAAATAACTACGGAGAGATTGTAATAA
AGCACAACAAAATTATATTAAATCCCAAGGAAGACGAAATAGAAAACTGCGATTATGGATTTA
GCGGATTTTTTGTTTTAATCAAAAACGGAAAGTATAAAAAAAATTTTAAAGAAACAAGGCACCC
AAGAACAATAATAGGAACTGATAAAAATAACAAGCATTTATTTCTTGTTACAATAGAAGGAAG
GGGTGTCAATAATAGCAAAGGGGCCTCTCTTAATGAAGCTATTGATTTTGCATTAAGCTACGGC
ATGACTAACGCTATTAATCTAGACGGGGGGGGCTCAAGCACTCTTGTTGTAAAATCAAATAACG
CTCCTTACAAATTAAACTTCACAGCAAACATCTTTGGACAGGAAAGACCTGTCCCATTTCATTT
AGGAATAAAACTTCCTAATTGA t30.nt (SEQ ID NO:304)
CTGTCCAAATCAATCACCAAAAAATCCAAATACAAAATTATTAGGGATTATTTCATAAACAGCA
ATTATGTTCTGGTGAAAATTGAAAATAAAGATCTAAAATTTACCATATCAAAACCTATTTACGA
CAAAAAGCTAAATAATTACTTCTTTAAAGGCCAAACAACAAGCCATTTCTTAATTTCTAACAAT
GTTGACATTGCAATTAACACAAGTCCATACGAAGTTAAACAAAACATGTTTTTCCCAAAAGGAC
TATACATATATAATAAAAAAATGATTTCAAAACAAATAAATAACTACGGAGAGATTGTAATAA
AGCACAACAAAATTATATTAAATCCCAAGGAAGACGAAATAGAAAACTGCGATTATGGATTTA
GCGGATTTTTTGTTTTAATCAAAAACGGAAAGTATAAAAAAAATTTTAAAGAAACAAGGCACCC
AAGAACAATAATAGGAACTGATAAAAATAACAAGCATTTATTTCTTGTTACAATAGAAGGAAG
GGGTGTCAATAATAGCAAAGGGGCCTCTCTTAATGAAGCTATTGATTTTGCATTAAGCTACGGC
ATGACTAACGCTATTAATCTAGACGGGGGGGGCTCAAGCACTCTTGTTGTAAAATCAAATAACG
CTCCTTACAAATTAAACTTCACAGCAAACATCTTTGGACAGGAAAGACCTGTCCCATTTCATTT
AGGAATAAAACTTCCTAATTGA f308.aa (SEQ ID NO:305)
MQLLKNKYPFKRALLDLFLVYAIVYLASPFVNVNSEFWNVDENHFYFWISRSFLIIFIIYFFK
LTSSYDDFRVEFFIPKFKFIFLWDSVLIFIKTILIAMIVIFLIAFLLEYLLPESVLVYYFQNNAGFNWKISS
KKAFFLMTFTSFFTGAFEELFYRAFVITKFTQMGFPVVATAILSSMFFAYGHLYYGILGFLVTFILGIF
FAFTYLRYKNVYYVIFIHSFYNIIVSSLLLFLN t308.aa (SEQ ID NO:306)
NSEFWNVDENHFYFWISRSFLIIFIIYFFKLTSSYDDFRVEFFIPKFKFIFLWDSVLIFIKTILIAMIVIFLI
AFLLEYLLPESVLVYYFQNNAGFNWKISSKKAFFLMTFTSFFTGAFEELFYRAFVITKFTQMGFPVV
ATAILSSMFFAYGHLYYGILGFLVTFILGIFFAFTYLRYKNVYYVIFIHSFYNIIVSSLLLFLN f308.nt (SEQ ID NO:307)
ATGCAATTGTTAAAAAATAAATATCCATTCAAGCGGGCTTTGCTTGATCTTTTTTTGGTCTATGC
TATTGTTTATTTGGCATCTCCTTTTGTAAATGTTAATTCAGAATTTTGGAATGTTGATGAAAATC
ATTTTTATTTTTGGATTTCAAGATCTTTTTTAATTATTTTTATAATTTATTTTTTTAAACTTACCA
GTTCTTATGATGATTTTAGAGTAGAGTTTTTTATTCCTAAATTTAAATTTATTTTTCTTTGGGATT
CTGTTTTAATTTTTATTAAAACAATATTGATTGCAATGATAGTCATTTTTTTAATAGCTTTTTTGC
TTGAATATTTGTTGCCAGAATCGGTACTTGTCTATTATTTTCAAAACAATGCTGGATTTAATTGG
AAGATTAGCAGTAAAAAAGCATTTTTTTTAATGACTTTTTACCTCTTTTTTTTACAGGAGCTTTTGA
AGAACTTTTTTACAGGGCTTTTGTTATTACTAAGTTTACACAAATGGGATTTCCTGTTGTAGCTA
CCGCCATTCTTAGTAGTATGTTTTTTGCTTATGGGCATTTATATTATGGAATTTTAGGATTTTTG
GTTACATTTATATTAGGGATATTTTTTGCTTTTACTTATTTAAGGTATAAAAATGTATATTATGT
GATTTTTTATACAGTTTTTATAATATTATTGTTAGCAGCTTGTTGCTTTTTTTGAATTAA t308.nt (SEQ ID NO:308)
AATTCAGAATTTTGGAATGTTGATGAAAATCATTTTTATTTTTGGATTTCAAGATCTTTT
TTAATTATTTTTATAATTTATTTTTTTAAACTTACCAGTTCTTATGATGATTTTAGAGTAGAGTTT
TTTATTCCTAAATTTAAATTTATTTTTCTTTGGGATTCTGTTTTAATTTTTATTAAAACAATATTG
ATTGCAATGATAGTCATTTTTTTAATAGCTTTTTTGCTTGAATATTTGTTGCCAGAATCGGTACT
TGTCTATTATTTTCAAAACAATGCTGGATTTAATTGGAAGATTAGCAGTAAAAAAGCATTTTTTT
TAATGACTTTTTACCTCTTTTTTTACAGGAGCTTTTGAAGAACTTTTTTACAGGGCTTTTGTTATT
ACTAAGTTTACACAAATGGGATTTCCTGTTGTAGCTACCGCCATTCTTAGTAGTATGTTTTTTGC
TTATGGGCATTTATATTATGGAATTTTAGGATTTTTGGTTACATTTATATTAGGGATATTTTTTG
CTTTTACTTATTTAAGGTATAAAAATGTATATTATGTGATTTTTTATACAGTTTTTATAATATT
ATTGTTAGCAGCTTGTTGCTTTTTTTGAATTAA f31.aa (SEQ ID NO:309)
MKKYLFFILFLISSNNLIVSYPLSFGGGFSYQFTNYTDKTGATKFAPNFTRADHGINLNLFFDANYVL
FEMSYKEAFVVTHNGRYFSLGLYGTYPMVFKEQVRMLFPLIGFKYAFDLSSNNFNLFFLSMGLAAD
LFIPDLDGLYIRPLFMLSISPFSNYKNFSGLTTEIMLGFNIGWRFFN t31.aa (SEQ ID NO:310)
IVSYPLSFGGGFSYQFTNYTDKTGATKFAPNFTRADHGINLNLFFDANYVLFEMSYKEAFVVTHNG
RYFSLGLYGTYPMVFKEQVRMLFPLIGFKYAFDLSSNNFNLFFLSMGLAADLFIPDLDGLYIRPLFML

TABLE 1-continued

Nucleotide and Amino Acid Sequences.

SISPFSNYKNFSGLTTEIMLGFNIGWRFFN f31.nt (SEQ ID NO:311)
ATGAAGAAATATCTTTTTTTTATTTTATTTCTCATCTCTTCTAATAATTTAATTGTTTCTTATCCA
CTTTCTTTTGGTGGAGGTTTTTCTTATCAATTTACTAATTATACTGATAAAACAGGCGCCACTAA
ATTTGCTCCAAATTTTACCAGAGCAGATCATGGGATTAATTTGAATTTATTTTTTGATGCAAATT
ATGTACTTTTTGAAATGTCTTACAAAGAGGCTTTTGTTGTTACTCACAATGGGAGATATTTCTCG
CTTGGGCTTTATGGAACATATCCAATGGTTTTCAAAGAGCAGGTTAGAATGCTTTTCCCATTAA
TTGGGTTTAAATATGCTTTTGATTTAAGCTCTAATAACTTCAATCTCTTTTTTTTAAGCATGGGG
CTTGCTGCTGATCTTTTTATTCCCGATCTTGATGGTTTATATATTAGGCCTTTGTTTATGCTTTCT
ATTTCTCCATTTTCTAATTATAAAAATTTTTCTGGGTTAACAACTGAGATTATGCTTGGATTTAA
TATCGGTTGGAGATTTTTCAATTAG t31.nt (SEQ ID NO:312)
ATTGTTTCTTATCCACTTTCTTTTGGTGGAGGTTTTTCTTATCAATTTACTAATTATACTGATAAA
ACAGGCGCCACTAAATTTGCTCCAAATTTTACCAGAGCAGATCATGGGATTAATTTGAATTTAT
TTTTTGATGCAAATTATGTACTTTTGAAATGTCTTACAAAGAGGCTTTTGTTGTTACTCACAAT
GGGAGATATTTCTCGCTTGGGCTTTATGGAACATATCCAATGGTTTCAAAGAGCAGGTTAGAA
TGCTTTTCCCATTAATTGGGTTTAAATATGCTTTTGATTTAAGCTCTAATAACTTCAATCTCTTTT
TTTTAAGCATGGGGCTTGCTGCTGATCTTTTTATTCCCGATCTTGATGGTTTATATATTAGGCCT
TTGTTTATGCTTTCTATTTCTCCATTTTCTAATTATAAAAATTTTTCTGGGTTAACAACTGAGATT
ATGCTTGGATTTAATATCGGTTGGAGATTTTTCAATTAG f939.aa (SEQ ID NO:313)
MKQKYENYFKKRLILNLLIFLLLACSSESIFSQLGNLQKIKHEYNILGSSSPRGISLVGETLYIAAMHLF
KKENGKIEKIDLSNSYEFINDIVNISGKTYLLAQNKEEELEVCELNGKDWTLKFKKPLKAYKFLKSV
GRDGVKEAYILAIDKNNREKIFDLQGSDKTPPQATENDKFYQISNEENLITGNSLKIWQMNNNTYTN
IDYQQAKEIMPIIKTSIRGSSEVLVMTGGYNNLDTKFKVYSNTNNYTTPIFIQDEVGEFSSYFAREFND
AILIGSNNGFAEFTKNKEGIFALRAPSKSVEPGAYNGSQLSKTGLNDIIPVSNNTIYILTQGKGLWKLE
NRKLTKE f939.aa (SEQ ID NO:314)
CSSESIFSQLGNLQKIKHEYNILGSSSPRGISLVGETLYIAAMHLFKKENGKIEKIDLSNSYEFINDIVNI
SGKTYLLAQNKEEELEVCELNGKDWTLKFKKPLKAYKFLKSVGRDGVKEAYILAIDKNNREKTIDL
QGSDKTPPQATENDKFYQISNEENLITGNSLKIWQMNNNTYTNIDYQQAKEIMPIIKTSIRGSSEVLV
MTGGYNNLDTKFKVYSNTNNYTTPIFIQDEVGEFSSYFAREFNDAILIGSNNGFAEFTKNKEGIFALR
APSKSVEPGAYNGSQLSKTGLNDIIPVSNNTIYILTQGKGLWKLENR
KLTKE f939.nt (SEQ ID NO:315)
ATGAAACAAAAATACGAAAACTATTTTAAAAAAAGATTAATTTTAAACCTATTAATATTTTTAC
TACTAGCATGCTCAAGCGAATCCATATTTTCACAATTAGGAAATCTGCAAAAAATAAAACATGA
ATACAATATTTTGGGCAGTTCAAGTCCAAGAGGAATTTCTCTAGTAGGAGAAACTCTCTACATT
GCAGCCATGCATTTATTTAAAAAAGAAAACGGCAAGATTGAAAAAATTGATTTGAGCAATTCTT
ATGAGTTTATAAACGACATTGTAAATATATCTGGAAAAACCTATCTTTTAGCGCAAAACAAAGA
AGAAGAATTAGAAGTTTGCGAGCTAAATGGAAAAGATTGGACATTAAAATTTAAAAAACCGCT
AAAAGCATATAAATTCTTAAAATCCGTAGGAAGAGATGGCGTAAAAGAAGCATATATTTTAGC
TATAGATAAAAATAATCGTGAGAAAATTTTTGATCTACAAGGATCTGACAAAACACCACCACAA
GCTACTGAAAATGACAAATTTTATCAAATATCAAATGAAGAAAACTTAATTACAGGAAATTCAC
TCAAAATATGGCAAATGAATAACAATACATACACAAACATAGACTATCAACAGGCCAAAGAAA
TAATGCCTATCATTAAAACAAGCATTAGGGGCTCTTCTGAAGTTTTAGTAATGACTGGTGGTTA
CAATAATTTAGATACAAAATTTAAAGTTTACTCAAATACAAATAATTACACAACGCCAATATTT
ATTCAAGACGAAGTAGGCGAATTTAGCAGCTACTTTGCAAGAGAATTTAATGATGCGATATTAA
TCGGAAGTAATAATGGATTTGCAGAATTTACAAAAAATAAAGAAGGAATTTTTGCCCTACGGGC
ACCCTCAAAATCTGTAGAACCTGGAGCTTATAACGGATCTCAGCTAAGCAAAACAGGCCTTAAT
GATATTATTCCTGTATCAAACAACACGATTTACATATTAACTCAGGGCAAGGGTTTGTGGAAAT
TGGAAAACAGAAAATTAACTAAAGAATAA t939.nt (SEQ ID NO:316)
TGCTCAAGCGAATCCATATTTTCACAATTAGGAAATCTGCAAAAAATAAAACATGAATACAATA
TTTTGGGCAGTTCAAGTCCAAGAGGAATTTCTCTAGTAGGAGAAACTCTCTACATTGCAGCCAT
GCATTTATTTAAAAAAGAAAACGGCAAGATTGAAAAAATTGATTTGAGCAATTCTTATGAGTTT
ATAAACGACATTGTAAATATATCTGGAAAAACCTATCTTTTAGCGCAAAACAAAGAAGAAGAA
TTAGAAGTTTGCGAGCTAAATGGAAAAGATTGGACATTAAAATTTAAAAAACCGCTAAAAGCA
TATAAATTCTTAAAATCCGTAGGAAGAGATGGCGTAAAAGAAGCATATATTTTAGCTATAGATA
AAAATAATCGTGAGAAAATTTTTGATCTACAAGGATCTGACAAAACACCACCACAAGCTACTGA
AAATGACAAATTTTATCAAATATCAAATGAAGAAACTTAATTACAGGAAATTCACTCAAAATA
TGGCAAATGAATAACAATACATACACAAACATAGACTATCAACAGGCCAAAGAAATAATGCCT
ATCATTAAAACAAGCATTAGGGGCTCTTCTGAAGTTTTAGTAATGACTGGTGGTTACAATAATT
TAGATACAAAATTTAAAGTTTACTCAAATACAAATAATTACACAACGCCAATATTTATTCAAGA
CGAAGTAGGCGAATTTAGCAGCTACTTTGCAAGAGAATTTAATGATGCGATATTAATCGGAAGT
AATAATGGATTTGCAGAATTTACAAAAAATAAAGAAGGAATTTTTGCCCTACGGGCACCCTCAA
AATCTGTAGAACCTGGAGCTTATAACGGATCTCAGCTAAGCAAAACAGGCCTTAATGATATTAT
TCCTGTATCAAACAACACGATTTACATATTAACTCAGGGCAAGGGTTTGTGGAAATTGGAAAAC
AGAAAATTAACTAAAGAATAA f739.aa (SEQ ID NO:317)

TABLE 1-continued

Nucleotide and Amino Acid Sequences.

MQSGLKIKLILFFCCFACSCDINYPEIKELDYKINYYFTENRLDYSMSFDFAIKVINSKDVFK
LSIENKNTNEFIQVINNNYSSFFIDSSLGKDILYCKDLRFNFFDKTFEDFTSCVRLFDKGMRVYNRELV
ISLGMSKYDLDDVHNYVYKSKDMEMLNKLSNSKVFFVKTYKDKLHPVSSVVRIDSIDILEIDKAFD
NYISFYYVEKNSNLFFKVG t739.aa (SEQ ID NO:318)
CCFACSCDINYPEIKELDYKINYYFTENRLDYSMSFDFAIKVINSKDVFKLSIENKNTNEFIQVINNNY
SSFFIDSSLGKDILYCKDLRFNFFDKTFEDFTSCVRLFDKGMRVYNRELVISLGMSKYDLDDVHNYV
YKSKDMEMLNKLSNSKVFFVKTYKDKLHPVSSVVRIDSIDILEIDKAFDNYISFYYVEKNSNLFFKV
G f739.nt (SEQ ID NO:319)
ATGCAGAGCGGATTAAAAATTAAATTAATATTGTTTTTTTGTTGTTTTGCTTGTTCTTGCGACAT
AAATTATCCGGAGATAAAAGAGCTTGATTATAAGATAAATTATTATTTTACTGAAAATCGCTTA
GATTACTCTATGAGTTTTGATTTTGCAATTAAAGTTATAAATTCAAAAGATGTTTTTAAATTATC
AATAGAGAATAAGAACACTAATGAGTTTATTCAAGTGATTAATAATAATTATAGCTCTTTTTTT
ATTGATTCTAGCCTTGGAAAGGATATTCTATATTGTAAGGATTTGAGGTTTAATTTTTTTGATAA
AACTTTTGAAGATTTTACCTCATGTGTTCGTCTTTTTGATAAGGGCATGAGAGTATACAATAGA
GAGCTTGTTATTTCTTTGGGTATGTCAAAATATGATTTAGATGATGTTCACAATTATGTATATAA
GTCTAAAGATATGGAAATGTTAAACAAGTTAAGCAATTCCAAAGTATTTTTTGTTAAAACTTAT
AAAGACAAACTACATCCGGTCTCTTCAGTTGTTAGAATTGATTCAATAGATATTCTAGAGATTG
ATAAAGCATTTGATAATTACATAAGTTTTTATTATGTCGAAAAAAATTCAAATCTTTTTTTTAAA
GTTGGCTGA t739.nt (SEQ ID NO:320)
TGTTGTTTTGCTTGTTCTTGCGACATAAATTATCCGGAGATAAAAGAGCTTGATTATAAGATAA
ATTATTATTTTACTGAAAATCGCTTAGATTACTCTATGAGTTTTGATTTTGCAATTAAAGTTATA
AATTCAAAAGATGTTTTTAAATTATCAATAGAGAATAAGAACACTAATGAGTTTATTCAAGTGA
TTAATAATAATTATAGCTCTTTTTTTATTGATTCTAGCCTTGGAAAGGATATTCTATATTGTAAG
GATTTGAGGTTTAATTTTTTTGATAAAACTTTTGAAGATTTTACCTCATGTGTTCGTCTTTTTGA
AAMGGGCATGAGAGTATACAATAGAGAGCTTGTTATTTCTTTGGGTATGTCAAAATATGATTTA
GATGATGTTCACAATTATGTATATAAGTCTAAAGATATGGAAATGTTAAACAAGTTAAGCAATT
CCAAAGTATTTTTTGTTAAAACTTATAAAGACAAACTACATCCGGTCTCTTCAGTTGTTAGAATT
GATTCAATAGATATTCTAGAGATTGATAAAGCATTTGATAATTACATAAGTTTTTATTATGTCG
AAAAAAATTCAAATCTTTTTTTTAAAGTTGGCTGA f742.aa (SEQ ID NO:321)
MNKKHTNFSVLLLLIFLLILSFGGFGYYIYQSKLNDKNREIMLNEVKNSVIDRNYKKAYSVA
KLLQDKYPQNEDIAMLTNTLAEIANSSPFESKDLQRDSANQILDKIKGQDNTKTNVNENFDIAFNNR
YIKDSTITENYSDRNDDVGIEDEDISEFKKSKIPEKIKPNTNPKEEDQIIQSPNPKLSVNDQKNLFNLEK
LKKNLSGKSNSENILNDSQKIENDKQNTNLSKEKNSENILKTPDNSKYSNNNNTTSLKKISSNSQKES
ELSPPSQTIIGKIYRPYSYLIKKELYEILDDINTGRVTLGKNRLKELIKKGLSNKFQKVNELIENSKNKE
ASNLLLTLIKKDIEPNLINIPKDPYKKEIFQLDKEDKKPQYLEDLKSKVHSIKPIDLENTKSRQQAIKD
LNEFLKNNPNDAQASKTLAQANKIQHLEDLKSKVHSIKPIDLENTKSRQQAIKDLNEFLKNNPNDAQ
ASKTLAQANKIQHLEDLKSKVHSIKPIDLENTKSRQQAIKDLNEFLKNNPNDAQASKTLAQANKIQH
LEDLKSKVHSIKPIDLENTKSRQQAIKDLNEFXKNNPNDAQASKTLAQANKIQHLEDLKSKVHSIKPI
DLENTKSRQQAIKDLNEFXKNNPNDAQASKTLAQANKIQHLEDLKSKVHSIKPIDLENTKSRQQAIK
DLNEFLKNNPNDAQASKTLAQANKIQHLEDLKSKVHSIKPIDLENTKSRQQAIKDLNEFXKNNPNDA
QASKTLAQAYENNGDLLKAENAYEKIIKLTNTQEDHYKLGIIRFKLKKYEHSIESFDQTIKLDPKHKK
ALHNKGIALMMLNKNKKAIESFEKAIQIDKNYGTAYYQKGIAEEKNGDMQQAFASFKNAYNLDKN
PNYALKAGIVSNNLGNFKQSEEYLNFFNANAKKPNEIAIYNLSIAKFENNKLEESLETINKAIDLNPE
KSEYLYLKASINLKKENYQNAISLYSLVIEKNPENTSAYINLAKAYEKSGNKSQAISTLEKIINKNNKL
ALNNLGILYKKEKNYQKAIEIFEKAIINSDIEAKYNLATTLIEINDNTRAKDLLREYTKLKPNNPEALH
ALGIIEYNENNNDQTLRELIKKFPNYKKNENIKKIIGI t742.aa (SEQ ID NO:322)
KLNDKNREIMLNEVKNSVIDRNYKKAYSVAKLLQDKYPQNEDIAMLTNTLAEIANSSPFES
KDLQRDSANQILDKIKGQDNTKTNVNENFDIAFNNRYIKDSTITENYSDRNDDVGIEDEDTSEFKKSK
IPEKIKPNTNPKEEDQIIQSPNPKLSVNDQKNLFNLEKLKKNLSGKSNSENILNDSQKIENDKQNTNLS
KEKNSENILKTPDNSKYSNNNTTSLKKISSNSQKESELSPPSQTIIGKIYRPYSYLIKKELYEILDDINT
GRVTLGKNRLKELIKKGLSNKFQKVNELIENSKNKEASNLLLTLIKKDIEPNLINIPKDPYKKEIFQLD
KEDKKPQYLEDLKSKVHSIKPIDLENTKSRQQAIKDLNEFLKNNPNDAQASKTLAQANKIQHLEDLK
SKVHSIKPIDLENTKSRQQAIKDLNEFLKNNPNDAQASKTLAQANKIQHLEDLKSKVHSIKPIDLENT
KSRQQAIKDLNEFLKNNPNDAQASKTLAQANKIQHLEDLKSKVHSIKPIDLENTKSRQQAIKDLNEF
XKNNPNDAQASKTLAQANKIQHLEDLKSKVHSIKPIDLENTKSRQQAIKDLNEFXKNNPNDAQASK
TLAQANKIQHLEDLKSKVHSIKPIDLENTKSRQQAIKDLNEFLKNNPNDAQASKTLAQANKIQHLED
LKSKVHSIKPIDLENTKSRQQAIKDLNEFXKNNPNDAQASKTLAQAYENNGDLLKAENAYEKIIKLT
NTQEDHYKLGIIRFKLKKYEHSIESFDQTIKLDPKHKKALHNKGIALMMLNKNKKAIESFEKAIQIDK
NYGTAYYQKGIAEEKNGDMQQAFASFKNAYNLDKNPNYALKAGIVSNNLGNFKQSEEYLNFFNAN
AKKPNEIAIYNLSIAKFENNKLEESLETINKAIDLNPEKSEYLYLKASINLKKENYQNAISLYSLVIEKN
PENTSAYINLAKAYEKSGNKSQAISTLEKIINKNNKLALNNLGILYKKEKNYQKAIEIFEKAIINSDIEA
KYNLATTLIEINDNTRAKDLLREYTKLKPNNPEALHALGIIEYNENNNDQTLRELIKKFPNKKKNENI
KKIIGI f742.nt (SEQ ID NO:323)
ATGAATAAAAAACATACAAATTTTTCGGTATTATTGCTTTTAATTTTCTTACTTATCTTA
TCATTTGGGGGCTTTGGTTACTATATATATCAAAGCAAATTAAATGACAAAAATCGAGAAATAA

TABLE 1-continued

Nucleotide and Amino Acid Sequences.

```
TGCTAAACGAAGTTAAAAATAGCGTAATAGATCGAAACTATAAAAAAGCATATTCTGTTGCAA
AACTTCTGCAAGACAAATACCCCCAAAATGAAGACATTGCAATGCTTACAAATACACTAGCAGA
AATTGCCAACAGTAGTCCTTTTGAATCAAAAGACTTGCAAAGAGATTCTGCTAATCAAATCTTA
GACAAGATCAAAGGTCAAGACAATACAAAAACAAATGTAAACGAAAATTTTGATATAGCATTT
AATAATAGATACATTAAAGACAGCACAATAACAGAAAACTACTCTGACAGAAACGATGATGTT
GGCATTGAAGATGAAGACATATCTGAATTTAAAAAAAGCAAAATCCCAGAAAAAATAAAACCA
AATACAAACCCAAAAGAAGAAGACCAAATAATACAATCTCCAAATCCGAAATTAAGTGTTAAT
GACCAAAAAATTTATTTAATTTGGAAAAACTAAAAAAAAATTTAAGTGGAAAATCAAATAGT
GAAAATATTTTAAACGATTCTCAAAAAATAGAAAATGATAAGCAAAACACAAATTTATCCAAA
GAAAAAAATTCGGAGAATATTTTAAAAACTCCGGACAACAGTAAATATTCAAACAATAACAAT
ACTACATCTTTAAAAAAAATTTCTTCAAATTCCCAAAAAGAAAGTGAGCTTTCTCCACCCAGTC
AAACAATAATAGGGAAAATTTATAGGCCATATAGCTACTTGATAAAAAAAGAGCTCTATGAAA
TATTAGACGATATTAATACCGGAAGAGTCACACTTGGAAAAAACAGATTAAAAGAATTAATTA
AAAAAGGTCTAAGCAACAAATTTCAAAAAGTAAATGAATTGATTGAAAATTCAAAAAATAAAG
AAGCTTCAAATTTACTATTAACCTTAATAAAAAAAGATATTGAACCAAATCTCATTAATATACC
AAAAGATCCTTACAAAAAAGAAATTTTTCAATTAGATAAAGAAGACAAAAAGCCTCAGTACCT
AGAGGACCTTAAATCTAAAGTTCATTCAATAAAACCCATTGATCTTGAAAACACAAAATCACGC
CAACAAGCCATTAAGGATCTAAACGAATTCTTGAAAAACAATCCCAATGACGCTCAGGCCTCTA
AAACTTTAGCTCAAGCTAATAAAATACAACACCTAGAGGACCTTAAATCTAAGGTTCATTCAAT
AAAACCCATTGATCTTGAAAACACAAAATCACGCCAACAAGCCATTAAGGATCTAAACGAATTC
TTGAAAAACAATCCCAATGACGCTCAGGCCTCTAAAACTTTAGCTCAAGCTAATAAAATACAAC
ACCTAGAGGACCTTAAATCTAAGGTTCATTCAATAAAACCCATTGATCTTGAAAACACAAAATC
ACGCCAACAAGCCATTAAGGATCTAAACGAATTCTTAAAAAACAATCCCAATGACGCCCAGGCC
TCTAAAACTTTAGCTCAAGCTAATAAAATACAACACCTGGAGGACCTTAAATCTAAGGTTCATT
CAATAAAACCCATTGATCTTGAAAACACAAAATCACGCCAACAAGCCATTAAGGATCTAAACG
AATTCTTAAAAACAATCCCAATGACGCCAGGCCTCTAAAACTTTAGCTCAAGCTAATAAAATAC
AACACCTGAGGACCTTAAATCTAAGGTTCATTCAATAAAACCCATTGATCTTGAAAACACAAAA
TCACGCCAACAAGCCATTAAGGATCTAAACGAATTCTTAAAAACAATCCCAATGACGCCAGGCC
TCTAAAACTTTAGCTCAAGCTAATAAAATACAACACCTAGAGGACCTTAAATCTAAGGTTCATT
CAATAAAACCCATTGATCTTGAAAACACAAAATCACGCCAACAAGCCATTAAGGATCTAAACG
AATTCTTAAAAACAATCCCAATGACGCCCAGGCCTCTAAAACTTTAGCTCAAGCTAATAAAAT
ACAACACCTGGAGGACCTTAAATCTAAGGTTCATTCAATAAAACCCATTGATCTTGAAAACACA
AAATCACGCCAACAAGCCATTAAGGATCTAAACGAATTCTTAAAAACAATCCCAATGACGCCCA
GGCCTCTAAAACTTTAGCTCAAGCTTATGAAAACAATGGAGATTTGCTAAAAGCAGAAAATGCA
TACGAAAAAATTATCAAACTCACAAATACCCAAGAAGATCACTATAAACTTGGAATCATTAGAT
TCAAGCTTAAAAAGTATGAACACTCAATAGAATCATTTGATCAAACAATAAAACTCGACCCAAA
ACATAAAAAAGCACTTCATAACAAAGGAATAGCTTTAATGATGCTAAATAAAAACAAAAAAGC
AATAGAATCTTTTGAGAAAGCAATACAAATTGATAAAAATTATGGCACCGCCTACTACCAAAAA
GGAATAGCAGAAGAAAAAAATGGCGATATGCAACAAGCATTTGCAAGCTTTAAAAATGCCTAC
AATCTCGACAAAAACCCCAATTATGCATTAAAAGCAGGAATAGTATCAAATAACTTGGGCAACT
TCAAACAAAGTGAAGAGTATTTAAATTTTTTTAATGCCAATGCAAAAAAACCTAACGAAATTGC
TATTTACAACCTATCAATAGCAAAATTTGAAAACAATAAACTTGAAGAATCTCTTGAAACAATA
AACAAAGCCATAGATTTAAATCCAGAAAAAAGTGAATATTTATATTTAAAAGCATCTATAAATC
TTAAAAAAGAAAATTACCAAAATGCTATATCACTTTACAGCTTAGTAATTGAAAAAAAACCCTGA
AAATACTTCAGCCTATATAAACCTGGCAAAAGCATATGAAAAATCAGGAAATAAAAGTCAAGC
AATCTCAACTCTTGAAAAGATAATAAAACAAAAATAATAAATTAGCCTTAAACAATCTTGGGATA
CTTTACAAAAAAGAAAAAAATTATCAAAAAGCAATTGAAATTTTTGAAAAAGCAATAATCAATT
CAGATATTGAAGCAAAATATAATCTTGCAACCACTCTAATTGAAATTAATGATAACACAAGAGC
TAAAGACCTTCTAAGAGAATATACAAAATTAAAACCAAACAATCCAGAGGCCTTACATGCACTA
GGAATAATAGAATATAATGAAAATAACAATGATCAAACACTAAGAGAACTTATAAAAAAATTT
CCAAATTACAAAAAAAATGAAAATATTAAAAAAATAATAGGAATATAA t742.nt (SEQ ID NO:324)
AAATTAAATGACAAAAATCGAGAAATAATGCTAAACGAAGTTAAAAATAGCGTAATAG
ATCGAAACTATAAAAAGCATATTCTGTTGCAAAACTTCTGCAAGACAAATACCCCCAAAATGA
AGACATTGCAATGCTTACAAATACACTAGCAGAAATTGCCAACAGTAGTCCTTTTGAATCAAAA
GACTTGCAAAGAGATTCTGCTAATCAAATCTTAGACAAGATCAAAGGTCAAGACAATACAAAA
ACAAATGTAAACGAAAATTTTGATATAGCATTTAATAATAGATACATTAAAGACAGCACAATAA
CAGAAAACTACTCTGACAGAAACGATGATGTTGGCATTGAAGATGAAGACATATCTGAATTTA
AAAAAAGCAAAATCCCAGAAAAAATAAAACCAAATACAAACCCAAAAGAAGAAGACCAAATA
ATACAATCTCCAAATCCGAAATTAAGTGTTAATGACCAAAAAATTTATTTAATTTGGAAAAAC
TAAAAAAAAATTTAAGTGGAAAATCAAATAGTGAAAATATTTTAAACGATTCTCAAAAAATAG
AAAATGATAAGCAAAACACAAATTTATCCAAAGAAAAAAATTCGGAGAATATTTTAAAAACTC
CGGACAACAGTAAATATTCAAACAATAACAATACTACATCTTTAAAAAAAATTTCTTCAAATTC
CCAAAAAGAAAGTGAGCTTTCTCCACCCAGTCAAACAATAATAGGGAAAATTTATAGGCCATAT
AGCTACTTGATAAAAAAAGAGCTCTATGAAATATTAGACGATATTAATACCGGAAGAGTCACA
CTTGGAAAAAACAGATTAAAAGAATTAATTAAAAAAGGTCTAAGCAACAAATTTCAAAAAGTA
AATGAATTGATTGAAAATTCAAAAAATAAAGAAGCTTCAAATTTACTATTAACCTTAATAAAAA
AAGATATTGAACCAAATCTCATTAATATACCAAAAGATCCTTACAAAAAAGAAATTTTTCAATT
AGATAAAGAAGACAAAAAGCCTCAGTACCTAGAGGACCTTAAATCTAAAGTTCATTCAATAAA
ACCCATTGATCTTGAAAACACAAAATCACGCCAACAAGCCATTAAGGATCTAAACGAATTCTTG
AAAAACAATCCCAATGACGCTCAGGCCTCTAAAACTTTAGCTCAAGCTAATAAAATACAACACC
TAGAGGACCTTAAATCTAAGGTTCATTCAATAAAACCCATTGATCTTGAAAACACAAAATCACG
CCAACAAGCCATTAAGGATCTAAACGAATTCTTGAAAAACAATCCCAATGACGCTCAGGCCTCT
AAAACTTTAGCTCAAGCTAATAAAATACAACACCTAGAGGACCTTAAATCTAAGGTTCATTCAA
TAAAACCCATTGATCTTGAAAACACAAAATCACGCCAACAAGCCATTAAGGATCTAAACGAATT
CTTAAAAAACAATCCCAATGACGCCCAGGCCTCTAAAACTTTAGCTCAAGCTAATAAAATACAA
```

TABLE 1-continued

Nucleotide and Amino Acid Sequences.

```
CACCTGGAGGACCTTAAATCTAAGGTTCATTCAATAAAACCCATTGATCTTGAAAACACAAAAT
CACGCCAACAAGCCATTAAGGATCTAAACGAATTCTTAAAAACAATCCCAATGACGCCCAGGCCT
CTAAAACTTTAGCTCAAGCTAATAAAATACAACACCTGAGGACCTTAAATCTAAGGTTCATTCA
ATAAAACCCATTGATCTTGAAAACACAAAATCACGCCAACAAGCCATTAAGGATCTAAACGAAT
TCTTAAAAACAATCCCAATGACGCCAGGCCTCTAAAACTTTAGCTCAAGCTAATAAAATACAAC
ACCTAGAGGACCTTAAATCTAAGGTTCATTCAATAAAACCCATTGATCTTGAAAACACAAATC
ACGCCAACAAGCCATTAAGGATCTAAACGAATTCTTAAAAAACAATCCCAATGACGCCCAGGCC
TCTAAAACTTTAGCTCAAGCTAATAAAATACAACACCTGGAGGACCTTAAATCTAAGGTTCATT
CAATAAAACCCATTGATCTTGAAAACACAAATCACGCCAACAAGCCATTAAGGATCTAAACG
AATTCTTAAAAACAATCCCAATGACGCCCAGGCCTCTAAAACTTTAGCTCAAGCTTATGAAAAC
AATGGAGATTTGCTAAAAGCAGAAAATGCATACGAAAAAATTATCAAACTCACAAATACCCAA
GAAGATCACTATAAACTTGGAATCATTAGATTCAAGCTTAAAAGTATGAACACTCAATAGAAT
CATTTGATCAAACAATAAAACTCGACCCAAAACATAAAAAAGCACTTCATAACAAAGGAATAG
CTTTAATGATGCTAAATAAAAACAAAAAGCAATAGAATCTTTTGAGAAAGCAATACAAATTG
ATAAAAATTATGGCACCGCCTACTACCAAAAAGGAATAGCAGAAGAAAAAAATGGCGATATGC
AACAAGCATTTGCAAGCTTTAAAAATGCCTACAATCTCGACAAAAACCCCAATTATGCATTAAA
AGCAGGAATAGTATCAAATAACTTGGGCAACTTCAAACAAAGTGAAGAGTATTTAAATTTTTTT
AATGCCAATGCAAAAAAACCTAACGAAATTGCTATTTACAACCTATCAATAGCAAAATTTGAA
ACAATAAACTTGAAGAATCTCTTGAAACAATAAACAAAGCCATAGATTTAAATCCAGAAAAAA
GTGAATATTTATATTTAAAAGCATCTATAAATCTTAAAAAAGAAAATTACCAAAATGCTATATC
ACTTTACAGCTTAGTAATTGAAAAAAACCCTGAAAATACTTCAGCCTATATAAACCTGGCAAAA
GCATATGAAAAATCAGGAAATAAAAGTCAAGCAATCTCAACTCTTGAAAAGATAATAAACAAA
AATAATAAATTAGCCTTAAACAATCTTGGGATACTTTACAAAAAAGAAAAAAATTATCAAAAA
GCAATTGAAATTTTTGAAAAAGCAATAATCAATTCAGATATTGAAGCAAAATATAATCTTGCAA
CCACTCTAATTGAAATTAATGATAACACAAGAGCTAAAGACCTTCTAAGAGAATATACAAAATT
AAAACCAAACAATCCAGAGGCCTTACATGCACTAGGAATAATAGAATATAATGAAAATAACAA
TGATCAAACACTAAGAGAACTATAAAAAAATTTCCAAATTACAAAAAAAATGAAAATATTAAA
AAAATAATAGGAATATAA f743.aa (SEQ ID NO:325)
MRIYLFLNKNYKIFILFLILILNSKLAYSQRLIRIGKEEMKNKNYIQAIETLSDAIKKYPKVQLGYYFLS
IAYRENNQLTEAEGALLDGIAVGGEIDYILYYELGNIMFNRGEGYYPLAIKYYSNSIKSRPNYDSALL
NRANAYVQQGKITSKEKEYQKAWDSYTMAIHDYSQFITLRSKTEKKDSILLIISYLRNEKINLEQLDK
SLKGRTEHIVYAKEDKNQILKDSFKDNLETNSLIELEKLNWQEELYIDE t743.aa (SEQ ID NO:326)
YSQRLIRIGKEEMKNKNYIQAIETLSDAIKKYPKVQLGYYFLSIAYRENNQLTEAEGALLDGIAVGGE
IDYILYYELGNIMFNRGEGYYPLAIKYYSNSIKSRPNYDSALLNRANAYVQQGKITSKEKEYQKAWD
SYTMAIHDYSQFITLRSKTEKKDSILLIISYLRNEKINLEQLDKSLKGRTEHIVYAKEDKNQILKDSFK
DNLETNSLIELEKLNWQEELYIDE f743.nt (SEQ ID NO:327)
ATGAGGATTTATTTATTTTTAAATAAAAATTACAAGATTTTTATTTTATTTTTAATTTTAATATT
AAATTCAAAATTGGCATATTCTCAAAGGCTAATTAGAATTGGCAAAGAAGAGATGAAAAACAA
AAATTACATTCAAGCAATCGAAACACTAAGTGATGCTATTAAAAAATATCCAAAAGTACAACTC
GGCTATTA TTTATCAATAGCATACAGAGAAATAATCAACTAACAGAAGCAGAAGGAGCA
TTGCTCGATGGAATTGCAGTAGGGGGTGAAATCGACTACATACTATATTATGAATTAGGCAACA
TAATGTTTAACAGAGGGGAAGGTTACTATCCTTTAGCAATAAAATATTATTCTAATTCTATTAA
AAGTAGACCTAATTATGACAGTGCGCTACTAAACAGAGCTAATGCCTATGTTCAACAGGGCAAA
ATAACTTCTAAAGAAAAAGAATACCAAAAAGCTTGGGACTCTTATACTATGGCTATCCACGACT
ACTCTCAATTTATTACCCTTAGATCAAAAACAGAAAAAAAAGACAGCATTTTGCTTATAATAAG
CTATTTAAGAAATGAAAAAATTAATCTTGAACAACTTGACAAAGTTTGAAGGGGCGAACCGA
GCATATTGTATACGCAAAAGAAGATAAAAATCAAATACTTAAAGATAGTTTTAAAGACAACCT
AGAAACAAATTCTAATTGAGCTAGAAAAACTTAATTGGCAAGAGGAGTTATACATAGATGA
ATAA t743.nt (SEQ ID NO:328)
TATTCTCAAAGGCTAATTAGAATTGGCAAAGAAGAGATGAAAAACAAAATTACATTC
AAGCAATCGAAACACTAAGTGATGCTATTAAAAAATATCCAAAAGTACAACTCGGCTATTACTT
TTTATCAATAGCATACAGAGAAATAATCAACTAACAGAAGCAGAAGGAGCATTGCTCGATGG
AATTGCAGTAGGGGGTGAAATCGACTACATACTATATTATGAATTAGGCAACATAATGTTTAAC
AGAGGGGAAGGTTACTATCCTTTAGCAATAAAATATTATTCTAATTCTATTAAAAGTAGACCTA
ATTATGACAGTGCGCTACTAAACAGAGCTAATGCCTATGTTCAACAGGGCAAAATAACTTCTAA
AGAAAAAGAATACCAAAAAGCTTGGGACTCTTATACTATGGCTATCCACGACTACTCTCAATTT
ATTACCCTTAGATCAAAAACAGAAAAAAAAGACAGCATTTTGCTTATAATAAGCTATTTAAGAA
ATGAAAAAATTAATCTTGAACAACTTGACAAAGTTTGAAGGGGCGAACCGAGCATATTGTAT
ACGCAAAAGAAGATAAAAATCAAATACTTAAAGATAGTTTTAAAGACAACCTAGAAACAAATT
CTTTAATTGAGCTAGAAAAACTTAATTGGCAAGAGGAGTTATACATAGATGAATAA f748.aa (SEQ ID NO:329)
MKFIINLLLSTIKIITFTVIVCLTILSIFQPIYILKENEISITTRLGKIQRTENLAGLKYKIPLIENVQIFPKII
LRWDGEPQRIPTGGEEKQLIWIDTTARWKIADINKFYTTIKTMSRAYVRIDAAIEPAVRGVIAKYPLL
EIIRSSNDPIQRLSNGILTPQETKINGIYKITKGRKIIEKEIIRIANNNTKDIGIEIVDVLIRKVTYDPSLIES
VNNRMISERQQIAEEQRSIGLAEKTEILGSIEKEKLKILSEAKATAAKIKAEGDREAAKIYSNAYGKNI
EFYKFWQALESYKAVLKDKRKIFSTDMDFFQYLHKRN t748.aa (SEQ ID NO:330)
```

TABLE 1-continued

Nucleotide and Amino Acid Sequences.

IFQPIYILKENEISITTRLGKIQRTENLAGLKYKIPLIENVQIFPKIILRWDGEPQRIPTGGEEKQ
LIWIDTTARWKIADINKFYTTIKTMSRAYVRIDAAIEPAVRGVIAKYPLLEIIRSSNDPIQRLSNGILTP
QETKINGIYKITKGRKIIEKEIIRIANNNTKDIGIEIVDVLIRKVTYDPSLIESVNNRMISERQQIAEEQRS
IGLAEKTEILGSIEKEKLKILSEAKATAAKIKAEGDREAAKIYSNAYGKNIEFYKFWQALESYKAVLK
DKRKIFSTDMDFFQYLHKRN f748.nt (SEQ ID NO:331)
ATGAAATTTATAATAAATCTTTTATTATCTACTATAAAGATTATAACCTTTACAGTAAT
AGTTTGCTTGACTATTTTGTCTATTTTCCAGCCAATTTATATTTTGAAAGAAAATGAAATTTCAA
TAACCACTCGACTTGGAAAAATTCAAAGAACTGAAAATTTAGCTGGACTTAAATATAAAATACC
ATTAATTGAAAATGTGCAAATATTTCCCAAAATCATTCTTAGATGGGATGGAGAACCTCAAAGA
ATCCCAACAGGAGGGGAAGAAAAGCAATTAATATGGATTGATACAACTGCTAGATGAAAATT
GCAGACATAAATAAATTTTACACAACAATAAAAACAATGAGTAGAGCTTACGTTAGAATTGAT
GCAGCAATTGAACCTGCTGTTAGGGGGGTTATTGCAAAATACCCTTTGCTTGAAATTATAAGAA
GCTCAAACGATCCTATTCAACGTTTGTCTAATGGAATACTCACCCCACAAGAAACAAAAATTAA
CGGTATTTATAAATAACAAAAGGACGAAAGATAATCGAAAAAGAAATAATTCGTATAGCAAA
CAACAATACCAAAGATATTGGAATTGAAATTGTAGACGTACTAATAAGAAAAGTTACTTATGAC
CCAAGCCTTATTGAATCTGTAAACAACAGAATGATCTCAGAAAGACAACAAATCGCAGAAGAA
CAAAGAAGCATAGGATTAGCTGAAAAAACAGAAATTCTTGGAAGCATAGAAAAAGAAAAACTG
AAAATATTAAGTGAAGCAAAAGCCACTGCTGCAAAAATAAAAGCCGAAGGGGATAGAGAAGCC
GCAAAAATTATTCAAATGCATATGGCAAAAATATTGAATTTTACAAATTCTGGCAGGCATTAG
AAAGCTATAAAGCAGTATTAAAAGATAAAAGAAAAATTTTCTCAACAGACATGGATTTCTTTCA
ATATCTTCACAAAAGAAATTGA t748.nt (SEQ ID NO:332)
ATTTTCCAGCCAATTTATATTTGAAAGAAAATGAAATTTCAATAACCACTCGACTTGG
AAAAATTCAAAGAACTGAAAATTTAGCTGGACTTAAATATAAAATACCATTAATTGAAAATGTG
CAAATATTTCCCAAAATCATTCTTAGATGGGATGGAGAACCTCAAAGAATCCCAACAGGAGGG
GAAGAAAAGCAATTAATATGGATTGATACAACTGCTAGATGAAAATTGCAGACATAAATAAA
TTTACACAACAATAAAAACAATGAGTAGAGCTTACGTTAGAATTGATGCAGCAATTGAACCTG
CTGTTAGGGGGGTTATTGCAAAATACCCTTTGCTTGAAATTATAAGAAGCTCAAACGATCCTAT
TCAACGTTTGTCTAATGGAATACTCACCCCACAAGAAACAAAAATTAACGGTATTTATAAAATA
ACAAAAGGACGAAAGATAATCGAAAAAGAAATAATTCGTATAGCAAACAACAATACCAAAGAT
ATTGGAATTGAAATTGTAGACGTACTAATAAGAAAAGTTACTTATGACCCAAGCCTTATTGAAT
CTGTAAACAACAGAATGATCTCAGAAAGACAACAAATCGCAGAAGAACAAAGAAGCATAGGAT
TAGCTGAAAAAACAGAAATTCTTGGAAGCATAGAAAAAGAAAAACTGAAAATATTAAGTGAAG
CAAAAGCCACTGCTGCAAAAATAAAAGCCGAAGGGGATAGAGAAGCCGCAAAAATTTATTCAA
ATGCATATGGCAAAAATATTGAATTTTACAAATTCTGGCAGGCATTAGAAAGCTATAAAGCAGT
ATTAAAAGATAAAAGAAAAATTTTCTCAACAGACATGGATTTCTTTCAATATCTTCACAAAAGA
AATTGA f764.aa (SEQ ID NO:333)
MSGPKKLAIIALLVISIQGCKESSIIEKQFNYAIIFSDATEYFFEIQTTPFIKNEILFINDKNLEIIK
DKLKTTKKILLTHKSNNEILNNEILKEKIFYLSKIKFSLKKSIDFLLNEKSIDLQKTLLFRDKSLNNEDL
EYLEKKGKEKNVNITLINEKNISYIQTFITSQIKTIILFSLRDNNIILKKILNSPFSKNIKFVLIGNTRKDL
KIIKLKYIITLKEPDLIKIAKDVEKDFQYEFNIYKQ f764.aa (SEQ ID NO:334)
EKQFNYAIIFSDATEYFFEIQTTPFIKNEILFINDKNLEIIKDKLKTTKKILLTHKSNNEILNNEI
LKEKIFYLSKIKFSLKKSIDFLLNEKSIDLQKTLLFRDKSLNNEDLEYLEKKGKEKNVNITLINEKNISY
IQTFITSQIKTIILFSLRDNNIILKKILNSPFSKNIKFVLIGNTRKDLKIIKLKYIITLKEPDLIKIAKDVEKD
FQYEFNIYKQ f764.nt (SEQ ID NO:335)
ATGTCTGGCCCTAAAAAACTTGCTATAATAGCGCTCTTAGTAATTTCAATACAAGGATG
CAAAGAATCTTCTATTATTGAAAAACAATTTAATTATGCAATAATTTTTCAGATGCAACTGAA
TATTTTTTTGAAATTCAAACAACTCCATTCATAAAAAACGAAATACTATTTATAAATGACAAAA
ATTTAGAAATTATAAAAGACAAGCTTAAAACAACAAAAAAAATACTATTAACTCATAAATCAA
ATAATGAAATTCTAAATAACGAAATTCTAAAAGAGAAATTTTTTATCTATCAAAAATAAAATT
TTCTCTAAAAAAATCTATTGACTTTCTGCTTAACGAAAAATCAATAGATTTGCAAAAAACATTA
CTATTTAGAGACAAATCTCTAAATAACGAAGACCTTGAATACTTGGAAAAAAAAGGCAAAGAA
AAAAATGTCAATATTACTCTAATAAACGAAAAAAACATATCCTATATTCAAACATTCATTACTT
CTCAAATAAAAACAATAATATTATTCTCTTTAAGAGATAATAATATTATTTTAAAAAGATACT
AAATTCGCCTTTTTCTAAAAATATAAAATTTGTATTAATTGGCAATACAAGAAAAGACTTAAAA
ATTATTAAGCTAAAATATATAATCACCCTTAAAGAGCCTGATTTGATAAAAATAGCAAAAGATG
TTGAAAAAGATTTTCAATATGAATTTAACATTTATAAACAATAA t764.nt (SEQ ID NO:336)
GAAAAACAATTTAATTATGCAATAATTTTTTCAGATGCAACTGAATATTTTTTTGAAAT
TCAAACAACTCCATTCATAAAAAACGAAATACTATTTATAAATGACAAAAATTTAGAAATTATA
AAAGACAAGCTTAAAACAACAAAAAAAATACTATTAACTCATAAATCAAATAATGAAATTCTA
AATAACGAAATTCTAAAAGAGAAATTTTTTATCTATCAAAAATAAAATTTTCTCTAAAAAAAT
CTATTGACTTTCTGCTTAACGAAAAATCAATAGATTTGCAAAAAACATTACTATTTAGAGACAA
ATCTCTAAATAACGAAGACCTTGAATACTTGGAAAAAAAAGGCAAAGAAAAAAATGTCAATAT
TACTCTAATAAACGAAAAAAACATATCCTATATTCAAACATTCATTACTTCTCAAATAAAAACA
ATAATATTATTCTCTTTAAGAGATAATAATATTATTTTAAAAAGATACTAAATTCGCCTTTTTC
TAAAAATATAAAATTTGTATTAATTGGCAATACAAGAAAAGACTTAAAAATTATTAAGCTAAAA

TABLE 1-continued

Nucleotide and Amino Acid Sequences.

TATATAATCACCCTTAAAGAGCCTGATTTGATAAAAATAGCAAAAGATGTTGAAAAAGATTTTC
AATATGAATTTAACATTTATAAACAATAA f770.aa (SEQ ID NO:337)
MINFSKSFFYPLPIGKIFVLSGDMGSGKTSFLKGLALNLGISYFTSPTYNIVNVYDFINFKFYH
IDLYRVSSLEEFELVGGLEILMDLDSIIAIEWPQIALSIVPKDRLFSLTFKIVGSGRVVELNG t770.aa (SEQ ID NO:338)
KTSFLKGLALNLGISYFTSPTYNIVNVYDFINFKFYHIDLYRVSSLEEFELVGGLEILMDLDSI
IAIEWPQIALSIVPKDRLFSLTFKIVGSGRVVELNG f770.nt (SEQ ID NO:339)
ATGATAAATTTTTCCAAATCTTTTTTTTATCCTTTGCCAATTGGTAAAATATTTGTTTTA
AGTGGTGACATGGGATCTGGAAAAACTAGTTTTTTAAAGGGACTTGCCCTTAACCTTGGAATTT
CTTATTTTACAAGTCCAACTTATAACATTGTTAATGTTTATGATTTTATAAATTTTAAATTTTATC
ATATTGATTTATATCGGGTGTCTTCTTTGGAAGAATTTGAGCTTGTTGGGGGATTGGAAATACT
TATGGATCTTGACTCGATTATTGCTATTGAATGGCCACAAATTGCTTTGAGCATTGTTCCAAAA
GATAGATTATTTTCTTTAACTTTTAAAATAGTAGGTTCAGGCAGGGTTGTAGAACTTAATGGTT
AA t770.nt (SEQ ID NO:340)
AAAACTAGTTTTTTAAAGGGACTTGCCCTTAACCTTGGAATTTCTTATTTTACAAGTCCAACTTA
TAACATTGTTAATGTTTATGATTTTATAAATTTTAAATTTTATCATATTGATTTATATCGGGTGT
CTTCTTTGGAAGAATTTGAGCTTGTTGGGGGATTGGAAATACTTATGGATCTTGACTCGATTAT
TGCTATTGAATGGCCACAAATTGCTTTGAGCATTGTTCCAAAAGATAGATTATTTTCTTTAACTT
TTAAAATAGTAGGTTCAGGCAGGGTTGTAGAACTTAATGGTTAA f790.aa (SEQ ID NO:341)
MNTKATTPLLLLFLIQSLAFSSEIFEFKYIKGSKFRLEGTDNQKIYFNGHYNSSSNTNIQISSEI
KDIKENFASIKAFFRILKRENINEPYLLNEEFEEIFSVNKQGEYTIGANQKRPSVRGIPRFPKTPIKTNEK
WSYLAEEYIEASKIDKSIKDFVVKFNVNYEYKGKEEHNGKHYHIILSNYESQYNVKNISSFYQKVDQK
IYFDNEIGNTYKYSDKYIFEINQNNNQHFKMIGNSLGRIVSIELPNDNLIETEVENYIREKKIKAIEVEK
NNKGINLSFDIEFYPNSFQILQKEYKKIDLIAKLLEKFKKNNILIEGHTEQFGLEEEMHELSEKRARAI
GNYLIKMKVKDKDQILFKGWGSQKPKYPKSSPLKAKNRRVEITILNN t790.aa (SEQ ID NO:342)
SEIFEFKYIKGSKFRLEGTDNQKIYFNGHYNSSSNTNIQISSEIKDIKENFASIKAFFRILKRENI
NEPYLLNEEFEEIFSVNKQGEYTIGANQKRPSVRGIPRFPKTPIKINEKWSYLAEEYIEASKIDKSIKDF
VVKFNVNYEYKGKEEHNGKHYHIILSNYESQYNVKNISFYQKVDQKIYFDNEIGNTYKYSDKYIFEI
NQNNNQHFKMIGNSLGRIVSIELPNDNLIETEVENYIREKKIKAIEVEKNNKGINLSFDIEFYPNSFQIL
QKEYKKIDITAKLLEKFKKNNILIEGHTEQFGLEEEMHELSEKRARAIGNYLIKMKVKDKDQILFKG
WGSQKPKYPKSSPLKAKNRRVEITILNN f790.nt (SEQ ID NO:343)
ATGAATACCAAGGCGACTACACCATTGTTGTTATTATTTTTAATTCAAAGCTTAGCTTT
TTCTTCTGAAATCTTTGAATTTAAATACATTAAAGGTTCAAAGTTTAGATTAGAAGGCACAGAT
AATCAAAAAATATATTTCAATGGCCATTATAATTCAAGCTCTAATACCAATATTCAAATTTCAA
GTGAAATAAAAGACATAAAAGAAAACTTTGCAAGCATTAAAGCTTTTTTTAGAATCTTAAAAAG
AGAAAATATTAATGAACCTTACCTATTAAATGAAGAGTTTGAAGAAATCTTCAGCGTAAATAAG
CAAGGAGAATATACAATAGGAGCAAATCAAAAAAGACCTTCTGTTAGAGGTATTCCAAGATTC
CCAAAAACACCAATCAAAATAAATGAAAAATGGTCATATCTTGCAGAAGAATATATAGAAGCG
TCAAAAATAGACAAAAGTATAAAAGATTTCGTTGTAAAATTTAATGTTAACTACGAATATAAAG
GCAAAGAAGAGCACAATGGCAAGCATTACCACATAATTCTTTCGAATTATGAATCACAATACAA
TGTAAAAAACATCTCTTTCTATCAAAAAGTAGACCAAAAAATTTATTTTGATAATGAAATTGGC
AATACATATAAATACAGCGATAAATATATATTTGAAATAAATCAGAACAACAACCAACATTTTA
AAATGATTGGAAACTCTCTTGGCAGAATAGTTTCAATTGAGCTTCCAAATGATAATCTTATTGA
AACTGAGGTTGAAAATTACATCCGAGAAAAAAAAATAAAAGCTATTGAAGTTGAAAAAAACAA
TAAAGGTATTAATTTAAGCTTTGACATTGAATTTTATCCTAACTCATTTCAAATACTACAAAAG
AATATAAAAAAATTGACCTTATAGCTAAACTTCTTGAAAAATTTAAAAAAAATAACATACTAAT
AGAAGGACATACTGAGCAATTTGGATTGGAAGAAGAGATGCACGAGCTATCTGAAAAAAGAGC
TCGTGCAATTGGAAATTATTTAATAAAAATGAAAGTAAAAGACAAAGACCAAATACTATTTAA
AGGATGGGGATCTCAAAAACCAAAATATCCTAAGTCCTCCCCATTAAAGGCTAAAAATAGGCG
AGTAGAAATTACAATATTAAATAACTAA t790.nt (SEQ ID NO:344)
TCTGAAATCTTTGAATTTAAATACATTAAAGGTTCAAAGTTTAGATTAGAAGGCACAGA
TAATCAAAAAATATATTTCAATGGCCATTATAATTCAAGCTCTAATACCAATATTCAAATTTCA
AGTGAAATAAAAGACATAAAAGAAAACTTTGCAAGCATTAAAGCTTTTTTTAGAATCTTAAAAA
GAGAAAATATTAATGAACCTTACCTATTAAATGAAGAGTTTGAAGAAATCTTCAGCGTAAATAA
GCAAGGAGAATATACAATAGGAGCAAATCAAAAAAGACCTTCTGTTAGAGGTATTCCAAGATT
CCCAAAAACACCAATCAAAATAAATGAAAAATGGTCATATCTTGCAGAAGAATATATAGAAGC
GTCAAAAATAGACAAAAGTATAAAAGATTTCGTTGTAAAATTTAATGTTAACTACGAATATAAA
GGCAAAGAAGAGCACAATGGCAAGCATTACCACATAATTCTTTCGAATTATGAATCACAATACA
ATGTAAAAAACATCTCTTTCTATCAAAAAGTAGACCAAAAATTTATTTTGATAATGAAATTGG
CAATACATATAAATACAGCGATAAATATATATTTGAAATAAATCAGAACAACAACCAACATTTT
AAAATGATTGGAAACTCTCTTGGCAGAATAGTTTCAATTGAGCTTCCAAATGATAATCTTATTG
AAACTGAGGTTGAAAATTACATCCGAGAAAAAAAAATAAAAGCTATTGAAGTTGAAAAAAACA

TABLE 1-continued

Nucleotide and Amino Acid Sequences.

```
ATAAAGGTATTAATTTAAGCTTTGACATTGAATTTTATCCTAACTCATTTCAAATACTACAAAAA
GAATATAAAAAAATTGACCTTATAGCTAAACTTCTTGAAAAATTTAAAAAAAATAACATACTAA
TAGAAGGACATACTGAGCAATTTGGATTGGAAGAAGAGATGCACGAGCTATCTGAAAAAAGAG
CTCGTGCAATTGGAAATTATTTAATAAAAATGAAAGTAAAAGACAAAGACCAAATACTATTTAA
AGGATGGGGATCTCAAAAACCAAAATATCCTAAGTCCTCCCCATTAAAGGCTAAAAATAGGCG
AGTAGAAATTACAATATTAAATAACTAA f792.aa (SEQ ID NO:345)
MKIFIYWVVIFFFSVFKVFSIYSLTDEEFFKKYSLFFVHKGFLSKNVNGKITKVQVNGINSRWVYPFY
KLVPSRITSIYEDVYSSSSFLTTSNNLYVSYDYSKNFRKLVGIDKFNSGAYITSSAFSQGDYKRIAIGT
AIHGIYLSVNGAISFKNLNRLIPQIYLGAGYYDIISAIEFSKEETNNLYFSSGVYGDIFLISQKSGFIKKIS
FPFKKQIIRILDLSSKNVEKILVRTYDNHFYSYINGQWVFIGKLSLQDQDFFEKSQRMQLAKNKGSIY
LTAYTLRNKKAVDERFKFIKDSGMNAVVIDFKDDNGNLTYSSKLSLPNKLRSVKNFIDVPYILKKAK
ELGIYVIARCVVFKDSKLYYYDNFKHALWNKKTNKPWAHLIKKVDSSGLVKYVQVEHWVDIFSPA
TWEYNISIAKEIQSFGVDEIQFDYIRFPSDGPVSLAISRMNKYEMQPVDALESFLIMAREQLYVPISVD
IYGYNGWFPTNSIGQNISMLSDYVDVISPMFYPSHYTDDFLPSNFYYTKRAYRIYKEGSDRALAFSL
DGVVIRPYVQAFLLGKERLVDDEIYLEYLKFQLKGIKESFGSGFSLWNASNVYYMIKGSLKEYLDSF t792.aa (SEQ ID NO:346)
IYSLTDEEFFKKYSLFFVHKGFLSKNVNGKITKVQVNGINSRWVYPFYKLVPSRITSIYEDV
YSSSSFLTTSNNLYVSYDYSKNFRKLVGIDKFNSGAYITSSAFSQGDYKRIAIGTAIHGIYLSVNGAISF
KNLNRLIPQIYLGAGYYDIISAIEFSKEETNNLYFSSGVYGDIFLISQKSGFIKKISFPFKKQIIRILDLSS
KNVEKILVRTYDNHFYSYINGQWVFIGKLSLQDQDFFEKSQRMQLAKNKGSIYLTAYTLRNKKAVD
ERFKFIKDSGMNAVVIDFKDDNGNLTYSSKLSLPNKLRSVKNFIDVPYILKKAKELGIYVIARCVVFK
DSKLYYYDNFKHALWNKKTNKPWAHLIKKVDSSGLVKYVQVEHWVDIFSPATWEYNISIAKEIQSF
GVDEIQFDYIRFPSDGPVSLAISRMNKYEMQPVDALESFLIMAREQLYVPISVDIYGYNGWFPTNSIG
QNISMLSDYVDVISPMFYPSHYTDDFLPSNFYYTKRAYRIYKEGSDRALAFSLDGVVIRPYVQAFLL
GKEFLVDDEIYLEYLKFQLKGIKESFGSGFSLWNASNVYYMIKGSLKEYLDSF f792.nt (SEQ ID NO:347)
ATGAAAATTTTTATCTATTGGGTAGTTATTTTCTTCTTTTCTGTTTTCAAGGTTTTTAGT
ATATATTCATTAACCGATGAAGAATTTTTTAAAAAATATAGTTTATTTTTTGTTCATAAAGGATT
TTTAAGTAAAAATGTTAATGGGAAATAACCAAAGTTCAAGTCAATGGGATAAATTCTAGGTG
GGTTTACCCTTTTTATAAGCTTGTTCCTAGTCGAATTACTTCTATTTATGAGGATGTTTATTCTTC
AAGTTCATTTTTGACTACAAGTAACAATCTTTATGTTTCTTATGATTATTCAAAAAATTTTAGAA
AATTAGTAGGAATTGATAAATTTAATAGCGGTGCATATATTACATCTAGTGCCTTTTCTCAAGG
AGATTACAAGCGTATTGCTATTGGAACTGCGATTCATGGTATTTATCTTAGTGTTAATGGAGCT
ATTAGTTTTAAAAATTTAAATCGTTTGATTCCGCAGATTTATTTAGGTGCAGGATATTACGATAT
TATTAGTGCTATTGAATTTTCAAAAGAAGAGACAAATAATTTATATTTTTCCTCTGGAGTTTATG
GAGATATTTTTTTAATTAGTCAGAAAAGTGGGATTTATTAAAAAAAATATCTTTTCCTTTCAAAAA
GCAAATAATACGTATTTTAGACTTATCTAGTAAGAATGTAGAAAAAATTTTAGTCAGAACATAT
GACAATCATTTTTATTCTTATATTAATGGGCAATGGGTATTTATTGGAAAATTATCTTTGCAGGA
TCAGGATTTTTTTGAAAAATCACAAAGGATGCAGCTTGCTAAAAATAAAGGGTCTATTTATTTTA
ACAGCATATACATTGCGTAATAAGAAGGCAGTTGATGAAAGATTTAAATTTATTAAAGATTCAG
GTATGAATGCTGTTGTAATTGATTTTAAAGATGATAATGGTAATTTGACTTATTCTAGCAAGCTT
TCTTTGCCCAATAAGTTGAGATCTGTTAAAAACTTTATTGATGTTCCTTATATTCTTAAAAAAGC
AAAAGAGCTTGGAATTTATGTTATTGCTAGATGTGTTGTATTTAAAGATTCAAAATTGTATTATT
ATGATAATTTTAAACACGCCCTTTGGAATAAAAAAACCAATAAACCTTGGGCTCATTTGATTAA
AAAGTTGATTCTAGTGGTCTTGTGAAATATGTACAAGTAGAGCATTGGGTAGATATTTTTTCT
CCTGCTACTTGGGAATATAATATTTCTATCGCAAAAGAAATTCAATCTTTTGGAGTTGACGAGA
TACAATTTGATTATATTAGATTTCCATCAGATGGGCCTGTGTCTCTTGCAATCTCAAGAATGAAT
AAGTATGAGATGCAACCCGTTGATGCACTTGAATCTTTTTTGATTATGGCCAAGAGAACAGCTTT
ATGTTCCTATTTCTGTTGATATTTATGGGTACAATGGCTGGTTTCCTACTAATAGTATTGGGCAA
AATATTTCAATGTTATCAGATTATGTTGACGTCATATCTCCTATGTTTTATCCTTCGCATTATAC
TGATGATTTTTTGCCAAGCAATTTTTATTACACAAAAAGAGCTTATAGGATTTATAAAGAGGGG
AGTGATAGAGCACTTGCTTTTTCTTTAGATGGGGTTGTTATTAGGCCTTATGTTCAAGCTTTTTT
ATTAGGGAAAGAAAGATTGGTGGATGACGAGATTTATTTGGAGTATTTAAAGTTTCAGCTTAAA
GGAATTAAAGAGTCATTTGGTAGTGGCTTTAGCCTTTGGAATGCATCTAATGTTTATTATATGA
TTAAAGGTAGTTTAAAAGAATATTTAGATTCTTTTTTA t792.nt (SEQ ID NO:348)
ATATATTCATTAACCGATGAAGAATTTTTTAAAAAATATAGTTTATTTTTTGTTCATAA
AGGATTTTTAAGTAAAAATGTTAATGGGAAATAACCAAAGTTCAAGTCAATGGGATAAATTCT
AGGTGGGTTTACCCTTTTTATAAGCTTGTTCCTAGTCGAATTACTTCTATTTATGAGGATGTTTA
TTCTTCAAGTTCATTTTTGACTACAAGTAACAATCTTTATGTTTCTTATGATTATTCAAAAAATT
TTAGAAAATTAGTAGGAATTGATAAATTTAATAGCGGTGCATATATTACATCTAGTGCCTTTTC
TCAAGGAGATTACAAGCGTATTGCTATTGGAACTGCGATTCATGGTATTTATCTTAGTGTTAAT
GGAGCTATTAGTTTTAAAAATTTAAATCGTTTGATTCCGCAGATTTATTTAGGTGCAGGATATT
ACGATATTATTAGTGCTATTGAATTTTCAAAAGAAGAGACAAATAATTTATATTTTTCCTCTGG
AGTTTATGGAGATATTTTTTTAATTAGTCAGAAAAGTGGGATTTATTAAAAAAAATATCTTTTCCTT
TCAAAAAGCAAATAATACGTATTTTAGACTTATCTAGTAAGAATGTAGAAAAAATTTTAGTCAG
AACATATGACAATCATTTTTATTCTTATATTAATGGGCAATGGGTATTTATTGGAAAATTATCTT
TGCAGGATCAGGATTTTTTTGAAAAATCACAAAGGATGCAGCTTGCTAAAAATAAAGGGTCTAT
TTATTTTAACAGCATATACATTGCGTAATAAGAAGGCAGTTGATGAAAGATTTAAATTTATTAAA
GATTCAGGTATGAATGCTGTTGTAATTGATTTTAAAGATGATAATGGTAATTTGACTTATTCTA
GCAAGCTTTCTTTGCCCAATAAGTTGAGATCTGTTAAAAACTTTATTGATGTTCCTTATATTCTT
AAAAAAGCAAAAGAGCTTGGAATTTATGTTATTGCTAGATGTGTTGTATTTAAAGATTCAAAAT
```

TABLE 1-continued

Nucleotide and Amino Acid Sequences.

TGTATTATTATGATAATTTTAAACACGCCCTTTGGAATAAAAAAACCAATAAACCTTGGGCTCA
TTTGATTAAAAAAGTTGATTCTAGTGGTCTTGTGAAATATGTACAAGTAGAGCATTGGGTAGAT
ATTTTTTCTCCTGCTACTTGGGAATATAATATTTCTATCGCAAAAGAAATTCAATCTTTTGGAGT
TGACGAGATACAATTTGATTATATTAGATTTCCATCAGATGGGCCTGTGTCTCTTGCAATCTCAA
GAATGAATAAGTATGAGATGCAACCCGTTGATGCACTTGAATCTTTTTTGATTATGGCAAGAGA
ACAGCTTTATGTTCCTATTTCTGTTGATATTTATGGGTACAATGGCTGGTTTCCTACTAATAGTA
TTGGGCAAAATATTTCAATGTTATCAGATTATGTTGACGTCATATCTCCTATGTTTTATCCTTCG
CATTATACTGATGATTTTTTGCCAAGCAATTTTTATTACACAAAAAGAGCTTATAGGATTTATAA
AGAGGGGAGTGATAGAGCACTTGCTTTTTCTTTAGATGGGGTTGTTATTAGGCCTTATGTTCAA
GCTTTTTTTATTAGGAAAAGAAAGATTGGTGGATGACGAGATTTATTTGGAGTATTTAAAGTTTC
AGCTTAAAGGAATTAAAGAGTCATTTGGTAGTGGCTTTAGCCTTTGGAATGCATCTAATGTTTA
TTATATGATTAAAGGTAGTTTAAAAGAATATTTAGATTCTTTTTAA f797.aa (SEQ ID NO:349)
MSIKKFILTLIILSLAKNSFSENEINIFENENYIVKENIKTEIKKLKQSFLLASVDVAISQPYIEL
ADLNGEPIKELEGISYSFINVFSKIGSSAIISFDLSNEASKKYKIIKLEFLSPDKGNFINQLSSLTSGKQQS
KKELAKDAYSFGTLRTESLSKTIAEYYKDNNWYYILAAITVENNINKETEKYEIRINPKIYNDFQKKL
RLHFKSNQIKKFPIPIIE t797.aa (SEQ ID NO:350)
KNSFSENEINIFENENYIVKENIKTEIKKLKQSFLLASVDVAISQPYIELADLNGEPIKELEGIS
YSFINVFSKIGSSAIISFDLSNEASKKYKIIKLEFLSPDKGNFINQLSSLTSGKQQSKKELAKDAYSFGT
LRTESLSKTIAEYYKDNNWYYILAAITVENNINKETEKYEIRINPKIYNDFQKKLRLHFKSNQIKKFPI
PIIE f797.nt (SEQ ID NO:351)
ATGAGCATTAAAAAATTTATTTTAACCTTGATAATTCTTTCTCTAGCTAAAAATAGCTTT
TCTGAAAACGAAATTAATATCTTCGAAAACGAAAATTATATTGTAAAAGAAAATATAAAACA
GAAATTAAAAAACTAAAACAAAGTTTTTTACTTGCATCTGTTGATGTCGCCATTAGCCAACCCT
ACATAGAATTGGCAGATTTAAATGGAGAACCGATAAAAGAACTTGAAGGGATTAGTTATTCAT
TTATAAATGTATTTTCAAAAATTGGATCTTCTGCTATTATTTCATTTGACCTATCAAACGAAGCT
TCCAAGAAATACAAAATCATAAAATTAGAATTTTTAAGTCCAGATAAAGGCAATTTTATTAACC
AGCTAAGCAGCCTTACTAGTGGAAAACAGCAATCAAAAAAAGAGCTTGCAAAAGACGCTTACT
CATTTGGTACATTAAGAACTGAATCTCTTTCAAAAACAATTGCAGAATATTACAAAGATAACAA
CTGGTATTATATTTTAGCAGCAATAACAGTAGAAAATAATATAAATAAGAAACTGAAAATA
CGAAATTAGAATTAACCCTAAAATATATAATGATTTTCAAAAAAAATTGAGATTACATTTTAAA
AGCAACCAAATAAAAAAATTTCCAATACCCATTATAGAATAA t797.nt (SEQ ID NO:352)
AAAAATAGCTTTTCTGAAAACGAAATTAATATCTTCGAAAACGAAAATTATATTGTAAA
AGAAAATATAAAACAGAAATTAAAAAACTAAAACAAAGTTTTTTACTTGCATCTGTTGATGTC
GCCATTAGCCAACCCTACATAGAATTGGCAGATTTAAATGGAGAACCGATAAAAGAACTTGAA
GGGATTAGTTATTCATTTATAAATGTATTTTCAAAAATTGGATCTTCTGCTATTATTTCATTTGA
CCTATCAAACGAAGCTTCCAAGAAATACAAAATCATAAAATTAGAATTTTTAAGTCCAGATAAA
GGCAATTTTATTAACCAGCTAAGCAGCCTTACTAGTGGAAAACAGCAATCAAAAAAAGAGCTT
GCAAAAGACGCTTACTCATTTGGTACATTAAGAACTGAATCTCTTTCAAAAACAATTGCAGAAT
ATTACAAAGATAACAACTGGTATTATATTTTAGCAGCAATAACAGTAGAAAATAATATAAATAA
AGAAACTGAAAAATACGAAATTAGAATTAACCCTAAAATATATAATGATTTTCAAAAAAAATTG
AGATTACATTTTAAAAGCAACCAAATAAAAAAATTTCCAATACCCATTATAGAATAA f799.aa (SEQ ID NO:353)
MKKHIIIGIIFVAILLFFKILLIPRIQNHENNKNNIKMIISYKQDKNRLSLKINIKTKKTTNLGK
AKLDIYLDSKLIESNLLYISSKNFTTYANIIYQNESLLSIILKSNGNNNVFYSKRIKPRGKI t799.aa (SEQ ID NO:354)
HENNKNNIKMIISYKQDKNRLSLKINIKTKKTTNLGKAKLDIYLDSKLIESNLLYISSKNFTTYANIIY
QNESLLSIILKSNGNNNVFYSKRIKPRGKI f799.nt (SEQ ID NO:355)
ATGAAACATATCATTATTGGGATAATCTTTGTTGCAATTCTTTTATTTTTTAAAATTTTATT
AATTCCCAGAATTCAAAATCACGAAAATAATAAAAATAATATCAAAATGATAATAAGCTACAA
GCAAGACAAAAACAGATTATCGCTAAAGATAAACATAAAAACAAAAAAAACTACCAACCTGGG
AAAAGCCAAACTAGATATTTATCTAGACAGTAAATTAATTGAAAGCAATTTGCTTTATATAAGC
AGCAAAAACTTTACAACATATGCTAATATAATCTATCAAAATGAAAGTTTATTAAGTATAATAT
TAAAGAGTAATGGCAATAATAATGTCTTTTATAGTAAAAGAATAAAACCTAGAGGTAAAATAT
GA t799.nt (SEQ ID NO:356)
CACGAAAATAATAAAAATAATATCAAAATGATAATAAGCTACAAGCAAGACAAAAACA
GATTATCGCTAAAGATAAACATAAAAACAAAAAAAACTACCAACCTGGGAAAAGCCAAACTAG
ATATTTATCTAGACAGTAAATTAATTGAAAGCAATTTGCTTTATATAAGCAGCAAAAACTTTAC
AACATATGCTAATATAATCTATCAAAATGAAAGTTTATTAAGTATAATATTAAAGAGTAATGGC
AATAATAATGTCTTTTATAGTAAAAGAATAAAACCTAGAGGTAAAATATGA f800.aa (SEQ ID NO:357)
MKKHYKALILSLLFAIISCNTKTLNELGEEQFKIPFGTLPGAIMPLNNKFTNSKFDIKTYNGL
VYIAEIKTNKLMIFNSYGKLIQTYQNGIFKTNPDLKIKKIDFEGIQAIYPLKDFIIVADKLNNKKSKFN

TABLE 1-continued

Nucleotide and Amino Acid Sequences.

QKENIAYFMRILILNKNSSVEILGQEGLNGMPFPQIYDVNVDENGNIAIISIYSEGYIIYSYNKEFSPLY
KIYVNKNLLKTIDNQKKKYNISIDKVFFEVNKKTLYVKTTYYENIGDNENINDLGIKIKDQYIYKMS
LKKNKELEVINKIALPKNLLDDKQESFINIIKIQKDKIIASTNMKNLSNNLIWKLDSKGSIKEQIALIEP
PNLMFLSESLSKDGILSILYGGKTGVSVYWWNLALLKL t800.aa (SEQ ID NO:358)
KTLNELGEEQFKIPFGTLPGAIMPLNNKFTNSKFDIKTYNGLVYIAEIKTNTKLMIFNSYGKLI
QTYQNGIFKTNTPDLKIKKIDFEGIQAIYPLKDFIIVADKLNNKKSKFNQKENIAYFMRILILNKNSSVEI
LGQEGLNGMPFPQIYDVNVDENGNIAIISIYSEGYIIYSYNKEFSPLYKIYVNKNLLKTIDNQKKKYNI
SIDKVFFEVNKKTLYVKTYYYENIGDNENINDLGIKIKDQYIYKMSLKKNKELEVINKIALPKNLLDD
KQESFINIIKIQKDKIIASTNMKNLSNNLIWKLDSKGSIKEQIALIEPPNLMFLSESLSKDGILSILYGGK
TGVSVYWWNLNALLKL f800.nt (SEQ ID NO:359)
ATGAAAAAACACTATAAAGCTCTTATATTAAGCTTGCTTTTTGCAATTATATCATGTAA
TACTAAAACTTTAAACGAATTAGGAGAAGAACAATTTAAAATACCATTTGGAACACTTCCTGGT
GCAATAATGCCTCTGAATAACAAATTTACAAATTCAAAATTTGACATCAAAACGTATAACGGGC
TAGTGTACATTGCAGAAATAAAAACAAATAAATTAATGATTTTCAACTCATACGGAAAACTAAT
ACAAACATATCAAAATGGAATATTTAAAACAAACCCCGATTTAAAAATAAAAAAAATAGATTTT
GAAGGAATTCAAGCAATATACCCACTAAAAGATTTTATTATTGTCGCAGACAAACTAAATAATA
AAAAATCAAAATTCAACCAAAAAGAGAATATTGCCTACTTCATGAGAATACTAATACTAAACAA
AAACTCATCTCTGTAGAAATTTTGGGTCAAGAAGGTTTAAACGGAATGCCATTTCCACAAATTTAT
GATGTTAATGTTGATGAAAATGGCAACATTGCAATAATATCAATATATAGCGAAGGATATATAA
TATATTCTTACAATAAAGAATTTTCCCCGCTTTATAAAATTTACGTCAACAAAAACCTGTTAAAA
ACAATAGACAATCAAAAGAAAAAATACAACATTTCAATAGATAAGGTTTTTTTTGAAGTCAACA
AAAAAAAACTCTTTATGTAAAAACTACTTACTATGAAAACATTGGTGACAATGAAAATATAAACGA
TCTTGGAATTAAAATTAAAGATCAATATATCTATAAAATGAGTTTGAAAAAAAACAAAGA
ATTAGAAGTGATAAATAAAATTGCTCTTCCTAAAAAACTTACTAGATGATAAACAAGAAAGCTTTATAA
ACATTATAAAAATACAAAAAGACAAAATAATAGCATCTACTAATATGAAAAATTTATCTAACAA
TTTAATATGGAAATTAGACAGCAAGGGCTCAATTAAAGAACAAATAGCTTTAATTGAGCCTCCA
AATTTAATGTTTCTCTCTGAGAGTTTATCTAAAGATGGAATACTTAGTATACTTTATGGCGGAA
AAACTGGTGTTAGTGTTTACTGGTGGAATTTAAATGCATTATTAAAATTATAA t800.nt (SEQ ID NO:360)
AAAACTTTAAACGAATTAGGAGAAGAACAATTTAAAATACCATTTGGAACACTTCCTG
GTGCAATAATGCCTCTGAATAACAAATTTACAAATTCAAAATTTGACATCAAAACGTATAACGG
GCTAGTGTACATTGCAGAAATAAAAACAAATAAATTAATGATTTTCAACTCATACGGAAAACTA
ATACAAACATATCAAAATGGAATATTTAAAACAAACCCCGATTTAAAAATAAAAAAAATAGAT
TTTGAAGGAATTCAAGCAATATACCCACTAAAAGATTTTATTATTGTCGCAGACAAACTAAATA
ATAAAAAATCAAAATTCAACCAAAAAGAGAATATTGCCTACTTCATGAGAATACTAATACTAAA
CAAAAACTCATCTGTAGAAATTTTGGGTCAAGAAGGTTTAAACGGAATGCCATTTCCACAAATT
TATGATGTTAATGTTGATGAAAATGGCAACATTGCAATAATATCAATATATAGCGAAGGATATA
TAATATATTCTTACAATAAAGAATTTTCCCCGCTTTATAAAATTTACGTCAACAAAAACCTGTTA
AAAACAATAGACAATCAAAAGAAAAAATACAACATTTCAATAGATAAGGTTTTTTTTGAAGTCA
ACAAAAAAAACTCTTTATGTAAAAACTACTTACTATGAAAACATTGGTGACAATGAAAATATAAA
CGATCTTGGAATTAAAATTAAAGATCAATATATCTATAAAATGAGTTTGAAAAAAAACAAAGA
ATTAGAAGTGATAAATAAAATTGCTCTTCCTAAAAAACTTACTAGATGATAAACAAGAAAGCTTT
ATAAACATTATAAAAATACAAAAAGACAAAATAATAGCATCTACTAATATGAAAAATTTATCTA
ACAATTTAATATGGAAATTAGACAGCAAGGGCTCAATTAAAGAACAAATAGCTTTAATTGAGCC
TCCAAATTTAATGTTTCTCTCTGAGAGTTTATCTAAAGATGGAATACTTAGTATACTTTATGGCG
GAAAAACTGGTGTTAGTGTTTACTGGTGGAATTTAAATGCATTATTAAAATTATAA f810.aa (SEQ ID NO:361)
MYKLFLFFIIFMFLSCDEKKSSKNLKSVKIGYVNWGGETAATNVLKVVFEKMGYNAEIFSV
TTSIMYQYLASGKIDGTVSSWVPTADKFYYEKLKTKFVDLGANYEGTIQGFVVPSYVPISSISELKG
KGDKFKNKMIGIDAGAGTQIVTEQALNYYGLSKEYELVPSSESVMLASLDSSIKRNEWILVPLWKPH
WAFSRYDIKFLDDPDLIMGGIESVHTLVRLGLENDDFDAYYVFDHFYWSDDLILPLMDKNDKEPGK
EYRNAVEFVEKNKEIVKTWVPEKYKTLFD t810.aa (SEQ ID NO:362)
CDEKKSSKNLKSVKIGYVNWGGETAATNVLKVVFEKMGYNAEIFSVTTSIMYQYLASGKIDGTVSS
WVPTADKFYYEKLKTKFVDLGANYEGTIQGFVVPSYVPISSISELKGKGDKFKNKMIGIDAGAGTQI
VTEQALNYYGLSKEYELVPSSESVMLASLDSSIKRNEWILVPLWKPHWAFSRYDIKFLDDPDLIMGG
IESVHTLVRLGLENDDFDAYYVFDHFYWSDDLILPLMDKNDKEPGKEYRNAVEFVEKNKEIVKTW
VPEKYKTLFD f810.nt (SEQ ID NO:363)
ATGTATAAATTATTTTTATTTTTTATTATTTTTTATGTTTTTGTCTTGTGATGAAAAAAAG
AGTTCAAAGAATTTAAAATCGGTAAAAATTGGATATGTGAATTGGGGTGGAGAAACGGCAGCT
ACAAATGTATTAAAGGTTGTTTTTGAGAAAATGGGCTACAATGCAGAAATATTTTCAGTTACTA
CGTCTATAATGTATCAATACTTAGCATCTGGAAAGATAGACGGTACGGTGTCTTCTTGGGTTCC
TACAGCCGATAAATTTTATTATGAAAAACTGAAAACAAAGTTTGTTGATCTTGGTGCAAATTAT
GAAGGAACCATTCAAGGTTTTGTGGTGCCAAGCTATGTTCCAATTTCCAGCATTAGTGAGCTTA
AGGGTAAAGGTGATAAGTTTAAAAACAAAATGATTGGCATAGATGCTGGTGCGGGAACTCAAA
TTGTTACAGAACAAGCGCTTAATTATTATGGATTAAGTAAAGAGTATGAGCTAGTTCCTTCAAG
TGAGAGTGTTATGCTTGCAAGTTTAGATTCTTCAATAAAGAGAAACGAATGGATTTTAGTTCCT
TTGTGGAAGCCTCATTGGGCTTTTTCTAGGTATGATATTAAGTTTCTTGATGATCCTGATTTAAT

TABLE 1-continued

Nucleotide and Amino Acid Sequences.

TATGGGGGGAATTGAGAGCGTGCATACTCTTGTTAGACTTGGTCTTGAAAATGATGATTTTGAT
GCATATTATGTTTTTGATCATTTTTATTGGAGCGATGATTTAATATTGCCCTTAATGGATAAAA
TGATAAAGAGCCAGGCAAAGAATACCGCAATGCGGTTGAATTTGTTGAAAAGAATAAAGAGAT
TGTAAAGACGTGGGTTCCAGAAAAATATAAGACCTTATTTGATTAA t810.nt (SEQ ID NO:364)
TGTGATGAAAAAAAGAGTTCAAAGAATTTAAAATCGGTAAAAATTGGATATGTGAATT
GGGGTGGAGAAACGGCAGCTACAAATGTATTAAAGGTTGTTTTTGAGAAAATGGGCTACAATG
CAGAAATATTTTCAGTTACTACGTCTATAATGTATCAATACTTAGCATCTGGAAAGATAGACGG
TACGGTGTCTTCTTGGGTTCCTACAGCCGATAAATTTTATTATGAAAAACTGAAAACAAAGTTT
GTTGATCTTGGTGCAAATTATGAAGGAACCATTCAAGGTTTTGTGGTGCCAAGCTATGTTCCAA
TTTCCAGCATTAGTGAGCTTAAGGGTAAAGGTGATAAGTTTAAAAACAAAATGATTGGCATAG
ATGCTGGTCGGGAACTCAAATTGTTACAGAACAAGCGCTTAATTATTATGGATTAAGTAAAGA
GTATGAGCTAGTTCCTTCAAGTGAGAGTGTTATGCTTGCAAGTTTAGATTCTTCAATAAAGAGA
AACGAATGGATTTTAGTTCCTTTGTGGAAGCCTCATTGGGCTTTTTCTAGGTATGATATTAAGTT
TCTTGATGATCCTGATTTAATTATGGGGGGAATTGAGAGCGTGCATACTCTTGTTAGACTTGGT
CTTGAAAATGATGATTTTGATGCATATTATGTTTTTGATCATTTTTATTGGAGCGATGATTTAAT
ATTGCCCTTAATGGATAAAAATGATAAAGAGCCAGGCAAAGAATACCGCAATGCGGTTGAATT
TGTTGAAAAGAATAAAGAGATTGTAAAGACGTGGGTTCCAGAAAAATATAAGACCTTATTTGA
TTAA f814.aa (SEQ ID NO:365)
MLVKRIVGKPITMLILFSLLLMISLYTFSRLKVDLLPGIDIPQISIHTVYPGASPREVEESVSRVLESGLS
SVKNLKNIYSVSSKESSTVSLEFYHGTDLDLVLNEIRDALELVKSSLPSKSQTPRIFRYNLKNIPVMEI
VINSVRPVSELKRYADEIIKPGLERLDGVAIVTVNGGSKKRVLIEVSQNRLESYGLSLSRISSIIASQNL
ELSAGNILENNLEYLVEVSGKFKSIEEIGNVVIAYKIPDISSGINSPIEIKLKDIANIKTDFEDLSEYVE
YNGLPSISLSVQKRSDSNSIAVSNVVMNEIEKLKLSMPKDMKLEIASDSTDFIKASISTVVNSAYFGA
MLAIFVIFFFLRSFRATIIIGISIPIAIVLTFCLMYFVNISLNIMSLAGLALGIGMVVDCSIVVIDNIYKYR
QKGAKLISSSILGAQEMMLPITSSTFTSICVFGPFLIFKSELGVYGDFFKDFTFTIVISLGVSLLVAIFLV
PVLSSHYVGLYTSFQKNIKNAFIRKIDAFFASIYYFLEFLYINLLNIVLNHKLIFGLIVFFSFIGSLLLGLL
LDVTTFTRGKENSITINLNFPHKTNLEYAKFYSNRFLEIVKSEAKGYKSIIATLRADRITFNVLFPLKEE
SRDNLTQSVDYDSIKYKIMNRIGNLYPEFNIEPSISGNALGGGDSIKIKISANDFEYIKDYGKILVSML
KKEIPELVNPRLSISDFQLQIGVEIDRALVYNYGIDMNTILNELKANINGVVAGQYVEKGLNYDIVLK
LDRMDVKNLKDLEKIFITNSSGVKIPFSSIATFEKTNKAESIYRENQALTIYLNAGISPDDNLTQVTAK
VVDFINNKVPHKEGITLKVEGEYNEFSNIMNQFKIIIMMAIIVVFGIMASQFESFLKPFIIIFTIPLTAIGV
VLIHFLAGEKLSIFAAIGMLMLVGVVVNTGIVLVDYTGLLIKRGFGLREAIIESCRSRLRPILMSSLTSII
GLIPMAFSSGSGNELLKPIAFTFIGGMTASTFLTLFFIPMLFEIFPTCFKFQI t814.aa (SEQ ID NO:366)
RLKVDLLPGIDIPQISIHTVYPGASPREVEESVSRVLESGLSSVKNLKNIYSVSSKESSTVSLEF
YHGTDLDLVLNEIRDALELVKSSLPSKSQTPRIFRYNLKNIPVMEIVINSVRPVSELKRYADEIIKPGL
ERLDGVAIVTVNGGSKKRVLIEVSQNRLESYGLSLSRISSIIASQNLELSAGNILENNLEYLVEVSGKF
KSIEEIGNVVIAYKIPDISSGINLSPIEIKLKDIANIKTDFEDLSEYVEYNGLPSISLSVQKRSDSNIAVS
NVVMNEIEKLKLSMPKDMKLEIASDSTDFIKASISTVVNSAYFGAMLAIFVIFFFLRSFPATIIIGISIPIA
IVLTFCLMYFVNISLNIMSLAGLALGIGMVVDCSIVVIDNIYKYRQKGAKLISSSILGAQEMMLPITSS
TFTSICVFGPFLIFKSELGVYGDFFKDFTFTIVISLGVSLLVAIFLVPVLSSHYVGLYTSFQKNIKNAFIR
KIDAFFASIYYFLEFLYIINLLNIVLNHKLIFGLIVFFSFIGSLLLGLLLDVTTFTRGKENSITTNLNFPHKT
NLEYAKFYSNRFLEIVKSEAKGYKSIIATLRADRITFNVLFPLKEESRDNLTQSVDYDSIKYKIMNRIG
NLYPEFNIEPSISGNALGGGDSIKIKISANDFEYIKDYGKILVSMLKKEIPELVNPRLSISDFQLQIGVEI
DRALVYNYGIDMNTILNEKLKANINGVVAGQYVEKGLNYDIVLKLDRMDVKNLKDLKIFITNSSGV
KIPSSIATEKTNKAESIYRENQALTIYLNAGISDDNLTQVTAKVVDFINNKVPHKEGITLKVEGEY
NEFSNIMNQFKIIIMMAIIVVFGIMASQFESFLKPFIIIFTIPLTAIGVVLIHFLAGEKLSIFAAIGMLMLV
GVVVNTGIVLDYTGLLIKRGFGLREAIIESCRSRLRPILMSSLTSIIGLIPMAFSSGSGNELLKPIAFTFI
GGMTASTFLTLFFIPMLFEIFPTCFKFQI f814.nt (SEQ ID NO:367)
ATGTTGGTAAAGAGAATAGTTGGCAAACCAATAACAATGTTGATTTATTTTCATTGTTATTGA
TGATAAGTTTGTATACCTTTTCAAGATTAAAAGTAGATCTTTTGCCGGGAATTGACATTCCCCA
AATAAGTATTCACACTGTTTATCCTGGCGCTTCTCCTAGAGAAGTTGAAGAGAGTGTTTCTAGA
GTCCTTGAGAGTGGCTTGAGTTCGGTAAAGAATTTAAAAAATATATATAGTGTATCTTCCAAAG
AAAGCAGCACCGTTTCACTTGAATTTTATCATGGAACCGATTTAGATTTGGTTTTAAATGAAAT
TCGAGATGCTCTTGAATTGGTAAAATCTTCATTGCCCAGCAAATCACAGACCCCAAGAATTTTT
AGATACAATCTTAAAAACATCCCTGTAATGGAAATTGTTATTAATTCTGTAAGGCCAGTTTCTG
AGCTTAAAAGATATGCCGATGAAATCATTAAACCTGGGCTTGAAAGGCTTGATGGAGTTGCAAT
TGTTACTGTTAATGGTGGAAGTAAAAAGCGTGTTTTAATTGAAGTTTCTCAAAACAGGCTGGAG
TCTTATGGGCTTTCTTTGTCAAGAATATCTTCAATTATAGCATCCCAAAATTTGGAACTTTCAGC
TGGCAATATATTGGAGAACAACTTGGAATATTTGGTTGAAGTTTCTGGAAAATTTAAATCAATT
GAAGAGATAGGTAATGTGGTCATAGCTTATAAGATACCCGACATTTCTTCTGGCATAAATTTAT
CTCCTATTGAGATAAAACTCAAAGATATTGCTAATATTAAAACCGATTTTGAAGATTTGTCTGA
ATATGTTGAATATAATGGGTTGCCTTCAATTTCTTTGTCGGTTCAAAACGTAGTGATTCTAATT
CTATTGCAGTTTCTAATGTTGTTATGAATGAAATAGAAAAATTGAAATTATCTATGCCTAAAGA
TATGAAATTGGAGATTGCTTCTGATAGTACTGATTTTATTAAAGCATCCATTTCAACGGTTGTA
AATTCAGCCTATTTTGGGGCCATGCTTGCAATATTTGTTATTTTTTTCTTTTTAAGAAGCTTTAG
GGCCACAATAATTATTGGAATTTCTATTCCAATAGCAATTGTTTTGACCTTTTGTTTAATGTATT
TTGTAAATATTTCTCTTAATATTATGAGTCTTGCGGGTCTTGCACTTGGGATTGGAATGGTTGTT
GACTGTTCAATTGTTGTAATAGACAATATATACAAATATAGGCAAAAGGAGCAAAGCTTATTT
CGTCTTCTATTCTCGGAGCTCAGGAGATGATGTTGCCTATTACATCTTCAACTTTTACTTCTATT

TABLE 1-continued

Nucleotide and Amino Acid Sequences.

TGTGTTTTTGGTCCATTTCTTATTTTCAAATCAGAACTTGGGGTATATGGAGATTTTTTCAAAGA
CTTTACATTTACGATTGTTATTTCCTTGGGTGTTTCTCTTTTAGTTGCAATTTTTTTGGTTCCTGT
TTTATCAAGCCACTATGTCGGTTTATACACAAGTTTCCAAAAGAATATTAAGAATGCTTTTATTA
GGAAAATCGATGCCTTTTTTTGCTAGTATTTATTATTTTTAGAGTTTTTGTATATCAATTTATTA
AATATAGTTTTAAATCACAAATTGATTTTTGGGTTGATTGTTTTTTTAGTTTTATTGGCAGCTT
GCTTTTAGGATTATTGTTAGATGTGACAACTTTTACTAGAGGGAAAGAGAACTCAATTACTATT
AATTTAAATTTTCCCCACAAAACTAATTTGGAATATGCAAAATTTTATTCTAATAGATTTTTAGA
AATTGTAAAAAGTGAGGCTAAAGGATATAAAAGTATTATTGCTACTTTGCGTGCTGATAGAATA
ACTTTCAACGTATTGTTTCCTCTCAAAGAAGAATCAAGAGATAATTTAACCCAAAGCGTAGATT
ACGATTCTATTAAATATAAAATTATGAATCGTATTGGTAATCTTTATCCTGAATTTAATATTGAG
CCTTCCATTAGTGGCAATGCTTTAGGTGGTGGAGATTCTATTAAAATTAAAATTTCGGCCAATG
ATTTTGAATATATAAAAGATTATGGAAAAATTTTAGTTTCCATGTTAAAAAAGGAAATTCCCGA
ACTTGTAAATCCAAGGCTTAGCATAAGTGATTTTCAGCTTCAAATTGGCGTTGAGATAGACAGA
GCGCTAGTTTATAATTATGGTATTGACATGAATACCATTTTAAATGAGTTGAAGGCCAATATTA
ATGGTGTTGTTGCTGGGCAATATGTGGAGAAGGGACTTAATTATGATATTGTTCTTAAGCTTGA
TAGAATGGATGTTAAAAATTTAAAAGATTTAGAAAAAATATTTATTACAAATTCATCTGGAGTT
AAAATTCCTTTTTCATCAATAGCCACCTTTGAAAAAACCAATAAAGCCGAATCTATTTACAGAG
AAAATCAAGCTTTAACCATTTATCTTAATGCGGGTATTTCTCCAGATGATAATTTAACCCAAGT
AACCGCAAAAGTTGTAGATTTTATTAATAATAAGGTGCCCCATAAAGAAGGCATAACTCTTAAG
GTTGAAGGAGAATATAATGAATTTTCAAATATCATGAATCAGTTTAAAATAATCATTATGATGG
CTATTATTGTTGTGTTTGGTATTATGGCTTCTCAATTTGAATCTTTTTTAAAACCCTTTATTATTA
TTTTACAATTCCTTTAACGGCAATAGGGGTTGTGCTTATACATTTTCTTGCAGGAGAAAAGCTT
TCTATTTTTGCTGCAATTGGTATGCTTATGCTTGTTGGTGTTGTTGGTAAATACAGGAATTGTTCT
TGTAGACTATACTGGTTTATTGATCAAGAGGGGATTTGGCCTAAGAGAAGCAATTATTGAATCT
TGTCGTTCAAGGCTTAGGCCAATTTTAATGTCTTCTTTGACCTCAATAATAGGGCTTATTCCAAT
GGCATTTTCTAGCGGAAGTGGAAATGAACTTCTAAAACCAATTGCATTTACTTTTATTGGCGGA
ATGACAGCTAGCACATTTCTTACTTTGTTTTTTATTCCCATGCTTTTTGAAATTTTTCCAACATGT
TTCAAGTTTCAAATCTAG t814.nt (SEQ ID NO:368)
AGATTAAAAGTAGATCTTTTGCCGGGAATTGACATTCCCCAAATAAGTATTCACACTGTTTATC
CTGGCGCTTCTCCTAGAGAAGTTGAAGAGAGTGTTTCTAGAGTCCTTGAGAGTGGCTTGAGTTC
GGTAAAGAATTTAAAAAATATATATAGTGTATCTTCCAAAGAAAGCAGCACCGTTTCACTTGAA
TTTTTATCATGGAACCGATTTAGATTTGGTTTTAAATGAAATTCGAGATGCTCTTGAATTGGTAA
AATCTTCATTGCCCAGCAAATCACAGACCCCAAGAATTTTTAGATACAATCTTAAAAACATCCC
TGTAATGGAAATTGTTATTAATTCTGTAAGGCCAGTTTCTGAGCTTAAAAGATATGCCGATGAA
ATCATTAAACCTGGGCTTGAAAGGCTTGATGGAGTTGCAATTGTTACTGTTAATGGTGGAAGTA
AAAAGCGTGTTTTAATTGAAGTTTCTCAAAACAGGCTGGAGTCTTATGGGCTTTCTTTGTCAAG
AATATCTTCAATTATAGCATCCCAAAATTTGGAACTTTCAGCTGGCAATATATTGGAGAACAAC
TTGGAATATTTGGTTGAAGTTTCTGGAAAATTTAAATCAATTGAAGAGATAGGTAATGTGGTCA
TAGCTTATAAGATACCCGACATTTCTTCTGGCATAAATTTATCTCCTATTGAGATAAAACTCAAA
GATATTGCTAATATTAAAACCGATTTTGAAGATTTGTCTGAATATGTTGAATATAATGGGTTGC
CTTCAATTTCTTTGTCGGTTCAAAAACGTAGTGATTCTAATTCTATTGCAGTTTCTAATGTTGTT
ATGAATGAAATAGAAAAATTGAAATTATCTATGCCTAAAGATATGAAATTGGAGATTGCTTCTG
ATAGTACTGATTTTATTAAAGCATCCATTTCAACGGTTGTAAATTCAGCCTATTTTGGGGCCATG
CTTGCAATATTTGTTATTTTTTCTTTTTAAGAAGCTTTAGGGCCACAATAATTATTGGAATTTC
TATTCCAATAGCAATTGTTTTGACCTTTTGTTTAATGTATTTTGTAAATATTTCTCTTAATATTAT
GAGTCTTGCGGGTCTTGCACTTGGGATTGGAATGGTTGTTGACTGTTCAATTGTTGTAATAGAC
AATATATACAAATATAGGCAAAAAGGAGCAAAGCTTATTTCGTCTTCTATTCTCGGAGCTCAGG
AGATGATGTTGCCTATTACATCTTCAACTTTTACTTCTATTTGTGTTTTTGGTCCATTTCTTATTT
TCAAATCAGAACTTGGGGTATATGGAGATTTTTTCAAAGACTTTACATTTACGATTGTTATTTCC
TTGGGTGTTTCTCTTTTAGTTGCAATTTTTTTGGTTCCTGTTTTATCAAGCCACTATGTCGGTTTA
TACACAAGTTTCCAAAAGAATATTAAGAATGCTTTTATTAGGAAAATCGATGCCTTTTTTTGCTA
GTATTTATTATTTTTAGAGTTTTTGTATATCAATTTATTAAATATAGTTTTAAATCACAAATTG
ATTTTTGGGTTGATTGTTTTTTTTAGTTTTATTGGCAGCTTGCTTTTAGGATTATTGTTAGATGTG
ACAACTTTTACTAGAGGGAAAGAGAACTCAATTACTATTAATTTAAATTTTCCCCACAAAACTA
ATTTGGAATATGCAAAATTTTATTCTAATAGATTTTTAGAAATTGTAAAAAGTGAGGCTAAAGG
ATATAAAAGTATTATTGCTACTTTGCGTGCTGATAGAATAACTTTCAACGTATTGTTTCCTCTCA
AAGAAGAATCAAGAGATAATTTAACCCAAAGCGTAGATTACGATTCTATTAAATATAAAATTAT
GAATCGTATTGGTAATCTTTATCCTGAATTTAATATTGAGCCTTCCATTAGTGGCAATGCTTTAG
GTGGTGGAGATTCTATTAAAATTAAAATTTCGGCCAATGATTTTGAATATATAAAAGATTATGG
AAAAATTTTAGTTTCCATGTTAAAAAAGGAAATTCCCGAACTTGTAAATCCAAGGCTTAGCATA
AGTGATTTTCAGCTTCAAATTGGCGTTGAGATAGACAGAGCGCTAGTTTATAATTATGGTATTG
ACATGAATACCATTTTAAATGAGTTGAAGGCCAATATTAATGGTGTTGTTGCTGGGCAATATGT
GGAGAAGGGACTTAATTATGATATTGTTCTTAAGCTTGATAGAATGGATGTTAAAAATTTAAAA
GATTTAGAAAAAATATTTATTACAAATTCATCTGGAGTTAAAATTCCTTTTTCATCAATAGCCAC
CTTTGAAAAAACCAATAAAGCCGAATCTATTTACAGAGAAAATCAAGCTTTAACCATTTATCTT
AATGCGGGTATTTCTCCAGATGATAATTTAACCCAAGTAACCGCAAAAGTTGTAGATTTTATTA
ATAATAAGGTGCCCCATAAAGAAGGCATAACTCTTAAGGTTGAAGGAGAATATAATGAATTTTC
AAATATCATGAATCAGTTTAAAATAATCATTATGATGGCTATTATTGTTGTGTTTGGTATTATGG
CTTCTCAATTTGAATCTTTTTTAAAACCCTTTATTATTATTTTTACAATTCCTTTAACGGCAATAG
GGGTTGTGCTTATACATTTTCTTGCAGGAGAAAAGCTTTCTATTTTTGCTGCAATTGGTATGCTT
ATGCTTGTTGGTGTTGTGTAAATACAGGAATTGTTCTTGTAGACTATACTGGTTTATTGATCAA
GAGGGGATTTGGCCTAAGAGAAGCAATTATTGAATCTTGTCGTTCAAGGCTTAGGCCAATTTTA
ATGTCTTCTTTGACCTCAATAATAGGGCTTATTCCAATGGCATTTTCTAGCGGAAGTGGAAATG
AACTTCTAAAACCAATTGCATTTACTTTTATTGGCGGAATGACAGCTAGCACATTCTTACTTTG
TTTTTTATTCCCATGCTTTTTGAAATTTTTCCAACATGTTTCAAGTTTCAAATCTAG

TABLE 1-continued

Nucleotide and Amino Acid Sequences.

f818.aa (SEQ ID NO:369)
MLKNHSKLIIQLKVVMMIYLKKMGNDMTKFYNYRIEIVSNLSLELDVFECIEKIEQELGESIYYSKIG
NVYGKGKKGEKHGNGVWPEENFILIIYTSNQSIVERLKDIVDDLNRSYPTEGINLFVLRNS t818.aa (SEQ ID NO:370)
KKMGNDMTKFYNYRIEIVSNLSLELDVFECIEKIEQELGESIYYSKIGNVYGKGKKGEKHG
NGVWPEENFILIIYTSNQSIVERLKDIVDDLNRSYPTEGINLFVLRNS f818.nt (SEQ ID NO:371)
ATGTTGAAAAATCATTCAAAATTAATAATTCAACTAAAAGTAGTTATGATGATTTATTTGAAGA
AGATGGGGAATGATATGACTAAATTTTATAATTATAGGATTGAAATAGTTTCTAACTTATCTTT
AGAGCTTGATGTTTTTGAATGTATAGAAAAAATAGAGCAAGAGTTAGGAGAGTCTATATATTAT
TCTAAGATAGGAAATGTTTATGGAAAAGGTAAGAAGGGAGAAAAGCATGGTAATGGCGTTTGG
CCTGAAGAAAATTTTATTTTGATTATTTATACCTCCAATCAGTCTATTGTTGAGCGATTAAAGGA
TATTGTGGATGATTTGAATCGTTCTTACCCTACAGAAGGGATTAATCTTTTTGTTTTGAGAAATT
CTTAA t818.nt (SEQ ID NO:372)
AAGAAGATGGGGAATGATATGACTAAATTTTATAATTATAGGATTGAAATAGTTTCTAACTTAT
CTTTAGAGCTTGATGTTTTTGAATGTATAGAAAAAATAGAGCAAGAGTTAGGAGAGTCTATATA
TTATTCTAAGATAGGAAATGTTTATGGAAAAGGTAAGAAGGGAGAAAAGCATGGTAATGGCGT
TTGGCCTGAAGAAAATTTTATTTTGATTATTTATACCTCCAATCAGTCTATTGTTGAGCGATTAA
AGGATATTGTGGATGATTTGAATCGTTCTTACCCTACAGAAGGGATTAATCTTTTTGTTTTGAG
AAATTCTTAA f820.aa (SEQ ID NO:373)
MLNNTYRIKTILTIFLAITLLTIYKYFTLMAFNNSPDNTISLKSNDIAKRGTIYDRNGKPIAFSSKSYSIG
TNPQKIENIVSTSETLGAILQINSRILKEKLSSNKGFLYIKRKIKREESDLIKRIQAEGRLSNITLYPDYT
RIYPFRNTTSNITGFVGTDNLGLEGIEFSLNSILGKDKTKQQFLNEEPETNNIHLTIDMDIQQGVSKIA
KKYFKENNPESLITLVMNSQNGEILSMVQFPQYDANFYSKYPEEIRKNLSSSLTYEPGSINKIFTVAIIL
ESGKLNLEEKFLDNGIYQKQFPSGEKITIKTLNPPYKHIDSTEILIYSSNVGIAYITEKVSNEYFYKKLL
DFGFGEKVGVPFPGETKGLLNHYSKWSGRSKATIGFGQEIGVSAVQILQAASILSNNGIMLKPRIIKKI
SNDKGENIKEFDKEEIRKVISKNSAQKVLKMMREVVNKGGIPNLKIKNLDISAKSGTSQAIDRKTGK
YSEEDYTSSILAIYPTEQPKYIIYIVYRYPKKIIYGTRIAAPMAKEIIEFIEHQQNTIAYKKIKMPSKIIKIP
KAETNYKNKTYLPNFINLSKREAIDILKYYKNTMKIKINGDGFVYKQSISPNTKLEDITELELYLK t820.aa (SEQ ID NO:374)
FNNSPDNTISLKSNDIAKRGTIYDRNGKPIAFSSKSYSIGTNPQKIENIVSTSETLGAILQINSRI
LKEKLSSNKGFLYIKRKIKREESDLIKRIQAEGRLSNITLYPDYTRIYPFRNTTSNITGFVGTDNLGLEG
IEFSLNSILGKDKTKQQFLNEEPETNNIHLTIDMDIQQGVSKIAKKYFKENNPESLITLVMNSQNGEIL
SMVQFPQYDANFYSKYPEEIRKNLSSSLTYEPGSINKIFTVAIILESGKLNLEEKFLDNGIYQKQFPSG
EKITIKTLNPPYKHIDSTEILIYSSNVGIAYITEKVSNEYFYKKLLDFGFGEKVGVPFPGETKGLLNHY
SKWSGRSKATIGFGQEIGVSAVQILQAASILSNNGIMLKPRIIKKISNDKGENIKEFDKEEIRKVISKNS
AQKVLKMMREVVNKGGIPNLKIKNLDISAKSGTSQAIDRKTGKYSEEDYTSSILAIYPTEQPKYIIYIV
YRYPKKIIYGTRIAAPMAKEIIEFIEHQQNTIAYKKIKMPSKIKIPKAETNYKNKTYLPNFINLSKREAEI
DILKYYKNTMKIKINGDGFVYKQSISPNTKLEDITELELYLK f820.nt (SEQ ID NO:375)
ATGCTTAATAACACTTATCGAATAAAAACAATATTAACAATATTCTTGGCTATAACTTTGTTAAC
TATTTACAAATATTTCACACTAATGGCCTTCAATAACAGCCCAGACAACACAATATCTTTAAAG
TCAAATGATATTGCCAAAAGAGGAACAATTTATGATAGAAATGGCAAACCAATAGCATTCTCTT
CAAAATCCTACTCAATTGGTACAAATCCTCAAAAAATAGAAAATATTGTAAGCACATCTGAAAC
TCTTGGTGCAATACTTCAAATTAATTCAAGAATTTTAAAGGAAAAGCTTCCTCTAACAAAGGG
TTTTTATATATAAAAAGAAAAATAAAAAGAGAAGAATCAGATTTAATAAAAAGAATTCAAGCT
GAAGGCAGGCTTTCAAACATCACTTTATATCCTGATTACACAAGAATTTATCCCTTCAGGAATA
CCACAAGCAATATTACTGGTTTTGTAGGAACAGATAATCTTGGCCTTGAGGGCATTGAATTTTC
CCTAAATAGCATATTAGGAAAAGATAAAACCAAGCAACAATTTTTAAATGAGGAGCCAGAAAC
AAACAACATCCACTTAACAATAGACATGGATATACAACAAGGTGTTAGCAAAATAGCTAAAAA
ATACTTTAAAGAAAATAATCCTGAAAGTTTAATTACCTTGGTAATGAACTCCCAAAATGGAGAA
ATATTATCCATGGTTCAATTTCCTCAATATGATGCAAACTTTTATTCTAAATATCCTGAAGAAAT
CCGAAAAAACCTTTCTTCATCTCTAACCTATGAGCCCGGAAGCATTAATAAAATTTTTACAGTT
GCAATAATATTAGAAAGTGGAAAATTAAATTTAGAAGAAAAATTTTTAGACAATGGAATATAT
CAAAAACAATTTCCATCAGGAGAAAAAATTACAATCAAAACATTAAATCCCCCCTATAAACATA
TCGACTCTACAGAGATTTTAATTTATTCATCAAATGTTGGAATAGCTTACATTACTGAAAAAGT
TAGCAATGAATACTTTTATAAAAAACTTTTAGATTTTGGCTTTGGGGAAAAAGTTGGAGTTCCA
TTTCCCGGAGAAACAAAAGGACTGCTAAATCATTATTCAAAATGGTCAGGACGAAGTAAAGCT
ACAATTGGATTTGGACAAGAAATAGGAGTGTCAGCGGTTCAAATATTACAAGCTGCAAGCATA
CTAAGCAATAATGGAATAATGCTAAAACCTAGAATAATAAAAAAAATAAGCAACGATAAAGGA
GAAAATATTAAAGAATTTGATAAAGAAGAAATAAGAAAGTAATATCCAAAAATTCAGCACAA
AAAGTTTTAAAAATGATGAGAGAAGTTGTAAATAAAGGTGGAATTCCAAATCTTAAAATTAAA
AATCTTGACATTTCTGCAAAAAGTGGAACATCTCAAGCTATTGATAGAAAAACGGGAAAATACT
CAGAAGAAGACTATACATCTTCTATATTGGCAATATACCCCACAGAACAACCAAAATATATTAT
TTACATTGTATACAGATACCCAAAAAAAATAATATACGGAACAAGAATAGCAGCCCCAATGGC
AAAAGAAATAATAGAATTTATTGAGCACCAACAAAATACAATAGCATATAAAAAAATTAAAAT
GCCATCAAAAATCAAGATCCCTAAAGCTGAAACTAATTACAAAAACAAAACATACTTACCAAAT
TTTATCAACCTTTCTAAAAGAGAAGCAATAGACATACTAAAATACTATAAAAATACTATGAAAA

TABLE 1-continued

Nucleotide and Amino Acid Sequences.

TAAAAATAAATGGCGATGGATTTGTTTACAAGCAAAGTATATCCCCCAATACAAAATTAGAAGA
TATAACAGAGCTTGAACTGTATTTAAAATAA t820.nt (SEQ ID NO:376)
TTCAATAACAGCCCAGACAACACAATATCTTTAAAGTCAAATGATATTGCCAAAAGAGGAACA
ATTTATGATAGAAATGGCAAACCAATAGCATTCTCTTCAAAATCCTACTCAATTGGTACAAATC
CTCAAAAAATAGAAAATATTGTAAGCACATCTGAAACTCTTGGTGCAATACTTCAAATTAATTC
AAGAATTTTAAAGGAAAAGCTTTCCTCTAACAAAGGGTTTTTATATATAAAAAGAAAAATAAAA
AGAGAAGAATCAGATTTAATAAAAAGAATTCAAGCTGAAGGCAGGCTTTCAAACATCACTTTAT
ATCCTGATTACACAAGAATTTATCCCTTCAGGAATACCACAAGCAATATTACTGGTTTTGTAGG
AACAGATAATCTTGGCCTTGAGGGCATTGAATTTTCCCTAAATAGCATATTAGGAAAAGATAAA
ACCAAGCAACAATTTTTAAATGAGGAGCCAGAAACAAACAACATCCACTTAACAATAGACATG
GATATACAACAAGGTGTTAGCAAAATAGCTAAAAAATACTTTAAAGAAAATAATCCTGAAAGT
TTAATTACCTTGGTAATGAACTCCCAAAATGGAGAAATATTATCCATGGTTCAATTTCCTCAAT
ATGATGCAAACTTTTATTCTAAATATCCTGAAGAAATCCGAAAAAACCTTTCTTCATCTCTAACC
TATGAGCCCGGAAGCATTAATAAAATTTTTACAGTTGCAATAATATTAGAAAGTGGAAAATTAA
ATTTAGAAGAAAAA TTTTTAGACAATGGAATATATCAAAAACAATTTCCATCAGGAGAAAAAA
TTACAATCAAAACATTAAATCCCCCCTATAAACATATCGACTCTACAGAGATTTTAATTTATTCA
TCAAATGTTGGAATAGCTTACATTACTGAAAAAGTTAGCAATGAATACTTTTATAAAAAACTTT
TAGATTTTGGCTTTGGGGAAAAAGTTGGAGTTCCATTTCCCGGAGAAACAAAAGGACTGCTAAA
TCATTATTCAAAATGGTCAGGACGAAGTAAAGCTACAATTGGATTTGGACAAGAAATAGGAGT
GTCAGCGGTTCAAATATTACAAGCTGCAAGCATACTAAGCAATAATGGAATAATGCTAAAACCT
AGAATAATAAAAAAAATAAGCAACGATAAAGGAGAAAATATTAAAGAATTTGATAAAGAAGA
AATAAGAAAAGTAATATCCAAAAATTCAGCACAAAAAGTTTTAAAAATGATGAGAGAAGTTGT
AAATAAAGGTGGAATTCCAAATCTTAAAATTAAAAATCTTGACATTTCTGCAAAAAGTGGAACA
TCTCAAGCTATTGATAGAAAAACGGGAAAATACTCAGAAGAGACTATACATCTTCTATATTGG
CAATATACCCCACAGAACAACCAAAATATATTATTTACATTGTATACAGATACCCAAAAAAAAT
AATATACGGAACAAGAATAGCAGCCCCAATGGCAAAAGAAATAATAGAATTTATTGAGCACCA
ACAAAATACAATAGCATATAAAAAAATTAAATGCCATCAAAAATCAAGATCCCTAAAGCTGA
AACTAATTACAAAAACAAAACATACTTACCAAATTTTATCAACCTTTCTAAAAGAGAAGCAATA
GACATACTAAAATACTATAAAAATACTATGAAAATAAAAATAAATGGCGATGGATTTGTTTACA
AGCAAAGTATATCCCCCAATACAAAATTAGAAGATATAACAGAGCTTGAACTGTATTTAAAATA
A f831.aa (SEQ ID NO:377)
MAKNNLLVFFIAIIFVFVSIIVVFYNSLGKDYVKSGGEIVENLEKDLNDYLKENDAKEREKIFLRIRELI
SKEKEISSYFISRFYLARAVYFQSQAQYDEAIKDLDIVIKAKGIESEIAFLNKAAVYEKMGLKEDALL
VYEDLINSTSLDFLKVRALLSKAILIEEKDKELAVKVYEEIVKFPYENNLYINMANNKILELKQN t831.aa (SEQ ID NO:378)
YNSLGKDYVKSGGEIVENLEKDLNDYLKENDAKEREKIFLRIRELISKEKEISSYFISRFYLARAVYFQ
SQAQYDEAIKDLDIVIKAKGIESEIAFLNKAAVYEKMGLKEDALLVYEDLINSTSLDFLKVRALLSKA
ILIEEKDKELAVKVYEEIVKFPYENNLYINMANNKILELKQN f831.nt (SEQ ID NO:379)
ATGGCTAAAAATAATCTTTTAGTTTTCTTTATTGCTATTATTTTTGTGTTTGTGTCTATTATTGTT
GTTTTTTATAATTCTTTAGGCAAGGATTATGTAAAGAGTGGCGGAGAAATAGTAGAAAATCTTG
AAAAAGATTTAAATGATTATTTAAAAGAAAATGATGCCAAAGAGAGAGAAAAAATATTTCTTA
GGATAAGGGAGCTTATTTCAAAGGAAAAAGAAATTTCATCTTATTTTATTTCAAGGTTCTATTT
AGCCAGAGCTGTTTATTTCCAAAGTCAAGCACAGTATGATGAGGCTATTAAAGATTTAGATATT
GTTATTAAGGCAAAAGGTATTGAAAGTGAAATTGCTTTTCTTAATAAAGCTGCAGTTTATGAAA
AAATGGGATTAAAAGAAGATGCTTTGTTAGTTTATGAAGATCTTATCAATAGTACTAGTTTGGA
TTTTTTAAAGGTAAGCTCTCTTTTGAGTAAGGCAATATTGATTGAGGAAAAAGATAAAGAGCTT
GCTGTGAAAGTATACGAAGAGATTGTTAAGTTTCCGTATGAAAATAATTTATATATAAATATGG
CAAATAATAAAATTTTAGAACTTAAGCAAAATTAA t831.nt (SEQ ID NO:380)
TATAATTCTTTAGGCAAGGATTATGTAAAGAGTGGCGGAGAAATAGTAGAAAATCTTGAAAAA
GATTTAAATGATTATTTAAAAGAAAATGATGCCAAAGAGAGAGAAAAAATATTTCTTAGGATA
AGGGAGCTTATTTCAAAGGAAAAAGAAATTTCATCTTATTTTATTTCAAGGTTCTATTTAGCCA
GAGCTGTTTATTTCCAAAGTCAAGCACAGTATGATGAGGCTATTAAAGATTTAGATATTGTTAT
TAAGGCAAAAGGTATTGAAAGTGAAATTGCTTTTCTTAATAAAGCTGCAGTTTATGAAAAAATG
GGATTAAAAGAAGATGCTTTGTTAGTTTATGAAGATCTTATCAATAGTACTAGTTTGGATTTTTT
AAAGCTAAGAGCTCTTTTGAGTAAGGCAATATTGATTGAGGAAAAAGATAAAGAGCTTGCTGT
GAAAGTATACGAAGAGATTGTTAAGTTTCCGTATGAAAATAATTTATATATAAATATGGCAAAT
AATAAAATTTTAGAACTTAAGCAAAATTAA f843.aa (SEQ ID NO:381)
MKAIGNAILLNMPLIFSIGISIGVARMGQGTAALGGLIGYLTFNITENYFIEAFSGLVEAETMSSVGRI
NFFGVQTLNTGIAGSLAVGLLVGYLHNKFYNMKLPKPFVFFSECHFVPIVIILPFCVFLAIFFCLIWSSF
DDLIASLGLFVFRFEYFGSFLYGFLNRLLLPLGLRSILSFPFEFTSLGGVEIVNGDTVRGLKNIFYAQLL
DPSLGKFSSGFAKISSGFYLSIMFGLPGAALGVYKGIVHEDKNKVAALLFSGALTAFLTGITEPLEFLF
IFTAPLLYFVHAAYSGFALLLANFFNVTIGNSFSTGFLDFFMFGILQGNSKTNWISVLPLGAMFFALY
YFTFSWLYRYFDFQIFVTDDPFFEGQEGKLESLGIAHLLIQGLGGFDNITKLDVCSTRLHVDVVNTEL
VDNNLLKEAGVLKIGLVNGKVQLFYGSNVYYIKNAIDTYSPKSLFEASVMVAVDNVKKGFKTYIE
MKEDKKLEKQGKSGKTYKLSELEED

TABLE 1-continued

Nucleotide and Amino Acid Sequences.

t843.aa (SEQ ID NO:382)
RMGQGTAALGGLIGYLTFNITENYFIEAFSGLVEAETMSSVGRINFFGVQTLNTGIAGSLAVGLLVG
YLHNKFYNMKLPKPFVFFSECHFVPIVIILPFCVFLAIFFCLIWSSFDDLIASLGLFVFRFEYFGSFLYGF
LNRLLLPGLHSILSFPFEFTSLGGVEIVNGDTVRGLKNFYAQLLDPSLGKFSSGFAKISSGFYLSIMF
GLPGAALGVYKGIVHEDKNKVAALLFSGALTAFLTGITEPLEFLFIFTAPLLYFVHAAYSGFALLLAN
FFNVTIGNSFSTGFLDFFMFGILQGNSKTNWISVLPLGAMFFALYYFTFSWLYRYFDFQIFVTDDPFF
EGQEGKLESLGIAHLLIQGLGGFDNITKLDVCSTRLHVDVVNTELVDNNLLKEAGVLKIGLVNGKV
QLFYGSNVYYIKNAIDTYSPKSLFEASVMVAVDNVKKGFKTYIEMKEDKKLEKQGKSGKTYKLSEL
EED f843.nt (SEQ ID NO:383)
ATGAAGGCTATAGGCAATGCTATTCTTCTCAATATGCCTTTAATTTTTTCTATTGGAATTTCTAT
TGGAGTTGCAAGAATGGGGCAGGGAACAGCGGCTTTGGGAGGCCTTATTGGTTATTTAACATTT
AATATTACTGAAAATTATTTTATTGAGGCTTTTTCAGGGCTTGTTGAAGCAGAGACAATGTCTT
CTGTTGGGCGTATAAATTTTTTTGGTGTTCAAACTTTAAATACGGGAATTGCAGGTTCTTTAGCG
GTAGGCCTTTTAGTTGGATATTTGCATAACAAATTTTATAATATGAAGCTACCCAAACCTTTTGT
GTTTTTTTCAGAGTGCCATTTTGTGCCTATAGTAATAATTTTACCCTTTTGTGTTTTTTGGCTAT
ATTTTTTTGTTTGATTTGGTCAAGTTTTGACGATTTAATTGCATCTTTAGGTTTGTTTGTTTTTAG
GTTTGAATATTTTGGCAGTTTTCTTTATGGATTTTTAAATAGGCTTTTATTGCCTTTGGGGTTGC
ATTCTATTTTATCTTTTCCTTTTGAGTTTACTTCTTTGGGAGGAGTGGAGATAGTTAATGGCGAT
ACTGTTAGAGGTCTTAAGAATATATTTTATGCTCAGCTATTAGACCCATCACTTGGTAAATTTTC
ATCAGGCTTTGCCAAAATTAGCAGTGGATTTTATCTATCTATTATGTTTGGACTGCCCGGAGCA
GCATTAGGGGTTTACAAGGGTATTGTTCATGAAGATAAAAATAAGGTTGCAGCACTTCTTTTCT
CTGGGGCCTTGACAGCTTTTTTAACAGGAATAACTGAGCCTTTAGAATTTTTATTTATTTTCACA
GCGCCTTTGCTTTATTTTGTTCATGCCGCTTATTCGGGGTTTGCATTGTTGCTTGCTAATTTTTTT
AATGTTACGATTGGCAATAGCTTTTCTACTGGATTTTTGGATTTTTTTATGTTTGGGATACTTCA
AGGAAATTCTAAGACAAATTGGATTAGTGTATTACCTTTGGGGGCAATGTTTTTTGCTCTTTATT
ATTTTACTTTTAGTTGGCTTTATAGATACTTTGATTTTCAGATATTTGTTACAGACGATCCATTT
TTTGAAGGCCAAGAAGGAAAGCTAGAGAGTCTCGGAATTGCGCATCTTTTAATTCAAGGTCTTG
GTGGATTTGATAATATTACAAAGCTTGATGTTTGTTCTACAAGATTGCATGTAGATGTTGTTAA
TACTGAGCTTGTTGATAATAATTTGCTTAAAGAGGCTGGAGTTCTTAAAATAGGGCTTGTTAAT
GGCAAGGTTCAGCTTTTTTATGGATCTAATGTTTATTATATTAAAAATGCCATTGATACCTATTC
TCCAAAGAGTCTTTTTGAAGCTAGTGTTATGGTTGCAGTTGATAATGTAAAAAAAGGTTTTAAA
ACTTATATTGAAATGAAAGAAGACAAAAAACTTGAAAAGCAAGGTAAATCAGGAAAAACCTAT
AAGCTTAGCGAATTAGAAGAAGATTAG t843.nt (SEQ ID NO:384)
AGAATGGGGCAGGGAACAGCGGCTTTGGGAGGCCTTATTGGTTATTTAACATTTAATATTACTG
AAAATTATTTTATTGAGGCTTTTTCAGGGCTTGTTGAAGCAGAGACAATGTCTTCTGTTGGGCG
TATAAATTTTTTTGGTGTTCAAACTTTAAATACGGGAATTGCAGGTTCTTTAGCGGTAGGCCTTT
TAGTTGGATATTTGCATAACAAATTTTATAATATGAAGCTACCCAAACCTTTTGTGTTTTTTTCA
GAGTGCCATTTTGTGCCTATAGTAATAATTTTACCCTTTTGTGTTTTTTGGCTATATTTTTTTGT
TTGATTTGGTCAAGTTTTGACGATTTAATTGCATCTTTAGGTTTGTTTGTTTTTAGGTTTGAATA
TTTTGGCAGTTTTCTTTATGGATTTTTAAATAGGCTTTTATTGCCTTTGGGGTTGCATTCTATTTT
ATCTTTTCCTTTTGAGTTTACTTCTTTGGGAGGAGTGGAGATAGTTAATGGCGATACTGTTAGA
GGTCTTAAGAATATATTTTATGCTCAGCTATTAGACCCATCACTTGGTAAATTTTCATCAGGCTT
TGCCAAAATTAGCAGTGGATTTTATCTATCTATTATGTTTGGACTGCCCGGAGCAGCATTAGGG
GTTTACAAGGGTATTGTTCATGAAGATAAAAATAAGGTTGCAGCACTTCTTTTCTCTGGGGCCT
TGACAGCTTTTTTAACAGGAATAACTGAGCCTTTAGAATTTTTATTTATTTTCACAGCGCCTTTG
CTTTATTTTGTTCATGCCGCTTATTCGGGGTTTGCATTGTTGCTTGCTAATTTTTTTAATGTTACG
ATTGGCAATAGCTTTTCTACTGGATTTTTGGATTTTTTTATGTTTGGGATACTTCAAGGAAATTC
TAAGACAAATTGGATTAGTGTATTACCTTTGGGGGCAATGTTTTTTGCTCTTTATTATTTTACTT
TTAGTTGGCTTTATAGATACTTTGATTTTCAGATATTTGTTACAGACGATCCATTTTTTGAAGGC
CAAGAAGGAAAGCTAGAGAGTCTCGGAATTGCGCATCTTTTAATTCAAGGTCTTGGTGGATTTG
ATAATATTACAAAGCTTGATGTTTGTTCTACAAGATTGCATGTAGATGTTGTTAATACTGAGCTT
GTTGATAATAATTTGCTTAAAGAGGCTGGAGTTCTTAAAATAGGGCTTGTTAATGGCAAGGTTC
AGCTTTTTTATGGATCTAATGTTTATTATATTAAAAATGCCATTGATACCTATTCTCCAAAGAGT
CTTTTTGAAGCTAGTGTTATGGTTGCAGTTGATAATGTAAAAAAAGGTTTTAAAACTTATATTG
AAATGAAAGAAGACAAAAAACTTGAAAAGCAAGGTAAATCAGGAAAAACCTATAAGCTTAGCG
AATTAGAAGAAGATTAG f850.aa (SEQ ID NO:385)
MRFKKIFLIIFIISNLKVYSYNYAIQYKNEGIDKYYFEILNDGFGFSLSDFFDDLRSGSLIFTYVSKYNFI
INLEAHMLTYRGYKDSPKSLISRTDLIEIGFMYYFPILLLINGKNFGEIDLGIGVKNLLFGDWGGHLM
QSIIHLILNQHRPIPSIKSYDSYNYRGFLSFALNYSYMNFLNLENYMDLSYFADYFIKNSIGITLKNENI
GFDIKLYSQIQNQIKSLKTYSKTQEAETGIGINYQFYSKNFFITNNLNIKNFSTKENFLSVGGFGIILTPE
EYKKISESNNEFNYISNNFYFGFDIMIPLKIRNSLFYKINENINHYFSISTNYYTNYNETNSFTNQLSSGI
MYEFLPQKTFNPYLISGLFFAYNQNNKDIKSISRPIRIKNILQVGIENELGFLFKMLKYRNTEYIFKIYS
KVNYIPIAYNLDEKKLEKHSINFNYLGIGIVVK t850.aa (SEQ ID NO:386)
YSYNYAIQYKNEGIDKYYFEILNDGFGFSLSDFFDDLRSGSLIFYVSKYNFIINLEAHMLTYRGYKD
SPKSLISRTDLIEIGFMYYFPILLLINGKNFGEIDLGIGVKNLLFGDWGGHLMQSIIHLILNQHRPIPSIK
SYDSYNYRGFLSFALNYSYMNFLNLENYMDLSYFADYFIKNSIGITLKNENIGFDIKLYSQIQNQIKSL
KTYSKTQEAETGIGINYQFYSKNFFITNNLNIKNFSTKENFLSVGGFGIIITPEEYKKISESNNEFNVISN
NFYFGFDIMIPLKIRNSLFYKINENINHYFSISTNYYTNYNETNSFTNQLSSGIMYEFLPQKTFNPYLIS
GLFFAYNQNNKDIKSISRPIRIKNILQVGIENELGFLFKMLKYRNTEYIFKIYSKVNYIPIAYNLDEKKL

TABLE 1-continued

Nucleotide and Amino Acid Sequences.

EKHSINFNYLGIGIVVK f850.nt (SEQ ID NO:387)
ATGCGGTTTAAAAAAATATTTTTAATAATATTTATAATTTCTAATTTAAAAGTTTATTCTTATAA
TTATGCAATCCAATATAAAAATGAAGGTATTGACAAATATTATTTTGAAATACTAAATGATGGA
TTCGGATTTTCATTAAGCGATTTTTTTGATGACTTGAGAAGTGGTTCTCTTATTTTTACCTATGT
TTCAAAATACAATTTTATAATAAATTTAGAAGCACACATGTTAACCTATAGGGGTTATAAAGAC
TCTCCGAAATCTTTAATTAGTAGAACAGACTTAATTGAAATAGGCTTCATGTACTATTTTCCAAT
TTTATTGCTAATTAATGGAAAAAATTTTGGAGAAATAGACTTGGGAATTGGAGTTAAAAACTTA
TTATTTGGAGACTGGGGAGGGCATTTAATGCAAAGCATAATTCACCTCATTTAAATCAACACC
GTCCAATTCCAAGTATAAAAAGCTACGACAGCTACAATTATAGAGGATTTTTAAGCTTTGCTCT
AAATTACTCTTACATGAATTTTTTAAATTTAGAAAATTATATGGACTTATCTTATTTTGCAGATT
ATTTTATTAAAAACAGTATTGGAATTACCTTAAAAAATGAAAATATTGGATTTGATATAAAACT
TTATTCCCAAATTCAAAATCAAATCAAAAGCCTCAAAACATATTCAAAAACACAAGAAGCAGA
AACAGGAATTGGAATAAATTATCAATTTTACTCTAAAAATTTTTTCATAACCAATAATTTAAAC
ATTAAAAATTTTTCAACCAAAGAAAATTTCTTAAGCGTTGGGGGATTTGGAATAATCATTACAC
CTGAAGAATACAAAAAATATCAGAATCAAATAATGAATTTAATGTTATAAGTAATAATTTA
CTTTGGATTTGATATTATGATCCCATTAAAAATAAGAAATTCATTATTTTATAAAATAAATGAA
AACATCAACCATTACTTTTCAATATCAACAAATTATTACACTAATTATAATGAAACTAATAGCTT0
TACAAATCAATTATCATCAGGCATCATGTATGAATTTTTACCACAAAAAACATTCAATCCTTACC
TAATTTCGGGATTATTTTTTGCCTATAATCAAAACAATAAAGATATCAAAAGCATCTCAAGACC
AATAAGAATAAAAAACATTCTTCAAGTTGGAATTGAAAATGAATTAGGATTTTTGTTCAAAATG
CTAAAATACCGCAACACTGAGTATATTTTCAAAATATATTCAAAAGTTAACTATATTCCTATAG
CTTATAACTTAGATGAAAAAAAATTAGAAAAACATTCTATTAACTTTAATTATTTAGGAATTGG
AATAGTCGTTAAATAA t850.nt (SEQ ID NO:388)
TATTCTTATAATTATGCAATCCAATATAAAAATGAAGGTATTGACAAATATTATTTTGAAATAC
TAAATGATGGATTCGGATTTTCATTAAGCGATTTTTTTGATGACTTGAGAAGTGGTTCTCTTATT
TTTACCTATGTTTCAAAATACAATTTTATAATAAATTTAGAAGCACACATGTTAACCTATAGGG
GTTATAAAGACTCTCCGAAATCTTTAATTAGTAGAACAGACTTAATTGAAATAGGCTTCATGTA
CTATTTTCCAATTTTATTGCTAATTAATGGAAAAAATTTTGGAGAAATAGACTTGGGAATTGGA
GTTAAAAACTTATTATTTGGAGACTGGGGAGGGCATTTAATGCAAAGCATAATTCACCTCATTT
TAAATCAACACCGTCCAATTCCAAGTATAAAAAGCTACGACAGCTACAATTATAGAGGATTTTT
AAGCTTTGCTCTAAATTACTCTTACATGAATTTTTTAAATTTAGAAAATTATATGGACTTATCTT
ATTTTGCAGATTATTTTATTAAAAACAGTATTGGAATTACCTTAAAAAATGAAAATATTGGATT
TGATATAAAACTTTATTCCCAAATTCAAATCAAATCAAAAGCCTCAAAACATATTCAAAAACA
CAAGAAGCAGAAACAGGAATTGGAATAAATTATCAATTTTACTCTAAAAATTTTTTCATAACCA
ATAATTTAAACATTAAAAATTTTTCAACCAAAGAAAATTTCTTAAGCGTTGGGGGATTTGGAAT
AATCATTACACCTGAAGAATACAAAAAAATATCAGAATCAAATAATGAATTTAATGTTATAAGT
AATAATTTTTACTTTGGATTTGATATTATGATCCCATTAAAAATAAGAAATTCATTATTTTATAA
AATAAATGAAAACATCAACCATTACTTTTCAATATCAACAAATTATTACACTAATTATAATGAA
ACTAATAGCTTTACAAATCAATTATCATCAGGCATCATGTATGAATTTTTACCACAAAAAACAT
TCAATCCTTACCTAATTTCGGGATTATTTTTTGCCTATAATCAAAACAATAAAGATATCAAAAGC
ATCTCAAGACCAATAAGAATAAAAAACATTCTTCAAGTTGGAATTGAAAATGAATTAGGATTTT
TGTTCAAAATGCTAAAATACCGCAACACTGAGTATATTTTCAAAATATATTCAAAAGTTAACTA
TATTCCTATAGCTTATAACTTAGATGAAAAAAAATTAGAAAAACATTCTATTAACTTTAATTATT
TAGGAATTGGAATAGTCGTTAAATAA f853.aa (SEQ ID NO:389)
MKSFLFWVILGTVGISSFAQNTPVAIINLYKNEIITKTGFDSKVDIFKKTQGRDLTDAEKKQV
LQVLIADVLFSQEASKQGIKISDDEVMQTIRTQFGLVNFTDEQIKQMIEKQGTNWGELLSSMKRSLSS
QKLVLKQAQPKFSEIKTPSEKEIVEYYEANKTKFVNPDISRVSHIFFSTKDKKRSDVLDQAKNILSQIR
SKKITFEEAVRKYSNDESSKAKNGDLGFLSRGDQNAQNLLGADFVKEVFNFNKGDISSPIASKEGFHI
VKVTEKYAQRFLGLNDKVSPTADLIVKDAIRNNMINVQQQQIVVQVQQDMYGKLNKSANIQILDSS
LK t853.aa (SEQ ID NO:390)
QNTPVAIINLYKNEIITKTGFDSKVDIFKKTQGRDLTDAEKKQVLQVLIADVLFSQEASKQGI
KISDDEVMQTIRTQFGLVNFTDEQIKQMIEKQGTNWGELLSSMKRSLSSQKLVLKQAQPKFSEIKTP
SEKEIVEYYEANKTKFVNPDISRVSHIFFSTKDKKRSDVLDQAKNILSQIRSKKITFEEAVRKYSNDES
SKAKNGDLGFLSRGDQNAQNLLGADFVKEVFNFNKGDISSPIASKEGFHIVKVTEKYAQRFLGLND
KVSPTADLIVKDAIRNNMINVQQQQIVVQVQQDMYGKLNKSANIQILDSSLK f853.nt (SEQ ID NO:391)
ATGAAGAGTTTTTTATTTTGGGTAATATTGGGAACTGTAGGGATTAGCTCTTTTGCTCAAAATA
CTCCTGTTGCTATTATTAATTTATATAAGAATGAAATTATTACTAAAACTGGTTTTGATTCTAAG
GTTGATATATTTAAAAAGACCCAAGGTAGAGACTTAACTGATGCGTGAGAAAAAGCAAGTTCTG
CAAGTTTTAATAGCAGATGTTCTTTTTAGTCAAGAGGCTTCAAAGCAAGGAATTAAAATCTCAG
ATGATGAGGTTATGCAAACAATTAGAACTCAATTTGGGCTTGTGAATTTTACTGATGAACAAAT
CAAGCAAATGATAGAAAAACAAGGTACAAATTGGGGCGAGCTTTTGTCTTCAATGAAAGATC
TCTGTCTTCTCAAAAGCTTGTTTTAAAGCAAGCTCAGCCTAAGTTTTCTGAAATTAAAACTCCTA
GTGAGAAAGAAATTGTTGAGTATTATGAGGCTAATAAAACTAAGTTTGTAAATCCCGATATTTC
AAGAGTTAGTCATATCTTTTTTTCTACTAAAGATAAAAAAGATCAGATGTTTAGATCAAGCA
AAAAATATTTTAAGCCAAATAAGATCAAAAAAAATTACTTTTGAAGAAGCTGTAAGAAAATATT
CAAATGACGAATCTTCTAAGGCTAAAAATGGTGATCTTGGGTTTTTATCAAGAGGTGATCAAAA
TGCTCAAAATCTTCTTGGAGCCGATTTTGTGAAAGAGGTTTTTAATTTTAATAAGGGTGATATA

TABLE 1-continued

Nucleotide and Amino Acid Sequences.

```
TCTTCGCCTATTGCTTCAAAGGAAGGGTTTCATATTGTTAAAGTTACAGAAAAATATGCTCAGA
GATTTTTAGGTTTGAATGATAAAGTGTCTCCTACTGCAGATTTGATTGTCAAAGATGCAATAAG
AAATAACATGATTAATGTTCAACAACAGCAAATTGTTGTTCAAGTACAGCAAGATATGTATGGT
AAGCTTAACAAGTCTGCAAATATACAAATCTTGGATTCTAGTCTAAAATAA t853.nt (SEQ ID NO:392)
CAAAATACTCCTGTTGCTATTATTAATTTATATAAGAATGAAATTATTACTAAAACTGG
TTTTGATTCTAAGGTTGATATATTTAAAAAGACCCAAGGTAGAGACTTAACTGATGCTGAGAAA
AAGCAAGTTCTGCAAGTTTTAATAGCAGATGTTCTTTTTAGTCAAGAGGCTTCAAAGCAAGGAA
TTAAAATCTCAGATGATGAGGTTATGCAAACAATTAGAACTCAATTTGGGCTTGTGAATTTTAC
TGATGAACAAATCAAGCAAATGATAGAAAACAAGGTACAAATTGGGGCGAGCTTTTGTCTTC
AATGAAAAGATCTCTGTCTTCTCAAAAGCTTGTTTTAAAGCAAGCTCAGCCTAAGTTTTCTGAA
ATTAAAACTCCTAGTGAGAAAGAAATTGTTGAGTATTATGAGGCTAATAAAACTAAGTTTGTAA
ATCCCGATATTTCAAGAGTTAGTCATATCTTTTTTTCTACTAAAGATAAAAAAAGATCAGATGTT
TTAGATCAAGCAAAAAATATTTTAAGCCAAATAAGATCAAAAAAAATTACTTTTGAAGAAGCTG
TAAGAAAATATTCAAATGACGAATCTTCTAAGGCTAAAAATGGTGATCTTGGGTTTTTATCAAG
AGGTGATCAAAATGCTCAAAATCTTCTTGGAGCCGATTTTGTGAAAGAGGTTTTTAATTTTAAT
AAGGGTGATATATCTTCGCCTATTGCTTCAAAGGAAGGGTTTCATATTGTTAAAGTTACAGAAA
AATATGCTCAGAGATTTTTAGGTTTGAATGATAAAGTGTCTCCTACTGCAGATTTGATTGTCAA
AGATGCAATAAGAAATAACATGATTAATGTTCAACAACAGCAAATTGTTGTTCAAGTACAGCAA
GATATGTATGGTAAGCTTAACAAGTCTGCAAATATACAAATCTTGGATTCTAGTCTAAAATAA f859.aa (SEQ ID NO:393)
MKLPKLYKLILLFLFTTRLFSVKDEKSDNKLELFSNVETKIKKNSKNYDSNSNSKKIKKESILKRDTN
SEKNINSNIYIQKSKKINYPNRNLGNNINQKTANDVNFTKTSYVKVYPNYKDDNFQEIKNANKFPAK
TEKTHMLIGPILKDNLGIIIKMLKTKGYTLIEYIEDNN t859.aa (SEQ ID NO:394)
VKDEKSDNKLELFSNVETKIKKNSKNYDSNSNSKKIKKESILKRDTNSEKNINSNIYIQKSKKINYPN
RNLGNNINQKTA f859.nt (SEQ ID NO:395)
ATGAAATTACCAAAACTTTACAAATTAATACTACTCTTTCTTTTTACAACAAGATTGTTTTCAGT
AAAAGATGAAAAATCAGACAATAAATTGGAATTATTTTCAAACGTAGAAACAAAAATCAAAAA
AAATTCTAAAAATTACGACTCAAATTCAAACAGCAAAAAGATCAAAAAGAATCAATTTTAA
AAGAGATACAAACAGCGAAAAAAATATAAATTCCAATATATACATACAAAAATCAAAAAAAAT
TAATTACCCCAACAGAAATTTAGGCAATAATATCAATCAAAAAACTGCAAATGATGTAAATTT
ACAAAAACTAGTTATGTTAAAGTTTATCCCAACTATAAAGACGATAACTTTCAAGAAATTAAAA
ATGCTAATAAATTTCCAGCTAAAACCGAAAAAACTCACATGCTAATCGGCCCAATATTAAAGA
TAATCTAGGAATAATAATTAAAATGCTAAAAACAAAGGGATACACTTTAATAGAATACATAGA
GGACAATAATTAA t859.nt (SEQ ID NO:396)
GTAAAAGATGAAAAATCAGACAATAAATTGGAATTATTTTCAAACGTAGAAACAAAAATCAAA
AAAAATTCTAAAAATTACGACTCAAATTCAAACAGCAAAAAGATCAAAAAGAATCAATTTTA
AAAAGAGATACAAACAGCGAAAAAAATATAAATTCCAATATATACATACAAAAATCAAAAAAA
ATTAATTACCCCAACAGAAATTTAGGCAATAATATCAATCAAAAAACTGCAAATGATGTAAATT
TTACAAAAACTAGTTATGTTAAAGTTTATCCCAACTATAAAGACGATAACTTTCAAGAAATTAA
AAATGCTAATAAATTTCCAGCTAAAACCGAAAAAACTCACATGCTAATCGGCCCAATATTAAAA
GATAATCTAGGAATAATAATTAAAATGCTAAAAACAAAGGGATACACTTTAATAGAATACATA
GAGGACAATAATTAA f861.aa (SEQ ID NO:397)
MKNFKEVIIIFDSGIGGLSYFKYIKSRIGGCQYVYVADNKNFPYGEKSPEYLLEAVLFLIEKLKKIYNI
GALVLACNTISVSVYNKLNFVFPVVYTLPDVSSVSDLVLKRVLLIATNTTLESKFVKDQVNIHNDLIV
KAAGELVNFVEYGENYKKYALRCLEALKFEVVNTGREIVFLGCTHYLHLKVMIEDFLKIPVYENRE
LVVKNLIRSMNFSEHKGNYYKNDFDFVDDEFYLTENKNLTFYQNFCKKYNLRFKGMIV t861.aa (SEQ ID NO:398)
RIGGCQYVYVADNKNFPYGEKSPEYLLEAVLFLIEKLKKIYNIGALVLACNTISVSVYNKLN
FVFPVVYTLPDVSSVSDLVLKRVLLIATNTTLESKFVKDQVNIHNDLIVKAAAGELVNFVEYGENYKK
YALRCLEALKFEVVNTGREIVFLGCTHYLHLKVMIEDFLKIPVYENRELVVKNLIRSMNFSEHKGNY
YKNDFDFVDDEFYLTENKNLTFYQNFCKKYNLRFKGMIV f861.nt (SEQ ID NO:399)
ATGAAAAATTTCAAAGAAGTAATAATTATTTTTGATTCAGGAATAGGAGGGCTTTCTTATTTTA
AATATATTAAAAGTAGAATAGGGGGATGCCAATATGTTTATGTTGCCGATAATAAAAATTTCCC
TTATGGAGAAAAAAGTCCTGAATATCTTCTAGAAGCAGTTTTGTTTTTGATTGAGAAGCTTAAA
AAAATCTATAATATTGGTGCATTAGTTTTGGCTTGTAATACAATTTCTGTTAGTGTATACAATAA
ATTAAATTTTGTTTTTCCAGTAGTCTATACTTTGCCAGATGTAAGTTCAGTTTCAGATCTTGTTT
TAAAAAGAGTTCTTTTGATTGCAACAAATACTACTCTTGAAAGCAAATTTGTTAAGGATCAAGT
AAATATACATAATGATTTGATTGTAAAAGCTGCTGGAGAGCTTGTTAATTTTGTTGAATATGGA
GAGAATTACAAAAAATATGCTCTTAGATGTTTAGAAGCTTTAAAATTTGAAGTTGTAAATACTG
GTAGAGAAATTGTTTTTCTTGGATGCACGCATTATTTGCATCTTAAGGTAATGATAGAAGATTT
TTTAAAAATTCCTGTTTATGAGAATCGTGAATTAGTGGTAAAAAATCTTATTAGATCAATGAAT
TTTTCTGAACACAAAGGTAATTATTATAAGAATGATTTTGATT TTTAGATGATGAGTTTTATTT
GACCGAAAATAAAAAATTTGACTTTTTATCAAAATTTTTGCAAAAAATATAATCTTCGCTTTAAG
```

TABLE 1-continued

Nucleotide and Amino Acid Sequences.

GGAATGATAGTTTGA t861.nt (SEQ ID NO:400)
AGAATAGGGGGATGCCAATATGTTTATGTTGCCGATAATAAAAATTTCCCTTATGGAGAAAAAA
GTCCTGAATATCTTCTAGAAGCAGTTTTGTTTTTGATTGAGAAGCTTAAAAAAATCTATAATATT
GGTGCATTAGTTTTGGCTTGTAATACAATTTCTGTTAGTGTATACAATAAATTAAATTTTGTTTTT
TCCAGTAGTCTATACTTTGCCAGATGTAAGTTCAGTTTCAGATCTTGTTTTAAAAAGAGTTCTTT
TGATTGCAACAAATACTACTCTTGAAAGCAAATTTGTTAAGGATCAAGTAAATACATAATGA
TTTGATTGTAAAAGCTGCTGGAGAGCTTGTTAATTTTGTTGAATATGGAGAGAATTACAAAAAA
TATGCTCTTAGATGTTTAGAAGCTTTAAAATTTGAAGTTGTAAATACTGGTAGAGAAATTGTTT
TTCTTGGATGCACGCATTATTTGCATCTTAAGGTAATGATAGAAGATTTTTTAAAAATTCCTGTT
TATGAGAATCGTGAATTAGTGGTAAAAAATCTTATTAGATCAATGAATTTTTCTGAACACAAAG
GTAATTATTATAAGAATGATTTTGATTTTGTAGATGATGAGTTTTATTTGACCGAAAATAAAAA
TTTGACTTTTTATCAAAATTTTTGCAAAAAATATAATCTTCGCTTTAAGGGAATGATAGTTTGA f363.aa (SEQ ID NO:401)
MIRLKVLILCLFGIFVLNGFADTNFEFNFGGGVAFPVSPFSSFYNEALEINAKLKQNLPSDLSPIEKEEI
VQNFSDLANIAKAGIRYGTYAQFGAKFDDFVSIGFELLFNINLLKAIKRSDGTANENFSFIMAITPRFY
TKLDFFVLALAFFTGPKINIATSSADSVLAELGTMGWDIGARLSFSFLILEGYYVWNIKNPKFSDFKF
GIGFEFGIV t363.aa (SEQ ID NO:402)
DTNFEFNFGGGVAFPVSPFSSFYNEALEINAKLKQNLPSDLSPIEKEEIVQNFSDLANIAKAGIRYGTY
AQFGAKFDDFVSIGFELLFNINLLKAIKRSDGTANENFSFIMAITPRFYTKLDFFVLALAFFTGPKINIA
TSSADSVLAELGTMGWDIGARLSFSFLILEGYYVWNIKNPKFSDFKFGIGFEFGIV f363.nt (SEQ ID NO:403)
ATGATTAGGCTTAAACTTTTAATTTTGTGTTTATTTGGGATTTTTGTGTTAAATGGTTTTGCAGA
TACTAATTTTGAATTCAATTTTGGTGGTGGGGTTGCTTTTCCTGTTAGTCCCTTTTCAAGCTTTT
ACAATGAGGCTTTAGAGATTAATGCAAAGCTTAAGCAAAATTTGCCTTCAGATTTATCCCCAAT
AGAAAAAGAAGAGATAGTCCAAAATTTTTCCGATTTAGCCAATATTGCTAAAGCTGGAATAAG
ATATGGAACTTACGCTCAATTTGGCGCTAAATTTGATGATTTTGTTTCTATTGGATTTGAGCTTT
TGTTTAACATTAATCTTCTTAAAGCAATAAAGCGTTCGGATGGAACTGCAAATGAAAATTCTC
GTTTATTATGGCAATAACACCAAGATTTTATACAAAATTAGATTTTTTGTTTTAGCTTTAGCGT
TTTTCACAGGTCCTAAGATCAATATAGCGACTTCTTCTGCGGATTCTGTTTTAGCAGAACTGGG
AACAATGGGCTGGGATATTGGTGCTAGACTTTCATTTTCTTTTTTAATTCTTGAAGGGTACTATG
TTTGGAATATTAAAAACCCTAAATTTTCTGATTTCAAGTTTGGAATAGGTTTTGAATTTG
GAATTGTGTAG t363.nt (SEQ ID NO:404)
GATACTAATTTTGAATTCAATTTTGGTGGTGGGGTTGCTTTTCCTGTTAGTCCCTTTTCAAGCTT
TTACAATGAGGCTTTAGAGATTAATGCAAAGCTTAAGCAAAATTTGCCTTCAGATTTATCCCCA
ATAGAAAAAGAAGAGATAGTCCAAAATTTTTCCGATTTAGCCAATATTGCTAAAGCTGGAATAA
GATATGGAACTTACGCTCAATTTGGCGCTAAATTTGATGATTTTGTTTCTATTGGATTTGAGCTT
TTGTTTAACATTAATCTTCTTAAAGCAATAAAGCGTTCGGATGGAACTGCAAATGAAAATTCT
CGTTTATTATGGCAATAACACCAAGATTTTATACAAAATTAGATTTTTTGTTTTAGCTTTAGCG
TTTTTCACAGGTCCTAAGATCAATATAGCGACTTCTTCTGCGGATTCTGTTTTAGCAGAACTGGG
AACAATGGGCTGGGATATTGGTGCTAGACTTTCATTTTCTTTTTTAATTCTTGAAGGGTACTATG
TTTGGAATATTAAAAACCCTAAATTTTCTGATTTCAAGTTTGGAATAGGTTTTGAATTTGGAATT
GTGTAG f368.aa (SEQ ID NO:405)
MIDLTQEKQEILIKNKFLAKVFGLMSIGLLISAVFAYATSENQTIKAIIFSNSMSFMAMILIQFGLVYAI
SGALNKISSNTATALFLLYSALTGVTLSSIFMIYTQGSIVFTFGITAGTFLGMSVYGYTTTTDLTKMGS
YLIMGLWGIIIASLVNMFFRSSGLNFLISILGVVIFTGLTAYDVQNISKMDKMLQDDTEIKNRMAVVA
SLKLYLDFINLFLYLLRFLGQRRND t368.aa (SEQ ID NO:406)
TSENQTIKAIIFSNSMSFMAMILIQFGLVYAISGALNKISSNTATALFLLYSALTGVTLSSIFMIYTQGSI
VFTFGITAGTFLGMSVYGYTTTTDLTKMGSYLIMGLWGIIIASLVNMFFRSSGLNFLISILGVVIFTGL
TAYDVQNISKMDKMLQDDTEIKNRMAVVASLKLYLDFINLFLYLLRFLGQRRND f368.nt (SEQ ID NO:407)
ATGATCGATTTAACACAAGAAAAACAAGAAATACTAATAAAAAACAAGTTTTTAGCCAAAGTTT
TCGGGCTTATGTCAATTGGACTTTTAATCTCAGCAGTATTTGCATATGCAACCTCAGAAAATCA
AACAATCAAAGCAATAATATTCTCAAATTCAATGTCATTTATGGCTATGATACTTATACAATTT
GGACTTGTATATGCAATAAGTGGTGCTCTTAATAAAAATATCAAGCAATACTGCAACAGCTCTTT
TCTTGCTCTACTCAGCACTAACAGGAGTAACATTATCTTCTATATTTATGATTTACACACAGGA
TCAATAGTATTCACATTCGGAATTACTGCTGGAACATTTCTTGGAATGTCTGTTTATGGATACAC
TACAACAACAGATCTAACAAAAATGGGAAGCTATTTAATAATGGGCTTATGGGGAATCATTATT
GCATCTCTTGTTAATATGTTTTTTAGAAGCTCAGGTCTTAATTTCCTTATATCTATTTTGGGCGT
AGTTATATTTACAGGCTTAACAGCTTATGATGTTCAAAATATTTCTAAAATGGACAAAATGCTA
CAAGACGACACTGAAATAAAAAACAGAATGGCGGTTGTAGCCTCACTTAAACTTTATTTAGATT
TTATAAATTTATTCTTATATCTTCTAAGATTTTTGGGCCAAAGAAGAAACGATTAA
t368.nt (SEQ ID NO:408)
ACCTCAGAAAATCAAACAATCAAAGCAATAATATTCTCAAATTCAATGTCATTTATGGCTATGA
TACTTATACAATTTGGACTTGTATATGCAATAAGTGGTGCTCTTAATAAAAATATCAAGCAATAC

TABLE 1-continued

Nucleotide and Amino Acid Sequences.

```
TGCAACAGCTCTTTTCTTGCTCTACTCAGCACTAACAGGAGTAACATTATCTTCTATATTTATGA
TTTACACACAAGGATCAATAGTATTCACATTCGGAATTACTGCTGGAACATTTCTTGGAATGTC
TGTTTATGGATACACTACAACAACAGATCTAACAAAAATGGGAAGCTATTTAATAATGGGCTTA
TGGGGAATCATTATTGCATCTCTTGTTAATATGTTTTTTAGAAGCTCAGGTCTTAATTTCCTTAT
ATCTATTTTGGGCGTAGTTATATTTACAGGCTTAACAGCTTATGATGTTCAAAATATTTCTAAAA
TGGACAAAATGCTACAAGACGACACTGAAATAAAAAACAGAATGGCGGTTGTAGCCTCACTTA
AACTTTATTTAGATTTTATAAATTTATTCTTATATCTTCTAAGATTTTTGGGCCAAAGAAGAAAC
GATTAA f371.aa (SEQ ID NO:409)
MKFFFLLQIALILLSNSSLLFGQSPPKEKEDSLLLYKEGKFKEAILNTLEEIRLNPSNLDARTILIWSLIA
IGEYKRAEKEAIIGLGIKKHDIRIIQALGEAYFPQKNYDNALKYFQEYISLDSKGARIIKVYNLIADSFY
ELKRYNEADFAYEHALRFSPNNQNLLIKLARSRINAKNKILAEEALIKILTISPNNLEAKNLLEELKKS
NNKP t371.aa (SEQ ID NO:410)
EDSLLLYKEGKFKEAILNTLEEIRLNPSNLDARTILIWSLIAIGEYKRAEKEAIIGLGIKKHDIRIIQALG
EAYFFQKNYDNALKYFQEYISLDSKGARIIKVYNLIADSFYELKRYNEADFAYEHALRFSPNNQNLLI
KLARSRINAKNKILAEEALIKILTISPNNLEAKNLLEELKKSNNKP f371.nt (SEQ ID NO:411)
ATGAAATTTTTTTTCTATTACAAATAGCTTTAATTCTACTATCCAATTCAAGCTTGTTATTTGG
ACAATCACCGCCTAAAGAAAAAGAAGACTCTCTTCTTCTATATAAAGAAGGAAAATTTAAAGA
AGCTATTTTAAACACGTTAGAAGAAATTCGACTAAATCCTAGTAACTTAGATGCTAGGACAATA
TTGATATGGAGCTTAATAGCCATAGGAGAATACAAGAGAGCTGAAAAAGAGGCGATTATAGGA
CTTGGCATTAAAAAACATGACATAAGAATTATTCAAGCACTAGGAGAAGCTTATTCTTTCAAA
AAAATTATGACAATGCATTAAAATACTTTCAAGAATACATTAGCCTTGATTCTAAAGGAGCAAG
AATAATAAAAGTTTATAATTTAATTGCAGATTCTTTTTATGAGCTAAAAAGATATAATGAAGCC
GATTTTGCATACGAACATGCATTACGTTTTTCTCCTAATAACCAAATCTATTAATAAAATTAGC
AAGATCAAGAATAAATGCAAAAAATAAAATATTAGCAGAAGAAGCACTAATTAAAATTCTTAC
AATCTCTCCTAATAATCTAGAGGCAAAAAATTTACTAGAAGAATTAAAAAAAAGCAACAACAA
ACCTTGA t371.nt (SEQ ID NO:412)
GAAGACTCTCTTCTTCTATATAAAGAAGGAAAATTTAAAGAAGCTATTTTAAACACGTTAGAAG
AAATTCGACTAAATCCTAGTAACTTAGATGCTAGGACAATATTGATATGGAGCTTAATAGCCAT
AGGAGAATACAAGAGAGCTGAAAAAGAGGCGATTATAGGACTTGGCATTAAAAAACATGACAT
AAGAATTATTCAAGCACTAGGAGAAGCTTATTCTTTCAAAAAAATTATGACAATGCATTAAAA
TACTTTCAAGAATACATTAGCCTTGATTCTAAAGGAGCAAGAATAATAAAAGTTTATAATTTAA
TTGCAGATTCTTTTTATGAGCTAAAAAGATATAATGAAGCCGATTTTGCATACGAACATGCATT
ACGTTTTTCTCCTAATAACCAAATCTATTAATAAAATTAGCAAGATCAAGAATAAATGCAAAA
AATAAAATATTAGCAGAAGAAGCACTAATTAAAATTCTTACAATCTCTCCTAATAATCTAGAGG
CAAAAAATTTACTAGAAGAATTAAAAAAAAGCAACAACAAACCTTGA f502.aa (SEQ ID NO:413)
MKKANFLSTNFLILLLVCFVNVNLFSKDIFKFKLVDQFFPFYYKNNKGEYEGLIFSILDKWAKDNNA
DIMVEHIDNLNESEIEDEAIYLGLTYNVKLNDFFYFKSELARSISILFFKNSNKKYKNTHSTFLSNFNIG
VIKNTIYEDILRLKNVNTIFLADNSQELVLALKNDKVDYIYGDCKTLHYIANNFLSEDLVIFTGDVFY
SIKNRVAISRNAPEIVKNLNLDLFSYLMKMPEELVFSFLDSNAKGSFVDVGLYNDYPPLSFINSQGKL
SGILVDLWNLLSRQHIFKPIFKGFSKEDIKKSLDGKSVGIFGGIISNDSVLENVNYVVSKPIYPLNFKFY
SKDLSNDAGPINSQFIDFNFNNIQLNKNKDIVNNFIDIVNNSYGFIENSITTKYLLKLNGYNGRLKSYD
SIFNKNRFLVIALDNRIYKVIKYILNSIFDDISFESLLQIDKNWLDKEEINSSRINSYKIMNKVKFNIEEK
IWLSKNNKLNLAVKNWYPIDYVEANNYKGINQFLLDKIRMFSGLRFNIIKVHSSLDLKKLIKSGKID
MLNTNATDSNLDNVFNIKLNSRIPLYIFSNKKRVLPSRSLEKFAILDFLYSKNLASNIKSKLILVSSFNE
ALLLLYKGKVDGIISDEYTAAAVFEELNIDDVEKIPTFRDLAFDLSLAIYNQDYILKEIIQKVVMRSNV
DSQMYLNDWKFDIYYKSRSIRFKNFKFLVITFIIFYFTFLGFVIIFMFRLSFEQKRRYSFVMNEKKIAE
AANAAKTIFIANVSHDIRTPINGIMAATELLDTTILTDVQKDYVRMINYSSDSLLSLIDDILYLSKIDV
NELYVESQEIDLESEMEMVLKAFQSQCAKKNIDLFSYSKSIFNNYIKGDIVKIKQVLINLIGNAFKFTD
DGVIVLNYEEVCRTRTDGNRVLVTVEFKVIDTGKGIEKENFSKIFEIFKQEDDSSSRVHEGAGLGLSIS
RELIRLMGGLGIAVDSKVGEGTTFSFMLPFLLGSELKSKKLSINRFQSVNGDNKVLNVLLSQKSIKIFE
HCSILLGCSSNVRYVASFEDAYKVFKKYPSYNFVINVNNDAAQEGIRLANNIERLNSDVQIIFLFYYL
DNKALKNLKYGYVKKPLMGLGICSILYKKEFNPEMDFEDLVPIDSALRIKEPINVLIAEDNQVNQKV
LKDILVVIGINENFIDVVDDGVKALKSLKDKKYTISFIDIRMPRYDGFSVAKEIRKFEKAKNLKPCVL
VAVTAHALQEYKDKCLASGMNDYISKPIHISSSIKTILKKYLQFEVDDIGENENLNQLVKFPNLDVNR
ALKELNLSYVSYSELCRGLVDFISTNIIDLEKAFDEEDLSLIKDISHSISGALSNMRSELYKDFQKIETSK
DSISELKKMYSFVKDDLFQLISDIKENILFESEIVSENKLYFKNNDQFLNLLNKLLIGIKTRKPREYKEI
LESINKYVLDDNIQVLFSDLRRNLRLYRFAESSKILEEIIEMLNNKRY t502.aa (SEQ ID NO:414)
CFVNVNLFSKDIFKFKLVDQFFPFYYKNNKGEYEGLIFSILDKWAKDNNADIMVEHIDNLNESEIEDE
AIYLGLTYNVKLNDFFYFKSELARSISILFFKNSNKKYKNTHSTFLSNFNIGVIKNTIYEDILRLKNVN
TIFLADNSQELVLALKNDKVDYIYGDCKTLHYIANNFLSEDLVIFTGDVFYSIKNRVAISRNAPEIVK
NLNLDLFSYLMKMPEELVFSFLDSNAKGSFVDVGLYNDYPPLSFINSQGKLSGILVDLWNLLSRQHI
FKPIFKGFSKEDIKKSLDGKSVGIFGGIISNDSVLENVNYVVSKPIYPLNFKFYSKDLSNDAGPINSQFI
DFNFNNIQLNKNKDIVNNFIDIVNNSYGFIENSITTKYLLKLNGYNGRLKSYDSIFNKNRFLVIALDNR
IYKVIKYILNSIFDDISFESLLQIDKNWLDKEEINSSRINSYKIMNKVKFNIEEKIWLSKNNKLNLAVKN
WYPIDYVEANNYKGINQFLLDKIRMFSGLRFNIIKVHSSLDLKKLIKSGKIDMLNTNATDSNLDNVF
```

TABLE 1-continued

Nucleotide and Amino Acid Sequences.

NIKLNSRIPLYIFSNKKRVLPSRSLEKFAILDFLYSKNLASNIKSKLILVSSFNEALLLLYKGKVDGIISD
EYTAAAVFEELNIDDVEKIPTFRDLAFDLSLAIYNQDYILKEIIQKVVMRSNVDSQMYLNDWKFDIY
YKSRSIRFKNFKFLVITFIIFYFTFLGFVIIFMFRLSFEQKRRYSFVMNEKKIAEAANAAKTIFIANVSHD
IRTPINGIMAATELLDTTILTDVQKDYVRMINYSSDSLISLTDDILYLSKIDVNELYVESQEIDLESEME
MVLKAFQSQCAKKNIDLFSYSKSIFNNYIKGDIVKIKQVLINLIGNAFK DDGVIVLNYEEVCRTRT
DGNRVLVTVEFKVIDTGKGIEKENFSKIFEIFKQEDDSSSRVHEGAGLGLSISRELIRLMGGLGIAVDS
KVGEGTTFSFMLPFLLGSELKSKKLSINRFQSVNGDNKVLNVLLSQKSIKIFEHCSILLGCSSNVRYVA
SFEDAYKVFKKYPSYNFVYINVNNDNIQEGIRLANNIERLNSDVQIIFLFYYLDNKALKNLKYGYVK
KPLMGLGICSILYKKEFNPEMDFEDLVPIDSALRIKEPINVLIAEDNQVNQKVLKDILVVIGINENFTD
VVDDGVKALKSLKDKKYTISFIDIRMPRYDGFSVAKEIRKFEKAKNLKPCVLVAVTAHALQEYKDK
CLASGMNDYISKPIHISSIKTILKKYLQFEVDDIGENENLNQLVKFPNLDYNRALKELNLSYVSYSEL
CRGLVDFISINIIDLEKAFDEEDLSLIKDISHSISGALSNMRSELYKDFQKIETSKDSISELKKMYSFVK
DDLFQLISDIKENILFESEIVSENKLYFKNNDQFLNLLNKLLIGIKTRKPREYKEILESINKYVLDDNIQ
VLFSDLRRNLRLYRFAESSKILEEIIEMLNNKRY f502.nt (SEQ ID NO:415)
ATGAAAAAAGCAAACTTTTTAAGTACTAATTTTTTAATTTTACTTTTGGTTTGCTTTGTCAACGT
CAATTTATTTTCTAAGGATATTTTCAAGTTTAAGCTTGTAGATCAATTTTTTCCTTTTTACTACA
AGAATAATAAAGGAGAATATGAAGGACTTATTTTTTCTATTTTAGATAAATGGGCAAAAGATAA
TAATGCTGATATTATGGTTGAGCATATTGATAATTTAAATGAAAGTGAAATTGAAGACGAAGCA
ATATATTTAGGATTAACTTATAATGTAAAATTAAATGATTTTTTTTATTTTAAAAGTGAGCTTGC
TAGGAGTATTTCAATTTTATTTTTTAAAAACTCTAATAAAAAATATAAAAATACCCATTCAACAT
TTTTATCCAATTTTAATATAGGAGTTATTAAAAATACAATATATGAAGATATCTTAAGGTTAAA
AAACGTTAACACCATTTTTTTGGCTGATAATTCTCAAGAGTTAGTATTGGCCTTAAAAAACGAT
AAAGTTGATTATATATATGGTGATTGCAAGACTTTACATTATATTGCAAATAACTTTTTAAGTG
AAGATCTTGTGATTTTTTACCGGGGATGTTTTTATAGTATCAAAAATAGAGTGGCTATTAGTAG
AAATGCTCCTGAGATAGTAAAGAATTTGAATTTAGATTTGTTTTCATATTTAATGAAAATGCCT
GAGGAACTTGTTTTTTCTTTTTTAGATAGCAATGCTAAGGGAAGTTTTGTTGATGTTGGTTTATA
TAATGATTATCCTCCTTTAAGTTTTATTAATTCACAGGGAAAATTGTCTGGCATTTTAGTGGATT
TGTGGAATCTTCTCTCAAGACAACATATCTTTAAACCTATTTTTAAGGGATTTTCCAAAGAGGA
TATTAAGAAATCATTAGATGGAAAATCAGTAGGTATTTTTGGAGGAATTATTAGCAATGATAGT
GTGTTGGAAAATGTTAATTATGTAGTAAGTAAGCCAATATATCCTCTTAATTTTAAATTTTATTC
TAAAGACCTAAGCAATGATGCTGGTCCAATAAATTCTCACTTTATTGATTTTAATTTTAATAATA
TTCAATTAAATAAGAATAAAGATATTGTTAATAACTTTATAGATATTGTTAATAATTCATATGG
GTTTATAGAAAATTCAATAACAACAAAATATTTGTTAAAATTAAATGGATATAACGGTAGATTA
AAATCTTACGATTCGATTTTTAATAAAAATAGGTTTTTAGTATTAGCCATTGATAATAGGATTTA
TAAGGTTATTAAATATATTCTCAATTCTATATTTGATGATATTTCATTTGAATCTTTGCTTCAAA
TAGATAAAAATTGGTTGGATAAAGAAGAGATTAATAGTTCTAGAATAAATAGTTATAAAATTAT
GAATAAGGTTAAATTTAATATAGAAGAAAAAATTTGGTTATCAAAAAATAATAAATTAAATCTT
GCTGTTAAAAATTGGTATCCAATAGATTATGTTGAGGCAAATAATTATAAAGGAATAAATCAAT
TTTTGCTTGATAAGATTAGAATGTTTTCAGGTTTGAGATTTAACATAATTAAAGTACACAGCAG
TTTAGATCTTAAAAAATTAATCAAATCTGGAAAAATCGATATGCTAAATACTAATGCAACCGAT
TCAAATTTAGATAATGTTTTCAACATAAAATTAAATTCTCGAATTCCACTTTATATTTTTTCAAA
TAAGAAAAGGGTGCTTCCATCTAGATCTTTAGAAAAGTTTGCTATACTTGATTTTTTATATAGTA
AAAATTTGGCTTCTAATATTAAATCAAAGCTTATTCTGGTAAGCAGTTTTAATGAAGCGTTGCTT
CTTCTTTATAAGGGAAAGGTAGATGGGATTATTAGCGATGAGTATACAGCTGCTGCTGTTTTTG
AGGAATTAAATATTGATGATGTTGAAAAAATTCCTACTTTTAGAGATTTGGCTTTTGATTTGAG
TCTTGCTATTTATAATCAAGATTATATCTTGAAAGAAATTATTCAAAAAGTTGTTATGCGTTCAA
ATGTTGACAGTCAGATGTATTTAAATGATTGGAAATTTGATATTTATTATAAATCCAGAAGTAT
CAGGTTTAAAAATTTCAAATTTTTAGTGATAACATTCATTATATTTTATTTTACTTTTTTAGGAT
TTGTAATTATATTTATGTTCAGATTATCATTTGAGCAGAAAAGAAGATATTCTTTTGTGATGAAT
GAAAAAAAGATTGCGGAAGCCGCTAATGCTGCTAAAACCATTTTTATAGCCAATGTCAGTCATG
ATATTCGTACCCCTATTAACGGAATAATGGCGGCTACTGAGCTTTTGGATACAACTATTCTTAC
AGATGTTCAAAAGATTATGTTAGGATGATAAATTATTCATCTGATTCTTTGCTTTCTTTAATTG
ATGGATATATTGTATTTGTCTAAAATAGATGTCAATGAATTATATGTTGAGAGTCAAGAGATTGA
TTTAGAGAGTGAAATGGAAATGGTTTTAAAAGCTTTTCAATCTCAATGTGCAAAGAAAAATATT
GATTTATTCTCTTATTCTAAATCTATTTTTAATAATTATATAAAGGGTGATATTGTAAAAATTAA
ACAAGTTTTAATTAATTTAATAGGAAATGCTTTTAAGTTTACAGATGATGGTGTTATTGTTTTAA
ATTATGAAGAAGTATGTAGAACAAGAACTGATGGTAATAGGGTTTTGGTTACAGTTGAATTTAA
GGTAATAGATACAGGCAAAGGGATTGAAAAAGAAAATTTTTCTAAGATATTTGAAATATTTAA
ACAAGAGGATGATTCTTCCTTCAAGGGTTCATGAAGGTGCAGGATTGGGATTGTCAATATCTAGA
GAGCTTATAAGACTAATGGGTGGTCTTGGTATTGCTGTTGATAGCAAGGTGGGAGAGGGTACA
ACTTTTTCATTTATGTTGCCCTTTTTATTGGGTAGTGAGCTTAAAAGTAAAAAATTGTCAATCAA
TAGATTTCAATCAGTAAATGGTGACAATAAAGTATTAAATGTGCTTTTAAGTCAAAAATCTATT
AAAATTTTTGAGCACTGTTCGATTTTATTGGGATGCTCTTCTAATGTGCGCTATGTAGCGTCTTT
TGAGGATGCTTATAAAGTCTTCAAGAAATACCCTTCTTATAATTTTGTTTATATAAATGTAAATA
ACGATAATATTCAAGAGGGTATTCGACTTGCCAATAATATTGAAAGACTAAATTCTGATGTACA
AATTATTTTTTATTTTATTATTTAGATAATAAAGCTCTAAAAAATTTAAAATATGGTTATGTTA
AAAAGCCTTTAATGGGGCTTGGTATATGCTCTATTCTTTATAAAAAAGAGTTTAACCCAGAAAT
GGATTTTGAGGATTTGGTTCCAATAGATAGTGCTTTAAGGATAAAAGAGCCCATTAATGTTTTA
ATAGCTGAAGATAATCAGGTAAATCAAAAAGTGTTGAAAGATATTCTTGTTGTTATAGGCATTA
ATGAAAATTTTATTGATGTTGTAGATGATGGAGTAAAGGCTTTAAAATCTTTAAAAGATAAAAA
ATATACTATCTTTTATTGATATACGAATGCCAAGATATGATGGATTTTCGGTGGCTAAGGAA
ATTAGAAAATTTGAAAAGGCAAAGAATTTAAAGCCTTGTGTTTTGGTTGCTGTAACAGCGCATG
CTTTTGCAAGAGTATAAAGACAAGTGTCTTGCAAGTGGTATGAATGATTATATCTCAAACCCAAT
ACACATAAGTTCAATTAAAACTATATTAAAAAAATACTTACAGTTTGAAGTTGATGATATTGGG
GAGAATGAAAATTTGAATCAACTTGTTAAGTTTCCTAATTTAGATGTTAATAGGGCTTTAAAAG

TABLE 1-continued

Nucleotide and Amino Acid Sequences.

AATTAAATCTTTCATATGTATCATATTCTGAATTATGTAGAGGGCTTGTTGATTTTATCTCTATT
AATATTATTGATTTGGAAAAGCTTTTGATGAGGAAGATTTGTCTTTAATTAAGGATATATCTC
ATTCAATATCTGGAGCTCTTTCTAATATGCGTAGCGAATTGTATAAAGATTTTCAAAAAATTGA
AACAAGTAAAGATTCAATTTCTGAGTTGAAAAAAATGTATTCTTTTGTAAAAGATGATTTATTT
CAACTAATAAGCGACATAAAGGAAAATATTTTGTTTGAGTCTGAGATTGTTAGTGAGAACAAGC
TATATTTTAAAAATAATGATCAATTTTTAAACCTTCTCAACAAACTTTTTAATTGGTATTAAGACT
AGAAAGCCAAGAGAATACAAAGAAATTCTTGAGAGCATTAATAAATATGTTTTAGACGATAAT
ATTCAGGTATTATTTAGTGATCTTCGCAGAAATTTAAGATTATATAGATTTGCTGAGAGCTCTA
AGATTCTTGAAGAGATTATTGAAATGCTTAATAATAAGAGATATTAG t502.nt (SEQ ID NO:416)
TGCTTTGTCAACGTCAATTTATTTTCTAAGGATATTTTCAAGTTTAAGCTTGTAGATCAATTTTT
TCCTTTTTACTACAAGAATAATAAAGGAGAATATGAAGGACTTATTTTTTCTATTTTAGATAAAT
GGGCAAAAGATAATAATGCTGATATTATGGTTGAGCATATTGATAATTTAAATGAAAGTGAAAT
TGAAGACGAAGCAATATATTTAGGATTAACTTATAATGTAAAATTAAATGATTTTTTTTATTTTA
AAAGTGAGCTTGCTAGGAGTATTTCAATTTTATTTTTTAAAAACTCTAATAAAAAATATAAAAA
TACCCATTCAACATTTTTATCCAATTTTAATATAGGAGTTATTAAAAATACAATATATGAAGAT
ATCTTAAGGTTAAAAAACGTTAACACCATTTTTTTGGCTGATAATTCTCAAGAGTTAGTATTGG
CCTTAAAAAACGATAAAGTTGATTATATATATGGTGATTGCAAGACTTTACATTATATTGCAAA
TAACTTTTTAAGTGAAGATCTTGTGATTTTTACCGGGGATGTTTTTTATAGTATCAAAAATAGAG
TGGCTATTAGTAGAAATGCTCCTGAGATAGTAAAGAATTTGAATTTAGATTTGTTTTCATATTTA
ATGAAAATGCCTGAGGAACTTGTTTTTTCTTTTTTAGATAGCAATGCTAAGGGAAGTTTTGTTG
ATGTTGGTTTATATAATGATTATCCTCCTTAAGTTTTATTAATTCACAGGGAAAATTGTCTGGC
ATTTTAGTGGATTTGTGGAATCTTCTCTCAAGACAACATATCTTTAAACCTATTTTTAAGGGATT
TTCCAAAGAGGATATTAAGAAATCATTAGATGGAAAATCAGTAGGTATTTTGGAGGAATTATT
AGCAATGATAGTGTGTTGGAAAATGTTAATTATGTAGTAAGTAAGCCAATATATCCTCTTAATT
TTAAATTTTATTCTAAAGACCTAAGCAATGATGCTGGTCCAATAAATTCTCAGTTTATTGATTTT
AATTTTAATAATATTCAATTAAATAAGAATAAAGATATTGTTAATAACTTTATAGATATTGTTA
ATAATTCATATGGGTTTATAGAAAATTCAATAACAACAAAATATTTGTTAAAATTAAATGGATA
TAACGGTAGATTAAAATCTTACGATTCGATTTTTAATAAAAATAGGTTTTTAGTATTAGCCATTG
ATAATAGGATTTATAAGGTTATTAAATATATTCTCAATTCTATATTTGATGATATTTCATTTGAA
TCTTTGCTTCAAATAGATAAAAATTGGTTGGATAAAGAAGAGATTAATAGTTCTAGAATAAATA
GTTATAAAATTATGAATAAGGTTAAATTTAATATAGAAGAAAAAATTTGGTTATCAAAAAATAA
TAAATTAAATCTTGCTGTTAAAAATTGGTATCCAATAGATTATGTTGAGGCAAATAATTATAAA
GGAATAAATCAATTTTTGCTTGATAAGATTAGAATGTTTTCAGGTTTGAGATTTAACATAATTA
AAGTACACAGCAGTTTAGATCTTAAAAAATTAATCAAATCTGGAAAAATCGATATGCTAAATAC
TAATGCAACCGATTCAAATTTAGATAATGTTTTCAACATAAAATTAAATTCTCGAATTCCACTTT
ATATTTTTTCAAATAAGAAAAGGGTGCTTCCATCTAGATCTTTAGAAAAGTTTGCTATACTTGAT
TTTTTATATAGTAAAAATTTGGCTTCTAATATTAAATCAAAGCTTATTCTGGTAAGCAGTTTTAA
TGAAGCGTTGCTTCTTCTTTATAAGGGAAAGGTAGATGGGATTATTAGCGATGAGTATACAGCT
GCTGCTGTTTTTGAGGAATTAAATATTGATGATGTTGAAAAAATTCCTACTTTTAGAGATTTGG
CTTTTGATTTGAGTCTTGCTATTTATAATCAAGATTATATCTTGAAAGAAATTATTCAAAAAGTT
GTTATGCGTTCAAATGTTGACAGTCAGATGTATTTAAATGATTGGAAATTTGATATTTATTATA
AATCCAGAAGTATCAGGTTTAAAAAATTTCAAATTTTTAGTGATAACATTCATTATATTTTATTTT
ACTTTTTTAGGATTTGTAATTATATTTATGTTCAGATTATCATTTGAGCAGAAAAGAAGATATTC
TTTTGTGATGAATGAAAAAAAGATTGCGGAAGCCGCTAATGCTGCTAAAACCATTTTTATAGCC
AATGTCAGTCATGATATTCGTACCCCTATTAACGGAATAATGGCGGCTACTGAGCTTTTGGATA
CAACTATTCTTACAGATGTTCAAAAAGATTATGTTAGGATGATAAATTATTCATCTGATTCTTTG
CTTTCTTTTAATTGATGATATATTGTATTTGTCTAAAATAGATGTCAATGAATTATATGTTGAGAG
TCAAGAGATTGATTTAGAGAGTGAAATGGAAATGGTTTTAAAAGCTTTTCAATCTCAATGTGCA
AAGAAAAATATTGATTTATTCTCTTATTCTAAATCTATTTTTAATAATTATATAAAGGGTGATAT
TGTAAAAATTAAACAAGTTTTAATTAATTTAATAGGAAATGCTTTTAAGTTTACAGATGATGGT
GTTATTGTTTTAAATTATGAAGAAGTATGTAGAACAAGAACTGATGGTAATAGGGTTTTGGTTA
CAGTTGAATTTAAGGTAATAGATACAGGCAAAGGGATTGAAAAGAAAATTTTTCTAAGGATAT
TTGAAATATTTAAACAAGAGGATGATTCTTCTTCAAGGGTTCATGAAGGTGCAGGATTGGGATT
GTCAATATCTAGAGAGCTTATAAGACTAATGGGTGGTCTTGGTATTGCTGTTGATAGCAAGGTG
GGAGAGGGTACAACTTTTTCATTTATGTTGCCCTTTTTATTGGGTAGTGAGCTTAAAAGTAAAA
AATTGTCAATCAATAGATTTCAATCAGTAAATGGTGACAATAAAGTATTAAATGTGCTTAAG
TCAAAAATCTATTAAAATTTTTGAGCACTGTTCGATTTTATTGGGATGCTCTTCTAATGTGCGCT
ATGTAGCGTCTTTTGAGGATGCTTATAAAGTCTTCAAGAAATACCCTTCTTATAATTTTGTTTAT
ATAAATGTAAATAACGATAATATTCAAGAGGGTATTCGACTTGCCAATAATATTGAAAGACTAA
ATTCTGATGTACAAATTATTTTTTTATTTTATTATTTAGATAATAAAGCTCTAAAAAATTTAAAA
TATGGTTATGTTAAAAAGCCTTTAATGGGGCTTGGTATATGCTCTATTCTTTATAAAAAAGAGT
TTAACCCAGAAATGGATTTTGAGGATTTGGTTCCAATAGATAGTGCTTTAAGGATAAAAGAGCC
CATTAATGTTTTAATAGCTGAAGATAATCAGGTAAATCAAAAAGTGTTGAAAGATATTCTTGTT
GTTATAGGCATTAATGAAAATTTTATTGATGTTGTAGATGATGGAGTAAAGGCTTTAAAATCTT
TAAAAGATAAAAAATATACTATCTCTTTTATTGATATACGAATGCCAAGATATGATGGATTTTC
GGTGGCTAAGGAAATTAGAAAATTTGAAAAGGCAAAGAATTTAAAGCCTTGTGTTTTGGTTGCT
GTAACAGCGCATGCTTTGCAAGAGTATAAAGACAAGTGTCTTGCAAGTGGTATGAATGATTATA
TCTCAAAACCAATACACATAAGTTCAATTAAAACTATATTAAAAAAATACTTACAGTTTGAAGT
TGATGATATTGGGGAGAATGAAAATTTGAATCAACTTGTTAAGTTTCCTAATTTAGATGTTAAT
AGGGCTTTAAAAGAATTAAATCTTTCATATGTATCATATTCTGAATTATGTAGAGGGCTTGTTG
ATTTTATCTCTATTAATATTATTGATTTGGAAAAAGCTTTTGATGAGGAAGATTTGTCTTTAATT
AAGGATATATCTCATTCAATATCTGGAGCTCTTTCTAATATGCGTAGCGAATTGTATAAAGATT
TTCAAAAAATTGAAACAAGTAAAGATTCAATTTCTGAGTTGAAAAAAATGTATTCTTTTGTAAA
AGATGATTTATTTCAACTAATAAGCGACATAAAGGAAAATATTTTGTTTGAGTCTGAGATTGTT
AGTGAGAACAAGCTATATTTTAAAAATAATGATCAATTTTTAAACCTTCTCAACAAACTTTTAA

TABLE 1-continued

Nucleotide and Amino Acid Sequences.

TTGGTATTAAGACTAGAAAGCCAAGAGAATACAAAGAAATTCTTGAGAGCATTAATAAATATG
TTTTAGACGATAATATTCAGGTATTATTTAGTGATCTTCGCAGAAATTTAAGATTATATAGATTT
GCTGAGAGCTCTAAGATTCTTGAAGAGATTATTGAAATGCTTAATAATAAGAGATATTAG f527.aa (SEQ ID NO:417)
MNLLVKIAKFILILFLFTSCNQKQSEIQNLTHLLKSSNKNRLDKFLIIDRVVNIYIANKNYEDALEIVN
NGIIDDESREYYPLYLYLMGNIYDSMGEDFVAFNIYKRVVDNFDDYVYENHSMKTRVAKKIVNLNI
DSIDKINYYKFILNMGIDNLNNEEKGNYFYNLALSLEDVQDYDESYFYYKKFLSIPRAHLKIDSRDYF
NVVTKINYFNNPEFVVYRNLGDLIQDVKNFVLSGNTSKLLNIRDKNNFFIQSWDQKGGKSNSINTNS
FLTTMIRLGGRRKNGIQFAKHLEADSSDDISYLESRGWDHIHEWYFVFKRIVYPKDPEINNGWTWIG
VYLGKK t527.aa (SEQID NO:418)
CNQKQSEIQNLTHLLKSSNKNRLDKFLIIDRVVNIYIANKNYEDALEIVNNGIIDDESREYYPLYLYL
MGNIYDSMGEDFVAFNIYKRVVDNFDDYVYENHSMKTRVAKKIVNLNIDSIDKINYYKFILNMGID
NLNNEEKGNYFYNLALSLEDVQDYDESYFYYKKFLSIPRAHLKIDSRDYFNVVTKINTYFNNPEFVVY
RNLGDLIQDVKNFVLSGNTSKLLNIRDKNNFFIQSWDQKGGKSNSINTNSFLTTMIRLGGRRKNGIQ
FAKHLEADSSDDISYLESRGWDHIHEWYFVFKRIVYPKDPEINNGWTWIGVYLGKK f527.nt (SEQ ID NO:419)
ATGAATCTATTGGTCAAAATTGCTAAATTTATTTTGATTTTGTTTTTATTTACTTCTTGCAACCA
AAAGCAAAGCGAGATTCAAAATCTTACACATCTTTTAAAATCTTCTAATAAAAATAGATTAGAT
AAATTTCTTATTATTGATAGAGTTGTTAACATATATATTGCAAATAAAAATTATGAAGATGCTTT
AGAAATTGTAAATAATGGAATTATTGATGATGAATCTAGAGAATATTATCCTTTGTATCTTTAT
TTAATGGGCAATATTTATGATTCCATGGGAGAAGATTTTGTAGCTTTTAATATTTACAAGCGTG
TTGTTGATAATTTTGATGATTATGTTTATGAAAACCATTCAATGAAAACAAGGGTTGCTAAAAA
GATTGTCAATTTAAATATTGATTCAATCGATAAAATCAATTATTACAAATTTATATTAAATATGG
GGATTGATAATTTAAATAATGAGGAAAAGGGTAATTATTTTTATAATCTTGCGCTAAGTTTGGA
AGATGTTCAAGATTACGATGAATCTTATTTTTATTATAAAAAATTTCTTCAATTCCAAGGGCAC
ATTTAAAAATAGATTCTAGAGACTATTTTAATGTTGTTACAAAAATTAATTACTTTAATAATCCA
GAGTTTGTTGTTTATAGAAATTTAGGAGATTTAATCCAGGATGTTAAAAATTTTGTTCTTTCTGG
TAATACTTCTAAATTGCTTAATATAAGAGATAAGAATAATTTTTTTATTCAAAGCTGGGATCAA
AAGGGTGGAAAGAGTAATTCCATTAATACTAATAGCTTTTTAACCACTATGATTAGGCTTGGGG
GGAGAAGAAAAAACGGAATACAATTTGCAAAGCATCTTGAGGCAGATTCTAGTGACGATATAT
CTTATCTTGAGTCAAGGGGCTGGGACCATATTCATGAATGGTATTTTGTTTTTAAAAGAATTGT
TTATCCTAAAGATCCAGAAATTAATAATGGCTGGACTTGGATAGGCGTGTATTTAGGTAAAAAA
TAA t527.nt (SEQ ID NO:420)
TGCAACCAAAAGCAAAGCGAGATTCAAAATCTTACACATCTTTTAAAATCTTCTAATAAAAATA
GATTAGATAAATTTCTTATTATTGATAGAGTTGTTAACATATATATTGCAAATAAAAATTATGA
AGATGCTTTAGAAATTGTAAATAATGGAATTATTGATGATGAATCTAGAGAATATTATCCTTTG
TATCTTTATTTAATGGGCAATATTTATGATTCCATGGGAGAAGATTTTGTAGCTTTTAATATTTA
CAAGCGTGTTGTTGATAATTTTGATGATTATGTTTATGAAAACCATTCAATGAAAACAAGGGTT
GCTAAAAAGATTGTCAATTTAAATATTGATTCAATCGATAAAATCAATTATTACAAATTTATAT
TAAATATGGGGATTGATAATTTAAATAATGAGGAAAAGGGTAATTATTTTTATAATCTTGCGCT
AAGTTTGGAAGATGTTCAAGATTACGATGAATCTTATTTTTATTATAAAAAATTTCTTTCAATTC
CAAGGGCACATTTAAAAATAGATTCTAGAGACTATTTTAATGTTGTTACAAAAATTAATTACTT
TAATAATCCAGAGTTTGTTGTTTATAGAAATTTAGGAGATTTAATCCAGGATGTTAAAAATTTT
GTTCTTTCTGGTAATACTTCTAAATTGCTTAATATAAGAGATAAGAATAATTTTTTTATTCAAAG
CTGGGATCAAAAGGGTGGAAAGAGTAATTCCATTAATACTAATAGCTTTTTAACCACTATGATT
AGGCTTGGGGGGAGAAGAAAAAACGGAATACAATTTGCAAAGCATCTTGAGGCAGATTCTAGT
GACGATATATCTTATCTTGAGTCAAGGGGCTGGGACCATATTCATGAATGGTATTTTGTTTTTA
AAAGAATTGTTTATCCTAAAGATCCAGAAATTAATAATGGCTGGACTTGGATAGGCGTGTATTT
AGGTAAAAAATAA f541.aa (SEQ ID NO:421)
MNKILLLILLESIVFLSCSGKGSLGSEIPKVSLIIDGTFDDKSFNESALNGVKKVKEEFKIELVLKESSS
NSYLSDLEGLKDAGSDLIWLIGYRFSDVAKVAALQNPDMKYAIIDPIYSNDPIPANLVGMTFRAQEG
AFLTGYIAAKLSKTGKIGFLGGIEGEIVDAFRYGYEAGAKYANKDIKISTQYIGSFADLEAGRSVATR
MYSDEIDIIHHAAGLGGIGAIEVAKELGSGHYIIGVDEDQAYLAPDNVITSTTKDVGRALNIFTSNHL
KTNTFEGGKLINYGLKEGVVGFVRNPKMISFELEKEIDNLSSKIINKEIIVPSNKESYEKFLKEFI t541.aa (SEQ ID NO:422)
CSGKGSLGSEIPKVSLIIDGTFDDKSFNESALNGVKKVKEEFKIELVLKESSSNSYLSDLEGLKDAGSD
LIWLIGYRFSDVAKVAALQNPDMKYAIIDPIYSNDPIPANLVGMTFRAQEGAFLTGYIAAKLSKTGKI
GFLGGIEGEIVDAFRYGYEAGAKYANKDIKISTQYIGSFADLEAGRSVATRMYSDEIDIIHHAAGLGG
IGAIEVAKELGSGHYIIGVDEDQAYLAPDNVITSTTKDVGRALNIFTSNHLKTNTFEGGKLINYGLKE
GVVGFVRNPKMISFELEKEIDNLSSKIINKEIIVPSNKESYEKFLKE
FI f541.nt (SEQ ID NO:423)
ATGAATAAAATATTGTTGTTGATTTTGCTTGAGAGTATTGTTTTTTATCTTGTAGTGGTAAAGG
TAGTCTTGGGAGCGAAATTCCTAAGGTATCTTTAATAATTGATGGAACTTTTGATGATAAATCT
TTTAATGAGAGTGCTTTAAATGGCGTAAAAAAAGTTAAAGAAGAATTTAAAATTGAGCTTGTTT
TAAAAGAATCCTCATCAAATTCTTATTTATCTGATCTTGAAGGGCTTAAGGATGCGGGCTCAGA
TTTAATTTGGCTTATTGGGTATAGATTTAGCGATGTGGCCAAGGTTGCGGCTCTTCCAAAATCCC

TABLE 1-continued

Nucleotide and Amino Acid Sequences.

GATATGAAATATGCAATTATTGATCCTATTTATTCTAACGATCCTATTCCTGCAAATTTGGTGGG
CATGACCTTTAGAGCTCAAGAGGGTGCATTTTTAACGGGTTATATTGCTGCAAAACTTTCTAAA
ACAGGTAAAATTGGATTTTTAGGGGGAATAGAAGGCGAGATAGTAGATGCTTTTAGGTATGGG
TATGAAGCTGGTGCTAAGTATGCTAATAAAGATATAAAGATATCTACTCAGTATATTGGTAGTT
TTGCTGACCTTGAAGCTGGTAGAAGCGTTGCAACTAGGATGTATTCTGATGAGATAGACATTAT
TCATCATGCTGCAGGCCTTGGAGGAATTGGGGCTATTGAGGTTGCAAAAGAACTTGGTTCTGGG
CATTACATTATTGGAGTTGATGAAGATCAAGCATATCTTGCTCCTGACAATGTAATAACATCTA
CAACTAAAGATGTTGGTAGAGCTTTAAATATTTTTACATCTAACCATTTAAAAACTAATACTTTC
GAAGGTGGCAAATTAATAAATTATGGCCTTAAAGAAGGAGTTGTGGGGTTTGTAAGAAATCCT
AAAATGATTTCCTTTGAACTTGAAAAAGAAATTGACAATCTTTCTAGCAAAATAATCAACAAAG
AAATTATTGTTCCATCTAATAAAGAAAGTTATGAGAAGTTTCTTAAAGAATTTATTTAA t541.nt (SEQ ID NO:424)
TGTAGTGGTAAAGGTAGTCTTGGGAGCGAAATTCCTAAGGTATCTTTAATAATTGATGGAACTT
TTGATGATAAATCTTTTTAATGAGAGTGCTTTAAATGGCGTAAAAAAAGTTAAAGAAGAATTTAA
AATTGAGCTTGTTTTAAAAGAATCCTCATCAAATTCTTATTTATCTGATCTTGAAGGGCTTAAGG
ATGCGGGCTCAGATTTAATTTGGCTTATTGGGTATAGATTTAGCGATGTGGCCAAGGTTGCGGC
TCTTCAAAATCCCGATATGAAATATGCAATTATTGATCCTATTTATTCTAACGATCCTATTCCTG
CAAATTTGGTGGGCATGACCTTTAGAGCTCAAGAGGGTGCATTTTTAACGGGTTATATTGCTGC
AAAACTTTCTAAAACAGGTAAAATTGGATTTTTAGGGGGAATAGAAGGCGAGATAGTAGATGC
TTTTAGGTATGGGTATGAAGCTGGTGCTAAGTATGCTAATAAAGATATAAAGATATCTACTCAG
TATATTGGTAGTTTTGCTGACCTTGAAGCTGGTAGAAGCGTTGCAACTAGGATGTATTCTGATG
AGATAGACATTATTCATCATGCTGCAGGCCTTGGAGGAATTGGGGCTATTGAGGTTGCAAAAG
AACTTGGTTCTGGGCATTACATTATTGGAGTTGATGAAGATCAAGCATATCTTGCTCCTGACAA
TGTAATAACATCTACAACTAAAGATGTTGGTAGAGCTTTAAATATTTTTACATCTAACCATTTAA
AAACTAATACTTTCGAAGGTGGCAAATTAATAAATTATGGCCTTAAAGAAGGAGTTGTGGGGTT
TGTAAGAAATCCTAAAATGATTTCCTTTGAACTTGAAAAAGAAATTGACAATCTTTCTAGCAAA
ATAATCAACAAAGAAATTATTGTTCCATCTAATAAAGAAAGTTATGAGAAGTTTCTTAAAGAAT
TTATTTAA f561.aa (SEQ ID NO:425)
MYKNGFFKNYLSLFLIFLVIACTSKDSSNEYVEEQEAENSSKPDDSKIDEHTIGHVFHAMGVVHSKK
DRKSLGKNIKVFYFSEEDGHFQTIPSKENAKLIVYFYDNVYAGEAPISISGKEAFIFVGITPDFKKIINS
NLHGAKSDLIGTFKDLNIKNSKLEITVDENNSDAKTFLESVNYIIDGVEKISPMLTN t561.aa (SEQ ID NO:426)
CTSKDSSNEYVEEQEAENSSKPDDSKIDEHTIGHVFHAMGVVHSKKDRKSLGKNIKVFYFSEEDGHF
QTIPSKENAKLIVYFYDNVYAGEAPISISGKEAFIFVGITPDFKKIINSNLHGAKSDLIGTFKDLNIKNS
KLEITVDENNSDAKTFLESVNYIIDGVEKISPMLTN f561.nt (SEQ ID NO:427)
ATGTATAAAAATGGTTTTTTTAAAAACTATTTGTCATTGTTTTTAATTTTTTTAGTAATTGCTTGT
ACTTCAAAAGATAGCTCAAATGAATATGTTGAGGAGCAAGAAGCGGAGAACTCTTCTAAGCCT
GATGATTCTAAAATAGATGAACATACTATTGGGCACGTTTTTCACGCTATGGGAGTAGTTCATT
CAAAAAAGGATCGAAAAAGTTTGGGGAAAAATATAAAGGTTTTTTATTTTTCTGAAGAAGATG
GACATTTTCAAACAATACCCTCAAAAGAGAATGCAAAGTTAATAGTTTATTTTTATGACAATGT
TTATGCAGGAGAGGCTCCAATTAGTATCTCTGGAAAAGAAGCCTTTATTTTTGTTGGGATTACC
CCTGACTTTAAAAAGATTATAAATAGCAATTTACATGGCGCTAAAAGTGATCTTATTGGTACTT
TTAAAGATCTTAATATTAAAAATTCAAAATTGGAAATTACAGTTGATGAGAATAATTCAGATGC
CAAGACCTTCCTTGAATCTGTTAATTACATTATCGACGGCGTTGAAAAAATTTCACCTATGTTAA
CGAATTAA t561.nt (SEQ ID NO:428)
TGTACTTCAAAAGATAGCTCAAATGAATATGTTGAGGAGCAAGAAGCGGAGAACTCTTCTAAG
CCTGATGATTCTAAAATAGATGAACATACTATTGGGCACGTTTTTCACGCTATGGGAGTAGTTC
ATTCAAAAAAGGATCGAAAAAGTTTGGGGAAAAATATAAAGGTTTTTTATTTTTCTGAAGAAGA
TGGACATTTTCAAACAATACCCTCAAAAGAGAATGCAAAGTTAATAGTTTATTTTTATGACAAT
GTTTATGCAGGAGAGGCTCCAATTAGTATCTCTGGAAAAGAAGCCTTTATTTTTGTTGGGATTA
CCCCTGACTTTAAAAAGATTATAAATAGCAATTTACATGGCGCTAAAAGTGATCTTATTGGTAC
TTTTAAAGATCTTAATATTAAAAATTCAAAATTGGAAATTACAGTTGATGAGAATAATTCAGAT
GCCAAGACCTTCCTTGAATCTGTTAATTACATTATCGACGGCGTTGAAAAAATTTCACCTATGTT
AACGAATTAA f604.aa (SEQ ID NO:429)
MSFNKTKKIGKKIKIVTLLMLAVSLIACNNNSEKEKLAFKVYIGGAPSSLDPHLVDETIGARILEQIFS
GLLTLNTKTGKLKPGLAKNWEASKDKKTYQFYLRDNLFWSDGVEITAEGIRKSFLRILNKETGSTN
VDMLKSIIKNGQEYFDGKVSDSELGIKAIDSKTLEITLTAPKPYFLELLLHYAFMPVPIHVIEKYKGN
WTSPENMVTSGPFKLKKRLPNEKIIFEKNERYYNAKEVELDELVYITSDNDLTVYNMYKNNEIDAIF
NSIPPDIVNEIKLQKDYYQHKSNAIYLYSFNTKIKPLDDARVREALTLAIDRETLTYKVLNDGTVPTR
EITPDLKNYNYGKKLALFDPEKSKKLLADAGYPNGKGFPMLTLKYNTNETHKKIAAFIQNQWKKIL
NINLMLTNENWPVLTNSRNTGNFEIIRVGRIGEYLDPHTYFTIFTRENSQLASYGYSNLEFDKLIRESD
LEKDPIKRKQLLRKAESIIIEKDFPAAPIYIYSGHYLFRNDKWTGWNPNVSEVYYLSELKPIKNAKHN t604.aa (SEQ ID NO:430)
CNNNSEKEKLAFKVYIGGAPSSLDPHLVDETIGARILEQIFSGLLTLNTKTGKLKPGLAKNWEASKD
KKTYQFYLRDNLFWSDGVEITAEGIRKSFLRILNKETGSTNVDMLKSIIKNGQEYFDGKVSDSELGIK
AIDSKTLEITLTAPKPYFLELLLHYAFMPVPIHVIEKYKGNWTSPENMVTSGPFKLKKRLPNEKIIFEK

TABLE 1-continued

Nucleotide and Amino Acid Sequences.

NERYYNAKEVELDELVYITSDNDLTVYNMYKNNEIDAIFNSIPPDIVNEIKLQKDYYQHKSNAIYLY
SFNTKIKPLDDARVREALTLAIDRETLTYKVLNDGTVPTREITPDLKNYNYGKKLALFDPEKSKKLL
ADAGYPNGKGFPMLTLKYNTNETHKKIAAFIQNQWKKILNINLMLTNENWPVLTNSRNTGNFEIIR
VGRIGEYLDPHTYFTIFTRENSQLASYGYSNLEFDKLIRESDLEKDPIKRKQLLRKAESIIIEKDFPAAP
IYIYSGHYLFRNDKWTGWNPNVSEVYYLSELKPIKNAKHN f604.nt (SEQ ID NO:431)
ATGAGCTTTAATAAAACTAAAAAAATCGGTAAAAAAATTAAAATAGTAACACTACTTATGCTTG
CTGTGTCTTTAATTGCATGCAATAATAATTCAGAAAAAGAAAAATTAGCATTTAAAGTATACAT
AGGGGGAGCGCCCTCATCGCTTGACCCTCATTTGGTAGATGAGACAATAGGAGCAAGAATTTTA
GAACAAATATTCTCAGGGCTTTTGACATTAAATACCAAAACAGGAAAGCTAAAGCCCGGACTTG
CTAAAAATTGGGAAGCCTCAAAAGATAAAAAAACATATCAATTTTATCTAAGGGACAACCTTTT
TTGGAGCGATGGAGTTGAAATTACCGCTGAAGGGATAAGAAAATCTTTTTTAAGAATTTTAAAT
AAAGAAACAGGATCTACAAATGTTGACATGCTCAAATCAATAATAAAAAATGGACAAGAGTAT
TTTGACGGGAAAGTATCCGATTCTGAACTTGGAATCAAGGCAATTGATAGTAAAACGCTGGAA
ATAACACTTACGGCCCCAAAGCCATATTTTCTTGAACTGCTTCTACATTACGCATTCATGCCAGT
ACCTATTCATGTGATTGAAAAATATAAGGGAAATTGGACAAGCCCTGAAAACATGGTTACTAGC
GGTCCTTTTAAATTAAAAAAAAGATTACCTAATGAAAAAATTATCTTTGAAAAAAACGAACGTT
ATTATAATGCAAAAGAAGTAGAACTTGATGAGCTTGTCTACATTACGTCTGACAATGATCTTAC
TGTGTACAATATGTACAAAAACAACGAAATTGATGCTATTTTTAACAGCATCCCGCCGGACATT
GTAAATGAAATAAAACTACAAAAAGACTATTACCAACACAAAAGTAATGCAATTTATTTATATT
CATTTAATACAAAAATAAAACCCCTTGATGATGCTAGAGTTAGAGAAGCTTTAACCTTAGCTAT
TGACAGAGAAACTTTTAACTTACAAAGTGCTAAATGATGGCACAGTTCCTACAAGAGAAATAACT
CCTGATCTTAAAAATTACAATTACGGTAAAAAATTGGCTTTATTTGATCCTGAAAAATCTAAAA
AGCTTTTGGCAGATGCAGGGTATCCTAATGGGAAAGGATTCCCAATGCTAACACTAAATATAA
TACAAACGAAACTCATAAAAAAATTGCTGCATTTATTCAAAACCAATGGAAAAAAATTCTAAAT
ATCAATCTTATGCTTACCAACGAAAATTGGCCTGTTCTTACCAACAGCAGAAATACTGGCAATT
TTGAAATAATAAGAGTTGGACGCATTGGGGAATATTTAGATCCACACACATACTTTACTATATT
CACAAGAGAAAATTCACAACTTGCATCATACGGATATTCAAACCTAGAATTTGACAAACTCATC
AGAGAATCAGATCTTGAAAAAGATCCTATAAAAAGAAAACAATTACTCAGAAAAGCAGAATCA
ATAATAATTGAAAAAGATTTTCCTGCTGCACCAATATACATATATTCTGGGCATTATCTTTTTAG
AAACGATAAATGGACTGGATGGAATCCTAATGTATCAGAGGTTTATTATCTTTCTGAATTAAAA
CCAATTAAAAATGCAAAACATAATTAA t604.nt (SEQ ID NO:432)
TGCAATAATAATTCAGAAAAAGAAAAATTAGCATTTAAAGTATACATAGGGGGAGCGCCCTCA
TCGCTTGACCCTCATTTGGTAGATGAGACAATAGGAGCAAGAATTTTAGAACAAATATTCTCAG
GGCTTTTGACATTAAATACCAAAACAGGAAAGCTAAAGCCCGGACTTGCTAAAAATTGGGAAG
CCTCAAAAGATAAAAAAACATATCAATTTTATCTAAGGGACAACCTTTTTTGGAGCGATGGAGT
TGAAATTACCGCTGAAGGGATAAGAAAATCTTTTTTAAGAATTTTAAATAAAGAAACAGGATCT
ACAAATGTTGACATGCTCAAATCAATAATAAAAAATGGACAAGAGTATTTTGACGGGAAAGTA
TCCGATTCTGAACTTGGAATCAAGGCAATTGATAGTAAAACGCTGGAAATAACACTTACGGCCC
CAAAGCCATATTTTCTTGAACTGCTTCTACATTACGCATTCATGCCAGTACCTATTCATGTGATT
GAAAAATATAAGGGAAATTGGACAAGCCCTGAAAACATGGTTACTAGCGGTCCTTTTAAATTA
AAAAAAAGATTACCTAATGAAAAATTATCTTTGAAAAAAACGAACGTTATTATAATGCAAAA
GAAGTAGAACTTGATGAGCTTGTCTACATTACGTCTGACAATGATCTTACTGTGTACAATATGT
ACAAAAACAACGAAATTGATGCTATTTTTAACAGCATCCCGCCGGACATTGTAAATGAAATAAA
ACTACAAAAAGACTATTACCAACACAAAAGTAATGCAATTTATTTATATTCATTTAATACAAAA
ATAAAACCCCTTGATGATGCTAGAGTTAGAGAAGCTTTAACCTTAGCTATTGACAGAGAAACTT
TAACTTACAAAGTGCTAAATGATGGCACAGTTCCTACAAGAGAAATAACTCCTGATCTTAAAAA
TTACAATTACGGTAAAAAATTGGCTTTATTTGATCCTGAAAAATCTAAAAAGCTTTTGGCAGAT
GCAGGGTATCCTAATGGGAAAGGATTCCCAATGCTAACACTAAAATATAACAAACGAAACT
CATAAAAAAATTGCTGCATTTATTCAAAACCAATGGAAAAAAATTCTAAATATCAATCTTATGC
TTACCAACGAAAATTGGCCTGTTCTTACCAACAGCAGAAATACTGGCAATTTTGAAATAATAAG
AGTTGGACGCATTGGGAATATTTAGATCCACACACATACTTTACTATATTCACAAGAGAAAAT
TCACAACTTGCATCATACGGATATTCAAACCTAGAATTTGACAAACTCATCAGAGAATCAGATC
TTGAAAAAGATCCTATAAAAAGAAAACAATTACTCAGAAAAGCAGAATCAATAATAATTGAAA
AAGATTTTCCTGCTGCACCAATATACATATATTCTGGGCATTATCTTTTTAGAAACGATAAATG
GACTGGATGGAATCCTAATGTATCAGAGGTTTATTATCTTTCTGAATTAAAACCAATTAAAAAT
GCAAAACATAATTAA f736.aa (SEQ ID NO:433)
MKKVIILIFMLSTSLLYNCKNQDNEKIVSIGGSTTVSPILDEMILRYNKINNNTKVTYDAQGSSVGIN
GLFNKIYKIAISSRDLTKEEIEQGAKETVFAYDALIFITSPEIKITNITEENLAKILNGEIQNWKQVGGP
DAKINFINRDSSSGSYSSIKDLLLNKIFKTHEEAQFRQDGIVVKSNGEVIEKTSLTPHSIGYIGLGYAK
NSIEKGLNILSVNSTYPTKETINSNKYTIKRNLIIVTNNKYEDKSVTQFIDFMTSSTGQDIVEEQGFLGI
KT t736.aa (SEQ ID NO:434)
CKNQDNEKIVSIGGSTTVSPILDEMILRYNKINNNTKVTYDAQGSSVGINGLFNKIYKIAISSRDLTKE
EIEQGAKETVFAYDALIFITSPEIKITNITEENLAKILNGEIQNWKQVGGPDAKINFINRDSSSGSYSSIK
DLLLNKIFKTHEEAQFRQDGIVVKSNGEVIEKTSLTPHSIGYIGLGYAKNSIEKGLNILSVNSTYPTKE
TINSNKYTIKRNLIIVTNNKYEDKSVTQFIDFMTSSTGQDIVEEQGFLGIKT f736.nt (SEQ ID NO:435)
ATGAAAAAAGTTATTATCTTAATTTTTATGCTATCAACAAGTTTATTATACAACTGTAAAAATCA
AGACAATGAAAAAATTGTATCAATTGGAGGATCTACAACTGTAAGCCCAATACTAGACGAAAT

TABLE 1-continued

Nucleotide and Amino Acid Sequences.

GATTTTAAGATATAATAAAATAAACAATAATACTAAAGTAACATACGATGCACAAGGAAGTAG
TGTTGGCATAAACGGGCTATTTAACCAAAATATATAAAATAGCAATATCATCAAGAGATTTAACA
AAAGAAGAAATTGAACAAGGGGCAAAAGAAACTGTATTTGCTTATGATGCTTTAATTTTCATTA
CAAGCCCTGAAATAAAAATTACAAATATTACAGAAGAAATCTAGCTAAAATACTAAATGGAG
AAATTCAAAATTGGAAACAAGTGGGAGGTCCTGATGCTAAAATCAACTTTATCAATCGAGACTC
TTCTTCTGGTTCTTATTCGTCTATAAAAGACCTACTTCTTAATAAAATATTCAAAACTCACGAAG
AAGCTCAATTTAGACAAGACGGAATAGTGGTAAAATCTAATGGAGAGGTAATTGAAAAAACAA
GCCTTACTCCCCACTCAATAGGATATATAGGTCTTGGATACGCAAAAAATTCAATAGAAAAGGG
TTTGAATATTCTTTCTGTTAACAGCACATATCCTACAAAAGAAACAATAAATAGCAATAAATAC
ACCATTAAAAGAAATTTAATAATAGTTACAAATAACAAATACGAGGATAAAAGCGTAACTCAA
TTTATTGATTTCATGACAAGCTCAACTGGACAAGATATTGTTGAAGAACAAGGCTTTTTAGGGA
TAAAAACATAA t736.nt (SEQ ID NO:436)
TGTAAAAATCAAGACAATGAAAAAATTGTATCAATGGAGGATCTACAACTGTAAGCCCAATA
CTAGACGAAATGATTTTAAGATATAATAAAATAAACAATAATACTAAAGTAACATACGATGCAC
AAGGAAGTAGTGTTGGCATAAACGGGCTATTTAACAAAATATATAAAATAGCAATATCATCAA
GAGATTTAACAAAAGAAGAAATTGAACAAGGGGCAAAAGAAACTGTATTTGCTTATGATGCTT
TAATTTTCATTACAAGCCCTGAAATAAAAATTACAAATATTACAGAAGAAATCTAGCTAAAAT
ACTAAATGGAGAAATTCAAAATTGGAAACAAGTGGGAGGTCCTGATGCTAAAATCAACTTTAT
CAATCGAGACTCTTCTTCTGGTTCTTATTCGTCTATAAAAGACCTACTTCTTAATAAAATATTCA
AAACTCACGAAGAAGCTCAATTTAGACAAGACGGAATAGTGGTAAAATCTAATGGAGAGGTAA
TTGAAAAAACAAGCCTTACTCCCCACTCAATAGGATATATAGGTCTTGGATACGCAAAAAATTC
AATAGAAAAGGGTTTGAATATTCTTTCTGTTAACAGCACATATCCTACAAAAGAAACAATAAAT
AGCAATAAATACACCATTAAAAGAAATTTAATAATAGTTACAAATAACAAATACGAGGATAAA
AGCGTAACTCAATTTATTGATTTCATGACAAGCTCAACTGGACAAGATATTGTTGAAGAACAAG
GCTTTTTAGGGATAAAAACATAA f752.aa (SEQ ID NO:437)
MNKKLNEVLLKLDQDLIKCVKGSLDLEISGVTYSSKLVLPRFVFFALPGIHFDGHDFIEIAIQKGSNV
VVCSRDVDFYSPNVTYIKVDDFNIRKFMSNFSNIFYDEPSKKLKVIGVTGTDGKSSVCYYIYLLFKK
KGVKVGFISTVFFDDGSGSLIKNPYRQSTPESTEIHSFLSTMVKNEAQYAILESTSHGLDLETARLIDV
NYFAVVFTNIGHEHLEFHGTIQNYLNVKLGLFRSVSDDAGFGVINLDDLYSSDFKNAVKKSFTYSLK
SSKADFFVSFIDEKTDSTRFEFYHKGVKYLANVSLLGSFNVENVMAALILVSQILNIDIQDIVDKLNCI
KSLDGRMDSINLGQNFSVIIDYAHTPGAFSKLFPIFKRFATNRLISVFGSAGERDVEKRFLQGQIADIY
SDLIILCDEDPRGENSMCIIKDIAKGIVNKVENKDLFFIADRKQAIEKAISLAKAGDLVVALGKGHESS
IIYKNREVFWNEQEVVKNAILSLEKSEKEK t752.aa (SEQ ID NO:438)
CVKGSLDLEISGVTYSSKLVLPRFVFFALPGIHFDGHDFIEIAIQKGSNVVVCSRDVDFYSPNVTYIKV
DDFNIRKFMSNFSNIFYDEPSKKLKVIGVTGTDGKSSVCYYIYLLFKKKGVKVGFISTVFFDDGSGSL
IKNPYRQSTPESTEIHSFLSTMVKNEAQYAILESTSHGLDLETARLIDVNYFAVVFTNIGHEHLEFHGT
IQNYLNVKLGLFRSVSDDAGFGVINLDDLYSSDFKNAVKKSFTYSLKSSKADFFVSFIDEKTDSTRFE
FYHKGVKYLANVSLLGSFNVENVMAALILVSQILNIDIQDIVDKLNCIKSLDGRMDSINLGQNFSVII
DYAHTPGAFSKLFPIFKRFATNRLISVFGSAGERDVEKRFLQGQIADIYSDLIILCDEDPRGENSMCIIK
DIAKGIVNKVENKDLFFIADRKQAIEKAISLAKAGDLVVALGKGHESSIIYKNREVFWNEQEVVKNA
ILSLEKSEKEK f752.nt (SEQ ID NO:439)
ATGAATAAAAAACTTAATGAAGTTTTATTAAAGTTAGATCAAGATTTAATAAAATGTGTAAAAG
GTTCTCTTGATTTAGAAATATCAGGAGTTACTTATAGTTCTAAATTGGTTTTGCCCAGGTTTGTG
TTTTTTTGCTCTTCCAGGAATTCATTTTGATGGGCATGATTTTATTGAAATTGCAATTCAAAAGGG
TAGTAATGTTGTTGTGTGTTCACGAGATGTGGATTTTTACAGTCCTAATGTTACTTATATTAAGG
TAGATGAGTTTAACATAAGAAAATTTATGTCTAATTTTTCAAATATTTTTTATGATGAGCCTTCA
AAAAAATTAAAAGTTATTGGAGTCACTGGCACTGACGGGAAAAGTTCTGTTTGTTATTATATAT
ATCTTCTTTTTAAAAAAAAGGGTGTTAAAGTAGGTTTTATATCGACAGTATTTTTTGATGATGG
GAGTGGAAGCTTGATTAAAAATCCTTACAGACAATCAACTCCCGAGTCTACGGAAATACATTCA
TTTTTAAGCACCATGGTTAAAAATGAAGCTCAATATGCAATTCTTGAATCTACTTCTCATGGGCT
TGACCTTGAAACAGCAAGGCTTATTGATGTTAATTATTTTGCAGTTGTTTTTACCAATATTGGAC
ATGAGCATCTTGAATTTCATGGCACAATTCAAAATTATTTGAATGTCAAGCTGGGTCTTTTTCG
GTCTGTTAGTGATGATGCTGGTTTTGGGGTTATTAATCTTGATGACCTTTATTCTTCTGATTTTA
AGAATGCTGTTAAGAAATCTTTTACTTATAGCTTAAAAAGCAGTAAAGCGGATTTTTTTGTTAG
TTTTATTGATGAGAAAACCGATTCTACTAGATTTGAATTTTATCACAAGGGGGTTAAATATCTT
GCTAATGTTAGCCTACTGGGGAGTTTTAATGTTGAGAATGTAATGGCTGCTCTTATTTTAGTTTC
TCAAATTTTAAATATCGATATTCAAGATATTGTTGATAAACTTAACTGCATTAAAAGTCTTGAT
GGGCGTATGGATAGTATTAATTTGGGGCAAAATTTTTGTAATAATTGATTATGCTCATACTC
CTGGTGCTTTTTCCAAGCTTTTTCCTATTTTTAAAAGATTTGCTACCAATAGATTGATTTCTGTTT
TTGGCTCTGCAGGAGAAAGAGATGTTGAAAAAAGATTTTTGCAAGGGCAAATCGCAGATATTT
ATTCTGATTTAATAATACTTTGCGATGAAGATCCAAGAGGCGAGAATAGTATGTGTATAATTAA
AGACATTGCAAAAGGAATTGTAAATAAAGTTGAAAATAAGGATTTATTTTTTATTGCTGATAGA
AAGCAGGCTATTGAAAAAGCAATAAGTCTTGCAAAAGCAGGAGATTTGGTTGTTGCTTTGGGC
AAAGGTCATGAAAGTTCAATAATTTATAAAAATAGAGAAGTTTTTTGGAATGAACAAGAGGTA
GTTAAAAATGCTATTTTAAGTTTAGAAAAATCAGAAAAGGAGAAGTGA t752.nt (SEQ ID NO:440)
TGTGTAAAAGGTTCTCTTGATTTAGAAATATCAGGAGTTACTTATAGTTCTAAATTGGTTTTGCC
CAGGTTTGTGTTTTTTGCTCTTCCAGGAATTCATTTTGATGGGCATGATTTTATTGAAATTGCAA

TABLE 1-continued

Nucleotide and Amino Acid Sequences.

TTCAAAAGGGTAGTAATGTTGTTGTGTGTTCACGAGATGTGGATTTTTACAGTCCTAATGTTAC
TTATATTAAGGTAGATGACTTTAACATAAGAAAATTTATGTCTAATTTTTCAAATATTTTTATG
ATGAGCCTTCAAAAAAATTAAAAGTTATTGGAGTCACTGGCACTGACGGGAAAAGTTCTGTTTG
TTATTATATATCTTCTTTTTAAAAAAAAGGGTGTTAAAGTAGGTTTTATATCGACAGTATTTT
TTGATGATGGGAGTGGAAGCTTGATTAAAAATCCTTACAGACAATCAACTCCCGAGTCTACGGA
AATACATTCATTTTTAAGCACCATGGTTAAAAATGAAGCTCAATATGCAATTCTTGAATCTACTT
CTCATGGGCTTGACCTTGAAACAGCAAGGCTTATTGATGTTAATTATTTTGCAGTTGTTTTTACC
AATATTGGACATGAGCATCTTGAATTTCATGGCACAATTCAAAATTATTTGAATGTCAAGCTGG
GTCTTTTTCGGTCTGTTAGTGATGATGCTGGTTTTGGGGTTATTAATCTTGATGACCTTTATTCT
TCTGATTTTAAGAATGCTGTTAAGAAATCTTTTACTTATAGCTTAAAAAGCAGTAAAGCGGATT
TTTTTGTTAGTTTTATTGATGAGAAAACCGATTCTACTAGATTTGAATTTTATCACAAGGGGTT
AAATATCTTGCTAATGTTAGCCTACTGGGGAGTTTTAATGTTGAGAATGTAATGGCTGCTCTTA
TTTTAGTTTCTCAAATTTTAAATATCGATATTCAAGATATTGTTGATAAACTTAACTGCATTAAA
AGTCTTGATGGGCGTATGGATAGTATTAATTTGGGGCAAAATTTTTCTGTAATAATTGATTATG
CTCATACTCCTGGTGCTTTTTCCAAGCTTTTTCCTATTTTTAAAAGATTTGCTACCAATAGATTG
ATTTCTGTTTTTGGCTCTGCAGGAGAAAGAGATGTTGAAAAAAGATTTTTGCAAGGGCAAATCG
CAGATATTTATTCTGATTTAATAATACTTTGCGATGAAGATCCAAGAGGCGAGAATAGTATGTG
TATAATTAAAGACATTGCAAAAGGAATTGTAAATAAAGTTGAAAATAAGGATTTATTTTTTATT
GCTGATAGAAAGCAGGCTATTGAAAAAGCAATAAGTCTTGCAAAAGCAGGAGATTTGGTTGTT
GCTTTGGGCAAAGGTCATGAAAGTTCAATAATTTATAAAAATAGAGAAGTTTTTTGGAATGAAC
AAGAGGTAGTTAAAAATGCTATTTTAAGTTTAGAAAAATCAGAAAAGGAGAAGTGA f798.aa (SEQ ID NO:441)
MVFRTYKHLELIMLPMLMLSCAFFKKPQSVHQDSNTGKPISDEKLHLISGKISNKKLPIINSNHDVTW
IKTKAMTILGEDGKEIPEFKNKFGYSYIISPVKMDGKYSYYASLLILFETTKNGDDEYEIEDVKFVTA
GSTLELKNSLLAVENSQEEGYVTAYPFGILMSDEIKNAFKLTYKNGHWNYMLADLTVKNKLTQET
KIYKISLNSKLIIEFLKEVLKENSILKDIAGDLFEDI t798.aa (SEQ ID NO:442)
CAFFKKPQSVHQDSNTGKPISDEKLHLISGKISNKKLPIINSNHDVTWIKTKAMTILGEDGKEIPEFKN
KFGYSYIISPVKMDGKYSYYASLLILFETTKNGDDEYEIEDVKFVTAGSTLELKNSLLAVENSQEEGY
VTAYPFGILMSDEIKNAFKLTYKNGHWNYMLADLTVKNKLTQETKIYKISLNSKLIIEFLKEVLKEN
SILKDIAGDLFEDI f798.nt (SEQ ID NO:443)
ATGGTATTTAGAACATATAAACATTTGGAACTAATAATGCTGCCCATGTTAATGCTGAGTTGCG
CTTTTTTTAAGAAACCACAATCTGTACATCAAGACAGCAATACTGGCAAACCAATAAGCGATGA
AAAATTACATTTAATATCAGGCAAAATTTCAAATAAAAAATTGCCAATCATAAATAGTAATCAT
GACGTAACTTGGATAAAAACAAAGGCAATGACAATCTTAGGCGAAGATGGAAAAGAAATACCA
GAATTTAAAAACAAATTTGGATATTCTTATATAATATCTCCTGTAAAAATGGATGGAAAATATA
GTTATTACGCGTCATTATTAATACTTTTGAAACAACTAAAAATGGAGATGATGAATATGAAAT
TGAAGATGTTAAATTTGTAACAGCTGGTTCCACCCTAGAACTTAAAAATTCTCTTTTAGCTGTTG
AAAATTCACAAGAAGAAGGATATGTTACTGCATACCCATTTGGAATATTGATGAGTGACGAGAT
TAAAAATGCTTTTAAATTAACATATAAAAATGGTCATTGGAATTATATGCTTGCAGATTTAACT
GTCAAAAATAAACTTACTCAAGAAACTAAAATTTATAAAATTTCTCTTAATTCAAAATTAATTA
TTGAATTTTTAAAAGAAGTGCTAAAAGAAAATTCTATATTAAAAGACATAGCTGGAGATTTATT
TGAAGATATATAA t798.nt (SEQ ID NO:444)
TGCGCTTTTTTTAAGAAACCACAATCTGTACATCAAGACAGCAATACTGGCAAACCAATAAGCG
ATGAAAAATTACATTTAATATCAGGCAAAATTTCAAATAAAAAATTGCCAATCATAAATAGTAA
TCATGACGTAACTTGGATAAAAACAAAGGCAATGACAATCTTAGGCGAAGATGGAAAAGAAAT
ACCAGAATTTAAAAACAAATTTGGATATTCTTATATAATATCTCCTGTAAAAATGGATGGAAAA
TATAGTTATTACGCGTCATTATTAATACTTTTGAAACAACTAAAAATGGAGATGATGAATATG
AAAATTGAAGATGTTAAATTTGTAACAGCTGGTTCCACCCTAGAACTTAAAAATTCTCTTTTAGCT
GTTGAAAATTCACAAGAAGAAGGATATGTTACTGCATACCCATTTGGAATATTGATGAGTGACG
AGATTAAAAATGCTTTTAAATTAACATATAAAAATGGTCATTGGAATTATATGCTTGCAGATTT
AACTGTCAAAAATAAACTTACTCAAGAAACTAAAATTTATAAAATTTCTCTTAATTCAAAATTA
ATTATTGAATTTTTAAAAGAAGTGCTAAAAGAAAATTCTATATTAAAAGACATAGCTGGAGATT
TATTTGAAGATATATAA f805.aa (SEQ ID NO:445)
MLRKLKDISKIVLVTDGLTPNCQTCGKLIANGDEVYIAEDGLFHSVKSNTIAGSTLTMIQGLKNLIEF
GFSLSDAVQASSYNPTRILNIDKKGLICHGYDANLNVLDKDFNLKLTMIESKIIFNNL t805.aa (SEQ ID NO:446)
CQTCGKLIANGDEVYIAEDGLFHSVKSNTIAGSTLTMIQGLKNLIEFGFSLSDAVQASSYNPTRILNID
KKGLICHGYDANLNVLDKDFNLKLTMIESKIIFNNL f805.nt (SEQ ID NO:447)
ATGCTTAGAAAGCTTAAAGATATAAGTAAAATAGTCCTTGTAACTGACGGACTTACTCCGAATT
GTCAAACTTGTGGAAAACTAATTGCAAACGGAGACGAAGTTTATATTGCAGAAGATGGATTATT
CCATAGCGTGAAAAGCAACACAATAGCTGGATCAACACTCACAATGATACAAGGTCTTAAAAA
TTTAATAGAATTTGGTTTCAGCTTAAGCGATGCTGTTCAAGCAAGCTCTTACAATCCAACAAGA
ATTCTCAATATTGATAAAAAGGGCTTAATATGTCATGGATATGATGCAAACCTCAATGTCCTAG
ATAAAGATTTTAATCTAAAGTTAACAATGATAGAATCTAAAATAATTTTTAACAATCTCTAA

TABLE 1-continued

Nucleotide and Amino Acid Sequences.

f805.nt (SEQ ID NO:448)
TGTCAAACTTGTGGAAAACTAATTGCAAACGGAGACGAAGTTTATATTGCAGAAGATGGATTAT
TCCATAGCGTGAAAAGCAACACAATAGCTGGATCAACACTCACAATGATACAAGGTCTTAAAA
ATTTAATAGAATTTGGTTTCAGCTTAAGCGATGCTGTTCAAGCAAGCTCTTACAATCCAACAAG
AATTCTCAATATTGATAAAAAGGGCTTAATATGTCATGGATATGATGCAAACCTCAATGTCCTA
GATAAAGATTTTAATCTAAAGTTAACAATGATAGAATCTAAAATAATTTTTAACAATCTCTAA f635.aa (SEQ ID NO:449)
MKILWLIILVNLFLSCGNESKEKSNLGLRLRELEISGGGSESKIEVYKEFIEKEDKNILKIVNSI
DKKARFFNLIGLEFFKLGQYGPAIEYFAKNLEINPNNYLSHFYIGVASYNLAKNLRVKDEVEKYIILA
ENSFLKSLSIRDDFKDSLFAISNMYVYDLDKQLEAKNYLNKLGDMGEDYFEFLMLRGANYYSLGDL
GNAILFYDKASKKASTEEQKEGVSRIMSNLK t635.aa (SEQ ID NO:450)
CGNESKEKSNLGLRLRELEISGGGSESKIEVYKEFIEKEDKNILKIVNSIDKKARFFNLIGLEFFKLGQY
GPAIEYFAKNLEINPNNYLSHFYIGVASYNLAKNLRVKDEVEKYIILAENSFLKSLSIRDDFKDSLFAI
SNMYVYDLDKQLEAKNYLNKLGDMGEDYFEFLMLRGANYYSLGDLGNAILFYDKASKKASTEEQ
KEGVSRIMSNLK f635.nt (SEQ ID NO:451)
ATGAAAATTTTGTGGTTAATAATTCTTGTTAATTTATTTTTATCTTGTGGCAATGAATCTAAAGA
AAAATCAAATCTTGGTCTTAGATTAAGAGAATTGGAAATTTCAGGTGGTGGATCTGAATCTAAG
ATTGAAGTTTATAAAGAATTTATTGAAAAAGAAGATAAGAATATTTTAAAGATAGTTAATTCCA
TTGATAAGAAAGCCAGATTTTTTAATTTAATTGGTCTTGAATTTTTTAAGCTTGGTCAGTACGGA
CCTGCTATTGAATATTTTGCTAAAAATTTAGAAATCAATCCCAATAATTATTTATCTCATTTTTA
TATAGGTGTTGCTTCTTATAATTTAGCTAAAAATTTAAGAGTAAAAGATGAAGTTGAAAAATAC
ATAATTCTTGCTGAAAATTCTTTTTTAAAATCACTTTCAATTAGAGATGATTTTAAAGATTCTCT
TTTTGCCATTTCTAATATGTACGTATATGATCTTGATAAACAACTTGAAGCTAAAAATTATTTAA
ATAAACTTGGTGATATGGGTGAGGACTATTTTGAGTTTTTAATGTTAAGAGGTGCAAATTATTA
TTCGCTGGGCGATCTTGGTAATGCTATATTGTTTTATGATAAAGCTAGTAAAAAGGCTTCAACT
GAAGAGCAAAAAGAAGGTGTTTCTAGGATCATGAGTAATTTGAAGTAA t635.nt (SEQ ID NO:452)
TGTGGCAATGAATCTAAAGAAAAATCAAATCTTGGTCTTAGATTAAGAGAATTGGAAATTTCAG
GTGGTGGATCTGAATCTAAGATTGAAGTTTATAAAGAATTTATTGAAAAAGAAGATAAGAATA
TTTTAAAGATAGTTAATTCCATTGATAAGAAAGCCAGATTTTTTAATTTAATTGGTCTTGAATTT
TTTAAGCTTGGTCAGTACGGACCTGCTATTGAATATTTTGCTAAAAATTTAGAAATCAATCCCA
ATAATTATTTATCTCATTTTTATATAGGTGTTGCTTCTTATAATTTAGCTAAAAATTTAAGAGTA
AAAGATGAAGTTGAAAAATACATAATTCTTGCTGAAAATTCTTTTTTAAAATCACTTTCAATTA
GAGATGATTTTAAAGATTCTCTTTTTGCCATTTCTAATATGTACGTATATGATCTTGATAAACAA
CTTGAAGCTAAAAATTATTTAAATAAACTTGGTGATATGGGTGAGGACTATTTTGAGTTTTTAA
TGTTAAGAGGTGCAAATTATTATTCGCTGGGCGATCTTGGTAATGCTATATTGTTTTATGATAA
AGCTAGTAAAAAGGCTTCAACTGAAGAGCAAAAAGAAGGTGTTTCTAGGATCATGAGTAATTT
GAAGTAA f314.aa (SEQ ID NO:453)
MNNCLIKFFIFLLVFSNSYVAFSKNVNVLIVTAMDSEFDQINKLMSNKEEIVLKEYGLNKKILKGKLS
NRNVMVIICGVGKVNAGVWTSYILSKYNISHVINSGVAGGVVSAKYKDIKVGDVVVSSEVAYHDV
DLTKFGYKVGQLTGGLPQKFNANKNLIKNAIEAIKSKVGGSNAYSGLIVSGDQFIDPTYINKIIGNFK
DVIAVEMEGAAIGHVSHMFNIPFIVIRSISDIVNKEGNEVEYSKFSKIAAFNSAKVVQEILRKL t314.aa (SEQ ID NO:454)
KNVNVLIVTAMDSEFDQINKLMSNKEEIVLKEYGLNKKILKGKLSNRNVMVIICGVGKVNAGVWTS
YILSKYNISHVINSGVAGGVVSAKYKDIKVGDVVVSSEVAYHDVDLTKFGYKVGQLTGGLPQKFNA
NKNLIKNAIEAIKSKVGGSNAYSGLIVSGDQFIDPTYINKIIGNFKDVIAVEMEGAAIGHVSHMFNIPFI
VIRSISDIVNKEGNEVEYSKFSKIAAFNSAKVVQEILRKL f314.nt (SEQ ID NO:455)
ATGAATAATTGTTTAATAAAGTTTTTTATTTTTTATTAGTTTTTTCAAACAGTTATGTTGCTTTT
TCTAAAAATGTCAATGTTTTAATAGTAACTGCTATGGACTCTGAGTTTGATCAGATAAATAAGC
TTATGTCTAATAAGGAAGAAATAGTTCTTAAGGAGTATGGTCTTAATAAAAAGATTTTAAAGGG
GAAGTTGTCTAATCGCAATGTTATGGTTATTATTTGTGGGGTTGGTAAGGTTAATGCTGGTGTG
TGGACTAGCTACATTTTGTCAAAATACAACATAAGTCATGTCATTAATTCTGGCGTTGCTGGTG
GCGTTGTTAGTGCTAAATACAAAGATATTAAAGTGGGAGATGTGGTGTCTTCAGAGGTTGC
ATATCATGATGTTGATTTGACTAAATTTGGATACAAGGTAGGACAGCTTACAGGAGGATTGCCT
CAAAAATTTAATGCCAATAAAAATTTAATTAAGAATGCCATAGAGGCCATTAAATCAAAGGTTG
GAGGTTCTAATGCATATTCAGGATTAATAGTTTCAGGAGATCAGTTTATTGATCCAACTTATAT
TAACAAAATTATAGGAAACTTTAAAGATGTAATAGCTGTTGAGATGGAAGGTGCAGCAATAGG
GCATGTTTCTCATATGTTTAATATACCTTTTATAGTTATTAGGTCAATATCTGACATTGTAAATA
AAGAAGGGAATGAGGTTGAATATAGTAAATTTTCTAAAATAGCTGCTTTCAATTCAGCCAAAGT
TGTACAAGAAATTTTAAGAAAACTTTAA t314.nt (SEQ ID NO:456)
AAAAATGTCAATGTTTTAATAGTAACTGCTATGGACTCTGAGTTTGATCAGATAAATAAGCTTA
TGTCTAATAAGGAAGAAATAGTTCTTAAGGAGTATGGTCTTAATAAAAAGATTTTAAGGGGA
AGTTGTCTAATCGCAATGTTATGGTTATTATTTGTGGGGTTGGTAAGGTTAATGCTGGTGTGTG
GACTAGCTACATTTTGTCAAAATACAACATAAGTCATGTCATTAATTCTGGCGTTGCTGGTGGC

TABLE 1-continued

Nucleotide and Amino Acid Sequences.

GTTGTTAGTGCTAAATACAAAGATATTAAAGTGGGAGATGTGGTGGTGTCTTCAGAGGTTGCAT
ATCATGATGTTGATTTGACTAAATTTGGATACAAGGTAGGACAGCTTACAGGAGGATTGCCTCA
AAAATTTAATGCCAATAAAAATTTAATTAAGAATGCCATAGAGGCCATTAAATCAAAGGTTGGA
GGTTCTAATGCATATTCAGGATTAATAGTTTCAGGAGATCAGTTTATTGATCCAACTTATATTAA
CAAAATTATAGGAAACTTTAAAGATGTAATAGCTGTTGAGATGGAAGGTGCAGCAATAGGGCA
TGTTTCTCATATGTTTAATATACCTTTTATAGTTATTAGGTCAATATCTGACATTGTAAATAAAG
AAGGGAATGAGGTTGAATATAGTAAATTTTCTAAAATAGCTGCTTTCAATTCAGCCAAAGTTGT
ACAAGAAATTTTAAGAAAACTTTAA f32.aa (SEQ ID NO:457)
MNTKTLYLISLILLACNKNNKIPLIQKLDLPKSSILGFSNKMGIIIKDYAFLSKSTKKNSELDVDYAILL
RKDEVVKIEKTLEKTERYGIEGNWILVNYKGTKRYIFSKDFNIVNNLIIDHSK t32.aa (SEQ ID NO:458)
CNKNNKIPLIQKLDLPKSSILGFSNKMGIIIKDYAFLSKSTKKNSELDYDYAILLRKDEVVKIEKTLEK
TERYGIEGNWILVNYKGTKRYIFSKDINIVNNLIIDHSK f32.nt (SEQ ID NO:459)
ATGAATACAAAAACATTATATTTAATATCCTTAATTCTTTAGCTTGCAATAAAAATAA
CAAAATTCCTCTCATTCAAAAATTAGATTTGCCCAAAAGCAGCATTCTTGGCTTTAGCAATAAA
ATGGGCATAATAATAAAAGATTATGCTTTTCTTAGTAAAAGCACTAAGAAAAATAGCGAATTGG
ATTATGATTACGCAATTCTACTCAGAAAAGACGAAGTCGTAAAAATTGAAAAAACACTAGAAA
AAACAGAGCGCTATGGAATTGAAGGAAATTGGATCCTAGTCAATTACAAGGGAACTAAAAGAT
ACATCTTTAGCAAAGACATCAATATAGTCAACAATTTAATAATTGATCATTCTAAATAG t32.nt (SEQ ID NO:460)
TGCAATAAAAATAACAAAATTCCTCTCATTCAAAAATTAGATTTGCCCAAAAGCAGCATTCTTG
GCTTTAGCAATAAAATGGGCATAATAATAAAAGATTATGCTTTTCTTAGTAAAAGCACTAAGAA
AAATAGCGAATTGGATTATGATTACGCAATTCTACTCAGAAAAGACGAAGTCGTAAAAATTGA
AAAAACACTAGAAAAACAGAGCGCTATGAATTGAAGGAAATTGGATCCTAGTCAATTACAA
GGGAACTAAAAGATACATCTTTAGCAAAGACATCAATATAGTCAACAATTTAATAATTGATCAT
TCTAAATAG f320.aa (SEQ ID NO:461)
MKSIYALLFLFINLSLLANNISKKDLEVLLKIAQAMNKECKNFIEKNPIQFLKEIKPLVDAEKNNLLTL
INKKIPIPENYKIPDLVNIDDFEDLKNLGAKTIKVRKILIEDLIRLIKDAKKFGIEIKIKSAYRTQEYQKF
LFDYNVKTYGRKVAETQSAIPGHSQHHMGTAIDFINIDDNLLNTKEGKWLYENSLKYGFSVSYPKG
YETDTGYAAEPWHYLYIGPKPCFIQKKYFNNLQHKLLEFWNQNKTNLINLIEKYAN t320.aa (SEQ ID NO:462)
NNISKKDLEVLLKIAQAMNKECKNFIEKNPIQFLKEIKPLVDAEKNNLLTLINKKIPIPENYKIPDLVNI
DDFEDLKNLGAKTIKVRKILIEDLIRLIKDAKKFGIEIKIKSAYRTQEYQKFLFDYNVKTYGRKVAET
QSAIPGHSQHHMGTAIDFINIDDNLLNTKEGKWLYENSLKYGFSVSYPKGYETDTGYKAEPWHYLY
IGPKPCFIQKKYFNNLQHKLLEFWNQNKTNLINLIEKYAN f320.nt (SEQ ID NO:463)
ATGAAATCAATTTATGCTTTATTATTTCTATTTATTAATTTATCTTTGTTGGCTAACAACATTTCA
AAAAAAGATTTAGAAGTACTGCTAAAGATTGCCCAAGCAATGAATAAGGAATGCAAAAATTTT
ATTGAAAAAAATCCTATTCAGTTCTTAAAAGAAATAAAACCCTTAGTAGATGCAGAAAAAAATA
ACCTCTTAACTCTAATAAATAAAAAAATACCAATTCCTGAAAATTATAAAATACCTGATCTGGT
AAATATTGATGATTTTGAAGATCTTAAAAATCTTGGAGCAAAGACTATTAAAGTAAGAAAAATA
TTAATCGAAGATTTAATTCGACTAATAAAAGATGCAAAAAAATTTGGGATTGAAATTAAAATCA
AATCTGCTTACAGAACGCAAGAATATCAAAAATTTTTATTTGATTACAATGTCAAAACTTATGG
CAGAAAAGTTGCAGAAACCCAATCAGCAATTCCAGGCCATTCTCAACATCATATGGGAACAGC
AATAGATTTTATAAATATAGATGATAATTTACTAAACACAAAAGAAGGAAAATGGCTTTATGAA
AACTCTCTAAAATACGGATTTTCCGTTTCATACCCAAAAGGATATGAAACGGACACTGGATATA
AAGCAGAGCCTTGGCACTACTTATACATAGGACCTAAGCCATGCTTTATTCAGAAAAAATATTT
TAATAATTTACAACATAAGCTTCTTGAATTTTGGAACCAGAACAAAACAAATCTTATTAACCTA
ATTGAAAAATATGCAAACTAA f320.nt (SEQ ID NO:464)
AACAACATTTCAAAAAAAGATTTAGAAGTACTGCTAAAGATTGCCCAAGCAATGAATAAGGAA
TGCAAAAATTTTATTGAAAAAAATCCTATTCAGTTCTTAAAAGAAATAAAACCCTTAGTAGATG
CAGAAAAAAATAACCTCTTAACTCTAATAAATAAAAAAATACCAATTCCTGAAAATTATAAAAT
ACCTGATCTGGTAAATATTGATGATTTTGAAGATCTTAAAAATCTTGGAGCAAAGACTATTAAA
GTAAGAAAAATATTAATCGAAGATTTAATTCGACTAATAAAAGATGCAAAAAAATTTGGGATT
GAAATTAAAATCAAATCTGCTTACAGAACGCAAGAATATCAAAAATTTTTATTTGATTACAATG
TCAAAACTTATGGCAGAAAAGTTGCAGAAACCCAATCAGCAATTCCAGGCCATTCTCAACATCA
TATGGGAACAGCAATAGATTTTATAAATATAGATGATAATTTACTAAACACAAAAGAAGGAAA
ATGGCTTTATGAAAACTCTCTAAAATACGGATTTTCCGTTTCATACCCAAAAGGATATGAAACG
GACACTGGATATAAAGCAGAGCCTTGGCACTACTTATACATAGGACCTAAGCCATGCTTTATTC
AGAAAAAATATTTTAATAATTTACAACATAAGCTTCTTGAATTTTGGAACCAGAACAAAACAAA
TCTTATTAACCTAATTGAAAAATATGCAAACTAA f342.aa (SEQ ID NO:465)
MLYLGDNKAMRTKIIIMTIIILLAPISGFSNSKESARGKFGAGIILPLPIALQINIGNFDLDIGLYSGVNN
LFSDWKTLFIALDYIFYIYTFPGAANILDFSVGAGGYGTIWFSRFGGSKSGSGPMSIGARLPLALNIAV

TABLE 1-continued

Nucleotide and Amino Acid Sequences.

FRKKFDIFLRIAPGLGMNVWSNGVGFRWEVFAGLGLRFWFT t342.aa (SEQ ID NO:466)
LAPISGFSNSKESARGKFGAGIILPLPIALQINIGNFDLDIGLYSGVNNLFSDWKTLFIALDYIFYIYTFP
GAANILDFSVGAGGYGTIWFSRFGGSKSGSGPMSIGARLPLALNIAVFRKKFDIFLRIAPGLGMNVWS
NGVGFRWEVFAGLGLRFWFT f342.nt (SEQ ID NO:467)
ATGCTATACTTAGGAGATAATAAAGCAATGAGAACAAAAATAATTATTATGACAATTATTATTT
TATTAGCCCCAATCTCAGGATTTTCTAATTCAAAAGAATCTGCAAGGGGTAAATTTGGAGCAGG
AATTTATACTTCCATTACCAATTGCTCTACAGATTAATATAGGAAACTTTGATCTTGACATTGGTC
TTTACAGCGGAGTAAATAATTTGTTTTCAGACTGGAAAACATTATTTATAGCATTAGACTATAT
TTTCTACATATACACATTCCCGGGAGCTGCTAATATTTTGGATTTTTCAGTTGGCGCAGGGGGA
TATGGAACAATATGGTTTTCAAGATTTGGAGGCAGTAAGTCAGGCTCAGGACCAATGAGCATTG
GAGCAAGATTGCCTTTGGCCTTAAATATTGCAGTATTTAGGAAGAAATTCGACATATTTTTACG
AATAGCACCCGGACTTGGAATGAATGTTTGGAGTAATGGCGTTGGATTTAGATGGGAAGTATTC
GCAGGATTGGGACTAAGATTCTGGTTTACTTAA t342.nt (SEQ ID NO:468)
TTAGCCCCAATCTCAGGATTTTCTAATTCAAAAGAATCTGCAAGGGGTAAATTTGGAGCAGGAA
TTTATACTTCCATTACCAATTGCTCTACAGATTAATATAGGAAACTTTGATCTTGACATTGGTCTT
TACAGCGGAGTAAATAATTTGTTTTCAGACTGGAAAACATTATTTATAGCATTAGACTATATTT
TCTACATATACACATTCCCGGGAGCTGCTAATATTTTGGATTTTTCAGTTGGCGCAGGGGGATA
TGGAACAATATGGTTTTCAAGATTTGGAGGCAGTAAGTCAGGCTCAGGACCAATGAGCATTGG
AGCAAGATTGCCTTTGGCCTTAAATATTGCAGTATTTAGGAAGAAATTCGACATATTTTTACGA
ATAGCACCCGGACTTGGAATGAATGTTTGGAGTAATGGCGTTGGATTTAGATGGGAAGTATTCG
CAGGATTGGGACTAAGATTCTGGTTTACTTAA f352.aa (SEQ ID NO:469)
MNKTKNRSLTYFIILSCISLFGANNNTISYSSIEIPLEDLSEEFKSSGNKSDQINTSKHLNKNIVSYEDPK
KGKDLKLPENIRDKKLPQKRMDENDLKSVIENYENKIKNIEKLLKTKNQKTSENENKKIESIEKKAK
KYEILTNKLKNEIVELKKLLNKKIKPKEDENYEKINIENIEEETDDDFEDNYEYNDEIEEQMRTITLLM
KE t352.aa (SEQ ID NO:470)
CISLFGANNNTISYSSIEIPLEDLSEEFKSSGNKSDQINTSKHLNKNIVSYEDPKKGKDLKLPENIRDKK
LPQKRMDENDLKSVIENYENKIKNIEKLLKTKNQKTSENENKKIESIEKKAKKYEILTNKLKNEIVEI
KKLLNKKIKPKEDENYEKINIENIEEETDDDFEDNYEYNDEIEEQMRTITLLMKE f352.nt (SEQ ID NO:471)
ATGAATAAAACAAAAAATCGAAGCCTTACGTATTTTATAATACTTTCATGTATATCATTATTTG
GGGCTAATAATAATACAATAAGCTACTCTAGCATTGAAATTCCTCTAGAAGACTTAAGTGAAGA
ATTTAAAAGTTCTGGGAATAAAAGCGATCAAATAAATACCTCAAAACATTTAAACAAAAACAT
AGTTTCTTATGAAGACCCAAAAAAGGGTAAAGATCTAAAATTGCCAGAAAATATAAGAGACAA
AAAACTACCCCAAAAAAGAATGGACGAAAATGATCTAAAATCTGTAATTGAAAATTATGAAAA
TAAAATTAAAAACATAGAAAAGCTTTTAAAAACCAAAAATCAAAAAACATCGGAAAATGAAAA
TAAAAAAATAGAATCAATCGAAAAAAAAGCAAAAAAATATGAAATTTTAACCAATAAATTAAA
AAACGAAATAGTAGAAATAAAAAAGCTCCTTAACAAAAAAATCAAGCCTAAAGAAGATGAAAA
TTACGAAAAAATAAATATTGAAAACATTGAAGAAGAAACTGATGATGATTTTGAAGACAATTA
TGAATATAATGATGAAATTGAAGAACAAATGAGGACAATTACCCTTCTAATGAAGGAATAA t352.nt (SEQ ID NO:472)
TGTATATCATTATTTGGGGCTAATAATAATACAATAAGCTACTCTAGCATTGAAATTCCTCTAG
AAGACTTAAGTGAAGAATTTAAAAGTTCTGGGAATAAAAGCGATCAAATAAATACCTCAAAAC
ATTTAAACAAAAACATAGTTTCTTATGAAGACCCAAAAAAGGGTAAAGATCTAAAATTGCCAG
AAAATATAAGAGACAAAAAACTACCCCAAAAAAGAATGGACGAAAATGATCTAAAATCTGTAA
TTGAAAATTATGAAAATAAAATTAAAAACATAGAAAAGCTTTTAAAAACCAAAAATCAAAAAA
CATCGGAAAATGAAAATAAAAAAATAGAATCAATCGAAAAAAAAGCAAAAAAATATGAAATTT
TAACCAATAAATTAAAAAACGAAATAGTAGAAATAAAAAAGCTCCTTAACAAAAAAATCAAGC
CTAAAGAAGATGAAAATTACGAAAAAATAAATATTGAAACATTGAAGAAGAAACTGATGATG
ATTTTGAAGACAATTATGAATATAATGATGAAATTGAAGAACAAATGAGGACAATTACCCTTCT
AATGAAGGAATAA f301.aa (SEQ ID NO:473)
MQIDGKIYSIISFPVRDSVSTLGVIGILICFDESLDIIENQLYSSLKFGSKNYNFFMLDRNYMPIFSNLNN
LQAKSFSTAYSENFLSKVIAYAKKDSSSSQYTFNYERDFYSLNFVKTDDFLTQGLILNVNSIPIMFKS
NWVIFVAFLLLSFAIIFYLCNTFVFSLINDFNRIVDYQKSKSDPFSLESPLEVKYSSSIISYISSKLDNLSS
KSNESFEKIKFYSEDLNEYLEQIETAISNTESIDSSILVYEQLRDTFSRFEKSIVDILKGFESIADPINDHN
KYISEISSNFEESVSFFYSIDKNLEIFNKVATINSTDIENIKSKVFDLNIVFENVKNFADLLSQTNSLQS
VNKLLVSISAQTNMLAMNAAIEAAKAGDAGKSFAVVAEEIRKLAINSGKYSKTIKDELKTVDSIIAVI
NSEIDTIYKNFIDIQDNVDNNFSRHEKVDLTLAKHFKEIGEFKERYLSHDTKIRDAKNMYKEIFNNHY
FISGKFNNFSQDLKEFKVSKMNLDAVSSLQEYSSLVKSSKDKILKTKELIQKINDEIKDILF t301.aa (SEQ ID NO:474)
CFDESLDIIENQLYSSLKFGSKNYNFFMLDRNYMPIFSNLNNLQAKSFSTAYSENFLSKVIAYAKKDS
SSSQYTFNYERDFYSLNFVKTDDFLTQGLILNVNSIPIMFKSNWVIFVAFLLLSFAIIFYLCNTFVFSLI
NDFNRIVDYQKSKSDPFSLESPLEVKYSSSIISYISSKLDNLSSKSNESFEKIKFYSEDLNEYLEQIETAI

TABLE 1-continued

Nucleotide and Amino Acid Sequences.

SNTESIDSSILVYEQLRDTFSRFEKSIVDILKGFESIADPINDHNKYISEISSNFEESVSFFYSIDKNLEIFN
KVATINSTDIENIKSKVFDLNIVFENVNKNFADLLSQTNSLQSVNKLLVSISAQTNMLAMNAAIEAAK
AGDAGKSFAVVAEEIRKLAINSGKYSKTIKDELKTVDSIIAVINSEIDTIYKNFIDIQDNVDNNFSRHE
KVDLTLAKHFKEIGEFKERYLSHDTKIRDAKNMYKEIFNNHYFISGKFNNFSQDLKEFKVSKMNLD
AVSSLQEYSSLVKSSKDKILKTKELIQKINDEIKDILF f301.nt (SEQ ID NO:475)
ATGCAAATAGATGGGAAAATTTATTCTATAATAAGTTTTCCAGTTAGAGATTCTGTTTCAACAT
TGGGTGTGATAGGGATTTTAATATGCTTTGATGAGTCGTTAGATATTATTGAAAATCAGTTGTA
TTCTTCTCTTAAATTTGGTAGTAAAAATTATAATTTTTTTATGCTTGACAGAAATTACATGCCCA
TTTTTTCAAACCTTAATAATCTTCAGGCCAAATCTTTTTCTACAGCTTATAGTGAGAATTTTTG
AGTAAAGTTATAGCTTATGCTAAAAAAGATTCTTCTAGCTCTCAGTACACTTTTAATTATGAAA
GAGATTTTTATTCTTTAAACTTTGTAAAAACCGATGATTTTTTGACTCAGGGGCTTATTTTAAAT
GTCAATTCCATTCCTATTATGTTTAAATCAAATTGGGTTATATTTGTTGCATTTTTATTATTGTCT
TTTGCAATTATTTTTTATTTATGCAATACTTTTGTTTTTTCATTAATTAATGATTTTAACAGAATT
GTTGACTATCAAAAATCAAAAAGCGATCCTTTTAGTCTTGAATCTCCCTTAGAGGTTAAGTATT
CTTCATCTATTATTTCTTATATTAGTTCAAAGCTAGATAATCTGTCTTCAAGAGTAATGAATCT
TTTGAGAAGATAAAATTTTATTCTGAAGATTTGAATGAATATTTGGAACAAATAGAAACTGCTA
TATCAAATACTGAGAGTATAGATTCTAGCATTTTAGTTTACGAACAACTAAGAGATACTTTTTC
TAGATTTGAAAAATCAATTGTTGATATTTTAAAAGGCTTTGAATCTATTGCTGATCCGATTAAT
GATCACAATAAATATATATCAGAAATCTCTTCAAATTTTGAAGAGAGTGTTAGTTTTTTCTATA
GTATAGATAAAAATTTAGAAATTTTTAATAAGGTTGCTACTATAAATTCTACTGATATTGAAAA
TATTAAAAGTAAGGTTTTTGATTTAAATATTGTTTTTGAAAATGTGAATAAAAATTTTGCAGAT
CTTTTGTCTCAAACAAATAGTTTGCAAAGTGTAAATAAACTTTTAGTTTCAATTTCAGCTCAGAC
CAATATGCTTGCTATGAATGCAGCAATTGAAGCAGCAAAAGCAGGTGATGCAGGTAAAAGTTT
TGCAGTTGTTGCTGAGGAGATTAGAAAGCTTGCTATTAATTCTGGAAAATATTCTAAAACCATT
AAAGATGAACTTAAAACGGTCGACAGCATTATTGCAGTAATTAATTCTGAGAGATTGATACAATTT
ATAAAAATTTCATAGACATTCAAGATAATGTGGACAACAATTTTTCAAGACACGAGAAAGTAG
ATCTTACTCTTGCTAAGCATTTTAAAGAAATTGGCGAGTTTAAAGAAAGGTATTGTCTCACGA
TACTAAGATCAGAGATGCTAAGAATATGTATAAAGAAATATTTAATAATCATTATTTTATTAGT
GGCAAGTTTAACAACTTTAGTCAAGATTTAAAAGAGTTTAAAGTTTCTAAGATGAATTTAGATG
CGGTAAGTTCTCTTCAAGAATATTCATCTTTAGTAAAGTCTTCTAAGGATAAGATATTAAAGAC
AAAGGAATTGATTCAAAAGATTAATGATGAGATTAAAGATATTCTTTTTTAG t301.nt (SEQ ID NO:476)
TGCTTTGATGAGTCGTTAGATATTATTGAAAATCAGTTGTATTCTTCTCTTAAATTTGGTAGTAA
AAATTATAATTTTTTTATGCTTGACAGAAATTACATGCCCATTTTTTCAAACCTTAATAATCTTC
AGGCCAAATCTTTTTCTACAGCTTATAGTGAGAATTTTTTGAGTAAAGTTATAGCTTATGCTAAA
AAAGATTCTTCTAGCTCTCAGTACACTTTTAATTATGAAAGAGATTTTTATTCTTTAAACTTTGT
AAAAACCGATGATTTTTTGACTCAGGGGCTTATTTTAAATGTCAATTCCATTCCTATTATGTTTA
AATCAAATTGGGTTATATTTGTTGCATTTTTATTATTGTCTTTTGCAATTATTTTTTATTTATGCA
ATACTTTTGTTTTTTCATTAATTAATGATTTTAACAGAATTGTTGACTATCAAAAATCAAAAAGC
GATCCTTTTAGTCTTGAATCTCCCTTAGAGGTTAAGTATTCTTCATCTATTATTTCTTATATTAGT
TCAAAGCTAGATAATCTGTCTTCAAGAGTAATGAATCTTTTGAGAAGATAAAATTTTATTCTG
AAGATTTGAATGAATATTTGGAACAAATAGAAACTGCTATATCAAATACTGAGAGTATAGATTC
TAGCATTTTAGTTTACGAACAACTAAGAGATACTTTTTCTAGATTTGAAAAATCAATTGTTGAT
ATTTTAAAAGGCTTTGAATCTATTGCTGATCCGATTAATGATCACAATAAATATATATCAGAAA
TCTCTTCAAATTTTGAAGAGAGTGTTAGTTTTTTCTATAGTATAGATAAAAATTTAGAAATTTTT
AATAAGGTTGCTACTATAAATTCTACTGATATTGAAAATATTAAAGTAAGGTTTTTGATTTAA
ATATTGTTTTTGAAAATGTGAATAAAAATTTTGCAGATCTTTTGTCTCAAACAAATAGTTTGCAA
AGCTTGTAAATAAACTTTTAGTTTCAATTTCAGCTCAGACCAATATGCTTGCTATGAATGCAGCAA
TTGAAGCAGCAAAAGCAGGTGATGCAGGTAAAAGTTTTGCAGTTGTTGCTGAGGAGATTAGAA
AGTGCTATTAATTCTGGAAAATATTCTAAAACCATTAAAGATGAACTTAAAACGGTCGACAG
CATTATTGCAGTAATTAATTCAGAGATTGATACAATTTATAAAAATTTCATAGACATTCAAGAT
AATGTGGACAACAATTTTTCAAGACACGAGAAAGTAGATCTTACTCTTGCTAAGCATTTTAAAG
AAATTGGCGAGTTTAAAGAAAGGTATTGTCTCACGATACTAAGATCAGAGATGCTAAGAATAT
GTATAAAGAAATATTTAATAATCATTATTTTATTAGTGGCAAGTTTAACAACTTTAGTCAAGAT
TTAAAAGAGTTTAAAGTTTCTAAGATGAATTTAGATGCGGTAAGTTCTCTTCAAGAATATTCAT
CTTTAGTAAAGTCTTCTAAGGATAAGATATTAAAGACAAAGGAATTGATTCAAAAGATTAATGA
TGAGATTAAAGATATTCTTTTTAG f346.aa (SEQ ID NO:477)
MSIDKVPDEAFAEKIVGDGIAILPTSNELLAPCDGKIGKIFKTNHAFSLETKEGVEIFVHFGIN
TLNLNGKGFTRVAEEGINVKQGEVIIRLDLEYLKEHSESVITPVVIANSDEVSSIEYSFGRLENDSEYIL
SSSTVLTEEIRHKISQTKPVIAGKDLVLRVKK t346.aa (SEQ ID NO:478)
CDGKIGKIFKTNHAFSLETKEGVEIFVHFGINTLNLNGKGFTRVAEEGINVKQGEVIIRLDLEYLKEHS
ESVITPVVIANSDEVSSIEYSFGRLENDSEYILSSSTVLTEEIRHKISQTKPVIAGKDLVLRVKK f346.nt (SEQ ID NO:479)
ATGTCAATTGATAAGGTTCCCGATGAAGCTTTTGCTGAAAAAATAGTTGGCGATGGAATTGCAA
TTCTTCCAACAAGCAATGAGTTGTTGGCGCCTTGTGATGGGAAAATAGGTAAAATTTTTAAAAC
CAATCATGCCTTTAGCCTTGAAACTAAAGAGGGCGTTGAAATTTTTGTCCATTTTGGAATTAAT
ACTCTTAATTTAAATGGTAAGGGTTTTACAAGAGTTGCTGAAGAGGGCATTAATGTTAAACAAG
GTGAAGTTATTATTAGGCTTGATCTTGAATATTTAAAAGAGCATTCAGAATCCGTTATTACTCC
GGTTGTTATTGCAAATTCTGATGAAGTTTCAAGTATAGAATATTCTTTTGGAAGGCTTGAAAAT

TABLE 1-continued

Nucleotide and Amino Acid Sequences.

GATTCTGAATATATTTTATCATCTTCAACTGTCTTGACAGAAGAAATTAGGCATAAAATATCTC
AAACAAAGCCTGTTATAGCGGGCAAAGATTTGGTGTTGCGAGTTAAAAAGTAA t346.nt (SEQ ID NO:480)
TGTGATGGGAAAATAGGTAAAATTTTTAAAACCAATCATGCCTTTAGCCTTGAAACTAAAGAGG
GCGTTGAAATTTTTGTCCATTTTGGAATTAATACTCTTAATTTAAATGGTAAGGGTTTTACAAGA
GTTGCTGAAGAGGGCATTAATGTTAAACAAGGTGAAGTTATTATTAGGCTTGATCTTGAATATT
TAAAAGAGCATTCAGAATCCGTTATTACTCCGGTTGTTATTGCAAATTCTGATGAAGTTTCAAG
TATAGAATATTCTGGAAGGCTTGAAAATGATTCTGAATATATTTTATCATCTTCAACTGTCT
TGACAGAAGAAATTAGGCATAAAATATCTCAAACAAAGCCTGTTATAGCGGGCAAAGATTTGG
TGTTGCGAGTTAAAAAGTAA f373.aa (SEQ ID NO:481)
MNYQRIKNYCKFTSVFLFFLFSCVSNELKLDQSLVKGKLVNGLRYYIYKNQTPKNAVNMGIVFNVG
SLNEEDNERGIAHYLEHMAFNGTKDYPGNSIVDVLKKFGMQFGADINAATSFDFTYYRLDLSDGNN
KDEIDESINILRNWASQISFMKEEIDLERNIIIEEKKLGETYPGRIYEKMDKFLTSGSLYEFRSPIGLEEQ
ILSFQPEDFKKFYRKWYRPELASVIVVGDIDPIEIEEKIKKQFVSWKNPTDKIKEVKVSLDVELKDKF
LLLEDLEVGEPSLMFFKKEIINFVKTKDDLLNAIKKSLLAALFENRFSELKTAGVKQFKNVSNKDFFS
FKSDNNTIVAKSISLNFNPDHLNEGIQDFFYELERIRKFGFTQGELEKVRSQFYKSLELRKKNINKTNS
WAIFQDLIEIAINGSNKFDMNEYCDLSFQYLEKIDLKTINNLVGREFDVKNCAIFYSYHGRAHPVLTL
EDIDNLQKIALKRELKPYENSLIEGKFFKKSLDDKDIIRENEFENEISSFVLENGVEVYFKYNDQKKG
VIDFSATSWGGLINEDLKLIPVLSFAPGVVSGSGYGDYSALQIEKYLSDKAVSLRVGVGAQESYISGS
SDKKDLETLFQLIYFTFKEPKIDDVSLQNAINNIKALIKSNENSSDYHFHKAISKFLNNNDPRFEDTKD
SDLQYFTKENILSFYKKRFTYANNFKFVLLETQIFRQ t373.aa (SEQ ID NO:482)
CVSNELKLDQSLVKGKLVNGLRYYIYKNQTPKNAVNMGIVFNVGSLNEEDNERGIAHYLE
RMAFNGTKDYPGNSIVDVLKKFGMQFGADINAATSFDFTYYRLDLSDGNNKDEIDESINILRNWAS
QISFMKEEIDLERNIIIEEKKLGETYPGRIYEKMDKFLTSGSLYEFRSPIGLEEQILSFQPEDFKKFYRK
WYRPELASVIVVGDIDPIEIEEKIKKQFVSWKNPTDKIKEVKVSLDVELKDKFLLLEDLEVGEPSLMF
FKKEIINFVKTKDDLLNAIKKSLLAALFENRFSELKTAGVKQFKNVSNKDFFSFKSDNNTIVAKSISLN
FNPDHLNEGIQDFFYELERIRKFGFTQGELEKVRSQFYKSLELRKKNINKTNSWAIFQDLIEIAINGSN
KFDMNEYCDLSFQYLEKIDLKTINNLVGREFDVKNCAIFYSYHGRAHPVLTLEDIDNLQKIALKREL
KPYENSLIEGKFFKKSLDDKDIIRENEFENEISSFVLENGVEVYFKYNDQKKGVIDFSATSWGGLINE
DLKLIPVLSFAPGVVSGSGYGDYSALQIEKYLSDKAVSLRVGVGAQESYISGSSDKKDLETLFQLIYF
TFKEPKTDDVSLQNAINNIKALIKSNENSSDYHFHKAISKFLNNNDPRFEDTKDSDLQYFTKENILSFY
KKRFTYANNFKFVLLETQIFRQ f373.nt (SEQ ID NO:483)
ATGAATTATCAAAGAATTAAGAATTATTGTAAATTTACAAGCGTTTTTCTATTTTTTTG
TTTTCCTGTGTTTCTAATGAGTTAAAGTTAGATCAAAGTTTGGTAAAAGGAAAACTTGTCAATG
GGCTAAGGTATTATATTTATAAAAATCAAACCCCAAAGAATGCCGTTAATATGGGAATTGTTTT
TAATGTGGGCTCACTTAATGAAGAAGATAATGAGAGGGAATAGCGCATTATCTTGAACATAT
GGCTTTTAATGGTACAAAAGATTATCCAGGGAATTCTATAGTTGATGTTCTTAAAAAATTTGGA
ATGCAATTTGGTGCTGACATTAATGCTGCTACAGTTTTTGATTTCACTTATTATAGACTTGATTT
GTCAGATGGTAATAATAAAGATGAAATTGATGAATCTATAAATATTTTGAGAAACTGGGCTTCT
CAAATCAGTTTCATGAAAGAAGAAATAGATCTAGAGCGAAATATTATTATTGAGGAAAAAAAG
CTTGGTGAGACTTATCCTGGAAGAATTTATGAGAAAATGGATAAGTTTTTGACAAGCGGAAGTC
TTTATGAATTTAGAAGTCCTATTGGACTTGAAGAGCAAATTTTATCTTTTCAGCCAGAAGATTTT
AAAAAATTTTATAGAAAGTGGTATAGGCCAGAACTTGCAAGTGTTATTGTGGTAGGAGATATTG
ATCCTATAGAAATTGAAGAGAAGATAAAGAAGCAATTTGTTTCTTGGAAAAATCCAACCGATA
AAATTAAAGAAGTAAAAGTAAGTTTAGACGTAGAGCTTAAGGATAAAATTTTTACTTTTAGAAGA
TTTGGAAGTTGGAGAGCCTACTTTAATGTTCTTAAAAAGGGAATTATTAACTTTGTAAAGACC
AAAGATGACCTTTTAAATGCTATTAAAAAGTCTTTATTAGCCGCTCTTTTTGAAAATAGATTTTC
TGAATTAAAGACTGCTGGGGTAAAGCAATTTAAAAATGTTTCAAATAAAGATTTTTTCTCATTT
AAATCAGATAACAATACCATTGTTGCAAAATCGATTTCTTTAAACTTTAATCCAGATCATTTGA
ACGAAGGAATACAAGACTTTTTTTATGAGCTTGAGAGGATAAGAAAATTTGGATTTACCCAAGG
TGAGCTTGAAAAAGTTAGATCTCAATTTTACAAATCTTTAGAATTAAGGAAAAAGAATATAAAT
AAAACAAATTCATGGGCTATTTTTCAGGATTTAATAGAAATTGCTATTAATGGTTCTAATAAAT
TTGATATGAATGAATATTGCGATCTTTCTTTTCAATATTTGGAAAAGATTGATTTAAAAACAAT
AAACAATCTTGTAGGAAGAGAGTTTGATGTAAAAAATTGTGCAATTTTTTATTCTTACCATGGA
AGAGCACATCCTGTTTTAACTCTTGAAGATATTGACAATCTTCAAAAGATAGCTTTAAAAAGAG
AGTTAAAGCCTTATGAGAATTCTTTAATTGAAGGTAAATTTTTTAAGAAGTCTTTAGATGATAA
AGATATTATTAGAGAAAATGAGTTTGAAAATGAAATTTCGTCATTTGTTCTTGAAAATGGGGTT
GAAGTTTATTTTAAATATAATGATCAAAAAAAAGGTGTAATTGATTTTAGTGCAACTTCTTGGG
GAGGTTTAATTAATGAAGATTTAAAACTTATTCCTGTTTTATCTTTTGCTCCCGGAGTAGTATCT
GGTTCGGGTTATGGTGATTATTCTGCATTACAGATTGAAAAATATTTATCAGATAAAGCTGTTT
CTTTAAGAGTTGGGGTTGGAGCTCAAGAATCATATATTTCTGGAAGTTCAGATAAAAAAGATCT
TGAAACTCTTTTTCAGCTTATATATTTTACTTTTAAGGAACCCAAAATTGATGATGTTTCTTTGC
AAAATGCTATTAATAATATAAAAGCATTAATAAAGAGCAATGAAAATAGTTCTGATTATCATTT
TCATAAAGCCATTAGTAAATTTTTAAACAATAATGATCCTAGATTTGAAGATACAAAAGATAGT
GATTTGCAATATTTTACAAAAGAAAATATTTTGTCTTTTTATAAGAAAAGGTTTACTTATGCAA
ATAATTTTAAGTTTGTCTTGCTGGAGACTCAGATATTCAGACAATAA t373.nt (SEQ ID NO:484)
TGTGTTTCTAATGAGTTAAAGTTAGATCAAAGTTTGGTAAAAGGAAAACTTGTCAATGGGCTAA
GGTATTATATTTATAAAAATCAAACCCCAAAGAATGCCGTTAATATGGGAATTGTTTTTAATGT

TABLE 1-continued

Nucleotide and Amino Acid Sequences.

GGGCTCACTTAATGAAGAAGATAATGAGAGGGGAATAGCGCATTATCTTGAACATATGGCTTTT
AATGGTACAAAAGATTATCCAGGGAATTCTATAGTTGATGTTCTTAAAAAATTTGGAATGCAAT
TTGGTGCTGACATTAATGCTGCTACTAGTTTTGATTTCACTTATTATAGACTTGATTTGTCAGAT
GGTAATAATAAAGATGAAATTGATGAATCTATAAATATTTTGAGAAACTGGGCTTCTCAAATCA
GTTTCATGAAAGAAGAAATAGATCTAGAGCGAAATATTATTATTGAGGAAAAAAAGCTTGGTG
AGACTTATCCTGGAAGAATTTATGAGAAAATGGATAAGTTTTTGACAAGCGGAAGTCTTTATGA
ATTTAGAAGTCCTATTGGACTTGAAGAGCAAATTTTATCTTTTCAGCCAGAAGATTTTAAAAAA
TTTTATAGAAAGTGGTATAGGCCAGAACTTGCAAGTGTTATTGTGGTAGGAGATATTGATCCTA
TAGAAATTGAAGAGAAGATAAAGAAGCAATTTGTTTCTTGGAAAAATCCAACCGATAAAATTA
AAGAAGTAAAAGTAAGTTTAGACGTAGAGCTTAAGGATAAATTTTTACTTTTAGAAGATTTGGA
AGTTGGAGAGCCTAGTTTAATGTTCTTTAAAAAGGAAATTATTAACTTTGTAAAGACCAAAGAT
GACCTTTTAAATGCTATTAAAAAGTCTTTATTAGCCGCTCTTTTTGAAAATAGATTTTCTGAATT
AAAGACTGCTGGGGTAAAGCAATTTAAAAATGTTTCAAATAAAGATTTTTTCTCATTTAAATCA
GATAACAATACCATTGTTGCAAAATCGATTTCTTTAAACTTTAATCCAGATCATTTGAACGAAG
GAATACAAGACTTTTTTTTATGAGCTTGAGAGGATAAGAAAATTTGGATTTACCCAAGGTGAGCT
TGAAAAAGTTAGATCTCAATTTTACAAATCTTTAGAATTAAGGAAAAAGAATATAAATAAAACA
AATTCATGGGCTATTTTTCAGGATTTAATAGAAATTGCTATTAATGGTTCTAATAAATTTGATAT
GAATGAATATTGCGATCTTTCTTTTCAATATTTGGAAAAGATTGATTTAAAAACAATAAACAAT
CTTGTAGGAAGAGAGTTTGATGTAAAAAATTGTGCAATTTTTTATTCTTACCATGGAAGAGCAC
ATCCTGTTTTAACTCTTGAAGATATTGACAATCTTCAAAAGATAGCTTTAAAAAGAGAGTTAAA
GCCTTATGAGAATTCTTTAATTGAAGGTAAATTTTTTAAGAAGTCTTTAGATGATAAAGATATT
ATTAGAGAAAATGAGTTTGAAAATGAAATTTCGTCATTTGTTCTTGAAAATGGGGTTGAAGTTT
ATTTTAAATATAATGATCAAAAAAAAGGTGTAATTGATTTTAGTGCAACTTCTTGGGGAGGTTT
AATTAATGAAGATTTAAAACTTATTCCTGTTTTATCTTTTGCTCCCGGAGTAGTATCTGGTTCGG
GTTATGGTGATTATTCTGCATTACAGATTGAAAAATATTTATCAGATAAAGCTGTTTCTTTAAG
AGTTGGGGTTGGAGCTCAAGAATCATATATTTCTGGAAGTTCAGATAAAAAAGATCTTGAAACT
CTTTTTCAGCTTATATATTTTACTTTTAAGGAACCCAAAATTGATGATGTTTCTTTGCAAAATGC
TATTAATAATATAAAAGCATTAATAAAGAGCAATGAAAATAGTTCTGATTATCATTTTCATAAA
GCCATTAGTAAATTTTTAAACAATAATGATCCTAGATTTGAAGATACAAAAGATAGTGATTTGC
AATATTTTACAAAAGAAAATATTTTGTCTTTTTATAAGAAAAGGTTTACTTATGCAAATAATTTT
AAGTTTGTCTTGCTGGAGACTCAGATATTCAGACAATAA t384.aa (SEQ ID NO:485)
MDWDFEKIIFLLNESTRLALSGCAKLILDFKSDGSIVTQVDKQIEQFLFKEIKKPGNFVLGEETISTYK
EEYIKDALISESTFIIDPIDGTSSFAAGLPSYGISLAYASGGKIIEGAISLPLSGEFFITSKDNVFYAKKNI
GSYPLKKDFNKFIFDNSKCYNIHSLLAVSRSIIRLFNLDISSHIHINGSCVYSFAKLFTGSYKAYFSFVG
LWDIAACLAIGNKLGMVGEFYCGNKMTLDILDSMYILEPNNHKRWSLKDFFIYSDNKSTIDIIRKDA
NKKINK t384.aa (SEQ ID NO:486)
CAKLILDFKSDGSIVTQVDKQIEQFLFKEIKKPGNFVLGEETISTKKEEYIKDALISESTFIIDPIDGTSSF
AAGLPSYGISLAYASGGKIIEGAISLPLSGEFFITSKDNVFYAKKNIGSYPLKKDFNKFIFDNSKCYNIH
SLLAVSRSIIRLFNLDISSHIHINGSCVYSFAKLFTGSYKAYFSFVGLWDIAACLAIGNKLGMVGEFYC
GNKMTLDILDSMYILEPNNHKRWSLKDFFIYSDNKSTIDIIRKDANKKINK f384.nt (SEQ ID NO:487)
ATGGATTGGGATTTTGAAAAAATTATATTTTTATTAAATGAATCAACTAGGCTTGCATTAAGTG
GTTGTGCTAAATTAATTTTAGATTTTAAATCTGATGGGTCTATTGTAACTCAGGTTGATAAGCA
AATTGAGCAATTCTTATTCAAAGAGATCAAAAAGCCTGGAAATTTTGTTCTTGGAGAAGAGACA
ATATCTACTTATAAAGAAGAGTATATCAAAGATGCTTTAATATCAGAGAGTACTTTTATTATTG
ATCCTATTGATGGAACTTCTTCTTTTGCAGCAGGCCTTCCTTCATATGGAATATCGCTAGCGTAT
GCTAGTGGCGGCAAAATTATTGAAGGAGCCATTTCTCTTCCTTTAAGCGGAGAGTTTTTTATTA
CTTCTAAAGATAATGTATTTTATGCTAAAAAAAACATTGGTAGCTATCCTTTAAAAAAGGATTT
TAATAAATTTATTTTTGATAATTCTAAATGTTACAATATTCATAGTTTACTTGCAGTTTCAAGGT
CTATTATAAGGTTATTTAATCTTGATATTTCTTCTCATATTCATATTAATGGTTCTTGTGTATATT
CTTTTGCTAAACTTTTTACAGGTTCTTATAAGGCCTACTTTTCTTTTGTAGGACTTTGGGATATT
GCAGCGTGTTTAGCTATTGGTAATAAATTGGGCATGGTTGGCGAATTTTATTGTGGTAATAAAA
TGACATTAGATATCTTAGATTCAATGTATATTTTAGAGCCTAATAATCATAAAAGATGGTCCTT
GAAAGATTTTTTATTTATTCTGATAATAAATCAACAATAGACATTATAAGAAAAGATGCAAAT
AAAAAAATCAATAAGTAA t384.nt (SEQ ID NO:488)
AGTGGTTGTGCTAAATTAATTTTTAGATTTTAAATCTGATGGGTCTATTGTAACTCAGGTTGATA
AGCAAATTGAGCAATTCTTATTCAAAGAGATCAAAAAGCCTGGAAATTTTGTTCTTGGAGAAGA
GACAATATCTACTTATAAAGAAGAGTATATCAAAGATGCTTTAATATCAGAGAGTACTTTTATT
ATTGATCCTATTGATGGAACTTCTTCTTTTGCAGCAGGCCTTCCTTCATATGGAATATCGCTAGC
GTATGCTAGTGGCGGCAAAATTATTGAAGGAGCCATTTCTCTTCCTTTAAGCGGAGAGTTTTTT
ATTACTTCTAAAGATAATGTATTTTATGCTAAAAAAAACATTGGTAGCTATCCTTTAAAAAAGG
ATTTTAATAAATTTATTTTTGATAATTCTAAATGTTACAATATTCATAGTTACTTGCAGTTTCA
AGGTCTATTATAAGGTTATTTAATCTTGATATTTCTTCATATTCATATTAATGGTTCTTGTGT
ATATTCTTTTGCTAAACTTTTTACAGGTTCTTATAAGGCCTACTTTTCTTTTGTAGGACTTTGGG
ATATTGCAGCGTGTTTAGCTATTGGTAATAAATTGGGCATGGTTGGCGAATTTTATTGTGGTAA
TAAAATGACATTAGATATCTTAGATTCAATGTATATTTTAGAGCCTAATAATCATAAAAGATGG
TCCTTGAAAGATTTTTTATTTATTCTGATAATAAATCAACAATAGACATTATAAGAAAAGATG
CAAATAAAAAAATCAATAAGTAA f860.aa (SEQ ID NO:489)

TABLE 1-continued

Nucleotide and Amino Acid Sequences.

MAFYKLNDNIALAEDLLKYLLSSILNECSQDMDFLENYIEKGLIKKLENVINSNFEVITYTKA
IEILENSKKNFEIKPYWGIDLQTDHERYLTEETFKKPVVVIDYPKNFKAFYMKANKDNKTVKGMDIL
VPKIGEIIGGSEREDDLQKLENRIKELNLNIEHLNWYLDLRRFGSAPHSGFGLGLERLVQYSTGISNIR
DSIPFPRTPKNLYF t860.aa (SEQ ID NO:490)
CSQDMDFLENYIEKGLIKKLENVINSNFEVITYTKAIEILENSKKNFEIKPYWGIDLQTDHERYLTEET
FKKPVVVIDYPKNFKAFYMKANKDNKTVKGMDILVPKIGEIIGGSEREDDLQKLENRIKELNLNIEH
LNWYLDLRRFGSAPHSGFGLGLERLVQYSTGISNIRDSIPFPRTPKNLYF f860.nt (SEQ ID NO:491)
ATGGCTTTTTATAAGCTTAACGACAATATTGCCCTAGCAGAAGATCTCTTGAAATATCT
TTTAAGTTCAATTTTAAACGAATGCTCACAAGATATGGATTTTTTAGAAAATTACATTGAAAAA
GGTTTAATTAAAAAACTAGAAAATGTAATAAATTCAAATTTTGAGGTTATTACCTATACTAAAG
CAATTGAAATTCTTGAAAACTCAAAAAAAAATTTTGAAATAAAACCTTACTGGGGAATAGATTT
GCAAACAGATCACGAAAGATACCTAACAGAAGAGACTTTTAAAAAACCGGTAGTGGTCATTGA
TTATCCAAAAAATTTCAAAGCATTTTACATGAAAGCAAATAAAGACAATAAAACTGTTAAAGGA
ATGGACATACTTGTTCCAAAAATTGGAGAGATTATAGGGGGAAGCGAAAGAGAAGATGACCTT
CAAAAATTAGAAATAGAATAAAAGAATTAAACTTAAACATTGAACATCTAAACTGGTATCTTG
ATCTAAGAAGATTTGGCTCGGCTCCTCATTCTGGCTTTGGACTTGGACTTGAAAGATTGGTGCA
ATACTCAACAGGAATATCTAATATAAGAGATTCAATACCATTCCCAAGGACTCCTAAAAATCTT
TATTTTTAA t860.nt (SEQ ID NO:492)
TGCTCACAAGATATGGATTTTTTAGAAAATTACATTGAAAAAGGTTTAATTAAAAAACTAGAAA
ATGTAATAAATTCAAATTTTGAGGTTATTACCTATACTAAAGCAATTGAAATTCTTGAAAACTC
AAAAAAAAATTTTGAAATAAAACCTTACTGGGGAATAGATTTGCAAACAGATCACGAAAGATA
CCTAACAGAAGAGACTTTTAAAAAACCGGTAGTGGTCATTGATTATCCAAAAAATTTCAAAGCA
TTTTACATGAAAGCAAATAAAGACAATAAAACTGTTAAAGGAATGGACATACTTGTTCCAAAA
ATTGGAGAGATTATAGGGGGAAGCGAAAGAGAAGATGACCTTCAAAAATTAGAAATAGAATA
AAAGAATTAAACTTAAACATTGAACATCTAAACTGGTATCTTGATCTAAGAAGATTTGGCTCGG
CTCCTCATTCTGGCTTTGGACTTGGACTTGAAAGATTGGTGCAATACTCAACAGGAATATCTAA
TATAAGAGATTCAATACCATTCCCAAGGACTCCTAAAAATCTTTATTTTTAA f446.aa (SEQ ID NO:493)
MKILRLCLLFLFFACTFDYDEYSSRSDVAKKFPSIQILGIKYYDVVYNKEQTVLNSLSFSYFNDYKIY
KAENGRFLYHSLDNEISGKFNNLEGSYITKDLDMRDSVEFKIEDKNNYYLLNSNRLLWKNKDKKLQ
SPPNELVLIRFNDSKINGKGFSYFLKSNVFYFDSGVEGIMN t446.aa (SEQ ID NO:494)
CTFDYDEYSSRSDVAKKFPSIQILGIKYYDVVYNKEQTVLNSLSFSYFNDYKIYKAENGRFLYHSLD
NEISGKFNNLEGSYITKDLDMRDSVEFKIEDKNNYYLLNSNRLLWKNKDKKLQSPPNELVLIRFNDS
KINGKGFSYFLKSNVFYFDSGVEGIMN f446.nt (SEQ ID NO:495)
ATGAAAATACTTAGACTTTGTTGTTGTTTTGTTTTTTGCTTGTACTTTTGATTATGAT
GAGTATTCTAGTAGATCTGATGTGGCCAAAAAGTTTCCTTCAATACAAATATTAGGAATCAAGT
ATTATGATGTTGTATACAATAAAGAGCAAACCGTTTTAAATTCTTTAAGCTTTAGTTATTTCAAT
GACTATAAAATTTATAAGGCAGAGAATGGAAGGTTTTTATATCATTCCCTAGATAATGAAATTT
CAGGGAAGTTTAATAATTTGGAAGGTTCTTATATTACAAAGGATTTGGATATGAGAGATTCTGT
AGAATTTAAAATAGAAGATAAAAATAATTATTATTTGCTTAATTCAAATAGGCTTTTATGGAAG
AATAAAGACAAGAAGTTGCAATCCCCCCCAAATGAGCTAGTATTAATTAGATTTAATGATAGCA
AAATAAACGGAAAAGGATTTTCTTATTTTTAAAGAGCAATGTTTTTATTTTGATTCTGGAGTT
GAAGGAATCATGAATTGA t446.nt (SEQ ID NO:496)
TGTACTTTTGATTATGATGAGTATTCTAGTAGATCTGATGTGGCCAAAAAGTTTCCTTCAATACA
AATATTAGGAATCAAGTATTATGATGTTGTATACAATAAAGAGCAAACCGTTTTAAATTCTTTA
AGCTTTAGTTATTTCAATGACTATAAAATTTATAAGGCAGAGAATGGAAGGTTTTTATATCATT
CCCTAGATAATGAAATTTCAGGGAAGTTTAATAATTTGGAAGGTTCTTATATTACAAAGGATTT
GGATATGAGAGATTCTGTAGAATTTAAAATAGAAGATAAAAATAATTATTATTTGCTTAATTCA
AATAGGCTTTTATGGAAGAATAAAGACAAGAAGTTGCAATCCCCCCCAAATGAGCTAGTATTAA
TTAGATTTAATGATAGCAAAATAAACGGAAAAGGATTTTCTTATTTTTAAAGAGCAATGTTTT
TTATTTTGATTCTGGAGTTGAAGGAATCATGAATTGA f457.aa (SEQ ID NO:497)
MKQKLSWILLFCFLSCRSESRLAENVLIEFFDSIKNFQSSPEIFFNYLNIPSDDDLKAKIRGLKSQAKDD
FIFYPLFFNNLRYEIIGRKNISKGFEFEVVIKNINFQNGIEKFLAKLNKIEGRSLNIKNLEKKERKKIFDN
LINEVIGELDDFDYTEVVHFFRVVKSSSESYKIELLGDVLNIQSRNKLINDLFLVLSPGI t457.aa (SEQ ID NO:498)
CFLSCRSESRLAENVLIEFFDSIKNFQSSPEIFFNYLNIPSDDDLKAKIRGLKSQAKDDFIFYPLFFNNLR
YEIIGRKNISKGFEFEVVIKNINFQNGIEKFLAKLNKIEGRSLNIKNLEKKERKKIFDNLINEVIGELDDF
DYTEVVHFFRVVKSSSESYKIELLGDVLNIQSRNKLINDLFLVLSPGI f457.nt (SEQ ID NO:499)
ATGAAGCAAAAATTAAGTTGGATTTTATTATTTTGTTTTTTGTCTTGTAGATCTGAATCT
AGATTGGCTGAAAATGTTTTAATAGAGTTTTTTGATTCTATTAAAAATTTTCAAAGCAGTCCTG

TABLE 1-continued

Nucleotide and Amino Acid Sequences.

AAATATTTTTTAATTATTTAAATATTCCAAGTGATGATGATCTGAAGGCAAAAATTCGTGGGTT
GAAATCTCAGGCAAAGGATGATTTCATTTTTTATCCTTTGTTTTTTAATAATCTAAGATATGAGA
TAATAGGTAGAAAAAATATTTCTAAGGGCTTTGAATTTGAAGTTGTTATTAAAAATATTAACTT
TCAAAACGGTATAGAAAAATTTTTGGCTAAATTAAATAAAATTGAAGGGAGATCTTTAAATATT
AAAAATTTAGAAAAAAAAGAGCGTAAAAAAATATTTGACAATTTAATAAATGAAGTTATTGGA
GAGTTGGATGATTTTGATTACACTGAAGTTGTTCATTTTTTAGAGTAGTTAAGAGTTCTTCTGA
AAGTTATAAAATAGAGCTTTTAGGAGATGTTTTAAATATACAGTCTAGAAATAAGCTTATTAAT
GATCTTTTTTTGGTTTTATCGCCTGGAATTTAA t457.nt (SEQ ID NO:500)
TGTTTTTTGTCTTGTAGATCTGAATCTAGATTGGCTGAAAATGTTTTAATAGAGTTTTTTGATTC
TATTAAAAATTTTCAAAGCAGTCCTGAAATATTTTTTAATTATTTAAATATTCCAAGTGATGATG
ATCTGAAGGCAAAAATTCGTGGGTTGAAATCTCAGGCAAAGGATGATTTCATTTTTTATCCTTT
GTTTTTTAATAATCTAAGATATGAGATAATAGGTAGAAAAAATATTTCTAAGGGCTTTGAATTT
GAAGTTGTTATTAAAAATATTAACTTTCAAAACGGTATAGAAAAATTTTTGGCTAAATTAAATA
AAATTGAAGGGAGATCTTTAAATATTAAAAATTTAGAAAAAAAAGAGCGTAAAAAAATATTTG
ACAATTTAATAAATGAAGTTATTGGAGAGTTGGATGATTTTGATTACACTGAAGTTGTTCATTT
TTTTAGAGTAGTTAAGAGTTCTTCTGAAAGTTATAAAATAGAGCTTTTAGGAGATGTTTTAAAT
ATACAGTCTAGAAATAAGCTTATTAATGATCTTTTTTTGGTTTTATCGCCTGGAATTTAA f542.aa (SEQ ID NO:501)
MRIVIFIFGILLTSCFSRNGIESSSKKIKISMLVDGVLDDKSFNSSANEALLRLKKDFPENIEEVFSCAIS
GVYSSYVSDLDNLKRNGSDLIWLVGYMLTDASLLVSSENPKISYGIIDPIYGDDVQIPENLIAVVFRV
EPRCFFGWLYCSQKKLFWQNRFYRGNEG t542.aa (SEQ ID NO:502)
CFSRNGIESSSKKIKISMLVDGVLDDKSFNSSANEALLRLKKDFPENIEEVFSCAISGVYSSYVSDLDN
LKRNGSDLIWLVGYMLTDASLLVSSENPKISYGIIDPIYGDDVQIPENLIAVVFRVEPRCFFGWLYCS
QKKLFWQNRFYRGNEG f542.nt (SEQ ID NO:503)
ATGAGAATTGTAATTTTTATATTCGGTATTTTGTTGACTTCTTGCTTTAGTAGAAATGGAATAGA
ATCTAGTTCAAAAAAAATTAAGATATCCATGTTGGTAGATGGTGTTCTTGACGACAAATCTTTT
AATTCTAGTGCTAATGAGGCTTTATTACGCTTGAAAAAAGATTTTCCAGAAAATATTGAAGAAG
TTTTTTCTTGTGCTATTTCTGGAGTTTATTCTAGTTATGTTTCAGATCTTGATAATTTAAAAAGG
AATGGCTCAGACTTGATTTGGCTTGTAGGGTACATGCTTACGGACGCATCTTTATTGGTTTCATC
GGAGAATCCAAAAATTAGCTATGGAATAATAGATCCCATTTATGGTGATGATGTTCAGATTCCT
GAAAACTTGATTGCTGTTGTTTTCAGAGTAGAGCCAAGGTGCTTTTTTGGCTGGCTATATTGCA
GCCAAAAAAAGCTTTTCTGGCAAAATAGGTTTTATAGGGGGAATGAAGGGTAA t542.nt (SEQ ID NO:504)
TGCTTTAGTAGAAATGGAATAGAATCTAGTTCAAAAAAAATTAAGATATCCATGTTGGTAGATG
GTGTTCTTGACGACAAATCTTTTAATTCTAGTGCTAATGAGGCTTTATTACGCTTGAAAAAAGA
TTTTCCAGAAAATATTGAAGAAGTTTTTTCTTGTGCTATTTCTGGAGTTTATTCTAGTTATGTTT
CAGATCTTGATAATTTAAAAAGGAATGGCTCAGACTTGATTTGGCTTGTAGGGTACATGCTTAC
GGACGCATCTTTATTGGTTTCATCGGAGAATCCAAAAATTAGCTATGGAATAATAGATCCCATT
TATGGTGATGATGTTCAGATTCCTGAAAACTTGATTGCTGTTGTTTTCAGAGTAGAGCCAAGGT
GCTTTTTTGGCTGGCTATATTGCAGCCAAAAAAAGCTTTTCTGGCAAAATAGGTTTTATAGGGG
GAATGAAGGGTAA f93.aa (SEQ ID NO:505)
MKRILAMHDISSMGRTSLTICIPVISSFNMQVCPFVTAVLSASTAYKKFEIVDLTDHLEKFINIWKEQN
EHFDILYTGFLGSEKQQITIEKIIKLIKFEKIVIDPVFADDGEIYPIFDNKIISGFRKIIKYANIITPNITELE
MLSKSSKLNNKDDIIKAILNLDTKATVVVTSVKRGNLLGNICYNPKNKEYSEFFLEGLEQNFSGTGD
LFTSLLIGYLEKFETEQALEKTTKAIHLIIKESIKENVSKKEGVRIENFLKNTF t93.aa (SEQ ID NO:506)
CIPVISSFNMQVCPFVTAVLSASTAYKKFEIVDLTDHLEKFINIWKEQNEHFDILYTGFLGSEKQQITI
EKIIKLIKFEKIVIDPVFADDGEIYPIFDNKIISGFRKIIKYANIITPNITELEMLSKSSKLNNKDDIIKAIL
NLDTKATVVVTSVKRGNLLGNICYNPKNKEYSEFFLEGLEQNFSGTGDLFTSLLIGYLEKFETEQAL
EKTTKAIHLIIKESIKENVSKKEGVRIENFLKNTF f93.nt (SEQ ID NO:507)
ATGAAAAGAATTTTAGCAATGCATGATATTTCAAGCATGGGAAGAACATCTCTTACAATATGCA
TACCAGTAATATCTTCGTTTAATATGCAAGTTTGTCCTTTTGTGACAGCTGTCCTTTCTGCTTCC
ACAGCTTATAAAAAATTTGAAATAGTGGATTTAACCGATCATTTAGAAAAATTTATCAATATAT
GGAAAGAACAAAATGAGCACTTTGACATACTCTATACCGGATTTCTGGGAAGCGAAAACAAC
AAATAACAATAGAGAAAATAATTAAATTAATAAAATTTGAAAAATTGTAATTGATCCTGTGTT
TGCTGACGATGGAGAAATTTACCCTATATTTGATAATAAAATAATTAGTGGATTTAGAAAAATC
ATAAAGTACGCAAACATAATAACACCCAATATCACAGAACTTGAAATGCTAAGCAAAAGCTCA
AAACTTAACAACAAAGATGATATCATAAAAGCAATATTAAATCTTGATACAAAAGCGACGGTA
GTTGTTACAAGCGTTAAAAGGGGAAATCTCTTGGGAAACATTTGCTACAATCCTAAAAACAAAG
AATACTCGGAGTTTTTTTTAGAAGGATTAGAACAAAATTTCAGTGGAACAGGAGATTTATTTAC
CAGCTTACTTATAGGATATTTGGAAAAATTTGAAACAGAGCAAGCCTTAGAAAAAACAACAAA
GGCTATTCACCTAATAATAAAAGAGTCAATTAAAGAAAATGTTTCAAAAAAAGAAGGGGTCCG
AATTGAAAATTTCTTAAAAAATACATTTTGA

TABLE 1-continued

Nucleotide and Amino Acid Sequences.

t93.nt (SEQ ID NO:508)
TGCATACCAGTAATATCTTCGTTTAATATGCAAGTTTGTCCTTTTGTGACAGCTGTCCTTTCTGC
TTCCACAGCTTATAAAAAATTTGAAATAGTGGATTTAACCGATCATTTAGAAAAATTTATCAAT
ATATGGAAAGAACAAAATGAGCACTTTGACATACTCTATACCGGATTTCTGGGAAGCGAAAAA
CAACAAATAACAATAGAGAAAATAATTAAATTAATAAAATTTGAAAAAATTGTAATTGATCCTG
TGTTTGCTGACGATGGAGAAATTTACCCTATATTTGATAATAAAATAATTAGTGGATTTAGAAA
AATCATAAAGTACGCAAACATAATAACACCCAATATCACAGAACTTGAAATGCTAAGCAAAAG
CTCAAAACTTAACAACAAAGATGATATCATAAAAGCAATATTAAATCTTGATACAAAAGCGAC
GGTAGTTGTTACAAGCGTTAAAAGGGGAAATCTCTTGGGAAACATTTGCTACAATCCTAAAAAC
AAAGAATACTCGGAGTTTTTTTTAGAAGGATTAGAACAAAATTTCAGTGGAACAGGAGATTTAT
TTACCAGCTTACTTATAGGATATTTGGAAAAATTTGAAACAGAGCAAGCCTTAGAAAAAACAAC
AAAGGCTATTCACCTAATAATAAAAGAGTCAATTAAAGAAAATGTTTCAAAAAAAGAAGGGGT
CCGAATTGAAAATTTCTTAAAAAATACATTTTGA f105.aa (SEQ ID NO:509)
MGLYLKLLRQSINLKSLFPLSVLFFSCNVVDTDFSVLEFKVANFNLNDDFSQGLLDSAYNILNRSFDL
IIIKNLKNKNVLDLINNRVLFRAFKNAYFIDQGSGLSVSILSKRKINIKVLSVMQDSCDLKLGLLVDFK
FENNHYGIVIYNLSKDFIKSIANLQISEQILYLKAQMDKLMFILDESEFVIFDLLIKNGFFSLINDSNYTS
MLANKIDFRVFSNFFARVSLYSFMFVIADYLHSNYVVENFPQKIVIN t105.aa (SEQ ID NO:510)
CNVVDTDFSVLEFKVANFNLNDDFSQGLLDSAYNILNRSFDLIIIKNLKNKNVLDLINNRVLFRAFKN
AYFIDQGSGLSVSILSKRKINIKVLSVMQDSCDLKLGLLVDFKFENNHYGIVIYNLSKDFIKSIANLQIS
EQILYLKAQMDKLMFILDESEFVIFDLLIKNGFFSLINDSNYTSMLANKIDFRVFSNFFARVSLYSFMF
VIADYLHSNYVVENFPQKIVIN f105.nt (SEQ ID NO:511)
ATGGGCTTGTATTTGAAGTTGTTGAGACAAAGTATCAACTTGAAGAGTTTATTTCCGCTTAGTG
TTTTTATTTTTTTCCTGTAATGTTGTAGATACAGATTTTAGTGTTTTGGAGTTTAAGGTTGCAAAT
TTTAATTTAAATGATGATTTTTCTCAAGGGTTACTTGATTCTGCTTATAATATTCTAAATCGAAG
TTTTGATTTAATAATTATTAAGAATCTTAAGAATAAAAATGTTCTTGATTTAATTAATAATAGAG
TTTTTATTTAGAGCTTTTAAGAATGCTTATTTTATTGATCAAGGTAGTGGCCTTTCTGTTAGCATT
CTTTCTAAGCGCAAAATAAATATTAAAGTTTTAAGTGTAATGCAAGATTCTTGCGATTTAAAAT
TAGGATTGCTTGTGGATTTAAAATTTGAGAATAATCACTATGGTATTGTTATTTATAATTTAAGC
AAGGATTTTATTAAAAGTATTGCCAATTTGCAAATTAGTGAACAAATTTTATATTTAAAAGCCC
AAATGGATAAATTGATGTTTATTTTAGATGAATCTGAATTTGTTATTTTTGATTATTAATCAAA
AATGGATTTTTTAGCTTAATAAATGATTCAAACTACACTTCAATGTTAGCAAATAAAATTGATTT
TAGAGTTTTTTCTAATTTTTTTGCTAGGGTTTCTTTATATTCATTTATGTTTGTAATTGCAGATTA
TTTGCATAGCAATTATGTTGTTGAGAATTTTCCTCAAAAAATAGTTATCAATTGA t105.nt (SEQ ID NO:512)
TGTAATGTTGTAGATACAGATTTTAGTGTTTTGGAGTTTAAGGTTGCAAATTTTAATTTAAATGA
TGATTTTTCTCAAGGGTTACTTGATTCTGCTTATAATATTCTAAATCGAAGTTTTGATTTAATAA
TTATTAAGAATCTTAAGAATAAAAATGTTCTTGATTTAATTAATAATAGAGTTTTATTTAGAGCT
TTTAAGAATGCTTATTTTATTGATCAAGGTAGTGGCCTTTCTGTTAGCATTCTTTCTAAGCGCAA
AATAAATATTAAAGTTTTAAGTGTAATGCAAGATTCTTGCGATTTAAAATTAGGATTGCTTGTG
GATTTTAAATTTGAGAATAATCACTATGGTATTGTTATTTATAATTTAAGCAAGGATTTTATTAA
AAGTATTGCCAATTTGCAAATTAGTGAACAAATTTTATATTTAAAAGCCCAAATGGATAAATTG
ATGTTTATTTTAGATGAATCTGAATTTGTTATTTTTGATTATTAATCAAAAATGGATTTTTTAG
CTTAATAAATGATTCAAACTACACTTCAATGTTAGCAAATAAAATTGATTTTAGAGTTTTTTCTA
ATTTTTTTGCTAGGGTTTCTTTATATTCATTTATGTTTGTAATTGCAGATTATTTGCATAGCAATT
ATGTTGTTGAGAATTTTCCTCAAAAAATAGTTATCAATTGA f150.aa (SEQ ID NO:513)
MKTFVIIGLSNLGIHLLEDLSRLDCQIIIIDTSKELIEEYDVISTESFVVEQFTKNALKRIIPVDTDAVVID
FDDDLGKSALVTHYCNLLGLKEICVKTENRDDAEILKTLGATKIIFPSKDAARRLTPLLVSPNLSTYN
IIGYDIIVAETVIPKEYVGKTLFEADLRRECGITVIAVRNLSNSRYEFVDGDYFFLKDDKIVICGKPDSI
ENFTNNKDLIKDLISGSKEDENLNKDAEKKSRFLGIFNFMKIFQKDRKDN t150.aa (SEQ ID NO:514)
CQIIIIDTSKELIEEYDVISTESFVVEQFTKNALKRIIPVDTDAVVIDFDDDLGKSALVTHYCNLLGLKE
ICVKTENRDDAEILKTLGATKIIFPSKDAARRLTPLLVSPNLSTYNIIGYDIIVAETVIPKEYVGKTLFE
ADLRRECGITVIAVRNLSNSRYEFVDGDYFFLKDDKIVICGKPDSIENFTNNKDLIKDLISGSKEDENL
NKDAEKKSRFLGIFNFMKIFQKDRKDN f150.nt (SEQ ID NO:515)
ATGAAAACATTTGTTATTATTGGACTTAGTAATTTAGGCATTCACTTACTTGAAGATTT
AAGCAGGCTTGATTGTCAAATTATTATTATAGATACATCTAAAGAGCTTATTGAAGAATATGAT
GTGATATCTACAGAAAGCTTTGTTGTTGAGCAATTCACTAAAAATGCTTTGAAAAGAATAATTC
CAGTAGATACAGACGCTGTTGTTATTGATTTTGATGATGATCTTGGCAAAAGTGCTCTTGTTACT
CACTATTGTAATCTTTTAGGTTTGAAAGAAATATGCGTTAAGACAGAAAATAGAGATGATGCTG
AAATCTTAAAAACTCTTGGGGCAACAAAAATTATATTTCCAAGTAAAGATGCTGCAAGAAGATT
AACTCCATTATTAGTATCTCCAAATCTTTCAACTTATAATATTATTGGGTATGATATTATTGTTG
CTGAAACTGTTATTCCCAAAGAATATGTTGGTAAAACTCTTTTTGAAGCCGATCTTAGAAGAGA
ATGTGGGATTACAGTTATTGCTGTTAGAAATTTAAGTAATTCTAGGTATGAATTTGTTGATGGC
GATTATTTTTTTTAAAAGATGATAAAATTGTAATTTGTGGTAAACCAGATAGCATTGAAAATT
TTACAAATAATAAAGATTTAATTAAAGATTTAATTTCAGGCTCTAAAGAGGATGAAAATTTAAA

TABLE 1-continued

Nucleotide and Amino Acid Sequences.

TAAAGATGCTGAGAAAAAATCTAGATTTTTAGGGATTTTCAATTTTATGAAAATTTTTCAAAAA
GATCGTAAGGATAATTAG t150.nt (SEQ ID NO:516)
TGTCAAATTATTATTATAGATACATCTAAAGAGCTTATTGAAGAATATGATGTGATATCTACAG
AAAGCTTTGTTGTTGAGCAATTCACTAAAAATGCTTTGAAAAGAATAATTCCAGTAGATACAGA
CGCTGTTGTTATTGATTTTGATGATGATCTTGGCAAAAGTGCTCTTGTTACTCACTATTGTAATC
TTTTTAGGTTTGAAAGAAATATGCGTTAAGACAGAAAATAGAGATGATGCTGAAATCTTAAAAA
CTCTTGGGGCAACAAAAATTATATTTCCAAGTAAAGATGCTGCAAGAAGATTAACTCCATTATT
AGTATCTCCAAATCTTTCAACTTATAATATTATTGGGTATGATATTATTGTTGCTGAAACTGTTA
TTCCCAAAGAATATGTTGGTAAAACTCTTTTTGAAGCCGATCTTAGAAGAGAATGTGGGATTAC
AGTTATTGCTGTTAGAAATTTAAGTAATTCTAGGTATGAATTTGTTGATGGCGATTATTTTTTT
TAAAAGATGATAAAATTGTAATTTGTGGTAAACCAGATAGCATTGAAAATTTTACAAATAATAA
AGATTTAATTAAAGATTTAATTTCAGGCTCTAAAGAGGATGAAAATTTAAATAAAGATGCTGAG
AAAAAAATCTAGATTTTTAGGGATTTTCAATTTTATGAAAATTTTTCAAAAAGATCGTAAGGATA
ATTAG f219.aa (SEQ ID NO:517)
MLIARIMNINTLFYGMIIIIFALISCNHKNIQYDKRIKKFLDKNKIEYKIDSENDFIAFKDINNNEKEEVI
IRSRLNSYKNSKIREIFGIVKVFDINTPKIKEISDSLMSDSYNNRVFGSWEIIHNAERGINSLVYIVKAE
EFANDTFLLDAIDEIASTISIFKKIITTNNENIDNNEENNNTNESNEQPTLKQEKTNSTKESNNELKED
QIEEELQEIKAQ t219.aa (SEQ ID NO:518)
CNHKNIQYDKRIKKFLDKNKIEYKIDSENDFIAFKDINNNEKEEVIIRSRLNSYKNSKIREIFGIVKVFD
INTPKIKEISDSLMSDSYNNRVFGSWEIIHNAERGINSLVYIVKAEEFANDTFLLDAIDEIASTISIFKKII
TTNNENIDNNEENNNTNESNEQPTLKQEKTNSTKESNNELKEDQIEEELQEIKAQ f219.nt (SEQ ID NO:519)
ATGCTAATTGCAAGAATAATGAATATTAATACATTATTCTACGGCATGATCATTATCATTTTTGC
ACTCATTTCTTGCAATCATAAGAATATACAGTACGACAAGAGAATTAAAAAATTTTTAGATAAA
AACAAAATTGAATATAAAATAGACTCAGAAAATGACTTTATAGCATTTAAAGATATAAACAATA
ACGAAAAGAAGAAGTAATCATCAGATCAAGACTAAACTCATATAAAAATTCAAAGATAAGAG
AAATATTTGGAATTGTTAAAGTATTTGATATAAACACACCAAAAATAAAAGAAATATCTGACTC
GCTTATGAGCGATAGTTATAATAACAGAGTATTTGGATCGTGGGAGATTATTCATAATGCAGAA
AGAGGAATCAACTCTTTGGTATATATTGTAAAAGCAGAAGAATTTGCAAATGATACATTTTTGC
TTGATGCAATTGATGAGATTGCCTCAACAATAAGTATTTTCAAAAAAATAATAACAACCAACAA
CGAAAACATTGATAATAATGAAGAAATAACAATACAAATGAATCAAATGAACAGCCCACCTT
AAAGCAAGAAAAAACAAATTCAACAAAAGAATCTAATAACGAACTTAAAGAAGATCAAATAGA
AGAAGAACTTCAAGAAATCAAAGCCCAATAA t219.nt (SEQ ID NO:520)
TGCAATCATAAGAATATACAGTACGACAAGAGAATTAAAAAATTTTTAGATAAAAACAAAATT
GAATATAAAATAGACTCAGAAAATGACTTTATAGCATTTAAAGATATAAACAATAACGAAAAA
GAAGAAGTAATCATCAGATCAAGACTAAACTCATATAAAAATTCAAAGATAAGAGAAATATTT
GGAATTGTTAAAGTATTTGATATAAACACACCAAAAATAAAAGAAATATCTGACTCGCTTATGA
GCGATAGTTATAATAACAGAGTATTTGGATCGTGGGAGATTATTCATAATGCAGAAAGAGGAA
TCAACTCTTTGGTATATATTGTAAAAGCAGAAGAATTTGCAAATGATACATTTTTGCTTGATGC
AATTGATGAGATTGCCTCAACAATAAGTATTTTCAAAAAAATAATAACAACCAACAACGAAAA
CATTGATAATAATGAAGAAATAACAATACAAATGAATCAAATGAACAGCCCACCTTAAAGCA
AGAAAAAACAAATTCAACAAAAGAATCTAATAACGAACTTAAAGAAGATCAAATAGAAGAAGA
ACTTCAAGAAATCAAAGCCCAATAA f229.aa (SEQ ID NO:521)
MRVDLLPLVELSLYINLSFCCKDFSIFNRILEELKCHLILLGHPIIKTLYIKHVDFCLSRQDNLKFIFTSL
SKYINLELLEEFTLEIIPGYVDFEKFKLLDEFCITRINLNVQSFSLEFRKIVGIPEISYKKLNILINNIRKFP
FDLNIDMTVNMPLQKKSHLKRDLQRIAFIYA t229.aa (SEQ ID NO:522)
CKDFSIFNRILEELKCHLILLGHPIIKTLYLKHVDFCLSRQDNLKFIFTSLSKYINLELLEEFTLEIIPGYV
DFEKFKLLDEFCITRINLNVQSFSLEFRKIVGIPEISYKKLNILINNIRKFPFDLNIDMTVNMPLQKKSH
LKRDLQRIAFIYA f229.nt (SEQ ID NO:523)
ATGAGAGTAGATCTTTTACCTCTTGTCGAGTTAAGTCTTTATATTAATTTGTCATTTTGTTGTAA
AGATTTTAGCATTTTTAATAGAATTTTAGAGGAATTAAAATGTCATTTAATCTTGCTGGGTCATC
CAATTATAAAAACACTTTACATTAAGCACGTAGATTTTTGTTTATCTAGGCAAGATAATTTAAA
ATTTATTTTCACTTCTTTGTCCAAGTATATTAATTTGGAGTTATTAGAAGAATTTACTTTAGAAA
TTATTCCGGGTTATGTTGATTTTGAAAAATTCAAACTTTTGGATGAATTTTGTATTACTAGAATT
AATCTTAATGTTCAAAGTTTTTCTTTAGAGTTTAGAAAGATTGTGGGATACCCGAAATTCTTA
TAAAAAATTGAATATTTTGATTAACAATATTAGAAAGTTTCCTTTTGATTTGAATATTGACATGA
CTGTCAATATGCCTTTGCAAAAAAAATCTCATCTCAAGCGAGATTTGCAAAGAATTGCTTTCAT
ATATGCCTGA t229.nt (SEQ ID NO:524)
TGTAAAGATTTTAGCATTTTTAATAGAATTTTAGAGGAATTAAAATGTCATTTAATCTTGCTGG
GTCATCCAATTATAAAAACACTTTACATTAAGCACGTAGATTTTTGTTTATCTAGGCAAGATAA

TABLE 1-continued

Nucleotide and Amino Acid Sequences.

```
TTTAAAATTTATTTTCACTTCTTTGTCCAAGTATATTAATTTGGAGTTATTAGAAGAATTTACTT
TAGAAATTATTCCGGGTTATGTTGATTTTGAAAAATTCAAACTTTTGGATGAATTTTGTATTACT
AGAATTAATCTTAATGTTCAAAGTTTTTCTTTAGAGTTTAGAAAGATTGTGGGGATACCCGAAA
TTTCTTATAAAAAATTGAATATTTTGATTAACAATATTAGAAAGTTTCCTTTTGATTTGAATATT
GACATGACTGTCAATATGCCTTTGCAAAAAAAATCTCATCTCAAGCGAGATTTGCAAAGAATTG
CTTTCATATATGCCTGA f22.aa (SEQ ID NO:525)
MLKTLTKIITISCLIVGCASLPYTPPKQNLNYLMELLPGANLYAHVNLIKNRSIYNSLSPKYKSVLGLI
SNLYFSYKKENNDFALLIMGNFPKDIFWGIHKNRNTESIGNIFTNPKWKLKNSNIYIIPNKARTSIAIT
QKDITAKDNNMLTTKYIGEIEKNEMFFWIQDPTLLLPNQIVSSKNLIPFSSGTLSINSLNQEEYIFKSLI
KTNNPPILKILSKKLIPTVLTNMTNLTISSHIKTTIKDQNTVEIEFNIQKSSVESLIEKLASNIQT t22.aa (SEQ ID NO:526)
CASLPYTPPKQNLNYLMELLPGANLYAHVNLIKNRSIYNSLSPKYKSVLGLISNLYFSYKKENNDFA
LLIMGNFPKDIFWGIHKNRNTESIGNIFTNPKWKLKNSNIYIIPNKARTSIAITQKDITAKDNNMLTTK
YIGEIEKNEMFFWIQDPTLLLPNQIVSSKNLIPFSSGTLSINSLNQEEYIFKSLIKTNNPPILKILSKKLIPT
VLTNMTNLTISSHIKTTIKDQNTVEIEFNIQKSSVESLIEKLASNIQT f22.nt (SEQ D NO:527)
ATGTTAAAAACATTAACAAAAATAATTACCATTTCATGCCTCATAGTGGGATGCGCAAGCCTGC
CTTACACTCCTCCAAAACAAAATCTAAATTACTTAATGGAACTTTTACCTGGCGCAAATTTATAC
GCCCATGTAAATTTAATTAAAAACAGGTCTATTTATAACTCTTTAAGCCCTAAATATAAATCAG
TTCTTGGGCTTATAAGCAATTTATACTTTAGCTATAAAAAAGAAAATAACGATTTTGCTCTACTA
ATAATGGGTAATTTCCCAAAAGATATTTTCTGGGGAATTCATAAAAATAGAAATACAGAATCAA
TAGGCAATATATTTACAAATCCAAAATGGAAACTTAAAAATTCAAATATATACATTATTCCAAA
CAAAGCTAGAACTAGCATTGCAATAACCCAAAAAGATATAACCGCAAAAGACAATAATATGCT
AACAACAAAATATATTGGGGAAATAGAAAAAAATGAAATGTTTTTTTGGATTCAAGATCCAAC
ATTATTGCTCCCAAACCAAATAGTAAGCAGCAAAAATTTAATTCCCTTTAGCAGTGGAACTTTG
TCTATAAACAGCTTAAATCAAGAAGAATATATTTTTAAATCCTTAATCAAACAAATAATCCAC
CAATACTAAAAATATTGTCAAAAAAGTTAATTCCAACCGTCTTGACAAACATGACAAACCTCAC
AATATCAAGCCACATAAAGACCACAATAAAAGACCAAAATACGGTTGAAATAGAATTTAATAT
TCAAAAATCTAGTGTTGAAAGCCTTATAGAAAAACTAGCTTCAAATATTCAAACCTAA t22.nt (SEQ ID NO:528)
TGCGCAAGCCTGCCTTACACTCCTCCAAAACAAAATCTAAATTACTTAATGGAACTTTTACCTG
GCGCAAATTTATACGCCCATGTAAATTTAATTAAAAACAGGTCTATTTATAACTCTTTAAGCCCT
AAATATAAATCAGTTCTTGGGCTTATAAGCAATTTATACTTTAGCTATAAAAAAGAAAATAACG
ATTTGCTCTACTAATAATGGGTAATTTCCCAAAAGATATTTTCTGGGGAATTCATAAAAATAG
AAATACAGAATCAATAGGCAATATATTTACAAATCCAAAATGGAAACTTAAAAATTCAAATATA
TACATTATTCCAAACAAAGCTAGAACTAGCATTGCAATAACCCAAAAAGATATAACCGCAAAA
GACAATAATATGCTAACAACAAAATATATTGGGGAAATAGAAAAAAATGAAATGTTTTTTTGG
ATTCAAGATCCAACATTATTGCTCCCAAACCAAATAGTAAGCAGCAAAAATTTAATTCCCTTTA
GCAGTGGAACTTTGTCTATAAACAGCTTAAATCAAGAAGAATATATTTTTAAATCCTTAATCAA
ACAAATAATCCACCAATACTAAAAATATTGTCAAAAAAGTTAATTCCAACCGTCTTGACAAAC
ATGACAAACCTCACAATATCAAGCCACATAAAGACCACAATAAAAGACCAAAATACGGTTGAA
ATAGAATTTAATATTCAAAAATCTAGTGTTGAAAGCCTTATAGAAAAACTAGCTTCAAATATTC
AAACCTAA f32.aa (SEQ ID NO:529)
MNTKTLYLISLILLACNKNNKIPLIQKLDLPKSSILGFSNKMGIIIKDYAFLSKSTKKNSELDYDYAILL
RKDEVKKIEKTLEKTERYGIEGNWILVNYKGTKRYIFSKDINIVNNLIIDHSK t32.aa (SEQ ID NO:530)
CNKNNKIPLIQKLDLPKSSILGFSNKMGIIIKDYAFLSKSTKKNSELDYDYAILLRKDEVVKIEKTLEK
TERYGIEGNWILVNYKGTKRYIFSKDINIVNNLIIDHSK f32.nt (SEQ ID NO:531)
ATGAATACAAAAACATTATATTTAATATCCTTAATTCTTTTAGCTTGCAATAAAAATAACAAAA
TTCCTCTCATTCAAAAATTAGATTTGCCCAAAAGCAGCATTCTTGGCTTTAGCAATAAAATGGG
CATAATAATAAAAGATTATGCTTTTCTTAGTAAAAGCACTAAGAAAAATAGCGAATTGGATTAT
GATTACGCAATTCTACTCAGAAAAGACGAAGTCGTAAAAATTGAAAAAACACTAGAAAAAACA
GAGCGCTATGGAATTGAAGGAAATTGGATCCTAGTCAATTACAAGGGAACTAAAAGATACATC
TTTAGCAAAGACATCAATATAGTCAACAATTTAATAATTGATCATTCTAAATAG t32.nt (SEQ ID NO:532)
TGCAATAAAAATAACAAAATTCCTCTCATTCAAAAATTAGATTTGCCCAAAAGCAGCATTCTTG
GCTTTAGCAATAAAATGGGCATAATAATAAAAGATTATGCTTTTCTTAGTAAAAGCACTAAGAA
AAATAGCGAATTGGATTATGATTACGCAATTCTACTCAGAAAAGACGAAGTCGTAAAAATTGA
AAAAACACTAGAAAAACAGAGCGCTATGGAATTGAAGGAAATTGGATCCTAGTCAATTACAA
GGGAACTAAAAGATACATCTTTAGCAAAGACATCAATATAGTCAACAATTTAATAATTGATCAT
TCTAAATAG f186.aa (SEQ ID NO:533)
MKKLIIIFTLFLSQACNLSTMHKIDTKEDMKILYSEIAELRKKLNLNHLEIDDTLEKVAKEYAIKLGEN
RTITHTLFGTTPMQRIHKYDQSFNLTREILASGIELNRVVNAWLNSPSHKEALINTDTDKIGGYRLKT
TDNIDIFVVLFGKRKYKN
```

TABLE 1-continued

Nucleotide and Amino Acid Sequences.

t186.aa (SEQ ID NO:534)
CNLSTMHKIDTKEDMKILYSEIAELRKKLNLNHLEIDDTLEKVAKEYAIKLGENRTITHTLFGTT
PMQRIHKYDQSFNLTREILASGIELNRVVNAWLNSPSHKEALINTDTDKIGGYRLKTTDNIDIFVVLF
GKRKYKN f186.nt (SEQ ID NO:535)
ATGAAAAAATTGATTATAATTTTTACACTGTTTTTATCTCAAGCATGCAATTTAAGTACAATGCA
TAAAATAGATACAAAAGAAGATATGAAAATTCTATATTCAGAAATTGCTGAATTGAGAAAAAA
ATTAAATCTAAACCATCTAGAAATAGATGATACCCTTGAAAAAGTTGCAAAAGAATATGCCATT
AAACTGGGAGAAAATAGAACAATAACTCACACCCTTTTTGGCACAACCCCAATGCAAAGAATA
CATAAATACGATCAATCCTTTAATTTAACAAGAGAAATACTGGCATCAGGAATTGAACTTAACA
GAGTAGTTAATGCATGGCTTAATAGTCCAAGCCACAAAGAAGCTCTTATTAATACAGATACCGA
TAAAATAGGTGGCTATAGATTAAAAACGACTGACAATATAGATATATTTGTAGTTCTTTTTGGA
AAAAGAAAATATAAGAATTGA t186.nt (SEQ ID NO:536)
TGCAATTTAAGTACAATGCATAAAATAGATACAAAAGAAGATATGAAAATTCTATATTCAGAA
ATTGCTGAATTGAGAAAAAAATTAAATCTAAACCATCTAGAAATAGATGATACCCTTGAAAAA
GTTGCAAAAGAATATGCCATTAAACTGGGAGAAAATAGAACAATAACTCACACCCTTTTTGGCA
CAACCCCAATGCAAAGAATACATAAATACGATCAATCCTTTAATTTAACAAGAGAAATACTGGC
ATCAGGAATTGAACTTAACAGAGTAGTTAATGCATGGCTTAATAGTCCAAGCCACAAAGAAGC
TCTTATTAATACAGATACCGATAAAATAGGTGGCTATAGATTAAAAACGACTGACAATATAGAT
ATATTTGTAGTTCTTTTTGGAAAAAGAAAATATAAGAATTGA f216.aa (SEQ ID NO:537)
MIRVLLGSLAVSFLFSICMVFLNYDNLFSKKVFYFHSSKGFVANLRYLRDEQNLKDNLDLLVKDFLL
GSNEGFSFGFLLSDSRFLYSFLKNGVYYVNLSREFYDSFNNGDYNESNESFDVKVNLFAMSLIKTMR
FNYPGKIKKIVILVEGCILKEQS t216.aa (SEQ ID NO:538)
CMVFLNYDNLFSKKVFYFHSSKGFVANLRYLRDEQNLKDNLDLLVKDFLLGSNEGFSFGFLLSDSRF
LYSFLKNGVYYVNLSREFYDSFNNGDYNESNESFDVKVNLFAMSLIKTMRFNYPGKIKKIVILVEGC
ILKEQS f216.nt (SEQ ID NO:539)
ATGATTAGGGTGCTTTTGGGGTCTTTGGCAGTAAGCTTTTTGTTTTCTATTTGTATGGTTTTTTT
AAATTATGATAATCTTTTTTCAAAAAAGGTTTTTTATTTTCATTCTAGCAAGGGATTTGTTGCTA
ATTTAAGATATTTAAGAGATGAACAAAATTTGAAAGATAATTTAGATCTTTTAGTAAAAGATTT
TCTTTTAGGAAGCAATGAAGGGTTTTCTTTTGGGTTTTTATTAAGTGATTCAAGATTTTTATATT
CTTTTTTAAAGAATGGAGTTTATTATGTAAATCTTTCAAGAGAATTTTATGATTCTTTTAATAAT
GGTGATTATAATGAATCTAATGAATCTTTTGATGTTAAGGTCAATCTTTTTGCTATGTCTTTAAT
AAAAACAATGCGCTTTAACTATCCTGGTAAGATAAAAAAGATTGTTATTCTTGTTGAAGGGTGT
ATCTTAAAGGAGCAAAGTTGA t216.nt (SEQ ID NO:540)
TGTATGGTTTTTTTAAATTATGATAATCTTTTTTCAAAAAAGGTTTTTTATTTTCATTCTAGCAA
GGGATTTGTTGCTAATTTAAGATATTTAAGAGATGAACAAAATTTGAAAGATAATTTAGATCTT
TTAGTAAAAGATTTTCTTTTAGGAAGCAATGAAGGGTTTTCTTTTGGGTTTTTATTAAGTGATTC
AAGATTTTTATATTCTTTTTTAAAGAATGGAGTTTATTATGTAAATCTTTCAAGAGAATTTTATG
ATTCTTTTAATAATGGTGATTATAATGAATCTAATGAATCTTTTGATGTTAAGGTCAATCTTTTT
GCTATGTCTTTAATAAAAACAATGCGCTTTAACTATCCTGGTAAGATAAAAAAGATTGTTATTC
TTGTTGAAGGGTGTATCTTAAAGGAGCAAAGTTGA f328.aa (SEQ ID NO:541)
MAIKYARENNIPFLGICLGLQLAVIEFARNVCGILDADTEENLARDKPLKSPVIHLLPEQKGIKDKGA
TMRLGGYPVILKKNTIAFKLYGQDRIIERFRHRYEVNNDYIDLFAKNGLIVSGFSSDFKMAKLIEIPEN
KFFVACQFHPELITRIENPAKLFLGLIKACI t328.aa (SEQ ID NO:542)
CLGLQLAVIEFARNVCGILDADTEENLARDKPLKSPVIHLLPEQKGIKDKGATMRLGGYPVILKKNTI
AFKLYGQDRIIERFRHRYEVNNDYIDLFAKNGLIVSGFSSDFKMAKLIEIPENKFFVACQFHPELITRIE
NPAKLF
LGLIKACI f328.nt (SEQ ID NO:543)
ATGGCTATTAAATATGCTCGTGAGAATAATATTCCCTTTCTTGGAATTTGTCTTGGTTTGCAGCT
TGCTGTAATAGAATTTGCTCGTAATGTTTGTGGAATACTTGATGCTGATGCGGAGAAAATTTA
GCAAGAGACAAGCCCTTAAAAAGTCCTGTTATCCATTTACTTCCTGAGCAAAAGGGAATTAAAG
ATAAGGGCGCTACAATGAGGCTTGGTGGATATCCTGTGATTCTTAAAAAGAATACAATAGCTTT
TAAACTTTATGGCCAAGATCGGATAATTGAAAGATTTAGACATAGGTATGAAGTCAATAATGAT
TATATAGATTTATTTGCAAAAAATGGGCTTATAGTATCTGGATTTTCAAGTGATTTTAAAATGG
CAAAATTAATAGAAATTCCTGAAAATAAAATTTTTCGTAGCTTGCCAGTTTCATCCAGAACTTATT
ACAAGAATAGAAAATCCAGCCAAGCTTTTTCTAGGATTAATTAAAGCTTGTATTTGA t328.nt (SEQ ID NO:544)
TGTCTTGGTTTGCAGCTTGCTGTAATAGAATTTGCTCGTAATGTTTGTGGAATACTTGATGCTGA

TABLE 1-continued

Nucleotide and Amino Acid Sequences.

TACGGAGGAAAATTTAGCAAGAGACAAGCCCTTAAAAAGTCCTGTTATCCATTTACTTCCTGAG
CAAAAGGGAATTAAAGATAAGGGCGCTACAATGAGGCTTGGTGGATATCCTGTGATTCTTAAA
AAGAATACAATAGCTTTTAAACTTTATGGCCAAGATCGGATAATTGAAAGATTTAGACATAGGT
ATGAAGTCAATAATGATTATATAGATTTATTTGCAAAAAATGGGCTTATAGTATCTGGATTTTC
AAGTGATTTTAAAATGGCAAAATTAATAGAAATTCCTGAAAATAAATTTTTCGTAGCTTGCCAG
TTTCATCCAGAACTTATTACAAGAATAGAAAATCCAGCCAAGCTTTTTCTAGGATTAATTAAAG
CTTGTATTTGA f352.aa (SEQ ID NO:545)
MNKTKNRSLTYFIILSCISLFGANNNTISYSSIEIPLEDLSEEFKSSGNKSDQINTSKHLNKNIVSYEDPK
KGKDLKLPENIRDKKLPQKRMDENDLKSVIENYENKIKNIEKLLKTKNQKTSENENKKIESIEKKAK
KYEILTNKLKNEIVEIKKLLNKKIKPKEDENYEKINIENIEEETDDDFEDNYEYNDEIEXTNEDNYPSN
EGIINNLKENLNENEKYYAINEKKIDELEDRINENENTILDLQRELRNFKKKDNSDKNLEEIEENLSSI
GRIINDLKRKISANEAINKENQKKIRTDKHKLKELEDKIKENEETILKLQKELNNFKKKEIYQKPLNE
ETFTPSITSKNDDLEENKKLKKEYLKPIEKKESRDLEENTKSTPKTTMIKTADFQIYPDIYLNNYKFK
EKGDQFAFKKENTYYIEIDPTNNLNEALKNHEIISKYKFEKYFINPILKNKEEFFRNLIEVKNIHELGIM
YKNLKPEFKQIKIIK t352.aa (SEQ ID NO:546)
CISLFGANNNTISYSSIEIPLEDLSEEFKSSGNKSDQINTSKHLNKNIVSYEDPKKGKDLKLPENIRDKK
LPQKRMDENDLKSVIENYENKIKNIEKLLKTKNQKTSENENKKIESIEKKAKKYEILTNKLKNETVEI
KKLLNKKIKPKEDENYEKINIENIEEETDDDFEDNYEYNDEIEXTNEDNYPSNEGIINNLKENLNENE
KYYAINEKKIDELEDRINENENTILDLQRELRNFKKKDNSDKNLEEIEENLSSIGRIINDLKRKISANEA
INKENQKKIRTDKHKLKELEDKIKENEETILKLQKELNNFKKKEIYQKPLNEETFTPSITSKNDDLEE
NKKLKKEYLKPIEKKESRDLEENTKSTPKTTMIKTADFQIYPDIYLNNYKFKEKGDQFAFKKENTYY
IEIDPTNNLNEALKNHEIISKYKFEKYFINPILKNKEEFFRNLIEVKNIHELGIMYKNLKPEFKQIKIIK f352.nt (SEQ ID NO:547)
ATGAATAAAACAAAAAATCGAAGCCTTACGTATTTTATAATACTTTCATGTATATCATTATTTG
GGGCTAATAATAATACAATAAGCTACTCTAGCATTGAAATTCCTCTAGAAGACTTAAGTGAAGA
ATTTAAAAGTTCTGGGAATAAAAGCGATCAAATAAATACCTCAAAACATTTAAACAAAAACAT
AGTTTCTTATGAAGACCCAAAAAAGGGTAAAGATCTAAAATTGCCAGAAAATATAAGAGACAA
AAAACTACCCCAAAAAAGAATGGACGAAAATGATCTAAAATCTGTAATTGAAAATTATGAAAA
TAAAATTAAAAACATAGAAAAGCTTTTAAAAACCAAAAATCAAAAAACATCGGAAAATGAAAA
TAAAAAAATAGAATCAATCGAAAAAAAAGCAAAAAAATATGAAATTTTAACCAATAAATTAAA
AAACGAAATAGTAGAAATAAAAAAGCTCCTTAACAAAAAAATCAAGCCTAAAGAAGATGAAAA
TTACGAAAAAATAAATATTGAAACATTGAAGAAGAAACTGATGATGATTTTGAAGACAATTA
TGAATATAATGATGAAATTGAAGAACAAATGAGGACAATTACCCTTCTAATGAAGGAATAATA
AACAATCTAAAAGAAATTCTTAATGAAAACGAAAAATATTATGCTATTAATGAAAAAAAATC
GATGAACTTGAAGACAGAATCAACGAGAATGAAAACACTATTTTAGACTTGCAAAGAGAATTA
AGGAATTTTAAAAAAAAGATAACTCAGATAAAAACTTAGAAGAAATTGAGGAAAATTTATCT
TCAATAGGAAGAATAATTAATGATCTAAAAAGAAAAATCAGCGCAAATGAAGCAATAAACAAA
GAAAATCAAAAAAAAATAAGAACTGATAAACACAAACTCAAAGAATTAGAAGATAAAATAAAG
GAAAATGAAGAGACTATTTTAAAACTTCAAAAAGAATTAAACAATTTTAAAAAAAAAGAAATT
TATCAAAACCCTTAAATGAAGAAACTTTCACTCCAAGCATTACAAGTAAAAATGACGACTTAG
AAGAAAATAAGAAATTAAAAAAGGAATATTTAAAGCCCATAGAAAAAAAGAAAGCCGAGAT
CTAGAAGAAAATACTAAAAGCACCCCAAAAACAACTATGATAAAACAGCAGATTTTCAAATC
TACCCTGACATATATCTTAATAATTATAAATTTAAAGAAAAGGGAGATCAATTTGCATTTAAAA
AAGAAAACACATACTATATTGAAATAGATCCCACTAACAATTTAAATGAGGCTTTAAAAAATCA
TGAAATAATCTCAAAATATAAATTTGAAAAATATTTCATTAACCCTATTCTAAAAAATAAAGAA
GAATTTTTTAGAAACTTAATAGAAGTCAAAAATATCCACGAACTAGGAATTATGTATAAAAATC
TAAAGCCTGAATTTAAGCAAATAAAAATAATTAAATAA t352.nt (SEQ ID NO:548)
TGTATATCATTATTTGGGGCTAATAATAATACAATAAGCTACTCTAGCATTGAAATTCCTCTAG
AAGACTTAAGTGAAGAATTTAAAAGTTCTGGGAATAAAAGCGATCAAATAAATACCTCAAAAC
ATTTAAACAAAAACATAGTTTCTTATGAAGACCCAAAAAAGGGTAAAGATCTAAAATTGCCAG
AAAATATAAGAGACAAAAACTACCCCAAAAAAGAATGGACGAAAATGATCTAAAATCTGTAA
TTGAAAATTATGAAAATAAAATTAAAAACATAGAAAAGCTTTTAAAAACCAAAAATCAAAAAA
CATCGGAAAATGAAAATAAAAAAATAGAATCAATCGAAAAAAAAGCAAAAAAATATGAAATTT
TAACCAATAAATTAAAAAACGAAATAGTAGAAATAAAAAAGCTCCTTAACAAAAAAATCAAGC
CTAAAGAAGATGAAAATTACGAAAAAATAAATATTGAAACATTGAAGAAGAAACTGATGATG
ATTTTGAAGACAATTATGAATATAATGATGAAATTGAAGAACAAATGAGGACAATTACCCTTCT
AATGAAGGAATAATAAACAATCTAAAAGAAATTCTTAATGAAAACGAAAAATATTATGCTATT
AATGAAAAAAAAATCGATGAACTTGAAGACAGAATCAACGAGAATGAAAACACTATTTTAGAC
TTGCAAAGAGAATTAAGGAATTTTAAAAAAAAGATAACTCAGATAAAAACTTAGAAGAAATT
GAGGAAAATTTATCTTCAATAGGAAGAATAATTAATGATCTAAAAAGAAAAATCAGCGCAAAT
GAAGCAATAAACAAAGAAAATCAAAAAAAAATAAGACTGATAAACACAAACTCAAAGAATTA
GAAGATAAAATAAAGGAAAATGAAGAGACTATTTTAAAACTTCAAAAAGAATTAAACAATTTT
AAAAAAAAAGAAATTTATCAAAACCCTTAAATGAAGAAACTTTCACTCCAAGCATTACAAGTA
AAAATGACGACTTAGAAGAAAATAAGAAATTAAAAAAGGAATATTTAAAGCCCATAGAAAAA
AAGAAAGCCGAGATCTAGAAGAAAATACTAAAAGCACCCCAAAAACAACTATGATAAAACAG
CAGATTTTCAAATCTACCCTGACATATATCTTAATAATTATAAATTTAAAGAAAAGGGAGATCA
ATTTGCATTTAAAAAAGAAAACACATACTATATTGAAATAGATCCCACTAACAATTTAAATGAG
GCTTTAAAAAATCATGAAATAATCTCAAAATATAAATTTGAAAAATATTTCATTAACCCTATTC
TAAAAAATAAAGAAGAATTTTTTAGAAACTTAATAGAAGTCAAAAATATCCACGAACTAGGAA
TTATGTATAAAAATCTAAAGCCTGAATTTAAGCAAATAAAAATAATTAAATAA

TABLE 1-continued

Nucleotide and Amino Acid Sequences.

f867.aa (SEQ ID NO:549)
MNTKGKVVGVNGNLVTIEVEGSVSMNEVLFVKTAGRNLKAEVIRIRGNEVDAQVFELTKGISVGDL
VEFTDKLLTVELGPGLLTQVYDGLQNPLPELAIQCGFFLERGVYLRPLNKDKKWNFKKTSKVGDIVI
AGDFLGFVIEGTVHHQIMIPFYKRDSYKIVEIVSDGDYSIDEQIAVIEDDSGMRHNITMSFHWPVKVP
ITNYKERLIPSEPMLTQTRIIDTFFPVAKGGTFCIPGPFGAGKTVLQQVTSRNADVDVVIIAACGERAG
EVVETLKEFPELMDPKTGKSLMDRTCIICNTSSMPVAAREASVYTAITIGEYYRQMGLDILLLADSTS
RWAQAMREMSGRLEEIPGEEAFPAYLESVIASFYERAGIVVLNNGDIGSVTVGGSVSPAGGNFEEPV
TQATLKVVGAFHGLTRERSDARKFPAISPLESWSKYKGVIDQKKTEYARSFLVKGNEINQMMKVV
GEEGISNDDFLIYLKSELLDSCYLQQNSFDSIDAAVSSERQNYMFDIVYNILKTNFEFSDKLQARDFIN
ELRQNLLDMNLSSFKDHKFNKLEHALGELINFKKVI t867.aa (SEQ ID NO:550)
GRNLKAEVIRIRGNEVDAQVFELTKGISVGDLVEFTDKLLTVELGPGLLTQVYDGLQNPLPELAIQC
GFFLERGVYLRPLNKDKKWNFKKTSKVGDIVIAGDFLGFVIEGTVHHQIMIPFYKRDSYKIVEIVSDG
DYSIDEQIAVIEDDSGMRHNITMSFHWPVKVPITNYKERLIPSEPMLTQTRIIDTFFPVAKGGTFCIPG
PFGAGKTVLQQVTSRNADVDVVIIAACGERAGEVVETLKEFPELMDPKTGKSLMDRTCIICNTSSMP
VAAREASVYTAITIGEYYRQMGLDILLLADSTSRWAQAMREMSGRLEEIPGEEAFPAYLESVIASFY
ERAGIVVLNNGDIGSVTVGGSVSPAGGNFEEPVTQATLKVVGAFHGLTRERSDARKFPAISPLESWS
KYKGVIDQKKTEYARSFLVKGNEINQMMKVVGEEGISNDDFLIYLKSELLDSCYLQQNSFDSIDAAV
SSERQNYMFDIVYNILKTNFEFSDKLQARDFINELRQNLLDMNLSSFKDHKFNKLEHALGELINFKK
VI f867.nt (SEQ ID NO:551)
ATGAATACAAAAGGAAAAGTCGTTGGAGTTAATGGAAACTTAGTTACTATTGAGGTAGAAGGT
TCAGTTTCTATGAATGAAGTTTTATTTGTAAAGACTGCTGGTAGGAATTTAAAAGCAGAAGTAA
TTCGTATTAGGGGCAATGAAGTTGATGCACAGGTTTTTGAATTGACAAAAGGGATATCTGTTGG
AGACCTAGTTGAATTTACAGACAAACTTTTAACAGTTGAACTCGGACCAGGGCTTTTAACTCAA
GTATATGATGGGCTTCAAAATCCTTTGCCTGAATTGGCTATTCAATGTGGATTTTTTTTAGAAAG
GGGAGTATATTTAAGGCCCTTGAATAAAGATAAAAAGTGGAATTTTAAAAAAACCTCCAAAGT
TGGAGATATCGTTATTGCAGGAGATTTTTTAGGTTTTGTAATTGAGGGAACTGTTCACCATCAA
ATAATGATTCCATTTTATAAAAGGGATTCTTATAAAATTGTGGAGATTGTAAGTGATGGCGACT
ATTCGATTGATGAGCAAATTGCTGTAATTGAAGATGATTCTGGTATGAGGCATAATATTACAAT
GTCTTTTCATTGGCCTGTTAAAGTTCCTATTACTAATTATAAGGAACGCCTTATTCCTAGTGAAC
CTATGTTGACTCAAACTAGAATTATAGATACATTTTTCCCAGTTGCCAAAGGTGGAACTTTTTGC
ATTCCGGGTCCTTTTGGAGCAGGAAAAACGGTTCTTCAGCAGGTTACAAGTCGAAATGCTGATG
TTGATGTAGTGATTATTGCAGCTTGTGGTGAGCGAGCAGGAGAAGTGGTAGAAACTCTTAAAG
AATTTCCCGAATTAATGGATCCAAAAACCGGCAAATCTTTAATGGACAGGACTTGTATTATTTG
TAATACATCTTCAATGCCAGTTGCAGCTAGAGAAGCTTCTGTTTATACTGCTATTACTATTGGTG
AGTATTACAGGCAAATGGGCCTTGATATTCTTCTTTTGGCAGATTCAACTTCAAGATGGGCTCA
AGCAATGAGAGAAATGTCTGGACGCCTTGAGGAAATTCCTGGCGAGGAGGCTTTTCCGGCATA
TCTTGAGTCTGTTATTGCTTCCTTTTATGAAAGGGCAGGTATTGTAGTTCTTAATAATGGGGATA
TTGGATCTGTAACAGTTGGTGGCTCTGTAAGTCCTGCTGGTGGTAATTTTGAAGAGCCAGTTAC
TCAAGCAACTTTAAAAGTTGTAGGAGCATTTCACGGGCTTACAAGAGAAAGGTCTGATGCTAG
GAAATTTCCAGCTATTAGTCCTCTTGAATCTTGGAGTAAATATAAAGGCGTTATTGATCAAAAA
AAGACTGAATATGCAAGATCTTTTTTGGTGAAAGGTAATGAAATTAATCAAATGATGAAAGTTG
TTGGAGAAGAAGGCATAAGTAACGATGATTTTTTAATTTATTTAAAATCCGAGCTACTTGATTC
GTGCTATTTGCAGCAAAATTCATTTGATTCTATTGATGCTGCTGTTAGTTCAGAGCGTCAAAATT
ATATGTTTGATATAGTTTATAACATTCTTAAAACTAACTTTGAGTTTTCTGATAAACTTCAAGCA
AGAGATTTTATAAATGAGTTAAGGCAAAATCTTTTAGACATGAATCTTTCTTCTTTTAAGGATC
ATAAGTTTAATAAATTGGAGCATGCTTTGGGTGAATTGATAAATTTTAAAAAGGTAATTTAG t867.nt (SEQ ID NO:552)
GGTAGGAATTTAAAAGCAGAAGTAATTCGTATTAGGGGCAATGAAGTTGATGCACAGGTTTTT
GAATTGACAAAAGGGATATCTGTTGGAGACCTAGTTGAATTTACAGACAAACTTTTAACAGTTG
AACTCGGACCAGGGCTTTTAACTCAAGTATATGATGGGCTTCAAAATCCTTTGCCTGAATTGGC
TATTCAATGTGGATTTTTTTTAGAAAGGGGAGTATATTTAAGGCCCTTGAATAAAGATAAAAAG
TGGAATTTTAAAAAAACCTCCAAAGTTGGAGATATCGTTATTGCAGGAGATTTTTTAGGTTTTG
TAATTGAGGGAACTGTTCACCATCAAATAATGATTCCATTTTATAAAAGGGATTCTTATAAAAT
TGTGGAGATTGTAAGTGATGGCGACTATTCGATTGATGAGCAAATTGCTGTAATTGAAGATGAT
TCTGGTATGAGGCATAATATTACAATGTCTTTTCATTGGCCTGTTAAAGTTCCTATTACTAATTA
TAAGGAACGCCTTATTCCTAGTGAACCTATGTTGACTCAAACTAGAATTATAGATACATTTTTCC
CAGTTGCCAAAGGTGGAACTTTTTGCATTCCGGGTCCTTTTGGAGCAGGAAAAACGGTTCTTCA
GCAGGTTACAAGTCGAAATGCTGATGTTGATGTAGTGATTATTGCAGCTTGTGGTGAGCGAGCA
GGAGAAGTGGTAGAAACTCTTAAAGAATTTCCCGAATTAATGGATCCAAAAACCGGCAAATCT
TTAATGGACAGGACTTGTATTATTTGTAATACATCTTCAATGCCAGTTGCAGCTAGAGAAGCTT
CTGTTTATACTGCTATTACTATTGGTGAGTATTACAGGCAAATGGGCCTTGATATTCTTCTTTTG
GCAGATTCAACTTCAAGATGGGCTCAAGCAATGAGAGAAATGTCTGGACGCCTTGAGGAAATT
CCTGGCGAGGAGGCTTTTCCGGCATATCTTGAGTCTGTTATTGCTTCCTTTTATGAAAGGGCAG
GTATTGTAGTTCTTAATAATGGGGATATTGGATCTGTAACAGTTGGTGGCTCTGTAAGTCCTGC
TGGTGGTAATTTTGAAGAGCCAGTTACTCAAGCAACTTTAAAAGTTGTAGGAGCATTTCACGGG
CTTACAAGAGAAAGGTCTGATGCTAGGAAATTTCCAGCTATTAGTCCTCTTGAATCTTGGAGTA
AATATAAAGGCGTTATTGATCAAAAAAAGACTGAATATGCAAGATCTTTTTTGGTGAAAGGTAA
TGAAATTAATCAAATGATGAAAGTTGTTGGAGAAGAAGGCATAAGTAACGATGATTTTTTAATT
TATTTAAAATCCGAGCTACTTGATTCGTGCTATTTGCAGCAAAATTCATTTGATTCTATTGATGC
TGCTGTTAGTTCAGAGCGTCAAAATTATATGTTTGATATAGTTTATAACATTCTTAAAACTAACT
TTGAGTTTTCTGATAAACTTCAAGCAAGAGATTTTATAAATGAGTTAAGGCAAAATCTTTTAGA

TABLE 1-continued

Nucleotide and Amino Acid Sequences.

CATGAATCTTTCTTCTTTTAAGGATCATAAGTTTAATAAATTGGAGCATGCTTTGGGTGAATTGA
TAAATTTTAAAAAGGTAATTTAG f868.aa (SEQ ID NO:553)
MKRVYSKIESIAGNVITVTAQGIKYGELAIVKAKDTSSLAEVIKLDREKVSLQVYGGTRGVSTSDEIK
FLGHSMQVSFSDNLLGRIFDGSGNPRDGGPSLDDNLIEIGGPSANPTKRIVPRNMIRTGLPMIDVFNT
LVESQKLPIFSVSGEPYNELLIRIALQAEVDLIILGGMGLKHDDYLTFKDSLEKGGALSRAIFFVHTAN
DSVVESLTVPDISLSVAEKFALKGKKVLVLLTDMTNFADAMKEISITMEQVPSNRGYPGDLYSQLA
YRYEKAIDFEGAGSITILAVTTMPGDDVTHPVPDNTGYITEGQYYLKGGRIEPFGSLSRLKQMVNSR
TRDDHRTIMDSMIKLYASSKESVEKKAMGFNMTKWDEKLLKYSNMFESKMMDLSVNIPLEEALDL
GWSILASCFSPKETGIKTDLIEKYWPKKETY t868.aa (SEQ ID NO:554)
QGIKYGELAIVKAKDTSSLAEVIKLDREKVSLQVYGGTRGVSTSDEIKFLGHSMQVSFSDNL
LGRIFDGSGNPRDGGPSLDDNLIEIGGPSANPTKRIVPRNMIRTGLPMIDVFNTLVESQKLPIFSVSGEP
YNELLIRIALQAEVDLIILGGMGLKHDDYLTFKDSLEKGGALSRAIFFVHTANDSVVESLTVPDISLSV
AEKFALKGKKVLVLLTDMTNFADAMKEISITMEQVPSNRGYPGDLYSQLAYRYEKAIDFEGAGSITI
LAVTTMPGDDVTHPVPDNTGYITEGQYYLKGGRIEPFGSLSRLKQMVNSRTRDDHRTIMDSMIKLY
ASSKESVEKKAMGFNMTKWDEKLLKYSNMFESKMMDLSVNIPLEEALDLGWSILASCFSPKETGIK
TDLIEKYWPKKETY f868.nt (SEQ ID NO:555)
ATGAAAAGAGTCTATAGTAAAATAGAGTCTATAGCAGGCAATGTAATAACTGTTACAGCTCAA
GGTATTAAGTATGGTGAGCTTGCTATTGTAAAAGCAAAAGATACAAGTTCTCTAGCCGAAGTAA
TTAAACTTGATCGAGAAAAAGTTTCTCTTCAGGTTTATGGTGGTACAAGAGGTGTTTCCACGTC
AGACGAGATAAAGTTTTTAGGGCATTCAATGCAGGTTTCATTTTCTGACAATTTGTTGGGCAGA
ATTTTTGATGGTTCTGGGAATCCTAGAGATGGGGGCCCTTCTCTTGATGATAATTTGATTGAAA
TTGGTGGGCCTTCTGCAAATCCTACAAAACGCATTGTTCCTAGAAATATGATAAGGACAGGGCT
TCCAATGATAGATGTTTTTAATACTCTTGTTGAATCTCAAAAATTGCCAATTTTTTCTGTTTCTG
GTGAGCCTTATAATGAGCTTCTTATAAGAATTGCACTTCAAGCAGAAGTTGATTTAATAATTCT
TGGCGGAATGGGACTTAAGCATGATGATTATTTAACTTTTAAAGATTCTTTAGAAAAGGGAGGT
GCTTTAAGTAGAGCAATTTTTTTTGTTCATACTGCTAATGATTCTGTTGTTGAATCTTTAACTGT
TCCTGATATTTCACTTTCTGTTGCTGAAAAGTTTGCTCTAAAGGGCAAAAAGTTTTGGTGCTTC
TCACAGACATGACAAATTTTGCTGATGCAATGAAAGAAATATCTATTACAATGGAACAAGTGCC
TTCTAATAGAGGTTATCCCGGGGATTTGTATTCTCAGCTTGCATATCGTTATGAGAAGGCTATT
GACTTTGAAGGCGCAGGATCAATTACAATACTTGCAGTTACAACAATGCCGGGTGACGATGTTA
CTCATCCTGTTCCTGACAATACTGGATACATTACAGAAGGTCAATACTATTTAAAAGGTGGCAG
AATAGAGCCTTTTGGGTCTCTTTCAAGACTTAAGCAAATGGTAAATAGTAGAACTAGAGACGAT
CACAGGACTATAATGGATTCAATGATCAAGCTTTATGCATCTTCAAAAGAGTCTGTAGAAAAAA
AGGCTATGGGATTTAATATGACTAAGTGGGATGAAAAATTGCTCAAGTATAGCAATATGTTTGA
AAGTAAGATGATGGATTTGTCTGTTAATATTCCTTTAGAAGAGGCTTTAGATTTAGGTTGGAGC
ATTCTTGCTAGTTGTTTTAGCCCAAAAGAAACGGGAATAAAAACAGATCTTATTGAAAAATATT
GGCCTAAAAAAGAGACTTATTGA t868.nt (SEQ ID NO:556)
CAAGGTATTAAGTATGGTGAGCTTGCTATTGTAAAAGCAAAAGATACAAGTTCTCTAGCCGAAG
TAATTAAACTTGATCGAGAAAAAGTTTCTCTTCAGGTTTATGGTGGTACAAGAGGTGTTTCCAC
GTCAGACGAGATAAAGTTTTTAGGGCATTCAATGCAGGTTTCATTTTCTGACAATTTGTTGGGC
AGAATTTTTGATGGTTCTGGGAATCCTAGAGATGGGGGCCCTTCTCTTGATGATAATTTGATTG
AAATTGGTGGGCCTTCTGCAAATCCTACAAAACGCATTGTTCCTAGAAATATGATAAGGACAGG
GCTTCCAATGATAGATGTTTTTAATACTCTTGTTGAATCTCAAAAATTGCCAATTTTTTCTGTTT
CTGGTGAGCCTTATAATGAGCTTCTTATAAGAATTGCACTTCAAGCAGAAGTTGATTTAATAAT
TCTTGGCGGAATGGGACTTAAGCATGATGATTATTTAACTTTTAAAGATTCTTTAGAAAAGGGA
GGTGCTTTAAGTAGAGCAATTTTTTTTGTTCATACTGCTAATGATTCTGTTGTTGAATCTTTAAC
TGTTCCTGATATTTCACTTTCTGTTGCTGAAAAGTTTGCTCTAAAGGGCAAAAAGTTTTGGTGC
TTCTCACAGACATGACAAATTTTGCTGATGCAATGAAAGAAATATCTATTACAATGGAACAAGT
GCCTTCTAATAGAGGTTATCCCGGGGATTTGTATTCTCAGCTTGCATATCGTTATGAGAAGGCT
ATTGACTTTGAAGGCGCAGGATCAATTACAATACTTGCAGTTACAACAATGCCGGGTGACGATG
TTACTCATCCTGTTCCTGACAATACTGGATACATTACAGAAGGTCAATACTATTTAAAAGGTGG
CAGAATAGAGCCTTTTGGGTCTCTTTCAAGACTTAAGCAAATGGTAAATAGTAGAACTAGAGAC
GATCACAGGACTATAATGGATTCAATGATCAAGCTTTATGCATCTTCAAAAGAGTCTGTAGAAA
AAAAGGCTATGGGATTTAATATGACTAAGTGGGATGAAAAATTGCTCAAGTATAGCAATATGTT
TGAAAGTAAGATGATGGATTTGTCTGTTAATATTCCTTTAGAAGAGGCTTTAGATTTAGGTTGG
AGCATTCTTGCTAGTTGTTTTAGCCCAAAAGAAACGGGAATAAAAACAGATCTTATTGAAAAAT
ATTGGCCTAAAAAAGAGACTTATTGA f872.aa (SEQ ID NO:557)
MRSAVLFFFALPFSISLYSSSNKNFPYWILLEKGRQFLYSKSEFSKSNLTHAINYLQEALLRK
GVYPEASYYLSVAYGMSGNAILEKLNLYKSFEDRYYLLDESFEKKILFSLAKMAELENNYVDTIDYL
NDILNKFSTKKDYYSYHDYSQGENSMSNNELNASFYLTSYLKQVRGAFGIDFTFNLYRFKNYNVID
THQLLSKVYLHLKAYELSITHGLIAAVGILTRMYDYVCYYEPVYQFKNLRSFVQKINKYKAIKNAFE
STDFWEIVYNVAAATYAYSNGNYKFRAIDTWKLVVDLAPRFSPYIAKSRSQIKNSVYLKKN t872.aa (SEQ ID NO:558)
SNKNFPYWILLEKGRQFLYSKSEFSKSNLTHAINYLQEALLRKGVYPEASYYLSVAYGMSGNAILEK
LNLYKSFEDRYYLLDESFEKKILFSLAKMAELENNYVDTIDYLNDILNKFSTKKDYYSYHPYSQGEN
SMSNNELNASFYLTSYLKQVRGAFGIDFTFNLYRFKNYNVIDTHQLLSKVYLHLKAYELSITHGLIA

TABLE 1-continued

Nucleotide and Amino Acid Sequences.

AVGILTRMYDYVCYYEPVYQFKNLRSFVQKINKYKAIKNAFESTDFWEIVYNVAAATYAYSNGNY
KFRAIDTWKLVVDLAPRFSPYIAKSRSQIKNSVYLKKN f872.nt (SEQ ID NO:559)
ATGAGAAGTGCGGTTTTATTTTTTTTGCTTTGCCTTTTTCTATTTCTTTGTATTCTTCAAGTAAT
AAAAATTTTCCGTATTGGATTTTACTTGAAAAAGGCAGGCAATTTCTTTATTCTAAATCTGAATT
TAGTAAGTCTAATCTTACACATGCTATTAATTATTTGCAGGAAGCTTTGCTTAGAAAAGGCGTT
TATCCTGAGGCTAGTTATTATTTGTCAGTAGCTTATGGTATGTCTGGCAATGCTATTCTTGAAAA
ATTAAACCTTTATAAGTCTTTTGAAGACAGATATTATTTGCTAGATGAATCTTTTGAAAAAAAA
ATACTTTTTTCTTTAGCTAAAATGGCTGAACTTGAGAATAATTATGTTGATACTATTGATTATTT
GAATGACATATTAAATAAGTTTTCAACTAAAAAAGATTATTATAGTTATCATGATTATTCTCAA
GGCGAAAACAGTATGTCAAATAATGAACTTAATGCTTCATTTTATTTAACTTCTTATTTAAAACA
AGTAAGAGGAGCTTTTGGTATTGATTTTACTTTTAATCTTTACAGATTTAAAAACTACAATGTTA
TTGATACTCATCAATTATTGTCAAAAGTTTATTTGCACTTAAAAGCTTATGAGCTTTCATTACT
CATGGACTTATAGCTGCAGTAGGAATTTTAACAAGAATGTATGATTATGTTGTTATTATGAAC
CTGTGTATCAGTTTAAAAATTTAAGGTCTTTTGTTCAAAAAATTAATAAGTATAAGGCAATAAA
AAATGCTTTTGAATCTACAGATTTTTGGGAAATAGTTTATAATGTTGCTGCTGCTACTTATGCAT
ATTCTAATGGCAATTATAAATTTAGAGCAATAGATACTTGGAAATTAGTAGTAGATCTTGCGCC
AAGGTTTTCTCCTTATATTGCTAAATCAAGAAGTCAAATTAAAAATTCTGTATATTTAAAAAAA
AATTAA t872.nt (SEQ ID NO:560)
AGTAATAAAAATTTTCCGTATTGGATTTTACTTGAAAAAGGCAGGCAATTTCTTTATTCTAAATC
TGAATTTAGTAAGTCTAATCTTACACATGCTATTAATTATTTGCAGGAAGCTTTGCTTAGAAAA
GGCGTTTATCCTGAGGCTAGTTATTATTTGTCAGTAGCTTATGGTATGTCTGGCAATGCTATTCT
TGAAAAATTAAACCTTTATAAGTCTTTTGAAGACAGATATTATTTGCTAGATGAATCTTTTGAA
AAAAAAATACTTTTTTCTTTAGCTAAAATGGCTGAACTTGAGAATAATTATGTTGATACTATTG
ATTATTTGAATGACATATTAAATAAGTTTTCAACTAAAAAAGATTATTATAGTTATCATGATTAT
TCTCAAGGCGAAAACAGTATGTCAAATAATGAACTTAATGCTTCATTTTATTTAACTTCTTATTT
AAAACAAGTAAGAGGAGCTTTTGGTATTGATTTTACTTTTAATCTTTACAGATTTAAAAACTAC
AATGTTATTGATACTCATCAATTATTGTCAAAAGTTTATTTGCACTTAAAAGCTTATGAGCTTTC
AATTACTCATGGACTTATAGCTGCAGTAGGAATTTTAACAAGAATGTATGATTATGTTGTTAT
TATGAACCTGTGTATCAGTTTAAAAATTTAAGGTCTTTTGTTCAAAAAATTAATAAGTATAAGG
CAATAAAAAATGCTTTTGAATCTACAGATTTTTGGGAAATAGTTTATAATGTTGCTGCTGCTACT
TATGCATATTCTAATGGCAATTATAAATTTAGAGCAATAGATACTTGGAAATTAGTAGTAGATC
TTGCGCCAAGGTTTTCTCCTTATATTGCTAAATCAAGAAGTCAAATTAAAAATTCTGTATATTTA
AAAAAAAATTAA f874.aa (SEQ ID NO:561)
MLKSNKVVLIGAGGVGSSFAYALTIDNSLVHELVIIDVNENKAKGEVMDLNHGQMFLKKNINVLFG
TYKDCANADIVVITAGLNQKPGETRLDLVDKNSKIFKDIITNVVSSGFDGIFVVASNPVDIMTYVTM
KYSKFPIHKVIGTGTILDTSRLRYFLSDHFNVNTQNIHSYIMGEHXDSSFATWDETKIAMKPLSEYLA
EGKITELELDEIHKKVVNAAYEVIKLKGATYYAIGLGIKNIVNAIIGDQNVILPISSYINGQYGGLIKDI
YIGAPAIVCKEGVKEVLNFKISPKELDKFNSSANQLKSYIDKMEF t874.aa (SEQ ID NO:562)
ALTIDNSLVHELVIIDVNENKAKGEVMDLNHGQMFLKKNINVLFGTYKDCANADIVVITAGLNQKP
GETRLDLVDKNSKIFKDIITNVVSSGFDGIFVVASNPVDIMTYVTMKYSKFPIHKVIGTGTILDTSRLR
YFLSDHFNVNTQNIHSYIMGEHXDSSFATWDETKIAMKPLSEYLAEGKITELELDEIHKKVVNAAYE
VIKLKGATYYAIGLGIKNIVNAIIGDQNVILPISSYINGQYGGLIKDIYIGAPAIVCKEGVKEVLNFKISP
KELDKFNSSANQLKSYIDKMEF f874.nt (SEQ ID NO:563)
ATGCCTAAGTCTAATAAAGTTGTTCTTATTGGAGCTGGTGGGGTTGGTTCAAGCTTTGCGTATG
CTTTAACAATAGACAATTCACTTGTACATGAACTTGTAATTATTGATGTTAATGAAAATAAAGC
AAAAGGGGAGGTCATGGACCTTAATCATGGCCAAATGTTTTTAAAGAAGAATATTAATGTATTG
TTTGGGACTTACAAAGATTGTGCTAATGCAGATATTGTTGTAATTACAGCAGGACTTAATCAAA
AGCCTGGTGAGACAAGACTTGATTTGGTTGATAAAAATTCTAAAATTTTTAAAGATATTATAAC
TAATGTTGTATCTAGCGGTTTTGATGGTATTTTTGTTGTTGCAAGCAATCCTGTAGACATTATGA
CTTATGTTACAATGAAATATTCCAAATTTCCTATTCATAAGGTTATTGGTACTGGGACTATTCTT
GATACTTCAAGACTTAGATATTTTTTAAGTGATCATTTTAATGTGAACACTCAAAATATACATTC
ATATATTATGGGTGAGCACGTGACAGTTCTTTTGCTACGTGGGATGAAACAAAAATAGCAATGA
AGCCTTTGTCAGAATATCTTGCTGAAGGCAAAATAACTGAGTTGGAGCTTGATGAAATTCATAA
AAAGGTTGTGAATGCTGCTTATGAAGTTATTAAGTTAAAGGGGGCAACCTATTATGCTATTGGA
CTTGGTATTAAGAATATTGTAAATGCAATAATTGGAGATCAGAATGTTATTCTGCCAATATCTT
CTTATATTAATGGCCAGTATGGGGGATTGATTAAAGATATTTATATTGGAGCGCCTGCTATAGT
TTGTAAGGAAGGAGTCAAAGAAGTTTTAAACTTTAAGATAAGCCCTAAAGAGCTTGATAAGTTT
AATAGTTCTGCTAATCAGCTTAAAAGCTATATTGATAAAATGGAATTTTAG t874.nt (SEQ ID NO:564)
GCTTTAACAATAGACAATTCACTTGTACATGAACTTGTAATTATTGATGTTAATGAAAATAAAG
CAAAAGGGGAGGTCATGGACCTTAATCATGGCCAAATGTTTTTAAAGAAGAATATTAATGTATT
GTTTGGGACTTACAAAGATTGTGCTAATGCAGATATTGTTGTAATTACAGCAGGACTTAATCAA
AAGCCTGGTGAGACAAGACTTGATTTGGTTGATAAAAATTCTAAAATTTTTAAAGATATTATAA
CTAATGTTGTATCTAGCGGTTTTGATGGTATTTTTGTTGTTGCAAGCAATCCTGTAGACATTATG
ACTTATGTTACAATGAAATATTCCAAATTTCCTATTCATAAGGTTATTGGTACTGGGACTATTCT
TGATACTTCAAGACTTAGATATTTTTTAAGTGATCATTTTAATGTGAACACTCAAAATATACATT

TABLE 1-continued

Nucleotide and Amino Acid Sequences.

CATATATTATGGGTGAGCACGTGACAGTTCTTTTGCTACGTGGGATGAAACAAAAATAGCAATG
AAGCCTTTGTCAGAATATCTTGCTGAAGGCAAAATAACTGAGTTGGAGCTTGATGAATTCATA
AAAAGGTTGTGAATGCTGCTTATGAAGTTATTAAGTTAAAGGGGGCAACCTATTATGCTATTGG
ACTTGGTATTAAGAATATTGTAAATGCAATAATTGGAGATCAGAATGTTATTCTGCCAATATCT
TCTTATATTAATGGCCAGTATGGGGGATTGATTAAAGATATTTATATTGGAGCGCCTGCTATAG
TTTGTAAGGAAGGAGTCAAAGAAGTTTTAAACTTTAAGATAAGCCCTAAAGAGCTTGATAAGTT
TAATAGTTCTGCTAATCAGCTTAAAAGCTATATTGATAAAATGGAATTTTAG f886.aa (SEQ ID NO:565)
MKKKQLILLLFMPQIIYAKSYFASDVFFNKYQKLNEKPKTGFYIEYYSVDDTEKLYLYKENNLIKYK
TIQIIENTKKITCYDTKDTKRKEEIYDNLNNKIQEIEYDSKGKTLETANYVYENENLISKNLKTINQKP
KLIYYSKDDNGKLLKITGSNFQIWNYGINGDIKSTYFDIKKATTKVIKYDDKKRNSNSTIIVNNKIKS
KEKNQYLDEEKIVNTFEEENTKIISTYKANNLIKEETYKNNELIKVNDFQYNESDMIIFQNTKEKDKD
QYTNTKIEYEYNKDNQLKSKKIYENDIIYLKTEYHNDNEYEEEIYYKKPALRVKHKNGKVTEEKPI
GTN t886.aa (SEQ ID NO:566)
SYFASDVFFNKYQKLNEKPKTGFYIEYYSVDDTEKLYLYKENNLIKYKTIQIIENTKKITCYDTKDTK
RKEEIYDNLNNKIQEIEYDSKGKTLETANYVYENENLISKNLKTINQKPKLIYYSKDDNGKLLKITGS
NFQIWNYGINGDIKSTYFDIKKATTKVIKYDDKKRNSNSTIIVNNKIKSKEKNQYLDEEKIVNTFEEE
NTKIISTYKANNLIKEETYKNNELIKVNDFQYNESDMIIFQNTKEKDKDQYTNTKIEYEYNKDNQLK
SKKIYENDIIYLKTEYHNDNEYEEEIYYNKKPALRVKHKNGKVTEEKPIGTN f886.nt (SEQ ID NO:567)
ATGAAAAAAAAACAATTAATACTTCTTCTATTTATGCCACAAATTATTTATGCAAAAAGCTATT
TTGCATCTGATGTATTTTTCAATAAATACCAAAAATTAAATGAAAAACCAAAAACGGGGTTTTA
TATTGAGTATTATTCTGTTGATGATACTGAAAAACTCTACCTATACAAAGAAAATAACTTAATA
AAATACAAAACAATTCAAATCATAGAAAACACAAAAAAAATTACATGTTATGATACAAAAGAT
ACAAAAAGAAAAGAAGAGATTTACGATAATTTAAATAACAAAATACAAGAAATTGAATATGAT
AGCAAAGGAAAAACTCTTGAAACAGCAAATTACGTTTATGAAAACGAAAACTTAATATCTAAA
AATTTAAAAACAATAAACCAAAAACCAAAATTAATATATTATTCTAAAGACGACAATGGTAAAT
TACTAAAAATAACAGGATCAAATTTCCAAATTTGGAACTATGGAATTAATGGCGACATAAAATC
TACATATTTTGACATCAAAAAAGCAACAACAAAAGTTATAAAATATGATGATAAAAAAGAAA
TTCAAACAGTACAATAATTGTTAATAATAAATAAATCCAAAGAAAAAACCAATATTTAGAT
GAAGAAAAAATAGTAAATACCTTTGAAGAAGAGAATACAAAAATCATATCTACCTACAAGGCA
AACAACCTAATTAAAGAAGAAACATATAAAAATAATGAACTTATAAAAGTAAATGATTTTCAAT
ACAACGAATCTGATATGATAATTTTTCAAAACACTAAAGAAAGGATAAAGACCAATACACCA
ATACTAAAATTGAATACGAATATAACAAAGACAATCAATTAAAAAGCAAAAAAATTTATGAGA
ACGATATAATTTATCTAAAAACTGAATACCACAATGACAATGAATATGAAGAAGAAATATACTA
CAATAAAAAACCTGCTCTTAGGGTAAAACACAAGAACGGAAAAGTCACCGAAGAAAAACCAAT
AGGAACAAATTAA t886.nt (SEQ ID NO:568)
AGCTATTTTGCATCTGATGTATTTTTCAATAAATACCAAAAATTAAATGAAAAACCAAAAACGG
GGTTTTATATTGAGTATTATTCTGTTGATGATACTGAAAAACTCTACCTATACAAAGAAAATAA
CTTAATAAAATACAAAACAATTCAAATCATAGAAAACACAAAAAAAATTACATGTTATGATACA
AAAGATACAAAAAGAAAAGAAGAGATTTACGATAATTTAAATAACAAAATACAAGAAATTGAA
TATGATAGCAAAGGAAAAACTCTTGAAACAGCAAATTACGTTTATGAAAACGAAAACTTAATA
TCTAAAAATTTAAAAACAATAAACCAAAAACCAAAATTAATATATTATTCTAAAGACGACAATG
GTAAATTACTAAAAATAACAGGATCAAATTTCCAAATTTGGAACTATGGAATTAATGGCGACAT
AAAATCTACATATTTTGACATCAAAAAAGCAACAACAAAAGTTATAAAATATGATGATAAAAA
AGAAATTCAAACAGTACAATAATTGTTAATAATAAAATAAAATCCAAAGAAAAAACCAATA
TTTAGATGAAGAAAAAATAGTAAATACCTTTGAAGAAGAGAATACAAAAATCATATCTACCTA
CAAGGCAAACAACCTAATTAAAGAAGAAACATATAAAAATAATGAACTTATAAAAGTAAATGA
TTTTCAATACAACGAATCTGATATGATAATTTTTCAAAACACTAAAGAAAGGATAAAGACCAA
TACACCAATACTAAAATTGAATACGAATATAACAAAGACAATCAATTAAAAAGCAAAAAAATT
TATGAGAACGATATAATTTATCTAAAAACTGAATACCACAATGACAATGAATATGAAGAAGAA
ATATACTACAATAAAAAACCTGCTCTTAGGGTAAAACACAAGAACGGAAAAGTCACCGAAGAA
AAACCAATAGGAACAAATTAA f888.aa (SEQ ID NO:569)
MEKLKLKLAIPLLVFTICKIHSQSNIEYNFSYIINTKKENIDLKKGIEKQLDKIYDKITEHIVNNDDKSII
EDIYINQDIIKTELEISKLKKEMDKKKLQNIITAKEKHNTKTKIDELKKNIQNINNKQKKFAEYFNNL
KKLVKVKKIEEQTNISNLNKEFFIREELFFINYIDLKKIENYYLLEISNITPEKIETKKAVFKTSSSVNE
IADHITKYSLKEILGREFLKININVKNNSDAKIYINEKFVSKGIYHDNIFDISKLPNKEIEIQITSANFEN
YSIKRTVKNADSIILDIDLKRTISKKVSIKSNVQSKVFKKGIFMGETPIEIEKPENQDIILLKSKGYKDK
FKLINKEEDQVEIEMIKTNKNRLIDTRDKFYVNLAVFFLSTTGAIFAGTLLNNSEVLYKITGNHFINKR
LTAEDVYMAKAEQMTATFLFGVGITLTTGSFISLITHLVEYIKEANMGE t888.aa (SEQ ID NO:570)
SNIEYNFSYIINTKKENIDLKKGIEKQLDKIYDKITEHIVNNDDKSIIEDIYINQDIIKTELEISKLKKEM
DKKKLQNIITAKEKHNTKTKIDELKKNIQNINNKQKKFAEYFNNLKKLVKVKKIEEQTNISNLNKE
FFIREELFFINYIDLKKIENYYLLEISNITPEKIETKKAVFKTSSSVNEIADHITKYSLKEILGREFLKININ
VKNNSDAKIYINEKFVSKGIYHDNIFDISKLPNKEIEIQITSANFENYSIKRTVKNADSIILDIDLKRTIS
KKVSIKSNVQSKVFKKGIFMGETPIEIEKPENQDIILLKSKGYKDKFKLINKEEDQVEIEMIKTNKNRL
IDTRDKFYVNLAVFFLSTIGAIFAGTLLNNSEVLYKITGNHFINKRLTAEDVYMAKAEQMTATFLFG
VGITLTIGSFISLITHLVEYIKEANMGE

TABLE 1-continued

Nucleotide and Amino Acid Sequences.

f888.nt (SEQ ID NO:571)
ATGGAAAAGCTTAAACTAAAGCTAGCAATACCATTGCTAGTATTTACAATATGCAAAATACATT
CTCAAAGTAATATTGAATACAATTTTTCCTATATCATTAATACAAAAAAAGAAAATATTGACCT
AAAAAAGGGTATTGAAAAACAATTGGACAAAATCTATGATAAAATAACAGAACATATAGTAAA
CAATGATGACAAGAGCATCATTGAAGACATTTATATAAATCAAGATATAATAAAAACAGAACT
TGAAATTAGCAAATTAAAAAAAGAAATGGATAAAAAAAAACTTCAAAACATAATAACCGCAAA
AGAAAAGCATAACACCAAAACCAAAATTGATGAGCTTAAAAAAAATATTCAAATATTAACAA
TAAACAAAAAAAATTTGCAGAATATTTTAACAATTTAAAAAAACTAAAAGTAAAATATAAAA
AATCGAAGAGCAAACAAATATATCAAATTTAAATAAAGAATTTTTTATAAGAGAAGAATTATTT
TTTATTAACTATATTGATCTTAAAAAAATAGAAAATTATTATTTGCTAGAAATTAGCAACATCA
CTCCTGAGAAAATTGAGACTAAAAAAGCGGTATTTAAAACATCATCTTCTGTTAATGAAATTGC
AGATCACATAACAAAATACAGCCTCAAAGAAATATTGGGCAGAGAATTTTTAAAAATCAACATT
AACGTCAAAAATAACTCGGATGCAAAAATCTACATAAATGAAAAATTTGTTTCAAAAGGAATCT
ATCACGATAATATTTTTGACATTTCTAAACTCCCAAACAAAGAAATTGAAATACAAATCACAAG
TGCAAATTTCGAAAACTATTCTATTAAAAGAACGGTAAAAAATGCAGACTCAATAATATTAGAT
ATTGACTTAAAAAGAACAATCTCTAAAAAAGTATCAATTAAAAGCAATGTACAATCTAAAGTTT
TTAAAAAAGGAATATTTATGGGAGAAACCCCAATTGAAATTGAAAAACCAGAAAATCAAGATA
TCATCTTGCTTAAATCTAAAGGATATAAAGATAAATTCAAGTTAATAAATAAAGAAGAAGATCA
AGTAGAAATAGAAATGATAAAAACTAACAAAAATAGACTTATCGACACAAGAGATAAATTTTA
TGTCAATCTGGCCGTCTTTACATTAAGCACAATAGGAGCCATTTTTGCAGGAACATTGCTTAAC
AATTCAGAAGTACTTTATAAAATAACAGGCAATCACTTTATTAACAAAAGATTAACAGCAGAAG
ATGTTTATATGGCAAAAGCGGAACAAATGACTGCAACATTTCTATTTGGAGTAGGAATCACTTT
AACTATTGGAAGCTTTATCTCATTAATAACTCATTTAGTAGAATATATTAAAGAAGCAAATATG
GGAGAATAG t888.nt (SEQ ID NO:572)
AGTAATATTGAATACAATTTTTCCTATATCATTAATACAAAAAAAGAAAATATTGACCTAAAAA
AGGGTATTGAAAAACAATTGGACAAAATCTATGATAAAATAACAGAACATATAGTAAACAATG
ATGACAAGAGCATCATTGAAGACATTTATATAAATCAAGATATAATAAAAACAGAACTTGAAA
TTAGCAAATTAAAAAAAGAAATGGATAAAAAAAAACTTCAAAACATAATAACCGCAAAAGAAA
AGCATAACACCAAAACCAAAATTGATGAGCTTAAAAAAAATATTCAAATATTAACAATAAAC
AAAAAAAATTTGCAGAATATTTTAACAATTTAAAAAAACTAAAAGTAAAATATAAAAAATCG
AAGAGCAAACAAATATATCAAATTTAAATAAAGAATTTTTTATAAGAGAAGAATTATTTTTTAT
TAACTATATTGATCTTAAAAAAATAGAAAATTATTATTTGCTAGAAATTAGCAACATCACTCCT
GAGAAAATTGAGACTAAAAAAGCGGTATTTAAAACATCATCTTCTGTTAATGAAATTGCAGATC
ACATAACAAAATACAGCCTCAAAGAAATATTGGGCAGAGAATTTTTAAAAATCAACATTAACGT
CAAAAATAACTCGGATGCAAAAATCTACATAAATGAAAAATTTGTTTCAAAAGGAATCTATCAC
GATAATATTTTTGACATTTCTAAACTCCCAAACAAAGAAATTGAAATACAAATCACAAGTGCAA
ATTTCGAAAACTATTCTATTAAAAGAACGGTAAAAAATGCAGACTCAATAATATTAGATATTGA
CTTAAAAAGAACAATCTCTAAAAAAGTATCAATTAAAAGCAATGTACAATCTAAAGTTTTTAAA
AAAGGAATATTTATGGGAGAAACCCCAATTGAAATTGAAAAACCAGAAAATCAAGATATCATC
TTGCTTAAATCTAAAGGATATAAAGATAAATTCAAGTTAATAAATAAAGAAGAAGATCAAGTA
GAAATAGAAATGATAAAAACTAACAAAAATAGACTTATCGACACAAGAGATAAATTTTATGTC
AATCTGGCCGTCTTTACATTAAGCACAATAGGAGCCATTTTTGCAGGAACATTGCTTAACAATT
CAGAAGTACTTTATAAAATAACAGGCAATCACTTTATTAACAAAAGATTAACAGCAGAAGATGT
TTATATGGCAAAAGCGGAACAAATGACTGCAACATTTCTATTTGGAGTAGGAATCACTTTAACT
ATTGGAAGCTTTATCTCATTAATAACTCATTTAGTAGAATATATTAAAGAAGCAAATATGGGAG
AATAG f893.aa (SEQ ID NO:573)
MVRFLGFLYLITTIPLIKSCDAAQFGDYKPLYFENENDLKTANEYINSLGYKTISEYTTKIDILDFPEN
KEITINEINKLNNLDLRKSIFLKKLSNLFNIEHKKLLYVENRFKSINFKNLKKELNINADIHSLDYKTKI
NFISSIIFLIIIILLIFLDPTNSIFTLIFLLISSLAFMISKEIMYFYPFTVLSYLLFLIISNFNKNYNKIYLKEINF
LTLMTKIKHLLFLFTFTALYFITITTFFTTNIDPTFIAFVAIPTLCIFLIFSWIKTESNFKDTFLFPIEIKEK
KIEGKKALKSKIAIHLLLFTLSLIPFAYSSYMLNSYENINYLYSKKLNYFDYLNPNNIYIMLGYNKDM
PNIIGYLSHILYQNELKYNITAKYGKIPKDIKENYFEIKNDKIEIHPKTVYEVDKSFIDEILKKDLASLF
LKNKNPILIYKENKNNINTDKKNYKILFFFSLPFFVLLFLFKAIRFTILLNIN
EKTYKKYIQG t893.aa (SEQ ID NO:574)
CDAAQFGDYKPLYFENENDLKTANEYINSLGYKTISEYTTKIDILDFPENKEITINEINKLNNLDLRKS
IFLKKLSNLFNIEHKKLLYVENRFKSINFKNLKKELNINADIHSLDYKTKINFISSIIFLIIIILLIFLDPTNS
IFTLIFLLISSLAFMISKEIMYFYPFTVLSYLLFLIISNFNKNYNKIYLKEINFLTLMTKIKHLLFLFTFTA
LYFITITTFFTTNIDPTFIAFVAIPTLCIFLIFSWIKTESNFKDTFLFPIEIKEKKIEGKKALKSKIAIHLLLF
TLSLIPFAYSSYMLNSYENINYLYSKKLNYFDYLNPNNIYIMLGYNKDMPNIIGYLSHILYQNELKYN
ITAKYGKIPKDIKENYFEIKNDKIEIHPKTVYEVDKSFIDEILKKDLASLFLKNKNPILIYKENKNNINT
DKKNYKILFFFSLPFFVLLFLFKAIRFTILLNLNEKTYKKYIQG f893.nt (SEQ ID NO:575)
ATGGTGCGTTTTTTAGGTTTTTTATATTTAATTACAACAATACCACTTATCAAATCCTGTGATGC
AGCTCAATTTGGAGACTACAAACCTTTATACTTTGAAAATGAAAATGATCTAAAAACTGCCAAT
GAATATATAAATTCACTAGGATACAAACAATCTCAGAATACACAACAAAAATTGACATTTTAG
ACTTTCCCGAAAATAAAGAAATCACAATAAATGAGATAAACAAACTTAACAATCTTGACCTGAG
AAAAAGCATATTTTAAAAAAGCTCTCCAATCTTTTCAACATAGAGCACAAAAAACTTCTTTAT
GTTGAAAACAGGTTTAAAAGTATAAATTTTAAAAACCTAAAAAAAGAACTCAATATTAATGCCG
ACATACATTCTCTTGACTACAAAACAAAAATTAATTTTATTTCAAGCATAATATTTCTAATCATA

TABLE 1-continued

Nucleotide and Amino Acid Sequences.

ATAATTTTATTAATTTTTTAGACCCAACAAACTCTATATTTACTTTAATTTTTCTATTAATTTCA
TCTCTTGCTTTTATGATAAGCAAAGAAATAATGTATTTTTATCCATTTACAGTTCTCTCTTATTT
GTTATTTTTAATAATCAGTAATTTTAACAAAAATTACAATAAAATATATTTAAAAGAAATAAAT
TTTTTAACACTAATGACAAAAATAAAACACTTACTATTTTTATTTACATTCACAGCTCTATATTT
CATTACAATCACAACCTTTTTTACTACAAATATTGATCCCACTTTTATTGCATTTGTCGCAATAC
CAACCCTTTGCATTTTCTTAATTTTCAGCTGGATAAAAACAGAAAGCAATTTTAAAGACACTTTC
TTATTCCCAATCGAGATTAAAGAGAAAAAAATAGAAGGAAAAAAAGCTTTAAAATCAAAAATA
GCAATACATCTACTACTATTTACACTCTCATTAATTCCTTTCGCTTATTCAAGCTATATGCTAAA
TTCTTATGAAAACATTAACTACCTTTACAGTAAAAAATTAAATTACTTTGATTATTTAAATCCTA
ATAACATTTATATAATGCTGGGATACAACAAAGACATGCCCAATATTATAGGGTACCTATCCCA
CATTCTTTATCAAAACGAACTAAAATACAATATTACCGCTAAGTATGGAAAAATTCCTAAAGAT
ATAAAAGAAAATTACTTTGAAATCAAAAACGACAAAATAGAAATTCATCCTAAAACTGTTTACG
AAGTAGACAAATCATTTATTGATGAAATTCTTAAAAAAGATCTTGCAAGTCTGTTTTTAAAAAA
TAAAAATCCAATCCTAATATATAAAGAAAACAAGAATAATATCAACACAGATAAAAAAAATTA
CAAAATACTTTTCTTTTTCTCTTTGCCCTTCTTTGTATTACTATTCCTATTTAAAGCAATAAGATT
TACAATTCTTTTAAACATAAATGAAAAAACCTATAAAAAATATATTCAAGGATAA t893.nt (SEQ ID NO:576)
TGTGATGCAGCTCAATTTGGAGACTACAAACCTTTATACTTTGAAAATGAAAATGATCTAAAAA
CTGCCAATGAATATATAAATTCACTAGGATACAAAACAATCTCAGAATACACAACAAAAATTGA
CATTTTAGACTTTCCCGAAAATAAAGAAATCACAATAAATGAGATAAACAAACTTAACAATCTT
GACCTGAGAAAAAGCATATTTTTAAAAAAGCTCTCCAATCTTTTCAACATAGAGCACAAAAAC
TTCTTTATGTTGAAAACAGGTTTAAAAGTATAAATTTTAAAAACCTAAAAAAAGAACTCAATAT
TAATGCCGACATACATTCTCTTGACTACAAAACAAAAATTAATTTTATTTCAAGCATAATATTTC
TAATCATAATAATTTTATTAATTTTTTAGACCCAACAAACTCTATATTTACTTTAATTTTTCTAT
TAATTTCATCTCTTGCTTTTATGATAAGCAAAGAAATAATGTATTTTATCCATTTACAGTTCTC
TCTTATTTGTTATTTTTAATAATCAGTAATTTTAACAAAAATTACAATAAAATATATTTAAAAGA
AATAAATTTTTTAACACTAATGACAAAAATAAAACACTTACTATTTTTATTTACATTCACAGCTC
TATATTTCATTACAATCACAACCTTTTTTACTACAAATATTGATCCCACTTTTATTGCATTTGTCG
CAATACCAACCCTTTGCATTTTCTTAATTTTCAGCTGGATAAAAACAGAAAGCAATTTTAAAGA
CACTTTCTTATTCCCAATCGAGATTAAAGAGAAAAAAATAGAAGGAAAAAAAGCTTTAAAATC
AAAAATAGCAATACATCTACTACTATTTACACTCTCATTAATTCCTTTCGCTTATTCAAGCTATA
TGCTAAATTCTTATGAAAACATTAACTACCTTTACAGTAAAAAATTAAATTACTTTGATTATTTA
AATCCTAATAACATTTATATAATGCTGGGATACAACAAAGACATGCCCAATATTATAGGGTACC
TATCCCACATTCTTTATCAAAACGAACTAAAATACAATATTACCGCTAAGTATGGAAAAATTCC
TAAAGATATAAAAGAAAATTACTTTGAAATCAAAAACGACAAAATAGAAATTCATCCTAAAAC
TGTTTACGAAGTAGACAAATCATTTATTGATGAAATTCTTAAAAAAGATCTTGCAAGTCTGTTT
TTAAAAAATAAAAATCCAATCCTAATATATAAAGAAAACAAGAATAATATCAACACAGATAAA
AAAAATTACAAAATACTTTTCTTTTTCTCTTTGCCCTTCTTTGTATTACTATTCCTATTTAAAGCA
ATAAGATTTACAATTCTTTTAAACATAAATGAAAAAACCTATAAAAAATATATTCAAGGATAA f895.aa (SEQ ID NO:577)
MIRALLTNDLFLSCLVSGISAQVIKYGIQTVKTRKLKLTPVHLLKKIFLETGGMPSSHSSTVTALSTSI
ALTEGIDTNFIIALAFALITIRDSFGVRYMSGVQAEYLNALSEKLKKEIKIDTTKIKVVKGHKKKEVLT
GIIIGIVSAYIVCYF t895.aa (SEQ ID NO:578)
AQVIKYGIQTVKTRKLKLTPVHLLKKIFLETGGMPSSHSSTVTALSTSIALTEGIDTNFIIALAFALITIR
DSFGVRYMSGVQAEYLNALSEKLKKEIKIDTTKIKVVKGHKKKEVLTGIIIGIVSAYIVCYF f895.nt (SEQ ID NO:579)
ATGATAAGGGCATTGCTTACCAATGATCTTTTTTTGTCTTGTCTTGTATCAGGAATTTCTGCTCA
AGTGATTAAATATGGTATCCAAACTGTAAAAACAAGAAAGTTAAAACTAACTCCAGTACATCTT
TTAAAAAAAATTTTTCTAGAAACAGGAGGCATGCCAAGTAGTCATTCATCAACGGTCACCGCTC
TTTCAACCTCAATCGCACTAACTGAAGGAATAGATACAAATTTTATAATAGCTCTTGCATTTGC
CCTTATTACAATAAGAGATTCTTTCGGCGTAAGATATATGTCTGGAGTTCAAGCAGAATATTTA
AATGCATTATCAGAAAAATTAAAAAAAGAAATAAAAATTGACACAACAAAAATAAAAGTGGTC
AAGGGGCACAAAAAGAAGAGGTTCTAACGGGCATAATAATAGGAATAGTCTCTGCGTATATT
GTGTGCTATTTTTAG t895.nt (SEQ ID NO:580)
GCTCAAGTGATTAAATATGGTATCCAAACTGTAAAAACAAGAAAGTTAAAACTAACTC
CAGTACATCTTTTAAAAAAAATTTTTCTAGAAACAGGAGGCATGCCAAGTAGTCATTCATCAAC
GGTCACCGCTCTTTCAACCTCAATCGCACTAACTGAAGGAATAGATACAAATTTTATAATAGCT
CTTGCATTTGCCCTTATTACAATAAGAGATTCTTTCGGCGTAAGATATATGTCTGGAGTTCAAGC
AGAATATTTAAATGCATTATCAGAAAAATTAAAAAAAGAAATAAAAATTGACACAACAAAAAT
AAAAGTGGTCAAGGGGCACAAAAAGAAGAGGTTCTAACGGGCATAATAATAGGAATAGTCTC
TGCGTATATTGTGTGCTATTTTTAG f605.aa (SEQ ID NO:581)
MYIGAAGKSFSIIIDSAFLSNCFLFIGSFSRSDSLMSLSNSRFEYPYDASCEFSLVNIVKYVCGSKYSPM
RPTLIISKLPVFLLLVRTGQFSLVSIRLIFRIFFHWF t605.aa (SEQ ID NO:582)
CFLFIGSFSRSDSLMSLSNSRFEYPYDASCEFSLVNIVKYVCGSKYSPMRPTLIISKLPVFLLL
VRTGQFSLVSIRLIFRIFFHWF

TABLE 1-continued

Nucleotide and Amino Acid Sequences.

f605.nt (SEQ ID NO:583)
ATGTATATTGGTGCAGCAGGAAAATCTTTTTCAATTATTATTGATTCTGCTTTTCTGAGT
AATTGTTTTCTTTTTATAGGATCTTTTTCAAGATCTGATTCTCTGATGAGTTTGTCAAATTCTAG
GTTTGAATATCCGTATGATGCAAGTTGTGAATTTTCTCTTGTGAATATAGTAAAGTATGTGTGT
GGATCTAAATATTCCCCAATGCGTCCAACTCTTATTATTTCAAAATTGCCAGTATTTCTGCTGTT
GGTAAGAACAGGCCAATTTTCGTTGGTAAGCATAAGATTGATATTTAGAATTTTTTTCCATTGG
TTTTGA t605.nt (SEQ ID NO:584)
TGTTTTCTTTTTATAGGATCTTTTTCAAGATCTGATTCTCTGATGAGTTTGTCAAATTCT
AGGTTTGAATATCCGTATGATGCAAGTTGTGAATTTTCTCTTGTGAATATAGTAAAGTATGTGT
GTGGATCTAAATATTCCCCAATGCGTCCAACTCTTATTATTTCAAAATTGCCAGTATTTCTGCTG
TTGGTAAGAACAGGCCAATTTTCGTTGGTAAGCATAAGATTGATATTTAGAATTTTTTTCCATTG
GTTTTGA f606.aa (SEQ ID NO:585)
MKLQRSLFLIIFFLTFLCCNNKERKEGVSFKISLGAEPSSLDPQLAEDNVASKMIDTMFRGIV
TGDPNTGGNKPGLAKGWDISSDGTVYTFNLREKITWSDGVAITAEGIRKSYLRILNKETGSKYVEM
VKSVIKNGQKYFDGQVTDSELGIRAIDEKTLEITLESPKPYFIDMLVHQSFIPVPVHVTEKYGQNWTS
PENMVTSGPFKLKERIPNEKYVFEKNNKYYDSNEVELEEITFYTTNDSSTAYKMYENEELDAIFGSIP
PDLIKNLKLRSDYYSSAVNAIYFYAFNTHIKPLDNVKIRKALTLAIDRETLTYKVLDNGTTPTRRATP
NFSSYSYAKSLELFNPEIAKTLLAEAGYPNGNGFPILKLKYNTNEANKKICEFIQNQWKKNLNIDVEL
ENEEWTTYLNTKANGNYEIARAGWIGDYADPLTFLSIFTQGYTQFSSHNYSNPEYNELIKKSDLELD
PIKRQDILRQAEEIIIEKDFPIAPIYIYGNSYLFRNDKWTGWNTNILERFDLSQLKLKNK t606.aa (SEQ ID NO:586)
CCNNKERKEGVSFKISLGAEPSSLDPQLAEDNVASKMIDTMFRGIVTGDPNTGGNKPGLAK
GWDISSDGTVYTFNLREKITWSDGVAITAEGIRKSYLRILNKETGSKYVEMVKSVIKNGQKYFDGQ
VTDSELGIRAIDEKTLEITLESPKPYFIDMLVHQSFIPVPVHVTEKYGQNWTSPENMVTSGPFKLKERI
PNEKYVFEKNNKYYDSNEVELEEITFYTTNDSSTAYKMYENEELDAIFGSIPPDLIKNLKLRSDYYSS
AVNAIYFYAFNTHIKPLDNVKIRKALTLAIDRETLTYKVLDNGTTPTRRATPNFSSYSYAKSLELFNP
EIAKTLLAEAGYPNGNGFPILKLKYNTNEANKKICEFIQNQWKKNLNIDVELENEEWTTYLNTKAN
GNYEIARAGWIGDYADPLTFLSIFTQGYTQFSSHNYSNPEYNELIKKSDLELDPIKRQDILRQAEEIIIE
KDFPIAPIYIYGNSYLFRNDKWTGWNTNILERFDLSQLKLKNK f606.nt (SEQ ID NO:587)
ATGAAATTACAAAGGTCATTATTTTTAATAATATTTTTTCTAACTTTTCTTTGTTGTAAT
AACAAGGAAAGAAAAGAAGGAGTATCATTTAAAATAAGCTTGGGAGCAGAGCCAAGCAGTCTT
GACCCTCAATTAGCAGAGGATAATGTCGCATCAAAAATGATTGACACAATGTTTAGAGGGATTG
TTACAGGAGATCCTAATACAGGGGGAAATAAACCGGGACTTGCAAAAGGGTGGGATATTTCTT
CTGATGGAACAGTTTACACATTTAACCTAAGAGAAAAAATCACTTGGAGTGACGGAGTTGCAAT
CACTGCAGAAGGAATTAGAAAATCTTATCTTAGAATTTTAAATAAAGAAACTGGCTCAAAGTAC
GTTGAAATGGTTAAATCGGTAATTAAAAATGGTCAAAAATATTTTTGATGGACAAGTGACTGACT
CTGAACTTGGAATTAGAGCGATTGATGAAAAAACATTAGAAATAACACTGGAATCACCAAAAC
CTTATTTTATTGATATGTTAGTACACCAATCATTTATTCCAGTACCAGTTCATGTTACCGAAAAG
TATGGACAAAACTGGACAAGCCCCGAAAACATGGTGACAAGTGGTCCTTTTAAATTAAAAGAA
AGAATTCCTAACGAAAAATATGTCTTTGAAAAAAAATAACAAATACTACGACTCAAATGAAGTA
GAATTAGAAGAGATTACATTTTACACAACAAATGACAGCTCAACAGCGTATAAAATGTATGAA
AATGAAGAGCTAGATGCAATTTTTGGTTCCATACCCCCAGATCTAATCAAAAATCTAAAATTAA
GAAGCGACTATTACTCATCAGCTGTTAATGCCATATACTTTTACGCGTTCAATACACACATCAA
ACCACTTGACAACGTTAAAATTAGAAAAGCCTTAACTCTTGCTATTGACAGAGAAACGCTTACA
TATAAAGTTCTTGACAACGGGACTACCCCTACAAGAAGAGCAACTCCCAACTTTAGTTCATATT
CTTATGCAAAAAGTTTAGAATTATTTAATCCTGAAATTGCAAAAACCCTTCTAGCTGAAGCTGG
ATATCCTAATGGCAATGGATTTCCAATTTTAAAATTAAAATACAATACAAACGAAGCAAATAAA
AAAATTTGTGAATTTATTCAAAACCAATGGAAAAAAAAATTTAAATATTGATGTGGAACTTGAAA
ACGAAGAATGGACAACATACTTAAACACTAAGGCAAATGGAAATAGCAAGAGCAG
GATGGATAGGCGATTATGCTGATCCTTTGACATTTTTAAGCATATTCACACAAGGATACACACA
ATTCTCATCTCATAATTACTCAAACCCAGAATACAACGAACTTATAAAGAAATCCGACCTTGAG
CTTGATCCAATAAAAAGACAAGACATTTTAAGACAAGCAGAAGAGATAATTATTGAAAAAGAT
TTTCCAATAGCACCAATATACATATATGGGAACAGTTACCTTTTCAGAAATGACAAATGGACAG
GGTGGAACACCAATATTTTAGAAAGATTTGATTTATCTCAGCTAAAATTAAAAAATAAATAA t606.nt (SEQ ID NO:588)
TGTTGTAATAACAAGGAAAGAAAAGAAGGAGTATCATTTAAAATAAGCTTGGGAGCAG
AGCCAAGCAGTCTTGACCCTCAATTAGCAGAGGATAATGTCGCATCAAAAATGATTGACACAAT
GTTTAGAGGGATTGTTACAGGAGATCCTAATACAGGGGGAAATAAACCGGGACTTGCAAAAGG
GTGGGATATTTCTTCTGATGGAACAGTTTACACATTTAACCTAAGAGAAAAAATCACTTGGAGT
GACGGAGTTGCAATCACTGCAGAAGGAATTAGAAAATCTTATCTTAGAATTTTAAATAAAGAA
ACTGGCTCAAAGTACGTTGAAATGGTTAAATCGGTAATTAAAAATGGTCAAAAATATTTTTGATG
GACAAGTGACTGACTCTGAACTTGGAATTAGAGCGATTGATGAAAAAACATTAGAAATAACAC
TGGAATCACCAAAACCTTATTTTATTGATATGTTAGTACACCAATCATTTATTCCAGTACCAGTT
CATGTTACCGAAAAGTATGGACAAAACTGGACAAGCCCCGAAAACATGGTGACAAGTGGTCCT
TTTAAATTAAAAGAAAGAATTCCTAACGAAAAATATGTCTTTGAAAAAAAATAACAAATACTACG
ACTCAAATGAAGTAGAATTAGAAGAGATTACATTTTACACAACAAATGACAGCTCAACAGCGT
ATAAAATGTATGAAAATGAAGAGCTAGATGCAATTTTTGGTTCCATACCCCCAGATCTAATCAA
AAATCTAAAATTAAGAAGCGACTATTACTCATCAGCTGTTAATGCCATATACTTTTACGCGTTC
AATACACACATCAAACCACTTGACAACGTTAAAATTAGAAAAGCCTTAACTCTTGCTATTGACA

TABLE 1-continued

Nucleotide and Amino Acid Sequences.

GAGAAACGCTTACATATAAAGTTCTTGACAACGGGACTACCCCTACAAGAAGAGCAACTCCCA
ACTTTAGTTCATATTCTTATGCAAAAAGTTTAGAATTATTTAATCCTGAAATTGCAAAAACCCTT
CTAGCTGAAGCTGGATATCCTAATGGCAATCGATTTCCAATTTTAAAATTAAAATACAATACAA
ACGAAGCAAATAAAAAAATTTGTGAATTTATTCAAAACCAATGGAAAAAAAATTTAAATATTG
ATGTGGAACTTGAAAACGAAGAATGGACAACATACTTAAACACTAAGGCAAATGGAAATTATG
AAATAGCAAGAGCAGGATGGATAGGCGATTATGCTGATCCTTTGACATTTTTAAGCATATTCAC
ACAAGGATACACACAATTCTCATCTCATAATTACTCAAACCCAGAATACAACGAACTTATAAAG
AAATCCGACCTTGAGCTTGATCCAATAAAAAGACAAGACATTTTAAGACAAGCAGAAGAGATA
ATTATTGAAAAAGATTTTCCAATAGCACCAATATACATATATGGGAACAGTTACCTTTTCAGAA
ATGACAAATGGACAGGGTGGAACACCAATATTTTAGAAAGATTTGATTTATCTCAGCTAAAATT
AAAAAATAAATAA f679.aa (SEQ ID NO:589)
MFNRSSCVLQNFLFLFLFLSLVSCFAKKEISGNNFIKAHSKEFDLNNLNWLWNFDYTKKNF
DKHFNIDPSSYIYVAYLFKKIGFEEKFVEYMKKAIANGDSIASQFAGIKLIEYFNSAKEYFASELIGEK
LYKKYENNKFIILGYFKSLYWQKKNDKALSLLNKLDKMKFSDYQENENILLKAVLYLNLSNVSESK
IYFNELFENLPANYLHVRAYDYFIIENKSRYFGANFLNLVRFKYEVANGNFNGAINILNKNGLNDYY
DNNIVLSDVYKAFISSGKVSNALTFFSKIKSKYKNYYLGILNLREKNNLGLLLLKEYLEGLDLNNEIN
RLDLLNTAFSNLIFTKSARDYFAESLPKFYTEGDKKNSTFIKILEEYILESIQLEDYGNLYKLYSNAQK
VISNSVLSKLAFINARLIYHKLIKPNVSGEYKSLLHSAVNYDKWSYSSFMSRYLLDQNIDEFFTGGSDI
KYEQSDYEIFLEGFLKFNLCNYVRGFISEDFRNGYKFSLDFYRKVYDELLKSENYYDATLVINYLVN
QDESALMENDYKRLYPYLYGSLIEYWAKRRGLEASVVFSLIKAESSFEKNAVSKPGAVGLMQYMPS
TANDISKELKYFNYDLKIPKDNIIIGTYYLKKRISTTGSLYKALASYNGGIGNVRKWEKSYGHLSKEL
FIEAIPFSQTRNYIKKILVYSVFYDALYEKKGIDSVIVKIMGEFPKN t679.aa (SEQ ID NO:590)
CFAKKEISGNNFIKAHSKEFDLNNLNWLWNFDYTKKNFDKHFNIDPSSYIYVAYLFKKIGFE
EKFVEYMKKAIANGDSIASQFAGIKLIEYFNSAKEYFASELIGEKLYKKYENNKFIILGYFKSLYWQK
KNDKALSLLNKLDKMKFSDYQENENILLKAVLYLNLSNVSESKIYFNELFENLPANYLHVRAYDYFI
IENKSRYFGANFLNLVRFKYEVANGNFNGAINILNKNGLNDYYDNNIVLSDVYKAFISSGKVSNALT
FFSKIKSKYYNYYLGILNLREKNNLGLLLLKEYLEGLDLNNEINRLDLLNTAFSNLIFTKSARDYFAE
SLPKFYTEGDKKNSTFIKILEEYILESIQLEDYGNLYKLYSNAQKVISNSVLSKLAFINARLIYHKLIKP
NVSGEYKSLLHSAVNYDKWSYSSFMSRYLLDQNIDEFFTGGSDIKYEQSDYEIFLEGFLKFNLCNYV
RGFISEDFRNGYKFSLDFYRKVYDELLKSENYYDATLVINYLVNQDESALMENDYKRLYPYLYGSLI
EYWAKRRGLEASVVFSLIKAESSFEKNAVSKPGAVGLMQVMPSTANDISKELKYFNYDLKIPKDNIII
GTYYLKKRISTTGSLYKALASYNGGIGNVRKWEKSYGHLSKELFIEAIPFSQTRNYIKKILVYSVFYD
ALYEKKGIDSVIVKIMGEFPKN f679.nt (SEQ ID NO:591)
ATGTTTAATAGAAGTTCTTGTGTATTACAAAATTTTCTTTTTCTTTTTTTATTTTTAAGTTTAGTT
TCTTGCTTTGCAAAAAAGAAATCTCAGGCAATAATTTTATTAAGGCGCATTCAAAAGAGTTTG
ATTTAAATAATTTAAATTGGTTATGGAATTTTGATTATACAAAAAAAAATTTTGATAAGCATTTT
AACATAGATCCAAGTTCTTACATATATGTTGCTTATTTATTTAAAAAAATAGGATTTGAAGAGA
AATTTGTAGAGTATATGAAAAAGGCCATAGCTAATGGAGATAGCATTGCATCCCAGTTTGCTGG
GATTAAGCTTATTGAATATTTTAACTCAGCAAAAGAGTATTTTGCATCTGAATTGATTGGAGAG
AAGCTTTATAAAAATACGAAAATAATAAATTTATTATACTGGGGTACTTTAAAAGTCTTTATT
GGCAAAAGAAAAACGATAAGGCACTTAGTCTTTTAAATAAGCTTGATAAGATGAAATTTTCTGA
TTATCAGGAAAATGAAAATATTTTATTAAAAGCAGTTCTTTACCTTAATCTTTCTAATGTAAGTG
AGTCAAAAATTTATTTTAATGAGCTTTTTGAGAACTTACCTGCAAATTATTTACATGTAAGAGCT
TATGATTATTTTATTATTGAAAATAAGCTCTAGGTATTTTGGTGCAAATTTTTTAAATCTTGTTAG
ATTTAAGTATGAAGTGGCAAATGGCAATTTTAATGGTGCAATAAATATATTAAATAAAAATGGT
TTAAATGATTATTATGACAATAACATTGTATTAAGTGATGTTTATAAGGCTTTTATTAGTTCTGG
CAAAGTTTCAAATGCTTTAACATTTTTTAGTAAAATAAAGAGCAAATATAAAAATTATTATTTA
GGTATTCTAAACCTTAGAGAGAAAATAATTTAGGACTTCTTCTTTTAAAAGAATATCTTGAAG
GTTTAGATCTTAACAATGAGATTAACAGGCTTGATTTGCTTAATACTGCTTTTAGCAATTTAATT
TTTACTAAGAGCGCAAGGGATTATTTTGCCGAAAGTTTACCCAAGTTTTATACCGAGGGCGATA
AAAAAAAATTCTACTTTTATTAAGATTTTAGAAGAGTATATTTTGGAATCAATTCAGCTTGAAGA
CTATGGCAATCTTTATAAGCTTTATTCTAATGCTCAAAAAGTTATTTCTAATTCTGTTTTGTCTA
AGCTTGCTTTTATTAATGCAAGGCTTATATATCATAAATTAATTAAACCTAACGTAAGCGGAGA
ATACAAGAGTCTTTTGCATTCTGCTGTTAATTATGATAAATGGTCTTATTCTTCATTTATGAGTA
GGTACTTATTAGATCAAAATATTGATGAATTTTTTACAGGTGGGTCTGATATTAAGTATGAGCA
ATCCGATTATGAGATTTTTTTGGAAGGGTTTTTAAAATTCAATCTTTGTAATTATGTTAGAGGGT
TTATTTCTGAGGATTTTAGGAATGGATATAAATTTTCACTTGATTTTATCGAAAAGTATACGAT
GAACTTTTAAAGAGTGAAAATTATTACGATGCAACTCTTGTGATTAATTATCTTGTAAATCAAG
ATGAATCTGCTTTAATGGAGAATGACTATAAAAGACTTTATCCTTATTTGTATGGATCTTTGATA
GAATATTGGGCTAAAAGGAGAGGGCTTGAAGCTAGTGTTGTATTTTCTTTAATAAAAGCAGAG
AGTAGCTTTGAAAAAAATGCTGTCTCAAAACCGGGTGCTGTTGGCCTTATGCAGGTTATGCCAT
CAACAGCAAATGATATTTCTAAAGAACTTAAGTATTTTAACTATGATTTAAAGATTCCAAAAGA
TAATATAATAATTGGAACATATTATTTAAAAAAAAGAATATCTACAACTGGCAGTCTTTATAAG
GCTCTTGCGTCTTATAATGGGGGTATTGGTAATGTTAGAAAGTGGGAGAAAAGTTATGGACATT
TGTCAAAAGAGCTTTTTATTGAGGCAATTCCCTTTAGTCAAACTAGGAATTATATTAAAAAAAT
ATTAGTTTATTCGGTATTTTATGATGCTTTGTATGAAAGAAGGGAATAGATTCAGTAATAGTT
AAAATTATGGGCGAATTCCCCAAAAATTAA t679.nt (SEQ ID NO:592)
TGCTTTGCAAAAAAGAAATCTCAGGCAATAATTTTATTAAGGCGCATTCAAAAGAGTTTGATT
TAAATAATTTAAATTGGTTATGGAATTTTGATTATACAAAAAAAAATTTTGATAAGCATTTTAA

TABLE 1-continued

Nucleotide and Amino Acid Sequences.

```
CATAGATCCAAGTTCTTACATATATGTTGCTTATTTATTTAAAAAAATAGGATTTGAAGAGAAA
TTTGTAGAGTATATGAAAAAGGCCATAGCTAATGGAGATAGCATTGCATCCCAGTTTGCTGGGA
TTAAGCTTATTGAATATTTTAACTCAGCAAAAGAGTATTTTGCATCTGAATTGATTGGAGAGAA
GCTTTATAAAAAATACGAAAATAATAAATTTATTATACTGGGGTACTTTAAAAGTCTTTATTGG
CAAAAGAAAAACGATAAGGCACTTAGTCTTTTAAATAAGCTTGATAAGATGAAATTTTCTGATT
ATCAGGAAAATGAAAATATTTTATTAAAAGCAGTTCTTTACCTTAATCTTTCTAATGTAAGTGA
GTCAAAAATTTATTTTAATGAGCTTTTTGAGAACTTACCTGCAAATTATTTACATGTAAGAGCTT
ATGATTATTTTATTATTGAAAATAAGTCTAGGTATTTTGGTGCAAATTTTTTAAATCTTGTTAGA
TTTAAGTATGAAGTGGCAAATGGCAATTTTAATGGTGCAATAAATATATTAAATAAAAATGGTT
TAAATGATTATTATGACAATAACATTGTATTAAGTGATGTTTATAAGGCTTTTATTAGTTCTGGC
AAAGTTTCAAATGCTTTAACATTTTTTAGTAAAATAAAGAGCAAATATAAAAATTATTATTTAG
GTATTCTAAACCTTAGAGAGAAAAATAATTTAGGACTTCTTCTTTTAAAAGAATATCTTGAAGG
TTTAGATCTTAACAATGAGATTAACAGGCTTGATTTGCTTAATACTGCTTTTAGCAATTTAATTT
TTACTAAGAGCGCAAGGGATTATTTTGCCGAAAGTTTACCCAAGTTTTATACCGAGGGCGATAA
AAAAAATTCTACTTTTATTAAGATTTTAGAAGAGTATATTTTGGAATCAATTCAGCTTGAAGAC
TATGGCAATCTTTATAAGCTTTATTCTAATGCTCAAAAAGTTATTTCTAATTCTGTTTTGTCTAA
GCTTGCTTTTATTAATGCAAGGCTTATATATCATAAATTAATTAAACCTAACGTAAGCGGAGAA
TACAAGAGTCTTTTGCATTCTGCTGTTAATTATGATAAATGTCTTATTCTTCATTTATGAGTAG
GTACTTATTAGATCAAAATATTGATGAATTTTTTACAGGTGGGTCTGATATTAAGTATGAGCAA
TCCGATTATGAGATTTTTTTGGAAGGGTTTTTAAAATTCAATCTTTGTAATTATGTTAGAGGGTT
TATTTCTGAGGATTTTAGGAATGGATATAAATTTTCACTTGATTTTTATCGAAAAGTATACGATG
AACTTTTAAAGAGTGAAAATTATTACGATGCAACTCTTGTGATTAATTATCTTGTAAATCAAGA
TGAATCTGCTTTTAATGGAGAATGACTATAAAAGACTTTATCCTTATTTGTATGGATCTTTGATAG
AATATTGGGCTAAAAGGAGAGGGCTTGAAGCTAGTGTTGTATTTTCTTTAATAAAAGCAGAGA
GTAGCTTTGAAAAAAATGCTGTCTCAAAACCGGGTGCTGTTGGCCTTATGCAGGTTATGCCATC
AACAGCAAATGATATTTCTAAAGAACTTAAGTATTTTAACTATGATTTAAAGATTCCAAAAGAT
AATATAATAATTGGAACATATTATTTAAAAAAAAGAATATCTACAACTGGCAGTCTTTATAAGG
CTCTTGCGTCTTATAATGGGGGTATTGGTAATGTTAGAAAGTGGGAGAAAAGTTATGGACATTT
GTCAAAAGAGCTTTTTATTGAGGCAATTCCCTTTAGTCAAACTAGGAATTATATTAAAAAAATA
TTAGTTTATTCGGTATTTTATGATGCTTTGTATGAAAAGAAGGGAATAGATTCAGTAATAGTTA
AAATTATGGGCGAATTCCCCAAAAATTAA f11-12.nt (SEQ ID NO:593)
TAAAAGGAGAATATTTTTATGAGAAAAAGTTTGTTTTTATATGCATTATTAATGGGAGGATTGA
TGTCTTGTAATCTAGATTCCAAATTATCTAGTAACAAAGAACAAAAAAATAACAATAATGTAAA
AGAAGTTTCGGATAGTGTTCAAGAAGATGGTCTTAATGATTTATATAATAATCAAGAAAAGCAA
AAAAGCTTTACTAAAAATTTTGGAGAACGGAAATATGAGGATTTAATTAATCCTATAGAGCCTA
TAATACCTTCAGAATCACCAAAGAATAAGGCTAATATACCAAATATTTCAATTGCGCATACTGA
AAAAAAAGAGACAAAAAAGGAGAATTTAATCCCTTCTACTAATGAAGAAAAGGAAGCTGATGC
AGCAATTAAATATTTAGAAGAAAATATTCTTAAAAACTCTAAATTTTCTGAATTAATTAGAGAAG
GTACGTGTAATTAAAGATGAATATGCTTTAATAAAAGCTGATTTGTATGATGTAATTGGAAAGA
TTAACAATAAAAAAACATCATTAATGGAGAATCCTAAGAACAATAGAGATAAGATAAATAAAT
TAACACAATTGTTGCAAAATAATTTAAAGATAGATAGTGAACTTGAGCAGCTTATAAATATGAT
TGATATGGCAGAAAATGAAATAAGCTCTGCGGCTTTCTTTTTTGACAACGCTCAGAAAAGGTTA
AAAGAAAGCATTATTAAAGATTAGAGAGTAAAAATAATAGATCTTATGCATTAAAATTGTCTA
GACAGGCTTTAAGTGACGCAAGAAGTGCTTTAAGTAATTTAGAATCTTTTGCCTCTAAAAGAAT
TGAACCAATGGTGAGAAGGAAGAAATAAAAGAGCTTATTAAACATGCAAAAACTGTTTTAGA
AAGTGTCAATAAAAAATAA t11-12.nt (SEQ ID NO:594)
TTGTAATCTAGATTCCAAATTATCTAGTAACAAAGAACAAAAAAATAACAATAATGTAAAAGA
AGTTTCGGATAGTGTTCAAGAAGATGGTCTTAATGATTTATATAATAATCAAGAAAAGCAAAAA
AGCTTTACTAAAAATTTTGGAGAACGGAAATATGAGGATTTAATTAATCCTATAGAGCCTATAA
TACCTTCAGAATCACCAAAGAATAAGGCTAATATACCAAATATTTCAATTGCGCATACTGAAAA
AAAAGAGACAAAAAGGAGAATTTAATCCCTTCTACTAATGAAGAAAGGAAGCTGATGCAGC
AATTAAATATTTAGAAGAAAATATTCTTAAAAACTCTAAATTTTCTGAATTAATTAGAGAAGTA
CGTGTAATTAAAGATGAATATGCTTTAATAAAAGCTGATTTGTATGATGTAATTGGAAAGATTA
ACAATAAAAAAACATCATTAATGGAGAATCCTAAGAACAATAGAGATAAGATAAATAATTAA
CACAATTGTTGCAAAATAATTTAAAGATAGATAGTGAACTTGAGCAGCTTATAAATATGATTGA
TATGGCAGAAAATGAAATAAGCTCTGCGGCTTTCTTTTTTGACAACGCTCAGAAAGGTTAAAA
GAAAGCATTATTAAAGATTAGAGAGTAAAAATAATAGATCTTATGCATTAAAATTGTCTAGAC
AGGCTTTAAGTGACGCAAGAAGTGCTTTAAGTAATTTAGAATCTTTTGCCTCTAAAAGAATTGA
ACCAATGGTGAGAAGGAAGAAATAAAAGAGCTTATTAAACATGCAAAAACTGTTTTAGAAAG
TCTCAATAAAAAA f11-12.aa (SEQ ID NO:595)
KENIFMRKSLFLYALLMGGLMSCNLDSKLSSNKEQKNNNNVKEVSDSVQEDGLNDLYNNQEKQKS
FTKNFGERKYEDLINPIEPIIPSESPKNKANIPNISIAHTEKKETKKENLIPSTNEEKEADAAIKYLEENI
LKNSKFSELIREVRVIKDEYALIKADLYDVIGKINNKKTSLMENPKNNRDKINKLTQLLQNNLKIDSE
LEQLINMIDMAENEISSAAFFFDNAQKRLKESIIKRLESKNNRSYALKLSRQALSDARSALSNLESFAS
KRIEPMVRKEEIKELIKHAKTVLESLNKK t11-12.aa (SEQ ID NO:596)
CNLDSKLSSNKEQKNNNNVKEVSDSVQEDGLNDLYNNQEKQKSFTKNFGERKYEDLINPI
EPIIPSESPKNKANIPNISIAHTEKKETKKENLIPSTNEEKEADAAIKYLEENILKNSKFSELIREVRVIK
DEYALIKADLYDVIGKINNKKTSLMENPKNNRDKINKLTQLLQNNLKIDSELEQLINMIDMAENEISS
AAFFFDNAQKRLKESIIKRLESKNNRSYALKLSRQALSDARSALSNLESFASKRIEPMVRKEEIKELIK
```

TABLE 1-continued

Nucleotide and Amino Acid Sequences.

HAKTVLESLNKK f11-4.nt (SEQ ID NO:597)
TAAAGGAGTTTACAAATGAGTAAACTAATATTGGCAATATCTATACTGCTAATAATTTCATGTA
AATGGTATGTAGACAATACCATTGATGAAGCAACTGTAGAAAGTAAATCAGCACTAACATCTAT
TGATCAAGTATTAGATGAGATAAGTGAAGCCACAGGCCTAAGTTCGGAAAAAATCACAAAATT
AACTCCGGAAGAGCTAGAAAATTTAGCAAAGGAAGCTCAAGATGACTCTGAAAAATCCAAAAA
AGAAATTGAAGATCAAAAAAATACCAAGGAAAGTAAAAACATAGAAGTAAAGGATACTCCTCG
CTTAATCAAATTGATAAAGAATTCATCAGAAAAAATTGATTCGGTTTTTCAAACACTAATTAAT
ATAGGTTATAATGCTACCTATGCAGCCAAAAGTAATTTGAAGAATGGACTAAAGATGGTGAAA
TTACTGGATGAGTTGCTAAAAATATCGGTAAGTAGCAATGGTGATAAAAGTACCCAAAAATAC
AATGAACTTAAAACCGTTGTAAATAAGTTTAATGCTGAAAATTCGGTAAGCGTTTCTTTTAAAG
AACATTCAAACAGTAAAATTGAAACTAAAAAATGTATTCAAACTCTTATGAAAAATGTAGAAAC
ATACTTTGAAGGTGTATGCAGCGAACTTAAAAACAAAAATGATGGTGAGTACGAAAAAACATT
GACAACTTTAAGCTAA t11-4.nt (SEQ ID NO:598)
ATGTAAATGGTATGTAGACAATACCATTGATGAAGCAACTGTAGAAAGTAAATCAGCACTAAC
ATCTATTGATCAAGTATTAGATGAGATAAGTGAAGCCACAGGCCTAAGTTCGGAAAAAATCAC
AAAATTAACTCCGGAAGAGCTAGAAAATTTAGCAAAGGAAGCTCAAGATGACTCTGAAAAATC
CAAAAAAGAAATTGAAGATCAAAAAAATACCAAGGAAAGTAAAAACATAGAAGTAAAGGATA
CTCCTCGCTTAATCAAATTGATAAAGAATTCATCAGAAAAAATTGATTCGGTTTTTCAAACACT
AATTAATATAGGTTATAATGCTACCTATGCAGCCAAAAGTAATTTGAAGAATGGACTAAAGATG
GTGAAATTACTGGATGAGTTGCTAAAAATATCGGTAAGTAGCAATGGTGATAAAAGTACCCAA
AAATACAATGAACTTAAAACCGTTGTAAATAAGTTTAATGCTGAAAATTCGGTAAGCGTTTCTT
TTAAAGAACATTCAAACAGTAAAATTGAAACTAAAAAATGTATTCAAACTCTTATGAAAAATGT
AGAAACATACTTTGAAGGTGTATGCAGCGAACTTAAAAACAAAAATGATGGTGAGTACGAAAA
A f11-4.aa (SEQ ID NO:599)
RSLQMSKLILAISILLIISCKWYVDNTIDEATVESKSALTSIDQVLDEISEATGLSSEKITKLTPEELENL
AKEAQDDSEKSKKEIEDQKNTKESKNIEVKDTPRLIKLIKNSSEKIDSVFQTLINIGYNATYAAKSNL
KNGLKMVKLLDELLKISVSSNGDKSTQKYNELKTVVNKFNAENSVSVSFKEHSNSKIETKKCIQTL
MKNVETYFEGVCSELKNKNDGEYEKTLTTLS t11-4.aa (SEQ ID NO:600)
CKWYVDNTIDEATVESKSALTSIDQVLDEISEATGLSSEKITKLTPEELENLAKEAQDDSEKSKKEIE
DQKNTKESKNIEVKDTPRLIKLIKNSSEKIDSVFQTLINIGYNATYAAKSNLKNGLKMVKLLDELLKI
SVSSNGDKSTQKYNELKTVVNKFNAENSVSVSFKEHSNSKIETKKCIQTLMKNVETYFEGVCSELK
NKNDGEYEK f112-1.nt (SEQ ID NO:601)
TGAATCTCTAAAGATTTTAGCAGGGGAGAAAATATGAAAAAAAGTTTTTTATCAATATACATGT
TAATTTCAATAAGTTTATTATCATGTGATGTTAGTAGATTAAATCAGAGAAATATTAATGAGCT
TAAAATTTTTGTTGAAAAGGCCAAGTATTATTCTATAAAATTAGACGCTATTTATAACGAATGT
ACAGGAGCATATAATGATATTATGACTTATTCGGAAGGTACATTTTCTGATCAAAGTAAGGTTA
ATCAAGCTATATCTATATTTAAAAAAGACAATAAAATTGTTAATAAGTTTAAGGAGCTTGAAAA
GATTATAGAAGAATACAAACCTATGTTTTTAAGTAAATTAATTGATGATTTTGCGGGATCCGTT t112-1.nt (SEQ ID NO:602)
ATGTGATGTTAGTAGATTAAATCAGAGAAATATTAATGAGCTTAAAATTTTTGTTGAAAAGGCC
AAGTATTATTCTATAAAATTAGACGCTATTTATAACGAATGTACAGGAGCATATAATGATATTA
TGACTTATTCGGAAGGTACATTTTCTGATCAAAGTAAGGTTAATCAAGCTATATCTATATTTAA
AAAAGACAATAAAATTGTTAATAAGTTTAAGGAGCTTGAAAAGATTATAGAAGAATACAAACC
TATGTTTTTAAGTAAATTAATTGATGATTTT f112-1.aa (SEQ ID NO:603)
ISKDFSRGEN MKKSFLSIYM LISISLLSCD VSRLNQRNIN ELKIFVEKAK YYSIKLDAIY
NECTGAYNDI MTYSEGTFSD QSKVNQAISI FKKDNKIVNK FKELEKIIEE YKPMFLSKLI
DDFAGSV t112-1.aa (SEQ ID NO:604)
CDVSRLNQRNINELKIFVEKAKYYSIKLDAIYNECTGAYNDIMTYSEGTFSDQSKVNQAISIFKKDNK
IVNKFKELEKIIEEYKPMFLSKLIDDF f14-8.nt (SEQ ID NO:605)
TAAATACAGAGCCATTCAAGGAGAGTATTTATGAAATACTATATATGTGTGTGTTTTTTTGC
TTTTGAATGCTTGCAATTCAGATTTTAGCACTAATCAAGAAGATATTAAATATCCATCTGATAA
AGAGAAATCAAAATCCAACATGGAAGCAAGCTCTAAAGAAGAAGATCCAAATAAAAAAATAAA
AAATACACTGCTTAATGATTTAATAAATTTGATAGAAATAGCTAATGAGCATAAAGAAAAATAT
GAAAAAAGAATGCAAGAAGAACCTTCAGATCAATACGGAATATTGGCTTTCCAGGAATTAGAC
TTGTCCGTTGGAAAAATATCTGAAGCACCCCGCAATCTAAAAAATTTAGAAAAAACACCTATT
CTCCCTTAAGCGCTATTGATGTCAATAAATTAAAAGATCTTTCAGAGATTATAAGAAATTCGGG
CCAAATACAAGGTTTATTTAATATTTTCAACAGATTCGGAGGCATTTTTGACGACTCACTTAATC
ACGTATATTCTAAAAAAGATATCCTAGGGGGACTAGAAATTTTGGATTTAGATAAACTAAAAAA
TTCGTTTGAAAAATTACTATCTATAAAAGAAACTTTCTCAAAAATGCTAAATCAACTTTTATTAG
ATTATAAAAAATGATAAAGATCATATACGAACAGAGACAAATAAACTTAAATCTCATACAACTGC

TABLE 1-continued

Nucleotide and Amino Acid Sequences.

ACTTTTCGAACAACTTGATAAAAAAGAAGACGAAGCATATGAACCTAAAAATCAGATATTTTCA
ATAAGTAACCTTTAA t14-8.nt (SEQ ID NO:606)
TTGCAATTCAGATTTTAGCACTAATCAAGAAGATATTAAATATCCATCTGATAAAGAGAAATCA
AAATCCAACATGGAAGCAAGCTCTAAAGAAGAAGATCCAAATAAAAAAATAAAAAATACACTG
CTTAATGATTTAATAAATTTGATAGAAATAGCTAATGAGCATAAAGAAAAATATGAAAAGA
ATGCAAGAAGAACCTTCAGATCAATACGGAATATTGGCTTTCCAGGAATTAGACTTGTCCGTTG
GAAAAATATCTGAAGACACCCCGCAATCTAAAAAATTTAGAAAAAACACCTATTCTCCCTTAAG
CGCTATTGATGTCAATAAATTAAAAGATCTTTCAGAGATTATAAGAAATTCGGGCCAAATACAA
GGTTTATTTAATATTTTCAACAGATTCGGAGGCATTTTTGACGACTCACTTAATCACGTATATTC
TAAAAAAGATATCCTAGGGGGACTAGAAATTTTGGATTTAGATAAACTAAAAAATTCGTTTGAA
AAATTACTATCTATAAAAGAAACTTTCTCAAAAATGCTAAATCAACTTTTATTAGATTATAAAA
ATGATAAAGATCATATACGAACAGAGACAAATAAACTTAAATCTCATACAACTGCACTTTTCGA
ACAACTTGATAAAAAAGAAGACGAAGCATATGAACCTAAAAATCAG f14-8.aa (SEQ ID NO:607)
IQSHSRRVFMKYYICVCVFLLLNACNSDFSTNQEDIKYPSDKEKSKSNMEASSKEEDPNKKIKNTLL
NDLINLIEIANEHKEKYEKRMQEEPSDQYGILAFQELDLSVGKISEDTPQSKKFRKNTYSPLSAIDVN
KLKDLSEIIRNSGQIQGLFNIFNRFGGIFDDSLNHVYSKKDILGGLEILDLDKLKNSFEKLLSIKETFSK
MLNQLLLDYKNDKDHIRTETNKLKSHTTALFEQLDKKEDEAYEPKNQIFSISNL t14-8.aa (SEQ ID NO:608)
CNSDFSTNQEDIKYPSDKEKSKSNMEASSKEEDPNKKIKNTLLNDLINLIEIANEHKEKYEKRMQEEP
SDQYGILAFQELDLSVGKISEDTPQSKKFRKNTYSPLSAIDVNKLKDLSEIIRNSGQIQGLFNIFNRFGG
IFDDSLNHVYSKKDILGGLEILDLDKLKNSFEKLLSIKETFSKMLNQLLLDYKNDKDHIRTETNKLKS
HTTALFEQLDKKEDEAYEPKNQ f17-6.nt (SEQ ID NO:609)
TAAAGGAGGGTATTTATGAAATACCACATAATTACAACTATATTTGTTTTTCTGTTTTTAGCTTG
CAGGCCGGATTTTAATATCGATCAAAAAGACATTAAATACCCGCCTACTGAAAAATCAAGGCCC
AAAACTGAAAGCTCTAAGCAAAAAGAATCAAAGCCTAAAACAGAAGAAGAGCTTAAGAAAAA
ACAACAAGAAGAAGAGCTTAAGAAAAAACAACAAGAAGAAGAGCTTAAGAAAAAACAACAAG
AAGAAGAGCTTAAGAAAAAACAACAAGAAGAAGAGAAGGAAGAACTAAGAAAACAACAACTA
AAAAATACGCTATCTAATGATTTAAAAAAGCAAATAGAATCGGCCTACAATTTTAAAGAAAAAT
ATGTAAAAAGTATGGAAAAAGAACCTGAAGACCATTACGGGATGACGTCTTTTAGGGGATTGA
ATTGGGGGCCAGGGACTGAAGATATATCTGACAATACCGAAAGATCTATAAGATATAGAAGAC
ACACTTATACTGTTTTAAGCCCCCTGGATCCTCATGAATTAAAGGAATTCGCAAATATTATTCA
AGATATAAATAAACTAGCATCAGTAGCAAGTATATTTAATTCTTTTAGCGCTATTGGAGGAGCT
CTTGACATAGTAAGTGATCACCTATATTTCAAAAAAGACAATCTAGACAAACTAGATATTGCAG
ATTTAGAAATACTTAAAAATTCATTTGAACAAATATTATATATAAAAGGAAGTGTTGCAGGAAA
AGCAAAAAAACTTTTATTAGATTATAAAAATCTAAAAACAGATATTAATAAGCTTAAATCTTAT
TCAAATGAACTGGTTAATGGAATTAAGCAACAAGCTCTAGAAGCAGAAAATCTAGAAGAGCTT
ATAGTGTCAAAATATAAACTTTAA t17-6.nt (SEQ ID NO:610)
TTGCAGGCCGGATTTTAATATCGATCAAAAAGACATTAAATACCCGCCTACTGAAAAATCAAGG
CCCAAAACTGAAAGCTCTAAGCAAAAAGAATCAAAGCCTAAAACAGAAGAAGAGCTTAAGAAA
AAACAACAAGAAGAAGAGCTTAAGAAAAAACAACAAGAAGAAGAGCTTAAGAAAAAACAACA
AGAAGAAGAGCTTAAGAAAAAACAACAAGAAGAAGAGAAGGAAGAACTAAGAAAACAACAAC
TAAAAAATACGCTATCTAATGATTTAAAAAAGCAAATAGAATCGGCCTACAATTTTAAAGAAAA
ATATGTAAAAAGTATGGAAAAAGAACCTGAAGACCATTACGGGATGACGTCTTTTAGGGGATT
GAATTGGGGGCCAGGGACTGAAGATATATCTGACAATACCGAAAGATCTATAAGATATAGAAG
ACACACTTATACTGTTTTAAGCCCCCTGGATCCTCATGAATTAAAGGAATTCGCAAATATTATTC
AAGATATAAATAAACTAGCATCAGTAGCAAGTATATTTAATTCTTTTAGCGCTATTGGAGGAGC
TCTTGACATAGTAAGTGATCACCTATATTTCAAAAAAGACAATCTAGACAAACTAGATATTGCA
GATTTAGAAATACTTAAAAATTCATTTGAACAAATATTATATATAAAAGGAAGTGTTGCAGGAA
AAGCAAAAAAACTTTTATTAGATTATAAAAATCTAAAAACAGATATTAATAAGCTTAAATCTTA
TTCAAATGAACTGGTTAATGGAATTAAGCAACAAGCTCTAGAAGCAGAAAATCTAGAAGAGCT
TATAGTGTCAAAATATAAACTT f17-6.aa (SEQ ID NO:611)
RRVFMKYHIITTIFVFLFLACRPDFNIDQKDIKYPPTEKSRPKTESSKQKESKPKTEEELKKKQQEEEL
KKKQQEELKKKQQEEELKKKQQEEEKEELRKQQLKNTLSNDLKKQIESAYNFKEKYVKSMEKEP
EDHYGMTSFRGLNWGPGTEDISDNTERSIRYRRHTYTVLSPLDPHELKEFANIIQDINKLASVASIFNS
FSAIGGALDIVSDHLYFKKDNLDKLDIADLEILKNSFEQILYIKGSVAGKAKKLLLDYKNLKTDINKL
KSYSNELVNGIKQQALEAENLEELIVSKYKL t17-6.aa (SEQ ID NO:612)
CRPDFNIDQKDIKYPPTEKSRPKTESSKQKESKPKTEEELKKKQQEEELKKKQQEEELKKKQQEEEL
KKKQQEEKEELRKQQLKNTLSNDLKKQIESAYNFKEKYVKSMEKEPEDHYGMTSFRGLNWGPGT
EDISDNTERSIRYRRHTYTVLSPLDPHELKEFANIIQDINKLASVASIFNSFSAIGGALDIVSDHLYFKK
DNLDKLDIADLEILKNSFEQILYIKGSVAGKAKKLLLDYKNLKTDINKLKSYSNELVNGIKQQALEA
ENLEELIVSKYKL f19-2.nt (SEQ ID NO:613)
TAAAGAAAGATTAAATCATATTCAAGGAGAGTATTTATGAAACACTATATAATTGTGCATATAT

TABLE 1-continued

Nucleotide and Amino Acid Sequences.

```
TTGTTTTTCTATTTTTAAATGCTTGTTATCCAGTTGCATCTAATAAAATAGAATTAAAACCTAAA
ACAGAAACAAGCTTAAATCAAGAAGAAGTCCCAAATCAAGAAGCAAACTACAAAGAAGAAAA
AGAAGCAAAAGAAGAAGGCATTAATAAAAAAACAGAAAACACGCTGCTTAATGATTTAAGAAA
TTTAATAGAAACAGCTAAAAAGATAATGATAAATATACACAAAAGTTAAAAGAAGAATCCTC
AAGCCAATACGGAATACTGGCTTTCAAAGATTTGTTCTGGCTAGATGGAACAAATGAACAATTG
TCCGCAAATACCGAAAGATCTAAAGCCTATAGAAAACGAGCTTATAGCATCTTAAATACTATTA
ATGACGCTTCCTTAAAGAATTTTTCAGAAATTGTAATGGCATCAGGACAAACACAGGGCATATT
TAATACCCTTAACTCACTTGGGGGTAATTTTGAAAAGATAGTTAATTGTTTGTATCCCAAAAAA
GACAATTTGGAAAAATTAGAGACTTCAGTTTTAAAAAAGCTTAAAGATTCTTTGGAAAATTTTT
TAGAGATAAAAAAAATCGCCTCAGAAATGATGCACAAGCTCTTATTAGACTATCAAAATAATAC
AAATCGTATACAAACAGATAAAAATGAACTTAAGTCTTATGCAGACACACTTTTCAATCAAATG
ACAAAAAAACCCGAAGAAGCACTAAAGCTAAAAAATACCATATGCTCAATAGAGGACCTTTAA t19-2.nt (SEQ ID NO:614)
TTGTTATCCAGTTGCATCTAATAAAATAGAATTAAAACCTAAACAGAAACAAGCTTAAATCAA
GAAGAAGTCCCAAATCAAGAAGCAAACTACAAAGAAGAAAAGAAGCAAAAGAAGAAGGCAT
TAATAAAAAAACAGAAAACACGCTGCTTAATGATTTAAGAAATTTAATAGAAACAGCTAAAAA
AGATAATGATAAATATACACAAAAGTTAAAAGAAGAATCCTCAAGCCAATACGGAATACTGGC
TTTCAAAGATTTGTTCTGGCTAGATGGAACAAATGAACAATTGTCCGCAAATACCGAAAGATCT
AAAGCCTATAGAAACGAGCTTATAGCATCTTAAATACTATTAATGACGCTTCCTTAAAGAATT
TTTCAGAAATTGTAATGGCATCAGGACAAACACAGGGCATATTTAATACCCTTAACTCACTTGG
GGGTAATTTTGAAAAGATAGTTAATTGTTTGTATCCCAAAAAAGACAATTTGGAAAATTAGAG
ACTTCAGTTTTAAAAAAGCTTAAAGATTCTTTGGAAAATTTTTTAGAGATAAAAAAAATCGCCT
CAGAAATGATGCACAAGCTCTTATTAGACTATCAAAATAATACAAATCGTATACAAACAGATAAA
AAATGAACTTAAGTCTTATGCAGACACACTTTTCAATCAAATGACAAAAAAACCCGAAGAAGC
ACTAAAG f19-2.aa (SEQ ID NO:615)
RKIKSYSRRVFMKHYIIVHIFVFLFLNACYPVASNKIELKPKTETSLNQEEVPNQEANYKEEKEAKEE
GINKKTENTLLNDLRNLIETAKKDNDKYTQKLKEESSSQYGILAFKDLFWLDGTNEQLSANTERSKA
YRKRAYSILNTINDASLKNFSEIVMASGQTQGIFNTLNSLGGNFEKIVNCLYPKKDNLEKLETSVLKK
LKDSLENFLEIKKIASEMMHKLLLDYQNNTNRIQTDKNELKSYADTLFNQMTKKPEEALKLKNTICS
IEDL t19-2.aa (SEQ ID NO:616)
CYPVASNKIELKPKTETSLNQEEVPNQEANYKEEKEAKEEGINKKTENTLLNDLRNLIETAKKDNDK
YTQKLKEESSSQYGILAFKDLFWLDGTNEQLSANTERSKAYRKRAYSILNTINDASLKNFSEIVMAS
GQTQGIFNTLNSLGGNFEKIVNCLYPKKDNLEKLETSVLKKLKDSLENFLEIKKIASEMMHKLLLDY
QNNTNRIQTDKNELKSYADTLFNQMTKKPEEALK f19-4.nt (SEQ ID NO:617)
TAATCTATACTAATTGAGGAGAATATTTTTATGAAAAACAACATAATTTTATGCATGTGTGTTTT
TTTACTTTTAAATAGCTGCACCGCTAACCATGAAGCTGAAGCGAAAATAAAAAAACATGTTGAT
AAAACAAAAAACGAATATATTAATGAAATAAAAAATTTAATAGCAACAACCAAAGAAATCATC
GAAAAACGAAAATTGCTACAAGCTAAACCAGTAGATCAAAACCCCGTAGATGATACAAACAAT
AAGAAAGTTTTCGAGATAGATAAAAGAGCTTTCGATTTTATAAATAGTTTTTTAACAGATGATG
AATTTAATAAATTTGTAACAATATTTCATAAACCAACACTAAAATCACCCGGAAAAGTATTAAA
TAGCATAGCAATTCTAGAGCTAAACATAGAGCAGGTAATTAATCACCTAGACTCAAAAAATGA
GACCTTAAATAAAGCAAGCTCTTTAGATTTGGAAAAGATCAAAAATTCCCTTGAACAGCTGTTC
TCTATAAGGAATTTTTTTTCAACAATCATAAAAAGGGTCTTATTAGATCATCAAAACAATGAAA
ATTCTATAAAACCAGATGATTCTAAATCAGGAACCTATTTCGATACGATATACGATCAGTTTAA
TGAAAAAAATAAAGAGGTTAGAAATCTGAAAAAAACCATATTATCACTGCCGAATTAA t19-4.nt (SEQ ID NO:618)
CTGCACCGCTAACCATGAAGCTGAAGCGAAAATAAAAAAACATGTTGATAAAACAAAAAACGA
ATATATTAATGAAATAAAAAATTTAATAGCAACAACCAAAGAAATCATCGAAAAACGAAAATT
GCTACAAGCTAAACCAGTAGATCAAAACCCCGTAGATGATACAAACAATAAGAAAGTTTTCGA
GATAGATAAAAGAGCTTTCGATTTTATAAATAGTTTTTTAACAGATGATGAATTTAATAAATTT
GTAACAATATTTCATAAACCAACACTAAAATCACCCGGAAAAGTATTAAATAGCATAGCAATTC
TAGAGCTAAACATAGAGCAGGTAATTAATCACCTAGACTCAAAAAATGAGACCTTAAATAAAG
CAAGCTCTTTAGATTTGGAAAAGATCAAAAATTCCCTTGAACAGCTGTTCTCTATAAGGAATTT
TTTTTCAACAATCATAAAAAGGGTCTTATTAGATCATCAAAACAATGAAAATTCTATAAAACCA
GATGATTCTAAATCAGGAACCTATTTCGATACGATATACGATCAGTTTAATGAAAAAAATAAAG
AGGTTAGAAATCTGAAAAAA f19-4.aa (SEQ ID NO:619)
SILIEENIFMKNNIILCMCVFLLLNSCTANHEAEAKIKKHVDKTKNEYINEIKNLIATTKEIIEK
RKLLQAKPVDQNPVDDTNNKKVFEIDKRAFDFINSFLTDDEFNKFVTIFHKPTLKSPGKVLNSIAILE
LNIEQVINHLDSKNETLNKASSLDLEKIKNSLEQLFSIRNFFSTIIKRVLLDHQNNENSIKPDDSKSGTY
FDTIYDQFNEKNKEVRNLKKTILSLPN t19-4.aa (SEQ ID NO:620)
CTANHEAEAKIKKHVDKTKNEYINEIKNLIATTKEIIEKRKLLQAKPVDQNPVDDTNNKKVFEIDKR
AFDFINSFLTDDEFNKFVTIFHKPTLKSPGKVLNSIAILELNIEQVINHLDSKNETLNKASSLDLEKIKN
SLEQLFSIRNFFSTIIKRVLLDHQNNENSIKPDDSKSGTYFDTIYDQFNEKNKEVRNLKK f19-6.nt (SEQ ID NO:621)
```

TABLE 1-continued

Nucleotide and Amino Acid Sequences.

TAAAGGAGAGTATTAATGAAATGCCATATAATTGCAACTATATTTGTTTTTCTATTTTT
AGCTTGCAGTACAGATTTTAATACTGATCAAAAAGGCATTAAATACCCGCCTACCGAAAAATCA
AAGCCCAAAACTGAAGACTCTAAGCAAAAAGAATTAAAGCCTAAAACAGAAAAAGAACTAAAG
AAAAAACAACAACTAAAAAATAAACTACTTAATGATTTAAAAAATTCAATAGAAACAGCTAAT
AAGCATAAAGAAAAGTATAAAAAAAGAATGAAAGAAGAACCCGAAGATCAATACGGGGTACA
GGCTTTCAAAGGATCGAATTGGGGGCCGGGGACTGAAGATGTATCTGCCAACACCGAAAGATC
TATAAGATTTAGAAGACATACTTATACTATTTTAAGCACGCTGAGTCTTCATGAATTAAAGGAA
TTCTCAAATATTGTTACAAATGAAAATAAACTGGTGCCAGTAGTAGATATGTTTAATTTCTTTA
GCTCTATTGGGACAGCTCTTGATATAACAACCGATAGCTTATATCCCAAAAAGACAATCTGGAC
AAACCAGATCTGTCGGATTTAG t19-6.nt (SEQ ID NO:622)
TTGCAGTACAGATTTTAATACTGATCAAAAAGGCATTAAATACCCGCCTACCGAAAAAT
CAAAGCCCAAAACTGAAGACTCTAAGCAAAAAGAATTAAAGCCTAAAACAGAAAAAGAACTAA
AGAAAAAACAACAACTAAAAAATAAACTACTTAATGATTTAAAAAATTCAATAGAAACAGCTA
ATAAGCATAAAGAAAAGTATAAAAAAAGAATGAAAGAAGAACCCGAAGATCAATACGGGGTA
CAGGCTTTCAAAGGATCGAATTGGGGGCCGGGGACTGAAGATGTATCTGCCAACACCGAAAGA
TCTATAAGATTTAGAAGACATACTTATACTATTTTAAGCACGCTGAGTCTTCATGAATTAAAGG
AATTCTCAAATATTGTTACAAATGAAAATAAACTGGTGCCAGTAGTAGATATGTTTAATTTCTT
TAGCTCTATTGGGACAGCTCTTGATATAACAACCGATAGCTTATATCCCAAAAAGACAATCTGG
ACAAACCAGATCTGTCGG f19-6.aa (SEQ ID NO:623)
RRVLMKCHIIATIFVFLFLACSTDFNTDQKGIKYPPTEKSKPKTEDSKQKELKPKTEKELKKKQQLK
NKLLNDLKNSIETANKHKEKYKKRMKEEPEDQYGVQAFKGSNWGPGTEDVSANTERSIRFRRHTY
TILSTLSLHELKEFSNIVTNENKLVPVVDMFNFFSSIGTALDITIDSLYPKKTIWTNQICRI t19-6.aa (SEQ ID NO:624)
CSTDFNTDQKGIKYPPTEKSKPKTEDSKQKELKPKTEKELKKKQQLKNKLLNDLKNSIETANKHKE
KYKKRMKEEPEDQYGVQAFKGSNWGPGTEDVSANTERSIRFRRHTYTILSTLSLHELKEFSNIVTNE
NKLVPVVDMFNFFSSIGTALDITTDSLYPKKTIWTNQICR f21-4.nt (SEQ ID NO:625)
TAGGAGACAATCTTTATGAATAAAAAAATAAAAATGTTTATTATTTGTGCTATTTTTATGCTGAT
AAGTTCTTGTAAGAATGATGTAACTAGTAAAGATTTAGAAGGGGCGGTGAAAGATTTAGAAAG
TTCAGAACAAAATGTAAAAAAAACAGAACAAGAGATAAAAAAACAAGTTGAAGGATTTTTAGA
AATTTTTAGAGACAAAAGATTTAAACACATTAGATACAAAAGAAATTGAAAAACAAATTCAAGA
ATTAAAGAATAAGATAGAAAAATTAGACTCTAAAAAAACTTCTATTGAAACATATTCTGGGTAT
GAAGAAAAAATAAACAAAATAAAAGAAAAATTAAACGGAAAAGGACTTGAAGATAAATTAAA
TGAACTTTCAGAGAGCTTAAAAAAAGAAAAAAGAGGAGAGAAAAAAAAGCTTTACAAGAGGCTAA
AAAGAAATTTGAAGAGTATAAAAACCAAGCTGAATCTGCAACTGGAGTAACGCATGGTTCTCA
AGTCCAAAGACAAGGTGGTGTTGGATTACAAGCTTGGCAGTGTGCTAATAGTTTGGGGTTTAAA
AATATGACTAGTGGTAATAATACTAGCGATATGACCAATGAAGTTATAACTAATTCGCTTAAAA
AGATTGAAGAAGAACTTAAAAATATTGGAGAAACTGTAGAAGGTAAAAAAGAATAA t21-4.nt (SEQ ID NO:626)
TTGTAAGAATGATGTAACTAGTAAAGATTTAGAAGGGGCGGTGAAAGATTTAGAAAGT
TCAGAACAAAATGTAAAAAAAACAGAACAAGAGATAAAAAAACAAGTTGAAGGATTTTTAGAA
ATTTTTAGAGACAAAAGATTTAAACACATTAGATACAAAAGAAATTGAAAAACAAATTCAAGAA
TTAAAGAATAAGATAGAAAAATTAGACTCTAAAAAAACTTCTATTGAAACATATTCTGGGTATG
AAGAAAAAATAAACAAAATAAAAGAAAAATTAAACGGAAAAGGACTTGAAGATAAATTAAAT
GAACTTTCAGAGAGCTTAAAAAAAGAAAAAAGAGGAGAGAAAAAAAAGCTTTACAAGAGGCTAA
AAAGAAATTTGAAGAGTATAAAAACCAAGCTGAATCTGCAACTGGAGTAACGCATGGTTCTCA
AGTCCAAAGACAAGGTGGTGTTGGATTACAAGCTTGGCAGTGTGCTAATAGTTTGGGGTTTAAA
AATATGACTAGTGGTAATAATACTAGCGATATGACCAATGAAGTTATAACTAATTCGCTTAAAA
AGATTGAAGAAGAACTTAAAAATATTGGAGAAACTGTAGAAGGTAAAAAAGAA f21-4.aa (SEQ ID NO:627)
ETIFMNKKIKMFIICAIFMLISSCKNDVTSKDLEGAVKDLESSEQNVKKTEQEIKKQVEGFLEILETKD
LNTLDTKEIEKQIQELKNKIEKLDSKKTSIETYSGYEEKINKIKEKLNGKGLEDKLNELSESLKKKKEE
RKKALQEAKKKFEEYKNQAESATGVTHGSQVQRQGGVGLQAWQCANSLGFKNMTSGNNTSDMT
NEVITNSLKKIEEELKNIGETVEGKKE t21-4.aa (SEQ ID NO:628)
CKNDVTSKDLEGAVKDLESSEQNVKKTEQEIKKQVEGFLEILETKDLNTLDTKEIEKQIQELKNKIE
KLDSKKTSIETYSGYEEKINKIKEKLNGKGLEDKLNELSESLKKKKEERKKALQEAKKKFEEYKNQA
ESATGVTHGSQVQRQGGVGLQAWQCANSLGFKNMTSGNNTSDMTNEVITNSLKKIEEELKNIGET
VEGKKE f14-1.nt (SEQ ID NO:629)
TAAGCTGGTAACACTGTAAAGACAGCTGAGGGGCTTCAAGTGGTACTGATGCAATTGGAGAA
GTTGTGGATAATGATGCTAAGGTTGCTGATAAGGCGAGTGTGACGGGATTGCTAAGGGGATA
AAGGAGATTGTTGAAGCTGCTAGGGGGAGTGAAAAGCTGAAAGTTGCTGCTGCTAAAGAGGGC
AATGAAAAGGCAGGGAAGTTGTTTGGGAAGGCTGGTGCTAATGCTCATGGGACAGTGAGGCT
GCTAGCAAGGCGGCTGGTGCTGTTAGTGCTGTTAGTGGGAGCAGATATTAAGTGCGATTGTTA
AGGCTGCGGATGCGGCTGAGCAGGATGGAAAGAAGCCTGCAGATGCTACAAATCCGATTGCTG
CTGCTATTGGGAATAAAGATGAGGATGCGGATTTTGGTGATGGGATGAAGAAGGATGATCAGA

TABLE 1-continued

Nucleotide and Amino Acid Sequences.

```
TTGCTGCTGCTATTGCTTTGAGGGGGATGGCTAAGGATGGAAAGTTTGCTGTGAAGAATGATGA
GAAAGGGAAGGCTGAGGGGGCTATTAAGGGAGCTGCTGCAATTGGAGAAGTTGTGGATAATGC
TGGTGCTGCGAAGGCTGCTGATAAGGATAGTGTGAAGGGGATTGCTAAGGGGATAAAGGAGAT
TGTTGAAGCTGCTGGGGGGAGTGAAAAGCTGAAAGCTGCTGCTGCTGAAGGGGAGAATAATAA
AAAAGGCAGGGAAGTTGTTTGGGAAAGTTGATGGTGCTGCTGGGGACAGTGAGGCTGCTAGCAA
GGCGGCTGGTGCTGTTAGTGCTGTTAGTGGGGAGCAGATATTAAGTGCGATTGTTAAGGCTGCT
GGTGAGGCTGAGCAGGATGGAGAGAAGCCTGAGGATGCTAAAAATCCGATTGCTGCTGCTATT
GGGAAGGGTAATGGGGATGGTGCGGAGTTTGATCAGGATGAGATGAAGAAGGATGATCAGATT
GCTGCTGCTATTGCTTTGAGGGGGATGGCTAAGGATGGAAAGTTTGCTGTGAAGGGTAATAAT
GAGAAAGAGAAGGCTGAGGGGGCTATTAAAGAAGTTAGCGAGTTGTTGGATAAGCTGGTAACA
GCTGTAAAGACAGCTGAGGGGGCTTCAAGTGGTACTGATGCAATTGGAGAAGTTGTGGATAAT
GNTGCNAAGGNTGCTGATAAGGCGAGTGTGACGGGGATTGCTAAGGGGATAAAGGAGATTGTT
GAAGCTGCTNGGGGAGTGAAAAGCTGAAAGTTGCTGCTGCTANAGNGGNNAATAATAAAGA
GGCAGGGAAGTTGTTTGGGAAGGCTGGTGCTGATGCTAATGGGGACAGTGAGGCTGCTAGCAA
GGCGGCTGGTGCTGTTAGTGCTGTTAGTGGGGAGCAGATATTAAGTGCGATTGTTAAGGCTGCG
GCTGCTGGTGCGGCTGATCAGGATGGAGAGAAGCCTGGGGATGCTAAAAATCCGATTGCTGCT
GCTATTGGGAAGGGTAATGCGGATGATGGTGCGGATTTTGGTGATGGGATGAAGAAGGATGAT
CAGATTGCTGCTGCTATTGCTTTGAGGGGGATGGCTAAGGATGGAAAGTTTGCTGTGAAGAAG
GATGAGAAAGGGAAGGCTGAGGGGGCTATTAAGGGAGCTAGCGAGTTGTTGGATAAGCTGGTA
AAAGCTGTAAAGACAGCTGAGGGGGCTTCAAGTGGTACTGCTGCAATTGGAGAAGTTGTGGAT
AATGCTGCGAAGGCTGCTGATAAGGATAGTGTGACGGGGATTGCTAAGGGGATAAAGGAGATT
GTTGAAGCTGCAGGGGGGAGTGAAAAGCTGAAAGTTGCTGCTGCTAAAGGGGAGAATAATAAA
GGGGCAGGGAAGTTGTTTGGGAAGGCTGGTGCTAATGCTCATGGGGACAGTGAGGCTGCTAGC
AAGGCGGCTGGTGCTGTTAGTGCTGTTAGTGGGGAACAGATATTAAGTGCGATTGTTAAGGCTG
CTGGTGAGGCTGCTGGTGATCAGGAGGGAAAGAAGCCTGAGGAGGCTAAAAATCCGATTGCTG
CTGCTATTGGGGATAAAGATGGGGATGCGGAGTTTAATCAGGATGGGATGAAGAAGGATGATC
AGATTGCTGCTGCTATTGCTTTGAGGGGGATGGCTAAGGATGGAAAGTTTGCTGTGAAGGATG
GTGGTGAGAAAGAGAAGGCTGAGGGGGCTATTAAAGGAGTTAGCGAGTTGTTGGATAAGCTGG
TAAAAGCTGTAAAGACAGCTGAGGGGGCTTCAAGTGGTACTGCTGCAATTGGAGAAGTTGTGG
CTGATGCTGCTAAGGTTGCTGATAAGGCGAGTGTGACGGGGATTGCTAAGGGGATAAAGGAGA
TTGTTGAAGCTGCTGGGGACAGTGAGGCTGCTAGCAAGGCGGCTGGTGCTGTTAGTGCTGTTAG
TGGGGAGCAGATATTAAGTGCGATTGTTAAGGCTGCGGCTGCTGGTGCGGCTGAGCAGGATGG
AGAGAAGCCTGCAGAGGCTAAAAATCCGATTGCTGCTGCTATTGGGAAGGGTGATGGGGATGC
GGATTTTGGTGAGGATGGGATGAAGAAGGATGATCAGATTGCTGCTGCTATTGCTTTGAGGGG
GATGGCTAAGGATGGAAAGTTTGCTGTGAAGAATGATGAGAAAGGGAAGGCTGAGGGGCTAT
TAAGGGAGCTGCTGCAATTGGAGAAGTTGTGGATAATGCTGGTGCTGCGAAGGCTGCTGATAA
GGATAGTGTGAAGGGGATTGCTAAGGGGATAAAGGAGATTGTTGAAGCTGCTGGGGGAGTGA
AAAGCTGAAAGCTGCTGCTGCTGAAGGGGAGAATAATAAAAAGGCAGGGAAGTTGTTTGGGAA
AGTTGATGGTGCTGCTGGGGACAGTGAGGCTGCTAGCAAGGCGGCTGGTGCTGTTAGTGCTGTT
AGTGGGGAGCAGATATTAAGTGCGATTGTTAAGGCTGCGGATGCGGCTGAGCAGGATGGAAAG
AAGCCTGCAGATGCTACAAATCCGATTGCTGCTGCTATTGGGAATAAAGATGAGGATGCGGATT
TTGGTGATGGGATGAAGAAGGATGATCAGATTGCTGCTGCTATTGCTTTGAGGGGGATGGCTA
AGGATGGAAAGTTTGCTGTGAAGGGTAATAATGAGAAAGGGAAGGCTGAGGGGGCTTCAAGTG
GTACTGATGCAATTGGAGAAGTTGTGGATAATGATGCGAAGGCTGCTGATAAGGCGAGTGTGA
CGGGGATTGCTAAGGGGATAAAGGAGATTGTTGAAGCTGCTGGGGGAGTGAAAAGCTGAAA
GCTGTTGCTGCTGCTACAAGGGAGAATAATAAAGAGGCAGGGAAGTTGTTTGGGAAAGTTGAT
GATGCTCATGCTGGGGACAGTGAGGCTGCTAGCAAGGCGGCTGGTGCTGTTAGTGCTGTTAGTG
GGGAGCAGATATTAAGTGCGATTGTTACGGCTGCGGCTGCTGGTGAGCAGGATGGAGAGAAGC
CTGCAGAGGCTACAAATCCGATTGCTGCTGCTATTGGGAAGGGTAATGAGGATGGTGCGGATTT
TGGTAAGGATGAGATGAAGAAGGATGATCAGATTGCTGCTGCTATTGCTTTGAGGGGGATGGC
TAAGGATGGAAAGTTTGCTGTGAAGAGTAATGATGGTGAGAAAGGGAAGGCTGAGGGGGCTAT
TAAGGAAGTTAGCGAGTTGTTGGATAAGCTGGTAAAAGCTGTAAAAGACAGCTGAGGGGGCTTC
AAGCGGTACTGATGCAATTGGAGAAGTTGTGGCTAATGCTGGTGCTGCGAAGGCTGCTGATAA
GGCGAGTGTGACGGGGATTGCTAAGGGGATAAAGGAGATTGTTGAAGCTGCTGGGGGAGTAA
AAAGCTGAAAGCTGCTGCTGCTGAAGGGGAGAATAATAAAAAGGCAGGGAAGTTGTTTGGGAA
GGCTGGTGCTGGTGCTGGTGCTAATGGGGACAGTGAGGCTGCTAGCAAGGCGGCTGGTGCTGT
TAGTGCTGGTTAG t24-1.nt (SEQ ID NO:630)
TGGTGAGGCTGAGCAGGATGGAGAGAAGCCTGAGGATGCTAAAAATCCGATTGCTGCTGCTAT
TGGGAAGGGTAATGGGGATGGTGCGGAGTTTGATCAGGATGAGATGAAGAAGGATGATCAGAT
TGCTGCTGCTATTGCTTTGAGGGGGATGGCTAAGGATGGAAAGTTTGCTGTGAAGGGTAATAAT
GAGAAAGAGAAGGCTGAGGGGGCTATTAAAGAAGTTAGCGAGTTGTTGGATAAGCTGGTAACA
GCTGTAAAGACAGCTGAGGGGGCTTCAAGTGGTACTGATGCAATTGGAGAAGTTGTGGATAAT
GNTGCNAAGGNTGCTGATAAGGCGAGTGTGACGGGGATTGCTAAGGGGATAAAGGAGATTGTT
GAAGCTGCTNGGGGGAGTGAAAAGCTGAAAGTTGCTGCTGCTANAGNGGNNAATAATAAAGA
GGCAGGGAAGTTGTTTGGGAAGGCTGGTGCTGATGCTAATGGGGACAGTGAGGCTGCTAGCAA
G f24-1.aa (SEQ ID NO:631)
AGNTVKTAEGASSGTDAIGEVVDNDAKVADKASVTGIAKGIKEIVEAARGSEKLKVAAAKEGNEK
AGKLFGKAGANAHGDSEAASKAAGAVSAVSGEQILSAIVKAADAAEQDGKKPADATNPIAAAIGN
KDEDADFGDGMKKDDQIAAAIALRGMAKDGKFAVKNDEKGKAEGAIKGAAAIGEVVDNAGAAK
AADKDSVKGIAKGIKEIVEAAGGSEKLKAAAAEGENNKKAGKLFGKVDGAAGDSEAASKAAGAVS
AVSGEQILSAIVKAAGEAEQDGEKPEDAKNPIAAAIGKGNGDGAEFQDEMKKDDQIAAAIALRGM
AKDGKFAVKGNNEKEKAEGAIKEVSELLDKLVTAVKTAEGASSGTDAIGEVVDNXAKXADKASVT
GIAKGIKEIVEAAXGSEKLKVAAAXXXNNKEAGKLFGKAGADANGDSEAASKAAGAVSAVSGEQI
```

TABLE 1-continued

Nucleotide and Amino Acid Sequences.

LSAIVKAAAAGAADQDGEKPGDAKNPIAAAIGKGNADDGADFGDGMKKDDQIAAAIALRGMAKD
GKFAVKKDEKGKAEGAIKGASELLDKLVKAVKTAEGASSGTAAIGEVVDNAAKAADKDSVTGIAK
GIKEIVEAAGGSEKLKVAAAKGENNKGAGKLFGKAGANAHGDSEAASKAAGAVSAVSGEQILSAIV
KAAGEAAGDQEGKKPEEAKNPIAAAIGDKDGDAEFNQDGMKKDDQIAAAIALRGMAKDGKFAVK
DGGEKEKAEGAIKGVSELLDKLVKAVKTAEGASSGTAAIGEVVADAAKVADKASVTGIAKGIKEIV
EAAGDSEAASKAAGAVSAVSGEQILSAIVKAAAAGAAEQDGEKPAEAKNPIAAAIGKGDGDADFGE
DGMKKDDQIAAAIALRGMAKDGKFAVKNDEKGKAEGAIKGAAAIGEVVDNAGAAKAADKDSVK
GIAKGIKEIVEAAGGSEKLKAAAAEGENNKKAGKLFGKVDGAAGDSEAASKAAGAVSAVSGEQILS
AIVKAADAAEQDGKKPADATNPIAAAIGNKDEDADFGDGMKKDDQIAAAIALRGMAKDGKFAVK
GNNEKGKAEGASSGTDAIGEVVDNDAKAADKASVTGIAKGIKEIVEAAGGSEKLKAVAAATRENN
KEAGKLFGKVDDAHAGDSEAASKAAGAVSAVSGEQILSAIVTAAAAGEQDGEKPAEATNPIAAAIG
KGNEDGADFGKDEMKKDDQIAAAIALRGMAKDGKFAVKSNDGEKGKAEGAIKEVSELLDKLVKA
VKTAEGASSGTDAIGEVVANAGAAKAADKASVTGIAKGIKEIVEAAGGSIKLKAAAAEGENNKKA
GKLFGKAGAGANGDSEAASKAAGAVSAG t24-1.aa (SEQ ID NO:632)
GEAEQDGEKPEDAKNPIAAAIGKGNGDGAEFDQDEMKKDDQIAAAIALRGMAKDGKFAVKGNNE
KEKAEGAIKEVSELLDKLVTAVKTAEGASSGTDAIGEVVDNXAKXADKASVTGIAKGIKEIVEAAX
GSEKLKVAAAXXXNNKEAGKLFGKAGADANGDSEAASK f28-2.nt (SEQ ID NO:633)
TAAAAAGGAAATATAAATATTATGCGATTATGTTTAATAAAAATTTTTATTATACCTAATTTAG
TATTTAGTTCTCTTTTTTTATTTGAAAGTTGTTCTGGTTTTCTATCTAAAAAATCTATAGAACAG
TTTGCATTAGCATTAAAAGATCATCAAGAAAATAAAAATACTACTAATACTTCAGTAGATAAAA
ATAGTAAGGAAATTGAATCTCCTAAAGACGTTACATCATCAAATAAAAAAACTTATGATCCAAT
CTTACAAGTAGGTTCTAATCAACATATGTCAGATGATCCTGGTGCTAATAATAAAGAATCCCTA
CCAAATTCAAGTCCAGCAATAATACAAAATGACTCGCATGCTCAAAATAATGTAAAGATGGAA
GAAAATAAATCAGCTACTCCACAACATGATCCAATTGAACAAAGTAATTTTAAAAATAGCCTTA
CTACAACAAGTAAAACTCCTGCTATTCCTTCAGAAGAAGAAATTAAAGCTAACTTAGATGAATT
TGCACAAGAAGAGTATGAGCAAACATCTCTTTCAGAAATTAAAAATGCCACGCAAATTGTTAAT
CATGCTAATCCTGAAAACAAATTAAACAATACACTCCTTGAGTTTGAAAAAGATTATGAAACTT
TATCAAACTTGTTATTCTCTAATTTAGACGCATCTCCTTTGAATAGAAAAATAAAGACTATTATG
CCTAAATTACAAGAAATGCGTTCTTTTATGGAGCAAGCAACTAATTCTTGGGTATCTGCTAAAG
GCATGCTAGATGAGGCTAAGGATAAACTAGCAGAATCTATTTATAAAAGACTATACAATGGCA
ATTCATACCGGTTCGGTGGCAGTTTTAACGGACGTGATATGCAACATGCAAAAAATTTAGCATA
CAGAGCTATAGACTTTGCTTCTGCATGCATTGAATATACACAAAAAGCTATTGATTATCTTCAA
CAGGGAAATTCTTGCAAAAAAGAAATAGAAAATATATTCAAGCTTTAA t28-2.nt (SEQ ID NO:634)
AAAAGATCATCAAGAAAATAAAAATACTACTAATACTTCAGTAGATAAAAATAGTAAGGAAAT
TGAATCTCCTAAAGACGTTACATCATCAAATAAAAAAACTTATGATCCAATCTTACAAGTAGGT
TCTAATCAACATATGTCAGATGATCCTGGTGCTAATAATAAAGAATCCCTACCAAATTCAAGTC
CAGCAATAATACAAAATGACTCGCATGCTCAAAATAATGTAAAGATGGAAGAAAATAAATCAG
CTACTCCACAACATGATCCAATTGAACAAAGTAATTTTAAAAATAGCCTTACTACAACAAGTAA
AACTCCTGCTATTCCTTCAGAAGAAGAAATTAAAGCTAACTTAGATGAATTTGCACAAGAAGAG
TATGAGCAAACATCTCTTTCAGAAATTAAAAATGCCACGCAAATTGTTAATCATGCTAATCCTG
AAAACAAATTAAACAATACACTCCTTGAGTTTGAAAAAGATTATGAAACTTTATCAAACTTGTT
ATTCTCTAATTTAGACGCATCTCCTTTGAATAGAAAAATAAAGACTATTATGCCTAAATTACAA
GAAATGCGTTCTTTTATGGAGCAAGCAACTAATTCTTGGGTATCTGCTAAAGGCATGCTAGATG
AGGCTAAGGATAAACTAGCAGAATCTATTTATAAAAGACTATACAATGGCAATTCATACCGGTT
CGGTGGCAGTTTTAACGGACGTGATATGCAACATGCAAAAAATTTAGCATACAGAGCTATAGA
CTTTGCTTCTGCATGCATTGAATATACACAAAAAGCTATTGATTATCTTCAACAGGGAAATTCTT
GCAAAAAAGAAATAGAAAATATATTCAAG f28-2.aa (SEQ ID NO:635)
KGNINIMRLCLIKIFIIPNLVFSSLFLFESCSGFLSKKSIEQFALALKDHQENKNTTNTSVDKNSKEIESP
KDVTSSNKKTYDPILQVGSNQHMSDDPGANNKESLPNSSPAIIQNDSHAQNNVKMEENKSATPQHD
PIEQSNFKNSLTTTSKTPAIPSEEEIKANLDEFAQEEYEQTSLSEIKNATQIVNHANPENKLNNTLLEFE
KDYETLSNLLFSNLDASPLNRKIKTIMPKLQEMRSFMEQATNSWVSAKGMLDEAKDKLAESIYKRL
YNGNSYRFGGSFNGRDMQHAKNLAYRAIDFASACIEYTQKAIDYLQQGNSCKKEIENIFKL t28-2.aa (SEQ ID NO:636)
KDHQENKNTTNTSVDKNSKEIESPKDVTSSNKKTYDPILQVGSNQHMSDDPGANNKESLPNSSPAII
QNDSHAQNNVKMEENKSATPQHDPIEQSNFKNSLTTTSKTPAIPSEEEIKANLDEFAQEEYEQTSLSE
IKNATQIVNHANPENKLNNTLLEFEKDYETLSNLLFSNLDASPLNRKIKTIMPKLQEMRSFMEQATN
SWVSAKGMLDEAKDKLAESIYKRLYNGNSYRFGGSFNGRDMQHAKNLAYRAIDFASACIEYTQKA
IDYLQQGNSCKKEIENIFK f28-3.nt (SEQ ID NO:637)
TAGATGAATTTAATTGCTAAATTATTTATTTTATCCACTTTAGTTTCAATTCCAAATATCCTCTCT
TGTAACCTATATGATAATCTTGCAGACAACGCTGAGCAGGTTACAGACATACTAGACAACAACA
AGTCTTTTAATACTTTAGGAAGCAGCAATGAGAGTAGAAGTCGCAGGCCTAGAAGTACAAATA
ATGCTTATATGAAACAAAACATAGACAAAAATCATTTAGTTGTTGCAGATATGCAAAATGATAA
TAGTAGCAGCAGTCTTCCCCAACAAGTTAATAGTGAATCCAGTAAAGCTAATGAAGATAGTAAT
ATTATGAAGGAAATTGAATCTTCTACAGAAGAGTGCGCTAGACTAAGAAAAGATTTAGAAACT
ATAAAACAAATACTTGATAATATAGAAAGCTTGCTTAATACAGCTAATTCTTATTTAGAACG
CTAGAAAAGCACCTAAATCTAATCAAGATAATCAAACCTTATTGCTTAGCCTGCACCAAGCTAT

TABLE 1-continued

Nucleotide and Amino Acid Sequences.

TGCTAAGGTTAAGAGTAGTCATACTTCTTTTATCATTTGTTATAATGATGCATTTAATTCCCTGG
GAATAGCTGATACTGCCTTTAAAGATGCAAAGAGAAAGGCAGTTGAGGCATAA t28-3.nt (SEQ ID NO:638)
TTGTAACCTATATGATAATCTTGCAGACAACGCTGAGCAGGTTACAGACATACTAGACAACAAC
AAGTCTTTTAATACTTTAGGAAGCAGCAATGAGAGTAGAAGTCGCAGGCCTAGAAGTACAAAT
AATGCTTATATGAAACAAAACATAGACAAAAATCATTTAGTTGTTGCAGATATGCAAAATGATA
ATAGTAGCAGCAGTCTTCCCCAACAAGTTAATAGTGAATCCAGTAAAGCTAATGAAGATAGTAA
TATTATGAAGGAAATTGAATCTTCTACAGAAGAGTGCGCTAGACTAAGAAAAGATTTAGAAAC
TATAAAACAAATACTTGATAATATAGAAAGCTTGCTTAATACAGCTAATTCTTATTTAGAGAAC
GCTAGAAAAGCACCTAAATCTAATCAAGATAATCAAACCTTATTGCTTAGCCTGCACCAAGCTA
TTGCTAAGGTTAAGAGTAGTCATACTTCTTTTATCATTTGTTATAATGATGCATTTAATTCCCTG
GGAATAGCTGATACTGCCTTTAAAGATGCAAAGAGAAAGGCAGTTGAGGCA f28-3.aa (SEQ ID NO:639)
MNLIAKLFILSTLVSIPNILSCNLYDNLADNAEQVTDILDNNKSFNTLGSSNESRSRRPRSTNNAYMK
QNIDKNHLVVADMQNDNSSSSLPQQVNSESSKANEDSNIMKEIESSTEECARLRKDLETIKQILDNIE
SLLNTANSYLENARKAPKSNQDNQTLLLLSLHQAIAKVKSSHTSFIICYNDAFNSLGIADTAFKDAKR
KAVEA t28-3.aa (SEQ ID NO:640)
CNLYDNLADNAEQVTDILDNNKSFNTLGSSNESRSRRPRSTNNAYMKQNIDKNHLVVADMQNDNS
SSSLPQQVNSESSKANEDSNIMKEIESSTEECARLRKDLETIKQILDNIESLLNTANSYLENARKAPKS
NQDNQTLLLLSLHQAIAKVKSSHTSFIICYNDAFNSLGIADTAFKDAKRKAVEA f31-2.nt (SEQ ID NO:641)
TAAAAAAATAAGGAGGTATTAATGAAAAGGAAAAGCAATATATGTATTTCACTTCTAG
TCACAATATTATTTGTGTCTTGCAAGTTTTTTGGAAATAAAAGCGCAAGTAAAGAAAAAGAAGA
AACTTCTTTTTCTGATACTGCTAGCAAGATTAGTAAGTCGGGAACAGCTGCTTCTTCAGACAAA
CAAGAAAAAAATACAAGTGATGTTACAGGTGACGCCAAAAAGCATACTAGTAGCCCTTACATG
CTTGCTGATGCCCTTATTGTTAGTGATACTACTAATAGAGATAGAGATAAGCAAGAAAATAAAG
ATAAATTAAATGAAGAAGATAAAAAAAAGCTTAATGCTTTTTTTAGCACAACTAAAACATATCA
ATCTAGCCTAGATTCCATTTATAACAAATATACAGGCTATTATAATACCATTGATACCTATGGC
AGCTGTGATACGTATCGCATTGAGTGTTTTAGTGTAGGACCTTCTGAAAAACGTAAACAAGCTC
TTGCTGATCTAGAGAAGTTAAAACTAGACGAAAAGTACACTCAGCTTAGCACAATGTTAAAGA
GTGCTGTGCCTAGTTATTACAAAAAAAATTTAGATGATTCTATTGCACAGTATAAGGAAGCCAT
AAAGCAGGCTATTGAAGCTGAAAGTAAAATAGAGACAGTAAAAGACTATGCAACAGCTCAAAG
TGCTGCCGATGACGAAAAGAAAAGAAATATAGATAATTTAAAAATAGTTAGAGATGTTCTTCTT
ATTATTAAAAAAACTATTGAGAAAGCCAGCCGATCTTATGCTGATGCTTTTGCTATTGCAACAT
CTAGCTTATCTTGTAGCGAATTTAAGCAAGCTGTTAAAGAGTTTAATGATGCTGCTAAACAATA
TGCTAATGGAAATAAAGGAGACAATGCTGTCAATGTTATTGTAGGCACTATTTCTAGTATGCCT
TATGTCAAATTTAAAGATGAGTTTGCAAGAGCAAAAATGTTTGCTCGTAATTATAGAGGAGACG
AGGTAGACAAGATGATAAGAGCTATCGACAAGCTGTGTGATGTTTATAAAAAAGTTGCGCTTTA
G t31-2.nt (SEQ ID NO:642)
TTGCAAGTTTTTTGGAAATAAAAGCGCAAGTAAAGAAAAAGAAGAAACTTCTTTTTCTGATACT
GCTAGCAAGATTAGTAAGTCGGGAACAGCTGCTTCTTCAGACAAACAAGAAAAAAATACAAGT
GATGTTACAGGTGACGCCAAAAAGCATACTAGTAGCCCTTACATGCTTGCTGATGCCCTTATTG
TTAGTGATACTACTAATAGAGATAGAGATAAGCAAGAAAATAAAGATAAATTAAATGAAGAAG
ATAAAAAAAAGCTTAATGCTTTTTTTAGCACAACTAAAACATATCAATCTAGCCTAGATTCCAT
TTATAACAAATATACAGGCTATTATAATACCATTGATACCTATGGCAGCTGTGATACGTATCGC
ATTGAGTGTTTTAGTGTAGGACCTTCTGAAAAACGTAAACAAGCTCTTGCTGATCTAGAGAAGT
TAAAACTAGACGAAAAGTACACTCAGCTTAGCACAATGTTAAAGAGTGCTGTGCCTAGTTATTA
CAAAAAAAATTTAGATGATTCTATTGCACAGTATAAGGAAGCCATAAAGCAGGCTATTGAAGC
TGAAAGTAAAATAGAGACAGTAAAAGACTATGCAACAGCTCAAAGTGCTGCCGATGACGAAAA
GAAAAGAAATATAGATAATTTAAAAATAGTTAGAGATGTTCTTCTTATTATTAAAAAAACTATT
GAGAAAGCCAGCCGATCTTATGCTGATGCTTTTGCTATTGCAACATCTAGCTTATCTTGTAGCG
AATTTAAGCAAGCTGTTAAAGAGTTTAATGATGCTGCTAAACAATATGCTAATGGAAATAAAGG
AGACAATGCTGTCAATGTTATTGTAGGCACTATTTCTAGTATGCCTTATGTCAAATTTAAAGAT
GAGTTTGCAAGAGCAAAAATGTTTGCTCGTAATTATAGAGGAGACGAGGTAGACAAGATGATA
AGAGCTATCGACAAG f31-2.aa (SEQ ID NO:643)
KNKEVLMKRKSNICISLLVTILFVSCKFFGNKSASKEKEETSFSDTASKISKSGTAASSDKQEKNTSD
VTGDAKKHTSSPYMLADALIVSDTTNRDRDKQENKDKLNEEDKKKLNAFFSTTKTYQSSLDSIYNK
YTGYYNTIDTYGSCDTYRIECFSVGPSEKRKQALADLEKLKLDEKYTQLSTMLKSAVPSYYKKNLD
DSIAQYKEAIKQAIEAESKIETVKDYATAQSAADDEKKRNIDNLKIVRDVLLIIKKTIEKASRSYADAF
AIATSSLSCSEFKQAVKEFNDAAKQYANGNKGDNAVNVIVGTISSMPYVKFKDEFARAKMFARNY
RGDEVDKMIRAIDKLCDVYKKVAL t31-2.aa (SEQ ID NO:644)
CKFFGNKSASKEKEETSFSDTASKISKSGTAASSDKQEKNTSDVTGDAKKHTSSPYMLADALIVSDT
TNRDRDKQENKDKLNEEDKKKLNAFFSTTKTYQSSLDSIYNKYTGYYNTIDTYGSCDTYRIECFSV
GPSEKRKQALADLEKLKLDEKYTQLSTMLKSAVPSYYKKNLDDSIAQYKEAIKQAIEAESKIETVKD
YATAQSAADDEKKRNIDNLKIVRDVLLIIKKTIEKASRSYADAFAIATSSLSCSEFKQAVKEFNDAAK
QYANGNKGDNAVNVIVGTISSMPYVKFKDEFARAKMFARNYRGDEVDKMIRAIDK

TABLE 1-continued

Nucleotide and Amino Acid Sequences.

f32-4.nt (SEQ ID NO:645)
TAAGGAAATATGAGGAATATTAGCAATTGTATCAAATATATTATATTAACAATGCTTATTGGAT
TATTAATTTTTTGTTGTGCAACCTTTGTTTGGTTGATTGGAATTTTTTATTCAAATAACTTTAAA
GAAGAGCGGAATTATTCAATAAGCCCAATAGATAGTGTTATTATGCGTAAATGTTATTTTAAAG
AATTTAAGTCTGGACTTATTAAAAGCGTATTCTTTAAGAAATTAGATGTAAATGTTAACTCTAA
AAATTTTAAGGAGCTAAATAAGGTAGATAAACAAAATCTGCTAAATTCTTATCCATCTTATCAT
ATGGAGTTTGTCGTAGTTGATAATGGATTTTTAATGAATTTTAAAAATGTTATTTTAATGGTAT
AGATGATGCTAAATTATACGATCAACGTGATATGGTTTACGGAGGATTTAGATACTCAAAAGAG
GCTTATTTCCAAATTATTGGCAATTATGATGTTAAATTAAATAAAATGAACAATATACTCCAG
CAATTGTAGTAAATGTTTTCAAAATTAACATTAATGATGCTTTATTTAACTCGTTATTAAAGCAA
AAAACTTTAAAAGTTACTTTGATTTCCCATAATAATAAAGAGTATATTTTACAAACTAATAATTT
CTTATCAAAGTATAATTTTCAAACACCAGAAAAGGAGAATAGTTCTTACTAA t32-4.nt (SEQ ID NO:646)
AAATAACTTTAAAGAAGAGCGGAATTATTCAATAAGCCCAATAGATAGTGTTATTATGCGTAAA
TGTTATTTTAAAGAATTTAAGTCTGGACTTATTAAAAGCGTATTCTTTAAGAAATTAGATGTAA
ATGTTAACTCTAAAAATTTTAAGGAGCTAAATAAGGTAGATAAACAAAATCTGCTAAATTCTTA
TCCATCTTATCATATGGAGTTTGTCGTAGTTGATAATGGATTTTTAATGAATTTTAAAAATGTTA
TTTTTAATGGTATAGATGATGCTAAATTATACGATCAACGTGATATGGTTTACGGAGGATTTAG
ATACTCAAAAGAGGCTTATTTCCAAATTATTGGCAATTATGATGTTAAATTAAATAAAATGAAA
CAATATACTCCAGCAATTGTAGTAAATGTTTTCAAAATTAACATTAATGATGCTTTATTTAACTC
GTTATTAAAGCAAAAAACTTTAAAAGTTACTTTGATTTCCCATAATAATAAAGAGTATATTTTA
CAAACTAATAATTTCTTATCAAAGTATAATTTTCAAACACCAGAAAAGGAGAATAGTTCTTAC f32-4.aa (SEQ ID NO:647)
GNMRNISNCIKYIILTMLIGLLIFCCATFVWLIGIFYSNNFKEERNYSISPIDSVIMRKCYFKEFKSGLIK
SVFFKKLDVNVNSKNFKELNKVDKQNLLNSYPSYHMEFVVVDNGFLMNFKNVIFNGIDDAKLYDQ
RDMVYGGFRYSKEAYFQIIGNYDVKLNKMKQYTPAIVVNVFKININDALFNSLLKQKTLKVTLISHN
NKEYILQTNNFLSKYNFQTPEKENSSY t32-4.aa (SEQ ID NO:648)
NNFKEERNYSISPIDSVIMRKCYFKEFKSGLIKSVFFKKLDVNVNSKNFKELNKVDKQNLLNSYPSY
HMEFVVVDNGFLMNFKNVIFNGIDDAKLYDQRDMVYGGFRYSKEAYFQIIGNYDVKLNKMKQYT
PAIVVNVFKININDALFNSLLKQKTLKVTLISHNNKEYILQTNNFLSKYNFQTPEKENSSY f4-15.nt (SEQ ID NO:649)
TAAATGAGCAAAAAGTAATTTTAATATTACTAGAAATTTTGATCTTGTCTTGTGATTTATCTAT
AAATAAAGAACAAAAAACCAAAGAAAAAACATCTGAAAAGCAAGAATCTGAAAAACAAAATA
TTGAAAAACAAGAGCCTGAAAAACAGAAACAAAATGCAGCAAAAATAATCCCTACGGTATCAA
TTCAAACGGTAGAAATAAGGGAATCAAATCAAATTCCAAAAAGCATTGAGAAGTACTACAAGC
AAGCTTATCCGATTCAAACATTCACTCTTGATTTTAGCATCACAAGAGAAAAGGAATTTCTAAA
ACCAGAAGATAAAATCTTGCCCACACAGGGGAAAGTGGAGTCTTTGAGCATCTTAATAAATAA
AAAATTGTTAGACTTTAAAGCCCCAGAAAATCCAAAAAGCTCAACTTTAAAAAATTTCAAAGAA
ATTAAAAATATTGAGAATTTCTTCCAAAATCAAGACTTATTATTTGTCTTAACCCTTAAAGATAA
AAATAACAACAACACTATTAACATCATGCTCAATCCCCCAAACGACATCCAAAAACCCAAAGAT
TATATTTTAAAAGACCTTAAAGACACAATTAAAAAGGGTACTGGTGAGAAATACTTAAATCCTA
TCTATAGATTTCAAATAAAAAACAAAAAAGATTATCATTCAATAGATTACAACAAAGTGACTAT
TAGCGAAAAAACAATAGAATTGGACCTACTGCCTCACGAACAAGTCTTTCAAATGAATAAAAAT
TTCACTAAAATTTTAGACACAATAACAGACTTAAATAATCTAAAATTAGTAATTCAAAAAGAAT
TAGTGTAA t4-15.nt (SEQ ID NO:650)
TTGTGATTTATCTATAAATAAAGAACAAAAAACCAAAGAAAAAACATCTGAAAAGCAAGAATC
TGAAAAACAAAATATTGAAAAACAAGAGCCTGAAAAACAGAAACAAAATGCAGCAAAAATAAT
CCCTACGGTATCAATTCAAACGGTAGAAATAAGGGAATCAAATCAAATTCCAAAAAGCATTGA
GAAGTACTACAAGCAAGCTTATCCGATTCAAACATTCACTCTTGATTTTAGCATCACAAGAGAA
AAGGAATTTCTAAACCAGAAGATAAAATCTTGCCCACACAGGGGAAAGTGGAGTCTTTGAGC
ATCTTAATAAATAAAAAATTGTTAGACTTTAAAGCCCCAGAAAATCCAAAAAGCTCAACTTTAA
AAAATTTCAAAGAAATTAAAAATATTGAGAATTTCTTCCAAAATCAAGACTTATTATTTGTCTT
AACCCTTAAAGATAAAAATAACAACAACACTATTAACATCATGCTCAATCCCCCAAACGACATC
CAAAAACCCAAAGATTATATTTTAAAAGACCTTAAAGACACAATTAAAAAGGGTACTGGTGAG
AAATACTTAAATCCTATCTATAGATTTCAAATAAAAAACAAAAAAGATTATCATTCAATAGATT
ACAACAAAGTGACTATTAGCGAAAAAACAATAGAATTGGACCTACTGCCTCACGAACAAGTCTT
TCAAATGAATAAAAATTTCACTAAA f4-15.aa (SEQ ID NO:651)
MSKKVILILLEILILSCDLSINKEQKTKEKTSEKQESEKQNIEKQEPEKQKQNAAKIIPTVSIQTVEIRES
NQIPKSIEKYYKQAYPIQTFTLDFSITREKEFLKPEDKILPTQGKVESLSILINKKLLDFKAPENPKSSTL
KNFKEIKNIENFFQNQDLLFVLTLKDKNNNNTINIMLNPPNDIQKPKDYILKDLKDTIKKGTGEKYLN
PIYRFQIKNKKDYHSIDYNKVTISEKTIELDLLPHEQVFQMNKNFTKILDTITDLNNLKLVIQKELV t4-15.aa (SEQ ID NO:652)
CDLSINKEQKTKEKTSEKQESEKQNIEKQEPEKQKQNAAKIIPTVSIQTVEIRESNQIPKSIEKYYKQA
YPIQTFTLDFSITREKEFLKPEDKILPTQGKVESLSILINKKLLDFKAPENPKSSTLKNFKEIKNIENFFQ
NQDLLFVLTLKDKNNNNTINIMLNPPNDIQKPKDYILKDLKDTIKKGTGEKYLNPIYRFQIKNKKDY
HSIDYNKVTISEKTIELDLLPHEQVFQMNKNFTK

TABLE 1-continued

Nucleotide and Amino Acid Sequences.

f4-50.nt (SEQ ID NO:653)
TAGAAGGAGGAAAAAATGAAAATTGGAAAGCTAAATTCAATAGTTATAGCCTTGTTTTTAAAC
TATTGGTCGCATGTAGTATTGGATTAGTAGAAAGAACAAATGCAGCTCTTGAATCGTCCTCTAA
GGATTTAAAAAACAAAATTTTAAAAATAAAAAAAGAAGCCACGGGAAAAGGTGTACTTTTTGA
AGCTTTTACAGGTCTTAAAACCGGTTCCAAGGTAACAAGTGGTGGACTAGCCTTAAGAGAAGCA
AAAGTACAAGCCATTGTTGAAACAGGAAAGTTCCTTAAGATAATAGAAGAAGAAGCTTTAAAG
CTTAAAGAAACTGGAAACAGTGGTCAATTCTTGGCTATGTTTGACTTAATGCTTGAGGTTGTAG
AATCGCTAGAAGACGTTGGAATAATAGGCTTAAAAGCCCGTGTTTTAGAGGAATCTAAAAATA
ATCCTATAAACACAGCTGAAAGATTGCTTGCGGCTAAAGCTCAAATAGAAAATCAACTTAAAGT
GGTTAAGGAAAAACAAAATATTGAAAATGGTGGAGAGAAAAAAAATAATAAAAGCAAAAAAA
AGAAATAA t4-50.nt (SEQ ID NO:654)
ATGTAGTATTGGATTAGTAGAAAGAACAAATGCAGCTCTTGAATCGTCCTCTAAGGATTTAAAA
AACAAAATTTTAAAAATAAAAAAAGAAGCCACGGGAAAAGGTGTACTTTTTGAAGCTTTTACA
GGTCTTAAAACCGGTTCCAAGGTAACAAGTGGTGGACTAGCCTTAAGAGAAGCAAAAGTACAA
GCCATTGTTGAAACAGGAAAGTTCCTTAAGATAATAGAAGAAGAAGCTTTAAAGCTTAAAGAA
ACTGGAAACAGTGGTCAATTCTTGGCTATGTTTGACTTAATGCTTGAGGTTGTAGAATCGCTAG
AAGACGTTGGAATAATAGGCTTAAAAGCCCGTGTTTTAGAGGATCTAAAAATAATCCTATAAA
CACAGCTGAAAGATTGCTTGCGGCTAAAGCTCAAATAGAAAATCAACTTAAAGTGGTTAAGGA
AAAACAAAATATTGAAAATGGTGGAGAGAAAAAAAATAATAAAAGCAAAAAAAAGAAA f4-50.aa (SEQ ID NO:655)
KEEKMKIGKLNSIVIALFFKLLVACSIGLVERTNAALESSSKDLKNKILKIKKEATGKGVLFEAFTGL
KTGSKVTSGGLALREAKVQAIVETGKFLKIIEEEALKLKETGNSGQFLAMFDLMLEVVESLEDVGIIG
LKARVLEESKNNPINTAERLLAAKAQIENQLKVVKEKQNIENGGEKKNNKSKKKK t4-50.aa (SEQ ID NO:656)
CSIGLVERTNAALESSSKDLKNKILKIKKEATGKGVLFEAFTGLKTGSKVTSGGLALREAKVQAIVET
GKFLKIIEEEALKLKETGNSGQFLAMFDLMLEVVESLEDVGIIGLKARVLEESKNNPINTAERLLAAK
AQIENQLKVVKEKQNIENGGEKKNNKSKKKK f4-66.nt (SEQ ID NO:657)
TAATTTTTAAAATTTAAATATTTACATAATAGTAATGTGTGTGGGAGACGTATGAAAAATATTT
TATTATTTGTTATTTTATTATTCTTTTCTTGTAAAGAATTTAATTATTCTGATCTTAGGAGAAGG
CCTTCAAAGGTTTTAAATGCTTCTAATGGTGCATCAAATAAAGAACTTAAAATTTCTTTTGTAG
ATTCTTTAAATGATGATCAAAAAGAAGCTTTGTTTTTTCTTGAACAGGTAGTTCTTGATAGCAAT
CCCGACAAGTTTAATCAAATTTTTAATTTAAATGAAGAGAAGGTAAAAGAAATGCTTGTTACTG
TTGTTAAGTGTTTAAAGGCCAAAAGAAAGGCTAAAATGGCTCTTGAGAGCTCAAATGTTGCAA
ATGTTGCCAATGCTAAACAGCAATTGCTACAGGTTGAAAAAACTTACATAGATAATTTGCGACA
ATCTTTTATGACTACTAAAAACATTGAAGAGGCTTGTAATCTTGTAAAAAATTATGATGCATCT
GCTTCGTTTTAA t4-66.nt (SEQ ID NO:658)
TTGTAAAGAATTTAATTATTCTGATCTTAGGAGAAGGCCTTCAAAGGTTTTAAATGCTTCTAAT
GGTGCATCAAATAAAGAACTTAAAATTTCTTTTGTAGATTCTTTAAATGATGATCAAAAAGAAG
CTTTGTTTTTTCTTGAACAGGTAGTTCTTGATAGCAATCCCGACAAGTTTAATCAAATTTTTAAT
TTAAATGAAGAGAAGGTAAAAGAAATGCTTGTTACTGTTGTTAAGTGTTTAAAGGCCAAAAGA
AAGGCTAAAATGGCTCTTGAGAGCTCAAATGTTGCAAATGTTGCCAATGCTAAACAGCAATTGC
TACAGGTTGAAAAAACTTACATAGATAATTTGCGACAATCTTTTATGACTACTAAAAACATTGA
AGAGGCTTGTAATCTTGTAAAAAATTATGATGCATCTGCTTCGTTT f4-66.aa (SEQ ID NO:659)
FLKFKYLHNSNVCGRRMKNILLFVILLFFSCKEFNYSDLRRRPSKVLNASNGASNKELKISFVDSLND
DQKEALFFLEQVVLDSNPDKFNQIFNLNEEKVKEMLVTVVKCLKAKRKAKMALESSNVANVANAK
QQLLQVEKTYIDNLRQSFMTTKNIEEACNLVKNYDASASF t4-66.aa (SEQ ID NO:660)
CKEFNYSDLRRRPSKVLNASNGASNKELKISFVDSLNDDQKEALFFLEQVVLDSNPDKFNQIFNLNE
EKVKEMLVTVVKCLKAKRKAKMALESSNVANVANAKQQLLQVEKTYIDNLRQSFMTTKNIEEAC
NLVKNYDASASF f42-1.nt (SEQ ID NO:661)
TAATTATTAAAATCTAAGGAGAAGAGATTTATGAACAAAAAATTTTCTATTTCATTATTATCTA
CAATATTAGCCTTCTTGTTAGTATTAGGTTGTGATTTGTCAAGCAATAATGCTGAAAACAAAAT
GGATGATATTTTTAATTTAGAAAAGAAATACATGGATAATTCAAATTATAAATGTTTAAGTAAA
AATGAGGCTATAGTTAAAAATTCTAAAATTAAATTAGGTGTAAATAATACTAGAAGTCGTTCTT
ATTCTTCTAGAGAGACTAATGTTTCGGATTCCTATAATAAAACCTATTCATATTGCAAAAGCAA
CTGA t42-1.nt (SEQ ID NO:662)
TTGTGATTTGTCAAGCAATAATGCTGAAAACAAAATGGATGATATTTTTAATTTAGAAAAGAAA
TACATGGATAATTCAAATTATAAATGTTTAAGTAAAAATGAGGCTATAGTTAAAAATTCTAAAA
TTAAATTAGGTGTAAATAATACTAGAAGTCGTTCTTATTCTTCTAGAGAGACTAATGTTTCGGA
TTCCTATAATAAAACCTATTCATATTGCAAAAGCAAC

TABLE 1-continued

Nucleotide and Amino Acid Sequences.

f42-1.aa (SEQ ID NO:663)
LLKSKEKRFMNKKFSISLLSTILAFLLVLGCDLSSNNAENKMDDIFNLEKKYMDNSNYKCLSKNEAI
VKNSKIKLGVNNTRSRSYSSRETNVSDSYNKTYSYCKSN t42-1.aa (SEQ ID NO:664)
CDLSSNNAENKMDDIFNLEKKYMDNSNYKCLSKNEAIVKNSKIKLGVNNTRSRSYSSRETNVSDSY
NKTYSYCKSN f43-3.nt (SEQ ID NO:665)
TGAATATTAATAATAAAAAAAGGAATAANAATGAAAATTATCAACATATTATTTTGTTTATTTT
TACTAATGCTAAACAGCTGTAATTCTAATGATACTAATACTAGCCAAACAAAAAGTAGACAAAA
ACGTGATTTAACCCAAAAAGAAGCAACACAAGAAAAACCAAAATCTAAAGAAGACCTGCTTAG
AGAAAAGCTATCTGAAGACCAAAAAACACATCTTGACTGGTTAAAAACCGCTTTAACTGGTGCT
GGAGAATTTGATAAATTTTTAGGATATGACGAAGACAAAATAAAAGGTGCACTTAATCATATA
AAGAGTGAACTTGATAAGTGTACTGGGGATAATTCTGAACAACAAAAAAGCACCTTCAAAGAG
GTGGTTAAGGGGGCTCTTGGTGGCGGTATAGATAGTTTTGCAACTAGTGCAAGTAGTACCTGCC
AAGCTCAGCAATAA t43-3.nt (SEQ ID NO:666)
CTGTAATTCTAATGATACTAATACTAGCCAAACAAAAAGTAGACAAAAACGTGATTTAACCCAA
AAAGAAGCAACACAAGAAAAACCAAAATCTAAAGAAGACCTGCTTAGAGAAAAGCTATCTGAA
GACCAAAAAACACATCTTGACTGGTTAAAAACCGCTTTAACTGGTGCTGGAGAATTTGATAAAT
TTTTAGGATATGACGAAGACAAAATAAAAGGTGCACTTAATCATATAAAGAGTGAACTTGATA
AGTGTACTGGGGATAATTCTGAACAACAAAAAAGCACCTTCAAAGAGGTGGTTAAGGGGGCTC
TTGGTGGCGGTATAGATAGTTTTGCAACTAGTGCAAGTAGTACCTGCCAAGCTCAGCAA f43-3.aa (SEQ ID NO:667)
ILIIKKGIXMKIINILFCLFLLMLNSCNSNDTNTSQTKSRQKRDLTQKEATQEKPKSKEDLLREKLSED
QKTHLDWLKTALTGAGEFDKFLGYDEDKIKGALNHIKSELDKCTGDNSEQQKSTFKEVVKGALGG
GIDSFATSASSTCQAQQ t43-3.aa (SEQ ID NO:668)
CNSNDTNTSQTKSRQKRDLTQKEATQEKPKSKEDLLREKLSEDQKTHLDWLKTALTGAGEFDKFL
GYDEDKIKGALNHIKSELDKCTGDNSEQQKSTFKEVVKGALGGGIDSFATSASSTCQAQQ f45-2.nt (SEQ ID NO:669)
TAGGAGAGAATAATTATGAATAAAAAAACATTGATTATTTGTGCTGTTTTTGCGCTGATAATTT
CTTGCAAGAATTTTGCAACTGGTAAAGATATAAAACAAAATTCAGAAGGGAAAATTAAAGGAT
TTGTAAATAAGATTTTAGATCCAGTAAAGGATAAAATTGCTTCAAGTGGTACAAAAGTAGATGA
AGTAGCAAAAAAATTACAAGAAGAAGAAAAAGAAGAATTAATGCAGGGCGATGATCCTAATGG
CAGTGGAATAAATCCGCCACCAGTATTGCCGGAAAATATTCACAATAATGCATTAGTATTAAAA
GCAATAGAACAAAGTGATGGTCAACAAGAAAAAAAAGTAGAAGAAGCTGAAGCTAAAGTTGA
AGAAAATAAAGAAAAACAAGAGAATACAGAAGAAAACATTAAAGAAAAAGAAATAATAGACG
AACAAAACAAACAAGAATTAGCTAAAGCTAAAGAAGAAGAACAACAAAAAGAACAAAAAAGA
CATCAAGAAGAGCAACAAAGAAAAGCTAAAGCAGAAAAAGAAAAAAGAGAAAGAGAAGAGGC
AGAACAACAAAAACGACAACAAGAAGAGGAAGAAAAAAGGCAAGTTGATAACCAAATTAAAA
CACTTATAGCTAAAATAGATGAGATCAATGAAAATATTGATGTTATAAAATGGCAAACGACTGT
AGGCCCACAAGGCGTTATAGATAGAATTACTGGGCCTGTGTATGATGATTTTACCAATGGCAAT
AATTCTATACGCGAAACTTGGGAGGGGTTAGAAGAGGAATCAGAAGACGAAGGATTAGGAAAA
TTATTGAAAGAATTGAGTGATGCTAGGGACGCGCTAAGAACTAAATTAAATGAAGGCAATAAA
CCATATACTGGTTACGAAGAGCCTAAGTTAAAAGAAAGTGTAAATGTTAGCGAAATTAAAGAA
GATTTAGAAAAATTAAAATCAAAATTAGAAGAAGTTAAAAAATATCTTAAAGATAGTTCTAAAT
TTGAAGAAATTAAAGGATACATCAGTGACAGTCAGTAA t45-2.nt (SEQ ID NO:670)
TTGCAAGAATTTTGCAACTGGTAAAGATATAAAACAAAATTCAGAAGGGAAAATTAAAGGATT
TGTAAATAAGATTTTAGATCCAGTAAAGGATAAAATTGCTTCAAGTGGTACAAAAGTAGATGA
AGTAGCAAAAAAATTACAAGAAGAAGAAAAAGAAGAATTAATGCAGGGCGATGATCCTAATGG
CAGTGGAATAAATCCGCCACCAGTATTGCCGGAAAATATTCACAATAATGCATTAGTATTAAAA
GCAATAGAACAAAGTGATGGTCAACAAGAAAAAAAAGTAGAAGAAGCTGAAGCTAAAGTTGA
AGAAAATAAAGAAAAACAAGAGAATACAGAAGAAAACATTAAAGAAAAAGAAATAATAGACG
AACAAAACAAACAAGAATTAGCTAAAGCTAAAGAAGAAGAACAACAAAAAGAACAAAAAAGA
CATCAAGAAGAGCAACAAAGAAAAGCTAAAGCAGAAAAAGAAAAAAGAGAAAGAGAAGAGGC
AGAACAACAAAAACGACAACAAGAAGAGGAAGAAAAAAGGCAAGTTGATAACCAAATTAAAA
CACTTATAGCTAAAATAGATGAGATCAATGAAAATATTGATGTTATAAAATGGCAAACGACTGT
AGGCCCACAAGGCGTTATAGATAGAATTACTGGGCCTGTGTATGATGATTTTACCAATGGCAAT
AATTCTATACGCGAAACTTGGGAGGGGTTAGAAGAGGAATCAGAAGACGAAGGATTAGGAAAA
TTATTGAAAGAATTGAGTGATGCTAGGGACGCGCTAAGAACTAAATTAAATGAAGGCAATAAA
CCATATACTGGTTACGAAGAGCCTAAGTTAAAAGAAAGTGTAAATGTTAGCGAAATTAAAGAA
GATTTAGAAAAATTAAAATCAAAATTAGAAGAAGTTAAAAAATATCTTAAAGATAGTTCTAAAT
TTGAAGAAATTAAAGGATACATCAGTGACAGTCAG f45-2.aa (SEQ ID NO:671)
ERIIMNKKTLIICAVFALIISCKNFATGKDIKQNSEGKIKGFVNKILDPVKDKIASSGTKVDEVAKKLQ
EEEKEELMQGDDPNGSGINPPPVLPENIHNNALVLKAIEQSDGQQEKKVEEAEAKVEENKEKQENT
EENIKEKEIIDEQNKQELAKAKEEEQQKEQKRHQEEQQRKAKAEKEKREREEAEQQKRQQEEEEKR
QVDNQIKTLIAKIDEINENIDVIKWQTTVGPQGVIDRITGPVYDDFTNGNNSIRETWEGLEEESEDEG

TABLE 1-continued

Nucleotide and Amino Acid Sequences.

LGKLLKELSDARDALRTKLNEGNKPYTGYEEPKLKESVNVSEIKEDLEKLKSKLEEVKKYLKDSSKF
EEIKGYISDSQ t45-2.aa (SEQ ID NO:672)
CKNFATGKDIKQNSEGKIKGFVNKILDPVKDKIASSGTKVDEVAKKLQEEEKEELMQGDDPNGSGI
NPPPVLPENIHNNALVLKAIEQSDGQQEKKVEEAEAKVEENKEKQENTEENIKEKEIIDEQNKQELA
KAKEEEQQKEQKRHQEEQQRKAKAEKEKREREEAEQQKRQQEEEEKRQVDNQIKTLIAKIDEINEN
IDVIKWQTTVGPQGVIDRITGPVYDDFTNGNNSIRETWEGLEEESEDEGLGKLLKELSDARDALRTK
LNEGNKPYTGYEEPKLKESVNVSEIKEDLEKLKSKLEEVKKYLKDSSKFEEIKGYISDSQ f47-2.nt (SEQ ID NO:673)
TGAATATTAATAATAAAAAAAGGAGTAACAATGAAAATCATCAACATATTATTTTGTATATCTT
TGCTACTACTAAATAGCTGTAATTCCAATGATAATGACACTTTAAAAAACAATGCCCAACAAAC
AAAAAGCAGGAAAAAACGTGATTTAAGCCAAGAAGAACTGCCACAACAAGAAAAAATCACTTT
AACATCCGACGAAGAAAAAATGTTTACTTCATTAATCAATGTGTTTAAATACACAATTGAAAAA
TTAAACAATGAAATACAAGGGTGCATGAATGGAAACAAAAGTAAATGTAATGACTTCTTTGATT
GGCTTTCTGAAGATATTCAAAAACAAAAGAATTAGCTGGTGCTTTTACCAAGGTTTACAACTT
CTTAAAATCAAAAGCACAAAATGAAACTTTTGATACTTATATTAAAGGAGCTATTGATTGTAAA
AAAAACACTCCACAAGATTGTAATAAAAATAATGAAATATGGGGAGGTGGACAACTTANTAGN
GCAATATTTTAG t47-2.nt (SEQ ID NO:674)
CTGTAATTCCAATGATAATGACACTTTAAAAAACAATGCCCAACAAACAAAAAGCAGGAAAAA
ACGTGATTTAAGCCAAGAAGAACTGCCACAACAAGAAAAAATCACTTTAACATCCGACGAAGA
AAAAATGTTTACTTCATTAATCAATGTGTTTAAATACACAATTGAAAAATTAAACAATGAAATA
CAAGGGTGCATGAATGGAAACAAAAGTAAATGTAATGACTTCTTTGATTGGCTTTCTGAAGATA
TTCAAAAACAAAAGAATTAGCTGGTGCTTTTACCAAGGTTTACAACTTCTTAAAATCAAAAGC
ACAAAATGAAACTTTTGATACTTATATTAAAGGAGCTATTGATTGTAAAAAAAAACACTCCACAA
GATTGTAATAAAAATAATGAA f47-2.aa (SEQ ID NO:675)
ILIIKKGVTMKIINILFCISLLLLNSCNSNDNDTLKNNAQQTKSRKKRDLSQEELPQQEKITLTSDEEK
MFTSLINVFKYTIEKLNNEIQGCMNGNKSKCNDFFDWLSEDIQKQKELAGAFTKVYNFLKSKAQNE
TFDTYIKGAIDCKKNTPQDCNKNNEIWGGGQLXXAIF t47-2.aa (SEQ ID NO:676)
CNSNDNDTLKNNAQQTKSRKKRDLSQEELPQQEKITLTSDEEKMFTSLINVFKYTIEKLNNEIQGCM
NGNKSKCNDFFDWLSEDIQKQKELAGAFTKVYNFLKSKAQNETFDTYIKGAIDCKKNTPQDCNKN
NE f49-2.nt (SEQ ID NO:677)
TAAATGTTCAAAACAATCATTAAACAAAAAAATATGAAAAAAATTTCAAGTGCAATTTTATTAA
CAACTTTCTTTGTTTTTATTAATTGTAAAAGCCAAGTTGCTGATAAGGCGAGTGTGACGGGGAT
TGCTAAGGGAATAAAGGAGATTGTTGAAGCTGCTGGGGGGAGTGAAAAGCTGAAAGTTGCTGC
TGCTGAAGGGGAGAATAATGAAAAGGCAGGGAAGTTGTTTGGGAAGGCTGGTGCTGGTAATGC
TGGGGACAGTGAGGCTGCTAGCAAGGCGGCTGGTGCTGTTAGTGCTGTTAGTGGGGAGCAGAT
ATTAAGTGCGATTGTTAAGGCTGCTGGTGAGGCTGCGCAGGATGGAGAGAAGCCTGGGGAGGC
TAAAAATCCGATTGCTGCTGCTATTGGGAAGGGTAATGAGGATGGTGCGGAGTTTAAGGATGA
GATGAAGAAGGATGATCAGATTGCTGCTGCTATTGCTTTGAGGGGGATGGCTAAGGATGGAAA
GTTTGCTGTGAAGAATGATGAGAAAGGGAAGGCTGAGGGGGCTATTAAGGGAGCTGGCGAGTT
GTTGGATAAGCTGGTAAAAGCTGTAAAGACAGCTGAGGGGGCTTCAAGTGGTACTGCTGCAAT
TGGAGAAGTTGTGGCTGATGATAATGCTGCGAAGGTTGCTGATAAGGCGAGTGTGAAGGGGAT
TGCTAAGGGGATAAAGGAGATTGTTGAAGCTGCTGGGGGGAGTGAAAAAGCTGAAAGTTGCTGC
TGCTAAAGAGGGCAATGAAAAGGCAGGGAAGTTGTTTGGGAAAGTTGATGCTGCTCATGCTGG
GGACAGTGAGGCTGCTAGCAAGGCGGCTGGTGCTGTTAGTGCTGTTAGTGGGGAGCAGATATT
AAGTGCGATTGTTAAGGCTGCTGGTGCGGCTGCTGGTGATCAGGAGGGAAAGAAGCCTGGGGA
TGCTAAAAATCCGATTGCTGCTGCTATTGGGAAGGGTGATGCGGAGTTTAAGGATGGTGCGGAGTTTAA
TCATGATGGGATGAAGAAGGATGATCAGATTGCTGCTGCTATTGCTTTGAGGGGGATGGCTAA
GGATGGAAAGTTTGCTGTGAAGAGTGGTGGTGGTGAGAAAGGGAAGGCTGAGGGGGCTATTAA
GGGAGCTGCTGAGTTGTTGGATAAGCTGGTAAAAGCTGTAAAGACAGCTGAGGGGGCTTCAAG
TGGTACTGATGCAATTGGAGAAGTTGTGGCTAATGCTGGTGCTGCAAAGGTTGCTGATAAGGC
GAGTGTGACGGGGATTGCTAAGGGGATAAAGGAGATTGTTGAAGCTGCTGGGGGGAGTGAAAA
GCTGAAAGTTGCTGCTGCTACAGGGGAGAGTAATAAAGGGGCAGGGAAGTTGTTTGGGAAGGC
TGGTGCTGGTGCTAATGCTGGGGACAGTGAGGCTGCTAGCAAGGCGGCTGGTGCTGTTAGTGC
TGTTAGTGGGGAGCAGATATTAAGTGCGATTGTTAAGGCTGCTGATGCGGCTGATCAGGAGGG
AAAGAAGCCTGGGGATGCTANAAATCCGATTGCTGCTGCTATTGGGAAGGGTNATGNGGAGAA
TGGTGCGGAGTTTAANNATGANGGATGA t49-2.nt (SEQ ID NO:678)
TTGTAAAAGCCAAGTTGCTGATAAGGCGAGTGTGACGGGGATTGCTAAGGGAATAAAGGAGAT
TGTTGAAGCTGCTGGGGGGAGTGAAAAGCTGAAAGTTGCTGCTGCTGAAGGGGAGAATAATGA
AAAGGCAGGGAAGTTGTTTGGGAAGGCTGGTGCTGGTAATGCTGGGGACAGTGAGGCTGCTAG
CAAGGCGGCTGGTGCTGTTAGTGCTGTTAGTGGGGAGCAGATATTAAGTGCGATTGTTAAGGCT
GCTGGTGAGGCTGCGCAGGATGGAGAGAAGCCTGGGGAGGCTAAAAATCCGATTGCTGCTGCT
ATTGGGAAGGGTAATGAGGATGGTGCGGAGTTTAAGGATGAGATGAAGAAGGATGATCAGATT
GCTGCTGCTATTGCTTTGAGGGGGATGGCTAAGGATGGAAAGTTTGCTGTGAAGAATGATGAG
AAAGGGAAGGCTGAGGGGGCTATTAAG

TABLE 1-continued

Nucleotide and Amino Acid Sequences.

f49-2.aa (SEQ ID NO:679)
MFKTIIKQKNMKKISSAILLTTFFVFINCKSQVADKASVTGIAKGIKEIVEAAGGSEKLKVAAAEGEN
NEKAGKLFGKAGAGNAGDSEAASKAAGAVSAVSGEQILSAIVKAAGEAAQDGEKPGEAKNPIAAAI
GKGNEDGAEFKDEMKKDDQIAAAIALRGMAKDGKFAVKNDEKGKAEGAIKGAGELLDKLVKAVK
TAEGASSGTAAIGEVVADDNAAKVADKASVKGIAKGIKEIVEAAGGSKKLKVAAAKEGNEKAGKL
FGKVDAAHAGDSEAASKAAGAVSAVSGEQFLSAIVKAAGAAAGDQEGKKPGDAKNPIAAAIGKGD
AENGAEFNHDGMKKDDQIAAAIALRGMAKDGKFAVKSGGGEKGKAEGAIKGAAELLDKLVKAVK
TAEGASSGTDAIGEVVANAGAAKVADKASVTGIAKGIKEIVEAAGGSEKLKVAAATGESNKGAGK
LFGKAGAGANAGDSEAASKAAGAVSAVSGEQILSAIVKAADAADQEGKKPGDAXNPIAAAIGKGX
XENGAEFXXXG t49-2.aa (SEQ ID NO:680)
CKSQVADKASVTGIAKGIKEIVEAAGGSEKLKVAAAEGENNEKAGKLFGKAGAGNAGDSEAASKA
AGAVSAVSGEQILSAIVKAAGEAAQDGEKPGEAKNPIAAAIGKGNEDGAEFKDEMKKDDQIAAAIA
LRGMAKDGKFAVKNDEKGKAEGAIK f5-14.nt (SEQ ID NO:681)
TAGAAATTCAAAACAAAGGAGAAAACAAAAAGTATGAATAAAAAAATATTGATTATTTTTGCT
GTTTTTGCACTTATAATTTCTTGTAAAAATTATGCAACTGGTAAAGATATAAAACAAAATGCAA
AAGGGAAAATTAAAGGATTTTTAGATAAGGTTTTAGATCCAGCAAAAGATAAAATTACTTCAA
GTAGTTCAAAAGTAGATGAATTAGCAAAAAAATTACAAGAAGAAGATGAAGATAATGAATTAA
TGCAGGGCGATGATCCTAATAACAGAGCAATAGCACTGTTACCAGTATTGCCGGAAAATAGTC
ATGACAATCCACCAGTACCAAAAGTAAAAGCAGCAGCACAAAGTGGTGGTCAACAAGAAGACC
AAAAAGCAAAAGAATCTAAAGATAAAGTTGAGGAAGAAAAAGAAGTTGTAGAGGAGAAAAAA
GAAGAACAAGATAGTAAAAAGAAAAAGTGGAGAAGCAAAGTCAAAAGCAAAAGAAGAAGA
GAGAAACTCTAAAGAAGAACAACAAAAACAAGAAGAAGCAAAAGCTAGAGCAGATAGAGAAA
GAGAAGAACGACTAAAACAACAAGAACAAAAAAGCAACAGGAAGAAGCTAGGGTTAAAGCA
GAAAAAGAAAAACAAGAAAGAGAGGAACAACAAAAACAAGAAGAAGAAAAGAAAGTTAAATA
TAAAATTAAAACACTTACAGACAAAATAGATGAAATAAATAAGGATATTGATGGTATAAATGG
TAAAACAATTGTAGGAGCAGAAGAAGTTATAGATAAAATTACGGGGCCTGTATATGATGATTTT
ACTGATGGGAATAAAGCTATATACAAAACTTGGGGAGATTTAGAGGATGAAGAAGGCGAAGAA
TTAGGAAAATTATTGAAAGAATTGAGTGATACTAGACATAATTTAAGAACCAAATTAAATGAG
GGTAATAAAGCATATATTGTTCTAGAAAAGGAGCCTAATTTAAAAGAAAATGTAAATGTTAGT
GATATTCAATCAGATTTAGAAAAATTAAAATCAGGATTAGAAGAAGTTAAAAAATATTTTGAA
AATGAAGATAATTTTGAAGAAATTAAAGGATACATTGAGGATAGTAATTCATATTGA t5-14.nt (SEQ ID NO:682)
TTGTAAAAATTATGCAACTGGTAAAGATATAAAACAAAATGCAAAAGGGAAAATTAAAGGATT
TTTAGATAAGGTTTTAGATCCAGCAAAAGATAAAATTACTTCAAGTAGTTCAAAAGTAGATGAA
TTAGCAAAAAAATTACAAGAAGAAGATGAAGATAATGAATTAATGCAGGGCGATGATCCTAAT
AACAGAGCAATAGCACTGTTACCAGTATTGCCGGAAAATAGTCATGACAATCCACCAGTACCAA
AAGTAAAAGCAGCAGCACAAAGTGGTGGTCAACAAGAAGACCAAAAAGCAAAAGAATCTAAA
GATAAAGTTGAGGAAGAAAAAGAAGTTGTAGAGGAGAAAAAAGAAGAACAAGATAGTAAAAA
AGAAAAAGTGGAGAAGCAAAGTCAAAAGCAAAAGAAGAAGAGAGAAACTCTAAAGAAGAAC
AACAAAAACAAGAAGAAGCAAAAGCTAGAGCAGATAGAGAAAGAGAAGAACGACTAAAACAA
CAAGAACAAAAAAGACAACAGGAAGAAGCTAGGGTTAAAGCAGAAAAAGAAAAACAAGAAAG
AGAGGAACAACAAAAACAAGAAGAAGAAAAGAAAGTTAAATATAAAATTAAAACACTTACAG
ACAAAATAGATGAAATAAATAAGGATATTGATGGTATAAATGGTAAAACAATTGTAGGAGCAG
AAGAAGTTATAGATAAAATTACGGGGCCTGTATATGATGATTTTACTGATGGGAATAAAGCTAT
ATACAAAACTTGGGGAGATTTAGAGGATGAAGAAGGCGAAGAATTAGGAAAATTATTGAAAGA
ATTGAGTGATACTAGACATAATTTAAGAACCAAATTAAATGAGGGTAATAAAGCATATATTGTT
CTAGAAAAGGAGCCTAATTTAAAAGAAAATGTAAATGTTAGTGATATTCAATCAGATTTAGAA
AAATTAAAATCAGGATTAGAAGAAGTTAAAAAATATTTTGAAAATGAAGATAATTTTGAAGAA
ATTAAAGGATACATTGAGGATAGTAATTCATAT f5-14.aa (SEQ ID NO:683)
KFKTKEKTKSMNKKILIIFAVFALIISCKNYATGKDIKQNAKGKIKGFLDKVLDPAKDKITSSSSKVD
ELAKKLQEEDEDNELMQGDDPNNRAIALLPVLPENSHDNPPVPKVKAAAQSGGQQEDQKAKESKD
KVEEEKEVVEEKKEEQDSKKEKVEKQSQKQKEEERNSKEEQQKQEEAKARADREREERLKQQEQK
RQQEEARVKAEKEKQEREEQQKQEEEKKVKYKIKTLTDKIDEINKDIDGINGKTIVGAEEVIDKITGP
VYDDFTDGNKAIYKTWGDLEDEEGEELGKLLKELSDTRHNLRTKLNEGNKAYIVLEKEPNLKENV
NVSDIQSDLEKLKSGLEEVKKYFENEDNFEEIKGYIEDSNSY t5-14.aa (SEQ ID NO:684)
CKNYATGKDIKQNAKGKIKGFLDKVLKPAKDKITSSSSKVDELAKKLQEEDEDNELMQGDDPNNR
AIALLPVLPENSHDNPPVPKVKAAAQSGGQQEDQKAKESKDKVEEEKEVVEEKKEEQDSKKEKVE
KQSQKQKEEERNSKEEQQKQEEAKARADREREERLKQQEQKRQQEEARVKAEKEKQEREEQQKQ
EEEKKVKYKIKTLTDKIDEINKDIDGINGKTIVGAEEVIDKITGPVYDDFTDGNKAIYKTWGDLEDEE
GEELGKLLKELSDTRHNLRTKLNEGNKAYIVLEKEPNLKENVNVSDIQSDLEKLKSGLEEVKKYFEN
EDNFEEIKGYIEDSNSY f5-15.nt (SEQ ID NO:685)
TAACTTATGAATAAGAAAATGAAAATGTTATTATTTGTGCTGTTTTTGCATTGATGATTTCTTG
CAAGAATTATGCAAGTGGTGAAAATCTAAAAAATTCAGAACAAAATCTAGAAAGTTCAGAACA
AAATGTAAAAAAAACAGAACAAGAGATAAAAAAACAAGTTGAAGGATTTTTAGAAATTCTAGA
GACAAAAGATTTATCTAAATTAGATGAAAAGATACAAAAGAAATTGAAAAACAAATTCAAGA
ATTAAAGAATAAAAATAGAAAAATTAGATTCTAAAAAAACTTCTATTGAAACATATTCTGAGTAT

TABLE 1-continued

Nucleotide and Amino Acid Sequences.

GAAGAAAAAATAAACAAAATAAAAGAAAAATTGAAAGGAAAAGGACTTGAAGATAAATTTAA
GGAGCTTGAAGAGAGTTTAGCAAAGAAAAAGGGGGAGAGAAAAAAAGCTTTACAAGAGGCCA
AACAGAAATTTGAAGAATATAAAAAACAAGTAGATACTTCAACTGGGAAAACTCAAGGCGACA
GGTCTAAAAACCGAGGTGGTGTTGGAGTGCAAGCTTGGCAGTGTGCCAATGAATTAGGTTTGG
GTGTAAGTTATTCTAATGGCGGCAGTGACAACAGCAATACTGATGAATTAGCAAACAAAGTTAT
AGATGATTCTCTTAAAAAGATTGAAGAAGAACTTAAGGGAATAGAAGAAGATAAAAAAGAATA
A t5-15.nt (SEQ ID NO:686)
TTGCAAGAATTATGCAAGTGGTGAAAATCTAAAAAATTCAGAACAAAATCTAGAAAGTTCAGA
ACAAAATGTAAAAAAAACAGAACAAGAGATAAAAAAACAAGTTGAAGGATTTTTAGAAATTCT
AGAGACAAAAGATTTATCTAAATTAGATGAAAAGATACAAAAGAAATTGAAAAACAAATTCA
AGAATTAAAGAATAAAATAGAAAAATTAGATTCTAAAAAAACTTCTATTGAAACATATTCTGAG
TATGAAGAAAAATAAACAAAATAAAAGAAAAATTGAAAGGAAAAGGACTTGAAGATAAATTT
AAGGAGCTTGAAGAGAGTTTAGCAAAGAAAAAGGGGGAGAGAAAAAAAGCTTTACAAGAGGC
CAAACAGAAATTTGAAGAATATAAAAAACAAGTAGATACTTCAACTGGGAAAACTCAAGGCGA
CAGGTCTAAAAACCGAGGTGGTGTTGGAGTGCAAGCTTGGCAGTGTGCCAATGAATTAGGTTT
GGGTGTAAGTTATTCTAATGGCGGCAGTGACAACAGCAATACTGATGAATTAGCAAACAAAGT
TATAGATGATTCTCTTAAAAAGATTGAAGAAGAACTTAAGGGAATAGAAGAAGATAAAAAAGA
A f5-15.aa (SEQ ID NO:687)
LMNKKMKMFIICAVFALMISCKNYASGENLKNSEQNLESSEQNVKKTEQEIKKQVEGFLEILETKDL
SKLDEKDTKEIEKQIQELKNKIEKLDSKKTSIETYSEYEEKINKIKEKLKGKGLEDKFKELEESLAKK
KGERKKALQEAKQKFEEYKKQVDTSTGKTQGDRSKNRGGVGVQAWQCANELGLGVSYSNGGSD
NSNTDELANKVIDDSLKKIEEELKGIEEDKKE t5-15.aa (SEQ ID NO:688)
CKNYASGENLKNSEQNLESSEQNVKKTEQEIKKQVEGFLEILETKDLSKLDEKDTKEIEKQIQELKN
KIEKLDSKKTSIETYSEYEEKINKIKEKLKGKGLEDKFKELEESLAKKKGERKKALQEAKQKFEEYK
KQVDTSTGKTQGDRSKNRGGVGVQAWQCANELGLGVSYSNGGSDNSNTDELANKVIDDSLKKIEE
ELKGIEEDKKE f51-2.nt (SEQ ID NO:689)
TAATTGTTTGGGGTTGTGGTAAACTTAAGGCTTATGGAGTGGATTATGAATAAAAAAATGAAAA
TATTTATTATTTGTGCTGTATTTGTGCTGATAAGTTCTTGCAAGATTGATGCAACTGGTAAAGAT
GCAACTGGTAAAGATGCAACTGGTAAAGATGCAACTGGTAAAGATGCAACTGGTAAAAATGCA
GAACAAAATATAAAAGGGAAAGTTCAAGGATTTTTAGAAAAGATTTTAGATCCAGTAAAGGAT
AAAATTGCTTCAAATGGTCCAATAGCAGATGAATTGGCAAAAAAATTACAAGAAGAAAAAG
GTAAATAACGGGGAAGAAGAAAATGATAAAGCTGTCTTTTTAGGAGAAGAATCAAAAGAGGAT
GAAGAAGAAAATGAGCAAGCTGTTAATTTAGAAGAAAAAAATGCGGAAGAGGATAAGAAAGT
TGTTAATTTAGAAGAGAAAGAATTAGAAGTTAAAAAAGAGACTGAAGAAGATGAAGATAAAGA
AGAAATAGAGAAACAAAAACAAGAAGTGGAAAAAGCACAAGAAAGAAAACAACGACAAGAAG
AAAAGAAACGAAAAAAACAAGAACAGCAAGAAGAAAAGAAACGAAAACGACAAGAACAAAGA
AAAGAAAGGAGAGCTAAAAACAAAATTAAAAAACTTGCGGATAAAATAGATGAGATAAGTTGG
AATATTGATGGTATAGAAAGTCAAACAAGTGTAAAACCGAAAGCAGTTATAGATAAAATTACG
GGGCCTGTATATGATTATTTTACCGATGACAACAAAAAAGCTATATATAAAACATGGGGAGATT
TAGAAGATGAAGAAGGCGAAGGATTGGGAAAATTATTGAAAGAATTGAGTGATACTAGAGATG
AGTTAAGAACCAAATTAAATAAAGATAATAAAAAATATTATGCCCATGAAAATGAGCCTCCTCT
AAAAGAAAATGTAGATGTCAGCGAAATTAAAGAAGATTTAGAAAAAGTAAAATCAGGATTAGA
AAAGGTTAAAGAATATCTTAAAGACAATTCTAAATTTGAAGAAATTAAAGGATACATCAGTTAC
AGTCAGTAA t51-2.nt (SEQ ID NO:690)
TTGCAAGATTGATGCAACTGGTAAAGATGCAACTGGTAAAGATGCAACTGGTAAAGATGCAAC
TGGTAAAGATGCAACTGGTAAAAATGCAGAACAAAATATAAAAGGGAAAGTTCAAGGATTTTT
AGAAAAGATTTTAGATCCAGTAAAGGATAAAATTGCTTCAAATGGTCCAATAGCAGATGAATT
GGCAAAAAAATTACAAGAAGAAGAAAAGGTAAATAACGGGGAAGAAGAAAATGATAAAGCTG
TCTTTTTAGGAGAAGAATCAAAAGAGGATGAAGAAGAAAATGAGCAAGCTGTTAATTTAGAAG
AAAAAAATGCGGAAGAGGATAAGAAAGTTGTTAATTTAGAAGAGAAAGAATTAGAAGTTAAAA
AAGAGACTGAAGAAGATGAAGATAAAGAAGAAATAGAGAAACAAAAACAAGAAGTGGAAAAA
GCACAAGAAAGAAAACAACGACAAGAAGAAAAGAAACGAAAAACAAGAACAGCAAGAAGA
AAAGAAACGAAAACGACAAGAACAAAGAAAAGAAAGGAGAGCTAAAAACAAAATTAAAAAAC
TTGCGGATAAAATAGATGAGATAAGTTGGAATATTGATGGTATAGAAAGTCAAACAAGTGTAA
AACCGAAAGCAGTTATAGATAAAATTACGGGGCCTGTATATGATTATTTTACCGATGACAACAA
AAAAGCTATATATAAAACATGGGGAGATTTAGAAGATGAAGAAGGCGAAGGATTGGGAAAATT
ATTGAAAGAATTGAGTGATACTAGAGATGAGTTAAGAACCAAATTAAATAAAGATAATAAAAA
ATATTATGCCCATGAAAATGAGCCTCCTCTAAAAGAAAATGTAGATGTCAGCGAAATTAAAGA
AGATTTAGAAAAAGTAAAATCAGGATTAGAAAAGGTTAAAGAATATCTTAAAGACAATTCTAA
ATTTGAAGAAATTAAAGGATACATCAGTTACAGTCAG f51-2.aa (SEQ ID NO:691)
LFGVVVNLRLMEWIMNKKMKIFIICAVFVLISSCKIDATGKDATGKDATGKDATGKDATGKNAEQN
IKGKVQGFLEKILDPVKDKIASNGPIADELAKKLQEEEKVNNGEEENDKAVFLGEESKEDEENEQA
VNLEEKNAEEDKKVVNLEEKELEVKKETEEDEDKEEIEKQKQEVEKAQERKRQEEKKRKKQEQQ
EEKKRKRQEQRKERRAKNKIKKLADKIDEISWNIDGIESQTSVKPKAVIDKITGPVYDYFTDDNKKA
IYKTWGDLEDEEGEGLGKLLKELSDTRDELRTKLNKDNKKYYAHENEPPLKENVDVSEIKEDLEKV

TABLE 1-continued

Nucleotide and Amino Acid Sequences.

KSGLEKVKEYLKDNSKFEEIKGYISYSQ t51-2.aa (SEQ ID NO:692)
CKIDATGKDATGKDATGKDATGKDATGKNAEQNIKGKVQGFLEKILDPVKDKIASNGPIADELAKK
LQEEEKVNNGEEENDKAVFLGEESKEDEEENEQAVNLEEKNAEEDKKVVNLEEKELEVKKETEED
EDKEEIEKQKQEVEKAQERKQRQEEKKRKKQEQQEEKKRKRQEQRKERRAKNKIKKLADKIDEIS
WNIDGIESQTSVKPKAVIDKITGPVYDYFTDDNKKAIYKTWGDLEDEEGEGLGKLLKELSDTRDEL
RTKLNKDNKKYYAHENEPPLKENVDVSEIKEDLEKVKSGLEKVKEYLKDNSKFEEIKGYISYSQ f6-21.nt (SEQ ID NO:693)
TAGGCAAAATTTAAATTTATAAAAACTTGTAAGGATGCTTGTATGAAAATATTGATAAAAAAGT
TAAAAGTTGTATTATTTCTCAATTTAATTTTACTTATTTCTTGTGTTAATGAAAGTAATAGAAAC
AAAATTGGTTTTTAAGCTAAATATTGGAAGTGAGCCTGCTACTTTAGATGCTCAATTAATAAACG
ATACGGTTGGATCAGGGATTGTAAGCCAAATGTTTCTTGGCATTTTAGATGGAGATCCCAGGAC
TGGAGGATACAGACCGGGACTTGCTAAAAGTTGGGATATTTCTGATGACGGAGTAGTTTATACG
TTTCATTTAAGAGATAATCTTGTTTGGAGTGATGGAGTTTCCATTACTGCCGAAGAATAA t6-21.nt (SEQ ID NO:694)
TTGTGTTAATGAAAGTAATAGAAACAAATTGGTTTTTAAGCTAAATATTGGAAGTGAGCCTGCT
ACTTTAGATGCTCAATTAATAAACGATACGGTTGGATCAGGGATTGTAAGCCAAATGTTTCTTG
GCATTTTAGATGGAGATCCCAGGACTGGAGGATACAGACCGGGACTTGCTAAAAGTTGGGATA
TTTCTGATGACGGAGTAGTTTATACGTTTCATTTAAGAGATAATCTTGTTTGGAGTGATGGAGT
TTCCATTACTGCCGAAGAA f6-21.aa (SEQ ID NO:695)
AKFKFIKTCKDACMKILIKKLKVVLFLNLILLISCVNESNRNKLVFKLNIGSEPATLDAQLINDTVGSG
IVSQMFLGILDGDPRTGGYRPGLAKSWDISDDGVVYTFHLRDNLVWSDGVSITAEE t6-21.aa (SEQ ID NO:696)
CVNESNRNKLVFKLNIGSEPATLDAQLINDTVGSGIVSQMFLGILDGDPRTGGYRPGLAKSWDISDD
GVVYTFHLRDNLVWSDGVSITAEE f6-27.nt (SEQ ID NO:697)
TAAAGAAAAGCTTGCATAAAAAGTATAACAAATTCTTTAATAATTAAAATCAAAAAGAATATA
ATTATTGCACTAAAATTAAATTTATACAGTTATATAGAATACTTAAGGAACAAAAAATGAAAT
ACCTTAAAAACATTTCCTTATTTTTGTTAATTTTAGGTTGCAAATCCATCCCAAATGGTAATTTC
AATCTACACGATACAAACCATAAATTAGGAAAACTAAAATTTCAAGAAGACTCGATAATAAGC
AGAAAATTATGATAATAAAATATCCATTGTGGGAGTATACAACCCTTTAACAGAAAAAGAAAATT
TTAAAGTCAATATTTTCATCAAAAAAAAAGGATTACAAATAGATCCTGAAAATATTTTGATAAA
TGAAGAAAAAATTAATTATTCAAAATATAAAGCAGAACTCAAAGTAAAATCTAGGTTTAATAAA
AGCATTATCAGTATTTCACTAACTAATTCAAGAGATCTATTAACCTACATTTACGATAAAAGCA
CAGGGAAATACATTAACATTGAGTTTAAGGACAATTGGAACGTATCGCACAGTATAAAATTTAA
TAAGGAGTATATTTTAGCATATATAACAGATTTTGATAAAGAATTAAAATATCTAAAAATATT
TTGCAAAAACGTATTGATAATAGAAAAATTGAAATTGAAAAAACAGAGCTTAAAACAGAATAT
AATGAAATAGAGGATTATTACATCTACAGTATGAAAATTCCAAAATTATTTGAAAAATCAGACG
CTCCCTCTGAAACTTACGAAACATTTGTTATAGCAAATTATTACCCCTGTGAAAATTTAAATATA
CTGTTTTTGAATTTAAGCTTATACTCTGATAAATTACGCTTTCTAAACTCTATTTATGATGAGAA
TGATAGAAAATTAAAAATGGAGCCTCCTGTGAGAGCCTTAAAGAATTCAAAAACAATAAAAGA
AACATTAAATATAGTATTAAGTCCTCAAAAAATAATAGAGCTAGCAAAAAACATTGAAAAAGA
TATTACTCTAAAATTAAAATCTTACGGAGAAAAGGGAGAATTCACATTTGAAATATATAAACCA
CTTCTTTTAAAATTCTTAAAAGAAGTAGATCATTGCATAAAAAATTTGCAATCAAGTAGGCATA
AATTTTAA t6-27.nt (SEQ ID NO:698)
TTGCAAATCCATCCCAAATGGTAATTTCAATCTACACGATACAAACCATAAATTAGGAA
AACTAAAATTTCAAGAAGACTCGATAATAAGCAGAAATTATGATAATAAAATATCCATTGTGGG
AGTATACAACCCTTTAACAGAAAAAGAAAATTTTAAAGTCAATATTTTCATCAAAAAAAAAGGA
TTACAAATAGATCCTGAAAATATTTTGATAATGAAGAAAAAATTAATTATTCAAAATATAAAG
CAGAACTCAAAGTAAAATCTAGCTTTAATAAAAGCATTATCAGTATTTCACTAACTAATTCAAG
AGATCTATTAACCTACATTTACGATAAAGCACAGGGAAATACATTAACATTGACTTTAAGGAC
AATTGGAACGTATCGCACAGTATAAAATTTAATAAGGAGTATATTTTAGCATATATAACAGATT
TTGATAAAGAATTAAAATATCTAAAAATATTTTGCAAAAACGTATTGATAATAGAAAAATTGA
AATTGAAAAAACAGAGCTTAAAACAGAATATAATGAAATAGAGGATTATTACATCTACAGTAT
GAAAATTCCAAAATTATTTGAAAAATCAGACGCTCCCTCTGAAACTTACGAAACATTTGTTATA
GCAAATTATTACCCCTGTGAAAATTTAAATATACTGTTTTTGAATTTAAGCTTATACTCTGATAA
ATTACGCTTTCTAAACTCTATTTATGATGAGAATGATAGAAAATTAAAAATGGAGCCTCCTGTG
AGAGCCTTAAAGAATTCAAAAACAATAAAAGAAACATTAAATATAGTATTAAGTCCTCAAAAA
ATAATAGAGCTAGCAAAAAACATTGAAAAAGATATTACTCTAAAATTAAAATCTTACGGAGAA
AAGGGAGAATTCACATTTGAAATATATAAACCACTTCTTTTAAAATTCTTAAAAGAAGTAGATC
ATTGCATAAAAAATTTGCAATCAAGTAGGCATAAATTT f6-27.aa (SEQ ID NO:699)
RKACIKSITNSLIIKIKKNIIIALKLNLYSYIESLKEQKMKYLKNISLFLLILGCKSIPNGNFNLHDTNHK
LGKLKFQEDSIISRNYDNKISIVGVYNPLTEKENFKVNIFIKKKGLQIDPENILINEEKINYSKYKAELK
VKSSFNKSIISISLTNSRDLLTYIYDKSTGKYINIDFKDNWNVSHSIKFNKEYILAYITDFDKEIKISKNI
LQKRIDNRKIEIEKTELKTEYNEIEDYYIYSMKIPKLFEKSDAPSETYETFVIANYYPCENLNILFLNLS
LYSDKLRFLNSIYDENDPKLKMEPPVRALKNSKTIKETLNIVLSPQKIIELAKNIEKDITLKLKSYGEK

TABLE 1-continued

Nucleotide and Amino Acid Sequences.

GEFTFEIYKPLLLKFLKEVDHCIKNLQSSRHKF t6-27.aa (SEQ ID NO:700)
CKSIPNGNFNLHDTNHKLGKLKFQEDSIISRNYDNKISIVGVYNPLTEKENFKVNIFIKKKGLQIDPEN
ILINEEKINYSKYKAELKVKSSFNKSIISISLTNSRDLLTYIYDKSTGKYINIDFKDNWNVSHSIKFNKE
YILAYITDFDKEIKISKNILQKRIDNRKIEIEKTELKTEYNEIEDYYIYSMKIPKLFEKSDAPSETYETFV
IANYYPCENLNILFLNLSLYSDKLRFLNSIYDENDRKLKMEPPVRALKNSKTIKETLNIVLSPQKIIELA
KNIEKDITLKLKSYGEKGEFTFEIYKPLLLKFLKEVDHCIKNLQSSRHKF f6-5.nt (SEQ ID NO:701)
TAAATGAAGAAGTTTTTAATATCCGTTTATTTTTTATTGTTTTATGGTTGTTCAACTATATCTTTG
GTAAAAATACCAGAAAAGATAAAATAAATTTAACTGTTTTATCATCTTTAATGAATTATCCTG
ATTTGAAGATTTCAAATTTTAAAATAAAAGACTACGAACATTTGCATTATTCATCTGATTTTGAA
AGCTTGAGTGATACTAAAAATAGTGCTTATATTTACGTTGATGAATCTAGTTTCAATAATAATA
TTAATTTTATTAAAGATCTTTTTATTTATAATAAGAAATTATATAGAATACTTATTGCTTATAGC
TTGACCCAAGGTGCATCTTTTAAGGCAGAAGTTTTATCTTATCTTGAAAAACAAAAAATTATGA
AAAATTTTTCATTGAAAATAAATTTTCCAACTGCTAAAAAATTTATGGATAATAAGTATTGGAT
TGTAATTGCAAAAAACCATTTAGATTCTCTTGTTAAGAGTAAAAATTATTTAGTCTTGGCGAAT
GTAAAGATGGAATATATACTCAAAAAGTTTTTAACTTGA t6-5.nt (SEQ ID NO:702)
TTGTTCAACTATATCTTTGGTAAAAATACCAGAAAAGATAAAATAAATTTAACTGTTTTATCA
TCTTTAATGAATTATCCTGATTTGAAGATTTCAAATTTTAAAATAAAAGACTACGAACATTTGC
ATTATTCATCTGATTTTGAAAGCTTGAGTGATACTAAAAATAGTGCTTATATTTACGTTGATGA
ATCTAGTTTCAATAATAATATTAATTTTATTAAAGATCTTTTTATTTATAATAAGAAATTATATA
GAATACTTATTGCTTATAGCTTGACCCAAGGTGCATCTTTTAAGGCAGAAGTTTTATCTTATCTT
GAAAAACAAAAAATTATGAAAAATTTTTCATTGAAAATAAATTTTCCAACTGCTAAAAAATTTA
TGGATAATAAGTATTGGATTGTAATTGCAAAAAACCATTTAGATTCTCTTGTTAAGAGTAAAAA
T f6-5.aa (SEQ ID NO:703)
MKKFLISVYFLLFYGCSTISLVKIPEKDKINLTVLSSLMNYPDLKISNFKIKDYEHLHYSSDFESLSDT
KNSAYIYVDESSFNNNINFIKDLFIYNKKLYRILIAYSLTQGASFKAEVLSYLEKQKIMKNFSLKINFP
TAKKFMDNKYWIVIAKNHLDSLVKSKNYLVLANVKMEYILKKFLT t6-5.aa (SEQ ID NO:704)
CSTISLVKIPEKDKINLTVLSSLMNYPDLKISNFKIKDYEHLHYSSDFESLSDTKNSAYIYVDESSFNN
NINFIKDLFIYNKKLYRILIAYSLTQGASFKAEVLSYLEKQKIMKNFSLKINFPTAKKFMDNKYWIVIA
KNHLDSLVKSKN f7-30.nt (SEQ ID NO:705)
TAGAGACGAAGTCACAAGCAAAATGTTAAAAGATTTACAAAATCAAGTTCAAGGGGGCAAATA
ATGAAAAATTTAAAGACAAAAATTAATTTTTTAGGGATATTTTGGCTACTGTTACTATTTCTTTC
TTGCGAATCAATACCATCACTTCCCCAAAAACCAACCCTAACAAACAAAGAAGATATTGAAAAT
TTAATGCTCGATGAAGCAGAACTTTTTAGATACTCAACCGCACTAAATGTTTGGCTTTTGACTGT
AAAATCTTATGTGATCAAATACTATCCTAATGACAAATTTCCTGTGTTTGAAAATTTTGATCCCG
TGTTTGGCGATGAAAATGGAACTAAAGAAACAAATATACTAAAAAATCGAATTACCTACTACA
ATCGATACATAGAAAAAACCGAACCGATTGTATTTGGGTGTTACAAAAAATACAGCAGAAGAT
AA t7-30.nt (SEQ ID NO:706)
TTGCGAATCAATACCATCACTTCCCCAAAAACCAACCCTAACAAACAAAGAAGATATTGAAAAT
TTAATGCTCGATGAAGCAGAACTTTTTAGATACTCAACCGCACTAAATGTTTGGCTTTTGACTGT
AAAATCTTATGTGATCAAATACTATCCTAATGACAAATTTCCTGTGTTTGAAAATTTTGATCCCG
TGTTTGGCGATGAAAATGGAACTAAAGAAACAAATATACTAAAAAATCGAATTACCTACTACA
ATCGATACATAGAAAAAACCGAACCGATTGTATTTGGGTGTTACAAAAAATACAGCAGAAGA f7-30.aa (SEQ ID NO:707)
RRSHKQNVKRFTKSSSRGQIMKNLKTKINFLGIFWLLLLFLSCESIPSLPQKPTLTNKEDIENLMLDEA
ELFRYSTALNVWLLTVKSYVIKYYPNDKFPVFENFDPVFGDENGTKETNILKNRITYYNRYIEKTEPI
VFGCYKKYSRR t7-30.aa (SEQ ID NO:708)
CESIPSLPQKPTLTNKEDIENLMLDEAELFRYSTALNVWLLTVKSYVIKYYPNDKFPVFENFDPVFGD
ENGTKETNILKNRITYYNRYIEKTEPIVFGCYKKYSRR f76-1.nt (SEQ ID NO:709)
TGAATATTAATAATAAAAAAAGGAGTAACAATGAAAATTATCAACATATTATTTTGTTTGTTTT
TACTAATGCTAAACGGCTGTAATTCTAATGATACAAATACCAAGCAGACAAAAAGCAGACAAA
AGCGTGATTAACCCAAAAAGAAGCAACACAAGAAAAACCTAAATCTAAATCTAAAGAAGACC
TGCTTAGAGAAAAGCTATCTGATGATCAAAAAACACAACTTGACTGGTTAAAAACCGCTTTAAC
TGGTGTTGGAAAATTTGATAAATTCTTAGAAAATGATGAAGGCAAAATTAAATCAGCACTTGAA
CATATAAAGACTGAACTTGATAAATGTAATGGAAATGATGAAGGAAAAAACACCTTCAAAACT
ACCGTTCAAGGGTTTTTTAGCGGCGGCAATATAGATAATTTTGCAGATCAAGCAACTGCTACCT
GCAATTAA t76-1.nt (SEQ ID NO:710)

TABLE 1-continued

Nucleotide and Amino Acid Sequences.

CTGTAATTCTAATGATACAAATACCAAGCAGACAAAAAGCAGACAAAAGCGTGATTTAACCCA
AAAAGAAGCAACACAAGAAAAACCTAAATCTAAATCTAAAGAAGACCTGCTTAGAGAAAAGCT
ATCTGATGATCAAAAAACACAACTTGACTGGTTAAAAACCGCTTTAACTGGTGTTGGAAAATTT
GATAAATTCTTAGAAAATGATGAAGGCAAAATTAAATCAGCACTTGAACATATAAAGACTGAA
CTTGATAAATGTAATGGAAATGATGAAGGAAAAAACACCTTCAAAACTACCGTTCAAGGGTTTT
TTAGCGGCGGCAATATAGATAATTTTGCAGATCAAGCAACTGCTACCTGCAAT f76-1.aa (SEQ ID NO:711)
ILIIKKGVTMKIINILFCLFLLMLNGCNSNDTNTKQTKSRQKRDLTQKEATQEKPKSKSKEDLLREKL
SDDQKTQLDWLKTALTGVGKFDKFLENDEGKIKSALEHIKTELDKCNGNDEGKNTFKTTVQGFFSG
GNIDNFADQATATCN t76-1.aa (SEQ ID NO:712)
CNSNDTNTKQTKSRQKRDLTQKEATQEKPKSKSKEDLLREKLSDDQKTQLDWLKTALTGVGKFDK
FLENDEGKIKSALEHIKTELDKCNGNDEGKNTFKTTVQGFFSGGNIDNFADQATATCN f8-10.nt (SEQ ID NO:713)
TAAGTAAGGAGAATATTTATGAAATATAATACGATTATAAGCATATTTGTTTGTTTGTTTTTAAC
TGCTTGCAATCCAGATTTTAACACAAATAAGAAAAGAACTCTAAGTAAGGGGATAATTTCAAAT
CAAGATGCAGATTCTGATAAAATAATAAAAAATAAATTACTTGATGATTTAATAAATTTAATAG
AAAAAGCGAATGCAGATAGAGAAAAATATGTAAAAAAAATGGAAGAAGAACCTTCGGATCAAT
ATGGAATGTTGGCTGTTTTTGGAGGTATGTATTGGGCAGAATCACCACGGGAATTAATATCTGA
TACAGGTAGTGAGAGATCTATTAGGTATAGAAGGCGTGTTTATAGTATTTTATTAAATGCTATT
GAAACTAATGAATTAAAGAAATTTTCAGAAATTAGAATACTGTCAATAAAAGTACTAGAAATAT
TTAGCCTATTTAATCTATTTGGAAGTACTCTTGATGATGTGGTTGTTCACTTATATTCCAAAAAA
GATACTCTAGGTAAACTAGATATTTCAAATTTAAAAAGACTTAAAAATTTGTTTGAAAAATTAT
TATCTATAAAAACAATCGTTTCAAAGATGTCAAAACGTCTTTTATTGGATTATCAAAATAATGA
AAATTTTATAAAAACAGATAACGCCAAGCTTGGATCTTATGTGGTTGCACTTTCCAATCAAATT
CAAGAAAAATATAATGAAGCAGAAAGGCTGAAAAGCGAGATAATTTTAATATATACCCTTTAA t8-10.nt (SEQ ID NO:714)
TTGCAATCCAGATTTTAACACAAATAAGAAAAGAACTCTAAGTAAGGGGATAATTTCAAATCAA
GATGCAGATTCTGATAAAATAATAAAAAATAAATTACTTGATGATTTAATAAATTTAATAGAAA
AAGCGAATGCAGATAGAGAAAAATATGTAAAAAAAATGGAAGAAGAACCTTCGGATCAATATG
GAATGTTGGCTGTTTTTGGAGGTATGTATTGGGCAGAATCACCACGGGAATTAATATCTGATAC
AGGTAGTGAGAGATCTATTAGGTATAGAAGGCGTGTTTATAGTATTTTATTAAATGCTATTGAA
ACTAATGAATTAAAGAAATTTTCAGAAATTAGAATACTGTCAATAAAAGTACTAGAAATATTTA
GCCTATTTAATCTATTTGGAAGTACTCTTGATGATGTGGTTGTTCACTTATATTCCAAAAAAGAT
ACTCTAGGTAAACTAGATATTTCAAATTTAAAAAGACTTAAAAATTTGTTTGAAAAATTATTAT
CTATAAAAACAATCGTTTCAAAGATGTCAAAACGTCTTTTATTGGATTATCAAAATAATGAAAA
TTTTATAAAAACAGATAACGCCAAGCTTGGATCTTATGTGGTTGCACTTTCCAATCAAATTCAA
GAAAAATATAATGAAGCAGAAAGGCTGAAA f8-10.aa (SEQ ID NO:715)
VRRIFMKYNTIISIFVCLFLTACNPDFNTNKKRTLSKGIISNQDADSDKIIKNKLLDDLINLIEKANADR
EKYVKKMEEEPSDQYGMLAVFGGMYWAESPRELISDTGSERSIRYRRRVYSILLNAIETNELKKFSE
IRILSIKVLEIFSLFNLFGSTLDDVVVHLYSKKDTLGKLDISNLKRLKNLFEKLLSIKTIVSKMSKRLLL
DYQNNENFIKTDNAKLGSYVVALSNQIQEKYNEAERLKSEIILIYTL t8-10.aa (SEQ ID NO:716)
CNPDFNTNKKRTLSKGIISNQDADSDKIIKNKLLDDLINLIEKANADREKYVKKMEEEPSDQYGMLA
VFGGMYWAESPRELISDTGSERSIRYRRRVYSILLNAIETNELKKFSEIRILSIKVLEIFSLFNLFGSTLD
DVVVHLYSKKDTLGKLDISNLKRLKNLFEKLLSIKTIVSKMSKRLLLDYQNNENFIKTDNAKLGSYV
VALSNQIQEKYNEAERLK f8-14.nt (SEQ ID NO:717)
TAATATATATTCTTGATTAAGGGAAAGGAGAGTATTTTTATGAAAAAAAAAATGTTTTTATATA
CATTGTTAACGATAGGATTGATGTCTTGTAATCTAAATTCTAAATTATCTGGTAATAAAGAGGA
ACAAAAAAATAACAATGATATAAAAGAAGCTTTAAATGGCGTTCAAGAAAATGCTATTAATAA
TTTATATGGAAATAAAAAAGAAAAAAAAGATTTTATTAAAAATTCGGAAAAATTGAAAGACAA
GGGTTTAGACGTGACCACCCTCCCCTTAGAACCTGTAGTGGCGCCCTCCGTAGAATCTGCGGTG
TCTTTAGGAGAATCTAATAATAGGATTGGTATACCAACCATTTCAATTGAGCATAATCAAAAA
AAGAGATAAAGAAGAGGATTTTTTCCCTTCTACTGAGGAAGAAAAGCAAGCGGATAAAGCAA
TTAAAGATATAGAGAATCTTATTGGAGAATCTGGATTTCCCGAGTTAATTGAGAATGTGTGCTC
ACTTAAACATGAATATACTTTAATAAGAAGTGATTTTTATGATGTGATAACTAAGATTCAGAAT
AAAAAAAAATATCACTAATGAAAAATTCTCATAATAATAGAAATAAAATAAGGGAACTAGTACAA
TTGCAAAATAATTTAAAGATAGGAGACGAACTTGATAAAATTATGGGTTGCATTGATACTGCAG
AACAAGAGATAAGATCTGCCGCTTTCTTTTTGATGAAGCTAAGGAAAGCTTAAAAGAAGGTAT
TATTAAAAGATTGGAAAAAAGTAAAAATAGGGCAGCATCACAATTATCTAAAAAGGCTTTAAA
TAGAGCAGAGGATGCTTTAAGGTGCTTAGAAAATTATTCTTCTAAAAAAGGTGAGGCAATAGG
AAGAAGAAGCTTTATAAAAGAAGTTGTTGAACAGGCAAAAAATGCTTTAAGTAAGTCTTAA t8-14.nt (SEQ ID NO:718)
TTGTAATCTAAATTCTAAATTATCTGGTAATAAAGAGGAACAAAAAAATAACAATGATATAAAA
GAAGCTTTAAATGGCGTTCAAGAAAATGCTATTAATAATTTATATGGAAATAAAAAAGAAAAA
AAAGATTTTATTAAAAATTCGGAAAAATTGAAAGACAAGGGTTTAGACGTGACCACCCTCCCCT
TAGAACCTGTAGTGGCGCCCTCCGTAGAATCTGCGGTGTCTTTAGGAGAATCTAATAATAGGAT

TABLE 1-continued

Nucleotide and Amino Acid Sequences.

```
TGGTATACCAACCATTTCAATTGAGCATAATCAAAAAAAAGAGATAAAAGAAGAGGATTTTTTC
CCTTCTACTGAGGAAGAAAAGCAAGCGGATAAAGCAATTAAAGATATAGAGAATCTTATTGGA
GAATCTGGATTTCCCGAGTTAATTGAGAATGTGTGCTCACTTAAACATGAATATACTTTAATAA
GAAGTGATTTTTATGATGTGATAACTAAGATTCAGAATAAAAAAATATCACTAATGAAAAATTC
TCATAATAATAGAAATAAAATAAGGGAACTAGTACAATTGCAAAATAATTTAAAGATAGGAGA
CGAACTTGATAAAATTATGGGTTGCATTGATACTGCAGAACAAGAGATAAGATCTGCCGCTTTC
TTTTTTGATGAAGCTAAGGAAAGCTTAAAAGAAGGTATTATTAAAAGATTGGAAAAAAGTAAA
AATAGGGCAGCATCACAATTATCTAAAAAGGCTTTAAATAGAGCAGAGGATGCTTTAAGGTGC
TTAGAAAATTATTCTTCTAAAAAAGGTGAGGCAATAGGAAGAAGAAGCTTTATAAAAGAAGTT
GTTGAACAGGCAAAAAATGCTTTAAGTAAGTCT
``` f8-14.aa (SEQ ID NO:719)
```
YIFLIKGKESIFMKKKMFLYTLLTIGLMSCNLNSKLSGNKEEQKNNNDIKEALNGVQENAINNLYGN
KKEKKDFIKNSEKLKDKGLDVTTLPLEPVVAPSVESAVSLGESNNRIGIPTISIEHNQKKEIKEEDFFP
STEEEKQADKAIKDIENLIGESGFPELIENVCSLKHEYTLIRSDFYDVITKIQNKKISLMKNSHNNRNKI
RELVQLQNNLKIGDELDKIMGCIDTAEQEIRSAAFFFDEAKESLKEGIIKRLEKSKNRAASQLSKKAL
NRAEDALRCLENYSSKKGEAIGRRSFIKEVVEQAKNALSKS
``` t8-14.aa (SEQ ID NO:720)
```
CNLNSKLSGNKEEQKNNNDIKEALNGVQENAINNLYGNKKEKKDFIKNSEKLKDKGLDVTTLPLEP
VVAPSVESAVSLGESNNRIGIPTISIEHNQKKEIKEEDFFPSTEEEKQADKAIKDIENLIGESGFPELIEN
VCSLKHEYTLIRSDFYDVITKIQNKKISLMKNSHNNRNKIRELVQLQNNLKIGDELDKIMGCIDTAEQ
EIRSAAFFFDEAKESLKEGIIKRLEKSKNRAASQLSKKALNRAEDALRCLENYSSKKGEAIGRRSFIKE
VVEQAKNALSKS
``` f01A.nt BB001 (SEQ ID NO:721)
```
TGATTAATTTTTTTTAAGGATTACGTTTTGAAAAGAAACAAAATTTGGAAAACGTTAAA
ACTGTTTCAAATAACTTTACTGTTCTCATGCTCTTTTTATTCTAAATCAAACAACACAGAAGCGA
TAAGTGAATTACAATCAAGCCCTATTAAACTTGGAAAAATTAAAGTTTTACAAAAAACAGAAAA
GATTGTAAGCACCCAAAATCTTCAAAACTTACAACAAAGCCAGTTCTTTAAAAATGAAAAAGAA
AAAATAATTAAAAAAATTGCAAGAATTTGATGAGAATGAAAAATTGATTAATAAAATAGGT
CCAAATATCGAAATGTTTGCTCAAACAATAAAACACGGATATTCAAAAAATCGAACCTAATGATC
AATTTGGAATAAATAAAACTTTATTCACAGAAAAAAAAGACAATAATATTGACTTTATGTTAAA
AGACAATCGACTTAGAAGATTATTTTACTCATCTTTAAATTATGATGAAAATAAAATCAAAAAA
TTAGCCACAATACTCGCGCAAACATCAAGCTCAAACGACTACCATTACACACTTATTGGTTTAA
TTTTTTGGACAGGATTTAAAATCCAAGAAGCATTTGAAAGCGCTGTTAATATTTTAACTAAAGA
CGAGCAAAAGCGCCTAATTTTTAATTTTAGAACAAAAACAGTAAAAGAGATTCAGGAAAATTTT
GAAAAACTAATGCAAGAGAGAAATTCATGGATAAAAATCGTCGATAACATTATTGGCGAATAT
GACAAAAATACGGGAGGATGCAAAGCTGATGGAAAAATTCTCGGAGAAGTAATAAGGGTTGGA
TACGAGCATGAACTCGACTCAAATAAAAGTATGCAAATTTTAAACAATATTGAAACACCGCTAA
AAACCTGTTGTGACCACATACACTACTAA
``` t01A.nt BB001 (SEQ ID NO:722)
```
TGCTCTTTTTATTCTAAATCAAACAACACAGAAGCGATAAGTGAATTACAATCAAGCCC
TATTAAACTTGGAAAAATTAAAGTTTTACAAAAAACAGAAAAGATTGTAAGCACCCAAAATCTT
CAAAACTTACAACAAAGCCAGTTCTTTAAAAATGAAAAGAAAAAATAATTAAAAAAATTGCA
CAAGAATTTGATGAGAATGAAAAATTGATTAATAAAATAGGTCCAAATATCGAAATGTTTGCTC
AAACAATAAAACACGGATATTCAAAAAATCGAACCTAATGATCAATTTGGAATAAATAAAACTTT
ATTCACAGAAAAAAAAGACAATAATATTGACTTTATGTTAAAAGACAATCGACTTAGAAGATTA
TTTTACTCATCTTTAAATTATGATGAAAATAAAATCAAAAAATTAGCCACAATACTCGCGCAAA
CATCAAGCTCAAACGACTACCATTACACACTTATTGGTTTAATTTTTTGGACAGGATTTAAAATC
CAAGAAGCATTTGAAAGCGCTGTTAATATTTTAACTAAAGACGAGCAAAAGCGCCTAATTTTTA
ATTTTAGAACAAAAACAGTAAAAGAGATTCAGGAAAATTTTGAAAAACTAATGCAAGAGAGAA
ATTCATGGATAAAAATCGTCGATAACATTATTGGCGAATATGACAAAAATACGGGAGGATGCA
AAGCTGATGGAAAAATTCTCGGAGAAGTAATAAGGGTTGGATACGAGCATGAACTCGACTCAA
ATAAAAGTATGCAAATTTTAAACAATATTGAAACACCGCTAAAAACCTGTTGTGACCACATACA
CTAC
``` f01A.aa BB001 (SEQ ID NO:723)
```
LIFFKDYVLKRNKIWKTLKLFQITLLFSCSFYSKSNNTEAISELQSSPIKLGKIKVLQKTEKIVSTQNLQ
NLQQSQFFKNEKEKIIKKIAQEFDENEKLINKIGPNIEMFAQTINTDIQKIEPNDQFGINKTLFTEKKDN
NIDFMLKDNRLRRLFYSSLNYDENKIKKLATILAQTSSSNDYHYTLIGLIFWTGFKIQEAFESAVNILT
KDEQKRLIFNFRTKTVKEIQENFEKLMQERNSWIKIVDNIIGEYDKNTGGCKADGKILGEVIRVGYE
HELDSNKSMQILNNIETPLKTCCDHIHY
``` t01A.aa BB001 (SEQ ID NO:724)
```
CSFYSKSNNTEAISELQSSPIKLGKIKVLQKTEKIVSTQNLQNLQQSQFFNKNEKEKIIKKIAQEFDENE
KLINKIGPNIEMFAQTINTDIQKIEPNDQFGINKTLFTEKKDNNIDFMLKDNRLRRLFYSSLNYDENKI
KKLATILAQTSSSNDYHYTLIGLIFWTGFKIQEAFESAVNILTKDEQKRLIFNFRTKTVKEIQENFEKL
MQERNSWIKIVDNIIGEYDKNTGGCKADGKILGEVIRVGYEHELDSNKSMQILNNIETPLKTCCDHI
HY
``` f02A.nt BB002 (SEQ ID NO:725)
```
TAATTAATACTGGTTTTAATTTATAAGGAGAGTATTTTGAAAAAAGCCAAACTAAATATAATCA
AGATTAATATTATTACAATGATATTAACTTTAATTTGCATCTCATGTGCACCTTTTAACAAAATC
AATCCCAAGGCAAATGAAAACACCAAGCTTAAAAAAAAACACCAGACTGAAAAAACCCGCCAAT
CCAGGGGAAAACATCCAAAATTTTAAAGATAAATCTGGAGACCTTGGCGCTTCTGATGAAAAA
```

TABLE 1-continued

Nucleotide and Amino Acid Sequences.

TTTATGGGAACTACCGCTTCAGAGCTAAAAGCAATTGGTAAGGAGCTAGAAGATCGAAAAAAT
CAATACGATATACAAATAGCCAAAATTACTAATGAAGAATCTAACCTATTAGATACTTATATTC
GGGCTTATGAACTAGCTAACGAAAATGAAAAAATGCTTTTAAAAAGATTTCTTCTTTCATCTTT
AGATTATAAAAAAGAAAACATAGAGACATTAAAAGAAATTCTTGAAAAACTCATAAATAATTA
CGAAAACGACCCCAAAATTGCTGCAAATTTCCTTTATCGCATAGCGCTGGATATTCAATTAAAA
CTGGAAAAGCACTTAAAATCAATAAATGAAAAACTGGACACTCTAAGCAAAGAAAATTCAAAA
GAAGATTTAGAGGCGTTGCTAGAACAAGTAAAATCTGCCTTACAGCTACAAGAAAAGTTTAAA
AAAACCCTAAACAAAACTCTTGAAGATTACCGTAAAAATACTAACAACATTCAAGAAAATAAA
GTACTAGCAGAACACTTTAATAAATATTACAAAGACTCTGATTCTTTACAATCTGCCTTTTATTA
A t02A.nt BB002 (SEQ ID NO:726)
TGTGCACCTTTTAACAAAATCAATCCCAAGGCAAATGAAAACACCAAGCTTAAAAAAAACACC
AGACTGAAAAAACCCGCCAATCCAGGGGAAAACATCCAAAATTTTAAAGATAAATCTGGAGAC
CTTGGCGCTTCTGATGAAAAATTTATGGGAACTACCGCTTCAGAGCTAAAAGCAATTGGTAAGG
AGCTAGAAGATCGAAAAAATCAATACGATATACAAATAGCCAAAATTACTAATGAAGAATCTA
ACCTATTAGATACTTATATTCGGGCTTATGAACTAGCTAACGAAAATGAAAAAATGCTTTTAAA
AAGATTTCTTCTTTCATCTTTAGATTATAAAAAAGAAAACATAGAGACATTAAAAGAAATTCTT
GAAAAACTCATAAATAATTACGAAAACGACCCCAAAATTGCTGCAAATTTCCTTTATCGCATAG
CGCTGGATATTCAATTAAAACTGGAAAAGCACTTAAAATCAATAAATGAAAAACTGGACACTCT
AAGCAAAGAAAATTCAAAAGAAGATTTAGAGGCGTTGCTAGAACAAGTAAAATCTGCCTTACA
GCTACAAGAAAAGTTTAAAAAAACCCTAAACAAAACTCTTGAAGATTACCGTAAAAATACTAA
CAACATTCAAGAAAATAAAGTACTAGCAGAACACTTTAATAAATATTACAAAGACTCTGATTCT
TTACAATCTGCCTTTTAT f02A.aa BB002 (SEQ ID NO:727)
LILVLIYKESILKKAKLNIIKINIITMILTLICISCAPFNKINPKANENTKLKKNTRLKKPANPGENIQNF
KDKSGDLGASDEKFMGTTASELKAIGKELEDRKNQYDIQIAKITNEESNLLDTYIRAYELANENEKM
LLKRFLLSSLDYKKENIETLKEILEKLINNYENDPKIAANFLYRIALDIQLKLEKHLKSINEKLDTLSKE
NSKEDLEALLEQVKSALQLQEKFKKTLNKTLEDYRKNTNNIQENKVLAEHFNKYYKDSDSLQSAFY t02A.aa BB002 (SEQ ID NO:728)
CAPFNKINPKANENTKLKKNTRLKKPANPGENIQNFKDKSGDLGASDEKFMGTTASELKAIGKELE
DRKNQYDIQIAKITNEESNLLDTYIRAYELANENEKMLLKRFLLSSLDYKKENIETLKEILEKLTNNYE
NDPKIAANFLYRIALDIQLKLEKHLKSINEKLDTLSKENSKEDLEALLEQVKSALQLQEKFKKTLNKT
LEDYRKNTNNIQENKVLAEHFNKYYKDSDSLQSAFY f03A.nt BB006 (SEQ ID NO:729)
TGATTTAATGTAAATTTTAATTACCGCCTAAAAAAGGCTTTAAATGGTATAAAGGAAGAAGATC
TAATGGTATTTAGAACATATAAACATTTGGAACTAATAATGCTGCCCATGTTAATGCTGAGTTG
CGCTTTTTTTAAGAAACCACAATCTGTACATCAAGACAGCAATACTGGCAAACCAATAAGCGAT
GAAAAAATTACATTTAATATCAGGCAAAATTTCAAATAAAAAATTGCCAATCATAAATAGTAATC
ATGACGTAACTTGGATAAAAACAAAGGCAATGACAATCTTAGGCGAAGATGGAAAAGAAATAC
CAGAATTTAAAAACAAATTTGGATATTCTTATATAATATCTCCTGTAAAAATGGATGGAAAATA
TAGTTATTACGCGTCATTATTAATACTTTTTGAAACAACTAAAAATGGAGATGATGAATATGAA
ATTGAAGATGTTAAATTTGTAACAGCTGGTTCCACCCTAGAACTTAAAAATTCTCTTTTAGCTGT
TGAAAATTCACAAGAAGAAGGATATGTTACTGCATACCCATTTGGAATATTGATGAGTGACGA
GATTAAAAATGCTTTTAAATTAACATATAAAAATGGTCATTGGAATTATATGCTTGCAGATTTA
ACTGTCAAAAATAAACTTACTCAAGAAACTAAAATTTATAAAATTTCTCTTAATTCAAAATTAA
TTATTGAATTTTTAAAAGAAGTGCTAAAAGAAAATTCTATATTAAAAGACATAGCTGGAGATTT
ATTTGAAGATATATAA t03A.nt BB006 (SEQ ID NO:730)
TGCGCTTTTTTTAAGAAACCACAATCTGTACATCAAGACAGCAATACTGGCAAACCAATAAGCG
ATGAAAAAATTACATTTAATATCAGGCAAAATTTCAAATAAAAAATTGCCAATCATAAATAGTAA
TCATGACGTAACTTGGATAAAAACAAAGGCAATGACAATCTTAGGCGAAGATGGAAAAGAAAT
ACCAGAATTTAAAAACAAATTTGGATATTCTTATATAATATCTCCTGTAAAAATGGATGGAAAA
TATAGTTATTACGCGTCATTATTAATACTTTTTGAAACAACTAAAAATGGAGATGATGAATATG
AAATTGAAGATGTTAAATTTGTAACAGCTGGTTCCACCCTAGAACTTAAAAATTCTCTTTTAGCT
GTTGAAAATTCACAAGAAGAAGGATATGTTACTGCATACCCATTTGGAATATTGATGAGTGACG
AGATTAAAAATGCTTTTAAATTAACATATAAAAATGGTCATTGGAATTATATGCTTGCAGATTT
AACTGTCAAAAATAAACTTACTCAAGAAACTAAAATTTATAAAATTTCTCTTAATTCAAAATTA
ATTATTGAATTTTTAAAAGAAGTGCTAAAAGAAAATTCTATATTAAAAGACATAGCTGGAGATT
TATTTGAAGATATA f03A.aa BB006 (SEQ ID NO:731)
FNVNFNNNLKKALNGIKEEDLMVFRTYKHLELIMLPMLMLSCAFFKKPQSVHQDSNTGKPISDEKL
HLISGKISNKKLPIINSNHDVTWIKTKAMTILGEDGKEIPEFKNKFGYSYIISPVKMDGKYSYYASLLI
LFETTKNGDDEYEIEDVKFVTAGSTLELKNSLLAVENSQEEGYVTAYPFGILMSDEIKNAFKLTYKN
GHWNYMLADLTVKNKLTQETKIYKISLNSKLIIEFLKEVLKENSILKDIAGDLFEDI t03A.aa BB006 (SEQ ID NO:732)
CAFFKKPQSVHQDSNTGKPISDEKLHLISGKISNKKLPIINSNHDVTWIKTKAMTILGEDGKEIPEFKN
KFGYSYIISPVKMDGKYSYYASLLILFETTKNGDDEYEIEDVKFVTAGSTLELKNSLLAVENSQEEGY
VTAYPFGILMSDEIKNAFKLTYKNGHWNYMLADLTVKNKLTQETKIYKISLNSKLIIEFLKEVLKEN
SILKDIAGDLFEDI

TABLE 1-continued

Nucleotide and Amino Acid Sequences.

f04A.nt BB011 (SEQ ID NO:733)
TAATTACCAAAGATAAGTAAACTTGCAAATAAAACTACACGTATTGAAAGTAGATTTGAAATTT
CCATTATATTTATATATAATGGCACTAAATATCTGAAAATGAAGGAGAAGCGGGTGGGCAATA
AAATTTTTTATATTTCAGTGGTTTTAATTTTAATAGTTGGTTGCGACTGGGGAACTATTAAAGAT
AAAAGTACAGAAATTTCCAAGCTATTAAGAACGGACAAAGATAAGACTAAAAATCAAGATAGA
ATAGAATTGGGTGAAGATAATTTTGTATCTAAAAATAATATGTCTACTACTGATACGGGCATTA
CTAGTTTAGGAAGTCTAAACAACTTGGATTTAATTAATCGTTCACAGCGGGTCAGTGAACCACC
TATAATCTCAAATGAGAAAGCCATAGCTACTCAAGCAAAAGTAGATTTAATGAACAACATTAAT
GTTACTATAATAAACCCAAAACCAGCTCAAAATTTGGGAAATTCTTTAAACAATACTACTACTG
AAGATAGTGTGAAGTTTTTATCAATTGAAAACCAAGAGTGGCTTATTAGTAAAAAGATTTTGCC
CAGTAAGTTGGAAAATTTAGAAAGCTTTCTAAAAACACAACACGAAAAAGAAGCTTTTAAGAC
GGCTAAAACTATACAAAGTCTCATTAGTAATTCCAATATGGGTAAAGAAATTATTAAGTTTAAG
GAAGAATATTACAAACTTTATAATTTGTTGAAGGCATACAACAAAAATTCCATAGTCAAAGGA
ATTCATTTATAAAAGATACTAAATTTGGGGAAAATAGACAAAAAAATGCAGTTATATTTAAATC
CTTTTCATCTATAGAGAAAGAAATTAGAGATTTGAATTATAAGTTGNGTGAAATCCAAAGTAAT
TTTCAAATTGCAGATGTTAGCTGGAATAATGCAAACTCTCTTTTAAAAGAATCTATAGAAAAAT
TAATTCAGGCAATTGAAAAAAGGTATGACAATGAGAGTAGAAAGCAAGGTCAAATTGGTGGAC
CTGCTAATAGATGGGATAAAAATCAAGCTGACAATTTTGCTAAGGATGCAAAGTATAAGGCAG
AACATTCAGCAAATGATTTGGAAAATGCAGCCAACTATTTTAGATATAGTTGTTCAAATGAAAA
AGAAGCTAAAAAGCTATTAGAAGAAATTAAAAAAAGATTTGTACGAATTGGTATTAGCCTATA
A t04A.nt BB011 (SEQ ID NO:734)
TGCGACTGGGGAACTATTAAAGATAAAAGTACAGAAATTTCCAAGCTATTAAGAACGGACAAA
GATAAGACTAAAAATCAAGATAGAATAGAATTGGGTGAAGATAATTTTGTATCTAAAAATAAT
ATGTCTACTACTGATACGGGCATTACTAGTTTAGGAAGTCTAAACAACTTGGATTTAATTAATC
GTTCACAGCGGGTCAGTGAACCACCTATAATCTCAAATGAGAAAGCCATAGCTACTCAAGCAA
AAGTAGATTTAATGAACAACATTAATGTTACTATAATAAACCCAAAACCAGCTCAAAATTTGGG
AAATTCTTTAAACAATACTACTACTGAAGATAGTGTGAAGTTTTTATCAATTGAAAACCAAGAG
TGGCTTATTAGTAAAAAGATTTTGCCCAGTAAGTTGGAAAATTTAGAAAGCTTTCTAAAAACAC
AACACGAAAAGAAGCTTTTAAGACGGCTAAAACTATACAAAGTCTCATTAGTAATTCCAATAT
GGGTAAAGAAATTATTAAGTTTAAGGAAGAATATTACAAACTTTATAATTTGTTGAAGGCATA
CAACAAAAATTCCATAGTCAAAGGAATTCATTTATAAAAGATACTAAATTTGGGGAAATAGA
CAAAAAAATGCAGTTATATTTAAATCCTTTTCATCTATAGAGAAAGAAATTAGAGATTTGAATT
ATAAGTTGNGTGAAATCCAAAGTAATTTTTCAAATTGCAGATGTTAGCTGGAATAATGCAAACTC
TCTTTTAAAAGAATCTATAGAAAAATTAATTCAGGCAATTGAAAAAAGGTATGACAATGAGAG
TAGAAAGCAAGGTCAAATTGGTGGACCTGCTAATAGATGGGATAAAAATCAAGCTGACAATTT
TGCTAAGGATGCAAAGTATAAGGCAGAACATTCAGCAAATGATTTGGAAAATGCAGCCAACTA
TTTTAGATATAGTTGTTCAAATGAAAAAGAAGCTAAAAAGCTATTAGAAGAAATTAAAAAAAG
ATTTGTACGAATTGGTATTAGCCTA f04A.aa BB011 (SEQ ID NO:735)
LPKISKLANKTTRIESRFEISIIFIYNGTKYLKMKEKRVGNKIFYISVVLILIVGCDWGTIKDKS
TEISKLLRTDKDKTKNQDRIELGEDNFVSKNNMSTTDTGITSLGSLNNLDLINRSQRVSEPPIISNEKA
IATQAKVDLMNNINVTIINPKPAQNLGNSLNNTTTEDSVKFLSIENQEWLISKKILPSKLENLESFLKT
QHEKEAFKTAKTIQSLISNSNMGKEIIKFKEEYYKLYNLFEGIQQKFHSQRNSFIKDTKFGENRQKNA
VIFKSFSSIEKEIRDLNYKLXEIQSNFQIADVSWNNANSLLKESIEKLIQAIEKRYDNESRKQGQIGGPA
NRWDKNQADNFAKDAKYKAEHSANDLENAANYFRYSCSNEKEAKKLLEEIKKRFVRIGISL t04A.aa BB011 (SEQ ID NO:736)
CDWGTIKDKSTEISKLLRTDKDKTKNQDRIELGEDNFVSKNNMSTTDTGITSLGSLNNLDLINRSQR
VSEPPIISNEKAIATQAKVDLMNNINVTIINPKPAQNLGNSLNNTTTEDSVKFLSIENQEWLISKKILPS
KLENLESFLKTQHEKEAFKTAKTIQSLISNSNMGKEIIKFKEEYYKLYNLFEGIQQKFHSQRNSFIKDT
KFGENRQKNAVIFKSFSSIEKEIRDLNYKLXEIQSNFQIADVSWNNANSLLKESIEKLIQAIEKRYDNE
SRKQGQIGGPANRWDKNQADNFAKDAKYKAEHSANDLENAANYFRYSCSNEKEAKKLLEEIKKRF
VRIGISL f05A.nt BB009 (SEQ ID NO:737)
TAAATAAATTGTAGGATAAAAATGAAACAAAAATACGAAAACTATTTTAAAAAAAGATTAATT
TTAAACCTATTAATATTTTTACTACTAGCATGCTCAAGCGAATCCATATTTTCACAATTAGGAAA
TCTGCAAAAAATAAAACATGAATACAATATTTTGGGCAGTTCAAGTCCAAGAGGAATTTCTCTA
GTAGGAGAAACTCTCTACATTGCAGCCATGCATTTATTTAAAAAAGAAAACGGCAAGATTGAA
AAAATTGATTTGAGCAATTCTTATGAGTTTATAAACGACATTGTAAATATATCTGGAAAAACCT
ATCTTTTAGCGCAAAACAAAGAAGAAGAATTAGAAGTTTGCGAGCTAAATGGAAAAGATTGGA
CATTAAAATTTAAAAAACCGCTAAAAGCATATAAATTCTTAAAATCCGTAGAAGAGATGGCGTA
A t05A.nt BB009 (SEQ ID NO:738)
TGCTCAAGCGAATCCATATTTTCACAATTAGGAAATCTGCAAAAAATAAAACATGAATACAATA
TTTTGGGCAGTTCAAGTCCAAGAGGAATTTCTCTAGTAGGAGAAACTCTCTACATTGCAGCCAT
GCATTTATTTAAAAAAGAAAACGGCAAGATTGAAAAAATTGATTTGAGCAATTCTTATGAGTTT
ATAAACGACATTGTAAATATATCTGGAAAAACCTATCTTTTAGCGCAAAACAAAGAAGAAGAA
TTAGAAGTTTGCGAGCTAAATGGAAAAGATTGGACATTAAAATTTAAAAAACCGCTAAAAGCA
TATAAATTCTTAAAATCCGTAGAAGAGATGGCG f05A.aa BB009 (SEQ ID NO:739)
INCRIKMKQKYENYFKKRLILNLLIFLLLACSSESIFSQLGNLQKIKHEYNILGSSSPRGISLVGETLYIA

TABLE 1-continued

Nucleotide and Amino Acid Sequences.

AMHLFKKENGKIEKIDLSNSYEFINDIVNISGKTYLLAQNKEEELEVCELNGKDWTLKFKKPLKAYK
FLKSVEEMA t05A.aa BB009 (SEQ ID NO:740)
CSSESIFSQLGNLQKIKHEYNILGSSSPRGISLVGETLYIAAMHLFKKENGKIEKIDLSNSYEFINDIVNI
SGKTYLLAQNKEEELEVCELNGKDWTLKFKKPLKAYKFLKSVEEMA f06A.nt BB014 (SEQ ID NO:741)
TAAGGAGCATATATGAGGATTTTGGTTGGCGTTTGTATAATAGCATTGGCTTTATTGGGTTGTT
ATTTGCCTGATAATCAGGAACAAGCTGTTCAAACTTTTTTTGAGAATTCGGAAAGTAGTGATAT
GGGTTCCGATGAGATTGTTACTGAAGGCATATTTTCTAGTTTAAAATTATATGCGTCTGAACAT
CCTTTATTGGTTGAGATAAAAAAGACTTTAATTAGTTTAAAAGATCCTAATTATCNNGNTGTAG
TACNCCCAGTGAGTGACTATAATGAGGAGTATTTTAATAAATTCTTTCTAGATTTAGGGTCTGA
GCAATCTAAAGACCTGATTAAGTTGTTTATTATGGTAAAAAATGAGCAGAACAATAATAAATTT
ATGCGTATAGTTCGTTGGCTGTATTCATGTATAGAGGAGTTATATTCTCTAGATATTAAGTATTC
TGGCGAGGGGAGCCATGAGTATAATCGTAATATGCCTAGACCCACTGCTTATGAACAATATTTA
AAAGTGAAGAGGTATGATTATAATAGCCCAGTTTCTATTTTACCTACATAA t06A.nt BB014 (SEQ ID NO:742)
TGTTATTTGCCTGATAATCAGGAACAAGCTGTTCAAACTTTTTTTGAGAATTCGGAAAGTAGTG
ATATGGGTTCCGATGAGATTGTTACTGAAGGCATATTTTCTAGTTTAAAATTATATGCGTCTGA
ACATCGTTTATTGGTTGAGATAAAAAAGACTTTAATTAGTTTAAAAGATCCTAATTATCNNGNT
GTAGTACNCCCAGTGAGTGACTATAATGAGGAGTATTTTAATAAATTCTTTCTAGATTTAGGGT
CTGAGCAATCTAAAGACCTGATTAAGTTGTTTATTATGGTAAAAAATGAGCAGAACAATAATAA
ATTTATGCGTATAGTTCGTTGGCTGTATTCATGTATAGAGGAGTTATATTCTCTAGATATTAAGT
ATTCTGGCGAGGGGAGCCATGAGTATAATCGTAATATGCCTAGACCCACTGCTTATGAACAATA
TTTAAAAGTGAAGAGGTATGATTATAAT f06A.aa BB014 (SEQ ID NO:743)
GAYMRILVGVCIIALALLGCYLPDNQEQAVQTFFENSESSDMGSDEIVTEGIFSSLKLYASEHRLLVEI
KKTLISLKDPNYXXVVXPVSDYNEEYFNKFFLDLGSEQSKDLIKLFIMVKNEQNNNKFMRIVRWLY
SCIEELYSLDIKYSGEGSHEYNRNMPRPTAYEQYLKVKRYDYNSPVSILPT t06A.aa BB014 (SEQ ID NO:744)
CYLPDNQEQAVQTFFENSESSDMGSDEIVTEGIFSSLKLYASEHRLLVEIKKTLISLKDPNYXXVVXP
VSDYNEEYFNKFFLDLGSEQSKDLIKLFIMVKNEQNNNKFMRIVRWLYSCIEELYSLDIKYSGEGSH
EYNRNMPRPTAYEQYLKVKRYDYN f07A.nt BB023 (SEQ ID NO:745)
TAAAGTATTTTATTTTTTTTATTATCCACTGTTCTTTTTGCTCAAGAGACTGATGGATTA
GCAGAGGGTTCTAAAAGGGCAGAGCCTGGAGAATTAGTTTTAGATTTTGCCGAGCTTGCAAGA
GATCCAAGTTCAACTAGACTTGATCTTACAAATTATGTTGATTATGTATATTCGGGCGCTTCTGG
TATTGTTAAGCCGGAAGATATGGTTGTAGATCTTGGGATAAATAATTGGAGCGTTTTACTTACT
CCTTCTGCAAGGTTGCAGGCTTACGTTAAAAATTCAGTTGTTGCGCCCGCTGTTGTTAAGAGTG
AGTCAAAAAGGTACGCAGGTGATACTATTTTAGGGGTAAGAGTTTTGTTTCCAAGCTATTCTCA
ATCATCTGCTATGATTATGCCACCATTTAAAATTCCTTTTTATTCAGGGGAAAGTGGCAATCAAT
TTTTAGGCAAAGGTCTTATTGATAACATTAAAACCATGAAAGAAATTAAGGTATCTGTTTATAG
TTTAGGGTATGAGATAGATCTTGAGGTTTTATTTGAAGATATGAATGNCATGGAATATGCTTNN
TCTATGGGTACTTTAAAGTTTAAAGGGTGGGCTGATTTAATTTGGTCAAATCCTAACTATATTCC
TAATATATCATCCAGAATTATTAAAGACGATGTTCCAAATTATCCTCTTGCTTCAAGTAAAATG
AGATTTAAGGCTTTTAGAGTTTCAAAGTCACACAGTTCAAAAGAGCAAAATTTCATCTTTTATG
TTAAAGATTTAAGAGTTCTTTATGATAAGTTGAGTGTTTCAATAGATTCTGATATTGACAGTGA
GTCTGTATTTAAAGTTTATGAGACTAGCGGAACTGAATCCCTTCGTAAATTAAAGGCACACGNA
ACNTTTAAAAGNGTTTTAAAGCTTAGAGAAAAAATTTCTATGCCTGAAGGCTCTTTCCAAAACT
TTGTAGAAAAGATTGAGAGTGAAAAACCTGAAGAATCATCTCCGAAAAATTAG t07A.nt BB023 (SEQ ID NO:746)
GAGGGTTCTAAAAGGGCAGAGCCTGGAGAATTAGTTTTAGATTTTGCCGAGCTTGCAAGAGAT
CCAAGTTCAACTAGACTTGATCTTACAAATTATGTTGATTATGTATATTCGGGCGCTTCTGGTAT
TGTTAAGCCGGAAGATATGGTTGTAGATCTTGGGATAAATAATTGGAGCGTTTTACTTACTCCT
TCTGCAAGGTTGCAGGCTTACGTTAAAAATTCAGTTGTTGCGCCCGCTGTTGTTAAGAGTGAGT
CAAAAAGGTACGCAGGTGATACTATTTTAGGGGTAAGAGTTTTGTTTCCAAGCTATTCTCAATC
ATCTGCTATGATTATGCCACCATTTAAAATTCCTTTTTATTCAGGGGAAAGTGGCAATCAATTTT
TAGGCAAAGGTCTTATTGATAACATTAAAACCATGAAAGAAATTAAGGTATCTGTTTATAGTTT
AGGGTATGAGATAGATCTTGAGGTTTTATTTGAAGATATGAATGNCATGGAATATGCTTNNTCT
ATGGGTACTTTAAAGTTTAAAGGGTGGGCTGATTTAATTTGGTCAAATCCTAACTATATTCCTA
ATATATCATCCAGAATTATTAAAGACGATGTTCCAAATTATCCTCTTGCTTCAAGTAAAATGAG
ATTTAAGGCTTTTAGAGTTTCAAAGTCACACAGTTCAAAAGAGCAAAATTTCATCTTTTATGTT
AAAGATTTAAGAGTTCTTTATGATAAGTTGAGTGTTTCAATAGATTCTGATATTGACAGTGAGT
CTGTATTTAAAGTTTATGAGACTAGCGGAACTGAATCCCTTCGTAAATTAAAGGCACACGNAAC
NTTTAAAAGNGTTTTAAAGCTTAGAGAAAAAATTTCTATGCCTGAAGGCTCTTTCCAAAACTTT
GTAGAAAAGATTGAGAGTGAAAAACCTGAAGAATCATCTCCGAAAAAT f07A.aa BB023 (SEQ ID NO:747)
SILFFLLSTVLFAQETDGLAEGSKRAEPGELVLDFAELARDPSSTRLDLTNYVDYVYSGASGIVKPED
MVVDLGINNWSVLLTPSARLQAYVKNSVVAPVVKSESKRYAGDTILGVRVLFPSYSQSSAMIMPP
FKIPFYSGESGNQFLGKGLIDNIKTMKEIKVSVYSLGYEIDLEVLFEDMNXMEYAXSMGTLKFKGW

TABLE 1-continued

Nucleotide and Amino Acid Sequences.

ADLIWSNPNYIPNISSRIIKDDVPNYPLASSKMRFKAFRVSKSHSSKEQNFIFYVKDLRVLYDKLSVSI
DSDIDSESVFKVYETSGTESLRKLKAHXTFKXVLKLREKISMPEGSFQNFVEKIESEKPEESSPKN t07A.aa BB023 (SEQ ID NO:748)
EGSKRAEPGELVLDFAELARDPSSTRLDLTNYVDYVYSGASGIVKPEDMVVDLGINNWSVLLTPSA
RLQAYVKNSVVAPAVVKSESKRYAGDTILGVRVLFPSYSQSSAMIMPPFKIPFYSGESGNQFLGKGLI
DNIKTMKEIKVSVYSLGYEIDLEVLFEDMNXMEYAXSMGTLKFKGWADLIWSNPNYIPNISSRIIKD
DVPNYPLASSKMRFKAFRVSKSHSSKEQNFIFYVKDLRVLYDKLSVSIDSDIDSESVFKVYETSGTES
LRKLKAHXTFKXVLKLREKISMPEGSFQNFVEKIESEKPEESSPKN f08A.nt BB024 (SEQ ID NO:749)
TGAATATTAATAATAAAAAAAGGAGTAACAATGAAAATCATCAACATATTATTTTGTTTATTTT
TACTAATGCTAAACGGCTGTAATTCTAATGATAATGACACTTTAAAAAACAATGCCCAACAAAC
AAAAAGACGGGGAAAGCGTGATTTAACCCAAAAAGAAACAACACAAGAAAAACCAAAATCTA
AAGAAGAACTACTTAGAGAAAAGCTATCTGACGATCAAAAAACACATCTTGACTGGTTAAAAC
CCGCTTTAACTGGTGCTGGAGAATTTGACAAATTCTTAGAAAATGATGATGATAAAATAAAATC
AGCACTTGATCATATAAAAACTCAACTTGATAGTTGTAATGGTGATCAAGCAGAACAACAAAA
AACCCACTTTCAAAACTGTGGTTACAGAATTCTTTAAAAATGGTGATATAGATAATTTTGCAACT
GGAGCGGTTAGTAACTGCAATAATGGTGGCTAA t08A.nt BB024 (SEQ ID NO:750)
TGTAATTCTAATGATAATGACACTTTAAAAAACAATGCCCAACAAACAAAAAGACGGGGAAAG
CGTGATTTAACCCAAAAAGAAACAACACAAGAAAAACCAAAATCTAAAGAAGAACTACTTAGA
GAAAAGCTATCTGACGATCAAAAAACACATCTTGACTGGTTAAAACCCGCTTTAACTGGTGCTG
GAGAATTTGACAAATTCTTAGAAAATGATGATGATAAAATAAAATCAGCACTTGATCATATAAA
AACTCAACTTGATAGTTGTAATGGTGATCAAGCAGAACAACAAAAAACCCACTTTCAAAACTGTG
GTTACAGAATTCTTTAAAAATGGTGATATAGATAATTTTGCAACTGGAGCGGTTAGTAACTGCA
ATAATGGTGGC f08A.aa BB024 (SEQ ID NO:751)
ILIIKKGVTMKIINILFCLFLLMLNGCNSNDNDTLKNNAQQTKRRGKRDLTQKETTQEKPKSKEELLR
EKLSDDQKTHLDWLKPALTGAGEFDKFLENDDDKIKSALDHIKTQLDSCNGDQAEQQKTTFKTVV
TEFFKNGDIDNFATGAVSNCNNGG t08A.aa BB024 (SEQ ID NO:752)
CNSNDNDTLKNNAQQTKRRGKRDL51TQKETTQEKPKSKEELLREKLSDDQKTHLDWLKPALTGA
GEFDKFLENDDDKIKSALDHIKTQLDSCNGDQAEQQKTTFKTVVTEFFKNGDIDNFATGAVSNCNN
GG f09A.nt BB025 (SEQ ID NO:753)
TGAATATTAATAATAAAAAAAGGAATAATAATGAAAATTATCAACATATTATTTTGTTTATTTT
TACTAATGCTAAACGGCTGTAATTCTAATGATACTAATAATAGCCAAACAAAAAGTAGACAAAA
ACGTGATTTAACCCAAAAAGAAGCAACACAAGAAAAACCTAAATCTAAAGAAGAACTTCTTAG
AGAAAAGCTAAATGATAATCAAAAAACACACCTTGACTGGTTAAAAGAAGCTCTGGGCAATGA
TGGAGAATTTAATAAATTTTTAGGATATGATGAAAGCAAAATAAAATCTGCACTTGATCATATA
AAGAGTGAACTTGACAGTTGTACTGGAGATAAGGTTGAAAATAAAAATACCTTCAAGCAGGTC
GTTCAGGAGGCCCTTAAAGGGGGCATAGACGGCTTTGAAAATACTGCAAGTAGTACGTGCAAA
AATTCATAA t09A.nt BB025 (SEQ ID NO:754)
TGTAATTCTAATGATACTAATAATAGCCAAACAAAAAGTAGACAAAAACGTGATTTAACCCAAA
AAGAAGCAACACAAGAAAAACCTAAATCTAAAGAAGAACTTCTTAGAGAAAAGCTAAATGATA
ATCAAAAAACACACCTTGACTGGTTAAAAGAAGCTCTGGGCAATGATGGAGAATTTAATAAAT
TTTTAGGATATGATGAAAGCAAAATAAAATCTGCACTTGATCATATAAAGAGTGAACTTGACAG
TTGTACTGGAGATAAGGTTGAAAATAAAAATACCTTCAAGCAGGTCGTTCAGGAGGCCCTTAAA
GGGGGCATAGACGGCTTTGAAAATACTGCAAGTAGTACGTGCAAAAATTCA f09A.aa BB025 (SEQ ID NO:755)
ILIIKKGIMKIINILFCLFLLMLNGCNSNDTNNSQTKSRQKRDLTQKEATQEKPKSKEELLREKLNDN
QKTHLDWLKEALGNDGEFNKFLGYDESKIKSALDHIKSELDSCTGDKVENKNTFKQVVQEALKGGI
DGFENTASSTCKNS t09A.aa BB025 (SEQ ID NO:756)
CNSNDTNNSQTKSRQKRDLTQKEA51TQEKPKSKEELLREKLNDNQKTHLDWLKEALGNDGEFNK
FLGYDESKIKSALDHIKSELDSCTGDKVENKNTFKQVVQEALKGGIDGFENTASSTCKNS

TABLE 2

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f01A.aa | gi|2690256 | (AE000790) antigen, P35, putative [*Borrelia burgdorferi*] | 1523 | 5.90E-206 |
| f02A.aa | gi|2690286 | (AE000790) *B. burgdorferi* predicted coding region BBA69 [*Borrelia* | 1320 | 2.10E-174 |
| f02A.aa | gi|2690285 | (AE000790) *B. burgdorferi* predicted coding region BBA68 [*Borrelia* | 278 | 7.50E-71 |
| f02A.aa | gi|2690105 | (AE000789) *B. burgdorferi* predicted coding region BBI38 [*Borrelia* | 151 | 8.40E-54 |
| f02A.aa | gi|2690092 | (AE000789) antigen, P35, putative [*Borrelia burgdorferi*] | 151 | 2.70E-48 |
| f02A.aa | gi|2690183 | (AE000787) antigen, P35, putative [*Borrelia burgdorferi*] | 155 | 4.20E-22 |
| f02A.aa | gi|2690106 | (AE000789) *B. burgdorferi* predicted coding region BB139 [*Borrelia* | 154 | 1.30E-21 |
| f03A.aa | gi|2688051 | (AE001 127) antigen, S2, putative [*Borrelia burgdorferi*] | 1223 | 7.60E-164 |
| f03A.aa | gi|1063419 | S2 gene product [*Borrelia burgdorferi*] | 116 | 3.00E-22 |
| f03A.aa | gi|2690227 | (AE000790) antigen, S2 [*Borrelia burgdorferi*] > pir|D70207|D70207 | 116 | 9.70E-22 |
| f03A.aa | gi|2690128 | (AE000788) protein p23 [*Borrelia burgdorferi*] > pir|C70257|C70257 | 110 | 5.70E-19 |
| f03A.aa | gi|2689956 | (AE000785) protein p23 [*Borrelia burgdorferi*] > pir|D70225|D70225 | 104 | 7.90E-15 |
| f04A.aa | gi|2690078 | (AE000784) *B. burgdorferi* predicted coding region BBH18 [*Borrelia* | 1873 | 5.60E-250 |
| f04A.aa | gi|2690192 | (AE000787) *B. burgdorferi* predicted coding region BBJ13 [*Borrelia* | 167 | 1.40E-15 |
| f05A.aa | gi|2687919 | (AE001117) *B. burgdorferi* predicted coding region BB0028 [*Borrelia* | 696 | 4.20E-92 |
| f06A.aa | gi|2690129 | (AE000788) outer membrane protein [*Borrelia burgdorferi*] | 884 | 4.80E-124 |
| f06A.aa | gi|2690089 | (AE000789) conserved hypothetical protein [Borrelia burgdorferi] | 731 | 2.20E-118 |
| f06A.aa | gi|520783 | unknown [*Borrelia burgdorferi*] > gi|551742 unknown [*Borrelia* | 337 | 4.30E-58 |
| f07A.aa | gi|2688608 | (AE001168) flagellar filament outer layer protein (flaA) [*Borrelia* | 1668 | 2.50E-224 |
| f07A.aa | gi|1575447 | Fla A protein [*Borrelia burgdorferi*] > gi|1019754 orf [*Borrelia* | 1645 | 3.60E-221 |
| f07A.aa | gi|152896 | flagellar filament surface antigen [*Spirochaeta aurantia*] | 144 | 1.70E-38 |
| f07A.aa | gi|155059 | encloflagellar sheath protein [*Treponema pallidum*] | 139 | 3.80E-28 |
| f07A.aa | gi|433524 | flagellin FlaA1 [*Serpulina hyodysenteriae*] > gi|904393 endoflagellar | 119 | 3.00E-26 |
| f07A.aa | pir|A32814|A32814 | flagellar filament surface antigen - *Spirochaeta aurantia* | 116 | 9.40E-11 |
| f08A.aa | gi|1209837 | lipoprotein [*Borrelia burgdorferi*] | 508 | 2.10E-78 |
| f08A.aa | gi|2121280 | (AF000270) lipoprotein [*Borrelia burgdorferi*] > gi|3095109 | 547 | 4.00E-70 |
| f08A.aa | gi|1209873 | lipoprotein [*Borrelia burgdorferi*] | 303 | 3.70E-51 |
| f08A.aa | gi|1209843 | lipoprotein [*Borrelia burgdorferi*] | 395 | 2.20E-49 |
| f08A.aa | gi|1209849 | lipoprotein [*Borrelia burgdorferi*] | 219 | 2.60E-27 |
| f08A.aa | gi|3095105 | (AF046998) 2.9-8 lipoprotein [*Borrelia burgdorferi*] | 234 | 4.30E-27 |
| f08A.aa | gi|1209831 | lipoprotein [*Borrelia burgdorferi*] | 209 | 1.10E-22 |
| f08A.aa | gi|3095107 | (AF046999) 2.9-9 lipoprotein [*Borrelia burgdorferi*] | 200 | 1.80E-22 |
| f08A.aa | gi|1209857 | lipoprotein [*Borrelia burgdorferi*] | 200 | 2.50E-21 |
| f08A.aa | gnl|PID|e268244 | surface-exposed lipoprotein [*Borrelia afzelii*] | 142 | 1.80E-11 |
| f09A.aa | gi|1209843 | lipoprotein [*Borrelia burgdorferi*] | 453 | 8.60E-67 |
| f09A.aa | gi|2121280 | (AF000270) lipoprotein [*Borrelia burgdorferi*] > gi|3095109 | 379 | 1.00E-56 |
| f09A.aa | gi|1209873 | lipoprotein [*Borrelia burgdorferi*] | 282 | 1.10E-45 |
| f09A.aa | gi|1209837 | lipoprotein [*Borrelia burgdorferi*] | 357 | 7.10E-44 |
| f09A.aa | gi|1209849 | lipoprotein [*Borrelia burgdorferi*] | 143 | 1.60E-13 |
| f09A.aa | gnl|PID|e268244 | surface-exposed lipoprotein [*Borrelia afzelii*] | 111 | 3.60E-11 |
| f09A.aa | gi|3095105 | (AF046998) 2.9-8 lipoprotein [*Borrelia burgdorferi*] | 142 | 5.40E-13 |
| f101.aa | gi|2688708 | (AE001176) conserved hypothetical protein [*Borrelia burgdorferi*] | 1099 | 4.50E-152 |
| f105.aa | gi|2688693 | (AE001175) *B. burgdorferi* predicted coding region BB0758 [*Borrelia* | 1276 | 2.20E-177 |
| f11-12.aa | gi|2690139 | (AE000788) *B. burgdorferi* predicted coding region BBK01 [*Borrelia* | 1473 | 4.70E-193 |
| f11-12.aa | gi|2690030 | (AE000786) *B. burgdorferi* predicted coding region BBG01 [*Borrelia* | 1066 | 1.40E-138 |
| f11-12.aa | gi|2690074 | (AE000784) *B. burgdorferi* predicted coding region BBH37 [*Borrelia* | 173 | 6.20E-93 |
| f11-12.aa | gi|2690188 | (AE000787) *B. burgdorferi* predicted coding region BBJ08 [*Borrelia* | 192 | 2.70E-75 |
| f11-4.aa | gi|2690150 | (AE000788) *B. burgdorferi* predicted coding region BBK12 [*Borrelia* | 1144 | 2.70E-147 |
| f11-4.aa | gi|2690145 | (AE000788) *B. burgdorferi* predicted coding region BBK07 [*Borrelia* | 852 | 5.70E-127 |
| f11-4.aa | gi|2690095 | (AE000789) *B. burgdorferi* predicted coding region BBI10 [*Borrelia* | 153 | 1.30E-34 |
| f11-4.aa | gi|2690197 | (AE000787) *B. burgdorferi* predicted coding region BBJ31 [*Borrelia* | 115 | 1.40E-12 |
| f11-4.aa | gi|2690219 | (AE000787) *B. burgdorferi* predicted coding region BBJ45 [*Borrelia* | 115 | 1.40E-12 |
| f112-1.aa | gi|2690054 | (AE000784) *B. burgdorferi* predicted coding region BBH06 [*Borrelia* | 573 | 7.00E-75 |
| f12.aa | gi|2688785 | (AE001182) *B. burgdorferi* predicted coding region BB0838 [*Borrelia* | 6008 | 0 |
| f129.aa | gi|2688685 | (AE001174) *B. burgdorferi* predicted coding region BB0739 [*Borrelia* | 987 | 6.20E-133 |
| f14-8.aa | gi|2689955 | (AE000785) antigen, P35, putative [*Borrelia burgdorferi*] | 385 | 2.70E-75 |
| f14-8.aa | gi|2690120 | (AE000789) *B. burgdorferi* predicted coding region BBI34 [*Borrelia* | 330 | 2.60E-66 |
| f14-8.aa | gi|2690052 | (AE000784) antigen, P35, putative [*Borrelia burgdorferi*] | 287 | 4.00E-64 |
| f14-8.aa | gi|2690100 | (AE000789) *B. burgdorferi* predicted coding region BBI16 [*Borrelia* | 172 | 1.10E-38 |
| f14-8.aa | gi|2690115 | (AE000789) *B. burgdorferi* predicted coding region BBI28 [*Borrelia* | 173 | 1.70E-28 |
| f14-8.aa | gi|2690116 | (AE000789) *B. burgdorferi* predicted coding region BBI29 [*Borrelia* | 163 | 8.20E-24 |
| f14-8.aa | gi|2690207 | (AE000787) *B. burgdorferi* predicted coding region BBJ02 [*Borrelia* | 220 | 1.90E-23 |
| f14-8.aa | gi|2690099 | (AE000789) *B. burgdorferi* predicted coding region BBI15 [*Borrelia* | 140 | 3.60E-12 |
| f14-8.aa | gi|2690125 | (AE000788) antigen, P35, putative [*Borrelia burgdorferi*] | 111 | 1.00E-11 |
| f142.aa | gi|2688655 | (AE001172) glutamate transporter (gltP) [*Borrelia burgdorferi*] | 2233 | 7.19999999999982e-311 |
| f142.aa | gnl|PID|e233874 | hypothetical protein [*Bacillus subtilis*] > gnl|PID|e1 182902 | 727 | 2.60E-156 |
| f142.aa | gnl|PID|d10 | Proton/sodium-glutamate symport protein (Glutamate-aspartate | 762 | 6.60E-146 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f142.aa | gi|1574711 16231 | proton glutamate symport protein (gltP) [*Haemophilus influenzae*] | 903 | 2.10E-131 |
| f142.aa | gi|2983758 | (AE000735) proton/sodium-glutamate symport protein [*Aquifex*] | 111 | 8.40E-36 |
| f142.aa | gi|143000 | proton glutamate symport protein [*Bacillus stearothermophilus*] | 125 | 1.20E-30 |
| f142.aa | gi|143002 | proton glutamate symport protein [*Bacillus caldotenax*] | 125 | 1.90E-28 |
| f142.aa | gnl|PID|e11 83024 | proton/sodium-glutamate symport protein [*Bacillus subtilis*] | 122 | 2.20E-25 |
| f142.aa | gnl|PID|d10 22697 | glutamate transporter [*Caenorhabditis elegans*] | 121 | 1.80E-22 |
| f142.aa | gi|1255318 | coded for by *C. elegans* cDNA cm08h9; coded for by *C. elegans* cDNA | 121 | 2.10E-22 |
| f142.aa | gi|2388712 | (AF017105) amino acid transporter [*Chlamydia psittaci*] | 135 | 3.60E-22 |
| f142.aa | gi|2655021 | (AF018259) glutamate transporter 5A [*Ambystoma tigrinum*] | 125 | 7.70E-22 |
| f142.aa | gnl|PID|e14 9542 | gluT-R gene product [*Clostridium perfringens*] | 199 | 4.60E-21 |
| f142.aa | gi|396412 | gltP [*Escherichia coli*] > gi|147160 proton-glutamate [*Escherichia*] | 109 | 7.90E-21 |
| f147.aa | gi|2688656 | (AE001172) NADH oxidase, water-forming (nox) [*Borrelia burgdorferi*] | 2245 | 7.20E-303 |
| f147.aa | gi|642030 | NADH oxidase [*Serpulina hyodysenteriae*] | 318 | 9.20E-105 |
| f147.aa | gi|2650234 | (AE001077) NADH oxidase (noxA-2) [*Archeoglobus fulgidus*] | 303 | 2.90E-93 |
| f147.aa | gi|2792490 | (AF041467) coenzyme A disulfide reductase [*Staphylococcus aureus*] | 194 | 2.60E-90 |
| f147.aa | gi|2650383 | (AE001088) NADH oxidase (noxA-1) [*Archaeoglobus fulgidus*] | 286 | 3.30E-88 |
| f147.aa | gnl|PID|d10 09320 | H2O-forming NADH Oxidase [*Streptococcus mutans*] | 369 | 4.30-85 |
| f147.aa | gi|49023 | NADH peroxidase [*Enterococcus faecalis*] > pir|S18332|S18332 NADH | 638 | 3.20E-83 |
| f147.aa | gi|1591361 | NADH oxidase (nox) [*Methanococcus jannaschii*] > pir|A64381|A64381 | 535 | 4.80E-83 |
| f147.aa | gi|2622461 | (AE000898) NADH oxidase [*Methanobacterium thermoautotrophicum*] | 303 | 8.40E-72 |
| f147.aa | gi|47045 | NADH oxidase [*Enterococcus faecalis*] > pir|S26965|S26965 NADH oxidase | 547 | 8.80E-71 |
| f147.aa | gi|2650233 | (AE001077) NADH oxidase (nox A-3) [*Archaeoglobus fulgidus*] | 312 | 2.00E-63 |
| f147.aa | gi|1674132 | (AE000044) Mycoplasma pneumoniae, NADH oxidase: similar to | 175 | 7.00E-61 |
| f147.aa | gi|1045969 | NADH oxidase [*Mycoplasma genitalium*] > pir|D64230|D64230 NADH | 164 | 4.10E-51 |
| f147.aa | gi|2648692 | (AE000975) NADH oxidase (noxA-5) [*Archaeoglobus fulgidus*] | 143 | 2.00E-40 |
| f147.aa | gi|2983379 | (AE000709) NADH oxidase [*Aquifex aeolicus*] | 162 | 5.50E-30 |
| f150.aa | gi|2688659 | (AE001172) conserved hypothetical protein [*Borrelia burgdorferi*] | 1319 | 2.70E-179 |
| f150.aa | gi|2983887 | (AE000743) hypothetical protein [*Aquifex aeolicus*] | 238 | 1.40E-25 |
| f150.aa | gi|2581796 | (AF001974) putative Trk A [*Thermoanaerobacter ethanolicus*] | 175 | 5.80E-23 |
| f150.aa | gi|1377829 | unknown [*Bacillus subtilis*] > gnl|PID|d 1007628 orf4 [*Bacillus*] | 212 | 1.50E-21 |
| f150.aa | gnl|PID|e11 85982 | similar to hypothetical proteins [*Bacillus subtilis*] | 181 | 6.00E-17 |
| f150.aa | gnl|PID|d10 11497 | hypothetical protein [*Synechocystis* sp.] > pir|S75999|S75999 | 128 | 3.70E-11 |
| f152.aa | gi|2688660 | (AE001172) K+ transport protein (ntpJ) [*Borrelia burgdorferi*] | 2200 | 2.40000000001213e-313 |
| f152.aa | gi|2983882 | (AE000743) K+ transport protein homolog [*Aquifex aeolicus*] | 239 | 3.60E-106 |
| f152.aa | gnl|PID|e11 84940 | similar to Na+-transporting ATP synthase [*Bacillus subtilis*] | 158 | 6.60E-64 |
| f152.aa | gnl|PID|e11 85983 | similar to Na+-transporting ATP synthase [*Bacillus subtilis*] | 131 | 3.40E-62 |
| f152.aa | gnl|PID|d10 18749 | Na+-ATPase subunit J [*Synechocystis* sp.] > pir|S75455|S75455 | 141 | 1.70E-55 |
| f152.aa | gnl|PID|d10 04799 | Na+-ATPase subunit J [*Enterococcus hirae*] | 209 | 4.00E-45 |
| f152.aa | gi|2581795 | (AF001974) putative TrkG [*Thermoanaerobacter ethanolicus*] | 149 | 2.20E-29 |
| f152.aa | gi|1674061 | (AE000036) Mycoplasma pneumoniae, Na(+) translocating ATPase | 104 | 4.00E-28 |
| f152.a | gi|1046024 | Na+ ATPase subunit J [*Mycoplasma genitalium*] > pir|F64235|F64235 Na+ | 114 | 2.80E-27 |
| f152.aa | gi|567062 | HKT1 [*Triticum aestivum*] > pir|S47582|S47582 high-affinity potassium | 137 | 2.00E-17 |
| f154.aa | gi|2688664 | (AE001172) *B. burgdorferi* predicted coding region BB0722 [*Borrelia*] | 2456 | 0 |
| f157.aa | gi|2688641 | (AE001171) rod shape-determining protein (mreB-2) [*Borrelia*] | 2300 | 0 |
| f157.aa | gi|143657 | endospore forming protein [*Bacillus subtilis*] | 224 | 2.60E-61 |
| f157.aa | gi|580938 | internal open reading frame (AA 1-290) [*Bacillus subtilis*] | 224 | 2.60E-61 |
| f157.aa | gi|2982781 | (AE000670) rod shape determining protein RodA [*Aquifex aeolicus*] | 333 | 5.40E-61 |
| f157.aa | gi|580937 | spoVE gene product (AA 1-366) [*Bacillus subtilis*] > gnl|PID|e1185111 | 224 | 7.70E-59 |
| f157.aa | gi|147695 | rod-shape-determining protein [*Escherichia coli*] > gi|1778551 | 340 | 6.10E-58 |
| f157.aa | gnl|PID|e32 8589 | sfr [*Streptomyces coelicolor*] | 362 | 6.40E-58 |
| f157.aa | gi|1572976 | rod shape-determining protein (mreB) [*Haemophilus influenzae*] | 307 | 4.00E-56 |
| f157.aa | gnl|PID|e11 85075 | similar to cell-division protein [*Bacillus subtilis*] | 203 | 2.60E-45 |
| f157.aa | gi|1469784 | putative cell division protein ftsW [*Enterococcus hirae*] | 231 | 6.90E-45 |
| f157.aa | gi|1016213 | strong sequence similarity to FtsW, RodA, and Spo V-E [*Cyanophora*] | 206 | 3.00E-41 |
| f157.aa | gnl|PID|d10 19002 | rod-shape-determining protein [*Synechocystis* sp.] | 184 | 1.60E-38 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f157.aa | gi|146039 | cell division protein [*Escherichia coli*] > gi|40857 FtsW protein | 104 | 8.30E-35 |
| f157.aa | gi|1574692 | cell division protein (ftsW) [*Haemophilus influenzae*] | 114 | 3.30E-33 |
| f157.aa | gi|1165286 | FtsW [*Borrelia burgdorferi*] > gi|2688164 (AE001137) cell division | 170 | 6.20E-32 |
| f17-6.aa | gi|2690100 | (AE000789) *B. burgdorferi* predicted coding region BBI16 [*Borrelia* | 1250 | 1.70E-164 |
| f17-6.aa | gi|2690120 | (AE000789) *B. burgdorferi* predicted coding region BBI34 [*Borrelia* | 142 | 3.40E-59 |
| f17-6.aa | gi|2690115 | (AE000789) *B. burgdorferi* predicted coding region BBI28 [*Borrelia* | 447 | 6.70E-56 |
| f17-6.aa | gi|2690052 | (AE000784) antigen, P35, putative [*Borrelia burgdorferi*] | 182 | 1.10E-34 |
| f17-6.aa | gi|2689955 | (AE000785) antigen, P35, putative [*Borrelia burgdorferi*] | 196 | 6.60E-34 |
| f17-6.aa | gi|2690114 | (AE000789) *B. burgdorferi* predicted coding region BBI27 [*Borrelia* | 176 | 1.00E-16 |
| f17-6.aa | gnl|PID|d10 12343 | gene required for phosphoylation of oligosaccharides/has | 178 | 2.80E-15 |
| f17-6.aa | gi|2690207 | (AE000787) *B. burgdorferi* predicted coding region BBJ02 [*Borrelia* | 114 | 3.50E-13 |
| f17-6.aa | gnl|PID|e32 9895 | (AJ000496) cyclic nucleotide-gated channel beta subunit | 152 | 1.10E-11 |
| f170.aa | gi|2688652 | (AE001171) *B. burgdorferi* predicted coding region BB0708 [*Borrelia* | 524 | 2.60E-73 |
| f186.aa | gi|2688622 | (AE001169) *B. burgdorferi* predicted coding region BB0689 [*Borrelia* | 792 | 1.80E-105 |
| f186.aa | gi|2688622 | (AE001169) *B. burgdorferi* predicted coding region BB0689 [*Borrelia* | 792 | 1.80E-105 |
| f19-2.aa | gi|2690120 | (AE000789) *B. burgdorferi* predicted coding region BBI34 *Borrelia* | 1341 | 2.70E-177 |
| f19-2.aa | gi|2689955 | (AE000785) antigen, P35, putative [*Borrelia burgdorferi*] | 347 | 7.00E-53 |
| f19-2.aa | gi|2690052 | (AE000784) antigen, P35, putative [*Borrelia burgdorferi*] | 254 | 7.70E-53 |
| f19-2.aa | gi|2690100 | (AE000789) *B. burgdorferi* predicted coding region BBI16 [*Borrelia* | 142 | 6.60E-50 |
| f19-2.aa | gi|2690115 | (AE000789) *B. burgdorferi* predicted coding region BBI28 [*Borrelia* | 144 | 7.60E-34 |
| f19-2.aa | gi|2690116 | (AE000789) *B. burgdorferi* predicted coding region BBI29 [*Borrelia* | 183 | 2.20E-21 |
| f19-2.aa | gi|2690207 | (AE000787) *B. burgdorferi* predicted coding region BBJ02 [*Borrelia* | 171 | 2.00E-16 |
| f19-2.aa | gi|2690099 | (AE000789) *B. burgdorferi* predicted coding region BBI15 [*Borrelia* | 166 | 1.20E-15 |
| f19-2.aa | gi|2690125 | (AE000788) antigen, P35, putative [*Borrelia burgdorferi*] | 122 | 5.70E-14 |
| f19-4.aa | gi|2690116 | (AE000789) *B. burgdorferi* predicted coding region BBI29 [*Borrelia* | 1129 | 1.30E-150 |
| f19-4.aa | gi|2690099 | (AE000789) *B. burgdorferi* predicted coding region BBJ15 [*Borrelia* | 260 | 3.00E-30 |
| f19-4.aa | gi|2689955 | (AE000785) antigen, P35, putative [*Borrelia burgdorferi*] | 180 | 1.80E-23 |
| f19-4.aa | gi|2690120 | (AE000789) *B. burgdorferi* predicted coding region BBI34 [*Borrelia* | 183 | 1.50E-21 |
| f19-4.aa | gi|2690052 | (AE000784) antigen, P35, putative [*Borrelia burgdorferi*] | 192 | 1.20E-19 |
| f19-4.aa | gi|2690207 | (AE000787) *B. burgdorferi* predicted coding region BBJ02 [*Borrelia* | 149 | 8.90E-14 |
| f19-4.aa | gi|2690098 | (AE000789) *B. burgdorferi* predicted coding region BBI14 [*Borrelia* | 138 | 8.00E-12 |
| f19-6.aa | gi|2690115 | (AE000789) *B. burgdorferi* predicted coding region BBI28 [*Borrelia* | 995 | 1.20E-131 |
| f19-6.aa | gi|2690100 | (AE000789) *B. burgdorferi* predicted coding region BBI16 [*Borrelia* | 447 | 3.00E-55 |
| f19-6.aa | gi|2689955 | (AE000785) antigen, P35, putative [*Borrelia burgdorferi*] | 219 | 2.00E-36 |
| f19-6.aa | gi|2690120 | (AE000789) *B. burgdorferi* predicted coding region BBI34 [*Borrelia* | 144 | 3.50E-34 |
| f19-6.aa | gi|2690052 | (AE000784) antigen, P35, putative [*Borrelia burgdorferi*] | 130 | 6.30E-12 |
| f196.aa | gi|2688620 | (AE001169) methyl-accepting chemotaxis protein (mcp-5) [*Borrelia* | 3093 | 0 |
| f196.aa | gi|2688621 | (AE001169) methyl-accepting chemotaxis protein (mcp-4) [*Borrelia* | 615 | 1.90E-83 |
| f196.aa | gi|496484 | tlpC gene product [*Bacillus subtilis*] > pir|I40496|I40496 methylation | 180 | 6.90E-28 |
| f196.aa | gnl|PID|d10 07002 | methyl-accepting chemotaxis protein TlpC [*Bacillus subtilis*] | 180 | 4.90E-27 |
| f196.aa | gnl|PID|e11 73493 | methyl-accepting chemotaxis protein [*Bacillus subtilis*] | 162 | 5.10E-25 |
| f196.aa | gi|882594 | ORF_f506 [*Escherichia coli*] > gi|1789453 (AE000389) aerotaxis | 204 | 1.70E-24 |
| f196.aa | gi|148350 | tas [*Enterobacter aerogenes*] > pir|D32302|D32302 probable aspartate | 179 | 1.80E-24 |
| f196.aa | gi|1066850 | putative [*Rhodobacter capsulatus*] > pir|JC4735|JC4735 | 207 | 1.80E-24 |
| f196.aa | gi|154381 | chemoreceptor [*Salmonella typhimurium*] > pir|A47178|A47178 | 230 | 2.00E-24 |
| f196.aa | gi|459690 | transmembrane receptor [*Bacillus subtilis*] > gnl|PID|e1185997 | 212 | 1.40E-23 |
| f196.aa | gi|805015 | MCPA protein [*Rhodobacter sphaeroides*] > pir|S70094|S54262 | 237 | 2.10E-23 |
| f196.aa | gi|40424 | mcpA gene product [*Caulobacter crescentus*] > pir|S23064|S23064 mcpA | 238 | 7.30E-23 |
| f196.aa | gi|144913 | sensory transducer protein [*Clostridium thermocellum*] | 227 | 8.90E-23 |
| f196.aa | gi|1061063 | Trg sensory transducer protein [*Escherichia coli*] | 211 | 2.40E-20 |
| f196.aa | gnl|PID|d10 15762 | Methyl-accepting chemotaxis protein III (MCP-III) (Ribose and | 211 | 2.50E-20 |
| f197.aa | gi|2688621 | (AE001169) methyl-accepting chemotaxis protein (mcp-4) [*Borrelia* | 3724 | 0 |
| f197.aa | gi|2688620 | (AE001169) methyl-accepting chemotaxis protein (mcp-5) [*Borrelia* | 615 | 8.40E-83 |
| f197.aa | gi|1066850 | putative [*Rhodobacter capsulatus*] > pir|JC4735|JC4735 | 227 | 9.80E-27 |
| f197.aa | gi|882594 | ORF_f506 [*Escherichia coli*] > gi|1789453 (AE000389) aerotaxis | 217 | 1.00E-26 |
| f197.aa | gi|154381 | chemoreceptor [*Salmonella typhimurium*] > pir|A47178|A47178 | 239 | 2.80E-25 |
| f197.aa | gi|496484 | tlpC gene product [*Bacillus subtilis*] > pir|I40496|I40496 methylation | 202 | 5.10E-25 |
| f197.aa | gnl|PID|d10 07002 | methyl-accepting chemotaxis protein TlpC [*Bacillus subtilis*] | 202 | 5.10E-25 |
| f197.aa | gi|2564665 | (AF022807) putative methyl accepting chemotaxis protein [*Rhizobium* | 212 | 7.20E-24 |
| f197.aa | gi|459691 | transmembrane receptor [*Bacillus subtilis*] > gnl|PID|e1185996 | 215 | 1.10E-23 |
| f197.aa | gi|43218 | serine chemoreceptor [*Escherichia coli*] > bbs|127562 serine | 236 | 2.80E-23 |
| f197.aa | gi|537197 | CG Site No. 63; alternate gene name cheD [*Escherichia coli*] | 236 | 2.90E-23 |
| f197.aa | gi|148077 | methyl-accepting chemotaxis protein I [*Escherichia coli*] > gi|2367378 | 236 | 2.90E-23 |
| f197.aa | gnl|PID|1d10 09948 | transducer [*Pseudomonas aeruginosa*] | 178 | 4.20E-23 |
| f197.aa | gi|148349 | tse [*Enterobacter aerogenes*] > pir|C32302|C32302 serine transducer | 234 | 5.50E-23 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f197.aa | gi|2626835 | chemotactic transducer [*Pseudomonas aeruginosa*] | 177 | 5.70E-23 |
| f200.aa | gi|2688600 | (AE001168) ribose/galactose ABC transporter, permease protein | 1887 | 5.10E-266 |
| f200.aa | gnl|PID|e311453 | unknown [*Bacillus subtilis*] > gnl|PID|e1184234 similar to | 283 | 1.50E-63 |
| f200.aa | gi|2649711 | (AE001042) ribose ABC transporter, permease protein (rbsC-1) | 202 | 1.10E-47 |
| f200.aa | gi|2130609 | (AF000308) putative polytopic protein [*Mycoplasma fermentans*] | 119 | 2.10E-27 |
| f200.aa | gnl|PID|e311493 | unknown [*Bacillus subtilis*] > gnl|PID|e1184235 similar to | 112 | 1.10E-18 |
| f200.aa | gi|950073 | membrane forming protein [*Mycoplasma capricolum*] > pir|S77790|S77790 | 161 | 5.60E-16 |
| f200.aa | gi|2688599 | (AE001168) ribose/galactose ABC transporter, permease protein | 108 | 2.00E-14 |
| f208.aa | gi|2688610 | (AE001168) *B. burgdorferi* predicted coding region BB0674 [*Borrelia* | 1726 | 6.70E-244 |
| f21-4.aa | gi|1197833 | Bbk2.11 [*Borrelia burgdorferi*] > pir|S70531|S70531 bbk2.11 protein | 474 | 3.00E-70 |
| f21-4.aa | gi|2627267 | ErpL [*Borrelia burgdorferi*] | 477 | 6.30E-69 |
| f21-4.aa | gi|1707281 | putative outer membrane protein [*Borrelia burgdorferi*] | 503 | 6.60E-66 |
| f21-4.aa | gi|896042 | OspF [*Borrelia burgdorferi*] > pir|S70532|S70532 outer surface protein | 503 | 6.60E-66 |
| f21-4.aa | gi|1707287 | putative outer membrane protein [*Borrelia burgdorferi*] | 489 | 3.00E-60 |
| f21-4.aa | gi|1707290 | putative outer surface protein [*Borrelia burgdorferi*] | 342 | 3.20E-49 |
| f21-4.aa | gi|1663633 | ErpK [*Borrelia burgdorferi*] | 268 | 1.70E-48 |
| f21-4.aa | gi|466482 | outer surface protein F [*Borrelia burgdorferi*] > pir|I40287|I40287 | 321 | 3.80E-38 |
| f21-4.aa | gi|896038 | BbK2.10 precursor [*Borrelia burgdorferi*] > pir|S70534|S70534 bbK2.10 | 121 | 3.90E-34 |
| f21-4.aa | gi|896040 | BbK2.10 precursor [*Borrelia burgdorferi*] > pir|S70533|S70533 bbK2.10 | 118 | 2.30E-33 |
| f21-4.aa | gi|1051120 | outer surface protein G [*Borrelia burgdorferi*] > gi|1373118 ErpG | 107 | 3.30E-33 |
| f21-4.aa | gi|2444428 | (AF020657) ErpX protein [*Borrelia burgdorferi*] | 118 | 6.00E-14 |
| f210.aa | gi|2688603 | (AE001168) conserved hypothetical protein [*Borrelia burgdorferi*] | 867 | 2.60E-116 |
| f210.aa | gi|2688604 | (AE001168) chemotaxis response regulator (cheY-3) [*Borrelia* | 733 | 1.40E-97 |
| f210.aa | gi|1408274 | CheY [*Borrelia burgdorferi*] | 720 | 9.00E-96 |
| f210.aa | gi|1765976 | chemotaxis protein CheY [*Treponema pallidum*] | 405 | 6.60E-52 |
| f210.aa | gi|142682 | chemotactic response protein [*Bacillus subtilis*] > gnl|PID|185224 | 184 | 8.00E-30 |
| f210.aa | gi|940149 | CheY [*Thermotoga maritima*] | 171 | 1.50E-27 |
| f210.aa | gi|2649557 | (AE001031) chemotaxis response regulator (cheY) [*Archaeoglobus* | 168 | 1.50E-26 |
| f210.aa | gi|620085 | cheY gene product [*Listeria monocytogenes*] | 183 | 3.00E-26 |
| f210.aa | gnl|PID|e249646 | YneI [*Bacillus subtilis*] > gi|870926 response regulator | 166 | 4.00E-24 |
| f210.aa | gi|149620 | ORF2 [*Leptospira borgpetersenii*] > sp|P24086|YLB3_LEPIN HYPOTHETICAL | 121 | 4.70E-22 |
| f210.aa | gi|1408275 | orfX; putative OrfX protein [*Borrelia burgdorferi*] | 208 | 9.20E-22 |
| f210.aa | gi|994802 | cheY gene product [*Halobacterium salinarium*] > pir|A58645|S58645 CheY | 139 | 8.90E-18 |
| f210.aa | gi|143598 | spoOF [*Bacillus subtilis*] > gi|143601 SpoOF protein [*Bacillus* | 113 | 4.70E-11 |
| f216.aa | gi|2688586 | (AE001167) conserved hypothetical protein [*Borrelia burgdorferi*] | 804 | 1.20E-109 |
| f216.aa | gi|1575446 | orfA [*Borrelia burgdorferi*] | 472 | 1.10E-91 |
| f219.aa | gi|2688594 | (AE001167) *B. burgdorferi* predicted coding region BB0664 [*Borrelia* | 1122 | 3.10E-148 |
| f22.aa | gi|2688779 | (AE001181) *B. burgdorferi* predicted coding region BB0832 [*Borrelia* | 1400 | 4.90E-188 |
| f22.aa | gi|2688779 | (AE001181) *B. burgdorferi* predicted coding region BB0832 [*Borrelia* | 1400 | 4.90E-188 |
| f221.aa | gi|2688596 | (AE001167) *B. burgdorferi* predicted coding region BB0662 [*Borrelia* | 692 | 2.60E-93 |
| f229.aa | gi|2688591 | (AE001167) oxygen-independent coproporphyrinogen III oxidase, | 863 | 7.80E-120 |
| f24-1.aa | gi|2039285 | putative vls recombination cassette Vls6 [*Borrelia burgdorferi*] | 924 | 1.80E-114 |
| f24-1.aa | gi|2039284 | putative vls recombination cassette Vls5 [*Borrelia burgdorferi*] | 867 | 6.30E-107 |
| f24-1.aa | gi|2039287 | putative vls recombination cassette Vls8 [*Borrelia burgdorferi*] | 824 | 1.50E-104 |
| f24-1.aa | gi|2039289 | putative vls recombination cassette Vls10 [*Borrelia burgdorferi*] | 829 | 7.50E-102 |
| f24-1.aa | gi|2039320 | vmp-like sequence protein, VlsE [*Borrelia burgdorferi*] | 644 | 1.10E-98 |
| f24-1.aa | gi|2039288 | putative vls recombination cassette Vls9 [*Borrelia burgdorferi*] | 783 | 8.20E-96 |
| f24-1.aa | gi|2039330 | vmp-like sequence protein VlsE [*Borrelia burgdorferi*] | 742 | 6.30E-95 |
| f24-1.aa | gi|2039336 | vmp-like sequence protein VlsE [*Borrelia burgdorferi*] | 509 | 1.50E-92 |
| f24-1.aa | gi|2039286 | putative vls recombination cassette Vls7 [*Borrelia burgdorferi*] | 754 | 6.60E-92 |
| f24-1.aa | gi|2039324 | vmp-like sequence protein VlsE [*Borrelia burgdorferi*] | 488 | 8.10E-86 |
| f24-1.aa | gi|2039316 | vmp-like sequence protein VlsE [*Borrelia burgdorferi*] | 531 | 1.70E-85 |
| f24-1.aa | gi|2039312 | vmp-like sequence protein VlsE [*Borrelia burgdorferi*] | 531 | 1.20E-83 |
| f24-1.aa | gi|2039326 | vmp-like sequence protein VlsE [*Borrelia burgdorferi*] | 476 | 2.00E-82 |
| f24-1.aa | gi|2039332 | vmp-like sequence protein VlsE [*Borrelia burgdorferi*] | 474 | 5.10E-82 |
| f24-1.aa | gi|2039328 | vmp-like sequence protein VlsE [*Borrelia burgdorferi*] | 420 | 3.50E-59 |
| f253.aa | gi|2688567 | (AE001165) Na+/H+ antiporter (nhaC-1) [*Borrelia burgdorferi*] | 2247 | 0 |
| f253.aa | gi|2688566 | (AE001165) Na+/H+ antiporter (nhaC-2) [*Borrelia burgdorferi*] | 609 | 6.40E-155 |
| f253.aa | gi|2209268 | Na+/H+ antiporter [*Bacillus firmus*] > pir|A41594|A41594 | 158 | 9.40E-15 |
| f253.aa | gi|1574661 | Na+/H+ antiporter (nhaC) [*Haemophilus influenzae*] | 143 | 4.20E-14 |
| f253.aa | gnl|PID|e1185625 | similar to Na+/H+ antiporter [*Bacillus subtilis*] | 137 | 1.20E-11 |
| f253.aa | gnl|PID|e324972 | hypothetical protein [*Bacillus subtilis*] > gnl|PID|e1182969 | 133 | 2.00E-11 |
| f265.aa | gi|2688555 | (AE001164) conserved hypothetical protein [*Borrelia burgdorferi*] | 1196 | 9.90E-161 |
| f269.aa | gi|2688560 | (AE001164) *B. burgdorferi* predicted coding region BB0624 [*Borrelia* | 1654 | 5.50E-226 |
| f28-2.aa | gi|2690174 | (AE000788) *B. burgdorferi* predicted coding region BBK47 [*Borrelia* | 1683 | 2.80E-222 |
| f28-2.aa | gi|2690161 | (AE000788) *B. burgdorferi* predicted coding region BBK49 [*Borrelia* | 1068 | 2.20E-163 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f28-3.aa | gi|2690138 | (AE000788) immunogenic protein P37, putative [Borrelia burgdorferi] | 281 | 6.00E-48 |
| f28-3.aa | gi|2690127 | (AE000788) immunogenic protein P37, [Borrelia burgdorferi] | 209 | 3.20E-28 |
| f28-3.aa | gi|2459605 | immunogenic protein P37 [Borrelia burgdorferi] | 208 | 4.50E-28 |
| f28-3.aa | gi|2690137 | (AE000788) immunogenic protein P37, putative [Borrelia burgdorferi] | 172 | 5.50E-17 |
| f29.aa | gi|2688764 | (AE001180) B. burgdorferi predicted coding region BB0826 [Borrelia | 869 | 8.20E-116 |
| f290.aa | gi|2688537 | (AE001162) serine-type D-Ala-D-Ala carboxypeptidase (dacA) | 2046 | 1.50E-281 |
| f290.aa | gi|143439 | DD-carboxypeptidase [Bacillus subtilis] > pir|B42708|B42708 | 161 | 6.60E-36 |
| f290.aa | gnl|PID|e1185617 | D-alanyl-D-alanine carboxypeptidase (penicilin binding | 161 | 6.60E-36 |
| f290.aa | gnl|PID|d1016562 | Probable penicillin-binding protein. [Escherichia coli] | 131 | 3.30E-28 |
| f290.aa | sp|P37604|DACD_SALTY | PENICILLIN-BINDING PROTEIN 6B PRECURSOR | 135 | 9.10E-28 |
| f290.aa | gi|1572974 | penicillin-binding protein 5 (dacA) [Haemophilus influenzae] | 145 | 3.00E-27 |
| f290.aa | gi|580849 | D-alanine carboxypeptidase [Bacillus stearothermophilus] | 170 | 4.10E-27 |
| f290.aa | gi|778549 | penicillin-binding protein 5 [Escherichia coli] > gi|41212 precursor | 152 | 3.20E-26 |
| f290.aa | gi|142820 | penicillin-binding protein 5 [Bacillus subtilis] | 137 | 4.60E-26 |
| f290.aa | gi|410134 | penicillin-binding protein [Bacillus subtilis] > gnl|PID|e1185588 | 137 | 4.60E-26 |
| f290.aa | gi|41218 | precursor [Escherichia coli] | 136 | 1.30E-25 |
| f290.aa | gnl|PID|d1015262 | Penicillin-binding protein 6 precursor (D-alanyl-D-alanine | 136 | 1.30E-25 |
| f290.aa | gi|1864022 | penicillin binding protein 4 [Staphylococcus aureus] | 155 | 5.10E-22 |
| f290.aa | gnl|PID|e154145 | penicillin-binding protein 4 [Staphylococcus aureus] | 155 | 5.10E-22 |
| f290.aa | gnl|PID|e264682 | penicillin-binding protein 4 [Staphylococcus aureus] | 155 | 5.10E-22 |
| f291.aa | gi|2688538 | (AE001162) L-lactate permease (lctP) [Borrelia burgdorferi] | 2473 | 0 |
| f291.aa | gnl|PID|e274704 | lactate premease [Streptococcus iniae] | 586 | 1.20E-132 |
| f291.aa | gi|882504 | ORF_f560 [Escherichia coli] > gi|1789347 (AE000380) f560; This 560 aa | 345 | 3.60E-95 |
| f291.aa | gi|2313225 | (AE000535) L-lactate permease (lctP) [Helicobacter pylori] | 359 | 1.10E-94 |
| f291.aa | gi|2313224 | (AE000535) L-lactate permease (lctP) [Helicobacter pylori] | 348 | 2.90E-93 |
| f291.aa | gi|404693 | L-lactate permease [Escherichia coli] > gi|466741 aug is 3rd start | 331 | 7.20E-82 |
| f291.aa | gnl|PID|e313006 | hypothetical protein [Bacillus subtilis] > gnl|PID|e1186107 | 330 | 9.00E-80 |
| f291.aa | gnl|PID|d1022632 | lactate permease [Bacillus subtilis] | 300 | 1.70E-61 |
| f291.aa | gnl|PID|e1182258 | L-lactate permease [Bacillus subtilis] > pir|F69649|F69649 | 300 | 1.10E-60 |
| f291.aa | gnl|PID|d1009575 | homologue of L-lactate permease of E. coli [Bacillus | 265 | 6.40E-56 |
| f291.aa | gi|2649804 | (AE001049) L-lactate permease (lctP) [Archaeoglobus fulgidus] | 170 | 1.50E-47 |
| f291.aa | gnl|PID|e283914 | L-Lactate permease [Sulfolobus solfataricus] | 163 | 2.60E-44 |
| f291.aa | gi|1574148 | L-lactate permease (lctP) [Haemophilus influenzae] | 173 | 6.00E-35 |
| f296.aa | gi|2688517 | (AE001161) chaperonin, putative [Borrelia burgdorferi] | 1276 | 4.40E-177 |
| f296.aa | gi|840643 | mucZ gene product [Coxiella burnetii] > pir|I40852|I40852 mucZ | 101 | 7.90E-12 |
| f3.aa | gi|2688797 | (AE001183) B. burgdorferi predicted coding region BB0844 [Borrelia | 1604 | 1.40E-211 |
| f30.aa | gi|2688765 | (AE001180) B. burgdorferi predicted coding region BB0825 [Borrelia | 1343 | 2.00E-181 |
| f301.aa | gi|2688521 | (AE001161) methyl-accepting chemotaxis protein (mcp-3) [Borrelia | 2756 | 0 |
| f301.aa | gi|1805311 | methyl-accepting chemotaxis protein B [Treponema denticola] | 211 | 7.00E-20 |
| f301.aa | gi|2688522 | (AE001161) methyl-accepting chemotaxis protein (mcp-2) [Borrelia | 189 | 2.80E-18 |
| f301.aa | gi|2367665 | (AF016689) Mcp-2 [Treponema pallidum] | 189 | 3.50E-17 |
| f301.aa | gi|2352917 | (AF012922) methyl-accepting chemotaxis protein [Treponema | 187 | 5.70E-17 |
| f301.aa | gi|1354776 | MCP-1 [Treponema pallidum] | 189 | 5.90E-17 |
| f301.aa | gi|2619023 | (AF027868) YoaH [Bacillus subtilis] > gnl|PID|e1185333 similar to | 184 | 2.80E-16 |
| f301.aa | gi|1654421 | transducer-HtB protein [Halobacterium salinarum] | 177 | 2.20E-15 |
| f301.aa | gi|415694 | chemoreceptor [Desulfovibrio vulgaris] > pir|G36943|G36943 | 163 | 3.50E-15 |
| f301.aa | gi|459691 | transmembrane receptor [Bacillus subtilis] > gnl|PID|e1185996 | 163 | 4.90E-15 |
| f301.aa | gi|2104730 | ORF2 [Desulfurococcus sp. SY] | 173 | 5.80E-15 |
| f301.aa | gi|2914132 | methyl accepting chemotaxis homolog [Treponema denticola] | 170 | 1.10E-14 |
| f301.aa | gi|459689 | transmembrane receptor [Bacillus subtilis] > gnl|PID|e1185998 | 164 | 1.30E-14 |
| f301.aa | gi|496484 | tlpC gene product [Bacillus subtilis] > pir|I40496|I40496 methylation | 170 | 3.80E-14 |
| f301.aa | gi|2313163 | (AE000530) methyl-accepting chemotaxis transducer (tlpC) | 170 | 6.30E-14 |
| f308.aa | gi|2688527 | (AE001161) B. burgdorferi predicted coding region BB0592 [Borrelia | 1227 | 1.70E-176 |
| f31-2.aa | gi|2690202 | (AE000787) B. burgdorferi predicted coding region BBJ36 [Borrelia | 1771 | 7.20E-235 |
| f31-2.aa | gi|2690200 | (AE000787) B. burgdorferi predicted coding region BBJ34 [Borrelia | 423 | 4.60E-88 |
| f31.aa | gi|2688766 | (AE001180) B. burgdorferi predicted coding region BB0824 [Borrelia | 957 | 7.80E-133 |
| f314.aa | gi|2688509 | (AE001160) pfs protein (pfs-2) [Borrelia burgdorferi] | 1329 | 7.40E-180 |
| f314.aa | gi|2690087 | (AE000789) pfs protein (pfs) [Borrelia burgdorferi] | 335 | 1.50E-77 |
| f314.aa | gi|2688288 | (AE001143) pfs protein (pfs-1) [Borrelia burgdorferi] | 266 | 1.00E-65 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f314.aa | gi|2738591 | (AFO12886) Pfs [*Buchnera aphidicola*] | 115 | 1.70E-52 |
| f314.aa | gi|1552737 | similar to purine nucleoside phosphorylase (deoD) [*Escherichia*] | 133 | 6.90E-52 |
| f314.aa | gnl|PID|e11 83957 | similar to purine nucleoside phosphorylase [*Bacillus*] | 157 | 1.20E-49 |
| f314.aa | gi|147158 | pfs [*Escherichia coli*] > gi|457107 ORF [*Escherichia coli*] {SUB 9-219} | 133 | 2.50E-42 |
| f314.aa | gi|1574146 | pfs protein (pfs) [*Haemophilus influenzae*] > pir|C64169|C64169 pfs | 110 | 2.70E-37 |
| f314.aa | gi|2267164 | (AF009177) pfs protein homolog [*Helicobacter pylori*] | 118 | 3.30E-23 |
| f314.aa | gi|2313168 | (AE000530) pfs protein (pfs) [*Helocobacter pylori*] | 115 | 1.00E-22 |
| f314.aa | gi|1777939 | Pfs [*Treponema pallidum*] | 102 | 1.90E-20 |
| f314.aa | gi|2689970 | (AE000785) B. burgdorferi predicted coding region BBE07 [*Borrelia*] | 191 | 1.50E-19 |
| f314.aa | gnl|PID|e24 9405 | unknown [*Mycobacterium tuberculosis*] > sp|Q10889|Y05A_MYCTU | 105 | 7.60E-16 |
| f32-4.aa | gi|2690221 | (AE000787) B. burgdorferi predicted coding region BBJ47 [*Borrelia*] | 1192 | 4.00E-163 |
| f32-4.aa | gi|2689979 | (AE000785) B. burgdorferi predicted coding region BBE16 [*Borrelia*] | 103 | 4.10E-11 |
| f32.aa | gi|2688767 | (AE001180) B. burgdorferi predicted coding region BB0823 [*Borrelia*] | 623 | 1.80E-81 |
| f32.aa | gi|2688767 | (AE001180) B. burgdorferi predicted coding region BB0823 [*Borrelia*] | 623 | 1.80E-81 |
| f320.aa | gi|2688497 | (AE001159) carboxypeptidase, putative [*Borrelia burgdorferi*] | 1373 | 6.40E-186 |
| f320.aa | gi|2529473 | (AF006665) YokZ [*Bacillus subtilis*] | 136 | 9.80E-28 |
| f320.aa | gi|2415396 | (AF015775) carboxypeptidase [*Bacillus subtilis*] > gnl|PID|e1185433 | 136 | 1.90E-27 |
| f320.aa | gi|1209528 | D,D-carboxypeptidase [*Enterococcus faecalis*] > sp|Q47746|VANY_ENTFA | 148 | 3.30E-16 |
| f320.aa | gi|155044 | vanY [*Transposon Tn1546*] > gi|149126 D,D-carboxypeptidase [*Plasmid*] | 142 | 1.60E-13 |
| f328.aa | gi|2688502 | (AE001159) CTP synthase (pyrG) [*Borrelia burgdorferi*] | 869 | 6.10E-119 |
| f328.aa | gi|1591801 | CTP synthase (pyrG) [*Methanococcus jannaschii*] > pir|E64446|E64446 | 325 | 6.20E-59 |
| f328.aa | gi|2650385 | (AE001088) CTP synthase (pyrG) [*Archaeoglobus fulgidus*] | 304 | 4.20E-54 |
| f328.aa | gi|1399854 | CTP synthetase [*Synechococcus PCC7942*] > sp|Q54775|PYRG_SYNP7 CTP | 313 | 3.30E-52 |
| f328.aa | gnl|PID|d10 19032 | CTP synthetase [*Synechocystis sp.*] > pir|S75840|S75840 CTP | 295 | 1.80E-50 |
| f328.aa | gi|143597 | CTP synthetase [*Bacillus subtilis*] > gi|853762 CTP synthase [*Bacillus*] | 274 | 1.60E-49 |
| f328.aa | gi|2983754 | (AE000735) CTP synthetase [*Aquifex aeolicus*] | 271 | 1.50E-46 |
| f328.aa | gi|1574630 | CTP synthetase (pyrG) [*Haemophilus influenzae*] > pir|F64181|F64181 | 234 | 1.90E-44 |
| f328.aa | gi|413755 | CTP synthetase [*Spiroplasma citri*] > sp|P52200|PYRG_SPICI CTP | 231 | 3.00E-44 |
| f328.aa | gi|2621483 | (AE000826) CTP synthase [*Methanobacterium thermoautotrophicum*] | 257 | 2.80E-40 |
| f328.aa | gi|950067 | CTP synthetase [*Mycoplasma capricolum*] > pir|S77767|S77767 CTP synthase | 220 | 4.10E-39 |
| f328.aa | gi|904007 | cytidine triphosphate synthetase precursor [*Giardia intestinalis*] | 219 | 2.00E-38 |
| f328.aa | gi|147478 | CTP synthetase (EC 6.3.4.2) [*Escherichia coli*] | 217 | 2.90E-38 |
| f328.aa | gi|882674 | CTP synthetase (*Escherichia coli*) > gi|1789142 (AE000361) CTP | 214 | 7.70E-38 |
| f328.aa | gi|38688 | CTP synthase [*Azospirillum brasilense*] > pir|I39496|S25101 CTP | 132 | 3.20E-37 |
| f342.aa | gi|2688495 | (AE001158) B. burgdorferi predicted coding region BB0563 [*Borrelia*] | 944 | 5.30E-130 |
| f346.aa | gi|1272356 | phosphotransferase enzyme II [*Borrelia burgdorferi*] > gi|2688474 | 828 | 1.10E-108 |
| f346.aa | gi|145603 | PTS enzyme III glc [*Escherichia coli*] > gi|145605 PTS enzyme III glc | 385 | 8.80E-53 |
| f346.aa | gi|1314675 | glucose-specific component IIA of the PTS system [*Escherichia coli*] | 385 | 9.30E-53 |
| f346.aa | gi|47658 | III (Glc) (crr) (AA 1-169) [*Salmonella typhimurium*] | 382 | 2.30E-52 |
| f346.aa | gi|1574566 | glucose phosphotransferase enzyme III-glc (crr) [*Haemophilus*] | 397 | 8.70E-50 |
| f346.aa | gi|43819 | nagE gene product [*Klebsiella pneumoniae*] > pir|S18607|S18607 | 349 | 2.80E-41 |
| f346.aa | gi|146913 | N-acetylglucosamine transport protein [*Escherichia coli*] | 334 | 3.20E-39 |
| f346.aa | gi|1072418 | glcA [*Staphylococcus carnosus*] > pir|S46952|S46952 | 317 | 7.20E-37 |
| f346.aa | gi|1072419 | glcB [*Staphylococcus carnosus*] > pir|S63606|S46953 | 315 | 1.40E-36 |
| f346.aa | gi|1146177 | phosphotransferase system glucose-specific enzyme II [*Bacillus*] | 295 | 7.30E-36 |
| f346.aa | gi|529001 | PTS glucose-specific permease [*Bacillus stearothermophilus*] | 294 | 8.80E-36 |
| f346.aa | gnl|PID|e11 82187 | alternate gene name: yzfA; similar to phosphotransferase | 293 | 1.40E-33 |
| f346.aa | gi|580912 | enzyme III-glucose [*Bacillus subtilis*] | 257 | 1.20E-30 |
| f346.aa | gi|602681 | phosphocarrier protein (enzyme IIA) [*Mycoplasma capricolum*] | 243 | 1.00E-28 |
| f346.aa | gi|1432153 | cellobiose-specific PTS permease [*Klebsiella oxytoca*] | 257 | 1.20E-28 |
| f352.aa | gi|2688482 | (AE001157) B. burgdorferi predicted coding region BB0553 [*Borrelia*] | 2547 | 0 |
| f352.aa | gi|2688482 | (AE001157) B. burgdorferi predicted coding region BB0553 [*Borrelia*] | 1005 | 1.30E-132 |
| f363.aa | gi|2688468 | (AE001156) B. burgdorferi predicted coding region BB0543 [*Borrelia*] | 1109 | 5.40E-153 |
| f368.aa | gi|2688450 | (AE001155) conserved hypothetical integral membrane protein | 1133 | 4.10E-157 |
| f368.aa | gi|1787004 | (AE000181) o234; This 234 aa ORF is 26 pct identical (15 gaps) to | 417 | 1.40E-67 |
| f368.aa | gi|2314055 | (AE000601) conserved hypothetical integral membrane protein | 129 | 3.50E-16 |
| f368.aa | gnl|PID|e12 89272 | S1R [*Cowpox virus*] | 135 | 1.80E-14 |
| f368.aa | gnl|PID|d10 03176 | 24K membrane protein [*Pseudomonas aeruginosa*] | 108 | 9.00E-13 |
| f368.aa | gi|41284 | put. 23.5-kd protein [*Escherichia coli*] > gi|1787205 (AE000199) | 101 | 1.00E-11 |
| f371.aa | gi|2688452 | (AE001155) conserved hypothetical protein [*Borrelia burgdorferi*] | 1066 | 3.60E-143 |
| f371.aa | gi|2196997 | Orf256 [*Treponema pallidum*] | 154 | 1.10E-15 |
| f373.aa | gi|2688453 | (AE001155) zinc protease, putative [*Borrelia burgdorferi*] | 3663 | 0 |
| f373.aa | gi|1574200 | hypothetical [*Haemophilus influenzae*] > pir|E64171|E64171 | 295 | 2.70E-67 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f373.aa | gi\|1787770 | (AE000246) f931; residues 5–650 are 99 pct identical to YDDC_ECOLI | 289 | 1.10E-57 |
| f373.aa | gi\|535004 | cds106 gene product [Escherichia coli] | 289 | 3.20E-57 |
| f373.aa | gi\|799369 | metalloendopeptidase [Pisum sativum] | 148 | 7.10E-28 |
| f373.aa | gi\|2827039 | (AF008444) chloroplast processing enzyme [Arabidopsis thaliana] | 150 | 1.70E-26 |
| f373.aa | gi\|2983709 | (AE000732) processing protease [Aquifex aeolicus] | 136 | 4.30E-24 |
| f373.aa | gi\|2314155 | (AE000609) protease (pqqE) [Helicobacter pylori] > pir\|D64646\|D64646 | 115 | 5.30E-23 |
| f378.aa | gi\|2688458 | (AE001155) B. burgdorferi predicted coding region BB0531 [Borrelia | 1030 | 1.30E-136 |
| f384.aa | gi\|2688435 | (AE001154) inositol monophosphatase [Borrelia burgdorferi] | 1470 | 3.80E-201 |
| f4-15.aa | gi\|2690238 | (AE000790) surface lipoprotein P27 [Borrelia burgdorferi] | 1400 | 1.50E-185 |
| f4-15.aa | gi\|144008 | P27 [Borrelia burgdorferi] > pir\|S34995\|S34995 surface lipoprotein | 462 | 2.40E-96 |
| f4-50.aa | gi\|2690243 | (AE000790) decorin binding protein B (dbpB) [Borrelia burgdorferi] | 900 | 6.30E-117 |
| f4-50.aa | gi\|2062381 | decorin binding protein B [Borrelia burgdorferi] | 897 | 1.60E-116 |
| f4-50.aa | gi\|2809217 | (AF042796) putative decorin-binding protein precursor [Borrelia | 887 | 3.60E-115 |
| f4-50.aa | gi\|2809218 | (AF042796) decorin-binding protein precursor [Borrelia burgdorferi] | 172 | 2.00E-33 |
| f4-50.aa | gi\|2690249 | (AE000790) decorin binding protein A (dbpA) [Borrelia burgdorferi] | 176 | 9.50E-33 |
| f4-50.aa | gi\|2062379 | decorin binding protein A [Borrelia burgdorferi] | 177 | 6.10E-32 |
| f4-66.aa | gi\|2690229 | (AE000790) chpAI protein, putative [Borrelia burgdorferi] | 807 | 1.60E-107 |
| f4.aa | gi\|2688787 | (AE001183) conserved hypothetical integral membrane protein | 2408 | 0 |
| f4.aa | gi\|2697115 | (AF008219) unknown [Borrelia afzelii] | 1138 | 1.90E-305 |
| f4.aa | gi\|1573583 | H. influenzae predicted coding region HI0594 [Haemophilus | 337 | 2.10E-109 |
| f4.aa | gi\|1788636 | (AE000319) o513; This 513 aa ORF is 31 pct identical (30 gaps) to | 327 | 9.10E-80 |
| f4.aa | gnl\|PID\|d1009571 | homologue of hypothetical protein HI10594 of H. influenzae | 357 | 5.40E-69 |
| f42-1.aa | gi\|2689993 | (AE000794) conserved hypothetical protein [Borrelia burgdorferi] | 495 | 2.70E-62 |
| f42-1.aa | gi\|2689934 | (AE000793) conserved hypothetical protein [Borrelia burgdorferi] | 312 | 1.00E-37 |
| f43-3.aa | gi\|1209843 | lipoprotein [Borrelia burgdorferi] | 546 | 1.50E-69 |
| f43-3.aa | gi\|2121280 | (AF000270) lipoprotein [Borrelia burgdorferi] > gi\|3095109 | 442 | 1.80E-55 |
| f43-3.aa | gi\|1209837 | lipoprotein [Borrelia burgdorferi] | 365 | 3.10E-55 |
| f43-3.aa | gi\|1209873 | lipoprotein [Borrelia burgdorferi] | 269 | 5.30E-32 |
| f43-3.aa | gi\|1209849 | lipoprotein [Borrelia burgdorferi] | 141 | 1.70E-13 |
| f43-3.aa | gi\|3095105 | (AF046998) 2.9-8 lipoprotein [Borrelia burgdorferi] | 140 | 9.60E-13 |
| f43-3.aa | gi\|3095107 | (AF046999) 2.9-9 lipoprotein [Borrelia burgdorferi] | 132 | 1.40E-11 |
| f43.aa | gi\|2688752 | (AE001179) B. burgdorferi predicted coding region BB0811 [Borrelia | 2337 | 6.60000000084856e-315 |
| f446.aa | gi\|2688383 | (AE001151) B. burgdorferi predicted coding region BB0464 [Borrelia | 920 | 7.20E-124 |
| f45-2.aa | gi\|1699017 | ErpB2 [Borrelia burgdorferi] > gi\|1373133.ErpB [Borrelia | 364 | 7.50E-78 |
| f45-2.aa | gi\|2627270 | ErpJ [Borrelia burgdorferi] | 364 | 2.50E-77 |
| f45-2.aa | gi\|2627268 | ErpM [Borrelia burgdorferi] | 452 | 9.70E-60 |
| f45-2.aa | gi\|1373144 | ErpD [Borrelia burgdorferi] | 316 | 1.60E-58 |
| f45-2.aa | gi\|2444428 | (AF020657) ErpX protein [Borrelia burgdorferi] | 380 | 2.80E-55 |
| f45-2.aa | gi\|1051120 | outer surface protein G [Borrelia burgdorferi] > gi\|1373118 ErpG | 213 | 7.10E-35 |
| f45-2.aa | gi\|1663633 | ErpK [Borrelia burgdorferi] | 152 | 1.60E-21 |
| f45-2.aa | gnl\|PID\|e329895 | (AJ000496) cyclic nucleotide-gated channel beta subunit | 198 | 2.80E-16 |
| f45-2.aa | gi\|466482 | outer surface protein F [Borrelia burgdorferi] > pir\|I40287\|I40287 | 111 | 5.70E-14 |
| f45-2.aa | gi\|2246532 | ORF 73, contains large complex repeat CR 73 [Kaposi's | 174 | 5.90E-14 |
| f45-2.aa | gi\|160299 | glutamic acid-rich protein [Plasmodium falciparum] | 169 | 1.00E-13 |
| f45-2.aa | gi\|1707287 | putative outer membrane protein [Borrelia burgdorferi] | 101 | 2.20E-13 |
| f45-2.aa | gi\|1633572 | Herpes virus saimiri ORF73 homolog [Kaposi's sarcoma-associated | 175 | 4.10E-13 |
| f45-2.aa | gnl\|PID\|d1012343 | gene required for phosphoylation of oligosaccharides/has | 166 | 5.60E-13 |
| f45-2.aa | gi\|2690100 | (AE000789B. burgdorferi predicted coding region BBI16 [Borrelia | 161 | 2.70E-12 |
| f457.aa | gi\|2688369 | (AE001150) B. burgdorferi predicted coding region BB0456 [Borrelia | 1021 | 6.20E-139 |
| f469.aa | gi\|2688368 | (AE001150) Na+/H + antiporter (napA) [Borrelia burgdorferi] | 1544 | 1.10E-211 |
| f47-2.aa | gi\|1209849 | lipoprotein [Borrelia burgdorferi] | 742 | 2.30E-97 |
| f47-2.aa | gi\|1209857 | lipoprotein [Borrelia burgdorferi] | 407 | 7.80E-86 |
| f47-2.aa | gi\|1209831 | lipoprotein [Borrelia burgdorferi] | 393 | 5.00E-82 |
| f47-2.aa | gnl\|PID\|e268245 | surface-exposed lipoprotein [Borrelia burgdorferi] | 321 | 2.60E-73 |
| f47-2.aa | gi\|1209874 | lipoprotein [Borrelia burgdorferi] | 348 | 1.10E-64 |
| f47-2.aa | gnl\|PID\|e268239 | surface-exposed lipoprotein [Borrelia garinii] | 333 | 1.40E-57 |
| f47-2.aa | gnl\|PID\|e268244 | surface-exposed lipoprotein [Borrelia afzelii] | 292 | 9.60E-44 |
| f47-2.aa | gi\|3095107 | (AF046999) 2.9-9 lipoprotein [Borrelia burgdorferi] | 328 | 3.80E-40 |
| f47-2.aa | gnl\|PID\|e268242 | surface-exposed lipoprotein [Borrelia garinii] | 320 | 1.70E-39 |
| f47-2.aa | gi\|1209837 | lipoprotein [Borrelia burgdorferi] | 210 | 4.80E-29 |
| f47-2.aa | gi\|2121280 | (AF000270) lipoprotein [Borrelia burgdorferi] > gi\|3095109 | 205 | 1.10E-27 |
| f47-2.aa | gi\|3095105 | (AF046998) 2.9-8 lipoprotein [Borrelia burgdorferi] | 217 | 6.30E-25 |
| f47-2.aa | gi\|1209873 | lipoprotein [Borrelia burgdorferi] | 113 | 2.40E-11 |
| f477.aa | gi\|2688350 | (AE001149) fructose-bisphosphate aldolase (fba) [Borrelia | 1506 | 3.60E-202 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f477.aa | gi\|882454 | fructose 1,6-bisphosphate aldolase [*Escherichia coli*] > gi\|41423 | 651 | 1.10E-131 |
| f477.aa | gi\|2708661 | (AF037440) fructose 1,6-bisphosphate aldolase [*Edwardsiella* | 593 | 1.40E-124 |
| f477.aa | gi\|573507 | fructose bisphosphate aldolase (fba) [*Haemophilus influenzae*] | 560 | 8.50E-120 |
| f477.aa | gi\|671841 | fructose 1,6-bisphosphate aldolase [*Campylobacter jejuni*] | 856 | 3.80E-113 |
| f477.aa | gnl\|PID\|d10 04756 | fructose 1,6-bisphosphate aldolase [*Schizosaccharomyces* | 749 | 1.70E-98 |
| f477.aa | gi\|433637 | yeast fructose-bisphate-aldolase [*Saccharomyces cerevisiae*] > gi\|3696 | 459 | 1.20E-92 |
| f477.aa | gnl\|PID\|e19 0134 | fructose 1,6-bisphosphate aldolase [*Euglena gracilis*] | 701 | 6.30E-92 |
| f477.aa | gi\|1334980 | fructose 1,6-bisphosphate aldolase [*Neurospora crassa*] | 647 | 1.50E-84 |
| f477.aa | gi\|40495 | fructose bisphosphate aldolase [*Corynebacterium glutamicum*] | 204 | 6.80E-37 |
| f477.aa | gnl\|PID\|e31 5480 | Fba [*Mycobacterium tuberculosis*] | 207 | 1.50E-35 |
| f477.aa | gi\|1045692 | fructose bisphosphate aldolase [*Mycoplasma genitalium*] | 108 | 2.10E-23 |
| f477.aa | gnl\|PID\|d10 03809 | hypothetical protein [*Bacillus subtilis*] > gnl\|PID\|e1184692 | 102 | 2.70E-15 |
| f488.aa | gi\|2688338 | (AE001148) DNA gyrase, subunit A (gyrA) [*Borrelia burgdorferi*] | 3222 | 0 |
| f488.aa | gi\|1790876 | DNA gyrase subunit A [*Clostridium acetobutylicum*] | 822 | 1.80E-171 |
| f488.aa | gi\|2650163 | (AE001072) DNA gyrase, subunit A (gyrA) [*Archaeoglobus fulgidus*] | 483 | 1.10E-162 |
| f488.aa | gi\|40019 | ORF 821 (aa 1–821) [*Bacillus subtilis*] > gnl\|PID\|d1005785 A subunit of | 836 | 6.10E-159 |
| f488.aa | gi\|459929 | gyrase A subunit [*Pseudomonas aeruginosa*] > sp\|P48372\|GYRA_PSEAE DNA | 418 | 7.00E-155 |
| f488.aa | gi\|144206 | DNA gyrase A [*Campylobacter jejuni*] > pir\|A48902\|A48902 DNA gyrase | 508 | 7.50E-154 |
| f488.aa | gi\|466275 | gyrase A [*Mycobacterium tuberculosis*] > sp\|Q07702\|GYRA_MYCTU DNA | 395 | 3.50E-152 |
| f488.aa | gnl\|PID\|e26 6924 | GyrA [*Mycobacterium tuberculosis*] | 395 | 2.00E-151 |
| f488.aa | gi\|43485 | DNA gyrase A subunit [*Haloferax*] > pir\|S30571\|S30571 DNA topoisomerase | 275 | 6.10E-151 |
| f488.aa | gnl\|PID\|d10 25098 | (AB010081) A subunit of DNA gyrase [*Bacillus sp.*] | 549 | 1.20E-150 |
| f488.aa | gnl\|PID\|e21 4031 | DNA gyrase subunit A [*Mycobacterium smegmatis*] | 388 | 5.90E-150 |
| f488.aa | gi\|2731385 | DNA gyrase [*Serratia marcescens*] | 378 | 6.00E-148 |
| f488.aa | gnl\|PID\|e13 7038 | DNA topoisomerase (ATP-hydrolysing) [*Mycobacterium smegmatis*] | 388 | 7.30E-147 |
| f488.aa | gi\|41634 | gyrA gene product (AA 1–875) [*Escherichia coli*] > gi\|41636 DNA gyrase | 383 | 2.40E-146 |
| f488.aa | gi\|497648 | DNA gyrase subunit A [*Mycoplasma genitalium*] | 514 | 5.20E-146 |
| f49-2.aa | gi\|2039282 | putative vls recombination cassette Vls3 [*Borrelia burgdorferi*] | 943 | 2.30E-120 |
| f49-2.aa | gi\|2547241 | vmp-like sequence protein VlsE [*Borrelia burgdorferi*] | 434 | 4.10E-106 |
| f49-2.aa | gi\|2039324 | vmp-like sequence protein VlsE [*Borrelia burgdorferi*] | 458 | 3.00E-104 |
| f49-2.aa | gi\|2039281 | putative vls recombination cassette Vls2 [*Borrelia burgdorferi*] | 793 | 1.80E-100 |
| f49-2.aa | gi\|2039283 | putative vls recombination cassette Vls4 [*Borrelia burgdorferi*] | 729 | 4.60E-92 |
| f49-2.aa | gi\|2039308 | vmp-like sequence protein VlsE [*Borrelia burgdorferi*] | 652 | 1.40E-88 |
| f49-2.aa | gi\|2039288 | putative vls recombination cassette Vls9 [*Borrelia burgdorferi*] | 352 | 1.80E-88 |
| f49-2.aa | gi\|2039332 | vmp-like sequence protein VlsE [*Borrelia burgdorferi*] | 550 | 4.40E-88 |
| f49-2.aa | gi\|2039328 | vmp-like sequence protein VlsE [*Borrelia burgdorferi*] | 629 | 1.50E-85 |
| f49-2.aa | gi\|2039336 | vmp-like sequence protein VlsE [*Borrelia burgdorferi*] | 460 | 1.40E-82 |
| f49-2.aa | gi\|2039318 | vmp-like sequence protein VlsE [*Borrelia burgdorferi*] | 367 | 6.20E-82 |
| f49-2.aa | gi\|2039320 | vmp-like sequence protein VlsE [*Borrelia burgdorferi*] | 449 | 1.80E-77 |
| f49-2.aa | gi\|2483796 | VlsE1 [*Borrelia burgdorferi*] | 497 | 8.20E-76 |
| f49-2.aa | gi\|2039326 | vmp-like sequence protein VlsE [*Borrelia burgdorferi*] | 427 | 2.50E-64 |
| f49-2.aa | gi\|2039291 | putative vls recombination cassette Vls13 [*Borrelia burgdorferi*] | 409 | 1.30E-47 |
| f494.aa | gi\|2688346 | (AE001148) B. burgdorferi predicted coding region BB0428 [*Borrelia* | 547 | 8.20E-74 |
| f5-14.aa | gi\|2627268 | ErpM [*Borrelia burgdorferi*] | 1836 | 2.60E-236 |
| f5-14.aa | gi\|1373144 | ErpD [*Borrelia burgdorferi*] | 543 | 4.40E-87 |
| f5-14.aa | gi\|2627270 | ErpJ [*Borrelia burgdorferi*] | 503 | 4.30E-83 |
| f5-14.aa | gi\|1699017 | ErpB2 [*Borrelia burgdorferi*] > gi\|1373133 ErpB [*Borrelia* | 503 | 2.60E-82 |
| f5-14.aa | gi\|2444428 | (AF020657) ErpX protein [*Borrelia burgdorferi*] | 399 | 9.30E-57 |
| f5-14.aa | gnl\|PID\|e32 9895 | (AJ000496) cyclic nucleotide-gated channel beta subunit | 228 | 1.50E-20 |
| f5-14.aa | gnl\|PID\|d10 12343 | gene required for phosphoylation of oligosaccharides/has | 203 | 8.70E-18 |
| f5-14.aa | gi\|2246532 | ORF 73, contains large complex repeat CR 73 [Kaposi's | 197 | 3.30E-17 |
| f5-14.aa | gi\|1633572 | Herpes virus saimiri ORF73 homolog [Kaposi's sarcoma-associated | 192 | 1.20E-16 |
| f5-14.aa | gi\|3068583 | (AF000580) Rep-like [*Dictyostelium discoideum*] | 197 | 3.60E-16 |
| f5-14.aa | gi\|2690100 | (AE000789) B. burgdorferi predicted coding region BBI16 [*Borrelia* | 183 | 2.90E-15 |
| f5-14.aa | gi\|1825739 | No definition line found [*Caenorhabditis elegans*] | 168 | 1.60E-14 |
| f5-14.aa | gi\|3044185 | (AF056936) mature parasite-infected erythrocyte surface antigen | 166 | 2.00E-14 |
| f5-14.aa | gnl\|PID\|e34 9084 | E02A10.2 [*Caenorhabditis elegans*] | 176 | 2.30E-14 |
| f5-14.aa | gi\|1051120 | outer surface protein G [*Borrelia burgdorferi*] > gi\|1373118 ErpG | 157 | 3.30E-12 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f5-15.aa | gi|2627267 | ErpL [*Borrelia burgdorferi*] | 1152 | 4.40E-147 |
| f5-15.aa | gi|1197833 | Bbk2.11 [*Borrelia burgdorferi*] > pir|S70531|S70531 bbk2.11 protein | 856 | 3.30E-108 |
| f5-15.aa | gi|896042 | OspF [*Borrelia burgdorferi*] > pir|S70532|S70532 outer surface protein | 325 | 1.00E-72 |
| f5-15.aa | gi|1707281 | putative outer membrane protein [*Borrelia burgdorferi*] | 323 | 1.80E-72 |
| f5-15.aa | gi|1707287 | putative outer membrane protein [*Borrelia burgdorferi*] | 322 | 6.60E-70 |
| f5-15.aa | gi|466482 | outer surface protein F [*Borrelia burgdorferi*] > pir|I40287|I40287 | 448 | 6.80E-68 |
| f5-15.aa | gi|1707290 | putative outer surface protein [*Borrelia burgdorferi*] | 290 | 1.90E-52 |
| f5-15.aa | gi|1663633 | ErpK [*Borrelia burgdorferi*] | 172 | 8.70E-43 |
| f5-15.aa | gi|896038 | BbK2.10 precursor [*Borrelia burgdorferi*] > pir|S70534|S70534 bbK2.10 | 153 | 1.10E-42 |
| f5-15.aa | gi|896040 | BbK2.10 precursor [*Borrelia burgdorferi*] > pir|S70533|S70533 bbK2.10 | 124 | 4.30E-39 |
| f5-15.aa | gi|1051120 | outer surface protein G [*Borrelia burgdorferi*]> gi|1373118 ErpG | 105 | 3.10E-23 |
| f5-15.aa | gi|1373144 | ErpD [*Borrelia burgdorferi*] | 103 | 1.10E-14 |
| f50.aa | gi|2688754 | (AE001179) *B. burgdorferi* predicted coding region BB0806 [*Borrelia* | 2651 | 0 |
| f502.aa | gi|2688313 | (AE001146) sensory transduction histidine kinase, putative | 7570 | 0 |
| f502.aa | gnl|PID|d10 25877 | (AB006363) homologue of histidine kinase [*Candida albicans*] | 296 | 3.80E-58 |
| f502.aa | gi|1354473 | Os-1p [*Neurospora crassa*] | 275 | 3.30E-57 |
| f502.aa | gi|1679757 | two-component histidine kinase CHK-1 [*Glomerella cingulata*] | 382 | 4.20E-57 |
| f502.aa | gi|1262208 | Nik-1 [*Neurospora crassa*] > gi|1262210 Nik-1 [*Neurospora crassa*] | 273 | 6.30E-57 |
| f502.aa | gi|2460283 | (AF024654) hybrid histidine kinase DHKB [*Dictyostelium discoideum*] | 273 | 3.90E-55 |
| f502.aa | gnl|PID|d10 17789 | sensory transduction histidine kinase [*Synechocystis* sp.] | 288 | 8.50E-54 |
| f502.aa | gi|2623815 | (AF030352) two component sensor [*Pseudomonas aeruginosa*] | 252 | 4.00E-52 |
| f502.aa | gi|939724 | putative sensor kinase; regulatory protein for production of | 252 | 1.80E-50 |
| f502.aa | gi|151329 | regulatory protein [*Pseudomonas syringae*] > sp|P48027|LEMA_PSESY | 248 | 1.20E-49 |
| f502.aa | pir|B41863|B41863 | two-component regulatory protein lemA - *Pseudomonas syringae* | 248 | 1.30E-49 |
| f502.aa | gnl|PID|d10 18725 | sensory transduction histidine kinase [*Synechocystis* sp.] | 252 | 2.10E-49 |
| f502.aa | gnl|PID|d10 02185 | sensor-regulator protein [*Escherichia coli*] > gi|1789149 | 262 | 6.20E-49 |
| f502.aa | gi|463195 | pectate lyase [*Pseudomonas viridiflava*] | 247 | 7.50E-49 |
| f502.aa | gnl|PID|d10 18731 | sensory transduction histidine kinase [*Synechocystis* sp.] | 244 | 1.00E-48 |
| f51-2.aa | gi|2444428 | (AF020657) ErpX protein [*Borrelia burgdorferi*] | 1755 | 2.20E-227 |
| f51-2.aa | gi|2627268 | ErpM [*Borrelia burgdorferi*] | 399 | 3.20E-57 |
| f51-2.aa | gi|1373144 | ErpD [*Borrelia burgdorferi*] | 282 | 2.20E-50 |
| f51-2.aa | gi|2627270 | ErpJ [*Borrelia burgdorferi*] | 271 | 6.00E-34 |
| f51-2.aa | gi|1699017 | ErpB2 [*Borrelia burgdorferi*] > gi|1373133 ErpB [*Borrelia* | 271 | 2.50E-33 |
| f51-2.aa | gi|1051120 | outer surface protein G [*Borrelia burgdorferi*] > gi|1373118 ErpG | 109 | 3.70E-22 |
| f51-2.aa | gnl|PID|d10 12343 | gene required for phosphoylation of oligosaccharides/has | 203 | 5.40E-18 |
| f51-2.aa | gi|1707287 | putative outer membrane protein [*Borrelia burgdorferi*] | 111 | 7.50E-18 |
| f51-2.aa | gi|896042 | OspF [*Borrelia burgdorferi*] > pir|S70532|S70532 outer surface protein | 111 | 2.10E-17 |
| f51-2.aa | gi|1707281 | putative outer membrane protein [*Borrelia burgdorferi*] | 111 | 7.50E-17 |
| f51-2.aa | gnl|PID|e32 9895 | (AJ000496) cyclic nucleotide-gated channel beta subunit | 198 | 1.60E-16 |
| f51-2.aa | gi|2246532 | ORF 73, contains large complex repeat CR 73 [Kaposi's | 176 | 2.30E-14 |
| f51-2.aa | gnl|PID|e34 9084 | E02A10.2 [*Caenorhabditis elegans*] | 170 | 2.10E-13 |
| f51-2.aa | gi|160299 | glutamic acid-rich protein [*Plasmodium falciparum*] | 157 | 7.30E-12 |
| f516.aa | gi|2688326 | (AE001146) *B. burgdorferi* predicted coding region BB0409 [*Borrelia* | 1096 | 2.00E-150 |
| f517.aa | gi|2688320 | (AE001146) PTS system, fructose-specific IIABC component (fruA-1) | 1637 | 2.30E-228 |
| f517.aa | gnl|PID|e11 83221 | similar to fructose phosphotransferase system enzyme II | 256 | 4.00E-88 |
| f517.aa | gi|396296 | similar to phosphotransferase system enzyme II [*Escherichia coli*] | 305 | 9.10E-86 |
| f517.aa | gi|405893 | fructose-specific IIBC component [*Escherichia coli*] > gi|450372 | 224 | 4.30E-84 |
| f517.aa | gi|151932 | fructose enzyme II [*Rhodobacter capsulatus*] > gi|46021 fructose | 222 | 4.70E-79 |
| f517.aa | gi|1573422 | frustose-permease IIBC component (fruA) [*Haemophilus influenzae*] | 225 | 6.90E-69 |
| f517.aa | gi|2688554 | (AE001164) PTS system, fructose-specific IIABC component (fruA-2) | 236 | 8.20E-66 |
| f517.aa | gnl|PID|e11 85030 | phosphotransferase system (PTS) fructose-specific enzyme IIBC | 195 | 2.80E-65 |
| f517.aa | gi|155369 | PTS enzyme-II fructose [*Xanthomonas campestris*] pir|B40944|B40944 | 187 | 8.10E-62 |
| f517.aa | gi|305003 | similar to fructose-specific phosphotransferase enzyme II | 145 | 1.90E-39 |
| f517.aa | gnl|PID|d10 11544 | HrsA [*Escherichia coli*] > gi|1786951 (AE000176) | 148 | 2.80E-39 |
| f517.aa | gi|1813488 | phosphotransferase enzyme II [*Bacillus firmus*] | 226 | 3.90E-39 |
| f517.aa | gi|757734 | fruA gene product [*Bacillus amyloliquefaciens*] > pir|S59965|S59965 | 177 | 2.50E-36 |
| f517.aa | gnl|PID|d10 16984 | PTS SYSTEM, FRUCTOSE-SPECIFIC IIBC COMPONENT (EIIBC-FRU) | 173 | 1.10E-34 |
| f517.aa | gi|1673731 | (AE000010) *Mycoplasma pneumoniae*, fructose-permease IIBC component; | 143 | 9.00E-33 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f519.aa | gi|2688327 | (AE001146) B. burgdorferi predicted coding region BB0406 [Borrelia | 1060 | 5.70E-145 |
| f519.aa | gi|2688328 | (AE001146) B. burgdorferi predicted coding region BB0405 [Borrelia | 261 | 1.20E-47 |
| f520.aa | gi|2688328 | (AE001146) B. burgdorferi predicted coding region BB0405 [Borrelia | 1022 | 3.90E-138 |
| f520.aa | gi|2688327 | (AE001146) B. burgdorferi predicted coding region BB0406 [Borrelia | 261 | 4.00E-47 |
| f523.aa | gi|2688300 | (AE001145) glutamate transporter, putative [Borrelia burgdorferi] | 2007 | 9.90E-284 |
| f526.aa | gi|2688309 | (AE001145) B. burgdorferi predicted coding region BB0399 [Borrelia | 1087 | 1.60E-145 |
| f527.aa | gi|2688310 | (AE001145) B. burgdorferi predicted coding region BB0398 [Borrelia | 1814 | 7.60E-249 |
| f541.aa | gi|508421 | antigen P39 [Borrelia burgdorferi] > gi|2688281 (AE001143) basic | 1706 | 5.40E-230 |
| f541.aa | gi|1753225 | BmpA protein [Borrelia burgdorferi] | 1698 | 6.80E-229 |
| f541.aa | gnl|PID|e11 72833 | bmpA (p39, ORF1) [Borrelia burgdorferi] | 1695 | 1.70E-228 |
| f541.aa | gnl|PID|e11 72835 | membrane protein A [Borrelia burgdorferi] > gi|516592 membrane | 1642 | 3.40E-221 |
| f541.aa | gnl|PID|e11 72834 | membrane protein A [Borrelia burgdorferi] | 1638 | 1.20E-220 |
| f541.aa | gnl|PID|e11 72828 | bmpA (p39, ORF1) [Borrelia burgdorferi] | 1551 | 1.00E-208 |
| f541.aa | gnl|PID|e11 72829 | membrane protein A [Borrelia afzelii] | 1502 | 5.60E-202 |
| f541.aa | gnl|PID|e11 72831 | membrane protein A [Borrelia afzelii] | 1499 | 1.40E-201 |
| f541.aa | gnl|PID|e11 72837 | membrane protein A [Borrelia garinii] | 1496 | 3.70E-201 |
| f541.aa | gnl|PID|e11 72830 | membrane protein A [Borrelia afzelii] | 1493 | 9.60E-201 |
| f541.aa | gnl|PID|e11 72838 | membrane protein A [Borrelia garinii] | 1488 | 4.60E-200 |
| f541.aa | gnl|PID|e23 7214 | membrane protein A [Borrelia garinii] | 1216 | 1.20E-162 |
| f541.aa | gnl|PID|e23 7209 | membrane protein A [Borrelia garinii] | 1211 | 5.90E-162 |
| f541.aa | gnl|PID|e23 7236 | membrane protein A [Borrelia garinii] | 1098 | 2.00E-146 |
| f541.aa | gi|2688282 | (AE001143) basic membrane protein B (bmpB) [Borrelia burgdorferi] | 518 | 1.20E-123 |
| f542.aa | gi|508422 | [Borrelia burgdorferi immunodominant antigen P39 gene, complete | 711 | 1.70E-95 |
| f542.aa | gi|2688282 | (AE001143) basic membrane protein B (bmpB) [Borrelia burgdorferi] | 711 | 1.70E-95 |
| f542.aa | gi|551744 | membrane lipoprotein [Borrelia burgdorferi] | 708 | 8.60E-95 |
| f542.aa | gnl|PID|e11 72836 | bmpB (p39, ORF2) [Borrelia burgdorferi] | 699 | 8.20E-94 |
| f542.aa | gnl|PID|e11 72832 | bmpB (p39, ORF2) [Borrelia afzelii] | 634 | 1.00E-84 |
| f542.aa | gnl|PID|e11 72839 | bmpB (p39, ORF2) [Borrelia garinii] | 613 | 9.20E-82 |
| f542.aa | gnl|PID|e23 7209 | membrane protein A [Borrelia garinii] | 153 | 1.70E-32 |
| f532.aa | gnl|PID|e11 72828 | bmpA (p39, ORF1) [Borrelia burgdorferi] | 144 | 3.80E-32 |
| f542.aa | gnl|PID|e23 7214 | membrane protein A [Borrelia garinii] | 153 | 2.00E-31 |
| f542.aa | gi|1753225 | BmpA protein [Borrelia burgdorferi] | 155 | 2.80E-31 |
| f542.aa | gnl|PID|e11 72833 | bmpA (p39, ORF1) [Borrelia burgdorferi] | 155 | 2.80E-31 |
| f542.aa | gi|508421 | antigen P39 [Borrelia burgdorferi] > gi|2688281 (AE001143) basic | 155 | 2.80E-31 |
| f542.aa | gnl|PID|e11 72837 | membrane protein A [Borrelia garinii] | 156 | 1.00E-30 |
| f542.aa | gnl|PID|e11 72829 | membrane protein A [Borrelia afzelii] | 144 | 1.90E-30 |
| f542.aa | gnl|PID|e11 72830 | membrane protein A [Borrelia afzelii] | 144 | 2.70E-30 |
| f544.aa | gi|2688284 | (AE001143) Mg2+ transport protein (mgtE) [Borrelia burgdorferi] | 860 | 4.20E-119 |
| f544.aa | gi|1753228 | MgtE [Borrelia burgdorferi] | 855 | 2.20E-118 |
| f544.aa | gi|619724 | MgtE [Bacillus firmus] > pir|I40201|I40201 mgtE protein - Bacillus | 176 | 3.70E-37 |
| f544.aa | gi|780282 | extended ORF of mgtE gene; transcription from this start point is | 182 | 1.30E-34 |
| f544.aa | gnl|PID|e31 5479 | unknown [Mycobacterium tuberculosis] | 183 | 4.50E-31 |
| f544.aa | gnl|PID|d10 18132 | Mg2+ transporter [Synechocystis sp.] > pir|S77552|S77552 Mg2+ | 165 | 4.60E-31 |
| f544.aa | gnl|PID|e11 81529 | (AJ002571) YkoK [Bacillus subtilis]> gnl|PID|e1183350 similar | 142 | 2.30E-30 |
| f544.aa | gi|2621701 | (AE000843) Mg2+ transporter [Methanobacterium thermoautotrophicum] | 142 | 3.20E-21 |
| f545.aa | gi|2688284 | (AE001143) Mg2+ transport protein (mgtE) [Borrelia burgdorferi] | 860 | 4.20E-119 |
| f545.aa | gi|1753228 | MgtE [Borrelia burgdorferi] | 855 | 2.20E-118 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f545.aa | gi|619724 | MgtE [Bacillus firmus] > pir|I40201|I40201 mgtE protein - Bacillus | 176 | 3.70E-37 |
| f545.aa | gi|780282 | extended ORF of mgtE gene; transcpription from this start point is | 182 | 1.30E-34 |
| f545.aa | gnl|PID|e315479 | unknown [Mycobacterium tuberculosis] | 183 | 4.50E-31 |
| f545.aa | gnl|PID|d1018132 | Mg2+ transporter [Synechocystis sp.] > pir|S77552|S77552 Mg2+ | 165 | 4.60E-31 |
| f545.aa | gnl|PID|e1181529 | (AJ002571) YkoK [Bacillus subtilis] > gnl|PID|e1183350 similar | 142 | 2.30E-30 |
| f545.aa | gi|2621701 | (AE000843) Mg2+ transporter [Methanobacterium thermoautotrophicum] | 142 | 3.20E-21 |
| f561.aa | gi|49245 | lipoprotein [Borrelia burgdorferi] > gi|2688271 (AE001142) lipoprotein | 1000 | 1.30E-132 |
| f561.aa | gi|495738 | P22 [Borrelia burgdorferi] | 982 | 3.70E-130 |
| f577.aa | gi|2688261 | (AE001141) B. burgdorferi predicted coding region BB0352 [Borrelia | 1930 | 4.00E-264 |
| f584.aa | gi|2688246 | (AE001110) B. burgdorferi predicted coding region BB0346 [Borrelia | 1094 | 4.10E-147 |
| f596.aa | gi|2688241 | (AE001140) P26 [Borrelia burgdorferi] > pir|G70141|G70141 P26 | 1322 | 1.20E-180 |
| f596.aa | gi|2281465 | (AF000366) P26 [Borrelia burgdorferi] > gi|2281465 (AF000366) P26 | 1010 | 5.90E-137 |
| f598.aa | gi|2281462 | (AF000366) oligopeptide permease homolog D [Borrelia burgdorferi] | 652 | 1.20E-85 |
| f598.aa | gi|143607 | sporulation protein [Bacillus subtilis] | 372 | 1.20E-45 |
| f598.aa | gnl|PID|e1183166 | oligopeptide ABC transporter (ATP-binding protein) [Bacillus | 372 | 1.20E-45 |
| f598.aa | gi|1574676 | oligopeptide transport ATP-binding protein (oppD) [Haemophilus | 344 | 6.70E-42 |
| f598.aa | gi|677943 | AppD [Bacillus subtilis] > gnl|PID|e1183156 oligopeptide ABC | 344 | 8.00E-42 |
| f598.aa | gi|1787051 | (AE000185) o612; 48 pct identical (33 gaps) to 525 residues from | 346 | 2.50E-41 |
| f598.aa | gi|47346 | AmiE protein [Streptococcus pneumoniae] > pir|S11152|S11152 amiE | 338 | 1.10E-40 |
| f598.aa | gi|47805 | Opp D (AA 1–335) [Salmonella typhimurium] > sp|P04285|OPPD_SALTY | 332 | 5.70E-40 |
| f598.aa | pir|A03413|QREBOT | oligopeptide transport protein oppD - Salmonella typhimurium | 332 | 5.70E-40 |
| f598.aa | gi|1787499 | (AE000223) oligopeptide transport ATP-binding protein OppD | 332 | 5.90E-40 |
| f598.aa | gnl|PID|d1015494 | Oligopeptide transport ATP-binding protein OppD [Escherichia | 332 | 5.90E-40 |
| f598.aa | gi|495177 | ATP binding protein [Lactococcus lactis] > sp|P50980|OPPD_LACLC | 331 | 8.40E-40 |
| f598.aa | gnl|PID|e187587 | oligopeptidepermease [Steptococcus pyogenes] | 331 | 1.10E-39 |
| f598.aa | gi|308850 | ATP binding protein [Lactococcus lactis] > pir|A53290|A53290 | 329 | 1.60E-39 |
| f598.aa | gi|2313399 | (AE000548) dipeptide ABC transporter, ATP-binding protein (dppD) | 322 | 2.30E-39 |
| f6-21.aa | gi|2281468 | (AF000948) OppAIV [Borrelia burgdorferi] > gi|2689891 (AE000792) | 565 | 4.30E-73 |
| f6-21.aa | gi|2253286 | (AF005657) plasminogen binding protein [Borrelia burgdorferi] | 315 | 1.20E-37 |
| f6-21.aa | gi|2688228 | (AE001139) oligopeptide ABC transporter, periplasmic | 314 | 1.60E-37 |
| f6-21.aa | gi|2809544 | (AF043071) oligopeptide permease periplasmic binding protein | 314 | 1.60E-37 |
| f6-21.aa | gi|2281457 | (AF000366) oligopeptide permease homolog AI [Borrelia burgdorferi] | 314 | 1.60E-37 |
| f6-21.aa | gi|2688227 | (AE001139) oligopeptide ABC transporter, periplasmic | 290 | 3.90E-34 |
| f6-21.aa | gi|2281458 | (AF000366) oligopeptide permease homolog AII [Borrelia burgdorferi] | 290 | 3.90E-34 |
| f6-21.aa | gi|2281455 | (AF000365) oligopeptide permease homolog AV [Borrelia burgdorferi] | 279 | 9.90E-34 |
| f6-21.aa | gi|2690261 | (AE000790) oligopeptide ABC transporter, periplasmic | 282 | 5.30E-33 |
| f6-21.aa | gi|1616644 | P30 [Borrelia burgdorferi] | 271 | 6.70E-32 |
| f6-21.aa | gi|2688226 | (AE001139) oligopeptide ABC transporter, periplasmic | 268 | 5.00E-31 |
| f6-21.aa | gi|2281459 | (AF000366) oligopeptide permease homolog AIII [Borrelia | 268 | 5.00E-31 |
| f6-21.aa | gi|2809546 | (AF043071) oligopeptide permease periplasmic binding protein | 268 | 5.00E-31 |
| f6-21.aa | bbsl161785 | 60 kda antigen [Borrelia coriaceae, C053, ATCC 4338, Peptide, 514 | 255 | 2.90E-30 |
| f6-21.aa | gi|2983834 | (AE000740) transporter (extracellular solute binding protein family | 154 | 3.50E-14 |
| f6-27.aa | gi|2689911 | (AE000792) B. burgdorferi predicted coding region BBB09 [Borrelia | 1773 | 7.30E-240 |
| f6-5.aa | gi|2689905 | (AE000792) B. burgdorferi predicted coding region BBB27 [Borrelia | 932 | 7.50E-126 |
| f600.aa | gi|2281461 | (AF000366) oligopeptide permease homolog C [Borrelia burgdorferi] | 731 | 1.40E-100 |
| f600.aa | gi|2688244 | (AE001140) oligopeptide ABC transporter, permease protein (oppC-1) | 731 | 1.40E-100 |
| f600.aa | gi|143606 | sporulation protein [Bacillus subtilis] > pir|C38447|C38447 | 372 | 5.00E-48 |
| f600.aa | gi|40007 | OppC gene product [Bacillus subtilis] > gnl|PID|e1183165 oligopeptide | 372 | 5.00E-48 |
| f600.aa | gi|1574677 | oligopeptide transport system permease protein (oppC)C [Haemophilus | 372 | 7.30E-48 |
| f600.aa | gi|47804 | Opp C (AA 1–301) [Salmonella typhimurium] > pir|C29333|QREBOC | 366 | 4.20E-47 |
| f600.aa | gnl|PID|d1015493 | Oligopeptide transport system permease protein OppC. | 366 | 4.20E-47 |
| f600.aa | gnl|PID|e1181495 | (AJ002571) DppC [Bacillus subtilis] > gnl|PID-e1183314 | 267 | 1.70E-42 |
| f600.aa | gi|1732315 | transport system permease homolog [Listeria moncytogenes] | 335 | 5.30E-42 |
| f600.aa | gi|580851 | dciAC [Bacillus subtilis] > sp|P26904|DPPC_BACSU DIPEPTIDE TRANSPORT | 258 | 1.50E-40 |
| f600.aa | gnl|PID|d1011164 | oligopeptide transport system permease protein [Synechocystis | 240 | 2.50E-39 |
| f600.aa | gi|677947 | AppC [Bacillus subtilis] > gnl|PID|e1183160 oligopeptide ABC | 236 | 2.80E-37 |
| f600.aa | gi|1813497 | dipeptide transporter protein dppC [Bacillus firmus] | 281 | 1.20E-35 |
| f600.aa | sp|Q10623|Y021_MYCTU | PUTATIVE PEPTIDE TRANSPORT PERMEASE PROTEIN CY373.01C. | 290 | 1.50E-35 |
| f600.aa | gi|1532201 | BldKA [Streptomyces coelicolor] | 291 | 1.60E-35 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f603.aa | gi\|2281460 | (AF000366) oligopeptide permease homolog B [*Borrelia burgdorferi*] | 1522 | 5.80E-214 |
| f603.aa | gi\|1574678 | dipeptide transport system permease protein (dppB) [*Haemophilus*] | 392 | 1.30E-100 |
| f603.aa | gnl\|PID\|e1183164 | oligopeptide ABC transporter (permease) [*Bacillus subtilis*] | 374 | 3.40E-96 |
| f603.aa | gi\|580897 | OppB gene product [*Bacillus subtilis*] > pir\|S15231\|B38447 | 373 | 6.60E-96 |
| f603.aa | gi\|47803 | OppB (AA1–306) [*Salmonella typhimurium*] > pir\|B29333\|QREBOB | 371 | 6.70E-96 |
| f603.aa | gi\|1787497 | (AE000223) oligopeptide transport system permease protein OppB | 364 | 3.50E-95 |
| f603.aa | gnl\|PID\|d1015492 | Oligopeptide transport system permease protein OppB | 357 | 3.50E-94 |
| f603.aa | gi\|580850 | dciAB [*Bacillus subtilis*] > gnl\|PID\|e1181494 (AJ002571) DppB | 350 | 9.10E-90 |
| f603.aa | gi\|551726 | sporulation protein [*Bacillus subtilis*] > gi\|143605 sporulation | 374 | 2.40E-87 |
| f603.aa | gi\|349226 | transmembrane protein [*Escherichia coli*] > gi\|466682 dppB | 293 | 9.60E-79 |
| f603.aa | gi\|1787053 | (AE000185) o306; This 306 aa ORF is 46 pct identical (32 gaps) to | 284 | 3.80E-77 |
| f603.aa | gi\|972895 | DppB [*Haemophilus influenzae*] > gi\|1574114 dipeptide transport system | 301 | 2.50E-76 |
| f603.aa | gi\|2182464 | (AE000098) Y4tP [*Rhizobium* sp. NGR234] > sp\|Q53191\|Y4TP_RHISN | 294 | 9.10E-74 |
| f603.aa | gi\|2983140 | (AE000692) transporter (OppBC family) [*Aquifex aeolicus*] | 169 | 2.30E-73 |
| f603.aa | gi\|677946 | AppB [*Bacillus subtilis*] > gnl\|PID\|e1183159 oligopeptide ABC | 218 | 8.70E-73 |
| f604.aa | gi\|2281459 | (AF000366) oligopeptide permease homolog AIII [*Borrelia*] | 2818 | 0 |
| f604.aa | gi\|2809546 | (AF043071) oligopeptide permease periplasmic binding protein | 2818 | 0 |
| f604.aa | gi\|2688226 | (AE001139) oligopeptide ABC transporter, periplasmic | 2823 | 0 |
| f604.aa | gi\|2688227 | (AE001139) oligopeptide ABC transporter, periplasmic | 1738 | 1.40E-234 |
| f604.aa | gi\|2281458 | (AF000366) oligopeptide permease homolog AII [*Borrelia burgdorferi*] | 1731 | 1.30E-233 |
| f604.aa | gi\|2281468 | (AF000948) OppAIV [*Borrelia burgdorfer*] > gi\|2689891 (AE000792) | 1675 | 3.60E-229 |
| f604.aa | gi\|2688228 | (AE001139) oligopeptide ABC transporter, periplasmic | 718 | 1.60E-204 |
| f604.aa | gi\|2809544 | (AF043071) oligopeptide permease periplasmic binding protein | 718 | 3.00E-204 |
| f604.aa | gi\|2253286 | (AF005657) plasminogen binding protein [*Borrelia burgdorferi*] | 718 | 4.10E-204 |
| f604.aa | gi\|2281457 | (AF000366) oligopeptide permease homolog AI [*Borrelia burgdorferi*] | 714 | 2.00E-203 |
| f604.aa | bbs\|161785 | 60 kda antigen [*Borrelia coriaceae*, C053, ATCC 4338, Peptide, 514 | 704 | 1.20E-190 |
| f604.aa | gi\|2281455 | (AF000365) oligopeptide permease homolog AV [*Borrelia burgdorferi*] | 1402 | 1.80E-188 |
| f604.aa | gi\|2690261 | (AE000790) oligopeptide ABC transporter, periplasmic | 1400 | 3.40E-188 |
| f604.aa | gi\|1616644 | P30 [*Borrelia burgdorferi*] | 858 | 4.90E-117 |
| f604.aa | gi\|47802 | Opp A (AA1–542) [*Salmonella typhimurium*] > gi\|47808 precursor | 296 | 9.00E-114 |
| f606.aa | gi\|2281458 | (AF000366) oligopeptide permease homolog AII [*Borrelia burgdorferi*] | 2762 | 0 |
| f606.aa | gi\|2688227 | (AE001139) oligopeptide ABC transporter, periplasmic | 2774 | 0 |
| f606.aa | gi\|2281468 | (AF000948) OppAIV [*Borrelia burgdorferi*] > gi\|2689891 (AE000792) | 1817 | 6.50E-245 |
| f606.aa | gi\|2809546 | (AF043071) oligopeptide permease periplasmic binding protein | 1739 | 3.10E-234 |
| f606.aa | gi\|2688226 | (AE001139) oligopeptide ABC transporter, periplasmic | 1738 | 4.20E-234 |
| f606.aa | gi\|2281459 | (AF000366) oligopeptide permease homolog AIII [*Borrelia*] | 1733 | 2.00E-233 |
| f606.aa | bbs\|161785 | 60 kda antigen [*Borrelia coriaceae*, C053, ATCC 4338, Peptide 514 | 762 | 1.70E-202 |
| f606.aa | gi\|2281455 | (AF000365) oligopeptide permease homolog AV [*Borrelia burgdorferi*] | 1456 | 1.80E-195 |
| f606.aa | gi\|2690261 | (AE000790) oligopeptide ABC transporter, periplasmic | 1454 | 3.30E-195 |
| f606.aa | gi\|2253286 | (AF005657) plasminogen binding protein [*Borrelia burgdorferi*] | 751 | 2.00E-192 |
| f606.aa | gi\|2688228 | (AE001139) oligopeptide ABC transporter, periplasmic | 751 | 2.70E-192 |
| f606.aa | gi\|2809544 | (AF043071) oligopeptide permease periplasmic binding protein | 751 | 6.90E-192 |
| f606.aa | gi\|2281457 | (AF000366) oligopeptide permease homolog AI [*Borrelia burgdorferi*] | 748 | 2.40E-191 |
| f606.aa | gi\|1616644 | P30 [*Borrelia burgdorferi*] | 1220 | 7.30E-163 |
| f606.aa | gi\|47802 | Opp A (AA1–542) [*Salmonella typhimurium*] > gi\|47808 precursor | 285 | 7.80E-106 |
| f607.aa | gi\|2281457 | (AF000366) oligopeptide permease homolog AI [*Borrelia burgdorferi*] | 2694 | 0 |
| f607.aa | gi\|2253286 | (AF005657) plasminogen binding protein [*Borrelia burgdorferi*] | 2706 | 0 |
| f607.aa | gi\|2809544 | (AF043071) oligopeptide permease periplasmic binding protein | 2708 | 0 |
| f607.aa | gi\|2688228 | (AE001139) oligopeptide ABC transporter, periplasmic | 2714 | 0 |
| f607.aa | bbs\|161785 | 60 kda antigen [*Borrelia coriaceae*, C053, ATCC 4338, Peptide, 514 | 1272 | 3.80E-242 |
| f607.aa | gi\|2809546 | (AF043071) oligopeptide permease periplasmic binding protein | 718 | 1.40E-204 |
| f607.aa | gi\|2688226 | (AE001139) oligopeptide ABC transporter, periplasmic | 718 | 3.60E-204 |
| f607.aa | gi\|2281459 | (AF000366) oligopeptide permease homolog AIII [*Borrelia*] | 713 | 1.70E-203 |
| f607.aa | gi\|2688227 | (AE001139) oligopeptide ABC transporter, periplasmic | 751 | 2.40E-192 |
| f607.aa | gi\|2281458 | (AF000366) oligopeptide permease homolog AII [*Borrelia burgdorferi*] | 751 | 4.50E-192 |
| f607.aa | gi\|2281468 | (AF000948) OppAIV [*Borrelia burgdorferi*] > gi\|2689891 (AE000792) | 806 | 8.40E-189 |
| f607.aa | gi\|2690261 | (AE000790) oligopeptide ABC transporter, periplasmic | 601 | 1.20E-144 |
| f607.aa | gi\|2281455 | (AF000365) oligopeptide permease homolog AV [*Borrelia burgdorferi*] | 600 | 1.60E-144 |
| f607.aa | gi\|1616644 | P30 [*Borrelia burgdorferi*] | 709 | 5.40E-103 |
| f607.aa | gi\|47802 | Opp A (AA1–542) [*Salmonella typhimurium*] > gi\|47808 precursor | 261 | 8.50E-69 |
| f611.aa | gi\|2688231 | (AE001139) *B. burgdorferi* predicted coding region BB0325 [*Borrelia*] | 1907 | 1.10E-261 |
| f617.aa | gi\|2688213 | (AE001138) conserved hypothetical integral membrane protein | 1574 | 2.70E-226 |
| f617.aa | gi\|2649711 | (AE001042) ribose ABC transporter, permease protein (rbsC-1) | 109 | 7.00E-12 |
| f631.aa | gi\|1165286 | FtsW [*Borrelia burgdorferi*] > gi\|2688164 (AE001137) cell division | 1820 | 4.00E-259 |
| f631.aa | gnl\|PID\|e229592 | membrane protein [*Borrelia burgdorferi*] > gnl\|PID\|e228289 ftsW | 1815 | 2.10E-258 |
| f631.aa | gi\|146039 | cell division protein [*Escherichia coli*] > gi\|40857 FtsW protein | 362 | 1.30E-60 |
| f631.aa | gi\|580938 | internal open reading frame (AA 1–290) [*Bacillus subtilis*] | 407 | 4.90E-55 |
| f631.aa | gnl\|PID\|e315953 | FtsW [*Mycobacterium tuberculosis*] > sp\|O06223\|FTWH_MYCTU | 412 | 5.40E-55 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f631.aa | gi|580937 | spoVE gene product (AA 1–366) [*Bacillus subtilis*] > gnl|PID|e1185111 | 410 | 2.90E-53 |
| f631.aa | gi|143657 | endospore forming protein [*Bacillus subtilis*] | 405 | 1.20E-52 |
| f631.aa | gnl|PID|d10 19002 | rod-shape-determing protein [*Synechocystis* sp.] | 358 | 3.10E-51 |
| f631.aa | gnl|PID|e12 87793 | (AL022602) cell division protein FtsW [*Mycobacterium leprae*] | 396 | 6.70E-51 |
| f631.aa | gi|1016213 | strong sequence similarity to FtsW, RodA, and SpoV-E [*Cyanophora*] | 349 | 1.00E-50 |
| f631.aa | gi|1574692 | cell division protein (ftsW) [*Haemophilus influenzae*] | 304 | 4.20E-50 |
| f631.aa | gnl|PID|e11 85075 | similar to cell-division protein [*Bacillus subtilis*] | 281 | 1.80E-46 |
| f631.aa | gi|1469784 | putative cell division protein ftsW [*Enterococcus hirae*] | 247 | 1.60E-38 |
| f631.aa | gi|1572976 | rod shape-determining protein (mreB) [*Haemophilus influenzae*] | 196 | 1.20E-37 |
| f631.aa | gi|147695 | rod-shape-determining protein [*Escherichia coli*] > gi|1778551 | 194 | 5.00E-35 |
| f635.aa | gi|1165282 | orf7; Method: conceptual translation supplied by author [*Borrelia*] | 1166 | 1.00E-156 |
| f635.aa | gi|1448949 | ORF 224; The predicted gene product showed weak homology with the | 621 | 2.80E-125 |
| f647.aa | gi|2688180 | (AE001137) flagellar protein (flbB) [*Borrelia burgdorferi*] | 1032 | 1.00E-140 |
| f647.aa | gi|1196323 | putative [*Borrelia burgdorferi*] | 1031 | 1.50E-140 |
| f647.aa | gi|1165270 | orf19; Method: conceptual translation supplied by author [*Borrelia*] | 1019 | 7.10E-139 |
| f647.aa | gi|2108242 | 22.5K protein [*Treponema pallidum*] | 200 | 4.70E-24 |
| f65.aa | gi|2688737 | (AE001178) B. burgdorferi predicted coding region BB0792 [*Borrelia*] | 1095 | 8.10E-148 |
| f653.aa | gi|1165265 | MotB [*Borrelia burgdorferi*] > gi|1185054 flagellar motor apparatus | 1220 | 1.70E-164 |
| f653.aa | gi|1399286 | MotB [*Treponema phagedenis*] | 168 | 5.80E-57 |
| f653.aa | gi|2196896 | MotB [*Treponema pallidum*] | 179 | 1.30E-49 |
| f664.aa | gi|1185062 | flagellar export protein [*Borrelia burgdorferi*] | 1430 | 1.90E-199 |
| f664.aa | gi|1165257 | FlhB [*Borrelia burgdorferi*] > gi|2688194 (AE001137) flagellar | 1430 | 1.90E-199 |
| f664.aa | gi|1216382 | FlhB' [*Treponema pallidum*] > pir|PC4115|PC4115 flagellar protein | 272 | 5.30E-64 |
| f664.aa | gi|395390 | flagellar biosynethetic protein [*Bacillus subtilis*] | 433 | 1.30E-61 |
| f664.aa | gnl|PID|e11 85229 | flagella-associated protein [*Bacillus subtilis*] | 433 | 1.30E-61 |
| f664.aa | gi|1147737 | third gene in fliQ operon; membrane protein homolog [*Caulobacter*] | 353 | 1.70E-46 |
| f664.aa | gi|2313898 | (AE000589) flagellar biosynthetic protein (flhB) [*Helicobacter*] | 203 | 1.20E-44 |
| f664.aa | gi|2984250 | (AE000768) flagellar biosynthetic protein FlhB [*Aquifex aeolicus*] | 319 | 3.00E-44 |
| f664.aa | gi|2459702 | FlhB [*Agrobacterium tumefaciens*] | 347 | 6.20E-44 |
| f664.aa | gi|793892 | flhB [*Yersinia enterocolitica*] > pir|S54213|S54213 flhB protein | 330 | 1.30E-39 |
| f664.aa | gnl|PID|d10 16420 | Flagellar biosynthetic protein FlhB. [*Escherichia coli*] | 325 | 2.20E-39 |
| f664.aa | gi|475126 | yscU [*Yersinia pseudotuberculosis*] > gi|2996233 (AF053946) Yop | 309 | 9.80E-38 |
| f664.aa | gi|497216 | YscU [*Yersinia enterocolitica*] | 308 | 1.40E-37 |
| f664.aa | gnl|PID|d10 07477 | flagellar protein FlhB [*Salmonella typhimurium*] | 312 | 2.10E-37 |
| f664.aa | gnl|PID|e28 3684 | secretion system apparatus, SsaU [*Salmonella typhimurium*] | 312 | 8.20E-37 |
| f679.aa | gi|2688158 | (AE001136) B. burgdorferi predicted coding region BB0259 [*Borrelia*] | 3714 | 0 |
| f679.aa | gnl|PID|d10 11473 | soluble lytic transglycosylase [*Synechocystis* sp.] | 180 | 1.10E-25 |
| f679.aa | gnl|PID|e11 83177 | similar to lytic transglycosylase [*Bacillus subtilis*] | 108 | 2.10E-22 |
| f679.aa | gi|2984090 | (AE000756) hypothetical protein [*Aquifex acolicus*] | 111 | 9.30E-17 |
| f680.aa | gi|2688153 | (AE001136) bacitracin resistance protein (bacA) [*Borrelia*] | 769 | 3.90E-109 |
| f680.aa | gnl|PID|e11 85988 | similar to bacitracin resistance protein (undecaprenol | 174 | 7.30E-18 |
| f680.aa | gi|2622542 | (AE000905) bacitracin resistance protein [*Methanobacterium*] | 116 | 3.30E-16 |
| f680.aa | gi|2984378 | (AE000777) undecaprenol kinase [*Aquifex aeolicus*] | 152 | 3.90E-15 |
| f680.aa | gi|882579 | CG Site No. 29739 [*Exchericia coli*] > gi|1789437 (AE000387) | 139 | 2.60E-12 |
| f688.aa | gi|2688146 | (AE001135) conserved hypothetical integral membrane protein | 2497 | 0 |
| f688.aa | gi|2649351 | (AE001019) conserved hypothetical protein [*Archaeoglobus fulgidus*] | 110 | 3.70E-18 |
| f688.aa | gi|1592186 | M jannaschii predicted coding region MJ1562 [*Methanococcus*] | 174 | 1.10E-16 |
| f7-30.aa | gi|2690009 | (AE000786) conserved hypothetical protein [*Borrelia burgdorferi*] | 682 | 1.90E-90 |
| f704.aa | gi|2688137 | (AE001134) glycerol uptake facilitator (glpF) [*Borrelia*] | 1307 | 4.70E-181 |
| f704.aa | gi|142997 | glycerol uptake facilitator [*Bacillus subtilis*] > gnl|PID|e1182917 | 191 | 1.50E-50 |
| f704.aa | gi|521003 | C01G6.1 [*Caenorhabditis elegans*] | 152 | 1.60E-50 |
| f704.aa | gi|529582 | water channel protein [*Rattus norvegicus*] > pir|I59266|I59266 water | 142 | 5.80E-50 |
| f704.aa | dbj|AB0005 07_1 | (AB000507) aquaporin 7 [*Rattus norvegicus*] | 155 | 1.30E-49 |
| f704.aa | pir|A57119| A57119 | aquaporin 3-human | 149 | 4.20E-44 |
| f704.aa | gi|1109920 | coded for by *C. elegans* cDNA cm16b11; strong similarity to MIP | 168 | 9.30E-44 |
| f704.aa | gnl|PID|d10 19987 | (AB001325) aquaporin 3 [*Homo sapiens*] > sp|Q92482|AQP3_HUMAN | 148 | 5.30E-43 |
| f704.aa | gnl|PID|d10 25786 | (AB008775) aquaporin 9 [*Homo sapiens*] | 144 | 1.40E-42 |
| f704.aa | gi|146188 | glycerol diffusion facilitator [*Escherichia coli*] > gi|305030 CG Site | 146 | 1.30E-40 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f704.aa | gi\|1065485 | strong similarity to the MIP family of transmembrane channel | 179 | 1.40E-39 |
| f704.aa | sp\|P31140\|GLPF_SHIFL | GLYCEROL UPTAKE FACILITATOR PROTEIN | 146 | 3.30E-39 |
| f704.aa | gi\|2587035 | (AF026270) PduF [*Salmonella typhimurium*] > sp\|P37451\|PDUF_SALTY | 168 | 7.30E-39 |
| f704.aa | gi\|1399489 | glycerol diffusion facilitator [*Pseudomonas aeruginosa*] | 154 | 7.90E-39 |
| f704.aa | gi\|2649144 | (AE001005) glycerol uptake facilitator, MIP channel (glpF) | 150 | 1.30E-38 |
| f707.aa | gi\|2688143 | (AE001134) B. burgdorferi predicted coding region BB0238 [*Borrelia*] | 1300 | 3.90E-176 |
| f709.aa | gi\|2688131 | (AE001133) B. burgdorferi predicted coding region BB0236 [*Borrelia*] | 3437 | 0 |
| f730.aa | gi\|2688111 | (AE001132) gufA protein [*Borrelia burgdorferi*] > pir\|C70127\|C70127 | 1376 | 3.00E-192 |
| f730.aa | gi\|1707057 | coded for by C. elegans cDNA CEESS55F; coded for by C. elegans cDNA | 235 | 2.80E-83 |
| f730.aa | gi\|2621542 | (AE000831) conserved protein [*Methanobacterium thermoautotrophicum*] | 259 | 1.10E-74 |
| f730.aa | gnl\|PID\|e183440 | gufA gene product [*Myxococcus xanthus*] > gi\|49253 orfX gene | 175 | 2.30E-35 |
| f730.aa | gi\|2984109 | (AE000757) hypothetical protein [*Aquifex aeolicus*] | 171 | 7.00E-28 |
| f736.aa | gi\|2688115 | (AE001132) phosphate ABC transporter, periplasmic phosphate-binding | 1403 | 2.10E-186 |
| f736.aa | gi\|2622858 | (AE000929) phosphate-binding protein PstS [*Methanobacterium*] | 151 | 4.40E-30 |
| f736.aa | gi\|2622859 | (AE000929) phosphate-binding protein PstS homolog [*Methanobacterium*] | 145 | 2.80E-24 |
| f736.aa | gnl\|PID\|d1010224 | ORF108 [*Bacillus subtilis*] > gnl\|PID\|e1185766 alternate gene | 120 | 1.20E-11 |
| f739.aa | gi\|2688119 | (AE001132) B. burgdorferi predicted coding region BB0213 [*Borrelia*] | 1139 | 1.10E-156 |
| f742.aa | gi\|2688100 | (AE001131) surface-located membrane protein 1 (lmp1) [*Borrelia*] | 5654 | 0 |
| f742.aa | gi\|2621120 | (AE000799) O-linked GlcNAc transferase [*Methanobacterium*] | 200 | 9.30E-22 |
| f742.aa | gi\|2621106 | (AE000798) O-linked GlcNAc transferase [*Methanobacterium*] | 180 | 5.80E-17 |
| f742.aa | pir\|E69190\|E69190 | conserved hypothetical protein MTH68 - Methanobacterium | 154 | 1.60E-14 |
| f742.aa | gi\|1591608 | transformation sensitive protein [*Methanococcus jannaschii*] | 109 | 9.90E-14 |
| f742.aa | gi\|1589778 | SPINDLY [*Arabidopsis thaliana*] | 101 | 1.40E-13 |
| f742.aa | gi\|2984175 | (AE000762) hypothetical protein [*Aquifex aeolicus*] | 132 | 7.30E-13 |
| f742.aa | gi\|3037137 | (AF056198) Hsp70/Hsp90 organizing protein homolog [*Drosophila*] | 105 | 5.40E-11 |
| f743.aa | gi\|2688104 | (AE001131) B. burgdorferi predicted coding region BB0209 [*Borrelia*] | 1299 | 1.70E-174 |
| f748.aa | gi\|2688089 | (AE001130) Lambda CII stability-governing protein (hflC) [*Borrelia*] | 1615 | 5.10E-220 |
| f748.aa | gi\|436158 | putative integral membrane protease required for high frequency | 191 | 4.80E-35 |
| f748.aa | gi\|1573107 | Lambda CII stability-governing protein (hflC) [*Haemophilus*] | 193 | 4.90E-33 |
| f748.aa | gi\|507735 | HflC [*Vibrio parahaemolyticus*] > sp\|P40606\|HFLC_VIBPA HFLC PROTEIN | 212 | 6.10E-26 |
| f752.aa | gi\|2688092 | (AE001130) | 2585 | 0 |
| f752.aa | gi\|2984050 | (AE000754) UDP-MurNac-tripeptide synthetase [*Aquifex aeolicus*] | 202 | 9.10E-74 |
| f752.aa | gi\|40162 | murE gene product [*Bacillus subtilis*] > gnl\|PID\|e1185108 | 157 | 6.40E-70 |
| f752.aa | gnl\|PID\|d1011466 | UDP-MurNac-tripeptide synthetase [*Synechocystis* sp.] | 166 | 5.20E-57 |
| f752.aa | gnl\|PID\|e307808 | UDP-MurNac-tripeptide synthetase [*Rickettsia prowazekii*] | 108 | 2.30E-51 |
| f752.aa | gi\|1574688 | UDP-MurNac-tripeptide synthetase (murE) [*Haemophilus influenzae*] | 166 | 3.20E-50 |
| f752.aa | gnl\|PID\|e1287797 | (AL022602) udp-n-acetylmuramoylalanyl-d-glutamate | 183 | 3.20E-50 |
| f752.aa | gnl\|PID\|e316022 | MurE [*Mycobacterium tuberculosis*] | 181 | 4.10E-46 |
| f752.aa | gi\|581032 | UDP-MurNac-tripeptide synthetase (MurE) [*Escherichia coli*] | 175 | 1.30E-41 |
| f752.aa | gi\|2177098 | UDP-MurNac-Dipeptide: meso-diaminopimelate ligase [*Escherichia*] | 172 | 3.70E-41 |
| f752.aa | gi\|2314673 | (AE000648) UDP-MurNac-tripeptide synthetase (murE) [*Helicobacter*] | 137 | 9.80E-41 |
| f752.aa | gi\|840843 | UDP-N-acetylmuramoylalanyl-D-glutamate-2,6-diaminopimelate ligase | 135 | 1.70E-20 |
| f76-1.aa | gi\|1209837 | lipoprotein [*Borrelia burgdorferi*] | 395 | 2.80E-49 |
| f76-1.aa | gi\|1209873 | lipoprotein [*Borrelia burgdorferi*] | 250 | 7.00E-37 |
| f76-1.aa | gi\|1209843 | lipoprotein [*Borrelia burgdorferi*] | 267 | 7.30E-32 |
| f76-1.aa | gi\|2121280 | (AF000270) lipoprotein [*Borrelia burgdorferi*] > gi\|3095109 | 258 | 1.20E-30 |
| f76-1.aa | gnl\|PID\|e268244 | surface-exposed lipoprotein [*Borrelia afzelii*] | 116 | 2.40E-18 |
| f76-1.aa | gi\|1209849 | lipoprotein [*Borrelia burgdorferi*] | 146 | 8.30E-17 |
| f76-1.aa | gi\|3095105 | (AF046998) 2.9-8 lipoprotein [*Borrelia burgdorferi*] | 148 | 5.80E-14 |
| f76-1.aa | gi\|3095107 | (AF046999) 2.9-9 lipoprotein [*Borrelia burgdorferi*] | 127 | 7.20E-11 |
| f764.aa | gi\|2688084 | (AE001129) B. burgdorferi predicted coding region BB0193 [*Borrelia*] | 1218 | 1.20E-164 |
| f770.aa | gi\|2688077 | (AE001129) conserved hypothetical protein [*Borrelia burgdorferi*] | 646 | 7.60E-87 |
| f790.aa | gi\|2688065 | (AE001128) outer membrane protein (tpn50) [*Borrelia burgdorferi*] | 2013 | 2.50E-271 |
| f790.aa | gi\|458015 | TpN50 precursor [*Treponema pallidum*] | 134 | 4.30E-33 |
| f790.aa | sp\|P38369\|TP50_TREPA | OUTER MEMBRANE PROTEIN TPN50 PRECURSOR. | 134 | 4.30E-33 |
| f790.aa | gi\|532658 | antigen [*Treponema pallidum*] > pir\|S61867\|S61867 antigen tpp57- | 139 | 4.30E-31 |
| f792.aa | gi\|2688052 | (AE001127) B. burgdorferi predicted coding region BB0165 [*Borrelia*] | 3185 | 0 |
| f797.aa | gi\|2688056 | (AE001127) B. burgdorferi predicted coding region BB0159 [*Borrelia*] | 1116 | 5.30E-148 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f798.aa | gi\|2688051 | (AE001127) antigen, S2, putative [*Borrelia burgdorferi*] | 1223 | 9.70E-164 |
| f798.aa | gi\|1063419 | S2 gene product [*Borrelia burgdorferi*] | 116 | 4.70E-23 |
| f798.aa | gi\|2690227 | (AE000790) antigen, S2 [*Borrelia burgdorferi*] > pir\|D70207\|D70207 | 116 | 1.50E-22 |
| f798.aa | gi\|2690128 | (AE000788) protein p23 [*Borrelia burgdorferi*] > pir\|C70257\|C70257 | 110 | 1.40E-19 |
| f798.aa | gi\|2689956 | (AE000785) protein p23 [*Borrelia burgdorferi*] > pir\|D70225\|D70225 | 104 | 2.70E-15 |
| f799.aa | gi\|2688043 | (AE001126) *B. burgdorferi* predicted coding region BB0156 [*Borrelia* | 632 | 1.40E-83 |
| f8-10.aa | gi\|2690052 | (AE000784) antigen, P35, putative [*Borrelia burgdorferi*] | 1241 | 1.10E-167 |
| f8-10.aa | gi\|2689955 | (AE000785) antigen, P35, putative [*Borrelia burgdorferi*] | 298 | 1.70E-57 |
| f8-10.aa | gi\|2690120 | (AE000789) *B. burgdorferi* predicted coding region BBI34 [*Borrelia* | 254 | 3.80E-54 |
| f8-10.aa | gi\|2690100 | (AE000789) *B. burgdorferi* predicted coding region BBI16 [*Borrelia* | 182 | 2.90E-31 |
| f8-10.aa | gi\|2690207 | (AE000787) *B. burgdorferi* predicted coding region BBJ02 [*Borrelia* | 196 | 1.50E-20 |
| f8-10.aa | gi\|2690116 | (AE000789) *B. burgdorferi* predicted coding region BBI29 [*Borrelia* | 192 | 5.50E-20 |
| f8-10.aa | gi\|2690125 | (AE000788) antigen, P35, putative [*Borrelia burgdorferi*] | 129 | 5.80E-14 |
| f8-10.aa | gi\|2690206 | (AE000787) *B. burgdorferi* predicted coding region BBJ01 [*Borrelia* | 103 | 1.10E-13 |
| f8-10.aa | gi\|2690099 | (AE000789) *B. burgdorferi* predicted coding region BBI15 [*Borrelia* | 142 | 8.50E-13 |
| f8-10.aa | gi\|2690115 | (AE000789) *B. burgdorferi* predicted coding region BBI28 [*Borrelia* | 130 | 3.30E-12 |
| f8-14.aa | gi\|2690074 | (AE000784) *B. burgdorferi* predicted coding region BBH37 [*Borrelia* | 1560 | 2.60E-206 |
| f8-14.aa | gi\|2690188 | (AE000787) *B. burgdorferi* predicted coding region BBJ08 [*Borrelia* | 599 | 3.50E-123 |
| f8-14.aa | gi\|2690030 | (AE000786) *B. burgdorferi* predicted coding region BBG01 [*Borrelia* | 337 | 4.40E-106 |
| f8-14.aa | gi\|2690139 | (AE000788) *B. burgdorferi* predicted coding region BBK01 [*Borrelia* | 173 | 8.00E-91 |
| f8.aa | gi\|2688783 | (AE001182) *B. burgdorferi* predicted coding region BB0840 [*Borrelia* | 2765 | 0 |
| f8.aa | gi\|2697112 | (AF008219) unknown [*Borrelia afzelii*] | 1494 | 2.80E-205 |
| f800.aa | gi\|2688044 | (AE001126) *B. burgdorferi* predicted coding region BB0155 [*Borrelia* | 1936 | 1.00E-262 |
| f805.aa | gi\|2688039 | (AE001126) N-acetylglcosamine-6-phosphate deacetylase (nagA) | 641 | 6.30E-85 |
| f810.aa | gi\|2688024 | (AE001125) glycine betaine, L-proline ABC transporter, | 1527 | 4.20E-207 |
| f810.aa | gi\|984805 | glycine betaine-binding protein precursor [*Bacillus subtilis*] | 179 | 6.80E-21 |
| f810.aa | gi\|1850605 | ProX [*Steptococcus mutans*] | 181 | 2.30E-18 |
| f814.aa | pir\|D70117\|D70117 | acriflavine resistance protein (acrB) homolog - Lyme disease | 5105 | 0 |
| f814.aa | gi\|2688027 | (AE001125) acriflavine resistance protein (acrB) [Borrelia | 5111 | 0 |
| f814.aa | gi\|2983346 | (AE000707) cation efflux (AcrB/AcrD/AcrF family) [*Aquifex aeolicus*] | 325 | 4.80E-119 |
| f814.aa | gi\|2313726 | (AE000574) acriflavine resistance protein (acrB) [*Helicobacter* | 327 | 4.50E-111 |
| f814.aa | gi\|3068786 | (AF059041) RND pump protein [*Helicobacter pylori*] | 297 | 1.70E-110 |
| f814.aa | gnl\|PID\|e1182651 | similar to acriflavin resistance protein [*Bacillus subtilis*] | 257 | 8.90E-100 |
| f814.aa | gi\|1573914 | acriflavine resistance protein (acrB) [*Haemophilus influenzae*] | 294 | 2.10E-97 |
| f814.aa | gnl\|PID\|e256815 | mexF [*Pseudomonas aeruginosa*] | 300 | 2.00E-88 |
| f814.aa | gnl\|PID\|d1019295 | cation efflux system protein CzcA [*Synechocystis* sp.] | 198 | 1.30E-87 |
| f814.aa | gnl\|PID\|e285274 | membrane-bound cation-proton-aniporter [*Ralstonia eutropha*] | 283 | 2.20E-87 |
| f814.aa | gi\|438854 | envD homologue; ORFB [*Pseudomonas aeruginosa*] > pir\|S39630\|S39630 | 290 | 6.50E-87 |
| f814.aa | gnl\|PID\|d1011721 | CzcA [*Alcaligenes* sp.] > pir\|JC4700\|JC4700 cadmium, zinc, | 275 | 8.20E-87 |
| f814.aa | gi\|2314107 | (AE000605) cation efflux system protein (czcA) [*Helicobacter*] | 266 | 2.30E-86 |
| f814.aa | pir\|A33830\|A33830 | cation efflux system membrane protein czcA - Alcaligenes | 275 | 3.10E-86 |
| f814.aa | gnl\|PID\|d1017073 | envD gene product homolog [*Escherichia coli*] > gi\|1788814 | 283 | 8.30E-86 |
| f818.aa | gi\|2688032 | (AE001125) *B. burgdorferi* predicted coding region BB0139 [*Borrelia*] | 664 | 3.00E-87 |
| f82.aa | gi\|2688729 | (AE001177) *B. burgdorferi* predicted coding region BB0776 [*Borrelia*] | 991 | 2.20E-132 |
| f820.aa | gi\|2688029 | (AE001125) penicillin-binding protein (pbp-1) [*Borrelia*] | 3171 | 0 |
| f820.aa | gi\|580936 | SpoVD [*Bacillus subtilis*] > gnl\|PID\|e1185107 penicillin-binding | 149 | 3.00E-49 |
| f820.aa | gi\|150283 | penicillin-binding protein 2 [*Neisseria meningitidis*] | 154 | 6.90E-43 |
| f820.aa | gnl\|PID\|e1287798 | (AL022602) penicillin binding protein 2 [*Mycobacterium* | 182 | 4.20E-42 |
| f820.aa | gi\|509190 | penicillin-binding protein 2 [*Neisseria meningitidis*] | 158 | 1.70E-41 |
| f820.aa | gi\|509118 | penicillin-binding protein 2 [*Neisseria meningitidis*] | 151 | 7.10E-41 |
| f820.aa | gi\|840842 | penicillin-binding protein 3 [*Pseudomonas aeruginosa*] | 177 | 1.20E-40 |
| f820.aa | gi\|509065 | penicillin-binding protein 2 [*Neisseria meningitidis*] | 152 | 1.40E-40 |
| f820.aa | gi\|509043 | penicillin-binding protein 2 [*Neisseria meningitidis*] | 150 | 2.70E-40 |
| f820.aa | gi\|509159 | penicillin-binding protein 2 [*Neisseria meningitidis*] | 147 | 2.80E-40 |
| f820.aa | gi\|509120 | penicillin-binding protein 2 [*Neisseria meningitidis*] | 155 | 1.60E-39 |
| f820.aa | gi\|509157 | penicillin-binding protein 2 [*Neisseria meningitidis*] | 155 | 1.60E-39 |
| f820.aa | gi\|509126 | penicillin-binding protein 2 [*Neisseria meningitidis*] | 158 | 1.70E-39 |
| f820.aa | gi\|45178 | penicillin-binding protein 2 (AA 1–581) [*Neisseria meningitidis*] | 155 | 2.30E-38 |
| f820.aa | gi\|150279 | penicillin-binding protein 2 [*Neisseria gonorrhoeae*] | 154 | 8.70E-38 |
| f831.aa | gi\|2688018 | (AE001124) *B. burgdorferi* predicted coding region BB0126 [*Borrelia*] | 994 | 1.20E-133 |
| f843.aa | gi\|2688014 | (AE001124) PTS system, maltose and glucose-specific IIABC component | 2590 | 0 |
| f843.aa | gi\|2688579 | (AE001166) PTS system, glucose-specific IIBC component (ptsG) | 594 | 1.80E-129 |
| f843.aa | gi\|1072418 | glcA [*Staphylococcus carnosus*] > pir\|S46952\|S46952 | 283 | 1.00E-72 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f843.aa | gi\|1072419 | glcB [*Staphylococcus carnosus*] > pir\|S63606\|S46953 | 248 | 1.00E-66 |
| f843.aa | dbj\|D86417_11 | YflF [*Bacillus subtilis*] > gnl\|PID\|e1182760 similar to | 215 | 7.90E-65 |
| f843.aa | gi\|2197104 | (AF003742) MalX homolog [*Escherichia coli*] | 182 | 8.90E-64 |
| f843.aa | gi\|43819 | nagE gene product [*Klebiella pneumoniae*] > pir\|S18607\|S18607 | 264 | 8.50E-63 |
| f843.aa | gi\|146913 | N-acetylglucosamine transport protein [*Escherichia coli*] | 256 | 1.10E-62 |
| f843.aa | gi\|39956 | IIGlc [*Bacillus subtilis*] > gnl\|PID\|e1184979 phosphotransferase system | 315 | 5.20E-62 |
| f843.aa | dbj\|D87820_1 | NagE [*Vibrio cholerae* non-O1] > pir\|JC5651\|JC5651 | 263 | 3.80E-61 |
| f843.aa | gi\|2689888 | (AE000792) PTS system, maltose and glucose-specific IIABC component | 198 | 1.10E-60 |
| f843.aa | gi\|397363 | enzyme II-glc [*Salmonella typhimurium*] > pir\|S36620\|S36620 | 227 | 1.20E-58 |
| f843.aa | gi\|147393 | glucose-specific enzyme II of phosphotransferase system [*Escherichia* | 226 | 3.90E-57 |
| f843.aa | gnl\|PID\|e1182187 | alternate gene name: yzfA; similar to phosphotransferase | 180 | 9.00E-56 |
| f843.aa | gi\|1732194 | PTS permease for glucose [*Vibrio furnissii*] | 349 | 4.30E-50 |
| f850.aa | gi\|2687999 | (AE001123) B. burgdorferi predicted coding region BB0110 [*Borrelia* | 2374 | 0 |
| f853.aa | gi\|2687994 | (AE001123) basic membrane protein [*Borrelia burgdorferi*] | 1672 | 2.20E-224 |
| f853.aa | gi\|155055 | basic membrane protein precursor [*Treponema pallidum*] | 130 | 3.60E-24 |
| f859.aa | gi\|2688002 | (AE001123) B. burgdorferi predicted coding region BB0102 [*Borrelia* | 888 | 1.80E-115 |
| f86.aa | gi\|2688725 | (AE001177) flagellar P-ring protein (flgI) [*Borrelia burgdorferi*] | 1647 | 1.50E-217 |
| f86.aa | gi\|2920802 | (AF019213) FlgI [*Vibrio cholerae*] | 143 | 3.50E-14 |
| f86.aa | gi\|405550 | flagellar P-ring protein [*Pseudomonas putida*] > sp\|Q52082\|FLGI_PSEPU | 102 | 3.70E-13 |
| f86.aa | gi\|144241 | flagellin [*Caulobacter crescentus*] > pir\|A41891\|A41891 basal body | 110 | 6.70E-13 |
| f860.aa | gi\|2687998 | (AE001123) asparaginyl-tRNA synthetas (asnS) [*Borrelia* | 1110 | 2.40E-149 |
| f860.aa | gi\|1574761 | asparaginyl-tRNA synthetase (asnS) [*Haemophilus influenzae*] | 634 | 1.30E-83 |
| f860.aa | gi\|147935 | asparaginyl-tRNA synthetase (asnS) [*Escherichia coli*] > gi\|41000 | 622 | 6.10E-82 |
| f860.aa | gnl\|PID\|e1202698 | (AJ222644) asparaginyl-tRNA synthetase [*Arabidopsis thaliana*] | 404 | 2.40E-80 |
| f860.aa | gnl\|PID\|d1011495 | asparaginyl-tRNA synthetase [*Synechocystis* sp.] | 618 | 4.50E-80 |
| f860.aa | gi\|530408 | Asn-tRNA synthetase [*Mycoplasma capricolum*] > pir\|S77842\|S77842 | 439 | 1.60E-65 |
| f860.aa | gi\|1045792 | asparaginyl-tRNA synthetase [*Mycoplasma genitalium*] | 365 | 2.20E-62 |
| f860.aa | gi\|1674281 | (AE000057) *Mycoplasma pneumoniae*, asparaginyl-tRNA synthetase; | 338 | 3.10E-61 |
| f860.aa | gnl\|PID\|e1202700 | (AJ222645) asparaginyl-tRNA synthetase [*Arabidopsis thaliana*] | 364 | 3.90E-59 |
| f860.aa | gnl\|PID\|e264488 | YCR245c, len:492 [*Saccharomyces cerevisiae*] > pir\|S19435\|S19435 | 150 | 3.90E-47 |
| f860.aa | gnl\|PID\|e254305 | asparaginyl-tRNA synthetase [*Salmonella typhi*] | 370 | 1.70E-46 |
| f860.aa | gnl\|PID\|e188505 | asparagine--tRNA ligase [*Lactobacillus delbrueckii*] | 224 | 1.30E-44 |
| f860.aa | pir\|S71072\|S71072 | asparagine--tRNA ligase (EC 6.1.122) asnS1 - *Lactobacillus* | 224 | 1.30E-44 |
| f860.aa | gnl\|PID\|e188572 | asparagine--tRNA ligase [*Lactobacillus delbrueckii*] | 224 | 2.40E-44 |
| f860.aa | gi\|1146247 | asparaginyl-tRNA synthetase [*Bacillus subtilis*] > gnl\|PID\|e1183681 | 234 | 6.10E-44 |
| f861.aa | gi\|2687975 | (AE001122) glutamate racemase (murI) [*Borrelia burgdorferi*] | 1354 | 2.90E-186 |
| f861.aa | gi\|396314 | glutamate synthase [*Escherichia coli*] > gi\|290428 glutamate synthase | 168 | 1.20E-16 |
| f861.aa | gnl\|PID\|e1165353 | glutamate racemase [*Bacillus subtilis*] > gnl\|PID\|e1184088 | 120 | 1.80E-13 |
| f861.aa | pir\|JC5587\|JC5587 | glutamate racemase (EC 5.1.1.3) - *Bacillus pumilus* | 122 | 1.80E-13 |
| f861.aa | sp\|P52973\|MURI_HAEIN | PROBABLE GLUTAMATE RACEMASE (EC 5.1.1.3) | 114 | 8.10E-13 |
| f867.aa | gi\|2687979 | (AE001122) V-type ATPase, subunit A (atpA) [*Borrelia burgdorferi*] | 2826 | 0 |
| f867.aa | pir\|JC5532\|JC5532 | vacuolar-type ATPase (EC 3.-.-.-) A chain - *Desulurococcus* | 594 | 2.20E-162 |
| f867.aa | gi\|2104726 | V-ATPase A subunit [*Desulfurococcus* sp. SY] | 594 | 3.10E-162 |
| f867.aa | gi\|2605627 | ATPase alpha subunit [*Thermococcus* sp.] | 592 | 7.10E-161 |
| f867.aa | gnl\|PID\|d1003475 | Na+-ATPase alpha subunit [*Enterococcus hirae*] | 601 | 1.60E-153 |
| f867.aa | gi\|1590955 | H+-transporting ATP synthase, subunit A (atpA) [*Methanococcus* | 585 | 6.00E-147 |
| f867.aa | gi\|496904 | membrane ATPase [*Haloferax volcanii*] > pir\|S55895\|S45144 | 728 | 6.00E-147 |
| f867.aa | gi\|152927 | ATPase alpha subunit [*Sulfolobus acidocaldarius*] > pir\|A28652\|A28652 | 548 | 5.00E-163 |
| f867.aa | gi\|2649416 | (AE001023) H+-transporting ATP synthase, subunit A (atpA) | 748 | 2.00E-146 |
| f867.aa | gi\|2622052 | (AE000869) ATP synthase, subunit A [*Methanobacterium* | 607 | 9.40E-146 |
| f867.aa | gi\|168926 | vacuolar ATPase vma-1 [*Neurospora crassa*] > pir\|A30799\|PXNCV7 | 302 | 9.00E-145 |
| f867.aa | gi\|149820 | ATPase alpha subunit [*Methanosarcina barkeri*] > pir\|A34283\|A34283 | 743 | 1.40E-143 |
| f867.aa | gi\|160736 | vacuolar ATPase [*Plasmodium falciparum*] > pir\|A48582\|A48582 vacuolar | 305 | 9.40E-140 |
| f867.aa | gnl\|PID\|d1009732 | adenosine triphosphatase A subunit [*Acetabularia acetabulum*] | 307 | 9.00E-137 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f867.aa | gi\|49048 | ATPase alpha-subunit [*Thermus aquaticus thermophilus*] | 684 | 4.80E-136 |
| f868.aa | gi\|2687980 | (AE001122) V-type ATPase, subunit B (atpB) [*Borrelia burgdorferi*] | 2205 | 1.80E-298 |
| f868.aa | gi\|1590954 | H+-transporting ATP synthase, subunit B (atpB) [*Methanococcus* | 156 | 2.00E-114 |
| f868.aa | gi\|2605628 | ATPase beta subunit [*Thermococcus* sp.] | 151 | 3.30E-108 |
| f868.aa | gi\|2104727 | V-ATPase B subunit [*Desulfurococcus* sp. SY] | 151 | 1.10E-107 |
| f868.aa | gi\|43641 | ATP synthase subunit [*Halobacterium salinarium*] > pir\|S14733\|S14733 | 150 | 1.80E-107 |
| f868.aa | gi\|149821 | ATPase beta subunit [*Methanosarcina barkeri*] > pir\|B34283\|B34283 | 172 | 1.00E-105 |
| f868.aa | gnl\|PID\|d10 03476 | Na+-ATPase beta subunit [*Enterococcus hirae*] | 151 | 1.40E-105 |
| f868.aa | gi\|2649415 | (AE001023) H+-transporting ATP synthase, subunit B (atpB) | 151 | 1.70E-103 |
| f868.aa | gi\|496905 | membrane ATPase [*Haloferax volcanii*] > pir\|S55896\|S45145 | 153 | 5.80E-103 |
| f868.aa | gi\|1199639 | AlAO H+ ATPase, subunit B [*Methanosarcina mazeii*] | 173 | 2.20E-102 |
| f868.aa | gi\|2622051 | (AE000869) ATP synthase, subunit B [*Methyanobacterium* | 155 | 1.00E-101 |
| f868.aa | gnl\|PID\|d10 09734 | adenosine triphosphatase B subunit [*Acetabularia acetabulum*] | 159 | 1.30E-101 |
| f868.aa | gi\|1086645 | Similar to vacuolar ATP synthase (strong). [*Caenorhabditis elegans*] | 163 | 1.30E-101 |
| f868.aa | gi\|459198 | vacuolar H+-ATPase subunit B [*Gossypium hirsutum*] | 164 | 4.60E-101 |
| f868.aa | gi\|167108 | vacuolar ATPase B subunit [*Hordeum vulgare*] > sp\|Q40078\|VAT1_HORVU | 164 | 4.60E-101 |
| f872.aa | gi\|2687986 | (AE001122) *B. burgdorferi* predicted coding region BB0089 [*Borrelia* | 1684 | 1.60E-230 |
| f874.aa | gi\|2687965 | (AE001121) L-lactate dehydrogenase (ldh) [*Borrelia burgdorferi*] | 1603 | 2.80E-217 |
| f874.aa | gi\|39758 | L-lactate dehydrogenase [*Bacillus psychrosaccharolyticus*] | 520 | 3.10E-109 |
| f874.aa | pir\|S08183\|S08183 | L-lactate dehydrogenase (EC 1.1.1.27) X - *Bacillus* | 515 | 4.30E-109 |
| f874.aa | pir\|A25805\|A25805 | L-lactate dehydrogenase (EC 1.1.1.27) - *Bacillus subtilis* | 520 | 1.00E-107 |
| f874.aa | gi\|143136 | L-lactate dehydrogenase [*Bacillus megaterium*] > pir\|S00133\|DEBSLM | 430 | 5.20E-107 |
| f874.aa | gi\|143138 | lactate dehydrogenase (EC 1.1.1.27) [*Bacillus stearothermophilus*] | 514 | 6.60E-107 |
| f874.aa | gnl\|PID\|d10 09574 | L-lactate dehydrogenase [*Bacillus subtilis*] > gnl\|PID\|e1182257 | 512 | 8.90E-107 |
| f874.aa | gi\|143134 | lactate dehydrogenase (EC 1.1.1.27) [*Bacillus caldotenax*] | 516 | 1.70E-106 |
| f874.aa | gi\|143132 | lactate dehydrogenase (AC 1.1.1.27) [*Bacillus caldolyticus*] | 506 | 2.30E-106 |
| f874.aa | gi\|412392 | NAD-dependent dehydrogenase [unidentified] | 508 | 4.40E-106 |
| f874.aa | gi\|143130 | L-lactate dehydrogenase [*Bacillus caldotenax*] > pir\|S00019\|S00019 | 510 | 1.10E-105 |
| f874.aa | gi\|642256 | L-lactate dehydrogenase [*Pediococcus acidilactici*] | 560 | 1.70E-91 |
| f874.aa | gi\|847956 | L-lactate dehydrogenase [*Lactobacillus sake*] > sp\|P50934\|LDH_LACSK | 381 | 2.30E-91 |
| f874.aa | gi\|581305 | L-lactate dehydrogenase [*Lactobacillus plantarum*] > pir\|A36957\|A36957 | 547 | 2.30E-91 |
| f874.aa | gi\|149575 | L(+)-lactate dehydrogenase [*Lactobacillus casei*] | 386 | 3.20E-91 |
| f886.aa | gi\|2687958 | (AE001120) *B. burgdorferi* predicted coding region BB0077 [*Borrelia* | 1792 | 9.50E-237 |
| f888.aa | gi\|2687959 | (AE001120) *B. burgdorferi* predicted coding region BB0075 [*Borrelia* | 2351 | 3.59999944710933e-318 |
| f893.aa | gi\|2687962 | (AE001120) *B. burgdorferi* predicted coding region BB0071 [*Borrelia* | 2514 | 0 |
| f895.aa | gi\|2687954 | (AE001120) conserved hypothetical protein [*Borrelia burgdorferi*] | 747 | 3.60E-100 |
| f895.aa | gnl\|PID\|e11 84285 | similar to hypothetical proteins [*Bacillus subtilis*] | 103 | 2.50E-35 |
| f899.aa | gi\|2687946 | (AE001119) *B. burgdorferi* predicted coding region BB0066 [*Borrelia* | 1161 | 4.30E-158 |
| f924.aa | gi\|2687934 | (AE001118) *B. burgdorferi* predicted coding region BB0044 [*Borrelia* | 692 | 3.90E-93 |
| f925.aa | gi\|2687935 | (AE001118) *B. burgdorferi* predicted coding region BB0043 [*Borrelia* | 1771 | 7.50E-242 |
| f929.aa | gi\|2687916 | (AE001117) *B. burgdorferi* predicted coding region BB0038 [*Borrelia* | 2589 | 0 |
| f93.aa | gi\|2688703 | (AE001176) pyridoxal kinase (pdxK) [*Borrelia burgdorferi*] | 1334 | 6.60E-181 |
| f933.aa | gi\|2687917 | (AE001118) *B. burgdorferi* predicted coding region BB0034 [*Borrelia* | 902 | 1.90E-122 |
| f933.aa | gi\|2690091 | (AE000789) conserved hypothetical protein [*Borrelia burgdorferi*] | 136 | 3.10E-37 |
| f933.aa | gi\|2690225 | (AS000790) conserved hypothetical protein [*Borrelia burgdorferi*] | 149 | 4.50E-37 |
| f933.aa | gi\|2690045 | (AE000784) conserved hypothetical protein [*Borrelia burgdorferi*] | 126 | 5.70E-28 |
| f933.aa | gi\|2239281 | No definition line found [*Borrelia burgdorferi*] | 148 | 2.40E-14 |
| f939.aa | gi\|2687919 | (AE001117) *B. burgdorferi* predicted coding region BB0028 [*Borrelia* | 1796 | 7.50E-241 |
| f940.aa | gi\|2687920 | (AE001117) *B. burgdorferi* predicted coding region BB0027 [*Borrelia* | 1109 | 1.20E-152 |
| f943.aa | gi\|2687905 | (AE001116) *B. burgdorferi* predicted coding region BB0024 [*Borrelia* | 2001 | 5.00E-273 |
| f943.aa | gi\|411592 | L-sorbosone dehydrogenase [unidentified] | 175 | 2.30E-15 |
| f943.aa | gnl\|PID\|d10 06418 | L-sorbosone dehydrogenase [*Acetobacter liquefaciens*] | 173 | 4.40E-15 |
| f952.aa | gi\|2687880 | (AE001115) glpE protein (glpE) [*Borrelia burgdorferi*] | 628 | 2.90E-84 |
| f07A.aa | R33279 | 43 kD endoflagellum sheath protein | 120 | 6.10E-25 |
| f142.aa | R95044 | Apoptosis participating protein | 103 | 4.70E-18 |
| f147.aa | W18209 | *Staphylococcus aureus* Coenzyme A disulphide reductase (CoADR). | 194 | 4.80E-91 |
| f147.aa | W06425 | Water-forming NADH oxidase. | 369 | 8.00E-86 |
| f147.aa | R32089 | Benzene dioxygenase polypeptide V. | 104 | 4.70E-11 |
| f147.aa | R66733 | Aromatic dihydrodiol/catechol deoxygenase #5. | 105 | 9.00E-11 |
| f152.aa | R81549 | High affinity potassium uptake transporter HKT1. | 137 | 3.70E-18 |
| f157.aa | W15192 | *Staphylococcus aureus* cell surface protein. | 239 | 3.40E-37 |
| f17-6.aa | W30763 | Mannose-1-phosphate transferase protein MNN4. | 178 | 5.20E-16 |
| f17-6.aa | W03627 | Human follicle stimulating hormone GPR N-terminal sequence. | 145 | 1.30E-11 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f17-6.aa | W03626 | Human thyrotropin GPR N-terminal sequence. | 144 | 1.90E-11 |
| f17-6.aa | W21591 | Antibiotic potentiating peptide #3. | 141 | 5.10E-11 |
| f196.aa | W05196 | Helicobacter pylori 50 kDa protective antigen G3.8. | 183 | 2.70E-18 |
| f196.aa | W20916 | H. pylori inner membrane protein 14gp12015orf12. | 180 | 3.60E-17 |
| f196.aa | W20287 | H. pylori inner membrane protein, 24132293.aa | 169 | 6.50E-15 |
| f196.aa | W20769 | H. pylori inner membrane protein, 07ee20513orf28. | 169 | 1.40E-14 |
| f196.aa | W20767 | H. pylori cytoplasmic protein, 07ee20513orf1. | 140 | 6.10E-14 |
| f197.aa | W20769 | H. pylori inner membrane protein, 07ee20513orf28. | 190 | 2.30E-19 |
| f197.aa | W20287 | H. pylori inner membrane protein, 24132293.aa. | 190 | 2.00E-18 |
| f197.aa | W05196 | Helicobacter pylori 50 kDa protective antigen G3.8. | 179 | 4.00E-16 |
| f197.aa | W20916 | H. pylori inner membrane protein 14gp12015orf12. | 182 | 6.30E-16 |
| f197.aa | W20767 | H. pylori cytoplasmic protein, 07ee20513orf1. | 150 | 1.10E-12 |
| f21-4.aa | R69629 | B. burgdorferi OspF operon. | 321 | 7.00E-39 |
| f21-4.aa | R89476 | B. burgdorferi OspG lipoprotein. | 107 | 6.10E-34 |
| f24-1.aa | W22676 | Borrelia variable major protein (VMP)-like protein VlsE. | 412 | 4.60E-72 |
| f291.aa | W20152 | H. pylori transporter protein, 1464715.aa. | 336 | 1.70E-41 |
| f291.aa | W24682 | Helicobacter pylori transporter protein 4882763.aa. | 234 | 8.20E-27 |
| f291.aa | W20528 | H. pylori cell envelope transporter protein 4882763.aa. | 234 | 8.20E-27 |
| f291.aa | W20592 | H. pylori transporter protein, 01ce11513orf21. | 168 | 7.60E-17 |
| f301.aa | W20287 | H. pylori inner membrane protein, 24132293.aa. | 158 | 1.60E-13 |
| f301.aa | W20916 | H. pylori inner membrane protein 14gp12015orf12. | 158 | 1.90E-13 |
| f301.aa | W20769 | H. pylori inner membrane protein, 07ee20513orf28. | 158 | 2.40E-13 |
| f301.aa | W05196 | Helicobacter pylori 50 kDa protective antigen G3.8. | 157 | 2.80E-13 |
| f301.aa | W20767 | H. pylori cytoplasmic protein, 07ee20513orf1. | 138 | 4.30E-11 |
| f320.aa | R24300 | Glycopeptide resistance protein VanY from E. faecium. | 142 | 2.90E-14 |
| f328.aa | R15642 | CTP synthetase. | 274 | 3.00E-50 |
| f328.aa | W20778 | H. pylori cytoplasmic protein, 07ge20415orf6. | 122 | 1.90E-34 |
| f352.aa | W03626 | Human thyrotropin GPR N-terminal sequence. | 153 | 4.70E-12 |
| f352.aa | W21591 | Antibiotic potentiating peptide #3. | 152 | 6.60E-12 |
| f352.aa | W03627 | Human follicle stimulating hormone GPR N-terminal sequence. | 145 | 5.30E-11 |
| f4-50.aa | W07187 | B. garinii IP90 decorin binding protein. | 305 | 1.30E-41 |
| f4-50.aa | W07186 | B. afzelii strain pGau decorin binding protein. | 161 | 1.60E-34 |
| f4-50.aa | W07185 | B. burgdorferi HB-19 decorin binding protein. | 173 | 2.80E-34 |
| f4-50.aa | W07183 | B. burgdorferi B31 decorin binding protein. | 176 | 1.80E-33 |
| f4-50.aa | W07190 | B. burgdorferi JD1 decorin binding protein. | 177 | 1.80E-33 |
| f4-50.aa | W07182 | B. burgdorferi 297 decorin binding protein. | 177 | 1.10E-32 |
| f4-50.aa | W07189 | B. burgdorferi LP7 decorin binding protein. | 177 | 1.10E-32 |
| f4-50.aa | W07188 | B. burgdorferi LP4 decorin binding protein. | 177 | 3.90E-32 |
| f4-50.aa | W07184 | B. burgdorferi Sh.2.82 decorin binding protein. | 177 | 1.30E-31 |
| f45-2.aa | R89476 | B. burgdorferi OspG lipoprotein. | 213 | 1.30E-35 |
| f45-2.aa | R70491 | Leucocytozoan protozoa structural protein epitope. | 206 | 2.10E-20 |
| f45-2.aa | W03626 | Human thyrotropin GPR N-terminal sequence. | 211 | 6.10E-20 |
| f45-2.aa | W03627 | Human follicle stimulating hormone GPR N-terminal sequence. | 202 | 8.90E-19 |
| f45-2.aa | R69629 | B. burgdorferi OspF operon. | 111 | 1.10E-14 |
| f45-2.aa | W30763 | Mannose-1-phosphate transferase protein MNN4. | 166 | 1.00E-13 |
| f45-2.aa | R97866 | Chicken leucocytozoan immunogenic protein for use in vaccines. | 154 | 7.10E-12 |
| f488.aa | W15078 | M leprae gyrA precursor. | 390 | 2.70E-143 |
| f488.aa | R88733 | S. aureus mutant grlA protein. | 698 | 6.70E-122 |
| f488.aa | R88731 | S. aureus topoisomerase IV grlA subunit. | 698 | 6.70E-122 |
| f49-2.aa | W22676 | Borrelia variable major protein (VMP)-like protein VlsE. | 497 | 2.70E-75 |
| f5-14.aa | W03626 | Human thyrotropin GPR N-terminal sequence. | 234 | 6.60E-23 |
| f5-14.aa | W03627 | Human follicle stimulating hormone GPR N-terminal sequence. | 231 | 1.40E-22 |
| f5-14.aa | R70491 | Leucocytozoan protozoa structural protein epitope. | 221 | 1.00E-20 |
| f5-14.aa | W30763 | Mannose-1-phosphate transferase protein MNN4. | 203 | 1.60E-18 |
| f5-14.aa | R97866 | Chicken leucocytozoan immunogenic protein for use in vaccines. | 187 | 2.10E-15 |
| f5-14.aa | W21591 | Antibiotic potentiating peptide #3. | 176 | 4.60E-15 |
| f5-14.aa | R69629 | B. burgdorferi OspF operon. | 106 | 3.50E-13 |
| f5-14.aa | R89476 | B. burgdorferi OspG lipoprotein. | 157 | 6.20E-13 |
| f5-14.aa | W26536 | Trypanosoma cruzi antigen. | 143 | 5.00E-11 |
| f5-15.aa | R69629 | B. burgdorferi OspF operon. | 448 | 1.30E-68 |
| f5-15.aa | R89476 | B. burgdorferi OspG lipoprotein. | 105 | 5.80E-24 |
| f502.aa | R69852 | Ethylene response (ETR) mutant protein etr1-3. | 191 | 1.90E-35 |
| f502.aa | R69849 | Ethylene response (ETR) gene product. | 191 | 2.70E-35 |
| f502.aa | R69853 | Ethylene response (ETR) mutant protein etr1-4. | 191 | 2.70E-35 |
| f502.aa | R69850 | Ethylene response (ETR) mutant protein etr1-1. | 191 | 3.60E-35 |
| f502.aa | R69851 | Ethylene response (ETR) mutant protein etr1-2. | 191 | 3.60E-35 |
| f502.aa | R74632 | QETR ethylene response (ETR) protein from Arabidopsis thaliana. | 190 | 5.20E-26 |
| f502.aa | R74629 | Tornato ethylene response (TETR) protein. | 171 | 6.50E-23 |
| f502.aa | R74633 | Nr (never ripe) tomato ethylene response (ETR) protein. | 171 | 6.50E-23 |
| f502.aa | R74630 | Tornato TGETR1 ethylene response protein. | 123 | 1.20E-19 |
| f51-2.aa | W03626 | Human thyrotropin GPR N-terminal sequence. | 235 | 2.90E-23 |
| f51-2.aa | R89476 | B. burgdorferi OspG lipoprotein. | 109 | 6.90E-23 |

TABLE 2-continued

Closest matching sequences between the polypeptides of the present invention and sequences in GenBank and Derwent databases.

| Query | GenSeq Access No. | GenSeq Gene Description | BLAST Score | BLAST P-Value |
|---|---|---|---|---|
| f51-2.aa | W03627 | Human follicle stimulating hormone GPR N-terminal sequence. | 228 | 2.20E-22 |
| f51-2.aa | W30763 | Mannose-1-phosphate transferase protein MNN4. | 203 | 1.00E-18 |
| f51-2.aa | R70491 | *Leucocytozoan protozoa* structural protein epitope. | 191 | 7.50E-18 |
| f51-2.aa | R97866 | Chicken leucocytozoan immunogenic protein for use in vaccines. | 183 | 4.80E-16 |
| f51-2.aa | W21591 | Antibiotic potentiating peptide #3. | 159 | 6.20E-13 |
| f51-2.aa | R68838 | Plasmodium falciparum ABRA gene protein. | 142 | 1.10E-12 |
| f51-2.aa | R27530 | *Plasmodium falciparum* blood and liver stage ABRA antigen. | 142 | 2.80E-12 |
| f51-2.aa | W31186 | Human p160 polypeptide 160.2 | 148 | 2.30E-11 |
| f51-2.aa | W31185 | Human p160 polypeptide 160.1 | 148 | 2.40E-11 |
| f517.aa | W24296 | *Staphylococcus aureus* Gene #1 polypeptide sequence 2. | 237 | 6.80E-30 |
| f541.aa | R31013 | P39-alpha. | 1253 | 3.80E-229 |
| f541.aa | R33280 | P39-beta. | 504 | 1.90E-117 |
| f542.aa | R33280 | P39-beta. | 711 | 3.20E-96 |
| f542.aa | R31013 | P39-alpha. | 101 | 7.90E-16 |
| f561.aa | R69631 | *B. burgdorferi* T5 protein. | 982 | 6.90E-131 |
| f598.aa | W20289 | *H. pylori* transporter protein, 24218968.aa. | 264 | 9.90E-33 |
| f598.aa | W20640 | *H. pylori* transporter protein, 02ce11022orf8. | 264 | 1.00E-30 |
| f598.aa | W20101 | *H. pylori* transporter protein 11132778.aa. | 233 | 8.50E-27 |
| f598.aa | W20861 | *H. pylori* cell envelope transporter protein, 12ge10305orf16. | 233 | 9.60E-27 |
| f598.aa | W34202 | *Streptomyces efflux* pump protein (frenolicin gene D product). | 196 | 2.80E-21 |
| f598.aa | R71091 | *C. jejuni* PEB1A antigen from ORF3. | 168 | 1.20E-17 |
| f600.aa | W25527 | *Staphlococcus aureus* Gene #20 polypeptide sequence 2. | 209 | 3.40E-26 |
| f600.aa | W34201 | *Streptomyces efflux* pump protein (frenolicin gene C product). | 169 | 6.50E-19 |
| f600.aa | W20639 | *H. pylori* transporter protein, 02ce11022orf7. | 127 | 1.10E-14 |
| f603.aa | W34200 | *Streptomyces efflux* pump protein (frenolicin gene B product). | 155 | 7.40E-32 |
| f604.aa | R48035 | Hyaluronic acid synthase of *Streptococcus equisimilis*. | 110 | 2.30E-20 |
| f606.aa | R48035 | Hyaluronic acid synthase of *Streptococcus equisimilis*. | 116 | 1.20E-25 |
| f607.aa | R48035 | Hyaluronic acid synthase of *Streptococcus equisimilis*. | 141 | 1.50E-26 |
| f631.aa | W15192 | *Staphylococcus aureus* cell surface protein. | 160 | 7.30E-29 |
| f664.aa | W20105 | *H. pylori* flagella-associated protein, 1171928.aa. | 202 | 3.20E-46 |
| f664.aa | W20688 | *H. pylori* flagella-associated protein 04ge11713orf5. | 202 | 2.60E-45 |
| f664.aa | R97245 | Virulence gene cluster polypeptide product. | 158 | 3.90E-13 |
| f704.aa | R60153 | Nematode-inducible transmembrane pore protein. | 104 | 2.50E-18 |
| f704.aa | R33913 | Sequence encoded by TobRB7-5A which encodes a membrane channel | 104 | 2.50E-18 |
| f704.aa | R77082 | Tobacco root specific promoter RB7 from clone lambda5A (TobRB7-5A). | 104 | 2.50E-18 |
| f742.aa | W46499 | Amino acid sequence of the spindly (SPY) protein of *Arabidopsis*. | 101 | 2.50E-14 |
| f752.aa | W20733 | *H. pylori* cell envelope protein, 06cp11722orf15. | 141 | 3.00E-37 |
| f752.aa | W20358 | *H. pylori* cell envelope protein 26366312.aa. | 110 | 4.20E-18 |
| f814.aa | W20753 | *H. pylori* transporter protein, 06gp11202orf7. | 178 | 7.90E-35 |
| f814.aa | W20420 | *H. pylori* cell envelope transporter protein 33399142.aa. | 160 | 2.30E-21 |
| f843.aa | R14319 | Human T-cell immunosuppressive factor. | 167 | 1.20E-19 |
| f860.aa | W21894 | Asparaginyl-tRNA synthetase from *Staphylococcus aureus*. | 245 | 2.30E-38 |
| f860.aa | W33903 | *Streptococcus pneumoniae* asparaginyl tRNA synthetase. | 177 | 1.10E-22 |
| f867.aa | W34261 | An alpha subunit of a thermostable ATPase. | 592 | 1.30E-161 |
| f867.aa | R10098 | Alpha subunit of ATP-synthase. | 741 | 4.90E-144 |
| f867.aa | R31522 | Carrot reverse transcriptase. | 311 | 4.60E-130 |
| f867.aa | R10099 | Beta subunit of ATP-synthase. | 121 | 7.90E-14 |
| f867.aa | W34262 | A beta subunit of a thermostable ATPase. | 116 | 1.00E-12 |
| f868.aa | W34262 | A beta subunit of a thermostable ATPase. | 151 | 6.10E-109 |
| f868.aa | R10099 | Beta subunit of ATP-synthase. | 172 | 1.90E-106 |
| f868.aa | W34261 | An alpha subunit of a thermostable ATPase. | 117 | 3.10E-19 |
| f868.aa | R10098 | Alpha subunit of ATP-synthase. | 113 | 2.00E-18 |
| f868.aa | R31522 | Carrot reverse transcriptase. | 101 | 7.10E-15 |
| f874.aa | R10591 | L-lactic acid dehydrogenase. | 538 | 7.20E-109 |
| f874.aa | R08355 | Recombinant thermophilic NAD-dependant dehydrogenase. | 455 | 9.80E-99 |
| f874.aa | R09295 | Recombinant thermophilic NAD-dependant dehydrogenase. | 455 | 9.80E-99 |
| f874.aa | R15736 | L-lactic acid dehydrogenase. | 426 | 1.60E-85 |
| f874.aa | P91948 | Pig H4 isoenzyme. | 393 | 2.00E-82 |
| f874.aa | W33108 | Chicken lactic acid dehydrogenase type B subunit. | 390 | 2.20E-80 |
| f874.aa | W33107 | Chicken lactic acid dehydrogenase type B subunit. | 385 | 1.10E-79 |
| f874.aa | P80891 | Testis-specific lactate dehydrogenase subunit LDH-C4. | 339 | 5.50E-74 |
| f874.aa | R94013 | Heat resistant maleate dehydrogenase. | 255 | 1.30E-55 |
| f874.aa | R11119 | Recombinant L-2-hydroxyisocaproic acid dehydrogenase. | 224 | 7.90E-49 |
| f874.aa | R62605 | *P. falciparum* lactate dehydrogenase. | 255 | 2.00E-44 |
| f874.aa | W11476 | Eimeria lactate dehydrogenase. | 203 | 1.10E-25 |
| f943.aa | P91223 | Coenzyme-independent L-sorbosone dehydrogenase from *Gluconobacter* | 175 | 4.30E-16 |

TABLE 3

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

TABLE 4

Residues Comprising Epito-Bearing Fragments

| Query | Residues Comprising Epito-Bearing Fragments |
|---|---|
| f101.aa | from about Lys-62 to about Gly-64, from about Ser-111 to about Asp-113, from about Arg-136 to about Arg-139, from about Pro-189 to about Asn-193. |
| f11.aa | from about Pro-38 to about Lys-40, from about Glu-92 to about Lys-96. |
| f12.aa | from about Pro-288 to about Asp-290, from about Asn-336 to about Gly-338, from about Tyr-410 to about Gly-413, from about Asp-418 to about Arg-420, from about Pro-552 to about Val-555, from about Gln-643 to about Asp-645, from about Gln-1061 to about Arg-1063, from about Asn-1130 to about Lys-1132. |
| f129.aa | from about Glu-76 to about Arg-81, from about Lys-144 to about Asn-146. |
| f147.aa | from about Gln-94 to about Thr-96. |
| f152.aa | from about Gly-35 to about Gly-37, from about Gln-321 to about Gly-323. |
| f154.aa | from about Asn-39 to about Lys-41, from about Ser-74 to about Lys-77, from about Ser-213 to about Gly-215, from about Ser-303 to about Asp-306, from about Asp-422 to about Asn-424. |
| f157.aa | from about Lys-21 to about Asp-24, from about Ser-45 to about Tyr-47. |
| f17.aa | from about Arg-17 to about Asn-20, from about Thr-94 to about Gly-96. |
| f186.aa | from about Lys-305 to about Tyr-308. |
| f196.aa | from about Lys-121 to about Asn-123, from about Pro-278 to about Lys-282, from about Glu-576 to about Tyr-578. |
| f899.aa | from about Asn-174 to about Asp-177. |
| f925.aa | from about Lys-201 to about Asp-204, from about Phe-291 to about Lys-294. |
| f929.aa | from about Pro-139 to about Asn-141, from about Arg-211 to about Glu-214, from about Thr-370 to about Asn-375. |
| f933.aa | from about Ser-139 to about Lys-143. |
| f940.aa | from about Gly-143 to about Asn-148. |
| f943.aa | from about Asp-58 to about Asp-60, from about Lys-157 to about Asn-159, from about Asp-217 to about Asp-221, from about Lys-250 to about Asn-254, from about Pro-262 to about Asn-264, from about Gly-305 to about Trp-307. |
| f952.aa | from about Ser-52 to about Ser-54. |
| f4.aa | from about Arg-64 to about Arg-67. |
| f43.aa | from about Ser-84 to about Gln-87, from about Asp-231 to about Tyr-233, from about Arg-296 to about Asp-300. |
| f50.aa | from about Glu-136 to about Gly-138, from about Asp-153 to about Lys-155, from about Asp-289 to about Asp-291, from about Glu-458 to about Asn-461. |
| f65.aa | from about Glu-120 to about Asp-122, from about Pro-204 to about Tyr-206. |
| f8.aa | from about Pro-263 to about Arg-265, from about Asp-274 to about Lys-278. |

TABLE 4-continued

Residues Comprising Epito-Bearing Fragments

| Query | Residues Comprising Epito-Bearing Fragments |
|---|---|
| f82.aa | from about Tyr-66 to about Gly-68, from about Ser-116 to about Lys-119, from about Asp-121 to about Gly-123, from about Pro-128 to about Gly-131. |
| f86.aa | from about Asn-179 to about Asn-181, from about Lys-192 to about Asn-194, from about Lys-270 to about Asn-272, from about Lys-279 to about Lys-282, from about Asp-331 to about Asn-333. |
| f477.aa | from about Pro-250 to about Lys-253. |
| f488.aa | from about Lys-76 to about Lys-79, from about Asn-486 to about Asp-489, from about Lys-508 to about Gly-510, from about Asn-559 to about Gly-562. |
| f494.aa | from about Lys-76 to about Asn-78. |
| f516.aa | from about Lys-32 to about Asp-34. |
| f523.aa | from about Pro-202 to about Asn-206, from about Lys-255 to about Tyr-258. |
| f526.aa | from about Asn-85 to about Lys-88, from about Asp-136 to about Gly-138. |
| f577.aa | from about Cys-18 to about Lys-22, from about Asn-297 to about Gln-300. |
| f584.aa | from about Pro-131 to about Lys-133, from about Pro-200 to about Ser-202. |
| f596.aa | from about Arg-42 to about Asp-44, from about Asp-117 to about Tyr-119, from about Pro-205 to about Asp-207. |
| f600.aa | from about Pro-143 to about Asp-145. |
| f603.aa | from about Phe-35 to about Ser-37. |
| f607.aa | from about Gln-67 is about Lys-70, from about Asp-273 to about Tyr-275, from about Asp-333 to about Gly-338, from about Pro-359 to about Lys-362, from about Arg-409 to about Gly-411. |
| f611.aa | from about Arg-133 to about Gly-135. |
| f631.aa | from about Pro-132 to about Asn-136, from about Asn-159 to about Tyr-161, from about Pro-216 to about Asp-218, from about Pro-220 to about Lys-223. |
| f688.aa | from about Lys-266 to about Asp-268, from about Lys-271 to about Asn-273, from about Lys-315 to about Lys-318. |
| f704.aa | from about Lys-250 to about Lys-253. |
| f707.aa | from about Lys-131 to about Asp-134, from about Asp-246 to about Asn-249. |
| f709.aa | from about Tyr-39 to about Gly-42, from about Lys-148 to about Gly-150, from about Arg-269 to about Gly-272, from about Ser-466 to about Tyr-468, from about Asn-489 to about Asn-491, from about Lys-575 to about Asp-578, from about Pro-642 to about Lys-644. |
| f197.aa | from about Pro-217 to about Asp-219, from about Glu-675 to about Asp-678, from about Pro-687 to about Asn-689, from about Glu-694 to about Gln-696. |
| f200.aa | from about Arg-174 to about Phe-179. |
| f208.aa | from about Arg-326 to about Ser-328. |
| f210.aa | from about Pro-191 to about Ile-194. |
| f221.aa | from about Asn-133 to about Asn-135. |
| f253.aa | from about Arg-191 to about Gly-194. |
| f269.aa | from about Ser-271 to about Thr-273, from about Asp-284 to about Gly-286. |
| f29.aa | from about Pro-159 to about Ser-161. |
| f290.aa | from about Pro-240 to about Gly-244. |
| f291.aa | from about Gln-267 to about Lys-269. |
| f296.aa | from about Glu-98 to about Lys-101. |
| f3.aa | from about Asn-241 to about Lys-245. |
| f30.aa | from about Asn-156 to about Tyr-159, from about Asn-178 to about Lys-180. |
| f939.aa | from about Ser-245 to about Asn-249. |
| f739.aa | from about Asn-80 to about Tyr-82, from about Lys-208 to about Ser-210. |
| f742.aa | from about Ser-141 to about Asp-145, from about Asn-222 to about Gln-225, from about Asp-243 to about Tyr-247, from about Asn-249 to about Asn-251. |
| f743.aa | from about Arg-111 to about Gly-114, from about Pro-131 to about Asp-134. |
| f790.aa | from about Thr-40 to about Asn-42, from about Ser-53 to about Ser-55, from about Lys-215 to about Asp-218, from about Asn-274 to about Gly-277. |
| f792.aa | from about Val-82 to about Ser-84, from about Ser-102 to about Asn-104, from about Gln-127 to about Tyr-130, from about Lys-309 to about Asn-314, from about Lys-375 to about Thr-377, from about Pro-511 to about His-513, from about Thr-515 to about Asp-517. |

TABLE 4-continued

Residues Comprising Epito-Bearing Fragments

| Query | Residues Comprising Epito-Bearing Fragments |
|---|---|
| f797.aa | from about Pro-119 to about Gly-122, from about Lys-166 to about Asn-169. |
| f799.aa | from about Asn-31 to about Asn-34, from about Gln-44 to about Asn-47, from about Pro-123 to about Gly-125. |
| f814.aa | from about Ser-120 to about Ser-122, from about Arg-636 to about Asn-638, from about Cys-967 to about Ser-969. |
| f820.aa | from about Thr-563 to about Tyr-565. |
| f850.aa | from about Tyr-159 to about Tyr-164, from about Gln-375 to about Asp-379. |
| f853.aa | from about Thr-180 to about Lys-184, from about Arg-231 to about Asp-233, from about Asn-252 to about Gly-254. |
| f859.aa | from about Lys-46 to about Ser-52, from about Pro-88 to about Asn-91, from about Asn-117 to about Asp-120. |
| f861.aa | from about Asp-38 to about Lys-40, from about Lys-219 to about Asn-225. |
| f368.aa | from about Gln-228 to about Asn-231. |
| f371.aa | from about Tyr-109 to about Asn-111, from about Asn-162 to about Gln-164. |
| f502.aa | from about Asn-118 to about Lys-122, from about Ser-269 to about Gly-271, from about Lys-370 to about Asp-373, from about Asn-509 to about Lys-511, from about Lys-705 to about Arg-707, from about Thr-912 to about Gly-914, from about Pro-1213 to about Asp-1216, from about Asn-1491 to about Arg-1493. |
| f527.aa | from about Cys-20 to about Gln-22, from about Asn-38 to about Asn-40, from about Phe-112 to about Asp-114, from about Lys-160 to about Asn-162, from about Ser-199 to about Asp-201, from about Gln-258 to about Gly-261, from about Arg-282 to about Asn-284, from about Ser-297 to about Asp-299. |
| f541.aa | from about Ser-68 to about Asn-71. |
| f604.aa | from about Lys-77 to about Gly-79, from about Lys-201 to about Asn-203, from about Asp-252 to about Asp-254, from about Tyr-347 to about Gly-350, from about Asp-514 to about Trp-516. |
| f736.aa | from about Lys-20 to about Asn-24, from about Arg-147 to about Ser-153, from about Ser-231 to about Lys-233. |
| f752.aa | from about Thr-119 to about Lys-122, from about Pro-420 to about Gly-422. |
| f798.aa | from about Asp-33 to about Thr-36, from about Lys-180 to about His-183. |
| f635.aa | from about Pro-100 to about Asn-102, from about Asp-145 to about Phe-147. |
| f32.aa | from about Lys-18 to about Asn-20. |
| f320.aa | from about Asn-193 to about Leu-195, from about Gln-248 to about Lys-250. |
| f352.aa | from about Ser-46 to about Asn-49. |
| f301.aa | from about Lys-178 to about Lys-180, from about Ser-401 to about Tyr-404. |
| f373.aa | from about Gly-88 to about Lys-90, from about Asn-539 to about Lys-542, from about Glu-654 to about Ser-657. |
| f384.aa | from about Pro-250 to about Asn-252, from about Asp-266 to about Lys-268. |
| f446.aa | from about Asp-20 to about Ser-26, from about Asn-146 to about Lys-149. |
| f542.aa | from about Arg-86 to about Gly-88, from about Arg-163 to about Asn-165. |
| f93.aa | from about Asn-152 to about Asp-155. |
| f105.aa | from about Asp-48 to about Phe-50. |
| f150.aa | from about Thr-214 to about Asp-218, from about Asp-256 to about Asp-259. |
| f219.aa | from about Asn-77 to about Asn-81, from about Asp-111 to about Asn-115. |
| f229.aa | from about Gln-61 to about Asn-63. |
| f32.aa | from about Lys-18 to about Asn-20. |
| f186.aa | from about Lys-305 to about Tyr-308. |
| f216.aa | from about Ser-105 to about Asn-107. |
| f328.aa | from about Asn-105 to about Asp-107. |
| f352.aa | from about Ser-46 to about Asn-49. |
| f867.aa | from about Thr-3 to about Gly-5, from about Lys-156 to about Ser-159. |
| f868.aa | from about Arg-94 to about Gly-96, from about Pro-257 to about Gly-261, from about Pro-295 to about Asp-297, from about Arg-340 to about Asp-342. |
| f872.aa | from about Ser-19 to about Lys-23, from about Thr-139 to about Asp-142, from about Ser-282 to about Tyr-286, from about Ser-311 to about Ser-313. |
| f886.aa | from about Thr-83 to about Asp-85, from about Asp-106 to about Lys-108, from about Lys-143 to about Gly-147, from about Asp-186 to about Asn-191. |
| f888.aa | from about Asn-65 to about Asp-67. |
| f893.aa | from about Asn-203 to about Asn-207, from about Thr-446 to about Asn-450. |
| f605.aa | from about Arg-31 to about Asp-33. |
| f606.aa | from about Asn-68 to about Gly-71, from about Asn-136 to about Lys-139, from about Asn-223 to about Tyr-226, from about Ser-276 to about Tyr-279, from about Pro-362 to about Asn-365, from about Arg-503 to about Trp-507. |
| f679.aa | from about Lys-154 to about Asp-156, from about Lys-224 to about Arg-226, from about Asn-260 to about Asp-264, from about Glu-363 to about Lys-366, from about Asp-387 to about Gly-389, from about Tyr-441 to about Lys-443, from about Arg-501 to about Tyr-504. |
| f11-12.aa | from about Pro-91 to about Asn-93, from about Pro-181 to about Asp-186, from about Lys-244 to about Ser-248. |
| f11-4.aa | from about Asn-160 to about Lys-163. |
| f14-8.aa | from about Pro-92 to about Gln-95, from about Lys-123 to about Thr-125, from about Lys-215 to about Asp-219. |
| f17-6.aa | from about Pro-36 to about Glu-38. |
| f19-2.aa | from about Ser-104 to about Ser-106, from about Gln-230 to about Asn-232. |
| f19-4.aa | from about Val-79 to about Thr-82, from about Pro-195 to about Gly-201. |
| f19-6.aa | from about Asp-24 to about Lys-30, from about Pro-36 to about Glu-38. |
| f21-4.aa | from about Cys-24 to about Asn-26. |
| f28-2.aa | from about Ser-77 to about Lys-80, from about Tyr-274 to about Asn-277. |
| f28-3.aa | from about Glu-53 to about Arg-57, from about Gln-82 to about Asn-85, from about Gln-157 to about Asn-159. |
| f31-2.aa | from about Arg-95 to about Arg-97, from about Asn-297 to about Asn-299. |
| f4-15.aa | from about Pro-182 to about Asp-184, from about Lys-220 to about Asp-222. |
| f4-50.aa | from about Thr-109 to about Asn-111. |
| f42-1.aa | from about Asn-55 to about Asn-57, from about Arg-81 to about Ser-84, from about Asp-94 to about Asn-97. |
| f45-2.aa | from about Asn-83 to about Gly-86. |
| f47-2.aa | from about Ser-29 to about Asp-33, from about Asn-94 to about Lys-99, from about Pro-152 to about Lys-157. |
| f49-2.aa | from about Asn-452 to about Gly-454. |
| f5-14.aa | from about Glu-102 to about Asp-106, from about Thr-272 to about Asn-275, from about Glu-313 to about Asn-315, from about Ser-370 to about Ser-372. |
| f5-15.aa | from about Lys-170 to about Gly-173, from about Asn-194 to about Gly-196. |
| f51-2.aa | from about Asp-302 to about Lys-304. |
| f6-21.aa | from about Glu-38 to about Asn-42, from about Arg-84 to about Gly-87. |
| f6-27.aa | from about Asp-67 to about Asn-69, from about Arg-85 to about Asn-89, from about Lys-168 to about Gly-171, from about Lys-179 to about Asn-181, from about Ser-380 to about His-382. |
| f6-5.aa | from about Ser-67 to about Asn-71. |
| f7-30.aa | from about Pro-94 to about Asp-96, from about Lys-144 to about Arg-147. |
| f76-1.aa | from about Asn-30 to about Lys-35, from about Lys-113 to about Gly-116, from about Glu-119 to about Lys-121. |
| f8-10.aa | from about Pro-25 to about Lys-32, from about Ser-168 to about Thr-172. |
| f01a.aa__bb001 | from about Pro-123 to about Asp-125, from about Ser-179 to about Asp-181, from about Lys-255 to about Gly-259. |
| bb0011 | from about Ala8 about Arg 17, from about Tyr31 to about Gly40, from about Ser65 to about Lys78, from about Val93 to about Asp102, from about Ser120 to about Ile129, from about Pro156 to about Glu170, from about Lys187 to about Asn 196, from about His205 to about Lys214, from about Gly226 to about Glu235, from about Gln253 to about Asn266, from about |

TABLE 4-continued

Residues Comprising Epito-Bearing Fragments

| Query | Residues Comprising Epito-Bearing Fragments |
|---|---|
| | Glu283 to about Glu293, from about Leu311 to about Ile320, from about Arg326 to about Gly335, from about Pro340 to about Ala349 |
| f02a.aa _bb002 | from about Tyr-169 to about Asn-171, from about Tyr-242 to about Asn-245, from about Lys-264 to about Asp-267. |
| _bb9 | from about Met7 to about Lys16, from about Lys47 to about Ser57, from about Asn80 to about Ser89, from about Gly 103 to about Glu113, from about Lys125 to about Pro133, from about Lys138 to about Ala147 |
| f03a.aa _bb006 | from about Asp-54 to about Thr-57, from about Lys-201 to about His-204. |
| _bb014 | from about Pro23 to about Gln31, from about Ser37 to about Asp45, from about Leu76 to about Asn84, from about Leu76 to about Val84, from about Ser89 to about Asn97, from about Ser105 to about Lys113, from about Asn120 to about Met128, from about Asn159 to about Gly 167, from about Lys173 to about Bal181 |
| _bb023 | from about Asp17 to about Gly27, from about Arg40 to about Asp48, from about Val64 to about Asp72, from about Glu105 to about Thr113, from about Ser141 to about Gly150, from about Asp155 to about Ile163, from about Asn184 to about Lys198, from about Ile219 to about Pro227, from about Ser230 to about Phe238, from about Ser241 to about Asn250, from about Asp270 to about Val278, from about Ser285 to about Leu293, from about Glyu307 to about Ser315, from about Lys327 to about Asn335 |
| f08a.aa bb024 | from about Asn-30 to about Asp-33, from about Ser-116 to about Asn-118, from about Asn-154 to about Gly-156. |
| f09a.aa _bb025 | from about Asn-30 to about Ser-35, from about Thr-145 to about Asn-148. |

What is claimed is:

1. An isolated polynucleotide which encodes at least 50 contiguous amino acid residues of SEQ ID NO:627.

2. The isolated polynucleotide which is fully complementary to the polynucleotide of claim 1.

3. An isolated polynucleotide consisting of at least 100 contiguous nucleotides of SEQ ID NO:625.

4. The isolated polynucleotide which is fully complementary to the polynucleotide of claim 3.

5. The isolated polynucleotide of claim 3 consisting of at least 300 contiguous nucleotides of SEQ ID NO:625.

6. The isolated polynucleotide which is fully complementary to the polynucleotide of claim 5.

7. The isolated polynucleotide of claim 5 consisting of the full length sequence of SEQ ID NO:625.

8. A method of detecting *Borrelia* nucleic acids in a biological sample comprising:

(a) contacting the sample with the nucleic acid of claim 1, under conditions such that hybridization occurs, and (b) detecting hybridization of said nucleic acids to the one or more *Borrelia* nucleic acid sequences present in the biological sample.

9. A method of detecting *Borrelia* nucleic acids in a biological sample comprising:

(a) contacting the sample with the nucleic acid of claim 3, under conditions such that hybridization occurs, and (b) detecting hybridization of said nucleic acids to the one or more *Borrelia* nucleic acid sequences present in the biological sample.

* * * * *